(12) United States Patent
Bereznak et al.

(10) Patent No.: US 8,815,772 B2
(45) Date of Patent: Aug. 26, 2014

(54) FUNGICIDAL HETEROCYCLIC CARBOXAMIDES

(71) Applicant: E I du Pont de Nemours and Company, Wilmington, DE (US)

(72) Inventors: James Francis Bereznak, Newtown Square, PA (US); Steven Gutteridge, Wilmington, DE (US); Ravisekhara P Reddy, Andhra Pradesh (IN); Andrew Edmund Taggi, Newark, DE (US); Matthew James Campbell, Rising Sun, MD (US); Moumita Kar, Hyderabad (IN); Johan A. J. Desaeger, Elkton, MD (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/921,495

(22) Filed: Jun. 19, 2013

(65) Prior Publication Data

US 2014/0005231 A1    Jan. 2, 2014

Related U.S. Application Data

(60) Provisional application No. 61/666,531, filed on Jun. 29, 2012, provisional application No. 61/780,489, filed on Mar. 13, 2013.

(51) Int. Cl.
| | | |
|---|---|---|
| A01N 25/00 | (2006.01) |
| A01N 43/40 | (2006.01) |
| C07D 401/00 | (2006.01) |
| A01N 43/56 | (2006.01) |

(52) U.S. Cl.
CPC ..................................... A01N 43/56 (2013.01)
USPC ...................... 504/116.1; 514/341; 546/275.4

(58) Field of Classification Search
CPC ....................................................... A01N 43/56
USPC ...................... 504/116.1; 514/341; 546/275.4
See application file for complete search history.

(56) References Cited

U.S. PATENT DOCUMENTS

| 2006/0178513 A1* | 8/2006 | Dunkel et al. ............... 544/405 |
| 2007/0167491 A1 | 7/2007 | Mansfield et al. |
| 2009/0076113 A1 | 3/2009 | Dunkel et al. |
| 2010/0173966 A1 | 7/2010 | Stierli et al. |
| 2011/0136831 A1 | 6/2011 | Oda et al. |

FOREIGN PATENT DOCUMENTS

| EP | 1574511 A1 | 9/2005 |
| JP | 2009242244 A1 | 3/2008 |
| JP | 2009023994 A | 2/2009 |
| WO | 2007000246 A1 | 1/2007 |
| WO | 2007072999 A1 | 6/2007 |
| WO | 2007141009 A1 | 12/2007 |
| WO | 2008148570 A1 | 12/2008 |
| WO | WO 2008148570 A1 * | 12/2008 |
| WO | 2011048120 A1 | 4/2011 |
| WO | WO 2011157787 A1 * | 12/2011 |
| WO | 2013064519 A1 | 5/2013 |
| WO | 2013064520 A1 | 5/2013 |

OTHER PUBLICATIONS

Foye, W.O.; Lemke, T.L.; Williams, D.A. Principles of Medicinal Chemistry 1995, 4th Ed, Chapter 4.*
International Search Report and Written Opinion of corresponding PCT/US2013/044951 mailed Sep. 4, 2013.

* cited by examiner

Primary Examiner — Sean Basquill
Assistant Examiner — Andrew S Rosenthal

(57) ABSTRACT

Disclosed are compounds of Formula 1, including all stereoisomers, N-oxides, and salts thereof,

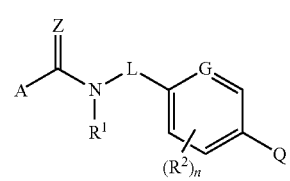

wherein
L is —C($R^{12a}$)$R^{12b}$—C($R^{13a}$)$R^{13b}$—, wherein the carbon atom bonded to $R^{12a}$ and $R^{12b}$ is also bonded to the carboxamide nitrogen atom in Formula 1; or 1,2-phenylene optionally substituted with up to 4 substituents independently selected from halogen and $C_1$-$C_2$ alkyl; and A, Z, $R^1$, $R^2$, n, G and Q are as defined in the disclosure.
Also disclosed are compositions containing the compounds of Formula 1 and methods for controlling plant disease caused by a fungal pathogen comprising applying an effective amount of a compound or a composition of the invention. Also disclosed are methods for controlling a phytophagous nematode comprising contacting the nematode or its environment with a nematocidally effective amount of a compound of Formula 1 wherein L is —C($R^{12a}$)$R^{12b}$—C($R^{13a}$)$R^{13b}$—; and A, Z, $R^1$, $R^2$, n, G and Q are as defined in the disclosure.

13 Claims, No Drawings

FUNGICIDAL HETEROCYCLIC CARBOXAMIDES

FIELD OF THE INVENTION

This invention relates to certain heterocyclic carboxamides, their N-oxides, salts and compositions, and methods of their use as fungicides and nematocides.

BACKGROUND OF THE INVENTION

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different sites of action.

The control of plant-parasitic nematodes is also extremely important in achieving high crop efficiency. Nematode-induced root damage can cause significant reduction in crop yields and quality and thereby result in increased costs to the consumer. The need continues for new compounds which are more effective, less costly, less toxic, environmentally safer or have different modes of action.

SUMMARY OF THE INVENTION

This invention is directed to compounds of Formula 1 (including all stereoisomers), N-oxides, and salts thereof, agricultural compositions containing them and their use as fungicides:

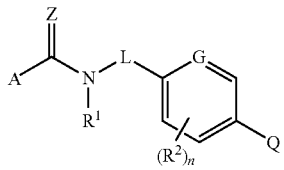

wherein

A is a radical selected from the group consisting of

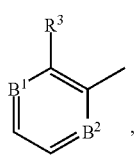
A-1

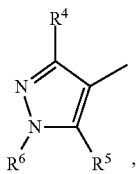
A-2

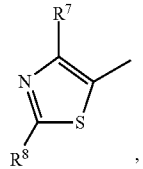
A-3

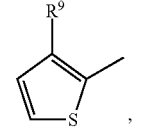
A-4

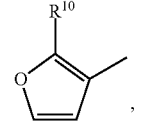
A-5

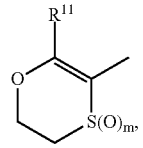
A-6

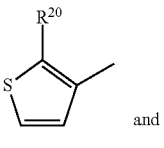
A-7 and

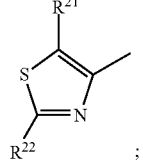
A-8

Z is O or S;
$R^1$ is H, cyclopropyl or $C_1$-$C_2$ alkoxy;
L is —C($R^{12a}$)$R^{12b}$—C($R^{13a}$)$R^{13b}$—, wherein the carbon atom bonded to $R^{12a}$ and $R^{12b}$ is also bonded to the carboxamide nitrogen atom in Formula 1; or 1,2-phenylene optionally substituted with up to 4 substituents independently selected from halogen and $C_1$-$C_2$ alkyl;
G is N or C—$R^{2a}$;
each $R^2$ is independently halogen, nitro, cyano, $C_1$-$C_2$ alkyl, $C_1$-$C_2$ haloalkyl, $C_1$-$C_2$ alkoxy or $C_1$-$C_2$ haloalkoxy;
n is 0, 1, 2 or 3;
$R^{2a}$ is H, halogen, nitro, cyano, $C_1$-$C_2$ alkyl, $C_1$-$C_2$ haloalkyl, $C_1$-$C_2$ alkoxy or $C_1$-$C_2$ haloalkoxy;
$B^1$ is CH or N;
$B^2$ is CH or N;
$R^3$ is halogen, $C_1$-$C_3$ alkyl or $C_1$-$C_3$ haloalkyl;
$R^4$ is halogen, $C_1$-$C_3$ alkyl or $C_1$-$C_3$ haloalkyl;
$R^5$ is H, halogen, $C_1$-$C_3$ alkyl or $C_1$-$C_3$ haloalkyl;
$R^6$ is $C_1$-$C_2$ alkyl;
$R^7$ is halogen, $C_1$-$C_3$ alkyl or $C_1$-$C_3$ haloalkyl;
$R^8$ is H, $C_1$-$C_2$ alkyl or $C_1$-$C_2$ haloalkyl;
$R^9$ is halogen, $C_1$-$C_3$ alkyl or $C_1$-$C_3$ haloalkyl;
$R^{10}$ is halogen, $C_1$-$C_3$ alkyl or $C_1$-$C_3$ haloalkyl;
$R^{11}$ is halogen, $C_1$-$C_3$ alkyl or $C_1$-$C_3$ haloalkyl;
m is 0, 1 or 2;

$R^{12a}$ and $R^{12b}$ are each independently H, $C_1$-$C_2$ alkyl or $C_1$-$C_2$ haloalkyl; or $R^{12a}$ and $R^{12b}$ are taken together as $C_2$-$C_4$ alkanediyl;

$R^{13a}$ is H, halogen, $C_1$-$C_2$ alkyl, $C_1$-$C_2$ haloalkyl, $C_1$-$C_2$ alkoxy, $C_1$-$C_2$ haloalkoxy, $C_1$-$C_2$ alkylthio or $C_1$-$C_2$ alkoxyamino;

$R^{13b}$ is H, halogen, $C_1$-$C_2$ alkyl or $C_1$-$C_2$ haloalkyl; or $R^{13a}$ and $R^{13b}$ are taken together as $C_2$-$C_4$ alkanediyl;

Q is a 5-membered unsaturated heterocyclic ring containing ring members selected from carbon atoms and up to 4 heteroatoms independently selected from up to 1O, up to 1S and up to 4N atoms, wherein up to 2 carbon atom ring members are independently selected from C(=O), the ring optionally substituted with one substituent on a ring member distal relative to the ring member connecting the heteroaromatic ring to the remainder of Formula 1, said optional substituent selected from $R^{14c}$ on carbon atom ring members and from $R^{14n}$ on nitrogen atom ring members, the heterocyclic ring further optionally substituted with substituents selected from $R^{15c}$ on carbon atom ring members and $R^{15n}$ on nitrogen atom ring members;

each $R^{14c}$ is independently halogen, cyano, $C_1$-$C_3$ alkyl, $C_1$-$C_3$ haloalkyl, $C_1$-$C_3$ alkoxy, $C_1$-$C_3$ haloalkoxy, $C_2$-$C_3$ alkoxycarbonyl or $C_2$-$C_4$ alkylcarbonyl; or a phenyl ring optionally substituted with up to 5 substituents independently selected from $R^{16}$; or a heteroaromatic ring optionally substituted with up to 4 substituents independently selected from $R^{17c}$ on carbon atom ring members and from $R^{17n}$ on nitrogen atom ring members;

each $R^{14n}$ is independently $C_1$-$C_3$ alkyl, $C_1$-$C_3$ haloalkyl or $C_1$-$C_3$ alkoxy; or a phenyl ring optionally substituted with up to 5 substituents independently selected from $R^{18}$; or a heteroaromatic ring optionally substituted with up to 4 substituents independently selected from $R^{19c}$ on carbon atom ring members and from $R^{19n}$ on nitrogen atom ring members;

each $R^{15c}$ is independently halogen, $C_1$-$C_3$ alkyl, $C_1$-$C_3$ haloalkyl or $C_1$-$C_3$ alkoxy;

each $R^{15n}$ is independently $C_1$-$C_3$ alkyl, $C_1$-$C_3$ haloalkyl or $C_1$-$C_3$ alkoxy;

each $R^{16}$, $R^{17c}$, $R^{18}$ and $R^{19c}$ is independently halogen, cyano, $C_1$-$C_2$ alkyl, $C_1$-$C_2$ haloalkyl, $C_1$-$C_2$ alkoxy or $C_1$-$C_2$ haloalkoxy;

each $R^{17n}$ and $R^{19n}$ is independently $C_1$-$C_2$ alkyl, $C_1$-$C_2$ haloalkyl or $C_1$-$C_2$ alkoxy;

$R^{20}$ is halogen, $C_1$-$C_3$ alkyl or $C_1$-$C_3$ haloalkyl;

$R^{21}$ is halogen, $C_1$-$C_3$ alkyl or $C_1$-$C_3$ haloalkyl; and $R^{22}$ is H, $C_1$-$C_2$ alkyl or $C_1$-$C_2$ haloalkyl;

provided that the compounds of Formula 1 are other than: 2-methyl-N-[2-[4-(1H-pyrazol-1-yl)phenyl]ethyl]-5-thiazolecarboxamide (CAS Registry No. 1280893-34-6), N-[2-[4-(3,5-dimethyl-1H-pyrazol-1-yl)phenyl]ethyl]-1,3,5-trimethyl-1H-pyrazole-4-carboxamide (CAS Registry No. 1252412-06-8), 2-bromo-N-[2-[4-(1H-pyrazol-1-yl)phenyl] ethyl]benzamide (CAS Registry No. 1169974-02-0), 3-methyl-N-[2-[4-(1H-pyrazol-1-yl)phenyl]ethyl]-2-thiophenecarboxamide (CAS Registry No. 1133718-61-2), 2-methyl-N-[2-[4-(1H-pyrazol-1-yl)phenyl]ethyl]benzamide (CAS Registry No. 1015521-08-0), 2-iodo-N-[2-[4-(1H-pyrazol-1-yl)phenyl]ethyl]benzamide (CAS Registry No. 1011617-47-2), 2-fluoro-N-[2-[4-(1H-pyrazol-1-yl)phenyl]ethyl]benzamide (CAS Registry No. 1011617-27-8), 2-chloro-N-[2-[4-(1H-pyrazol-1-yl)phenyl]ethyl]benzamide (CAS Registry No. 1008348-80-8), 5-chloro-1,3-dimethyl-N-[2-[4-(2-methyl-4-thiazolyl)phenyl]ethyl]-1H-pyrazole-4-carboxamide (CAS Registry No. 1295481-75-2), 2-methyl-N-[2-[4-(2-methyl-4-thiazolyl)phenyl]ethyl]benzamide (CAS Registry No. 1030712-80-1), 2-methyl-N-[2-[4-(2-methyl-4-thiazolyl)phenyl]ethyl]-3-furancarboxamide (CAS Registry No. 1010219-61-0), 2-fluoro-N-[2-[4-(2-methyl-4-thiazolyl) phenyl]ethyl]benzamide (CAS Registry No. 927077-70-1), 2-bromo-N-[2-[4-(2-methyl-4-thiazolyl)phenyl]ethyl]benzamide (CAS Registry No. 926832-81-7), 2-iodo-N-[2-[4-(2-methyl-4-thiazolyl)phenyl]ethyl]benzamide (CAS Registry No. 926764-00-3), N-[2-[4-(2-methyl-4-thiazolyl)phenyl]ethyl]-2-(trifluoromethyl)benzamide (CAS Registry No. 926763-25-9), and 2-chloro-N-[2-[4-(2-methyl-4-thiazolyl)phenyl]ethyl]benzamide (CAS Registry No. 926716-39-4).

More particularly, this invention pertains to a compound of Formula 1 (including all stereoisomers), an N-oxide or a salt thereof.

This invention also relates to a fungicidal composition comprising (a) a compound of the invention (i.e. in a fungicidally effective amount); and (b) at least one additional component selected from the group consisting of surfactants, solid diluents and liquid diluents.

This invention also relates to a fungicidal composition comprising (a) a compound of the invention; and (b) at least one other fungicide (e.g., at least one other fungicide having a different site of action).

This invention further relates to a method for controlling plant diseases caused by fungal plant pathogens comprising applying to the plant or portion thereof, or to the plant seed, a fungicidally effective amount of a compound of the invention (e.g., as a composition described herein).

The aforedescribed method can also be described as a method for protecting a plant or plant seed from diseases caused by fungal pathogens comprising applying a fungicidally effective amount of a compound of Formula 1, an N-oxide, or a salt thereof (e.g., as a composition described herein), to the plant (or portion thereof) or plant seed (directly or through the environment (e.g., growing medium) of the plant or plant seed).

This invention also provides a method for controlling a phytophagous nematode comprising contacting the nematode or its environment with a nematocidally effective amount of a compound of Formula 1, an N-oxide, or a salt thereof (e.g., as a composition described herein), wherein L is —C($R^{12a}$)$R^{12b}$—C($R^{13a}$)$R^{13b}$—, wherein the carbon atom bonded to $R^{12a}$ and $R^{12b}$ is also bonded to the carboxamide nitrogen atom in Formula 1;

and A, $R^1$, $R^2$, n, G and Q are as defined in the Summary of the Invention.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds.

As referred to herein, the term "seedling", used either alone or in a combination of words means a young plant developing from the embryo of a seed.

In the context of this disclosure "nematode control" means inhibition of nematode pest development (including mortality, feeding reduction, and/or mating disruption), and related expressions are defined analogously. Plant disease control refers to protecting plants preventatively and/or curatively from diseases caused by pathogens.

In the above recitations, the term "alkyl", used either alone or in compound words such as or "haloalkyl" includes straight-chain or branched alkyl such as methyl, ethyl, n-propyl, or i-propyl. "Alkanediyl", also known as alkylene, includes straight-chain or branched alkane divalent radicals, which in the context of $R^{12a}$ and $R^{12b}$, or $R^{13a}$ and $R^{13b}$, taken together are bonded through different carbon atoms to the remainder of the molecule. Examples of "alkanediyl" include —$CH_2CH_2$—, —$CH_2CH_2CH_2$—, —$CH_2CH(CH_3)$—, and the different butanediyl isomers.

"Alkoxy" includes, for example, methoxy, ethoxy, n-propyloxy and i-propyloxy. "Alkoxyamino" includes methoxyamine and ethoxyamine. "Alkylthio" includes methylthio and ethylthio.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$—, $ClCH_2$—, $CF_3CH_2$— and $CF_3CCl_2$—. The term "haloalkoxy" is defined analogously to the term "haloalkyl". Examples of "haloalkoxy" include $CF_3O$—, $CCl_3CH_2O$—, $HCF_2CH_2CH_2O$— and $CF_3CH_2O$—.

"Alkylcarbonyl" denotes a straight-chain or branched alkyl moieties bonded to a C(=O) moiety. Examples of "alkylcarbonyl" include $CH_3C(=O)$—, $CH_3CH_2CH_2C(=O)$— and $(CH_3)_2CHC(=O)$—. Examples of "alkoxycarbonyl" include $CH_3C(=O)$— and $CH_3CH_2OC(=O)$—.

The total number of carbon atoms in a substituent group is indicated by the "$C_i$-$C_j$" prefix where i and j are numbers from 1 to 3. For example, $C_1$-$C_3$ alkoxy designates $CH_3O$—, $CH_3CH_2O$—, $CH_3CH_2CH_2O$ and $(CH_3)_2CHO$—.

As used herein, the following definitions shall apply unless otherwise indicated. The term "optionally substituted" is used interchangeably with the phrase "substituted or unsubstituted". Unless otherwise indicated, an optionally substituted group may have a substituent at each substitutable position of the group, and each substitution is independent of the other.

When a compound is substituted with a substituent bearing a subscript that indicates the number of said substituents can exceed 1, said substituents (when they exceed 1) are independently selected from the group of defined substituents, e.g., $(R^2)_n$, n is 0, 1, 2, 3 or 4. When a group contains a substituent which can be hydrogen, for example $R^{2a}$, then when this substituent is taken as hydrogen, it is recognized that this is equivalent to said group being unsubstituted. When a variable group is shown to be optionally attached to a position, for example $(R^2)_n$, wherein n may be 0, then hydrogen may be at the position even if not recited in the variable group definition. When one or more positions on a group are said to be "not substituted" or "unsubstituted", then hydrogen atoms are attached to take up any free valency.

As referred to by the present disclosure and claims, an "unsaturated heterocyclic ring" is a heterocyclic ring wherein at least two ring member atoms are linked together by a double bond. Unless otherwise stated, an "unsaturated heterocyclic ring" (e.g., substituent Q) may be partially unsaturated or fully unsaturated. The expression "fully unsaturated heterocyclic ring" means a heterocyclic ring of atoms in which the bonds between carbon and/or nitrogen atoms in the ring are single or double bonds according to valence bond theory and furthermore the bonds between carbon and/or nitrogen atoms in the ring include as many double bonds as possible without double bonds being cumulative (i.e. no C=C=C, N=C=C, etc.). The term "partially unsaturated heterocyclic ring" denotes a heterocyclic ring comprising at least one ring member bonded to an adjacent ring member through a double bond and which conceptually potentially accommodates a number of non-cumulated double bonds between adjacent ring members (i.e. in its fully unsaturated counterpart form) greater than the number of double bonds present (i.e. in its partially unsaturated form). When a fully unsaturated heterocyclic ring satisfies Hückel's rule, then said ring is also called a "heteroaromatic ring" or "aromatic heterocyclic ring".

In the Summary of the Invention the unsaturated heterocyclic ring of Q is specified to be 5-membered, with ring members selected from carbon atoms and up to 4 heteroatoms independently selected from up to 1O, up to 1S and up to 4N atoms, wherein up to 2 carbon atoms are independently selected from C(=O). The heterocyclic ring is optionally substituted with one substituent selected from $R^{14c}$ or $R^{14n}$ on one ring member distal relative to the ring member connecting the heteroaromatic ring to the remainder of Formula 1. As depicted in Exhibit 1, in the five-membered heterocyclic ring of Q, a ring member distal relative to the ring member connecting the ring to the remainder of Formula 1 is linked through two ring bonds to the connecting ring member. The heterocyclic ring of Q is further optionally substituted with substituents selected from $R^{15c}$ on carbon atom ring members and $R^{15n}$ on nitrogen atom ring members.

Exhibit 1

Optional $R^{14c}$ or $R^{14n}$ Substitution on Q Ring of Formula 1

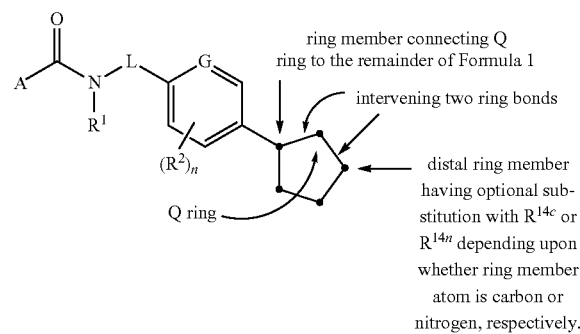

Certain heterocycles forming Q may have two distal ring members available for substitution. In this situation, only one of the distal ring members may be substituted with $R^{14c}$ or $R^{14n}$; the other distal ring member may be substituted with $R^{15c}$ or $R^{15n}$. If neither of the distal ring members of a heterocycle forming Q are available for substitution, then any substituents on the heterocycle are selected from $R^{15c}$ or $R^{15n}$. If a distal ring member can have two substituents, one substituent may be selected from $R^{14c}$ or $R^{14n}$ and the other substituent may be selected from $R^{15c}$ or $R^{15n}$. In other words, the Q ring is limited to one $R^{14c}$ or $R^{14n}$ substituent and this substituent must be bonded to a distal ring member; the Q ring can otherwise be substituted with $R^{15c}$ or $R^{15n}$ on any available ring member.

If an attachment point on a group (e.g., ring) is depicted as floating (e.g., as illustrated by the 5-membered unsaturated heterocyclic rings Q-1 through Q-21 in Exhibit 3) the group can be attached to the remainder of Formula 1 through any available carbon or nitrogen of the group by replacement of a hydrogen atom. If the attachment point of a substituent on a group (e.g., ring) is depicted as floating (e.g., as illustrated for $R^{14}$ and $R^{15}$ on the 5-membered unsaturated heterocyclic rings Q-1 through Q-21 in Exhibit 3), the substituent can be attached to any available carbon or nitrogen atom by replacing a hydrogen atom.

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

As specified in the Summary of the Invention and elsewhere in the present disclosure, linking group L in Formula 1 can be $—C(R^{12a})R^{12b}—C(R^{13a})R^{13b}—$, wherein the carbon atom bonded to $R^{12a}$ and $R^{12b}$ is also bonded to the carboxamide nitrogen atom in Formula 1. In this context, the carboxamide is an ordinary carboxamide when Z is O or a thiocarboxamide when Z is S. One skilled in the art recognizes the placement of parentheses in "$—C(R^{12a})R^{12b}—C(R^{13a})R^{13b}—$" is stylistic, and alternatives such as "$—C(R^{12a})(R^{12b})—C(R^{13a})(R^{13b})—$", "$—CR^{12a}R^{12b}—CR^{13a}R^{13b}—$", and variations thereof, denote the same molecular component.

Also as specified in the Summary of the Invention and elsewhere in the present disclosure, linking group L in Formula 1 can be 1,2-phenylene optionally substituted with up to 4 substituents independently selected from halogen and $C_1$-$C_2$ alkyl. As shown in Exhibit 1a, "1,2-phenylene" is understood to refer to a benzene ring that connected to the remainder of the molecule (e.g., Formula 1) at ortho positions (hence "1,2-") and optionally substituted with halogen and $C_1$-$C_2$ alkyl at the four remaining positions on the ring.

Exhibit 1a

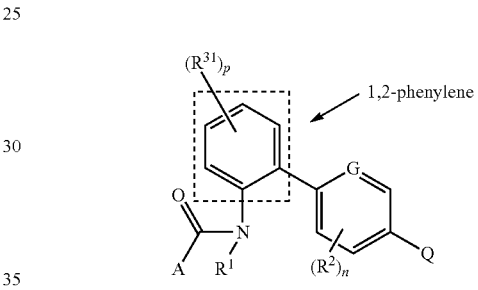

wherein each $R^{31}$ is independently halogen or $C_1$-$C_2$ alkyl, and p is 0, 1, 2, 3 or 4. Linking group L being optionally substituted 1,2-phenylene is further illustrated by Formula 1d in Schemes 16 and 18 and by the molecular structure depictions associated with Tables 1-2304 and Index Tables 4, 5 and 6.

The term "1,2-phenylene" as it relates to the present invention can alternatively described as "1,2-diphenylene", wherein recitation of "di" refers to 1,2-di-substitution of the ring connecting it to the remainder of the molecule (Formula 1). Although the present disclosure makes clear the intended meaning, the recitation of "di" might otherwise be interpreted to refer to number of phenyl rings, and therefore the term "1,2-phenylene" is now used throughout the present disclosure and claims.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form. For example, when $R^{12b}$ and $R^{13b}$ are both H, and $R^{12a}$ and $R^{13a}$ are other than H, then Formula 1 possesses chiral centers at the carbon atoms to which $R^{12b}$ and $R^{13b}$ are bonded, allowing for two racemic diastereomers, designated as anti and syn. Each racemic diastereomer is comprised of a pair of enantiomers, i.e. the anti diastereomer is comprised of enantiomers 1' and 1", and the syn diastereomer is comprised of enantiomers 2' and 2" as shown below in Exhibit 2, with the chiral centers identified with an asterisk (*).

Exhibit 2

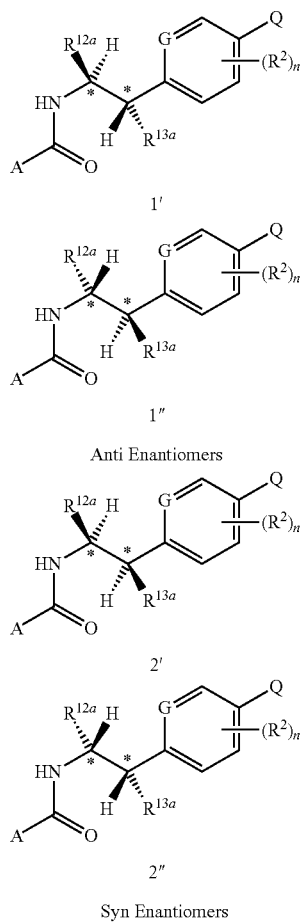

1'

1"

Anti Enantiomers

2'

2"

Syn Enantiomers

Molecular depictions drawn herein follow standard conventions for depicting stereochemistry. To indicate stereoconfiguration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereoconfiguration is intended to be specified.

This invention comprises racemic mixtures, for example, equal amounts of the enantiomers of Formulae 1' and 1". In addition, this invention includes compounds that are enriched compared to the racemic mixture in an enantiomer of Formula 1. Also included are the essentially pure enantiomers of compounds of Formula 1, for example, Formula 1' or Formula 1".

When enantiomerically enriched, one enantiomer is present in greater amounts than the other, and the extent of enrichment can be defined by an expression of enantiomeric excess ("ee"), which is defined as $(2x-1) \cdot 100\%$, where x is the mole fraction of the dominant enantiomer in the mixture (e.g., an ee of 20% corresponds to a 60:40 ratio of enantiomers).

Preferably the compositions of this invention have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Compounds of Formula 1 can comprise additional chiral centers. For example, substituents and other molecular constituents such as $R^2$ may themselves contain chiral centers. This invention comprises racemic mixtures as well as enriched and essentially pure stereoconfigurations at these additional chiral centers.

Compounds of this invention can exist as one or more conformational isomers due to restricted rotation about the amide bond (e.g., C(O)—N) in Formula 1. This invention comprises mixtures of conformational isomers. In addition, this invention includes compounds that are enriched in one conformer relative to others.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. Synthetic methods for the preparation of N-oxides of heterocycles and are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding non-salt forms, salts share the biological utility of the nonsalt forms. Thus a wide variety of salts of the compounds of Formula 1 are useful for control of plant diseases caused by fungal plant pathogens (i.e. are agriculturally suitable). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Compounds selected from Formula 1, stereoisomers, tautomers, N-oxides, and salts thereof, typically exist in more than one form, and Formula 1 thus includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures.

Embodiments of the present invention as described in the Summary of the Invention include (where Formula 1 as used in the following Embodiments includes N-oxides and salts thereof):

Embodiment 1. A compound of Formula 1 wherein A is A-1, A-2, A-3, A-4, A-5, A-6 or A-7.

Embodiment 1a. A compound of Formula 1 wherein A is A-1, A-2, A-3, A-4, A-5 or A-6.

Embodiment 1b. A compound of Formula 1 wherein A is A-1, A-2, A-3 or A-4.

Embodiment 1c. A compound of Formula 1 wherein A is A-1, A-2 or A-4.

Embodiment 2. A compound of Formula 1 wherein A is A-1 or A-2.

Embodiment 3. A compound of Formula 1 wherein A is A-1.

Embodiment 4. A compound of Formula 1 wherein A is A-2.

Embodiment 5. A compound of Formula 1 wherein A is A-3.

Embodiment 6. A compound of Formula 1 wherein A is A-4.

Embodiment 7. A compound of Formula 1 wherein A is A-5.

Embodiment 8. A compound of Formula 1 wherein A is A-6.

Embodiment 8a. A compound of Formula 1 wherein A is A-7.

Embodiment 8b. A compound of Formula 1 wherein A is A-8.

Embodiment 9. A compound of Formula 1 or any one of Embodiments 1 through 3 wherein $B^1$ is CH.

Embodiment 10. A compound of Formula 1 or any one of Embodiments 1 through 3 wherein $B^1$ is N.

Embodiment 11. A compound of Formula 1 or any one of Embodiments 1 through 3 or 9 and 10 wherein $B^2$ is CH.

Embodiment 12. A compound of Formula 1 or any one of Embodiments 1 through 3 or 9 and 10 wherein $B^2$ is N.

Embodiment 13. A compound of Formula 1 or any one of Embodiments 1 through 3 or 9 through 12 wherein $R^3$ is halogen, $C_1$-$C_2$ alkyl or $C_1$-$C_2$ haloalkyl.

Embodiment 14. A compound of Embodiment 13 wherein $R^3$ is halogen, $CH_3$ or $C_1$ haloalkyl.

Embodiment 15. A compound of Embodiment 14 wherein $R^3$ is F, Cl, Br, $CH_3$, $CHF_2$ or $CF_3$.

Embodiment 15a. A compound of Embodiment 15 wherein $R^3$ is F, Cl, Br, $CH_3$ or $CF_3$.

Embodiment 15b. A compound of Embodiment 15 wherein $R^3$ is Cl, Br, $CH_3$, $CHF_2$ or $CF_3$.

Embodiment 15c. A compound of Embodiment 15a or 15b wherein $R^3$ is Cl, Br, $CH_3$ or $CF_3$.

Embodiment 16. A compound of Formula 1 or any one of Embodiments 1, 1a, 1b, 1c, 2, 4 or 9 through 15c wherein $R^4$ is halogen, $C_1$-$C_2$ alkyl or $C_1$-$C_2$ haloalkyl.

Embodiment 17. A compound of Embodiment 16 wherein $R^4$ is halogen, $CH_3$ or $C_1$ haloalkyl.

Embodiment 18. A compound of Embodiment 17 wherein $R^4$ is F, Cl, Br, $CH_3$, $CHF_2$ or $CF_3$.

Embodiment 19. A compound of Formula 1 or any one of Embodiments 1, 1a, 1b, 1c, 2, 4 or 9 through 18 wherein $R^5$ is H, halogen, $C_1$-$C_2$ alkyl or $C_1$-$C_2$ haloalkyl.

Embodiment 20. A compound of Embodiment 16 wherein $R^5$ is H, halogen, $CH_3$ or $C_1$ haloalkyl.

Embodiment 21. A compound of Embodiment 17 wherein $R^5$ is H, F, Cl, Br, $CH_3$, $CHF_2$ or $CF_3$.

Embodiment 22. A compound of Formula 1 or any one of Embodiments 1, 1a, 1b, 1c, 2, 4 or 9 through 21 wherein $R^6$ is $CH_3$.

Embodiment 23. A compound of Formula 1 or any one of Embodiments 1, 1a, 1b, 5 or 9 through 22 wherein $R^7$ is halogen, $C_1$-$C_2$ alkyl or $C_1$-$C_2$ haloalkyl.

Embodiment 24. A compound of Embodiment 23 wherein $R^7$ is halogen, $CH_3$ or $C_1$ haloalkyl.

Embodiment 25. A compound of Embodiment 24 wherein $R^7$ is F, Cl, Br, $CH_3$, $CHF_2$ or $CF_3$.

Embodiment 26. A compound of Formula 1 or any one of Embodiments 1, 1a, 1b, 5 or 9 through 25 wherein $R^8$ is H or $CH_3$.

Embodiment 27. A compound of Formula 1 or any one of Embodiments 1, 1a, 1b, 1c, 6 or 9 through 26 wherein $R^9$ is halogen, $C_1$-$C_2$ alkyl or $C_1$-$C_2$ haloalkyl.

Embodiment 28. A compound of Embodiment 27 wherein $R^9$ is halogen, $CH_3$ or $C_1$ haloalkyl.

Embodiment 29. A compound of Embodiment 28 wherein $R^9$ is F, Cl, Br, $CHF_2$ or $CF_3$.

Embodiment 30. A compound of Formula 1 or any one of Embodiments 1, 1a, 7 or 9 through 29 wherein $R^{10}$ is halogen, $C_1$-$C_2$ alkyl or $C_1$-$C_2$ haloalkyl.

Embodiment 31. A compound of Embodiment 30 wherein $R^{10}$ is halogen, $CH_3$ or $C_1$ haloalkyl.

Embodiment 32. A compound of Embodiment 31 wherein $R^{10}$ is F, Cl, Br, $CH_3$, $CHF_2$ or $CF_3$.

Embodiment 33. A compound of Formula 1 or any one of Embodiments 1, 1a or 8 through 32 wherein $R^{11}$ is halogen, $C_1$-$C_2$ alkyl or $C_1$-$C_2$ haloalkyl.

Embodiment 34. A compound of Embodiment 33 wherein $R^{11}$ is halogen, $CH_3$ or $C_1$ haloalkyl.

Embodiment 35. A compound of Embodiment 34 wherein $R^{11}$ is F, Cl, Br, $CH_3$, $CHF_2$ or $CF_3$.

Embodiment 35a. A compound of Formula 1 or Embodiment 1 or 8a wherein $R^{20}$ is halogen, $C_1$-$C_2$ alkyl or $C_1$-$C_2$ haloalkyl.

Embodiment 35b. A compound of Embodiment 35a wherein $R^{20}$ is halogen, $CH_3$ or $C_1$ haloalkyl.

Embodiment 35c. A compound of Embodiment 35b wherein $R^{20}$ is F, Cl, Br, $CH_3$, $CHF_2$ or $CF_3$.

Embodiment 35d. A compound of Formula 1 or Embodiment 8b wherein $R^{21}$ is halogen, $C_1$-$C_2$ alkyl or $C_1$-$C_2$ haloalkyl.

Embodiment 35e. A compound of Embodiment 35d wherein $R^{21}$ is halogen, $CH_3$ or $C_1$ haloalkyl.

Embodiment 35f. A compound of Embodiment 35e wherein $R^{21}$ is F, Cl, Br, $CH_3$, $CHF_2$ or $CF_3$.

Embodiment 35g. A compound of Formula 1 or any one of Embodiments 8b, 35d, 35e or 35f wherein $R^{22}$ is H or $CH_3$.

Embodiment 35h. A compound of Formula 1 or anyone of Embodiments 1 through 35g wherein the compound is other than 3-(difluoromethyl)-N-[3'-fluoro-4'-[3-(trifluoromethyl)-1H-pyrazol-1-yl][1,1'-biphenyl]-2-yl]-2-pyridinecarboxamide or 3-(difluoromethyl)-N-[3',5'-difluoro-4'-[3-trifluoromethyl)-1H-pyrazol-1-yl][1,1'-biphenyl]-2-yl]-2-pyridinecarboxamide.

Embodiment 35i. A compound of Formula 1 or any one of Embodiments 1 through 35h wherein when A is A-1, $R^3$ is $CHF_2$ and $B^1$ is CH, then $B^2$ is CH.

Embodiment 35j. A compound of Formula 1 or any one of Embodiments 1 through 35i wherein when A is A-1 and $R^3$ is $CHF_2$, then $B^2$ is CH.

Embodiment 36. A compound of Formula 1 or any one of Embodiments 1 through 35j wherein $R^1$ is H.

Embodiment 37. A compound of Formula 1 or any one of Embodiments 1 through 36 wherein L is —$C(R^{12a})R^{12b}$—$C(R^{13a})R^{13b}$.

Embodiment 38. A compound of Formula 1 or any one of Embodiments 1 through 37 wherein $R^{12a}$ and $R^{12b}$ are each independently H, $C_1$-$C_2$ alkyl or $C_1$-$C_2$ haloalkyl;

Embodiment 38a. A compound of Formula 1 or any one of Embodiments 1 through 38 wherein $R^{13a}$ is H, halogen, $C_1$-$C_2$ alkyl, $C_1$-$C_2$ haloalkyl; $C_1$-$C_2$ alkoxy or $C_1$-$C_2$ haloalkoxy; and $R^{13b}$ is H, halogen, $C_1$-$C_2$ alkyl or $C_1$-$C_2$ haloalkyl.

Embodiment 38b. A compound of Formula 1 or any one of Embodiments 1 through 38a wherein $R^{12a}$ is H or $CH_3$.

Embodiment 39. A compound of Embodiment 38b wherein $R^{12a}$ is H.

Embodiment 40. A compound of Formula 1 or any one of Embodiments 1 through 39 wherein $R^{12b}$ is H or $CH_3$.

Embodiment 41. A compound of Embodiment 40 wherein $R^{12b}$ is H.

Embodiment 42. A compound of Formula 1 or any one of Embodiments 1 through 41 wherein $R^{13a}$ is H, $CH_3$ or $OCH_3$.

Embodiment 43. A compound of Embodiment 42 wherein $R^{13a}$ is H or $CH_3$.

Embodiment 44. A compound of Embodiment 43 wherein $R^{13a}$ is H.

Embodiment 45. A compound of Formula 1 or any one of Embodiments 1 through 44 wherein $R^{13b}$ is H or $CH_3$.

Embodiment 46. A compound of Embodiment 45 wherein $R^{13b}$ is H.

Embodiment 47. A compound of Formula 1 or any one of Embodiments 1 through 36 and 38 through 46 wherein when L comprises 1,2-phenylene, said 1,2-phenylene is optionally substituted with up to 2 substituents independently selected from F, Cl, Br and $CH_3$.

Embodiment 48. A compound of Embodiment 47 wherein when L comprises 1,2-phenylene, said 1,2-phenylene is optionally substituted with up to 2 substituents independently selected from F and $CH_3$.

Embodiment 49. A compound of Embodiment 48 wherein when L comprises 1,2-phenylene, said 1,2-phenylene is unsubstituted (except for the bonds to the remainder of Formula 1).

Embodiment 50. A compound of Formula 1 or any one of Embodiments 1 through 36 or 47 through 49 wherein L comprises 1,2-phenylene.

Embodiment 51. A compound of Formula 1 or any one of Embodiments 1 through 50 wherein G is C—$R^{2a}$.

Embodiment 52. A compound of Formula 1 or any one of Embodiments 1 through 51 wherein $R^{2a}$ is H, halogen, nitro, $C_1$-$C_2$ alkyl, $C_1$-$C_2$ haloalkyl, $C_1$-$C_2$ alkoxy or $C_1$-$C_2$ haloalkoxy.

Embodiment 52a. A compound of Embodiment 52 wherein $R^{2a}$ is H, halogen, $C_1$-$C_2$ alkyl, $C_1$-$C_2$ haloalkyl, $C_1$-$C_2$ alkoxy or $C_1$-$C_2$ haloalkoxy.

Embodiment 52b. A compound of Embodiment 52a wherein $R^{2a}$ is H, halogen, $C_1$-$C_2$ alkyl or $C_1$-$C_2$ haloalkyl.

Embodiment 52c. A compound of Embodiment 52b wherein $R^{2a}$ is H, F, Cl, Br or $CH_3$.

Embodiment 53. A compound of Embodiment 52c wherein $R^{2a}$ is H, F or Cl.

Embodiment 54. A compound of Embodiment 53 wherein $R^{2a}$ is H.

Embodiment 55. A compound of Embodiment 54 wherein $R^{2a}$ is F or Cl.

Embodiment 56. A compound of Embodiment 55 wherein $R^{2a}$ is F.

Embodiment 57. A compound of Embodiment 55 wherein $R^{2a}$ is Cl.

Embodiment 58. A compound of Formula 1 or any one of Embodiments 1 through 50 wherein G is N.

Embodiment 59. A compound of Formula 1 or any one of Embodiments 1 through 58 wherein each $R^2$ is independently halogen, nitro, $C_1$-$C_2$ alkyl, $C_1$-$C_2$ haloalkyl, $C_1$-$C_2$ alkoxy or $C_1$-$C_2$ haloalkoxy.

Embodiment 59a. A compound of Embodiment 59 wherein each $R^2$ is independently halogen, $C_1$-$C_2$ alkyl, $C_1$-$C_2$ haloalkyl, $C_1$-$C_2$ alkoxy or $C_1$-$C_2$ haloalkoxy.

Embodiment 59b. A compound of Formula 1 or any one of Embodiments 1 through 58 wherein each $R^2$ is independently halogen, cyano, $C_1$-$C_2$ alkyl or $C_1$-$C_2$ haloalkyl.

Embodiment 59c. A compound of Embodiment 59a or 59b wherein each $R^2$ is independently F, Cl, Br or $CH_3$.

Embodiment 60. A compound of Embodiment 59c wherein each $R^2$ is independently F or Cl.

Embodiment 61. A compound of Embodiment 60 wherein each $R^2$ is F.

Embodiment 62. A compound of Embodiment 60 wherein each $R^2$ is Cl.

Embodiment 63. A compound of Formula 1 or any one of Embodiments 1 through 62 wherein n is 0, 1 or 2.

Embodiment 64. A compound of Formula 1 or any one of Embodiments 1 through 63, provided that when G is N or $R^{2a}$ is H, then the ring comprising G is substituted with at least one instance of $R^2$.

Embodiment 64a. A compound of Formula 1 or any one of Embodiments 1 through 64 wherein when (1) L is —$C(R^{12a})R^{12b}$—$C(R^{13a})R^{13b}$— and (2) G is N or $R^{2a}$ is H, then the ring comprising G is substituted with $R^2$ ortho to the bond to L.

Embodiment 65. A compound of Formula 1 or any one of Embodiments 1 through 64a wherein when L comprises 1,2-phenylene, then the ring comprising G is substituted with at least one $R^2$ ortho to the bond to Q.

Embodiment 66. A compound of Embodiment 65 wherein when L comprises 1,2-phenylene, then the ring comprising G is substituted with two $R^2$ ortho to the bond to Q.

Embodiment 66a. A compound of Formula 1 or any one of Embodiments 1 through 66 wherein the compound is other than N-[2-[2-cyano-4-[3-(trifluoromethyl)-1H-pyrazol-1-yl]phenyl]ethyl]-3-(difluoromethyl)-1-methyl-1H-pyrazole-4-carboxamide or N-[2-[2-cyano-4-[3-(trifluoromethyl)-1H-pyrazol-1-yl]phenyl]ethyl]-3-(trifluoromethyl)-2-pyridinecarboxamide.

Embodiment 66b. A compound of Formula 1 or any one of Embodiments 1 through 66a wherein when L is —C($R^{12a}$)$R^{12b}$—C($R^{13a}$)$R^{13b}$— and the ring comprising G is substituted with $R^2$ or $R^{2a}$ ortho to the bond to L, then said $R^2$ or $R^{2a}$ is other than CN (cyano).

Embodiment 66c. A compound of Formula 1 or any one of Embodiments 1 through 66b wherein when the ring comprising G is substituted with $R^2$ or $R^{2a}$ ortho to the bond to L, then said $R^2$ or $R^{2a}$ is other than CN (cyano).

Embodiment 67. A compound of Formula 1 or any one of Embodiments 1 through 66c wherein the heterocyclic ring of Q contains at least one nitrogen atom ring member.

Embodiment 68. A compound of Embodiment 67 wherein the heterocyclic ring of Q contains two nitrogen atom ring members.

Embodiment 69. A compound of Formula 1 or any one of Embodiments 1 through 68 wherein the heterocyclic ring of Q is fully unsaturated (i.e. is heteroaromatic).

Embodiment 70. A compound of Formula 1 or any one of Embodiments 1 through 66c wherein the heterocyclic ring of Q is selected from furan, thiophene, pyrrole, oxazole, thiazole, imidazole, isoxazole, isothiazole, pyrazole, 1,2,4-oxadiazole, 1,2,5-oxadiazole, 1,3,4-oxadiazole, 1,2,4-thiadiazole, 1,2,5-thiadiazole, 1,3,4-thiadiazole, 1,2,3-triazole, 1,2,4-triazole, tetrazole, 4,5-dihydroisoxazole and 4,5-dihydropyrazole.

Embodiment 71. A compound of Embodiment 70 wherein the heterocyclic ring of Q is selected from other than 4,5-dihydroisoxazole and 4,5-dihydropyrazole.

Embodiment 72. A compound of Embodiment 70 wherein the heterocyclic ring of Q is selected from pyrazole.

Embodiment 73. A compound of Embodiment 70 wherein Q is selected from Q-1 through Q-21 depicted in Exhibit 3

Exhibit 3

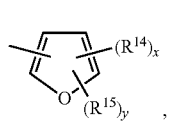
Q-1

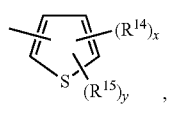
Q-2

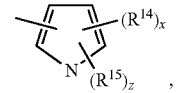
Q-3

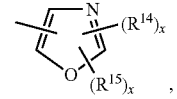
Q-4

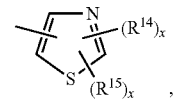
Q-5

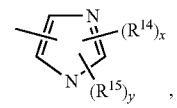
Q-6

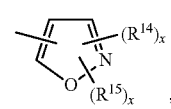
Q-7

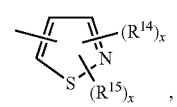
Q-8

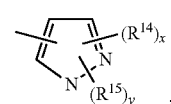
Q-9

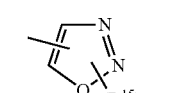
Q-10

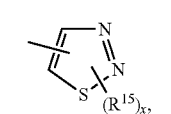
Q-11

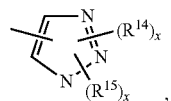
Q-12

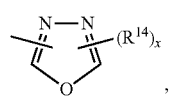
Q-13

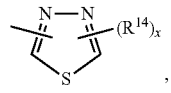
Q-14

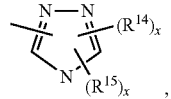
Q-15

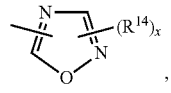
Q-16

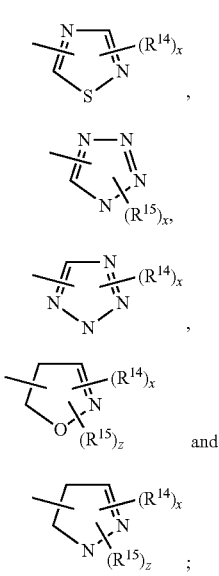

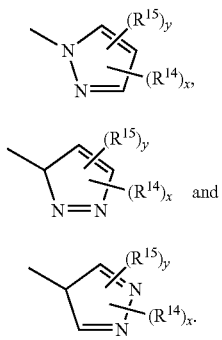

wherein
$R^{14}$ is bonded to a ring member distal relative to the ring member connecting the Q ring to the remainder of Formula 1, and independently selected from $R^{14c}$ on carbon atom ring members and $R^{14n}$ on nitrogen atom ring members;
each $R^{15}$ is independently selected from $R^{15c}$ on carbon atom ring members and $R^{15n}$ on nitrogen atom ring members;
each x is independently 0 or 1;
each y is independently 0, 1 or 2; and
each z is independently 0, 1, 2 or 3.

Embodiment 74. A compound of Embodiment 73 wherein Q is selected from Q-1 through Q-19.

Embodiment 75. A compound of Embodiment 73 wherein Q is selected from

Embodiment 76. A compound of Embodiment 75 wherein Q is Q-9A or Q-9B.

Embodiment 77. A compound of Embodiment 76 wherein Q is Q-9A.

Embodiment 78. A compound of any one of Embodiments 75 through 77 wherein y is 0 or 1.

Embodiment 78a. A compound of Formula 1 or any one of Embodiments 1 through 78 wherein when L comprises 1,2-phenylene and the 5-membered unsaturated heterocyclic ring of Q is substituted by $R^{15c}$ or $R^{15n}$ at an ortho position (i.e. adjacent ring position) relative to the bond connecting the ring of Q to the remainder of Formula 1, then the ring comprising G is substituted with at least one $R^2$ ortho to the bond to Q.

Embodiment 78b. A compound of Formula 1 or any one of Embodiments 1 through 78 wherein when L comprises 1,2-phenylene, then the 5-membered unsaturated heterocyclic ring of Q is not substituted by $R^{15c}$ or $R^{15n}$ at either ortho position (i.e. adjacent ring position) relative to the bond connecting the ring to the remainder of Formula 1.

Embodiment 78c. A compound of Formula 1 or any one of Embodiments 1 through 78 wherein the 5-membered unsaturated heterocyclic ring of Q is not substituted by $R^{15c}$ or $R^{15n}$ at either ortho position (i.e. adjacent ring position) relative to the bond connecting the ring to the remainder of Formula 1.

Embodiment 79. A compound of Formula 1 or any one of Embodiments 1 through 78c wherein each $R^{14c}$ is independently halogen, cyano, $C_1$-$C_3$ alkyl, $C_1$-$C_3$ haloalkyl, $C_1$-$C_3$ alkoxy, $C_1$-$C_3$ haloalkoxy or $C_2$-$C_3$ alkoxycarbonyl; or a phenyl ring optionally substituted with up to 5 substituents independently selected from $R^{16}$; or a heteroaromatic ring optionally substituted with up to 4 substituents independently selected from $R^{17c}$ on carbon atom ring members and from $R^{17n}$ on nitrogen atom ring members.

Embodiment 79a. A compound of Embodiment 79 wherein each $R^{14c}$ is independently halogen, cyano, $C_1$-$C_2$ alkyl, $C_1$-$C_2$ haloalkyl, $C_1$-$C_2$ alkoxy or $C_1$-$C_2$ haloalkoxy.

Embodiment 80. A compound of Embodiment 79a wherein each $R^{14c}$ is independently halogen, $CH_3$ or $C_1$ haloalkyl.

Embodiment 81. A compound of Embodiment 80 wherein each $R^{14c}$ is independently F, Cl, Br, $CH_3$, $CHF_2$ or $CF_3$.

Embodiment 82. A compound of Formula 1 or any one of Embodiments 1 through 81 wherein each $R^{14n}$ is independently $C_1$-$C_2$ alkyl or $C_1$-$C_2$ haloalkyl.

Embodiment 83. A compound of Embodiment 82 wherein each $R^{14n}$ is $C_1$-$C_2$ alkyl.

Embodiment 84. A compound of Embodiment 83 wherein each $R^{14n}$ is $CH_3$.

Embodiment 85. A compound of Formula 1 or any one of Embodiments 1 through 84 wherein each $R^{15c}$ is independently halogen, $C_1$-$C_2$ alkyl, $C_1$-$C_2$ haloalkyl or $C_1$-$C_2$ alkoxy.

Embodiment 86. A compound of Embodiment 85 wherein each $R^{15c}$ is independently halogen, $CH_3$ or $C_1$ haloalkyl.

Embodiment 87. A compound of Embodiment 86 wherein each $R^{15c}$ is independently F, Cl, Br, $CH_3$, $CHF_2$ or $CF_3$.

Embodiment 88. A compound of Formula 1 or any one of Embodiments 1 through 87 wherein each $R^{15n}$ is independently $C_1$-$C_2$ alkyl or $C_1$-$C_2$ haloalkyl.

Embodiment 89. A compound of Embodiment 88 wherein each $R^{15n}$ is $C_1$-$C_2$ alkyl.

Embodiment 90. A compound of Embodiment 89 wherein each $R^{15n}$ is $CH_3$.

Embodiment 91. A compound of Formula 1 or any one of Embodiments 1 through 79 wherein each $R^{16}$, $R^{17c}$, $R^{18}$ and $R^{19c}$ is independently halogen, $C_1$-$C_2$ alkyl, $C_1$-$C_2$ haloalkyl or $C_1$-$C_2$ alkoxy.

Embodiment 92. A compound of Embodiment 91 wherein each $R^{16}$, $R^{17c}$, $R^{18}$ and $R^{19c}$ is independently halogen, $CH_3$ or $C_1$ haloalkyl.

Embodiment 93. A compound of Embodiment 92 wherein each $R^{16}$, $R^{17c}$, $R^{18}$ and $R^{19c}$ is independently F, Cl, Br, $CH_3$, $CHF_2$ or $CF_3$.

Embodiment 94. A compound of Formula 1 or any one of Embodiments 1 through 79, or 91 through 93, wherein each $R^{17n}$ and $R^{19n}$ is independently $C_1$-$C_2$ alkyl or $C_1$-$C_2$ haloalkyl.

Embodiment 95. A compound of Embodiment 94 wherein each $R^{17n}$ and $R^{19n}$ is independently $C_1$-$C_2$ alkyl.

Embodiment 96. A compound of Embodiment 95 wherein each $R^{17n}$ and $R^{19n}$ is $CH_3$.

Embodiment 97. A compound of Formula 1 or any one of Embodiments 1 through 96 wherein Z is O.

Embodiments of this invention, including Embodiments 1-97 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-97 above as well as any other embodiments described herein, and any combination thereof, pertain to the compositions and methods of the present invention.

Of note as an embodiment of this invention is a compound of Formula 1, or an N-oxide or salt thereof, or a related composition, method, or starting or intermediate compound, wherein A is A-1, A-2, A-3, A-4, A-5 or A-6; Z is O; each $R^2$ is independently halogen, cyano, $C_1$-$C_2$ alkyl or $C_1$-$C_2$ haloalkyl; $R^{2a}$ is H, halogen, $C_1$-$C_2$ alkyl or $C_1$-$C_2$ haloalkyl; $R^{12a}$ and $R^{12b}$ are each independently H, $C_1$-$C_2$ alkyl or $C_1$-$C_2$ haloalkyl; $R^{13a}$ is H, halogen, $C_1$-$C_2$ alkyl, $C_1$-$C_2$ haloalkyl, $C_1$-$C_2$ alkoxy or $C_1$-$C_2$ haloalkoxy; and each $R^{14c}$ is independently halogen, cyano, $C_1$-$C_3$ alkyl, $C_1$-$C_3$ haloalkyl, $C_1$-$C_3$ alkoxy, $C_1$-$C_3$ haloalkoxy or $C_2$-$C_3$ alkoxycarbonyl; or a phenyl ring optionally substituted with up to 5 substituents independently selected from $R^{16}$; or a heteroaromatic ring optionally substituted with up to 4 substituents independently selected from $R^{17c}$ on carbon atom ring members and from $R^{17n}$ on nitrogen atom ring members. Also of note are embodiments, including Embodiments 1-97, including combinations thereof, applied as limitations to the aforedescribed embodiment of note.

Combinations of Embodiments 1-97 are further illustrated by:

Embodiment A. A compound of Formula 1 wherein
Z is O;
L is —$C(R^{12a})R^{12b}$—$C(R^{13a})R^{13b}$—; or 1,2-phenylene optionally substituted with up to 2 substituents independently selected from F, Cl, Br and $CH_3$;
each $R^2$ is independently F, Cl, Br or $CH_3$;
$R^{2a}$ is H, F, Cl, Br or $CH_3$;
$R^3$ is F, Cl Br, $CH_3$, $CHF_2$ or $CF_3$;
$R^4$ is F, Cl Br, $CH_3$, $CHF_2$ or $CF_3$;
$R^5$ is H, F, Cl Br, $CH_3$, $CHF_2$ or $CF_3$;
$R^6$ is $CH_3$;
$R^7$ is F, Cl Br, $CH_3$, $CHF_2$ or $CF_3$;
$R^8$ is H or $CH_3$;
$R^9$ is F, Cl Br, $CH_3$, $CHF_2$ or $CF_3$;
$R^{10}$ is F, Cl Br, $CH_3$, $CHF_2$ or $CF_3$;
$R^{11}$ is F, Cl Br, $CH_3$, $CHF_2$ or $CF_3$;
$R^{12a}$ is H or $CH_3$;
$R^{12b}$ is H;
$R^{13a}$ is H, $CH_3$, or $OCH_3$;
$R^{13b}$ is H;
each $R^{16}$, $R^{17c}$, $R^{18}$ and $R^{19c}$ is independently F, Cl, Br, $CH_3$, $CHF_2$ or $CF_3$; and
each $R^{17n}$ and $R^{19n}$ is $CH_3$.

Embodiment B. A compound of Embodiment A wherein
A is A-1, A-2, A-3 or A-4;
each $R^{14c}$ is independently F, Cl, Br, $CH_3$, $CHF_2$ or $CF_3$;
each $R^{14n}$ is $CH_3$;
each $R^{15c}$ is independently F, Cl, Br, $CH_3$, $CHF_2$ or $CF_3$; and
each $R^{15n}$ is $CH_3$.

Embodiment C. A compound of Embodiment B wherein
A is A-1, A-2 or A-4;
$B^2$ is N; and
Q is Q-9A or Q-9B.

Embodiment D. A compound of Embodiment C wherein
L is —$C(R^{12a})R^{12b}$—$C(R^{13a})R^{13b}$—;
$R^{2a}$ is H, F or Cl; and
each $R^2$ is F or Cl;
provided that when G is N or $R^{2a}$ is H, then the ring comprising G is substituted with $R^2$ ortho to the bond to L.

Embodiment E. A compound of Embodiment C wherein
L is 1,2-phenylene optionally substituted with up to 2 substituents independently selected from F, Cl, Br and $CH_3$;
$R^{2a}$ is H, F or Cl;
each $R^2$ is F or Cl; and
the ring comprising G is substituted with at least one $R^2$ ortho to the bond to Q.

Embodiment F. A compound of Formula 1, provided that when G is N or $R^{2a}$ is H, then the ring comprising G is substituted with at least one instance of $R^2$.

Embodiment G. A compound of Formula 1 wherein L is —$C(R^{12a})R^{12b}$—$C(R^{13a})R^{13b}$—.

Specific embodiments include compounds of Formula 1 selected from the group consisting of:

3-chloro-N-[2-chloro-4-(3-trifluoromethyl)-1H-pyrazol-1-yl]phenyl-1-methylethyl]-2-pyrazinecarboxamide (Compound 1), N-[2-[2-chloro-4-[3-(trifluoromethyl)-1H-pyrazol-1-yl]phenyl]ethyl-3-(trifluoromethyl)-2-pyridinecarboxamide (Compound 40), N-[3',5'-difluoro-4'-[3-(trifluoromethyl)-1H-pyrazol-yl][1,1'-biphenyl]-2-yl]-3-(trifluoromethyl)-2-pyridinecarboxamide (Compound 172), 3-(difluoromethyl)-N-[3',5'-difluoro-4'-[3-(trifluoromethyl)-1H-pyrazol-1-yl][1,1'-biphenyl]-2-yl]-1-methyl-1H-pyrazole-4-carboxamide (Compound 173), and N-[2-[3-chloro-5-[3-(trifluoromethyl)-1H-pyrazol-1-yl]-2-pyridinyl]ethyl]-2-(trifluoromethyl)benzamide (Compound 85).

This invention provides a fungicidal composition comprising a compound of Formula 1 (including all stereoisomers, N-oxides, and salts thereof) (in a fungicidally effective amount), and at least one other fungicide. Of note as embodiments of such compositions are compositions comprising a compound corresponding to any of the compound embodiments described above.

This invention provides a fungicidal composition comprising a compound of Formula 1 (including all stereoisomers, N-oxides, and salts thereof) (i.e. in a fungicidally effective amount), and at least one additional component selected from the group consisting of surfactants, solid diluents and liquid diluents. Of note as embodiments of such compositions are compositions comprising a compound corresponding to any of the compound embodiments described above.

This invention provides a method for controlling plant diseases caused by fungal plant pathogens comprising applying to the plant or portion thereof, or to the plant seed, a fungicidally effective amount of a compound of Formula 1 (including all stereoisomers, N-oxides, and salts thereof). Of note as embodiments of such method are methods comprising applying a fungicidally effective amount of a compound corresponding to any of the compound embodiments described above. Of particular note are embodiments where the compounds are applied as compositions of this invention.

This invention also provides a method for controlling a phytophagous nematode comprising contacting the phytophagous nematode or its environment with a nematocidally effective amount of a compound of Formula 1, an N-oxide, or a salt thereof, (e.g., as a composition described herein), wherein L is —C($R^{12a}$)$R^{12b}$—C($R^{13a}$)$R^{13b}$—. Of note as embodiments of this method are methods comprising applying a nematocidally effective amount of a compound corresponding to compound embodiments described above. Of particular note as embodiments of this method are methods comprising applying a nematocidally effective amount of a compound of Formula 1, an N-oxide, or a salt thereof, wherein A is A-1.

One or more of the following methods and variations as described in Schemes 1-19 can be used to prepare the compounds of Formula 1. The definitions of A, $R^1$, L, G, $R^2$ and n in the compounds of Formulae 1-38 below are as defined above in the Summary of the Invention unless otherwise noted. Formulae 1a-1f are various subsets of Formula 1, and all substituents for Formulae 1a-1f are as defined above for Formula 1 unless otherwise noted. Formulae 7a-7c are various subsets of Formula 7, and all substituents for Formulae 7a-7c are as defined for Formula 7 unless otherwise noted. Formulae 13a-13e are various subsets of Formula 13, and all substituents for Formulae 13a-13e are as defined for Formula 13 unless otherwise noted. Formula 16a is homologous to Formula 16, and all substituents are as defined for Formula 16, unless otherwise noted. Formula 19a is a subset of Formula 19, and all substituents for Formula 19a are as defined for Formula 19 unless otherwise noted. Formula 23a is a subset of Formula 23, and all substituents for Formula 23 unless otherwise noted.

As shown in Scheme 1, compounds of Formula 1a (i.e. Formula 1 wherein Z is O, and Q is a nitrogen-linked heterocycle denoted by $Q^N$) can be prepared by Buchwald-Hartwig coupling of compounds of Formula 2 with heterocycles of Formula 3 wherein a ring nitrogen is bonded to a hydrogen atom. These coupling reactions are typically conducted in an inert solvent in the presence of a suitable ligand, a copper (I) salt such as CuI or CuBr, and a base such as sodium or potassium carbonate. Typical ligands are 1,2-diaminocyclohexane and phenanthroline. Suitable solvents for the reaction are dioxane, 1,2-diethoxyethane or toluene, and the reaction is carried out at temperatures ranging from room temperature to reflux for a period ranging from 1-48 h. Conditions for Buchwald-Hartwig couplings are well-documented in the literature (see for example *Tetrahedron Letters*, 2010, 52(38), 5052 and *Journal of Medicinal Chemistry* 2010, 53(10), 31-8). Heterocycles of Formula 3 are commercially available or may be prepared by methods well known in the art.

As also shown in Scheme 1, compounds of Formula 1b (i.e. Formula 1 wherein Z is O, and Q is a carbon-linked heterocycle denoted by $Q^C$) can be prepared by Suzuki coupling of compounds of Formula 2 with boron intermediates of Formula 4, wherein a ring carbon is bonded to boron, in the presence of Pd(0) or Pd(II) salts, a suitable ligand, and a base. Suitable bases for this transformation are potassium carbonate or cesium carbonate, while Pd(II) salts such as Pd(OAc)$_2$ or PdCl$_2$ are used in conjunction with ligands such as triphenylphosphine or 1,1'-bis(diphenylphosphino)ferrocene (dppf). Conditions for Suzuki couplings are well documented in the literature (see for example *Angewandte Chemie International Edition*, 2006, 45, 3484 and *Tetrahedron Letters*, 2002, 58(14), 2885). Boron intermediates of Formula 4 are commercially available or can be prepared from the corresponding halides or trifluoromethanesulfonates by methods known in the literature (see for example PCT Patent Publication WO 2007/043278, U.S. Pat. No. 8,080,566, *Organic Letters*, 2011, 13(6), 1366 and *Organic Letters*, 2012, 14(2), 600).

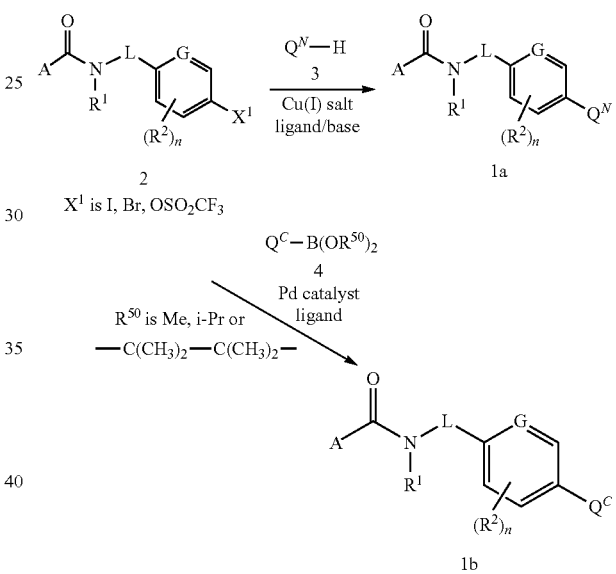

Alternatively, as shown in Scheme 2, compounds of Formula 1a can be prepared from boron intermediates 5 using Chan-Lam conditions for coupling with nitrogen heterocycles of Formula 3 in the presence of a Cu(II) salt, oxygen, and a base at temperatures ranging from ambient to reflux for 24-72 h. Examples of Cu(II) salts which can be used are Cu(OAc)$_2$, CuBr$_2$ and CuI$_2$. Suitable bases include pyridine, quinoline and triethylamine. Suitable solvents include dichloromethane, chloroform, diethyl ether and tetrahydrofuran. For representative conditions see *Tetrahedron Letters*, 1998, 38, 2941 and PCT Patent Publication WO2003/072547.

As also shown in Scheme 2, compounds of Formula 1b can prepared by coupling of compounds of Formula 5 with compounds of Formula 6 wherein a ring carbon is bonded to $X^2$. Conditions for carrying out such couplings are analogous to the Suzuki conditions described in Scheme 1. Compounds of Formula 6 are commercially available or can be prepared readily by methodologies described in the literature.

Scheme 2

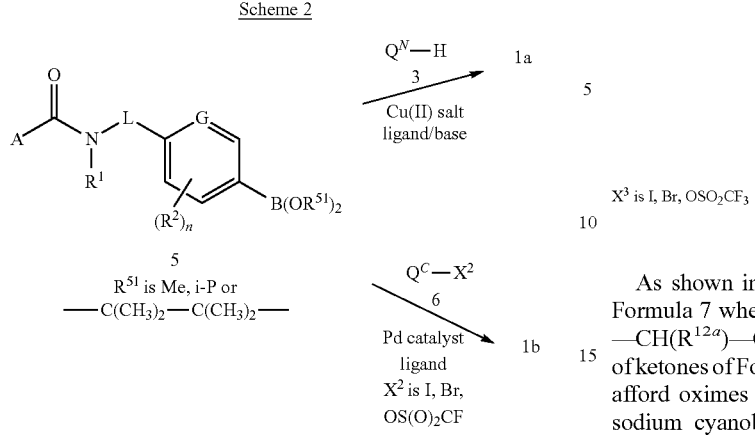

$R^{51}$ is Me, i-P or —C(CH$_3$)$_2$—C(CH$_3$)$_2$—

$X^2$ is I, Br, OS(O)$_2$CF

Compounds of Formula 5 can be prepared from compounds of Formula 2 using the methods cited in Scheme 1 for the preparation of compounds of Formula 4.

As shown in Scheme 3, compounds of Formula 2 can be prepared by acylation of amine derivatives of Formula 7. These types of acylations are well documented in the literature. (See for example March, *Advanced Organic Chemistry*, 3rd ed., John Wiley and Sons, New York, 1985, p. 1152).

Scheme 3

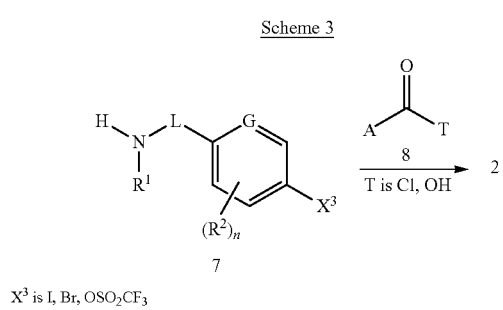

$X^3$ is I, Br, OSO$_2$CF$_3$

As shown in Scheme 4, compounds of Formula 7b (i.e. Formula 7 wherein $R^1$ is cyclopropyl) can be prepared by reacting primary amines of Formula 7a (i.e. Formula 7 wherein $R^1$ is H) by with 1-ethoxy-1-(trimethylsilyloxy)cyclopropane (9) in acetic acid/methanol in the presence of sodium cyanoborohydride. For representative procedures see *Journal of Medicinal Chemistry* 2008, 51(11), 3238 and US Patent Publication 2009/0176844. Primary amines of Formula 7a are prepared by methods known in the art, such as those found in PCT Patent Publications WO2007/141009, WO2010/075200, WO2011/124093 and WO2009/158426, US Patent Publication 2009/0069296, EP1574511 and *Applied Radiation & Isotopes*, 1993, 44(5), 821.

Scheme 4

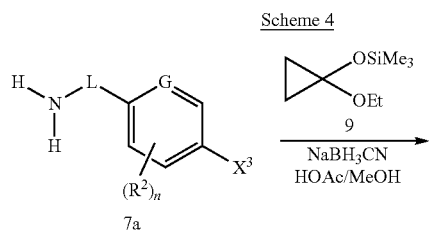

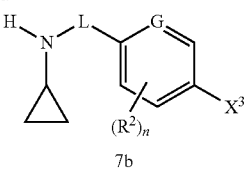

$X^3$ is I, Br, OSO$_2$CF$_3$

As shown in Scheme 5, compounds of Formula 7c (i.e. Formula 7 wherein $R^1$ is OR$^{30}$ (i.e. C$_1$-C$_2$ alkoxy) and L is —CH(R$^{12a}$)—C(R$^{13a}$)R$^{13b}$—) can be prepared by reaction of ketones of Formula 10 with alkoxyamines of Formula 11 to afford oximes of Formula 12, followed by reduction with sodium cyanoborohydride. Conditions for oximation and subsequent reduction with sodium cyanoborohydride can be found in US Patent Publication 2011/0230537 and PCT Patent Publications WO2011/147690 and WO2010/063700. Ketones of Formula 10 are either commercially available or can be prepared readily using well documented methods (see for example PCT Patent Publications WO2011/133875 and WO2007/063013 and US Patent Publication 2006/0154973).

Scheme 5

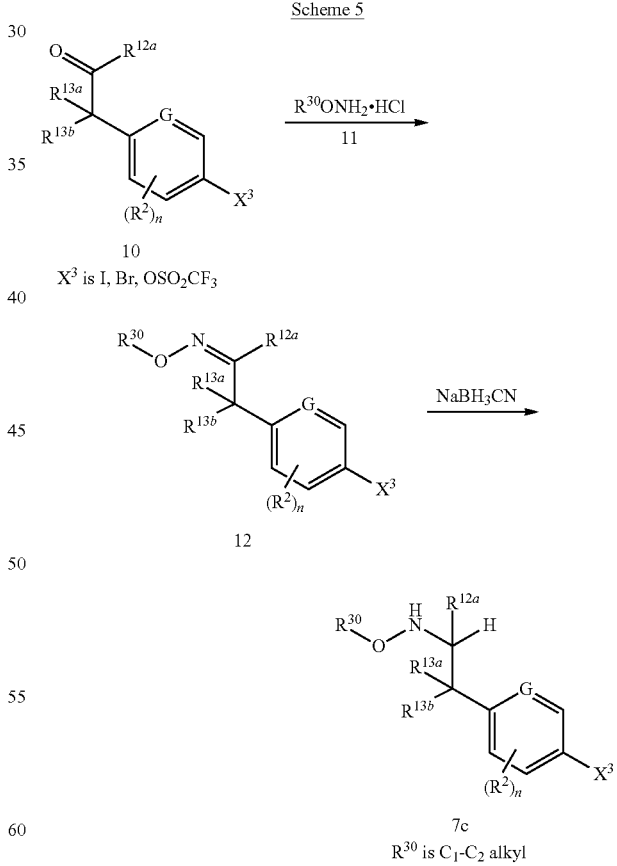

As shown in Scheme 6, compounds of Formula 1c (i.e. Formula 1 wherein Z is O, and $R^1$ is H) can be prepared by acylation of amines of Formula 13 by the methods cited for Scheme 3.

Scheme 6

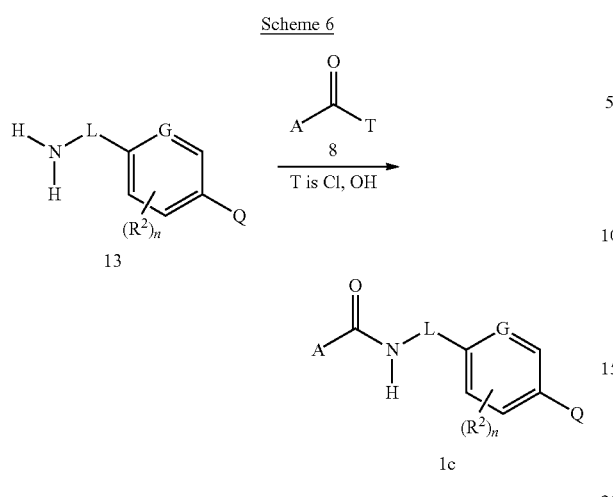

As shown in Scheme 7, amines of Formula 13 can be prepared from amines of Formula 7a. Amines of Formula 7a are first N-protected with a protecting group PG such as tert-butoxycarbonyl or benzyloxycarbonyl to afford compounds of Formula 14. Transformation of compounds of Formula 14 to compounds of Formula 15 can be carried out by the coupling reactions described in Scheme 1. N-deprotection of compounds of Formula 15 affords amines of Formula 13. Methods for N-protection and N-deprotection for use in this sequence can be found in Greene, *Protective Groups in Organic Synthesis*, John Wiley and Sons, New York, 1981.

Scheme 7

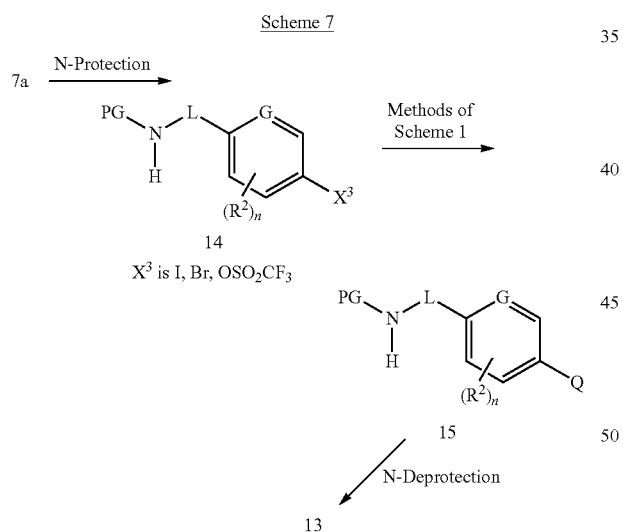

As shown in Scheme 8, amines of Formula 13a (i.e. Formula 13 wherein L is —CH($R^{12a}$)—CH($R^{13a}$)—) can be prepared by sodium borohydride reduction of nitroolefins of Formula 16 followed by reduction of the resultant nitro compound of Formula 17. Typical procedures for sodium borohydride reduction of nitroolefins are found in *ACS Medicinal Chemistry Letters,* 2010, 3(1), 5, and PCT Patent Publication WO2011/124704. Reduction of nitro compound 17 can be carried out using Fe, Zn or SnCl$_2$ in aqueous acidic media at temperatures ranging from ambient to reflux. Alcohol co-solvents such as methanol, ethanol and isopropanol may also be employed. Acids such as hydrochloric, hydrobromic and acetic acids, or ammonium chloride are typically employed. Conditions for such reductions can be found in *J. Labelled Compounds & Radiopharmaceuticals,* 2011, 54(5), 239 and PCT Patent Publication WO2011/138657. This method is applicable when $R^{13a}$ is H, alkyl or haloalkyl.

Scheme 8

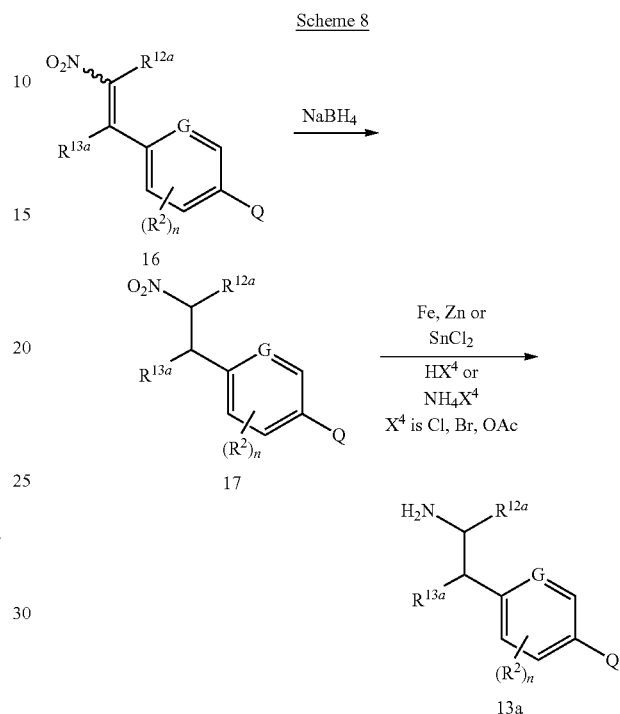

As shown in Scheme 9, nitroolefins of Formula 16 can be prepared by conversion of compounds of Formula 18 to compounds of Formula 19 by the coupling methods described for Scheme 1, followed by condensation of compounds of Formula 19 with nitro compounds of Formula 20. The condensation reaction is conducted in acetic acid in the presence of ammonium acetate in analogy to procedures disclosed in PCT Patent Publication WO2007/141009. This method is applicable when $R^{13a}$ is H, alkyl or haloalkyl.

Scheme 9

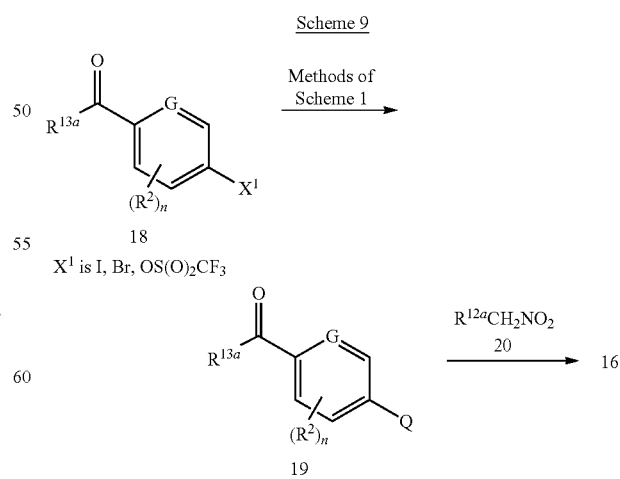

Amines of Formula 13b (i.e. Formula 13 wherein L is —CH($R^{12a}$)—CH($R^{13a}$)—, G is C—$R^{2a}$ and Q is a nitrogen-linked heterocycle denoted by $Q^N$) can be prepared as shown in Scheme 10. Compounds of Formula 21 are treated with heterocycles of Formula 3, wherein a ring nitrogen is bonded to a hydrogen atom, in the presence of bases such as sodium hydride, potassium carbonate, sodium carbonate and potassium tert-butoxide in aprotic solvents such as tetrahydrofuran, dimethylsulfoxide or N,N-dimethylformamide at temperatures ranging from ambient to reflux. The resulting compound of Formula 19a (i.e. Formula 19 wherein G is C—$R^{2a}$ and Q is a nitrogen-linked heterocycle denoted by $Q^N$) is then converted to compounds of Formula 13b by the methods described in Schemes 8 and 9. This method is applicable when $R^{13a}$ is H, alkyl, haloalkyl, alkoxy or haloalkoxy.

Scheme 10

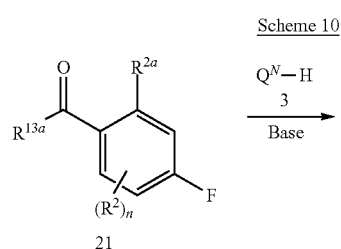

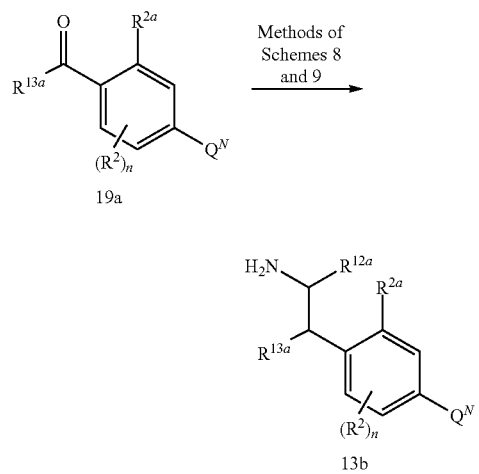

Amines of Formula 13c (i.e. Formula 13 wherein L is —CH($R^{12a}$)—C($R^{13a}$)($R^{13b}$)—) in which $R^{13a}$ is $C_1$-$C_2$ alkoxy, $C_1$-$C_2$ alkylthio or $C_1$-$C_2$ alkoxyamino can be prepared as shown in Scheme 11. Treatment of a nitroolefin of Formula 16a (homologous to Formula 16 except that the olefin substituent geminal to the ring comprising G is identified as $R^{13b}$ instead of $R^{13a}$) with an alcohol solution of a metal alkoxide (i.e. $M^{\oplus\ominus}OR^{52}$) affords an alkoxy intermediate of Formula 22 wherein $R^{13b}$ is $YR^{52}$, $R^{52}$ is $C_1$-$C_2$ alkyl and Y is O. Similarly, treatment of the nitroolefin with an alkanethiol or alkoxyamine of formula H—Y—$R^{52}$ wherein Y is S or —NH—O—, respectively, affords the corresponding compound of Formula 22. Conditions for these analogous transformations can be found in PCT Patent Publication WO2008/148570. Reduction of the intermediate of Formula 22 by the method described in Scheme 8 affords the corresponding amine of Formula 13c. This method is particularly useful when $R^{13b}$ is H, alkyl or haloalkyl. Compounds of Formula 16a can be prepared by methods for preparing compounds of Formula 16, for example, the method of Scheme 9.

Scheme 11

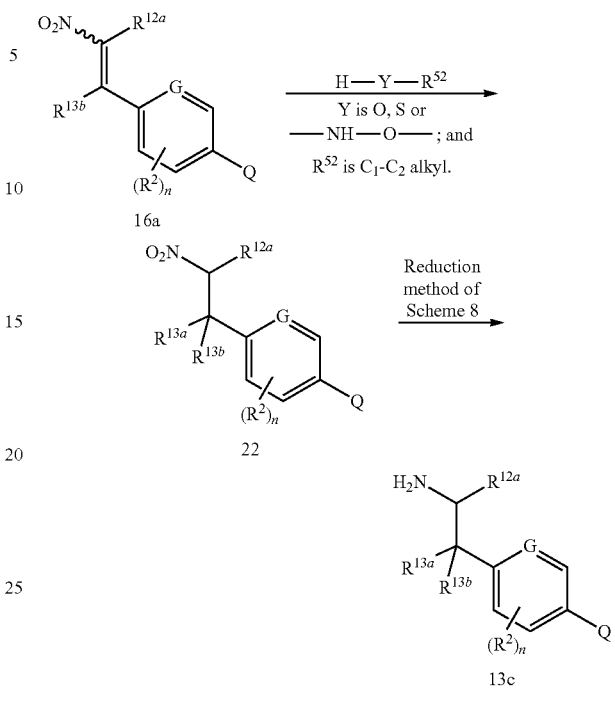

$R^{13a}$ is —Y—$R^{52}$; i.e. $C_1$-$C_2$ alkoxy, alkylthio or alkoxyamino.

As shown in Scheme 12, amines of Formula 13d (i.e. Formula 13 wherein L is —$CH_2CF_2$—) can be prepared from intermediates of Formula 23 by treatment with esters of Formula 24 in the presence of copper powder to give esters of Formula 25. Amidation of esters of Formula 25 followed by reduction of the resulting amides of Formula 26 affords amines of Formula 13d. Conditions for effecting this sequence can be found in *Bioorganic & Medicinal Chemistry Letters*, 2008, (18), 2865.

Scheme 12

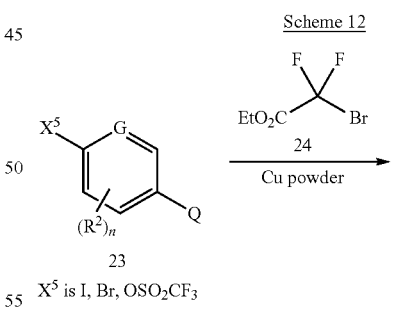

$X^5$ is I, Br, $OSO_2CF_3$

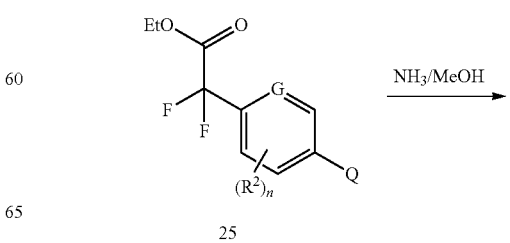

29

-continued

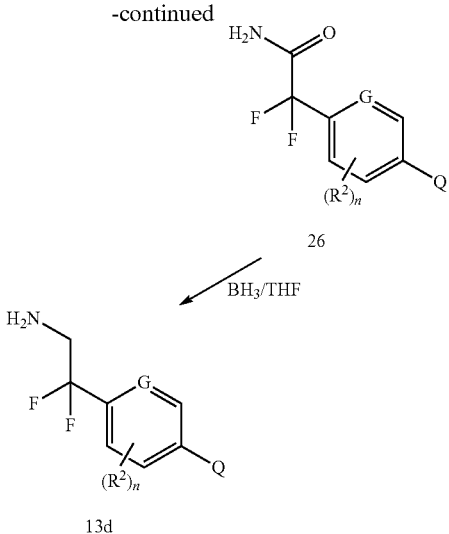

13d

As shown in Scheme 13, intermediates of Formula 23 can be prepared from boron intermediates 27 by employing the coupling methods described involving boron intermediates 4 and 5 in Schemes 1 and 2, respectively. The boron intermediates 27 are commercially available or are readily prepared by methods known in the literature (see, for example, *Tetrahedron Letters*, 2002, 58(14), 2885; *Tetrahedron*, 2010, 66(40), 8000; *European Journal of Organic Chemistry*, 2011, (2), 327; *European Journal of Organic Chemistry*, 2009, (25), 4325).

Scheme 13

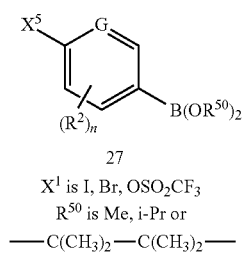

$X^1$ is I, Br, $OSO_2CF_3$
$R^{50}$ is Me, i-Pr or
—C(CH$_3$)$_2$—C(CH$_3$)$_2$—

As shown in Scheme 14, compounds of Formula 23a (i.e. Formula 23 wherein G is C—$R^{2a}$ and Q is a nitrogen-linked heterocycle denoted by $Q^N$) can also be prepared by reacting commercially available aryl fluorides of Formula 28 with heterocycles of Formula 3 wherein a ring nitrogen is bonded to a hydrogen atom analogous to the method described for Scheme 10.

Scheme 14

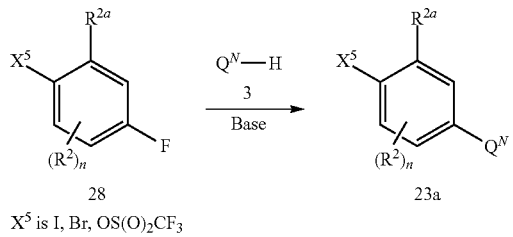

$X^5$ is I, Br, $OS(O)_2CF_3$

Compounds of Formula 13e (i.e. Formula 13 wherein L is —CH$_2$—C($R^{13a}$)($R^{13b}$)— and G is N) can be prepared as shown in Scheme 15. Subjecting compounds of Formula 29 to the coupling conditions described in Scheme 1 affords nitriles of Formula 30. Catalytic hydrogenation of nitriles of Formula 30 in the presence of acetic anhydride/acetic acid affords acetamide derivatives of Formula 31, which on hydrolysis with acid afford amines of Formula 13e. Nitriles of Formula 29 can be prepared by methods well known in the literature (see, for example, PCT Patent Application WO2011/124093).

Scheme 15

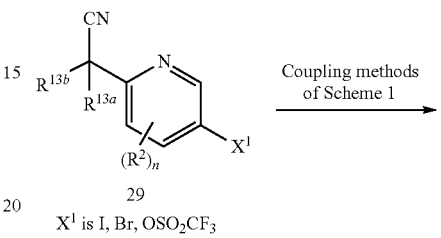

$X^1$ is I, Br, $OSO_2CF_3$

As shown in Scheme 16, compounds of Formula 1d (i.e. Formula 1 wherein Z is O, and L is 1,2-phenylene optionally substituted with up to 4 substituents independently selected from halogen and $C_1$-$C_2$ alkyl) can be prepared by coupling of boronates of Formula 32 with intermediates of Formula 33 under the Suzuki conditions described in Scheme 1. Alternatively trialkyl tin compounds of Formula 34 can be coupled with intermediates of Formula 33 under Stille conditions to give compounds of Formula 1d. Stille couplings typically are conducted in the presence of Pd(0) or a Pd(II) salt, a ligand and a Cu(I) salt such as copper(I) iodide. The reaction is run in a solvent such as dioxane, 1,2-dimethoxyethane or toluene at a temperature ranging from ambient to reflux. For conditions and reagents employed in Stille couplings see *Chemical Reviews*, 2007, 107(1), 133-173.

Scheme 16

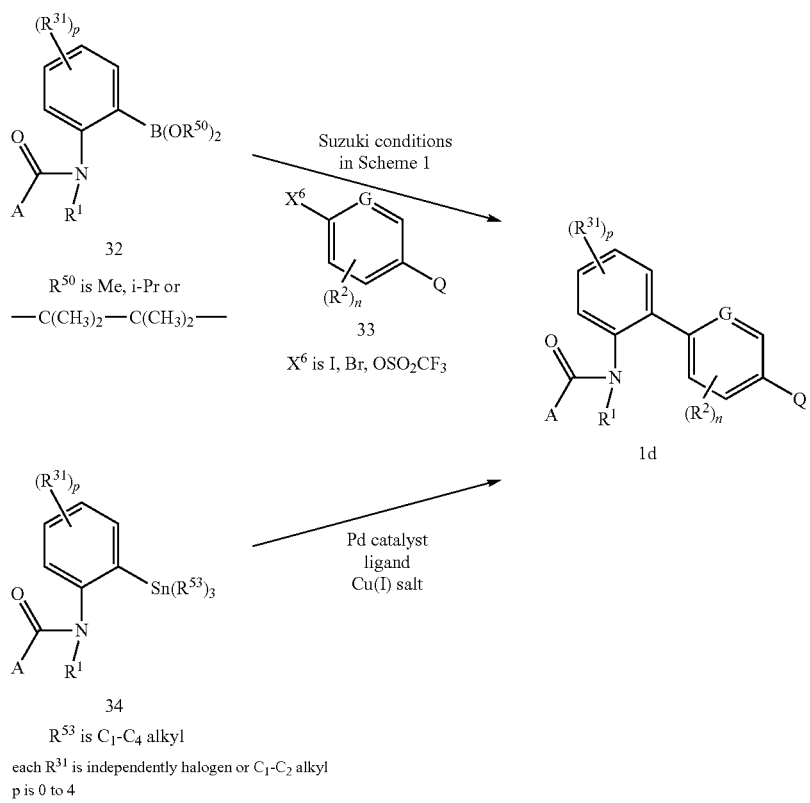

Intermediates of Formula 32 and 34 can be prepared using commercially available starting materials and the methods outlined in Schemes 3, 4 and 6.

Intermediates of Formula 33 are either commercially available or can be prepared as shown in Scheme 17 from intermediates of Formula 35 by a variety of methods known to one skilled in the art. For example, when Q in compounds of Formula 33 is a nitrogen-linked heterocycle denoted by $Q^N$, and J in compounds of Formula 35 is bromine, chlorine or trifluoromethanesulfonate, compounds of Formula 33 can be prepared using the Buchwald-Hartwig conditions described for Scheme 1. Alternatively, intermediates of Formula 35 wherein when J is a boronic acid or boronate ester, can be coupled with heterocycles of Formula 3 ($Q^N$-H) using the Chan-Lam conditions as described for Scheme 2 to provide compounds of Formula 33 wherein Q is $Q^N$. Compounds of Formula 33 wherein Q is a carbon-linked heterocycle denoted by $Q^C$ can be accessed by coupling precursors of Formula 35 wherein J is Br, Cl, I or trifluoromethanesulfonate with boronate-substituted heterocycles $Q^C$-B(OR$^{50}$)$_2$ (4) using the Suzuki conditions of Scheme 1 or with trialkyltin-substituted heterocycles $Q^C$-Sn(R$^{53}$)$_3$ using the Stille conditions of Scheme 16. Alternatively, compounds of Formula 35 wherein J is a boronate or trialkyltin group may also be coupled with halogen-substituted heterocycles $Q^C$-X using the methods shown in Schemes 1 or 16 to afford compounds of Formula 33 wherein Q is $Q^C$. The skilled chemist will realize that prudent choice of groups X and J in reactions involving compounds of Formula 35 is needed, and that isomeric products can occur in cases where groups X and J are similar in reactivity. In cases where regioisomeric mixtures are produced, the desired product can be isolated using routine separation techniques known in the art.

If J in Formula 35 is a functional group such as an alkene, alkyne, oxime, nitrile or ketone, the functional group can be converted to various heterocycles using methods described in Katritsky, Advances in Heterocyclic Chemistry, Elsevier, Vol. 1-104.

Scheme 17

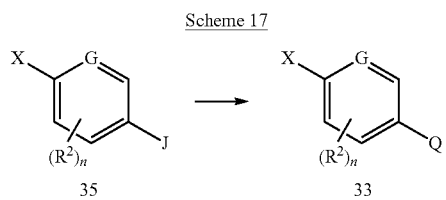

As shown in Scheme 18, compounds of Formula 1d can also be prepared by coupling intermediates analogous to those depicted in Scheme 16 wherein functional groups in the starting reagents have been interchanged. Thus coupling of intermediates of Formula 36 with boronates of Formula 37 and trialkyltin intermediates of Formula 38 using methods described in Scheme 16 affords compounds of Formula 1d.

Scheme 18

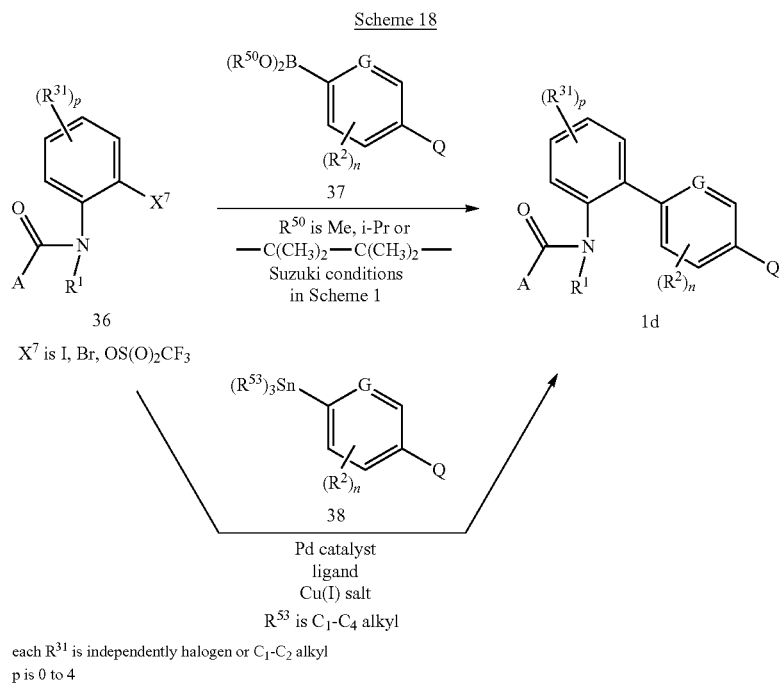

each $R^{31}$ is independently halogen or $C_1$-$C_2$ alkyl
p is 0 to 4

Compounds of Formula 1f (i.e. Formula 1 wherein Z is S) can be prepared as illustrated in Scheme 19. Treatment of a compound of Formula 1e (i.e. Formula 1 wherein Z is O) with phosphorus pentasulfide or Lawesson's Reagent (2,4-bis(4-methoxyphenyl)-1,3-dithia-2,4-diphosphetane-2,4-disulfide) in an inert solvent such as dioxane or toluene at temperatures ranging from 0° C. to the reflux temperature of the solvent for 0.1 to 72 h affords the corresponding thione compound of Formula 1f. This general transformation is well known in the literature; see, for example, U.S. Pat. No. 3,755,582.

Scheme 19

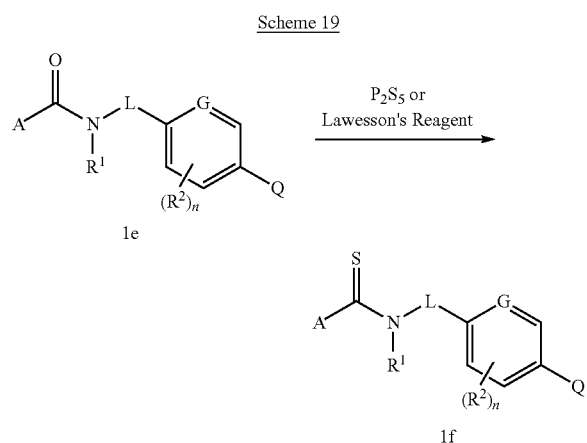

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1. One skilled in the art will also recognize that compounds of Formula 1 and the intermediates described herein can be subjected to various electrophilic, nucleophilic, radical, organometallic, oxidation, and reduction reactions to add substituents or modify existing substituents.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Synthesis Examples are, therefore, to be construed as merely illustrative, and not limiting of the disclosure in any way whatsoever. Steps in the following Synthesis Examples illustrate a procedure for each step in an overall synthetic transformation, and the starting material for each step may not have necessarily been prepared by a particular preparative run whose procedure is described in other Steps. Percentages are by weight except for chromatographic solvent mixtures or where otherwise indicated. Parts and percentages for chromatographic solvent mixtures are by volume unless otherwise indicated.

$^1$H NMR spectra are reported in ppm downfield from tetramethylsilane in CDCl$_3$ unless otherwise noted; "s" means singlet, "d" means doublet, "t" means triplet, "q" means quartet, "m" means multiplet, "br s" means broad singlet, "br m" means broad multiplet. Mass spectra are reported as the molecular weight of the highest isotopic abundance parent ion (M+1) formed by addition of H$^+$ (molecular weight of 1) to the molecule, or (M−1) formed by the loss of H$^+$ (molecular weight of 1) from the molecule, observed by using liquid chromatography coupled to a mass spectrometer (MS) using either atmospheric pressure chemical ionization (AP$^+$) or electrospray ionization (ESI$^+$), where "amu" stands for atomic mass units.

Synthesis Example 1

Preparation of 2-chloro-N-[3',5'-difluoro-4'-[3-(trifluoromethyl)-1H-pyrazol-1-yl][1,1'-biphenyl]-2-yl]-3-pyridinecarboxamide (Compound 170)

Step A: Preparation of 1-(2,6-difluoro-4-nitrophenyl)-3-trifluoromethyl)-1H-pyrazole A mixture of 1,2,3-trifluoro-5-nitrobenzene (2.00 g, 11.3 mmol), 3-(trifluoromethyl)-1H-pyrazole (1.61 g, 11.9 mmol) and potassium carbonate (3.90 g, 28.2 mmol) in acetonitrile (30 mL) was refluxed for 16 h. The reaction mixture was concentrated under reduced pressure and purified by medium pressure liquid chromatography on silica gel eluted with 0 to 40% ethyl acetate in hexanes to provide the title compound (2.39 g).
$^1$H NMR δ 8.04 (m, 2H), 7.82 (s, 1H), 6.84 (s, 1H).

Step B: Preparation of 3,5-difluoro-4-[3-(trifluoromethyl)-1H-pyrazol-1-yl]benzeneamine A mixture of 1-(2,6-difluoro-4-nitrophenyl)-3-trifluoromethyl)-1H-pyrazole (i.e. the product of Step A; 2.39 g, 8.15 mmol) and tin(II) chloride dihydrate (9.33 g, 41.3 mmol) in ethanol (173 mL) was refluxed for 2 h. The reaction mixture was concentrated under reduced pressure, and the residue was dissolved in ethyl acetate and washed successively with 1 N aqueous sodium hydroxide, and then water. The organic layer was dried (MgSO$_4$), filtered and concentrated under reduced pressure. The residue was purified by medium pressure liquid chromatography on silica gel eluted with 0 to 100% ethyl acetate in hexanes to provide the title compound (2.00 g).
$^1$H NMR δ 7.59 (s, H), 6.69 (d, 1H), 6.29 (m, 2H), 4.12 (br s, 2H).

Step C: Preparation of 1-(4-bromo-2,6-difluorophenyl)-3-(trifluoromethyl)-1H-pyrazole To a solution of copper(II) bromide (1.87 g, 8.36 mmol) in acetonitrile (20 mL) at 5° C. was added 3,5-difluoro-4-[3-(trifluoromethyl)-1H-pyrazol-1-yl]benzeneamine (i.e. the product of Step B; 2.00 g, 8.00 mmol) followed by tert-butyl nitrite (1.37 g, 14.0 mmol) dropwise over several minutes. The reaction mixture was allowed to slowly warm to room temperature overnight. An excess of 1 N HCl was added, and the mixture was then filtered through a pad of Celite® diatomaceous filter aid. The filtrate was extracted with ethyl acetate, dried (MgSO$_4$) and concentrated under reduced pressure. The residue was purified by medium pressure liquid chromatography on silica gel eluted with 0 to 40% ethyl acetate in hexanes. The resulting solid was then triturated with 1-chlorobutane and then air dried to yield the title compound (0.98 g).
$^1$H NMR δ 7.69 (s, 1H), 7.31 (m, 2H), 6.76 (d, 1H).

Step D: Preparation of 3',5'-difluoro-4'-[3-(trifluoromethyl)-1H-pyrazol-1-yl][1,1'-biphenyl]-2-amine A mixture of 1-(4-bromo-2,6-difluorophenyl)-3-(trifluoromethyl)-1H-pyrazole (i.e. the product of Step C, 1.83 g, 5.6 mmol), B-(2-aminophenyl)-boronic acid (0.90 g, 6.58 mmol), sodium carbonate (2.07 g, 19.5 mmol) and dichlorobis(triphenylphosphine)palladium(II) (0.33 g, 0.76 mmol) in 1,2-dimethoxyethane (46 mL) and water (11 mL) was heated at 85° C. for 16 h. The reaction mixture was then concentrated under reduced pressure, and the residue was purified by medium pressure liquid chromatography on silica gel eluted with 0 to 100% ethyl acetate in hexanes to yield the title compound (1.02 g).
$^1$H NMR δ 7.75 (s, 1H), 7.22 (m, 3H), 7.12 (m, 1H), 6.86 (m, 1H), 6.78 (m, 2H), 3.78 (br s, 2H).

Step E: Preparation of 2-chloro-N-[3',5'-difluoro-4'-[3-(trifluoromethyl)-1H-pyrazol-1-yl][1,1'-biphenyl]-2-yl]-3-pyridinecarboxamide A mixture of 3',5'-difluoro-4'-[3-(trifluoromethyl)-1H-pyrazol-1-yl][1,1'-biphenyl]-2-amine (i.e. the product of Step D; 0.17 g, 0.52 mmol), 2-chloro-3-pyridinecarbonyl chloride (0.092 g, 0.52 mmol) and triethylamine (0.050 g, 0.52 mmol) in dichloromethane (5 mL) was stirred for 16 h at room temperature. The reaction mixture was then concentrated under reduced pressure, and the residue was purified by medium pressure liquid chromatography on silica gel eluted with 0 to 100% ethyl acetate in hexanes. The resulting solid was triturated with 1-chlorobutane and hexanes to yield the title compound (0.090 g), a compound of the present invention.
$^1$H NMR δ 8.49 (br s, 1H), 8.26 (d, 1H), 8.15 (d, 1H), 8.03 (br s, 1H), 7.75 (br s, 1H), 7.53 (t, 1H), 7.36 (m, 3H), 7.20 (d, 2H), 6.78 (s, 1H).

Synthesis Example 2

Preparation of 3-difluoromethyl)-N-[3',5'-difluoro-4'-(1-methyl-1H-pyrazol-3-yl)[1,1'-biphenyl]-2-yl]-1-methyl-1H-pyrazole (Compound 232)

Step A: Preparation of 1-(4-bromo-2,6-difluorophenyl)-3-(dimethylamino)-2-propene-1-one A mixture of 1-(4-bromo-2,6-difluorophenyl)ethanone (prepared according to the method described in PCT Patent Publication WO 2004/72070; 4.56 g, 19.4 mmol) and N,N-dimethylacetamide dimethyl acetal (6.94 g, 58.2 mmol) in toluene (45 mL) was refluxed for 16 h. The reaction mixture was then concentrated under reduced pressure, and the residue was purified by medium pressure liquid chromatography on silica gel eluted with 0 to 100% ethyl acetate in hexanes to yield the title compound (4.78 g).
$^1$H NMR δ 7.79 (br s, 1H), 7.11 (m, 2H), 5.31 (br s, 1H), 3.12 (br s, 3H), 2.89 (s, 3H).

Step B: Preparation of 3-(4-bromo-2,6-difluorophenyl)-1-methyl-1H-pyrazole

A mixture of 1-(4-bromo-2,6-difluorophenyl)-3-(dimethylamino)-2-propene-1-one (i.e. the product of Step A, 2.39 g, 8.24 mmol) and methylhydrazine (0.42 g, 9.05 mmol) in methanol (50 mL) was stirred at room temperature overnight.

The reaction mixture was then concentrated under reduced pressure, and the residue was purified by medium pressure liquid chromatography on silica gel eluted with 0 to 100% ethyl acetate in hexanes to yield the title compound (0.86 g).
$^1$H NMR δ 7.59 (d, 1H), 7.23 (m, 2H), 6.38 (d, 1H), 3.78 (s, 3H).

Step C: Preparation of (3-difluoromethyl)-N-[3',5'-difluoro-4'-(1-methyl-1H-pyrazol-3-yl) [1,1'-biphenyl]-2-yl]-1-methyl-1H-pyrazole A mixture of 3-(difluoromethyl)-1-methyl-1H-pyrazole-4-carbonyl chloride (prepared from commercial 3-(difluoromethyl)-1-methyl-1H-pyrazole-4-carboxylic acid according to the procedure described in PCT Patent Application WO 2008/053043; 0.16 g, 0.91 mmol), 2-(4,4,5,5-tetramethyl-1,3,2-dioxaborolan-2-yl)-benzenamine (0.18 g, 0.83 mmol) and cesium carbonate (0.54 g, 1.65 mmol) in 1,2-dimethoxyethane (2.5 mL) was stirred at room temperature overnight. To this crude reaction mixture was added 3-(4-bromo-2,6-difluoro-phenyl)-1-methyl-1H-pyrazole (i.e. the product of Step B; 0.25 g, 0.91 mmol), dichloro-bis(triphenylphosphine) palladium(II) (0.03 g, 0.04 mmol), saturated aqueous sodium carbonate (0.6 mL) and additional 1,2-dimethoxyethane (2.5 mL). The mixture was then heated to 85° C. for 4 h, cooled to room temperature, diluted with brine and extracted with ethyl acetate. The combined organic extracts were dried (MgSO$_4$), concentrated under reduced pressure and purified by medium pressure liquid chromatography on silica gel eluted with 0 to 100% ethyl acetate in hexanes to yield the title compound (0.26 g), a compound of the present invention.
$^1$H NMR δ 8.25 (d, 1H), 7.88 (br s, 1H), 7.61 (s, 1H), 7.47 (m, 1H), 7.28 (m, 3H), 7.06 (m, 2H), 6.62 (m, 1H), 6.43 (d, 1H), 3.95 (s, 3H), 3.82 (s, 3H).

Synthesis Example 3

Preparation of 2-(trifluoromethyl)-N-[2-[4-[3-(trifluoromethyl)-1H-pyrazol-1-yl]phenyl]ethyl]benzamide (Compound 5)

Step A: Preparation of N-[2-(4-bromophenyl)ethyl]-2-(trifluoromethyl)benzamide

To a mixture of 2-(trifluoromethyl)benzoyl chloride (1.0 g, 5.3 mmol) in dichloromethane (5 mL) was added dropwise a solution of triethylamine (0.41 g, 4.0 mmol) and 4-bromophenethylamine (0.80 g, 4.0 mmol) in dichloromethane (5 mL). The resulting mixture was stirred at room temperature overnight. The reaction mixture was then diluted with dichloromethane and extracted with 1 N aqueous hydrochloric acid. The aqueous phase was separated and extracted with additional dichloromethane. The organic extracts were then combined, dried (MgSO$_4$), filtered, and concentrated under reduced pressure. The crude residue was purified by chromatography on a silica gel column eluted with 0 to 100% ethyl acetate:hexane to provide the title compound (1.10 g) as a white solid.
$^1$H NMR δ 7.68 (d, 1H), 7.55 (m, 2H), 7.45 (m, 3H), 7.15 (m, 2H), 5.78 (br m, 1H), 3.70 (m, 2H), 2.90 (m, 2H).

Step B: Preparation of 2-(trifluoromethyl)-N-[2-[4-[3-(trifluoromethyl) 11H-pyrazol-1-yl]phenyl]ethyl]benzamide To a mixture of 3-(trifluoromethyl)pyrazole (0.12 g, 0.89 mmol), N,N-dimethyl-cyclohexane-1,2-diamine (0.05 g, 0.36 mmol), copper(I) iodide (0.03 g, 0.18 mmol), and potassium carbonate (0.41 g, 3.0 mmol) in dioxane (5 mL) was added N-[2-(4-bromophenyl)ethyl]-2-(trifluoromethyl)benzamide (i.e. the product of Step A; 0.50 g, 1.3 mmol). The resulting mixture was then refluxed overnight, cooled to room temperature and partitioned between water and ethyl acetate. The layers were separated, and the aqueous phase was extracted with a second portion of ethyl acetate. The combined organic extracts were then dried (MgSO$_4$), filtered, and concentrated under reduced pressure. The residue was purified by column chromatography on silica gel eluted with 0 to 20% ethyl acetate:hexane to afford the title compound (0.19 g), a compound of the present invention, as a tan solid.
$^1$H NMR δ 7.96 (d, 1H), 7.67 (m, 3H), 7.53 (m, 2H), 7.44 (m, 1H), 7.35 (m, 2H), 6.71 (m, 1H), 5.85 (br m, 1H), 3.73 (m, 2H), 2.98 (m, 2H). MS 428 amu (AP$^+$).

Synthesis Example 4

Preparation of N-[2-[3-chloro-5-[(3-trifluoromethyl)-1H-pyrazol-1-yl]-2-pyridinyl]ethyl]-2-(trifluoromethyl)benzamide (Compound 85)

Step A: Preparation 5-bromo-3-chloro-2-pyridineacetonitrile

To a solution of 5-bromo-2,3-dichloropyridine (10.0 g, 0.044 mol) in N-methyl-2-pyrrolidone (70 mL) at 0° C. was added potassium hydroxide (5.4 g, 0.097 mol), and the resulting mixture was heated to 70° C. Ethyl cyanoacetate (5.65 mL, 0.53 mol) was added via syringe over 15 min, and then heating at 70° C. was continued for 3 h more. The pH of the reaction mixture was adjusted to 2 by careful addition of concentrated aqueous hydrochloric acid, and the resulting mixture was heated at 130° C. for 2 h. The reaction mixture was cooled to 20° C., treated with 1 N aqueous sodium hydroxide (15-16 mL) and extracted with three portions of methyl tert-butyl ether (3×100 mL). The combined organic extracts were washed with water, dried (Na$_2$SO$_4$) and concentrated under reduced pressure to afford the title compound (6.0 g) as a brown colored solid, which was used without further purification.
$^1$H NMR δ 8.60 (s, 1H), 7.79 (s, 1H), 4.01 (s, 2H).

Step B: Preparation of 3-chloro-5-[3-(trifluoromethyl)-1H-pyrazol-1-yl]-2-pyridineacetonitrile To a solution of 5-bromo-3-chloro-2-pyridineacetonitrile (i.e. the product of Step A; 6.0 g, 0.025 mol) in 1,4-dioxane (50 mL) was added 3-(trifluoromethyl)-1H-pyrazole (3.74 g, 0.027 mol), copper(I) iodide (0.49 g, 0.0025 mol), potassium carbonate (13.8 g, 0.1 mol) and trans-N,N'-dimethyl-1,2-cyclohexanediamine (1.42 g, 0.01 mol) under argon atmosphere at room temperature, and the resulting mixture was heated at 100° C. for 16 h. The cooled reaction mixture was diluted with ice water and extracted with dichloromethane (2×50 mL). The combined organic extracts were dried (Na$_2$SO$_4$) and concentrated under reduced pressure. The residue was purified by silica gel chromatography eluting with ethyl acetate-hexane (4:6) to afford the title compound (5.0 g) as a light yellow solid.
$^1$H NMR δ 8.60 (s, 1H), 8.25 (d, 1H), 7.79 (s, 1H), 7.44 (m, 1H), 6.80 (d, 1H), 4.10 (s, 2H).

Step C: Preparation of 3-chloro-5-[3-(trifluoromethyl)-1H-pyrazol-1-yl]-2-pyridineethanamine A solution of 3-chloro-5-[3-(trifluoromethyl)-1H-pyrazol-1-yl]-2-pyridineacetonitrile (i.e. the product of Step B; 5.0 g, 0.017 mol) in methanol (50 mL) was shaken in a Parr hydrogenation apparatus in the presence of Raney nickel (5.0 g) and a hydrogen pressure of 50 psi (345 kPa) at room temperature for 2 h. The mixture was filtered through a pad of Celite® diatomaceous filter aid, and the filter pad was washed with dichloromethane. The filtrate was concentrated under reduced pressure to afford the title compound (2.0 g), which was used without further purification.

Step D: Preparation of N-[2-[3-chloro-5-[(3-trifluoromethyl)-1H-pyrazol-1-yl]-2-pyridinyl]ethyl]-2-(trifluoromethyl)benzamide To a solution of 3-chloro-5-[3-(trifluoromethyl)-1H-pyrazol-1-yl]-2-pyridine-ethanamine (i.e. the product of Step C; 200 mg, 0.68 mmol) in dichloromethane (5 mL) at 0° C. was added triethylamine (0.14 mL, 1.02 mmol). The resulting mixture was stirred for 10 min, then 2-(trifluoromethyl)benzoyl chloride (156 mg, 0.74 mmol) was slowly added at 0° C., and the mixture stirred at room temperature for 16 h. Ice water was added to the mixture, the layers were separated, and the aqueous layer extracted with dichloromethane (2×). The combined organic layers were dried ($Na_2SO_4$) and concentrated under reduced pressure. The residue was purified by chromatography on silica gel eluted with ethyl acetate-hexane (8:2) to afford the title compound (130 mg, 41%), a compound of the present invention, as a white solid, mp 118-120° C.

$^1$H NMR δ 8.76 (d, 1H), 8.13 (d, 1H), 7.96 (s, 1H), 7.66 (d, 2H), 7.51 (d, 1H), 6.77 (s, 1H), 6.66 (br s, 1H), 4.01 (q, 2H), 3.27 (t, 2H). MS (AP$^+$) 463 amu.

Synthesis Example 5

Preparation of N-[2-[2-chloro-4-[3-(trifluoromethyl)-1H-pyrazol-1-yl]phenyl]ethyl]-3-(trifluoromethyl)-2-pyridinecarboxamide (Compound 40)

Step A: Preparation of 2-chloro-4-[3-(trifluoromethyl)-1H-pyrazol-1-yl]benzaldehyde A mixture of 2-chloro-4-fluorobenzaldehyde (5.0 g, 31.5 mmol), 3-(trifluoromethyl)-pyrazole (4.28 g, 31.5 mmol) and potassium carbonate (6.53 g, 47.3 mmol) in anhydrous N,N-dimethylformamide (40 mL) was stirred for 2 h at 110° C. The reaction mixture was cooled to 0° C., poured into ice water (500 mL) and stirred for 15 min. The precipitate formed was filtered and dried under reduced pressure to afford the title compound (8.1 g), which was used without further purification.

$^1$H NMR δ 10.4 (s, 1H), 8.00 (m, 2H), 7.85 (d, 1H), 7.77 (m, 1H), 6.70 (d, 1H). MS (AP$^+$) 275 amu.

Step B: Preparation of 1-[3-chloro-4-(2-nitroethenyl)phenyl]-3-(trifluoromethyl)-1H-pyrazole To a solution of 2-chloro-4-[3-(trifluoromethyl)-1H-pyrazol-1-yl]benzaldehyde (i.e. the product of Step A; 6.0 g, 0.025 mol) in acetic acid (24 mL) was added ammonium acetate (5.6 g, 73 mmol), and the resulting mixture was stirred for 15 min at 0° C. Nitromethane (12.5 g, 204 mmol) was then added, and the mixture was stirred at 80° C. for 2 h. The reaction mixture was poured into ice water and extracted with ethyl acetate (100 mL). The aqueous layer was extracted with ethyl acetate (2×250 mL), and the combined organic layers were washed with brine (200 mL), dried ($Na_2SO_4$) and concentrated under reduced pressure. The residue was purified by flash column chromatography on silica gel eluted with 30% ethyl acetate in hexanes to afford the title compound (7.1 g).

$^1$H NMR δ 8.30 (d, 1H), 7.90 (d, 1H), 7.80 (d, 1H), 7.60 (m, 2H), 7.55 (d, 1H), 6.70 (d, 1H).

Step C: Preparation of 2-chloro-4-[3-(trifluoromethyl)-1H-pyrazol-1-yl]benzeneethanamine hydrochloride (1:1)

To a cooled (0° C.) solution of sodium borohydride (238.6 mg, 6.28 mmol) in anhydrous tetrahydrofuran (8 mL) at 0° C. was added boron trifluoride diethyl etherate (1.13 g, 7.93 mmol) dropwise. The resultant solution was then stirred for 10 min at 0° C. and for 15 min at room temperature. A solution of 1-[3-chloro-4-(2-nitroethenyl)phenyl]-3-(trifluoromethyl)-1H-pyrazole (i.e. the product of Step B; 420 mg, 1.32 mmol) in anhydrous tetrahydrofuran (5.2 mL) was added dropwise via cannula, and the resulting mixture was refluxed for 7.5 h and then allowed to cool to room temperature. Water (17 mL) was added dropwise, followed by 1 N hydrochloric acid (17 mL). The reaction mixture was concentrated under reduced pressure, and the residue was triturated with petroleum ether to afford the title compound (320 mg).

$^1$H NMR δ 8.80 (d, 1H), 8.15 (br s, 2H), 1H), 8.00 (s, 1H), 7.80 (d, 1H), 7.60 (d, 1H), 7.00 (d, 1H), 3.40-3.60 (m, 4H). MS (AP$^+$) 291 amu.

Step D: Preparation of N-[2-[2-chloro-4-[3-(trifluoromethyl)-1H-pyrazol-1-yl]phenyl]ethyl]-3-(trifluoromethyl)-2-pyridinecarboxamide To a solution of 2-chloro-4-[3-(trifluoromethyl)-1H-pyrazol-1-yl]benzeneethanamine hydrochloride (1:1) (i.e. the product of Step C; 300 mg, 1.11 mmol), N-(3-dimethylaminopropyl)-N'-ethylcarbodiimide (297 mg, 1.66 mmol), 1-hydroxybenzotriazole (212 mg, 1.66 mmol) and N,N-diisopropylethylamine (0.9 mL, 5.55 mmol) in dichloromethane (15 mL) was added 3-(trifluoromethyl)pyridine-2-carboxylic acid (198 mg, 1.21 mmol), and the resulting mixture was stirred for 12 h. The reaction mixture was washed with water and brine, dried ($Na_2SO_4$) and concentrated under reduced pressure. The residue was purified by flash column chromatography on silica gel eluted with 50% ethyl acetate in hexanes to afford the title compound (210 mg) as a brown solid.

$^1$H NMR δ 8.60 (d, 1H), 8.10 (s, 1H), 7.80 (s, 1H), 7.70 (m, 2H), 7.40 (m, 2H), 7.30 (d, 1H), 6.80 (d, 1H), 3.70 (m, 2H), 3.10 (t, 2H). MS (AP$^+$) 464 amu.

Synthesis Example 6

Preparation of N-[2-[2-chloro-4-[3-(trifluoromethyl)-1H-pyrazol-1-yl]phenyl]-2,2-difluoroethyl]-3-(trifluoromethyl)-2-pyridinecarboxamide (Compound 150)

Step A: Preparation of 1-(3-chloro-4-iodophenyl)-3-(trifluoromethyl)-1H-pyrazole To a solution of 2-chloro-4-fluoro-1-iodo-benzene (3.6 g, 14.3 mmol) and 3-trifluoromethyl-1H-pyrazole (1.9 g, 14.4 mmol) in N,N-dimethylformamide (40 mL) was added potassium carbonate (2.4 g, 17.2 mmol), and the resulting mixture was heated at 135° C. for 12 h. The reaction mixture was cooled to room temperature, poured in cold water (80 mL) and extracted with dichloromethane (2×40 mL). The combined organic extracts were dried ($Na_2SO_4$) and concentrated under reduced pressure. The residue was purified by flash column chromatography on silica gel eluted with 10% ethyl acetate in hexanes to afford the title compound (4.2 g) as a white solid.

$^1$H NMR δ 10.4 (s, 1H), 7.88 (m, 2H), 7.80 (d, 1H), 7.27 (m, 1H), 6.68 (d, 1H). MS (AP$^+$) 373 amu.

Step B: Preparation of ethyl 2-chloro-α,α-difluoro-4-[3-trifluoromethyl)-1H-pyrazol-1-yl]benzeneacetate A mixture of ethyl bromodifluoroacetate (4 g, 20.1 mmol) and copper powder (2.5 g, 40.3 mmol) in dimethylsulfoxide (10 mL) was stirred at room temperature for 1 h. 1-(3-chloro-4-iodophenyl)-3-(trifluoromethyl)-1H-pyrazole (i.e. the product of Step A; 3.75 g, 10 mmol) was added, and stirring at room temperature was continued for 12 h. Saturated aqueous ammonium chloride (25 mL) was added, and the resulting solution was extracted with dichloromethane (2×25 mL). The combined organic extracts were washed with water and brine, dried (MgSO$_4$) and concentrated under reduced pressure. The resulting crude was purified by flash column chromatography on silica gel eluted with 15% ethyl acetate in hexanes to afford the title compound (2.2 g) as a colorless oil.

$^1$H NMR δ 7.94 (d, 1H), 7.83 (s, 1H), 7.78 (d, 1H), 7.65 (d, 1H), 6.70 (d, 1H), 4.30 (q, 2H), 1.25 (t, 3H). MS (AP$^+$) 370 amu.

Step C: Preparation of 2-chloro-β,β-difluoro-4-[3-trifluoromethyl)-1H-pyrazol-1-yl]benzeneethanamine hydrochloride (1:1)

To a solution of ethyl 2-chloro-α,α-difluoro-4-[3-trifluoromethyl)-1H-pyrazol-1-yl]benzeneacetate (i.e. the product of Step B; 500 mg, 1.35 mmol in methanol was added dropwise ammonia in methanol (2 M, 3.37 mL, 6.75 mmol), and the resulting mixture was stirred for 24 h at room temperature. The solvent was removed under reduced pressure to afford crude 2-chloro-α,α-difluoro-4-[3-trifluoromethyl)-1H-pyrazol-1-yl]benzeneacetamide, which was used without further purification.

$^1$H NMR δ 7.92 (d, 1H), 7.83 (s, 1H), 7.80 (d, 1H), 7.65 (d, 1H), 6.70 (d, 1H), 6.49 (br s, 1H), 5.91 (br s, 1H). MS (AP$^+$) 341 amu.

The crude 2-chloro-α,α-difluoro-4-[3-trifluoromethyl)-1H-pyrazol-1-yl]benzeneacetamide was dissolved in tetrahydrofuran, and to the resulting solution was added slowly borane in tetrahydrofuran (1 M, 3.4 mL, 3.34 mmol). The reaction mixture was heated at 70° C. for 12 h. The reaction mixture was cooled to room temperature, quenched with water (10 mL) and extracted with dichloromethane (2×10 mL). The combined organic extracts were washed with brine (15 mL), dried (MgSO$_4$) and concentrated under reduced pressure. To the residue was added 4 M hydrochloric acid in dioxane (1 mL). The residual solid was triturated with hexanes, filtered and dried under reduced pressure to afford the title compound (340 mg) as a solid.

$^1$H NMR δ 8.92 (d, 1H), 7.83 (s, 1H), 8.77 (br s, 2H), 8.22 (s, 1H), 8.07 (d, 1H), 7.85 (d, 1H), 7.13 (d 1H), 3.83 (t, 2H). MS (AP$^+$) 327 amu.

Step D: Preparation of N-[2-[2-chloro-4-[(3-trifluoromethyl)-1H-pyrazol-1-yl]phenyl]-2,2-difluoroethyl]-3-(trifluoromethyl)-2-pyridinecarboxamide To a solution of 2-chloro-β,β-difluoro-4-[3-trifluoromethyl)-1H-pyrazol-1-yl]-benzeneethanamine hydrochloride (1:1) (i.e. the product of Step C; 150 mg, 0.46 mmol), N-(3-dimethylaminopropyl)-N-ethylcarbodiimide (132 mg, 1.66 mmol), 1-hydroxybenzotriazole (93 mg, 1.55 mmol) and N,N-diisopropylethylamine (0.23 mL, 5.55 mmol) in dichloromethane was added 3-(trifluoromethyl)pyridine-2-carboxylic acid (105 mg, 0.6 mmol), and the resulting mixture was stirred for 12 h. The reaction mixture was washed with water and brine, dried (Na$_2$SO$_4$) and concentrated under reduced pressure. The residue was purified by flash column chromatography on silica gel eluted with 15% ethyl acetate in hexanes to yield the title compound (160 mg), a compound of the present invention, as a white solid.

$^1$H NMR 8.67 (d, 1H), 8.09 (d, 1H), 8.00 (t, 1H), 7.91 (d, 1H), 7.82 (d, 1H), 7.68 (d, 1H), 7.60 (dd, 1H), 7.52 (dd, 1H), 4.29 (td, 2H). MS (AP$^+$) 500 amu.

By the procedures described herein together with methods known in the art, the compounds disclosed in the Tables that follow can be prepared. The following abbreviations are used in the Tables which follow: Me means methyl, Et means ethyl, Ph means phenyl, MeO or OMe means methoxy, EtO means ethoxy and CN means cyano. "(R$^2$)$_n$ is H" means that n is 0 and the ring comprising G is not substituted with R$^2$. The structures of individual "A" substituents in the Tables are depicted in Exhibit 4.

Exhibit 4

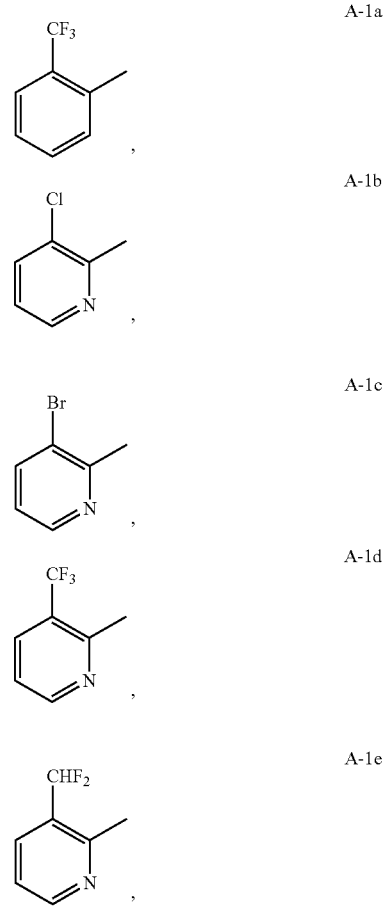

-continued
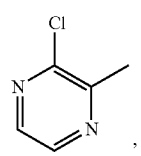 A-1f
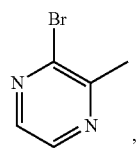 A-1g
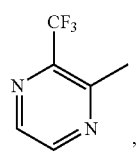 A-1h
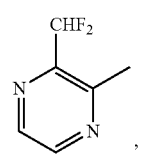 A-1i
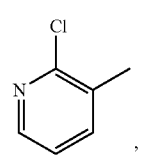 A-1j
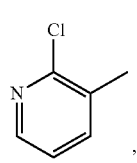 A-1k
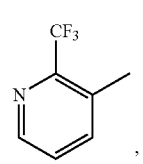 A-1l
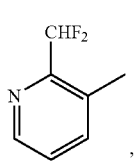 A-1m
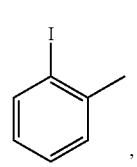 A-1n
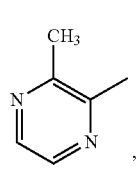 A-1o
-continued
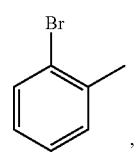 A-1p
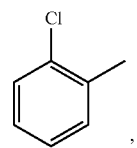 A-1q
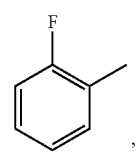 A-1r
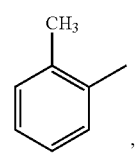 A-1s
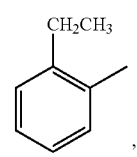 A-1t
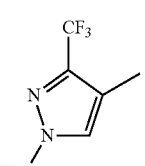 A-2a
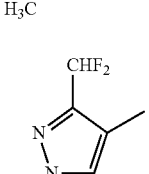 A-2b
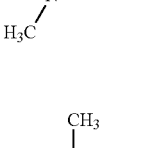 A-2c
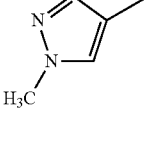 A-2d -continued
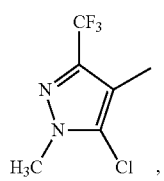 A-2e
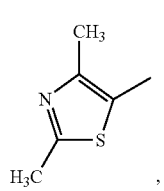 A-3a
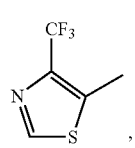 A-3b
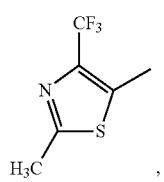 A-3c
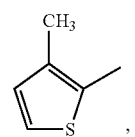 A-4a
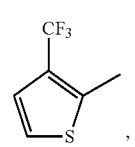 A-4b
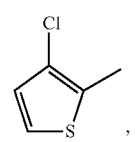 A-4c
-continued
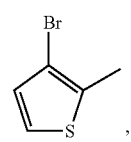 A-4d
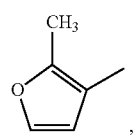 A-5a
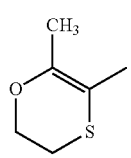 A-6a
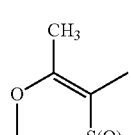 A-6b
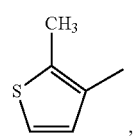 A-7a
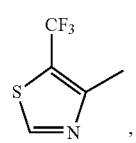 A-8a
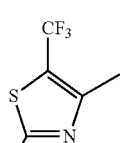 A-8b
and
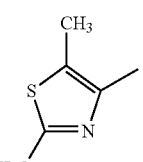 A-8c

TABLE 1

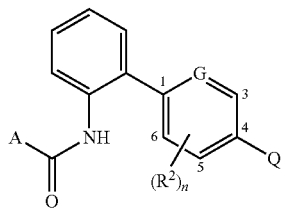

A is A-1a, $(R^2)_n$ is H, and G is CH.

| Q | Q | Q |
|---|---|---|
| 3-CF$_3$—1H-pyrazol-1-yl | 3-Me—1H-pyrazol-1-yl | 3-F—1H-pyrazol-1-yl |
| 3-Br—1H-pyrazol-1-yl | 4-CF$_3$—1H-pyrazol-1-yl | 4-Me—1H-pyrazol-1-yl |
| 4-F—1H-pyrazol-1-yl | 4-Br—1H-pyrazol-1-yl | 5-CF$_3$—1H-pyrazol-1-yl |
| 5-Me—1H-pyrazol-1-yl | 5-F—1H-pyrazol-1-yl | 5-Br—1H-pyrazol-1-yl |
| 3-CHF$_2$—1H-pyrazol-1-yl | 3-Et—1H-pyrazol-1-yl | 3-Cl—1H-pyrazol-1-yl |
| 3-I—1H-pyrazol-1-yl | 4-CHF$_2$—1H-pyrazol-1-yl | 4-Et—1H-pyrazol-1-yl |
| 4-Cl—1H-pyrazol-1-yl | 4-I—1H-pyrazol-1-yl | 5-CHF$_2$—1H-pyrazol-1-yl |
| 5-Et—1H-pyrazol-1-yl | 5-Cl—1H-pyrazol-1-yl | 3-I—1H-pyrazol-1-yl |
| 3-MeO—1H-pyrazol-1-yl | 3-CN—1H-pyrazol-1-yl | 3-CF$_3$O—1H-pyrazol-1-yl |
| 3-CHF$_2$O—1H-pyrazol-1-yl | 4-MeO—1H-pyrazol-1-yl | 4-CN—1H-pyrazol-1-yl |
| 4-CF$_3$O—1H-pyrazol-1-yl | 4-CHF$_2$O—1H-pyrazol-1-yl | 5-CF$_3$O—1H-pyrazol-1-yl |
| 5-CN—1H-pyrazol-1-yl | 5-CF$_3$O—1H-pyrazol-1-yl | 5-CHF$_2$O—1H-pyrazol-1-yl |
| 3-MeO(O=)C—1H-pyrazol-1-yl | 3-Ph—1H-pyrazol-1-yl | 3,5-di-Me—1H-pyrazol-1-yl |
| 3,5-di-F—1H-pyrazol-1-yl | 4-MeO(O=)C—1H-pyrazol-1-yl | 4-Ph—1H-pyrazol-1-yl |
| 3,5-di-CF$_3$—1H-pyrazol-1-yl | 3,5-di-Cl—1H-pyrazol-1-yl | 5-MeO(O=)C—1H-pyrazol-1-yl |
| 5-Ph—1H-pyrazol-1-yl | 3,5-di-CHF$_2$—1H-pyrazol-1-yl | 3,5-di-Br—1H-pyrazol-1-yl |
| 3-CF$_3$-5-Me-1H-pyrazol-1-yl | 3,4-di-Me—1H-pyrazol-1-yl | 3,4-di-CF$_3$—1H-pyrazol-1-yl |
| 3,4-di-Br—1H-pyrazol-1-yl | 3,4-di-Cl—1H-pyrazol-1-yl | 1H-pyrazol-1-yl |
| 3-Me—1H-[1,2,4]triazol-1-yl | 3-CF$_3$—1H-[1,2,4]triazol-1-yl | 3-CHF$_2$—1H-[1,2,4]triazol-1-yl |
| 3-F—1H-[1,2,4]triazol-1-yl | 3-Cl—1H-[1,2,4]triazol-1-yl | 3-Br—1H-[1,2,4]triazol-1-yl |
| 3,5-di-Me—1H-[1,2,4]triazol-1-yl | 3,5-di-CF$_3$—1H-[1,2,4]triazol-1-yl | 3,5-di-CHF$_2$—1H-[1,2,4]triazol-1-yl |
| 3,5-di-Cl—1H-[1,2,4]triazol-1-yl | 3,5-di-Br—1H-[1,2,4]triazol-1-yl | 3-Ph—1H-[1,2,4]triazol-1-yl |
| 1H-[1,2,4]triazol-1-yl | 4-Me—2H-[1,2,3]triazol-2-yl | 4-CF$_3$—2H-[1,2,3]triazol-2-yl |
| 4-CHF$_2$—2H-[1,2,3]triazol-2-yl | 4-F—2H-[1,2,3]triazol-2-yl | 4-Cl—2H-[1,2,3]triazol-2-yl |
| 4-Br—2H-[1,2,3]triazol-2-yl | 4-Ph—2H-[1,2,3]triazol-2-yl | 4,5-di-Me—2H-[1,2,3]triazol-2-yl |
| 4,5-di-CF$_3$—2H-[1,2,3]triazol-2-yl | 4,5-di-Cl—2H-[1,2,3]triazol-2-yl | 4,5-di-Br—2H-[1,2,3]triazol-2-yl |
| 2H-[1,2,3]triazol-2-yl | 4-Me—1H-[1,2,3]triazol-1-yl | 4-CF$_3$—1H-[1,2,3]triazol-1-yl |
| 4-CHF$_2$—1H-[1,2,3]triazol-1-yl | 4-F—1H-[1,2,3]triazol-1-yl | 4-Cl—1H-[1,2,3]triazol-1-yl |
| 4-Br—1H-[1,2,3]triazol-1-yl | 4-Ph—1H-[1,2,3]triazol-1-yl | 1H-[1,2,3]triazol-1-yl |
| 3-Me—1H-pyrrol-1-yl | 3-CF$_3$—1H-pyrrol-1-yl | 3-CHF$_2$—1H-pyrrol-1-yl |
| 3,4-di-Me—1H-pyrrol-1-yl | 2,4-di-Me—1H-pyrrol-1-yl | 3,4-di-CF$_3$—1H-pyrrol-1-yl |
| 2,4-di-CF$_3$—1H-pyrrol-1-yl | 3,4-di-Br—1H-pyrrol-1-yl | 3,4-di-Cl—1H-pyrrol-1-yl |
| 1H-pyrrol-1-yl | 1-Me—1H-pyrazol-3-yl | 1-CF$_3$—1H-pyrazol-3-yl |
| 1-Et—1H-pyrazol-3-yl | 1-i-Pr—1H-pyrazol-3-yl | 1-(F$_3$CCH$_2$)—1H-pyrazol-3-yl |
| 1-Ph—1H-pyrazol-3-yl | 1,4-di-Me—1H-pyrazol-3-yl | 1-Me-4-CF$_3$—1H-pyrazol-3-yl |
| 1-Me—1H-pyrazol-4-yl | 1-CF$_3$—1H-pyrazol-4-yl | 1-Et—1H-pyrazol-4-yl |
| 1-i-Pr—1H-pyrazol-4-yl | 1-(F$_3$CCH$_2$)—1H-pyrazol-4-yl | 1-Ph—1H-pyrazol-4-yl |
| 1,3-di-Me—1H-pyrazol-4-yl | 1-Me-3-CF$_3$—1H-pyrazol-4-yl | 3-Me-1-CF$_3$—1H-pyrazol-4-yl |
| 1-Me—1H-[1,2,4]triazol-3-yl | 1-CF$_3$—1H-[1,2,4]triazol-3-yl | 1-Et—1H-[1,2,4]triazol-3-yl |
| 1-i-Pr—1H-[1,2,4]triazol-3-yl | 1-Ph—1H-[1,2,4]triazol-3-yl | 5-Ph-4,5-dihydro-isoxazol-3-yl |
| 5-CF$_3$-2,4-dihydro-3-oxopyrazol-1-yl | 5-Me-2,4-dihydro-3-oxopyrazol-1-yl | |

The present disclosure also includes Tables 2 through 1728, each of which is constructed the same as Table 1 above, except that the row heading in Table 1 (i.e. "A is A-1a, $(R^2)_n$ is H, and G is CH.") is replaced with the respective row heading shown below. For example, in Table 2 the row heading is "A is A-1a, $(R^2)_n$ is 3-F, and G is CH." and Q is as defined in Table 1 above. Thus, the first entry in Table 2 specifically discloses N-[3'-fluoro-4'-[3-(trifluoromethyl)-1H-pyrazol-1-yl][1,1'-biphenyl]-2-yl]-2-(trifluoromethyl)benzamide. Tables 3 through 1728 are constructed similarly.

TABLES 2-1728

| Table | Row Heading |
|---|---|
| 2 | A is A-1a, $(R^2)_n$ is 3-F and G is CH. |
| 3 | A is A-1a, $(R^2)_n$ is 3,5-di-F and G is CH. |
| 4 | A is A-1a, $(R^2)_n$ is 3-Cl and G is CH. |
| 5 | A is A-1a, $(R^2)_n$ is 3,5-di-Cl and G is CH. |
| 6 | A is A-1a, $(R^2)_n$ is 3-Br and G is CH. |
| 7 | A is A-1a, $(R^2)_n$ is 3,5-di-Br and G is CH. |
| 8 | A is A-1a, $(R^2)_n$ is 3-Me and G is CH. |
| 9 | A is A-1a, $(R^2)_n$ is 3,5-di-Me and G is CH. |
| 10 | A is A-1a, $(R^2)_n$ is 3-CF$_3$ and G is CH. |
| 11 | A is A-1a, $(R^2)_n$ is 3,5-di-CF$_3$ and G is CH. |
| 12 | A is A-1a, $(R^2)_n$ is 3-MeO and G is CH. |
| 13 | A is A-1a, $(R^2)_n$ is 3,5-di-MeO and G is CH. |
| 14 | A is A-1a, $(R^2)_n$ is 3-CN and G is CH. |
| 15 | A is A-1a, $(R^2)_n$ is 3,5-di-CN and G is CH. |
| 16 | A is A-1a, $(R^2)_n$ is 3,6-di-F and G is CH. |
| 17 | A is A-1a, $(R^2)_n$ is 3,6-di-Cl and G is CH. |
| 18 | A is A-1a, $(R^2)_n$ is 3,6-di-Br and G is CH. |
| 19 | A is A-1a, $(R^2)_n$ is 3,6-di-Me and G is CH. |
| 20 | A is A-1a, $(R^2)_n$ is 3,6-di-CF$_3$ and G is CH. |
| 21 | A is A-1a, $(R^2)_n$ is 3,6-di-MeO and G is CH. |

TABLES 2-1728-continued

| Table | Row Heading |
|---|---|
| 22 | A is A-1a, $(R^2)_n$ is 3,6-di-CN and G is CH. |
| 23 | A is A-1a, $(R^2)_n$ is 6-F and G is CH. |
| 24 | A is A-1a, $(R^2)_n$ is 6-Cl and G is CH. |
| 25 | A is A-1a, $(R^2)_n$ is 6-Br and G is CH. |
| 26 | A is A-1a, $(R^2)_n$ is 6-Me and G is CH. |
| 27 | A is A-1a, $(R^2)_n$ is 6-CF$_3$ and G is CH. |
| 28 | A is A-1a, $(R^2)_n$ is 6-MeO and G is CH. |
| 29 | A is A-1a, $(R^2)_n$ is 6-CN and G is CH. |
| 30 | A is A-1a, $(R^2)_n$ is 6-F and G is C—F. |
| 31 | A is A-1a, $(R^2)_n$ is 6-Cl and G is C—Cl. |
| 32 | A is A-1a, $(R^2)_n$ is 6-Br and G is C—Br. |
| 33 | A is A-1a, $(R^2)_n$ is 6-Me and G is C—Me. |
| 34 | A is A-1a, $(R^2)_n$ is 6-CF$_3$ and G is C—CF$_3$. |
| 35 | A is A-1a, $(R^2)_n$ is 6-MeO and G is C—OMe. |
| 36 | A is A-1a, $(R^2)_n$ is H and G is N. |
| 37 | A is A-1a, $(R^2)_n$ is 3-F and G is N. |
| 38 | A is A-1a, $(R^2)_n$ is 3,5-di-F and G is N. |
| 39 | A is A-1a, $(R^2)_n$ is 3-Cl and G is N. |
| 40 | A is A-1a, $(R^2)_n$ is 3,5-di-Cl and G is N. |
| 41 | A is A-1a, $(R^2)_n$ is 3-Br and G is N. |
| 42 | A is A-1a, $(R^2)_n$ is 3,5-di-Br and G is N. |
| 43 | A is A-1a, $(R^2)_n$ is 3-Me and G is N. |
| 44 | A is A-1a, $(R^2)_n$ is 3,5-di-Me and G is N. |
| 45 | A is A-1a, $(R^2)_n$ is 3-CF$_3$ and G is N. |
| 46 | A is A-1a, $(R^2)_n$ is 3,5-di-CF$_3$ and G is N. |
| 47 | A is A-1a, $(R^2)_n$ is 3-MeO and G is N. |
| 48 | A is A-1a, $(R^2)_n$ is 3,5-di-MeO and G is N. |
| 49 | A is A-1a, $(R^2)_n$ is 3-CN and G is N. |
| 50 | A is A-1a, $(R^2)_n$ is 3,5-di-CN and G is N. |
| 51 | A is A-1a, $(R^2)_n$ is 3,6-di-F and G is N. |
| 52 | A is A-1a, $(R^2)_n$ is 3,6-di-Cl and G is N. |
| 53 | A is A-1a, $(R^2)_n$ is 3,6-di-Br and G is N. |
| 54 | A is A-1a, $(R^2)_n$ is 3,6-di-Me and G is N. |
| 55 | A is A-1a, $(R^2)_n$ is 3,6-di-CF$_3$ and G is N. |
| 56 | A is A-1a, $(R^2)_n$ is 3,6-di-MeO and G is N. |
| 57 | A is A-1a, $(R^2)_n$ is 3,6-di-CN and G is N. |
| 58 | A is A-1a, $(R^2)_n$ is 6-F and G is N. |
| 59 | A is A-1a, $(R^2)_n$ is 6-Cl and G is N. |
| 60 | A is A-1a, $(R^2)_n$ is 6-Br and G is N. |
| 61 | A is A-1a, $(R^2)_n$ is 6-Me and G is N. |
| 62 | A is A-1a, $(R^2)_n$ is 6-CF$_3$ and G is N. |
| 63 | A is A-1a, $(R^2)_n$ is 6-MeO and G is N. |
| 64 | A is A-1a, $(R^2)_n$ is 6-CN and G is N. |
| 65 | A is A-1b, $(R^2)_n$ is H and G is CH. |
| 66 | A is A-1b, $(R^2)_n$ is 3-F and G is CH. |
| 67 | A is A-1b, $(R^2)_n$ is 3,5-di-F and G is CH. |
| 68 | A is A-1b, $(R^2)_n$ is 3-Cl and G is CH. |
| 69 | A is A-1b, $(R^2)_n$ is 3,5-di-Cl and G is CH. |
| 70 | A is A-1b, $(R^2)_n$ is 3-Br and G is CH. |
| 71 | A is A-1b, $(R^2)_n$ is 3,5-di-Br and G is CH. |
| 72 | A is A-1b, $(R^2)_n$ is 3-Me and G is CH. |
| 73 | A is A-1b, $(R^2)_n$ is 3,5-di-Me and G is CH. |
| 74 | A is A-1b, $(R^2)_n$ is 3-CF$_3$ and G is CH. |
| 75 | A is A-1b, $(R^2)_n$ is 3,5-di-CF$_3$ and G is CH. |
| 76 | A is A-1b, $(R^2)_n$ is 3-MeO and G is CH. |
| 77 | A is A-1b, $(R^2)_n$ is 3,5-di-MeO and G is CH. |
| 78 | A is A-1b, $(R^2)_n$ is 3-CN and G is CH. |
| 79 | A is A-1b, $(R^2)_n$ is 3,5-di-CN and G is CH. |
| 80 | A is A-1b, $(R^2)_n$ is 3,6-di-F and G is CH. |
| 81 | A is A-1b, $(R^2)_n$ is 3,6-di-Cl and G is CH. |
| 82 | A is A-1b, $(R^2)_n$ is 3,6-di-Br and G is CH. |
| 83 | A is A-1b, $(R^2)_n$ is 3,6-di-Me and G is CH. |
| 84 | A is A-1b, $(R^2)_n$ is 3,6-di-CF$_3$ and G is CH. |
| 85 | A is A-1b, $(R^2)_n$ is 3,6-di-MeO and G is CH. |
| 86 | A is A-1b, $(R^2)_n$ is 3,6-di-CN and G is CH. |
| 87 | A is A-1b, $(R^2)_n$ is 6-F and G is CH. |
| 88 | A is A-1b, $(R^2)_n$ is 6-Cl and G is CH. |
| 89 | A is A-1b, $(R^2)_n$ is 6-Br and G is CH. |
| 90 | A is A-1b, $(R^2)_n$ is 6-Me and G is CH. |
| 91 | A is A-1b, $(R^2)_n$ is 6-CF$_3$ and G is CH. |
| 92 | A is A-1b, $(R^2)_n$ is 6-MeO and G is CH. |
| 93 | A is A-1b, $(R^2)_n$ is 6-CN and G is CH. |
| 94 | A is A-1b, $(R^2)_n$ is 6-F and G is C—F. |
| 95 | A is A-1b, $(R^2)_n$ is 6-Cl and G is C—Cl. |
| 96 | A is A-1b, $(R^2)_n$ is 6-Br and G is C—Br. |
| 97 | A is A-1b, $(R^2)_n$ is 6-Me and G is C—Me. |
| 98 | A is A-1b, $(R^2)_n$ is 6-CF$_3$ and G is C—CF$_3$. |
| 99 | A is A-1b, $(R^2)_n$ is 6-MeO and G is C—OMe. |
| 100 | A is A-1b, $(R^2)_n$ is H and G is N. |
| 101 | A is A-1b, $(R^2)_n$ is 3-F and G is N. |
| 102 | A is A-1b, $(R^2)_n$ is 3,5-di-F and G is N. |
| 103 | A is A-1b, $(R^2)_n$ is 3-Cl and G is N. |
| 104 | A is A-1b, $(R^2)_n$ is 3,5-di-Cl and G is N. |
| 105 | A is A-1b, $(R^2)_n$ is 3-Br and G is N. |
| 106 | A is A-1b, $(R^2)_n$ is 3,5-di-Br and G is N. |
| 107 | A is A-1b, $(R^2)_n$ is 3-Me and G is N. |
| 108 | A is A-1b, $(R^2)_n$ is 3,5-di-Me and G is N. |
| 109 | A is A-1b, $(R^2)_n$ is 3-CF$_3$ and G is N. |
| 110 | A is A-1b, $(R^2)_n$ is 3,5-di-CF$_3$ and G is N. |
| 111 | A is A-1b, $(R^2)_n$ is 3-MeO and G is N. |
| 112 | A is A-1b, $(R^2)_n$ is 3,5-di-MeO and G is N. |
| 113 | A is A-1b, $(R^2)_n$ is 3-CN and G is N. |
| 114 | A is A-1b, $(R^2)_n$ is 3,5-di-CN and G is N. |
| 115 | A is A-1b, $(R^2)_n$ is 3,6-di-F and G is N. |
| 116 | A is A-1b, $(R^2)_n$ is 3,6-di-Cl and G is N. |
| 117 | A is A-1b, $(R^2)_n$ is 3,6-di-Br and G is N. |
| 118 | A is A-1b, $(R^2)_n$ is 3,6-di-Me and G is N. |
| 119 | A is A-1b, $(R^2)_n$ is 3,6-di-CF$_3$ and G is N. |
| 120 | A is A-1b, $(R^2)_n$ is 3,6-di-MeO and G is N. |
| 121 | A is A-1b, $(R^2)_n$ is 3,6-di-CN and G is N. |
| 122 | A is A-1b, $(R^2)_n$ is 6-F and G is N. |
| 123 | A is A-1b, $(R^2)_n$ is 6-Cl and G is N. |
| 124 | A is A-1b, $(R^2)_n$ is 6-Br and G is N. |
| 125 | A is A-1b, $(R^2)_n$ is 6-Me and G is N. |
| 126 | A is A-1b, $(R^2)_n$ is 6-CF$_3$ and G is N. |
| 127 | A is A-1b, $(R^2)_n$ is 6-MeO and G is N. |
| 128 | A is A-1b, $(R^2)_n$ is 6-CN and G is N. |
| 129 | A is A-1c, $(R^2)_n$ is H and G is CH. |
| 130 | A is A-1c, $(R^2)_n$ is 3-F and G is CH. |
| 131 | A is A-1c, $(R^2)_n$ is 3,5-di-F and G is CH. |
| 132 | A is A-1c, $(R^2)_n$ is 3-Cl and G is CH. |
| 133 | A is A-1c, $(R^2)_n$ is 3,5-di-Cl and G is CH. |
| 134 | A is A-1c, $(R^2)_n$ is 3-Br and G is CH. |
| 135 | A is A-1c, $(R^2)_n$ is 3,5-di-Br and G is CH. |
| 136 | A is A-1c, $(R^2)_n$ is 3-Me and G is CH. |
| 137 | A is A-1c, $(R^2)_n$ is 3,5-di-Me and G is CH. |
| 138 | A is A-1c, $(R^2)_n$ is 3-CF$_3$ and G is CH. |
| 139 | A is A-1c, $(R^2)_n$ is 3,5-di-CF$_3$ and G is CH. |
| 140 | A is A-1c, $(R^2)_n$ is 3-MeO and G is CH. |
| 141 | A is A-1c, $(R^2)_n$ is 3,5-di-MeO and G is CH. |
| 142 | A is A-1c, $(R^2)_n$ is 3-CN and G is CH. |
| 143 | A is A-1c, $(R^2)_n$ is 3,5-di-CN and G is CH. |
| 144 | A is A-1c, $(R^2)_n$ is 3,6-di-F and G is CH. |
| 145 | A is A-1c, $(R^2)_n$ is 3,6-di-Cl and G is CH. |
| 146 | A is A-1c, $(R^2)_n$ is 3,6-di-Br and G is CH. |
| 147 | A is A-1c, $(R^2)_n$ is 3,6-di-Me and G is CH. |
| 148 | A is A-1c, $(R^2)_n$ is 3,6-di-CF$_3$ and G is CH. |
| 149 | A is A-1c, $(R^2)_n$ is 3,6-di-MeO and G is CH. |
| 150 | A is A-1c, $(R^2)_n$ is 3,6-di-CN and G is CH. |
| 151 | A is A-1c, $(R^2)_n$ is 6-F and G is CH. |
| 152 | A is A-1c, $(R^2)_n$ is 6-Cl and G is CH. |
| 153 | A is A-1c, $(R^2)_n$ is 6-Br and G is CH. |
| 154 | A is A-1c, $(R^2)_n$ is 6-Me and G is CH. |
| 155 | A is A-1c, $(R^2)_n$ is 6-CF$_3$ and G is CH. |
| 156 | A is A-1c, $(R^2)_n$ is 6-MeO and G is CH. |
| 157 | A is A-1c, $(R^2)_n$ is 6-CN and G is CH. |
| 158 | A is A-1c, $(R^2)_n$ is 6-F and G is C—F. |
| 159 | A is A-1c, $(R^2)_n$ is 6-Cl and G is C—Cl. |
| 160 | A is A-1c, $(R^2)_n$ is 6-Br and G is C—Br. |
| 161 | A is A-1c, $(R^2)_n$ is 6-Me and G is C—Me. |
| 162 | A is A-1c, $(R^2)_n$ is 6-CF$_3$ and G is C—CF$_3$. |
| 163 | A is A-1c, $(R^2)_n$ is 6-MeO and G is C—OMe. |
| 164 | A is A-1c, $(R^2)_n$ is H and G is N. |
| 165 | A is A-1c, $(R^2)_n$ is 3-F and G is N. |
| 166 | A is A-1c, $(R^2)_n$ is 3,5-di-F and G is N. |
| 167 | A is A-1c, $(R^2)_n$ is 3-Cl and G is N. |
| 168 | A is A-1c, $(R^2)_n$ is 3,5-di-Cl and G is N. |
| 169 | A is A-1c, $(R^2)_n$ is 3-Br and G is N. |
| 170 | A is A-1c, $(R^2)_n$ is 3,5-di-Br and G is N. |
| 171 | A is A-1c, $(R^2)_n$ is 3-Me and G is N. |
| 172 | A is A-1c, $(R^2)_n$ is 3,5-di-Me and G is N. |
| 173 | A is A-1c, $(R^2)_n$ is 3-CF$_3$ and G is N. |
| 174 | A is A-1c, $(R^2)_n$ is 3,5-di-CF$_3$ and G is N. |
| 175 | A is A-1c, $(R^2)_n$ is 3-MeO and G is N. |
| 176 | A is A-1c, $(R^2)_n$ is 3,5-di-MeO and G is N. |
| 177 | A is A-1c, $(R^2)_n$ is 3-CN and G is N. |

TABLES 2-1728-continued

| Table | Row Heading |
|---|---|
| 178 | A is A-1c, $(R^2)_n$ is 3,5-di-CN and G is N. |
| 179 | A is A-1c, $(R^2)_n$ is 3,6-di-F and G is N. |
| 180 | A is A-1c, $(R^2)_n$ is 3,6-di-Cl and G is N. |
| 181 | A is A-1c, $(R^2)_n$ is 3,6-di-Br and G is N. |
| 182 | A is A-1c, $(R^2)_n$ is 3,6-di-Me and G is N. |
| 183 | A is A-1c, $(R^2)_n$ is 3,6-di-CF$_3$ and G is N. |
| 184 | A is A-1c, $(R^2)_n$ is 3,6-di-MeO and G is N. |
| 185 | A is A-1c, $(R^2)_n$ is 3,6-di-CN and G is N. |
| 186 | A is A-1c, $(R^2)_n$ is 6-F and G is N. |
| 187 | A is A-1c, $(R^2)_n$ is 6-Cl and G is N. |
| 188 | A is A-1c, $(R^2)_n$ is 6-Br and G is N. |
| 189 | A is A-1c, $(R^2)_n$ is 6-Me and G is N. |
| 190 | A is A-1c, $(R^2)_n$ is 6-CF$_3$ and G is N. |
| 191 | A is A-1c, $(R^2)_n$ is 6-MeO and G is N. |
| 192 | A is A-1c, $(R^2)_n$ is 6-CN and G is N. |
| 193 | A is A-1d, $(R^2)_n$ is H and G is CH. |
| 194 | A is A-1d, $(R^2)_n$ is 3-F and G is CH. |
| 195 | A is A-1d, $(R^2)_n$ is 3,5-di-F and G is CH. |
| 196 | A is A-1d, $(R^2)_n$ is 3-Cl and G is CH. |
| 197 | A is A-1d, $(R^2)_n$ is 3,5-di-Cl and G is CH. |
| 198 | A is A-1d, $(R^2)_n$ is 3-Br and G is CH. |
| 199 | A is A-1d, $(R^2)_n$ is 3,5-di-Br and G is CH. |
| 200 | A is A-1d, $(R^2)_n$ is 3-Me and G is CH. |
| 201 | A is A-1d, $(R^2)_n$ is 3,5-di-Me and G is CH. |
| 202 | A is A-1d, $(R^2)_n$ is 3-CF$_3$ and G is CH. |
| 203 | A is A-1d, $(R^2)_n$ is 3,5-di-CF$_3$ and G is CH. |
| 204 | A is A-1d, $(R^2)_n$ is 3-MeO and G is CH. |
| 205 | A is A-1d, $(R^2)_n$ is 3,5-di-MeO and G is CH. |
| 206 | A is A-1d, $(R^2)_n$ is 3-CN and G is CH. |
| 207 | A is A-1d, $(R^2)_n$ is 3,5-di-CN and G is CH. |
| 208 | A is A-1d, $(R^2)_n$ is 3,6-di-F and G is CH. |
| 209 | A is A-1d, $(R^2)_n$ is 3,6-di-Cl and G is CH. |
| 210 | A is A-1d, $(R^2)_n$ is 3,6-di-Br and G is CH. |
| 211 | A is A-1d, $(R^2)_n$ is 3,6-di-Me and G is CH. |
| 212 | A is A-1d, $(R^2)_n$ is 3,6-di-CF$_3$ and G is CH. |
| 213 | A is A-1d, $(R^2)_n$ is 3,6-di-MeO and G is CH. |
| 214 | A is A-1d, $(R^2)_n$ is 3,6-di-CN and G is CH. |
| 215 | A is A-1d, $(R^2)_n$ is 6-F and G is CH. |
| 216 | A is A-1d, $(R^2)_n$ is 6-Cl and G is CH. |
| 217 | A is A-1d, $(R^2)_n$ is 6-Br and G is CH. |
| 218 | A is A-1d, $(R^2)_n$ is 6-Me and G is CH. |
| 219 | A is A-1d, $(R^2)_n$ is 6-CF$_3$ and G is CH. |
| 220 | A is A-1d, $(R^2)_n$ is 6-MeO and G is CH. |
| 221 | A is A-1d, $(R^2)_n$ is 6-CN and G is CH. |
| 222 | A is A-1d, $(R^2)_n$ is 6-F and G is C—F. |
| 223 | A is A-1d, $(R^2)_n$ is 6-Cl and G is C—Cl. |
| 224 | A is A-1d, $(R^2)_n$ is 6-Br and G is C—Br. |
| 225 | A is A-1d, $(R^2)_n$ is 6-Me and G is C—Me. |
| 226 | A is A-1d, $(R^2)_n$ is 6-CF$_3$ and G is C—CF$_3$. |
| 227 | A is A-1d, $(R^2)_n$ is 6-MeO and G is C—OMe. |
| 228 | A is A-1d, $(R^2)_n$ is H and G is N. |
| 229 | A is A-1d, $(R^2)_n$ is 3-F and G is N. |
| 230 | A is A-1d, $(R^2)_n$ is 3,5-di-F and G is N. |
| 231 | A is A-1d, $(R^2)_n$ is 3-Cl and G is N. |
| 232 | A is A-1d, $(R^2)_n$ is 3,5-di-Cl and G is N. |
| 233 | A is A-1d, $(R^2)_n$ is 3-Br and G is N. |
| 234 | A is A-1d, $(R^2)_n$ is 3,5-di-Br and G is N. |
| 235 | A is A-1d, $(R^2)_n$ is 3-Me and G is N. |
| 236 | A is A-1d, $(R^2)_n$ is 3,5-di-Me and G is N. |
| 237 | A is A-1d, $(R^2)_n$ is 3-CF$_3$ and G is N. |
| 238 | A is A-1d, $(R^2)_n$ is 3,5-di-CF$_3$ and G is N. |
| 239 | A is A-1d, $(R^2)_n$ is 3-MeO and G is N. |
| 240 | A is A-1d, $(R^2)_n$ is 3,5-di-MeO and G is N. |
| 241 | A is A-1d, $(R^2)_n$ is 3-CN and G is N. |
| 242 | A is A-1d, $(R^2)_n$ is 3,5-di-CN and G is N. |
| 243 | A is A-1d, $(R^2)_n$ is 3,6-di-F and G is N. |
| 244 | A is A-1d, $(R^2)_n$ is 3,6-di-Cl and G is N. |
| 245 | A is A-1d, $(R^2)_n$ is 3,6-di-Br and G is N. |
| 246 | A is A-1d, $(R^2)_n$ is 3,6-di-Me and G is N. |
| 247 | A is A-1d, $(R^2)_n$ is 3,6-di-CF$_3$ and G is N. |
| 248 | A is A-1d, $(R^2)_n$ is 3,6-di-MeO and G is N. |
| 249 | A is A-1d, $(R^2)_n$ is 3,6-di-CN and G is N. |
| 250 | A is A-1d, $(R^2)_n$ is 6-F and G is N. |
| 251 | A is A-1d, $(R^2)_n$ is 6-Cl and G is N. |
| 252 | A is A-1d, $(R^2)_n$ is 6-Br and G is N. |
| 253 | A is A-1d, $(R^2)_n$ is 6-Me and G is N. |
| 254 | A is A-1d, $(R^2)_n$ is 6-CF$_3$ and G is N. |
| 255 | A is A-1d, $(R^2)_n$ is 6-MeO and G is N. |
| 256 | A is A-1d, $(R^2)_n$ is 6-CN and G is N. |
| 257 | A is A-1e, $(R^2)_n$ is H and G is CH. |
| 258 | A is A-1e, $(R^2)_n$ is 3-F and G is CH. |
| 259 | A is A-1e, $(R^2)_n$ is 3,5-di-F and G is CH. |
| 260 | A is A-1e, $(R^2)_n$ is 3-Cl and G is CH. |
| 261 | A is A-1e, $(R^2)_n$ is 3,5-di-Cl and G is CH. |
| 262 | A is A-1e, $(R^2)_n$ is 3-Br and G is CH. |
| 263 | A is A-1e, $(R^2)_n$ is 3,5-di-Br and G is CH. |
| 264 | A is A-1e, $(R^2)_n$ is 3-Me and G is CH. |
| 265 | A is A-1e, $(R^2)_n$ is 3,5-di-Me and G is CH. |
| 266 | A is A-1e, $(R^2)_n$ is 3-CF$_3$ and G is CH. |
| 267 | A is A-1e, $(R^2)_n$ is 3,5-di-CF$_3$ and G is CH. |
| 268 | A is A-1e, $(R^2)_n$ is 3-MeO and G is CH. |
| 269 | A is A-1e, $(R^2)_n$ is 3,5-di-MeO and G is CH. |
| 270 | A is A-1e, $(R^2)_n$ is 3-CN and G is CH. |
| 271 | A is A-1e, $(R^2)_n$ is 3,5-di-CN and G is CH. |
| 272 | A is A-1e, $(R^2)_n$ is 3,6-di-F and G is CH. |
| 273 | A is A-1e, $(R^2)_n$ is 3,6-di-Cl and G is CH. |
| 274 | A is A-1e, $(R^2)_n$ is 3,6-di-Br and G is CH. |
| 275 | A is A-1e, $(R^2)_n$ is 3,6-di-Me and G is CH. |
| 276 | A is A-1e, $(R^2)_n$ is 3,6-di-CF$_3$ and G is CH. |
| 277 | A is A-1e, $(R^2)_n$ is 3,6-di-MeO and G is CH. |
| 278 | A is A-1e, $(R^2)_n$ is 3,6-di-CN and G is CH. |
| 279 | A is A-1e, $(R^2)_n$ is 6-F and G is CH. |
| 280 | A is A-1e, $(R^2)_n$ is 6-Cl and G is CH. |
| 281 | A is A-1e, $(R^2)_n$ is 6-Br and G is CH. |
| 282 | A is A-1e, $(R^2)_n$ is 6-Me and G is CH. |
| 283 | A is A-1e, $(R^2)_n$ is 6-CF$_3$ and G is CH. |
| 284 | A is A-1e, $(R^2)_n$ is 6-MeO and G is CH. |
| 285 | A is A-1e, $(R^2)_n$ is 6-CN and G is CH. |
| 286 | A is A-1e, $(R^2)_n$ is 6-F and G is C—F. |
| 287 | A is A-1e, $(R^2)_n$ is 6-Cl and G is C—Cl. |
| 288 | A is A-1e, $(R^2)_n$ is 6-Br and G is C—Br. |
| 289 | A is A-1e, $(R^2)_n$ is 6-Me and G is C—Me. |
| 290 | A is A-1e, $(R^2)_n$ is 6-CF$_3$ and G is C—CF$_3$. |
| 291 | A is A-1e, $(R^2)_n$ is 6-MeO and G is C—OMe. |
| 292 | A is A-1e, $(R^2)_n$ is H and G is N. |
| 293 | A is A-1e, $(R^2)_n$ is 3-F and G is N. |
| 294 | A is A-1e, $(R^2)_n$ is 3,5-di-F and G is N. |
| 295 | A is A-1e, $(R^2)_n$ is 3-Cl and G is N. |
| 296 | A is A-1e, $(R^2)_n$ is 3,5-di-Cl and G is N. |
| 297 | A is A-1e, $(R^2)_n$ is 3-Br and G is N. |
| 298 | A is A-1e, $(R^2)_n$ is 3,5-di-Br and G is N. |
| 299 | A is A-1e, $(R^2)_n$ is 3-Me and G is N. |
| 300 | A is A-1e, $(R^2)_n$ is 3,5-di-Me and G is N. |
| 301 | A is A-1e, $(R^2)_n$ is 3-CF$_3$ and G is N. |
| 302 | A is A-1e, $(R^2)_n$ is 3,5-di-CF$_3$ and G is N. |
| 303 | A is A-1e, $(R^2)_n$ is 3-MeO and G is N. |
| 304 | A is A-1e, $(R^2)_n$ is 3,5-di-MeO and G is N. |
| 305 | A is A-1e, $(R^2)_n$ is 3-CN and G is N. |
| 306 | A is A-1e, $(R^2)_n$ is 3,5-di-CN and G is N. |
| 307 | A is A-1e, $(R^2)_n$ is 3,6-di-F and G is N. |
| 308 | A is A-1e, $(R^2)_n$ is 3,6-di-Cl and G is N. |
| 309 | A is A-1e, $(R^2)_n$ is 3,6-di-Br and G is N. |
| 310 | A is A-1e, $(R^2)_n$ is 3,6-di-Me and G is N. |
| 311 | A is A-1e, $(R^2)_n$ is 3,6-di-CF$_3$ and G is N. |
| 312 | A is A-1e, $(R^2)_n$ is 3,6-di-MeO and G is N. |
| 313 | A is A-1e, $(R^2)_n$ is 3,6-di-CN and G is N. |
| 314 | A is A-1e, $(R^2)_n$ is 6-F and G is N. |
| 315 | A is A-1e, $(R^2)_n$ is 6-Cl and G is N. |
| 316 | A is A-1e, $(R^2)_n$ is 6-Br and G is N. |
| 317 | A is A-1e, $(R^2)_n$ is 6-Me and G is N. |
| 318 | A is A-1e, $(R^2)_n$ is 6-CF$_3$ and G is N. |
| 319 | A is A-1e, $(R^2)_n$ is 6-MeO and G is N. |
| 320 | A is A-1e, $(R^2)_n$ is 6-CN and G is N. |
| 321 | A is A-1f, $(R^2)_n$ is H and G is CH. |
| 322 | A is A-1f, $(R^2)_n$ is 3-F and G is CH. |
| 323 | A is A-1f, $(R^2)_n$ is 3,5-di-F and G is CH. |
| 324 | A is A-1f, $(R^2)_n$ is 3-Cl and G is CH. |
| 325 | A is A-1f, $(R^2)_n$ is 3,5-di-Cl and G is CH. |
| 326 | A is A-1f, $(R^2)_n$ is 3-Br and G is CH. |
| 327 | A is A-1f, $(R^2)_n$ is 3,5-di-Br and G is CH. |
| 328 | A is A-1f, $(R^2)_n$ is 3-Me and G is CH. |
| 329 | A is A-1f, $(R^2)_n$ is 3,5-di-Me and G is CH. |
| 330 | A is A-1f, $(R^2)_n$ is 3-CF$_3$ and G is CH. |
| 331 | A is A-1f, $(R^2)_n$ is 3,5-di-CF$_3$ and G is CH. |
| 332 | A is A-1f, $(R^2)_n$ is 3-MeO and G is CH. |
| 333 | A is A-1f, $(R^2)_n$ is 3,5-di-MeO and G is CH. |

TABLES 2-1728-continued

| Table | Row Heading |
|---|---|
| 334 | A is A-1f, $(R^2)_n$ is 3-CN and G is CH. |
| 335 | A is A-1f, $(R^2)_n$ is 3,5-di-CN and G is CH. |
| 336 | A is A-1f, $(R^2)_n$ is 3,6-di-F and G is CH. |
| 337 | A is A-1f, $(R^2)_n$ is 3,6-di-Cl and G is CH. |
| 338 | A is A-1f, $(R^2)_n$ is 3,6-di-Br and G is CH. |
| 339 | A is A-1f, $(R^2)_n$ is 3,6-di-Me and G is CH. |
| 340 | A is A-1f, $(R^2)_n$ is 3,6-di-$CF_3$ and G is CH. |
| 341 | A is A-1f, $(R^2)_n$ is 3,6-di-MeO and G is CH. |
| 342 | A is A-1f, $(R^2)_n$ is 3,6-di-CN and G is CH. |
| 343 | A is A-1f, $(R^2)_n$ is 6-F and G is CH. |
| 344 | A is A-1f, $(R^2)_n$ is 6-Cl and G is CH. |
| 345 | A is A-1f, $(R^2)_n$ is 6-Br and G is CH. |
| 346 | A is A-1f, $(R^2)_n$ is 6-Me and G is CH. |
| 347 | A is A-1f, $(R^2)_n$ is 6-$CF_3$ and G is CH. |
| 348 | A is A-1f, $(R^2)_n$ is 6-MeO and G is CH. |
| 349 | A is A-1f, $(R^2)_n$ is 6-CN and G is CH. |
| 350 | A is A-1f, $(R^2)_n$ is 6-F and G is C—F. |
| 351 | A is A-1f, $(R^2)_n$ is 6-Cl and G is C—Cl. |
| 352 | A is A-1f, $(R^2)_n$ is 6-Br and G is C—Br. |
| 353 | A is A-1f, $(R^2)_n$ is 6-Me and G is C—Me. |
| 354 | A is A-1f, $(R^2)_n$ is 6-$CF_3$ and G is C—$CF_3$. |
| 355 | A is A-1f, $(R^2)_n$ is 6-MeO and G is C—OMe. |
| 356 | A is A-1f, $(R^2)_n$ is H and G is N. |
| 357 | A is A-1f, $(R^2)_n$ is 3-F and G is N. |
| 358 | A is A-1f, $(R^2)_n$ is 3,5-di-F and G is N. |
| 359 | A is A-1f, $(R^2)_n$ is 3-Cl and G is N. |
| 360 | A is A-1f, $(R^2)_n$ is 3,5-di-Cl and G is N. |
| 361 | A is A-1f, $(R^2)_n$ is 3-Br and G is N. |
| 362 | A is A-1f, $(R^2)_n$ is 3,5-di-Br and G is N. |
| 363 | A is A-1f, $(R^2)_n$ is 3-Me and G is N. |
| 364 | A is A-1f, $(R^2)_n$ is 3,5-di-Me and G is N. |
| 365 | A is A-1f, $(R^2)_n$ is 3-$CF_3$ and G is N. |
| 366 | A is A-1f, $(R^2)_n$ is 3,5-di-$CF_3$ and G is N. |
| 367 | A is A-1f, $(R^2)_n$ is 3-MeO and G is N. |
| 368 | A is A-1f, $(R^2)_n$ is 3,5-di-MeO and G is N. |
| 369 | A is A-1f, $(R^2)_n$ is 3-CN and G is N. |
| 370 | A is A-1f, $(R^2)_n$ is 3,5-di-CN and G is N. |
| 371 | A is A-1f, $(R^2)_n$ is 3,6-di-F and G is N. |
| 372 | A is A-1f, $(R^2)_n$ is 3,6-di-Cl and G is N. |
| 373 | A is A-1f, $(R^2)_n$ is 3,6-di-Br and G is N. |
| 374 | A is A-1f, $(R^2)_n$ is 3,6-di-Me and G is N. |
| 375 | A is A-1f, $(R^2)_n$ is 3,6-di-$CF_3$ and G is N. |
| 376 | A is A-1f, $(R^2)_n$ is 3,6-di-MeO and G is N. |
| 377 | A is A-1f, $(R^2)_n$ is 3,6-di-CN and G is N. |
| 378 | A is A-1f, $(R^2)_n$ is 6-F and G is N. |
| 379 | A is A-1f, $(R^2)_n$ is 6-Cl and G is N. |
| 380 | A is A-1f, $(R^2)_n$ is 6-Br and G is N. |
| 381 | A is A-1f, $(R^2)_n$ is 6-Me and G is N. |
| 382 | A is A-1f, $(R^2)_n$ is 6-$CF_3$ and G is N. |
| 383 | A is A-1f, $(R^2)_n$ is 6-MeO and G is N. |
| 384 | A is A-1f, $(R^2)_n$ is 6-CN and G is N. |
| 385 | A is A-1g, $(R^2)_n$ is H and G is CH. |
| 386 | A is A-1g, $(R^2)_n$ is 3-F and G is CH. |
| 387 | A is A-1g, $(R^2)_n$ is 3,5-di-F and G is CH. |
| 388 | A is A-1g, $(R^2)_n$ is 3-Cl and G is CH. |
| 389 | A is A-1g, $(R^2)_n$ is 3,5-di-Cl and G is CH. |
| 390 | A is A-1g, $(R^2)_n$ is 3-Br and G is CH. |
| 391 | A is A-1g, $(R^2)_n$ is 3,5-di-Br and G is CH. |
| 392 | A is A-1g, $(R^2)_n$ is 3-Me and G is CH. |
| 393 | A is A-1g, $(R^2)_n$ is 3,5-di-Me and G is CH. |
| 394 | A is A-1g, $(R^2)_n$ is 3-$CF_3$ and G is CH. |
| 395 | A is A-1g, $(R^2)_n$ is 3,5-di-$CF_3$ and G is CH. |
| 396 | A is A-1g, $(R^2)_n$ is 3-MeO and G is CH. |
| 397 | A is A-1g, $(R^2)_n$ is 3,5-di-MeO and G is CH. |
| 398 | A is A-1g, $(R^2)_n$ is 3-CN and G is CH. |
| 399 | A is A-1g, $(R^2)_n$ is 3,5-di-CN and G is CH. |
| 400 | A is A-1g, $(R^2)_n$ is 3,6-di-F and G is CH. |
| 401 | A is A-1g, $(R^2)_n$ is 3,6-di-Cl and G is CH. |
| 402 | A is A-1g, $(R^2)_n$ is 3,6-di-Br and G is CH. |
| 403 | A is A-1g, $(R^2)_n$ is 3,6-di-Me and G is CH. |
| 404 | A is A-1g, $(R^2)_n$ is 3,6-di-$CF_3$ and G is CH. |
| 405 | A is A-1g, $(R^2)_n$ is 3,6-di-MeO and G is CH. |
| 406 | A is A-1g, $(R^2)_n$ is 3,6-di-CN and G is CH. |
| 407 | A is A-1g, $(R^2)_n$ is 6-F and G is CH. |
| 408 | A is A-1g, $(R^2)_n$ is 6-Cl and G is CH. |
| 409 | A is A-1g, $(R^2)_n$ is 6-Br and G is CH. |
| 410 | A is A-1g, $(R^2)_n$ is 6-Me and G is CH. |
| 411 | A is A-1g, $(R^2)_n$ is 6-$CF_3$ and G is CH. |
| 412 | A is A-1g, $(R^2)_n$ is 6-MeO and G is CH. |
| 413 | A is A-1g, $(R^2)_n$ is 6-CN and G is CH. |
| 414 | A is A-1g, $(R^2)_n$ is 6-F and G is C—F. |
| 415 | A is A-1g, $(R^2)_n$ is 6-Cl and G is C—Cl. |
| 416 | A is A-1g, $(R^2)_n$ is 6-Br and G is C—Br. |
| 417 | A is A-1g, $(R^2)_n$ is 6-Me and G is C—Me. |
| 418 | A is A-1g, $(R^2)_n$ is 6-$CF_3$ and G is C—$CF_3$. |
| 419 | A is A-1g, $(R^2)_n$ is 6-MeO and G is C—OMe. |
| 420 | A is A-1g, $(R^2)_n$ is H and G is N. |
| 421 | A is A-1g, $(R^2)_n$ is 3-F and G is N. |
| 422 | A is A-1g, $(R^2)_n$ is 3,5-di-F and G is N. |
| 423 | A is A-1g, $(R^2)_n$ is 3-Cl and G is N. |
| 424 | A is A-1g, $(R^2)_n$ is 3,5-di-Cl and G is N. |
| 425 | A is A-1g, $(R^2)_n$ is 3-Br and G is N. |
| 426 | A is A-1g, $(R^2)_n$ is 3,5-di-Br and G is N. |
| 427 | A is A-1g, $(R^2)_n$ is 3-Me and G is N. |
| 428 | A is A-1g, $(R^2)_n$ is 3,5-di-Me and G is N. |
| 429 | A is A-1g, $(R^2)_n$ is 3-$CF_3$ and G is N. |
| 430 | A is A-1g, $(R^2)_n$ is 3,5-di-$CF_3$ and G is N. |
| 431 | A is A-1g, $(R^2)_n$ is 3-MeO and G is N. |
| 432 | A is A-1g, $(R^2)_n$ is 3,5-di-MeO and G is N. |
| 433 | A is A-1g, $(R^2)_n$ is 3-CN and G is N. |
| 434 | A is A-1g, $(R^2)_n$ is 3,5-di-CN and G is N. |
| 435 | A is A-1g, $(R^2)_n$ is 3,6-di-F and G is N. |
| 436 | A is A-1g, $(R^2)_n$ is 3,6-di-Cl and G is N. |
| 437 | A is A-1g, $(R^2)_n$ is 3,6-di-Br and G is N. |
| 438 | A is A-1g, $(R^2)_n$ is 3,6-di-Me and G is N. |
| 439 | A is A-1g, $(R^2)_n$ is 3,6-di-$CF_3$ and G is N. |
| 440 | A is A-1g, $(R^2)_n$ is 3,6-di-MeO and G is N. |
| 441 | A is A-1g, $(R^2)_n$ is 3,6-di-CN and G is N. |
| 442 | A is A-1g, $(R^2)_n$ is 6-F and G is N. |
| 443 | A is A-1g, $(R^2)_n$ is 6-Cl and G is N. |
| 444 | A is A-1g, $(R^2)_n$ is 6-Br and G is N. |
| 445 | A is A-1g, $(R^2)_n$ is 6-Me and G is N. |
| 446 | A is A-1g, $(R^2)_n$ is 6-$CF_3$ and G is N. |
| 447 | A is A-1g, $(R^2)_n$ is 6-MeO and G is N. |
| 448 | A is A-1g, $(R^2)_n$ is 6-CN and G is N. |
| 449 | A is A-1h, $(R^2)_n$ is H and G is CH. |
| 450 | A is A-1h, $(R^2)_n$ is 3-F and G is CH. |
| 451 | A is A-1h, $(R^2)_n$ is 3,5-di-F and G is CH. |
| 452 | A is A-1h, $(R^2)_n$ is 3-Cl and G is CH. |
| 453 | A is A-1h, $(R^2)_n$ is 3,5-di-Cl and G is CH. |
| 454 | A is A-1h, $(R^2)_n$ is 3-Br and G is CH. |
| 455 | A is A-1h, $(R^2)_n$ is 3,5-di-Br and G is CH. |
| 456 | A is A-1h, $(R^2)_n$ is 3-Me and G is CH. |
| 457 | A is A-1h, $(R^2)_n$ is 3,5-di-Me and G is CH. |
| 458 | A is A-1h, $(R^2)_n$ is 3-$CF_3$ and G is CH. |
| 459 | A is A-1h, $(R^2)_n$ is 3,5-di-$CF_3$ and G is CH. |
| 460 | A is A-1h, $(R^2)_n$ is 3-MeO and G is CH. |
| 461 | A is A-1h, $(R^2)_n$ is 3,5-di-MeO and G is CH. |
| 462 | A is A-1h, $(R^2)_n$ is 3-CN and G is CH. |
| 463 | A is A-1h, $(R^2)_n$ is 3,5-di-CN and G is CH. |
| 464 | A is A-1h, $(R^2)_n$ is 3,6-di-F and G is CH. |
| 465 | A is A-1h, $(R^2)_n$ is 3,6-di-Cl and G is CH. |
| 466 | A is A-1h, $(R^2)_n$ is 3,6-di-Br and G is CH. |
| 467 | A is A-1h, $(R^2)_n$ is 3,6-di-Me and G is CH. |
| 468 | A is A-1h, $(R^2)_n$ is 3,6-di-$CF_3$ and G is CH. |
| 469 | A is A-1h, $(R^2)_n$ is 3,6-di-MeO and G is CH. |
| 470 | A is A-1h, $(R^2)_n$ is 3,6-di-CN and G is CH. |
| 471 | A is A-1h, $(R^2)_n$ is 6-F and G is CH. |
| 472 | A is A-1h, $(R^2)_n$ is 6-Cl and G is CH. |
| 473 | A is A-1h, $(R^2)_n$ is 6-Br and G is CH. |
| 474 | A is A-1h, $(R^2)_n$ is 6-Me and G is CH. |
| 475 | A is A-1h, $(R^2)_n$ is 6-$CF_3$ and G is CH. |
| 476 | A is A-1h, $(R^2)_n$ is 6-MeO and G is CH. |
| 477 | A is A-1h, $(R^2)_n$ is 6-CN and G is CH. |
| 478 | A is A-1h, $(R^2)_n$ is 6-F and G is C—F. |
| 479 | A is A-1h, $(R^2)_n$ is 6-Cl and G is C—Cl. |
| 480 | A is A-1h, $(R^2)_n$ is 6-Br and G is C—Br. |
| 481 | A is A-1h, $(R^2)_n$ is 6-Me and G is C—Me. |
| 482 | A is A-1h, $(R^2)_n$ is 6-$CF_3$ and G is C—$CF_3$. |
| 483 | A is A-1h, $(R^2)_n$ is 6-MeO and G is C—OMe. |
| 484 | A is A-1h, $(R^2)_n$ is H and G is N. |
| 485 | A is A-1h, $(R^2)_n$ is 3-F and G is N. |
| 486 | A is A-1h, $(R^2)_n$ is 3,5-di-F and G is N. |
| 487 | A is A-1h, $(R^2)_n$ is 3-Cl and G is N. |
| 488 | A is A-1h, $(R^2)_n$ is 3,5-di-Cl and G is N. |
| 489 | A is A-1h, $(R^2)_n$ is 3-Br and G is N. |

TABLES 2-1728-continued

| Table | Row Heading |
|---|---|
| 490 | A is A-1h, $(R^2)_n$ is 3,5-di-Br and G is N. |
| 491 | A is A-1h, $(R^2)_n$ is 3-Me and G is N. |
| 492 | A is A-1h, $(R^2)_n$ is 3,5-di-Me and G is N. |
| 493 | A is A-1h, $(R^2)_n$ is 3-CF$_3$ and G is N. |
| 494 | A is A-1h, $(R^2)_n$ is 3,5-di-CF$_3$ and G is N. |
| 495 | A is A-1h, $(R^2)_n$ is 3-MeO and G is N. |
| 496 | A is A-1h, $(R^2)_n$ is 3,5-di-MeO and G is N. |
| 497 | A is A-1h, $(R^2)_n$ is 3-CN and G is N. |
| 498 | A is A-1h, $(R^2)_n$ is 3,5-di-CN and G is N. |
| 499 | A is A-1h, $(R^2)_n$ is 3,6-di-F and G is N. |
| 500 | A is A-1h, $(R^2)_n$ is 3,6-di-Cl and G is N. |
| 501 | A is A-1h, $(R^2)_n$ is 3,6-di-Br and G is N. |
| 502 | A is A-1h, $(R^2)_n$ is 3,6-di-Me and G is N. |
| 503 | A is A-1h, $(R^2)_n$ is 3,6-di-CF$_3$ and G is N. |
| 504 | A is A-1h, $(R^2)_n$ is 3,6-di-MeO and G is N. |
| 505 | A is A-1h, $(R^2)_n$ is 3,6-di-CN and G is N. |
| 506 | A is A-1h, $(R^2)_n$ is 6-F and G is N. |
| 507 | A is A-1h, $(R^2)_n$ is 6-Cl and G is N. |
| 508 | A is A-1h, $(R^2)_n$ is 6-Br and G is N. |
| 509 | A is A-1h, $(R^2)_n$ is 6-Me and G is N. |
| 510 | A is A-1h, $(R^2)_n$ is 6-CF$_3$ and G is N. |
| 511 | A is A-1h, $(R^2)_n$ is 6-MeO and G is N. |
| 512 | A is A-1h, $(R^2)_n$ is 6-CN and G is N. |
| 513 | A is A-1i, $(R^2)_n$ is H and G is CH. |
| 514 | A is A-1i, $(R^2)_n$ is 3-F and G is CH. |
| 515 | A is A-1i, $(R^2)_n$ is 3,5-di-F and G is CH. |
| 516 | A is A-1i, $(R^2)_n$ is 3-Cl and G is CH. |
| 517 | A is A-1i, $(R^2)_n$ is 3,5-di-Cl and G is CH. |
| 518 | A is A-1i, $(R^2)_n$ is 3-Br and G is CH. |
| 519 | A is A-1i, $(R^2)_n$ is 3,5-di-Br and G is CH. |
| 520 | A is A-1i, $(R^2)_n$ is 3-Me and G is CH. |
| 521 | A is A-1i, $(R^2)_n$ is 3,5-di-Me and G is CH. |
| 522 | A is A-1i, $(R^2)_n$ is 3-CF$_3$ and G is CH. |
| 523 | A is A-1i, $(R^2)_n$ is 3,5-di-CF$_3$ and G is CH. |
| 524 | A is A-1i, $(R^2)_n$ is 3-MeO and G is CH. |
| 525 | A is A-1i, $(R^2)_n$ is 3,5-di-MeO and G is CH. |
| 526 | A is A-1i, $(R^2)_n$ is 3-CN and G is CH. |
| 527 | A is A-1i, $(R^2)_n$ is 3,5-di-CN and G is CH. |
| 528 | A is A-1i, $(R^2)_n$ is 3,6-di-F and G is CH. |
| 529 | A is A-1i, $(R^2)_n$ is 3,6-di-Cl and G is CH. |
| 530 | A is A-1i, $(R^2)_n$ is 3,6-di-Br and G is CH. |
| 531 | A is A-1i, $(R^2)_n$ is 3,6-di-Me and G is CH. |
| 532 | A is A-1i, $(R^2)_n$ is 3,6-di-CF$_3$ and G is CH. |
| 533 | A is A-1i, $(R^2)_n$ is 3,6-di-MeO and G is CH. |
| 534 | A is A-1i, $(R^2)_n$ is 3,6-di-CN and G is CH. |
| 535 | A is A-1i, $(R^2)_n$ is 6-F and G is CH. |
| 536 | A is A-1i, $(R^2)_n$ is 6-Cl and G is CH. |
| 537 | A is A-1i, $(R^2)_n$ is 6-Br and G is CH. |
| 538 | A is A-1i, $(R^2)_n$ is 6-Me and G is CH. |
| 539 | A is A-1i, $(R^2)_n$ is 6-CF$_3$ and G is CH. |
| 540 | A is A-1i, $(R^2)_n$ is 6-MeO and G is CH. |
| 541 | A is A-1i, $(R^2)_n$ is 6-CN and G is CH. |
| 542 | A is A-1i, $(R^2)_n$ is 6-F and G is C—F. |
| 543 | A is A-1i, $(R^2)_n$ is 6-Cl and G is C—Cl. |
| 544 | A is A-1i, $(R^2)_n$ is 6-Br and G is C—Br. |
| 545 | A is A-1i, $(R^2)_n$ is 6-Me and G is C—Me. |
| 546 | A is A-1i, $(R^2)_n$ is 6-CF$_3$ and G is C—CF$_3$. |
| 547 | A is A-1i, $(R^2)_n$ is 6-MeO and G is C—OMe. |
| 548 | A is A-1i, $(R^2)_n$ is H and G is N. |
| 549 | A is A-1i, $(R^2)_n$ is 3-F and G is N. |
| 550 | A is A-1i, $(R^2)_n$ is 3,5-di-F and G is N. |
| 551 | A is A-1i, $(R^2)_n$ is 3-Cl and G is N. |
| 552 | A is A-1i, $(R^2)_n$ is 3,5-di-Cl and G is N. |
| 553 | A is A-1i, $(R^2)_n$ is 3-Br and G is N. |
| 554 | A is A-1i, $(R^2)_n$ is 3,5-di-Br and G is N. |
| 555 | A is A-1i, $(R^2)_n$ is 3-Me and G is N. |
| 556 | A is A-1i, $(R^2)_n$ is 3,5-di-Me and G is N. |
| 557 | A is A-1i, $(R^2)_n$ is 3-CF$_3$ and G is N. |
| 558 | A is A-1i, $(R^2)_n$ is 3,5-di-CF$_3$ and G is N. |
| 559 | A is A-1i, $(R^2)_n$ is 3-MeO and G is N. |
| 560 | A is A-1i, $(R^2)_n$ is 3,5-di-MeO and G is N. |
| 561 | A is A-1i, $(R^2)_n$ is 3-CN and G is N. |
| 562 | A is A-1i, $(R^2)_n$ is 3,5-di-CN and G is N. |
| 563 | A is A-1i, $(R^2)_n$ is 3,6-di-F and G is N. |
| 564 | A is A-1i, $(R^2)_n$ is 3,6-di-Cl and G is N. |
| 565 | A is A-1i, $(R^2)_n$ is 3,6-di-Br and G is N. |
| 566 | A is A-1i, $(R^2)_n$ is 3,6-di-Me and G is N. |
| 567 | A is A-1i, $(R^2)_n$ is 3,6-di-CF$_3$ and G is N. |
| 568 | A is A-1i, $(R^2)_n$ is 3,6-di-MeO and G is N. |
| 569 | A is A-1i, $(R^2)_n$ is 3,6-di-CN and G is N. |
| 570 | A is A-1i, $(R^2)_n$ is 6-F and G is N. |
| 571 | A is A-1i, $(R^2)_n$ is 6-Cl and G is N. |
| 572 | A is A-1i, $(R^2)_n$ is 6-Br and G is N. |
| 573 | A is A-1i, $(R^2)_n$ is 6-Me and G is N. |
| 574 | A is A-1i, $(R^2)_n$ is 6-CF$_3$ and G is N. |
| 575 | A is A-1i, $(R^2)_n$ is 6-MeO and G is N. |
| 576 | A is A-1i, $(R^2)_n$ is 6-CN and G is N. |
| 577 | A is A-1j, $(R^2)_n$ is H and G is CH. |
| 578 | A is A-1j, $(R^2)_n$ is 3-F and G is CH. |
| 579 | A is A-1j, $(R^2)_n$ is 3,5-di-F and G is CH. |
| 580 | A is A-1j, $(R^2)_n$ is 3-Cl and G is CH. |
| 581 | A is A-1j, $(R^2)_n$ is 3,5-di-Cl and G is CH. |
| 582 | A is A-1j, $(R^2)_n$ is 3-Br and G is CH. |
| 583 | A is A-1j, $(R^2)_n$ is 3,5-di-Br and G is CH. |
| 584 | A is A-1j, $(R^2)_n$ is 3-Me and G is CH. |
| 585 | A is A-1j, $(R^2)_n$ is 3,5-di-Me and G is CH. |
| 586 | A is A-1j, $(R^2)_n$ is 3-CF$_3$ and G is CH. |
| 587 | A is A-1j, $(R^2)_n$ is 3,5-di-CF$_3$ and G is CH. |
| 588 | A is A-1j, $(R^2)_n$ is 3-MeO and G is CH. |
| 589 | A is A-1j, $(R^2)_n$ is 3,5-di-MeO and G is CH. |
| 590 | A is A-1j, $(R^2)_n$ is 3-CN and G is CH. |
| 591 | A is A-1j, $(R^2)_n$ is 3,5-di-CN and G is CH. |
| 592 | A is A-1j, $(R^2)_n$ is 3,6-di-F and G is CH. |
| 593 | A is A-1j, $(R^2)_n$ is 3,6-di-Cl and G is CH. |
| 594 | A is A-1j, $(R^2)_n$ is 3,6-di-Br and G is CH. |
| 595 | A is A-1j, $(R^2)_n$ is 3,6-di-Me and G is CH. |
| 596 | A is A-1j, $(R^2)_n$ is 3,6-di-CF$_3$ and G is CH. |
| 597 | A is A-1j, $(R^2)_n$ is 3,6-di-MeO and G is CH. |
| 598 | A is A-1j, $(R^2)_n$ is 3,6-di-CN and G is CH. |
| 599 | A is A-1j, $(R^2)_n$ is 6-F and G is CH. |
| 600 | A is A-1j, $(R^2)_n$ is 6-Cl and G is CH. |
| 601 | A is A-1j, $(R^2)_n$ is 6-Br and G is CH. |
| 602 | A is A-1j, $(R^2)_n$ is 6-Me and G is CH. |
| 603 | A is A-1j, $(R^2)_n$ is 6-CF$_3$ and G is CH. |
| 604 | A is A-1j, $(R^2)_n$ is 6-MeO and G is CH. |
| 605 | A is A-1j, $(R^2)_n$ is 6-CN and G is CH. |
| 606 | A is A-1j, $(R^2)_n$ is 6-F and G is C—F. |
| 607 | A is A-1j, $(R^2)_n$ is 6-Cl and G is C—Cl. |
| 608 | A is A-1j, $(R^2)_n$ is 6-Br and G is C—Br. |
| 609 | A is A-1j, $(R^2)_n$ is 6-Me and G is C—Me. |
| 610 | A is A-1j, $(R^2)_n$ is 6-CF$_3$ and G is C—CF$_3$. |
| 611 | A is A-1j, $(R^2)_n$ is 6-MeO and G is C—OMe. |
| 612 | A is A-1j, $(R^2)_n$ is H and G is N. |
| 613 | A is A-1j, $(R^2)_n$ is 3-F and G is N. |
| 614 | A is A-1j, $(R^2)_n$ is 3,5-di-F and G is N. |
| 615 | A is A-1j, $(R^2)_n$ is 3-Cl and G is N. |
| 616 | A is A-1j, $(R^2)_n$ is 3,5-di-Cl and G is N. |
| 617 | A is A-1j, $(R^2)_n$ is 3-Br and G is N. |
| 618 | A is A-1j, $(R^2)_n$ is 3,5-di-Br and G is N. |
| 619 | A is A-1j, $(R^2)_n$ is 3-Me and G is N. |
| 620 | A is A-1j, $(R^2)_n$ is 3,5-di-Me and G is N. |
| 621 | A is A-1j, $(R^2)_n$ is 3-CF$_3$ and G is N. |
| 622 | A is A-1j, $(R^2)_n$ is 3,5-di-CF$_3$ and G is N. |
| 623 | A is A-1j, $(R^2)_n$ is 3-MeO and G is N. |
| 624 | A is A-1j, $(R^2)_n$ is 3,5-di-MeO and G is N. |
| 625 | A is A-1j, $(R^2)_n$ is 3-CN and G is N. |
| 626 | A is A-1j, $(R^2)_n$ is 3,5-di-CN and G is N. |
| 627 | A is A-1j, $(R^2)_n$ is 3,6-di-F and G is N. |
| 628 | A is A-1j, $(R^2)_n$ is 3,6-di-Cl and G is N. |
| 629 | A is A-1j, $(R^2)_n$ is 3,6-di-Br and G is N. |
| 630 | A is A-1j, $(R^2)_n$ is 3,6-di-Me and G is N. |
| 631 | A is A-1j, $(R^2)_n$ is 3,6-di-CF$_3$ and G is N. |
| 632 | A is A-1j, $(R^2)_n$ is 3,6-di-MeO and G is N. |
| 633 | A is A-1j, $(R^2)_n$ is 3,6-di-CN and G is N. |
| 634 | A is A-1j, $(R^2)_n$ is 6-F and G is N. |
| 635 | A is A-1j, $(R^2)_n$ is 6-Cl and G is N. |
| 636 | A is A-1j, $(R^2)_n$ is 6-Br and G is N. |
| 637 | A is A-1j, $(R^2)_n$ is 6-Me and G is N. |
| 638 | A is A-1j, $(R^2)_n$ is 6-CF$_3$ and G is N. |
| 639 | A is A-1j, $(R^2)_n$ is 6-MeO and G is N. |
| 640 | A is A-1j, $(R^2)_n$ is 6-CN and G is N. |
| 641 | A is A-1k, $(R^2)_n$ is H and G is CH. |
| 642 | A is A-1k, $(R^2)_n$ is 3-F and G is CH. |
| 643 | A is A-1k, $(R^2)_n$ is 3,5-di-F and G is CH. |
| 644 | A is A-1k, $(R^2)_n$ is 3-Cl and G is CH. |
| 645 | A is A-1k, $(R^2)_n$ is 3,5-di-Cl and G is CH. |

TABLES 2-1728-continued

| Table | Row Heading |
|---|---|
| 646 | A is A-1k, (R$^2$)$_n$ is 3-Br and G is CH. |
| 647 | A is A-1k, (R$^2$)$_n$ is 3,5-di-Br and G is CH. |
| 648 | A is A-1k, (R$^2$)$_n$ is 3-Me and G is CH. |
| 649 | A is A-1k, (R$^2$)$_n$ is 3,5-di-Me and G is CH. |
| 650 | A is A-1k, (R$^2$)$_n$ is 3-CF$_3$ and G is CH. |
| 651 | A is A-1k, (R$^2$)$_n$ is 3,5-di-CF$_3$ and G is CH. |
| 652 | A is A-1k, (R$^2$)$_n$ is 3-MeO and G is CH. |
| 653 | A is A-1k, (R$^2$)$_n$ is 3,5-di-MeO and G is CH. |
| 654 | A is A-1k, (R$^2$)$_n$ is 3-CN and G is CH. |
| 655 | A is A-1k, (R$^2$)$_n$ is 3,5-di-CN and G is CH. |
| 656 | A is A-1k, (R$^2$)$_n$ is 3,6-di-F and G is CH. |
| 657 | A is A-1k, (R$^2$)$_n$ is 3,6-di-Cl and G is CH. |
| 658 | A is A-1k, (R$^2$)$_n$ is 3,6-di-Br and G is CH. |
| 659 | A is A-1k, (R$^2$)$_n$ is 3,6-di-Me and G is CH. |
| 660 | A is A-1k, (R$^2$)$_n$ is 3,6-di-CF$_3$ and G is CH. |
| 661 | A is A-1k, (R$^2$)$_n$ is 3,6-di-MeO and G is CH. |
| 662 | A is A-1k, (R$^2$)$_n$ is 3,6-di-CN and G is CH. |
| 663 | A is A-1k, (R$^2$)$_n$ is 6-F and G is CH. |
| 664 | A is A-1k, (R$^2$)$_n$ is 6-Cl and G is CH. |
| 665 | A is A-1k, (R$^2$)$_n$ is 6-Br and G is CH. |
| 666 | A is A-1k, (R$^2$)$_n$ is 6-Me and G is CH. |
| 667 | A is A-1k, (R$^2$)$_n$ is 6-CF$_3$ and G is CH. |
| 668 | A is A-1k, (R$^2$)$_n$ is 6-MeO and G is CH. |
| 669 | A is A-1k, (R$^2$)$_n$ is 6-CN and G is CH. |
| 670 | A is A-1k, (R$^2$)$_n$ is 6-F and G is C—F. |
| 671 | A is A-1k, (R$^2$)$_n$ is 6-Cl and G is C—Cl. |
| 672 | A is A-1k, (R$^2$)$_n$ is 6-Br and G is C—Br. |
| 673 | A is A-1k, (R$^2$)$_n$ is 6-Me and G is C—Me. |
| 674 | A is A-1k, (R$^2$)$_n$ is 6-CF$_3$ and G is C—CF$_3$. |
| 675 | A is A-1k, (R$^2$)$_n$ is 6-MeO and G is C—OMe. |
| 676 | A is A-1k, (R$^2$)$_n$ is H and G is N. |
| 677 | A is A-1k, (R$^2$)$_n$ is 3-F and G is N. |
| 678 | A is A-1k, (R$^2$)$_n$ is 3,5-di-F and G is N. |
| 679 | A is A-1k, (R$^2$)$_n$ is 3-Cl and G is N. |
| 680 | A is A-1k, (R$^2$)$_n$ is 3,5-di-Cl and G is N. |
| 681 | A is A-1k, (R$^2$)$_n$ is 3-Br and G is N. |
| 682 | A is A-1k, (R$^2$)$_n$ is 3,5-di-Br and G is N. |
| 683 | A is A-1k, (R$^2$)$_n$ is 3-Me and G is N. |
| 684 | A is A-1k, (R$^2$)$_n$ is 3,5-di-Me and G is N. |
| 685 | A is A-1k, (R$^2$)$_n$ is 3-CF$_3$ and G is N. |
| 686 | A is A-1k, (R$^2$)$_n$ is 3,5-di-CF$_3$ and G is N. |
| 687 | A is A-1k, (R$^2$)$_n$ is 3-MeO and G is N. |
| 688 | A is A-1k, (R$^2$)$_n$ is 3,5-di-MeO and G is N. |
| 689 | A is A-1k, (R$^2$)$_n$ is 3-CN and G is N. |
| 690 | A is A-1k, (R$^2$)$_n$ is 3,5-di-CN and G is N. |
| 691 | A is A-1k, (R$^2$)$_n$ is 3,6-di-F and G is N. |
| 692 | A is A-1k, (R$^2$)$_n$ is 3,6-di-Cl and G is N. |
| 693 | A is A-1k, (R$^2$)$_n$ is 3,6-di-Br and G is N. |
| 694 | A is A-1k, (R$^2$)$_n$ is 3,6-di-Me and G is N. |
| 695 | A is A-1k, (R$^2$)$_n$ is 3,6-di-CF$_3$ and G is N. |
| 696 | A is A-1k, (R$^2$)$_n$ is 3,6-di-MeO and G is N. |
| 697 | A is A-1k, (R$^2$)$_n$ is 3,6-di-CN and G is N. |
| 698 | A is A-1k, (R$^2$)$_n$ is 6-F and G is N. |
| 699 | A is A-1k, (R$^2$)$_n$ is 6-Cl and G is N. |
| 700 | A is A-1k, (R$^2$)$_n$ is 6-Br and G is N. |
| 701 | A is A-1k, (R$^2$)$_n$ is 6-Me and G is N. |
| 702 | A is A-1k, (R$^2$)$_n$ is 6-CF$_3$ and G is N. |
| 703 | A is A-1k, (R$^2$)$_n$ is 6-MeO and G is N. |
| 704 | A is A-1k, (R$^2$)$_n$ is 6-CN and G is N. |
| 705 | A is A-1l, (R$^2$)$_n$ is H and G is CH. |
| 706 | A is A-1l, (R$^2$)$_n$ is 3-F and G is CH. |
| 707 | A is A-1l, (R$^2$)$_n$ is 3,5-di-F and G is CH. |
| 708 | A is A-1l, (R$^2$)$_n$ is 3-Cl and G is CH. |
| 709 | A is A-1l, (R$^2$)$_n$ is 3,5-di-Cl and G is CH. |
| 710 | A is A-1l, (R$^2$)$_n$ is 3-Br and G is CH. |
| 711 | A is A-1l, (R$^2$)$_n$ is 3,5-di-Br and G is CH. |
| 712 | A is A-1l, (R$^2$)$_n$ is 3-Me and G is CH. |
| 713 | A is A-1l, (R$^2$)$_n$ is 3,5-di-Me and G is CH. |
| 714 | A is A-1l, (R$^2$)$_n$ is 3-CF$_3$ and G is CH. |
| 715 | A is A-1l, (R$^2$)$_n$ is 3,5-di-CF$_3$ and G is CH. |
| 716 | A is A-1l, (R$^2$)$_n$ is 3-MeO and G is CH. |
| 717 | A is A-1l, (R$^2$)$_n$ is 3,5-di-MeO and G is CH. |
| 718 | A is A-1l, (R$^2$)$_n$ is 3-CN and G is CH. |
| 719 | A is A-1l, (R$^2$)$_n$ is 3,5-di-CN and G is CH. |
| 720 | A is A-1l, (R$^2$)$_n$ is 3,6-di-F and G is CH. |
| 721 | A is A-1l, (R$^2$)$_n$ is 3,6-di-Cl and G is CH. |
| 722 | A is A-1l, (R$^2$)$_n$ is 3,6-di-Br and G is CH. |
| 723 | A is A-1l, (R$^2$)$_n$ is 3,6-di-Me and G is CH. |
| 724 | A is A-1l, (R$^2$)$_n$ is 3,6-di-CF$_3$ and G is CH. |
| 725 | A is A-1l, (R$^2$)$_n$ is 3,6-di-MeO and G is CH. |
| 726 | A is A-1l, (R$^2$)$_n$ is 3,6-di-CN and G is CH. |
| 727 | A is A-1l, (R$^2$)$_n$ is 6-F and G is CH. |
| 728 | A is A-1l, (R$^2$)$_n$ is 6-Cl and G is CH. |
| 729 | A is A-1l, (R$^2$)$_n$ is 6-Br and G is CH. |
| 730 | A is A-1l, (R$^2$)$_n$ is 6-Me and G is CH. |
| 731 | A is A-1l, (R$^2$)$_n$ is 6-CF$_3$ and G is CH. |
| 732 | A is A-1l, (R$^2$)$_n$ is 6-MeO and G is CH. |
| 733 | A is A-1l, (R$^2$)$_n$ is 6-CN and G is CH. |
| 734 | A is A-1l, (R$^2$)$_n$ is 6-F and G is C—F. |
| 735 | A is A-1l, (R$^2$)$_n$ is 6-Cl and G is C—Cl. |
| 736 | A is A-1l, (R$^2$)$_n$ is 6-Br and G is C—Br. |
| 737 | A is A-1l, (R$^2$)$_n$ is 6-Me and G is C—Me. |
| 738 | A is A-1l, (R$^2$)$_n$ is 6-CF$_3$ and G is C—CF$_3$. |
| 739 | A is A-1l, (R$^2$)$_n$ is 6-MeO and G is C—OMe. |
| 740 | A is A-1l, (R$^2$)$_n$ is H and G is N. |
| 741 | A is A-1l, (R$^2$)$_n$ is 3-F and G is N. |
| 742 | A is A-1l, (R$^2$)$_n$ is 3,5-di-F and G is N. |
| 743 | A is A-1l, (R$^2$)$_n$ is 3-Cl and G is N. |
| 744 | A is A-1l, (R$^2$)$_n$ is 3,5-di-Cl and G is N. |
| 745 | A is A-1l, (R$^2$)$_n$ is 3-Br and G is N. |
| 746 | A is A-1l, (R$^2$)$_n$ is 3,5-di-Br and G is N. |
| 747 | A is A-1l, (R$^2$)$_n$ is 3-Me and G is N. |
| 748 | A is A-1l, (R$^2$)$_n$ is 3,5-di-Me and G is N. |
| 749 | A is A-1l, (R$^2$)$_n$ is 3-CF$_3$ and G is N. |
| 750 | A is A-1l, (R$^2$)$_n$ is 3,5-di-CF$_3$ and G is N. |
| 751 | A is A-1l, (R$^2$)$_n$ is 3-MeO and G is N. |
| 752 | A is A-1l, (R$^2$)$_n$ is 3,5-di-MeO and G is N. |
| 753 | A is A-1l, (R$^2$)$_n$ is 3-CN and G is N. |
| 754 | A is A-1l, (R$^2$)$_n$ is 3,5-di-CN and G is N. |
| 755 | A is A-1l, (R$^2$)$_n$ is 3,6-di-F and G is N. |
| 756 | A is A-1l, (R$^2$)$_n$ is 3,6-di-Cl and G is N. |
| 757 | A is A-1l, (R$^2$)$_n$ is 3,6-di-Br and G is N. |
| 758 | A is A-1l, (R$^2$)$_n$ is 3,6-di-Me and G is N. |
| 759 | A is A-1l, (R$^2$)$_n$ is 3,6-di-CF$_3$ and G is N. |
| 760 | A is A-1l, (R$^2$)$_n$ is 3,6-di-MeO and G is N. |
| 761 | A is A-1l, (R$^2$)$_n$ is 3,6-di-CN and G is N. |
| 762 | A is A-1l, (R$^2$)$_n$ is 6-F and G is N. |
| 763 | A is A-1l, (R$^2$)$_n$ is 6-Cl and G is N. |
| 764 | A is A-1l, (R$^2$)$_n$ is 6-Br and G is N. |
| 765 | A is A-1l, (R$^2$)$_n$ is 6-Me and G is N. |
| 766 | A is A-1l, (R$^2$)$_n$ is 6-CF$_3$ and G is N. |
| 767 | A is A-1l, (R$^2$)$_n$ is 6-MeO and G is N. |
| 768 | A is A-1l, (R$^2$)$_n$ is 6-CN and G is N. |
| 769 | A is A-1m, (R$^2$)$_n$ is H and G is CH. |
| 770 | A is A-1m, (R$^2$)$_n$ is 3-F and G is CH. |
| 771 | A is A-1m, (R$^2$)$_n$ is 3,5-di-F and G is CH. |
| 772 | A is A-1m, (R$^2$)$_n$ is 3-Cl and G is CH. |
| 773 | A is A-1m, (R$^2$)$_n$ is 3,5-di-Cl and G is CH. |
| 774 | A is A-1m, (R$^2$)$_n$ is 3-Br and G is CH. |
| 775 | A is A-1m, (R$^2$)$_n$ is 3,5-di-Br and G is CH. |
| 776 | A is A-1m, (R$^2$)$_n$ is 3-Me and G is CH. |
| 777 | A is A-1m, (R$^2$)$_n$ is 3,5-di-Me and G is CH. |
| 778 | A is A-1m, (R$^2$)$_n$ is 3-CF$_3$ and G is CH. |
| 779 | A is A-1m, (R$^2$)$_n$ is 3,5-di-CF$_3$ and G is CH. |
| 780 | A is A-1m, (R$^2$)$_n$ is 3-MeO and G is CH. |
| 781 | A is A-1m, (R$^2$)$_n$ is 3,5-di-MeO and G is CH. |
| 782 | A is A-1m, (R$^2$)$_n$ is 3-CN and G is CH. |
| 783 | A is A-1m, (R$^2$)$_n$ is 3,5-di-CN and G is CH. |
| 784 | A is A-1m, (R$^2$)$_n$ is 3,6-di-F and G is CH. |
| 785 | A is A-1m, (R$^2$)$_n$ is 3,6-di-Cl and G is CH. |
| 786 | A is A-1m, (R$^2$)$_n$ is 3,6-di-Br and G is CH. |
| 787 | A is A-1m, (R$^2$)$_n$ is 3,6-di-Me and G is CH. |
| 788 | A is A-1m, (R$^2$)$_n$ is 3,6-di-CF$_3$ and G is CH. |
| 789 | A is A-1m, (R$^2$)$_n$ is 3,6-di-MeO and G is CH. |
| 790 | A is A-1m, (R$^2$)$_n$ is 3,6-di-CN and G is CH. |
| 791 | A is A-1m, (R$^2$)$_n$ is 6-F and G is CH. |
| 792 | A is A-1m, (R$^2$)$_n$ is 6-Cl and G is CH. |
| 793 | A is A-1m, (R$^2$)$_n$ is 6-Br and G is CH. |
| 794 | A is A-1m, (R$^2$)$_n$ is 6-Me and G is CH. |
| 795 | A is A-1m, (R$^2$)$_n$ is 6-CF$_3$ and G is CH. |
| 796 | A is A-1m, (R$^2$)$_n$ is 6-MeO and G is CH. |
| 797 | A is A-1m, (R$^2$)$_n$ is 6-CN and G is CH. |
| 798 | A is A-1m, (R$^2$)$_n$ is 6-F and G is C—F. |
| 799 | A is A-1m, (R$^2$)$_n$ is 6-Cl and G is C—Cl. |
| 800 | A is A-1m, (R$^2$)$_n$ is 6-Br and G is C—Br. |
| 801 | A is A-1m, (R$^2$)$_n$ is 6-Me and G is C—Me. |

TABLES 2-1728-continued

| Table | Row Heading |
|---|---|
| 802 | A is A-1m, $(R^2)_n$ is 6-CF$_3$ and G is C—CF$_3$. |
| 803 | A is A-1m, $(R^2)_n$ is 6-MeO and G is C—OMe. |
| 804 | A is A-1m, $(R^2)_n$ is H and G is N. |
| 805 | A is A-1m, $(R^2)_n$ is 3-F and G is N. |
| 806 | A is A-1m, $(R^2)_n$ is 3,5-di-F and G is N. |
| 807 | A is A-1m, $(R^2)_n$ is 3-Cl and G is N. |
| 808 | A is A-1m, $(R^2)_n$ is 3,5-di-Cl and G is N. |
| 809 | A is A-1m, $(R^2)_n$ is 3-Br and G is N. |
| 810 | A is A-1m, $(R^2)_n$ is 3,5-di-Br and G is N. |
| 811 | A is A-1m, $(R^2)_n$ is 3-Me and G is N. |
| 812 | A is A-1m, $(R^2)_n$ is 3,5-di-Me and G is N. |
| 813 | A is A-1m, $(R^2)_n$ is 3-CF$_3$ and G is N. |
| 814 | A is A-1m, $(R^2)_n$ is 3,5-di-CF$_3$ and G is N. |
| 815 | A is A-1m, $(R^2)_n$ is 3-MeO and G is N. |
| 816 | A is A-1m, $(R^2)_n$ is 3,5-di-MeO and G is N. |
| 817 | A is A-1m, $(R^2)_n$ is 3-CN and G is N. |
| 818 | A is A-1m, $(R^2)_n$ is 3,5-di-CN and G is N. |
| 819 | A is A-1m, $(R^2)_n$ is 3,6-di-F and G is N. |
| 820 | A is A-1m, $(R^2)_n$ is 3,6-di-Cl and G is N. |
| 821 | A is A-1m, $(R^2)_n$ is 3,6-di-Br and G is N. |
| 822 | A is A-1m, $(R^2)_n$ is 3,6-di-Me and G is N. |
| 823 | A is A-1m, $(R^2)_n$ is 3,6-di-CF$_3$ and G is N. |
| 824 | A is A-1m, $(R^2)_n$ is 3,6-di-MeO and G is N. |
| 825 | A is A-1m, $(R^2)_n$ is 3,6-di-CN and G is N. |
| 826 | A is A-1m, $(R^2)_n$ is 6-F and G is N. |
| 827 | A is A-1m, $(R^2)_n$ is 6-Cl and G is N. |
| 828 | A is A-1m, $(R^2)_n$ is 6-Br and G is N. |
| 829 | A is A-1m, $(R^2)_n$ is 6-Me and G is N. |
| 830 | A is A-1m, $(R^2)_n$ is 6-CF$_3$ and G is N. |
| 831 | A is A-1m, $(R^2)_n$ is 6-MeO and G is N. |
| 832 | A is A-1m, $(R^2)_n$ is 6-CN and G is N. |
| 833 | A is A-1n, $(R^2)_n$ is H and G is CH. |
| 834 | A is A-1n, $(R^2)_n$ is 3-F and G is CH. |
| 835 | A is A-1n, $(R^2)_n$ is 3,5-di-F and G is CH. |
| 836 | A is A-1n, $(R^2)_n$ is 3-Cl and G is CH. |
| 837 | A is A-1n, $(R^2)_n$ is 3,5-di-Cl and G is CH. |
| 838 | A is A-1n, $(R^2)_n$ is 3-Br and G is CH. |
| 839 | A is A-1n, $(R^2)_n$ is 3,5-di-Br and G is CH. |
| 840 | A is A-1n, $(R^2)_n$ is 3-Me and G is CH. |
| 841 | A is A-1n, $(R^2)_n$ is 3,5-di-Me and G is CH. |
| 842 | A is A-1n, $(R^2)_n$ is 3-CF$_3$ and G is CH. |
| 843 | A is A-1n, $(R^2)_n$ is 3,5-di-CF$_3$ and G is CH. |
| 844 | A is A-1n, $(R^2)_n$ is 3-MeO and G is CH. |
| 845 | A is A-1n, $(R^2)_n$ is 3,5-di-MeO and G is CH. |
| 846 | A is A-1n, $(R^2)_n$ is 3-CN and G is CH. |
| 847 | A is A-1n, $(R^2)_n$ is 3,5-di-CN and G is CH. |
| 848 | A is A-1n, $(R^2)_n$ is 3,6-di-F and G is CH. |
| 849 | A is A-1n, $(R^2)_n$ is 3,6-di-Cl and G is CH. |
| 850 | A is A-1n, $(R^2)_n$ is 3,6-di-Br and G is CH. |
| 851 | A is A-1n, $(R^2)_n$ is 3,6-di-Me and G is CH. |
| 852 | A is A-1n, $(R^2)_n$ is 3,6-di-CF$_3$ and G is CH. |
| 853 | A is A-1n, $(R^2)_n$ is 3,6-di-MeO and G is CH. |
| 854 | A is A-1n, $(R^2)_n$ is 3,6-di-CN and G is CH. |
| 855 | A is A-1n, $(R^2)_n$ is 6-F and G is CH. |
| 856 | A is A-1n, $(R^2)_n$ is 6-Cl and G is CH. |
| 857 | A is A-1n, $(R^2)_n$ is 6-Br and G is CH. |
| 858 | A is A-1n, $(R^2)_n$ is 6-Me and G is CH. |
| 859 | A is A-1n, $(R^2)_n$ is 6-CF$_3$ and G is CH. |
| 860 | A is A-1n, $(R^2)_n$ is 6-MeO and G is CH. |
| 861 | A is A-1n, $(R^2)_n$ is 6-CN and G is CH. |
| 862 | A is A-1n, $(R^2)_n$ is 6-F and G is C—F. |
| 863 | A is A-1n, $(R^2)_n$ is 6-Cl and G is C—Cl. |
| 864 | A is A-1n, $(R^2)_n$ is 6-Br and G is C—Br. |
| 865 | A is A-1n, $(R^2)_n$ is 6-Me and G is C—Me. |
| 866 | A is A-1n, $(R^2)_n$ is 6-CF$_3$ and G is C—CF$_3$. |
| 867 | A is A-1n, $(R^2)_n$ is 6-MeO and G is C—OMe. |
| 868 | A is A-1n, $(R^2)_n$ is H and G is N. |
| 869 | A is A-1n, $(R^2)_n$ is 3-F and G is N. |
| 870 | A is A-1n, $(R^2)_n$ is 3,5-di-F and G is N. |
| 871 | A is A-1n, $(R^2)_n$ is 3-Cl and G is N. |
| 872 | A is A-1n, $(R^2)_n$ is 3,5-di-Cl and G is N. |
| 873 | A is A-1n, $(R^2)_n$ is 3-Br and G is N. |
| 874 | A is A-1n, $(R^2)_n$ is 3,5-di-Br and G is N. |
| 875 | A is A-1n, $(R^2)_n$ is 3-Me and G is N. |
| 876 | A is A-1n, $(R^2)_n$ is 3,5-di-Me and G is N. |
| 877 | A is A-1n, $(R^2)_n$ is 3-CF$_3$ and G is N. |
| 878 | A is A-1n, $(R^2)_n$ is 3,5-di-CF$_3$ and G is N. |
| 879 | A is A-1n, $(R^2)_n$ is 3-MeO and G is N. |
| 880 | A is A-1n, $(R^2)_n$ is 3,5-di-MeO and G is N. |
| 881 | A is A-1n, $(R^2)_n$ is 3-CN and G is N. |
| 882 | A is A-1n, $(R^2)_n$ is 3,5-di-CN and G is N. |
| 883 | A is A-1n, $(R^2)_n$ is 3,6-di-F and G is N. |
| 884 | A is A-1n, $(R^2)_n$ is 3,6-di-Cl and G is N. |
| 885 | A is A-1n, $(R^2)_n$ is 3,6-di-Br and G is N. |
| 886 | A is A-1n, $(R^2)_n$ is 3,6-di-Me and G is N. |
| 887 | A is A-1n, $(R^2)_n$ is 3,6-di-CF$_3$ and G is N. |
| 888 | A is A-1n, $(R^2)_n$ is 3,6-di-MeO and G is N. |
| 889 | A is A-1n, $(R^2)_n$ is 3,6-di-CN and G is N. |
| 890 | A is A-1n, $(R^2)_n$ is 6-F and G is N. |
| 891 | A is A-1n, $(R^2)_n$ is 6-Cl and G is N. |
| 892 | A is A-1n, $(R^2)_n$ is 6-Br and G is N. |
| 893 | A is A-1n, $(R^2)_n$ is 6-Me and G is N. |
| 894 | A is A-1n, $(R^2)_n$ is 6-CF$_3$ and G is N. |
| 895 | A is A-1n, $(R^2)_n$ is 6-MeO and G is N. |
| 896 | A is A-1n, $(R^2)_n$ is 6-CN and G is N. |
| 897 | A is A-1p, $(R^2)_n$ is H and G is CH. |
| 898 | A is A-1p, $(R^2)_n$ is 3-F and G is CH. |
| 899 | A is A-1p, $(R^2)_n$ is 3,5-di-F and G is CH. |
| 900 | A is A-1p, $(R^2)_n$ is 3-Cl and G is CH. |
| 901 | A is A-1p, $(R^2)_n$ is 3,5-di-Cl and G is CH. |
| 902 | A is A-1p, $(R^2)_n$ is 3-Br and G is CH. |
| 903 | A is A-1p, $(R^2)_n$ is 3,5-di-Br and G is CH. |
| 904 | A is A-1p, $(R^2)_n$ is 3-Me and G is CH. |
| 905 | A is A-1p, $(R^2)_n$ is 3,5-di-Me and G is CH. |
| 906 | A is A-1p, $(R^2)_n$ is 3-CF$_3$ and G is CH. |
| 907 | A is A-1p, $(R^2)_n$ is 3,5-di-CF$_3$ and G is CH. |
| 908 | A is A-1p, $(R^2)_n$ is 3-MeO and G is CH. |
| 909 | A is A-1p, $(R^2)_n$ is 3,5-di-MeO and G is CH. |
| 910 | A is A-1p, $(R^2)_n$ is 3-CN and G is CH. |
| 911 | A is A-1p, $(R^2)_n$ is 3,5-di-CN and G is CH. |
| 912 | A is A-1p, $(R^2)_n$ is 3,6-di-F and G is CH. |
| 913 | A is A-1p, $(R^2)_n$ is 3,6-di-Cl and G is CH. |
| 914 | A is A-1p, $(R^2)_n$ is 3,6-di-Br and G is CH. |
| 915 | A is A-1p, $(R^2)_n$ is 3,6-di-Me and G is CH. |
| 916 | A is A-1p, $(R^2)_n$ is 3,6-di-CF$_3$ and G is CH. |
| 917 | A is A-1p, $(R^2)_n$ is 3,6-di-MeO and G is CH. |
| 918 | A is A-1p, $(R^2)_n$ is 3,6-di-CN and G is CH. |
| 919 | A is A-1p, $(R^2)_n$ is 6-F and G is CH. |
| 920 | A is A-1p, $(R^2)_n$ is 6-Cl and G is CH. |
| 921 | A is A-1p, $(R^2)_n$ is 6-Br and G is CH. |
| 922 | A is A-1p, $(R^2)_n$ is 6-Me and G is CH. |
| 923 | A is A-1p, $(R^2)_n$ is 6-CF$_3$ and G is CH. |
| 924 | A is A-1p, $(R^2)_n$ is 6-MeO and G is CH. |
| 925 | A is A-1p, $(R^2)_n$ is 6-CN and G is CH. |
| 926 | A is A-1p, $(R^2)_n$ is 6-F and G is C—F. |
| 927 | A is A-1p, $(R^2)_n$ is 6-Cl and G is C—Cl. |
| 928 | A is A-1p, $(R^2)_n$ is 6-Br and G is C—Br. |
| 929 | A is A-1p, $(R^2)_n$ is 6-Me and G is C—Me. |
| 930 | A is A-1p, $(R^2)_n$ is 6-CF$_3$ and G is C—CF$_3$. |
| 931 | A is A-1p, $(R^2)_n$ is 6-MeO and G is C—OMe. |
| 932 | A is A-1p, $(R^2)_n$ is H and G is N. |
| 933 | A is A-1p, $(R^2)_n$ is 3-F and G is N. |
| 934 | A is A-1p, $(R^2)_n$ is 3,5-di-F and G is N. |
| 935 | A is A-1p, $(R^2)_n$ is 3-Cl and G is N. |
| 936 | A is A-1p, $(R^2)_n$ is 3,5-di-Cl and G is N. |
| 937 | A is A-1p, $(R^2)_n$ is 3-Br and G is N. |
| 938 | A is A-1p, $(R^2)_n$ is 3,5-di-Br and G is N. |
| 939 | A is A-1p, $(R^2)_n$ is 3-Me and G is N. |
| 940 | A is A-1p, $(R^2)_n$ is 3,5-di-Me and G is N. |
| 941 | A is A-1p, $(R^2)_n$ is 3-CF$_3$ and G is N. |
| 942 | A is A-1p, $(R^2)_n$ is 3,5-di-CF$_3$ and G is N. |
| 943 | A is A-1p, $(R^2)_n$ is 3-MeO and G is N. |
| 944 | A is A-1p, $(R^2)_n$ is 3,5-di-MeO and G is N. |
| 945 | A is A-1p, $(R^2)_n$ is 3-CN and G is N. |
| 946 | A is A-1p, $(R^2)_n$ is 3,5-di-CN and G is N. |
| 947 | A is A-1p, $(R^2)_n$ is 3,6-di-F and G is N. |
| 948 | A is A-1p, $(R^2)_n$ is 3,6-di-Cl and G is N. |
| 949 | A is A-1p, $(R^2)_n$ is 3,6-di-Br and G is N. |
| 950 | A is A-1p, $(R^2)_n$ is 3,6-di-Me and G is N. |
| 951 | A is A-1p, $(R^2)_n$ is 3,6-di-CF$_3$ and G is N. |
| 952 | A is A-1p, $(R^2)_n$ is 3,6-di-MeO and G is N. |
| 953 | A is A-1p, $(R^2)_n$ is 3,6-di-CN and G is N. |
| 954 | A is A-1p, $(R^2)_n$ is 6-F and G is N. |
| 955 | A is A-1p, $(R^2)_n$ is 6-Cl and G is N. |
| 956 | A is A-1p, $(R^2)_n$ is 6-Br and G is N. |
| 957 | A is A-1p, $(R^2)_n$ is 6-Me and G is N. |

TABLES 2-1728-continued

| Table | Row Heading |
|---|---|
| 958 | A is A-1p, $(R^2)_n$ is 6-CF$_3$ and G is N. |
| 959 | A is A-1p, $(R^2)_n$ is 6-MeO and G is N. |
| 960 | A is A-1p, $(R^2)_n$ is 6-CN and G is N. |
| 961 | A is A-2a, $(R^2)_n$ is H and G is CH. |
| 962 | A is A-2a, $(R^2)_n$ is 3-F and G is CH. |
| 963 | A is A-2a, $(R^2)_n$ is 3,5-di-F and G is CH. |
| 964 | A is A-2a, $(R^2)_n$ is 3-Cl and G is CH. |
| 965 | A is A-2a, $(R^2)_n$ is 3,5-di-Cl and G is CH. |
| 966 | A is A-2a, $(R^2)_n$ is 3-Br and G is CH. |
| 967 | A is A-2a, $(R^2)_n$ is 3,5-di-Br and G is CH. |
| 968 | A is A-2a, $(R^2)_n$ is 3-Me and G is CH. |
| 969 | A is A-2a, $(R^2)_n$ is 3,5-di-Me and G is CH. |
| 970 | A is A-2a, $(R^2)_n$ is 3-CF$_3$ and G is CH. |
| 971 | A is A-2a, $(R^2)_n$ is 3,5-di-CF$_3$ and G is CH. |
| 972 | A is A-2a, $(R^2)_n$ is 3-MeO and G is CH. |
| 973 | A is A-2a, $(R^2)_n$ is 3,5-di-MeO and G is CH. |
| 974 | A is A-2a, $(R^2)_n$ is 3-CN and G is CH. |
| 975 | A is A-2a, $(R^2)_n$ is 3,5-di-CN and G is CH. |
| 976 | A is A-2a, $(R^2)_n$ is 3,6-di-F and G is CH. |
| 977 | A is A-2a, $(R^2)_n$ is 3,6-di-Cl and G is CH. |
| 978 | A is A-2a, $(R^2)_n$ is 3,6-di-Br and G is CH. |
| 979 | A is A-2a, $(R^2)_n$ is 3,6-di-Me and G is CH. |
| 980 | A is A-2a, $(R^2)_n$ is 3,6-di-CF$_3$ and G is CH. |
| 981 | A is A-2a, $(R^2)_n$ is 3,6-di-MeO and G is CH. |
| 982 | A is A-2a, $(R^2)_n$ is 3,6-di-CN and G is CH. |
| 983 | A is A-2a, $(R^2)_n$ is 6-F and G is CH. |
| 984 | A is A-2a, $(R^2)_n$ is 6-Cl and G is CH. |
| 985 | A is A-2a, $(R^2)_n$ is 6-Br and G is CH. |
| 986 | A is A-2a, $(R^2)_n$ is 6-Me and G is CH. |
| 987 | A is A-2a, $(R^2)_n$ is 6-CF$_3$ and G is CH. |
| 988 | A is A-2a, $(R^2)_n$ is 6-MeO and G is CH. |
| 989 | A is A-2a, $(R^2)_n$ is 6-CN and G is CH. |
| 990 | A is A-2a, $(R^2)_n$ is 6-F and G is C—F. |
| 991 | A is A-2a, $(R^2)_n$ is 6-Cl and G is C—Cl. |
| 992 | A is A-2a, $(R^2)_n$ is 6-Br and G is C—Br. |
| 993 | A is A-2a, $(R^2)_n$ is 6-Me and G is C—Me. |
| 994 | A is A-2a, $(R^2)_n$ is 6-CF$_3$ and G is C—CF$_3$. |
| 995 | A is A-2a, $(R^2)_n$ is 6-MeO and G is C—OMe. |
| 996 | A is A-2a, $(R^2)_n$ is H and G is N. |
| 997 | A is A-2a, $(R^2)_n$ is 3-F and G is N. |
| 998 | A is A-2a, $(R^2)_n$ is 3,5-di-F and G is N. |
| 999 | A is A-2a, $(R^2)_n$ is 3-Cl and G is N. |
| 1000 | A is A-2a, $(R^2)_n$ is 3,5-di-Cl and G is N. |
| 1001 | A is A-2a, $(R^2)_n$ is 3-Br and G is N. |
| 1002 | A is A-2a, $(R^2)_n$ is 3,5-di-Br and G is N. |
| 1003 | A is A-2a, $(R^2)_n$ is 3-Me and G is N. |
| 1004 | A is A-2a, $(R^2)_n$ is 3,5-di-Me and G is N. |
| 1005 | A is A-2a, $(R^2)_n$ is 3-CF$_3$ and G is N. |
| 1006 | A is A-2a, $(R^2)_n$ is 3,5-di-CF$_3$ and G is N. |
| 1007 | A is A-2a, $(R^2)_n$ is 3-MeO and G is N. |
| 1008 | A is A-2a, $(R^2)_n$ is 3,5-di-MeO and G is N. |
| 1009 | A is A-2a, $(R^2)_n$ is 3-CN and G is N. |
| 1010 | A is A-2a, $(R^2)_n$ is 3,5-di-CN and G is N. |
| 1011 | A is A-2a, $(R^2)_n$ is 3,6-di-F and G is N. |
| 1012 | A is A-2a, $(R^2)_n$ is 3,6-di-Cl and G is N. |
| 1013 | A is A-2a, $(R^2)_n$ is 3,6-di-Br and G is N. |
| 1014 | A is A-2a, $(R^2)_n$ is 3,6-di-Me and G is N. |
| 1015 | A is A-2a, $(R^2)_n$ is 3,6-di-CF$_3$ and G is N. |
| 1016 | A is A-2a, $(R^2)_n$ is 3,6-di-MeO and G is N. |
| 1017 | A is A-2a, $(R^2)_n$ is 3,6-di-CN and G is N. |
| 1018 | A is A-2a, $(R^2)_n$ is 6-F and G is N. |
| 1019 | A is A-2a, $(R^2)_n$ is 6-Cl and G is N. |
| 1020 | A is A-2a, $(R^2)_n$ is 6-Br and G is N. |
| 1021 | A is A-2a, $(R^2)_n$ is 6-Me and G is N. |
| 1022 | A is A-2a, $(R^2)_n$ is 6-CF$_3$ and G is N. |
| 1023 | A is A-2a, $(R^2)_n$ is 6-MeO and G is N. |
| 1024 | A is A-2a, $(R^2)_n$ is 6-CN and G is N. |
| 1025 | A is A-2b, $(R^2)_n$ is H and G is CH. |
| 1026 | A is A-2b, $(R^2)_n$ is 3-F and G is CH. |
| 1027 | A is A-2b, $(R^2)_n$ is 3,5-di-F and G is CH. |
| 1028 | A is A-2b, $(R^2)_n$ is 3-Cl and G is CH. |
| 1029 | A is A-2b, $(R^2)_n$ is 3,5-di-Cl and G is CH. |
| 1030 | A is A-2b, $(R^2)_n$ is 3-Br and G is CH. |
| 1031 | A is A-2b, $(R^2)_n$ is 3,5-di-Br and G is CH. |
| 1032 | A is A-2b, $(R^2)_n$ is 3-Me and G is CH. |
| 1033 | A is A-2b, $(R^2)_n$ is 3,5-di-Me and G is CH. |
| 1034 | A is A-2b, $(R^2)_n$ is 3-CF$_3$ and G is CH. |
| 1035 | A is A-2b, $(R^2)_n$ is 3,5-di-CF$_3$ and G is CH. |
| 1036 | A is A-2b, $(R^2)_n$ is 3-MeO and G is CH. |
| 1037 | A is A-2b, $(R^2)_n$ is 3,5-di-MeO and G is CH. |
| 1038 | A is A-2b, $(R^2)_n$ is 3-CN and G is CH. |
| 1039 | A is A-2b, $(R^2)_n$ is 3,5-di-CN and G is CH. |
| 1040 | A is A-2b, $(R^2)_n$ is 3,6-di-F and G is CH. |
| 1041 | A is A-2b, $(R^2)_n$ is 3,6-di-Cl and G is CH. |
| 1042 | A is A-2b, $(R^2)_n$ is 3,6-di-Br and G is CH. |
| 1043 | A is A-2b, $(R^2)_n$ is 3,6-di-Me and G is CH. |
| 1044 | A is A-2b, $(R^2)_n$ is 3,6-di-CF$_3$ and G is CH. |
| 1045 | A is A-2b, $(R^2)_n$ is 3,6-di-MeO and G is CH. |
| 1046 | A is A-2b, $(R^2)_n$ is 3,6-di-CN and G is CH. |
| 1047 | A is A-2b, $(R^2)_n$ is 6-F and G is CH. |
| 1048 | A is A-2b, $(R^2)_n$ is 6-Cl and G is CH. |
| 1049 | A is A-2b, $(R^2)_n$ is 6-Br and G is CH. |
| 1050 | A is A-2b, $(R^2)_n$ is 6-Me and G is CH. |
| 1051 | A is A-2b, $(R^2)_n$ is 6-CF$_3$ and G is CH. |
| 1052 | A is A-2b, $(R^2)_n$ is 6-MeO and G is CH. |
| 1053 | A is A-2b, $(R^2)_n$ is 6-CN and G is CH. |
| 1054 | A is A-2b, $(R^2)_n$ is 6-F and G is C—F. |
| 1055 | A is A-2b, $(R^2)_n$ is 6-Cl and G is C—Cl. |
| 1056 | A is A-2b, $(R^2)_n$ is 6-Br and G is C—Br. |
| 1057 | A is A-2b, $(R^2)_n$ is 6-Me and G is C—Me. |
| 1058 | A is A-2b, $(R^2)_n$ is 6-CF$_3$ and G is C—CF$_3$. |
| 1059 | A is A-2b, $(R^2)_n$ is 6-MeO and G is C—OMe. |
| 1060 | A is A-2b, $(R^2)_n$ is H and G is N. |
| 1061 | A is A-2b, $(R^2)_n$ is 3-F and G is N. |
| 1062 | A is A-2b, $(R^2)_n$ is 3,5-di-F and G is N. |
| 1063 | A is A-2b, $(R^2)_n$ is 3-Cl and G is N. |
| 1064 | A is A-2b, $(R^2)_n$ is 3,5-di-Cl and G is N. |
| 1065 | A is A-2b, $(R^2)_n$ is 3-Br and G is N. |
| 1066 | A is A-2b, $(R^2)_n$ is 3,5-di-Br and G is N. |
| 1067 | A is A-2b, $(R^2)_n$ is 3-Me and G is N. |
| 1068 | A is A-2b, $(R^2)_n$ is 3,5-di-Me and G is N. |
| 1069 | A is A-2b, $(R^2)_n$ is 3-CF$_3$ and G is N. |
| 1070 | A is A-2b, $(R^2)_n$ is 3,5-di-CF$_3$ and G is N. |
| 1071 | A is A-2b, $(R^2)_n$ is 3-MeO and G is N. |
| 1072 | A is A-2b, $(R^2)_n$ is 3,5-di-MeO and G is N. |
| 1073 | A is A-2b, $(R^2)_n$ is 3-CN and G is N. |
| 1074 | A is A-2b, $(R^2)_n$ is 3,5-di-CN and G is N. |
| 1075 | A is A-2b, $(R^2)_n$ is 3,6-di-F and G is N. |
| 1076 | A is A-2b, $(R^2)_n$ is 3,6-di-Cl and G is N. |
| 1077 | A is A-2b, $(R^2)_n$ is 3,6-di-Br and G is N. |
| 1078 | A is A-2b, $(R^2)_n$ is 3,6-di-Me and G is N. |
| 1079 | A is A-2b, $(R^2)_n$ is 3,6-di-CF$_3$ and G is N. |
| 1080 | A is A-2b, $(R^2)_n$ is 3,6-di-MeO and G is N. |
| 1081 | A is A-2b, $(R^2)_n$ is 3,6-di-CN and G is N. |
| 1082 | A is A-2b, $(R^2)_n$ is 6-F and G is N. |
| 1083 | A is A-2b, $(R^2)_n$ is 6-Cl and G is N. |
| 1084 | A is A-2b, $(R^2)_n$ is 6-Br and G is N. |
| 1085 | A is A-2b, $(R^2)_n$ is 6-Me and G is N. |
| 1086 | A is A-2b, $(R^2)_n$ is 6-CF$_3$ and G is N. |
| 1087 | A is A-2b, $(R^2)_n$ is 6-MeO and G is N. |
| 1088 | A is A-2b, $(R^2)_n$ is 6-CN and G is N. |
| 1089 | A is A-2c, $(R^2)_n$ is H and G is CH. |
| 1090 | A is A-2c, $(R^2)_n$ is 3-F and G is CH. |
| 1091 | A is A-2c, $(R^2)_n$ is 3,5-di-F and G is CH. |
| 1092 | A is A-2c, $(R^2)_n$ is 3-Cl and G is CH. |
| 1093 | A is A-2c, $(R^2)_n$ is 3,5-di-Cl and G is CH. |
| 1094 | A is A-2c, $(R^2)_n$ is 3-Br and G is CH. |
| 1095 | A is A-2c, $(R^2)_n$ is 3,5-di-Br and G is CH. |
| 1096 | A is A-2c, $(R^2)_n$ is 3-Me and G is CH. |
| 1097 | A is A-2c, $(R^2)_n$ is 3,5-di-Me and G is CH. |
| 1098 | A is A-2c, $(R^2)_n$ is 3-CF$_3$ and G is CH. |
| 1099 | A is A-2c, $(R^2)_n$ is 3,5-di-CF$_3$ and G is CH. |
| 1100 | A is A-2c, $(R^2)_n$ is 3-MeO and G is CH. |
| 1101 | A is A-2c, $(R^2)_n$ is 3,5-di-MeO and G is CH. |
| 1102 | A is A-2c, $(R^2)_n$ is 3-CN and G is CH. |
| 1103 | A is A-2c, $(R^2)_n$ is 3,5-di-CN and G is CH. |
| 1104 | A is A-2c, $(R^2)_n$ is 3,6-di-F and G is CH. |
| 1105 | A is A-2c, $(R^2)_n$ is 3,6-di-Cl and G is CH. |
| 1106 | A is A-2c, $(R^2)_n$ is 3,6-di-Br and G is CH. |
| 1107 | A is A-2c, $(R^2)_n$ is 3,6-di-Me and G is CH. |
| 1108 | A is A-2c, $(R^2)_n$ is 3,6-di-CF$_3$ and G is CH. |
| 1109 | A is A-2c, $(R^2)_n$ is 3,6-di-MeO and G is CH. |
| 1110 | A is A-2c, $(R^2)_n$ is 3,6-di-CN and G is CH. |
| 1111 | A is A-2c, $(R^2)_n$ is 6-F and G is CH. |
| 1112 | A is A-2c, $(R^2)_n$ is 6-Cl and G is CH. |
| 1113 | A is A-2c, $(R^2)_n$ is 6-Br and G is CH. |

TABLES 2-1728-continued

| Table | Row Heading |
|---|---|
| 1114 | A is A-2c, $(R^2)_n$ is 6-Me and G is CH. |
| 1115 | A is A-2c, $(R^2)_n$ is 6-CF$_3$ and G is CH. |
| 1116 | A is A-2c, $(R^2)_n$ is 6-MeO and G is CH. |
| 1117 | A is A-2c, $(R^2)_n$ is 6-CN and G is CH. |
| 1118 | A is A-2c, $(R^2)_n$ is 6-F and G is C—F. |
| 1119 | A is A-2c, $(R^2)_n$ is 6-Cl and G is C—Cl. |
| 1120 | A is A-2c, $(R^2)_n$ is 6-Br and G is C—Br. |
| 1121 | A is A-2c, $(R^2)_n$ is 6-Me and G is C—Me. |
| 1122 | A is A-2c, $(R^2)_n$ is 6-CF$_3$ and G is C—CF$_3$. |
| 1123 | A is A-2c, $(R^2)_n$ is 6-MeO and G is C—OMe. |
| 1124 | A is A-2c, $(R^2)_n$ is H and G is N. |
| 1125 | A is A-2c, $(R^2)_n$ is 3-F and G is N. |
| 1126 | A is A-2c, $(R^2)_n$ is 3,5-di-F and G is N. |
| 1127 | A is A-2c, $(R^2)_n$ is 3-Cl and G is N. |
| 1128 | A is A-2c, $(R^2)_n$ is 3,5-di-Cl and G is N. |
| 1129 | A is A-2c, $(R^2)_n$ is 3-Br and G is N. |
| 1130 | A is A-2c, $(R^2)_n$ is 3,5-di-Br and G is N. |
| 1131 | A is A-2c, $(R^2)_n$ is 3-Me and G is N. |
| 1132 | A is A-2c, $(R^2)_n$ is 3,5-di-Me and G is N. |
| 1133 | A is A-2c, $(R^2)_n$ is 3-CF$_3$ and G is N. |
| 1134 | A is A-2c, $(R^2)_n$ is 3,5-di-CF$_3$ and G is N. |
| 1135 | A is A-2c, $(R^2)_n$ is 3-MeO and G is N. |
| 1136 | A is A-2c, $(R^2)_n$ is 3,5-di-MeO and G is N. |
| 1137 | A is A-2c, $(R^2)_n$ is 3-CN and G is N. |
| 1138 | A is A-2c, $(R^2)_n$ is 3,5-di-CN and G is N. |
| 1139 | A is A-2c, $(R^2)_n$ is 3,6-di-F and G is N. |
| 1140 | A is A-2c, $(R^2)_n$ is 3,6-di-Cl and G is N. |
| 1141 | A is A-2c, $(R^2)_n$ is 3,6-di-Br and G is N. |
| 1142 | A is A-2c, $(R^2)_n$ is 3,6-di-Me and G is N. |
| 1143 | A is A-2c, $(R^2)_n$ is 3,6-di-CF$_3$ and G is N. |
| 1144 | A is A-2c, $(R^2)_n$ is 3,6-di-MeO and G is N. |
| 1145 | A is A-2c, $(R^2)_n$ is 3,6-di-CN and G is N. |
| 1146 | A is A-2c, $(R^2)_n$ is 6-F and G is N. |
| 1147 | A is A-2c, $(R^2)_n$ is 6-Cl and G is N. |
| 1148 | A is A-2c, $(R^2)_n$ is 6-Br and G is N. |
| 1149 | A is A-2c, $(R^2)_n$ is 6-Me and G is N. |
| 1150 | A is A-2c, $(R^2)_n$ is 6-CF$_3$ and G is N. |
| 1151 | A is A-2c, $(R^2)_n$ is 6-MeO and G is N. |
| 1152 | A is A-2c, $(R^2)_n$ is 6-CN and G is N. |
| 1153 | A is A-2d, $(R^2)_n$ is H and G is CH. |
| 1154 | A is A-2d, $(R^2)_n$ is 3-F and G is CH. |
| 1155 | A is A-2d, $(R^2)_n$ is 3,5-di-F and G is CH. |
| 1156 | A is A-2d, $(R^2)_n$ is 3-Cl and G is CH. |
| 1157 | A is A-2d, $(R^2)_n$ is 3,5-di-Cl and G is CH. |
| 1158 | A is A-2d, $(R^2)_n$ is 3-Br and G is CH. |
| 1159 | A is A-2d, $(R^2)_n$ is 3,5-di-Br and G is CH. |
| 1160 | A is A-2d, $(R^2)_n$ is 3-Me and G is CH. |
| 1161 | A is A-2d, $(R^2)_n$ is 3,5-di-Me and G is CH. |
| 1162 | A is A-2d, $(R^2)_n$ is 3-CF$_3$ and G is CH. |
| 1163 | A is A-2d, $(R^2)_n$ is 3,5-di-CF$_3$ and G is CH. |
| 1164 | A is A-2d, $(R^2)_n$ is 3-MeO and G is CH. |
| 1165 | A is A-2d, $(R^2)_n$ is 3,5-di-MeO and G is CH. |
| 1166 | A is A-2d, $(R^2)_n$ is 3-CN and G is CH. |
| 1167 | A is A-2d, $(R^2)_n$ is 3,5-di-CN and G is CH. |
| 1168 | A is A-2d, $(R^2)_n$ is 3,6-di-F and G is CH. |
| 1169 | A is A-2d, $(R^2)_n$ is 3,6-di-Cl and G is CH. |
| 1170 | A is A-2d, $(R^2)_n$ is 3,6-di-Br and G is CH. |
| 1171 | A is A-2d, $(R^2)_n$ is 3,6-di-Me and G is CH. |
| 1172 | A is A-2d, $(R^2)_n$ is 3,6-di-CF$_3$ and G is CH. |
| 1173 | A is A-2d, $(R^2)_n$ is 3,6-di-MeO and G is CH. |
| 1174 | A is A-2d, $(R^2)_n$ is 3,6-di-CN and G is CH. |
| 1175 | A is A-2d, $(R^2)_n$ is 6-F and G is CH. |
| 1176 | A is A-2d, $(R^2)_n$ is 6-Cl and G is CH. |
| 1177 | A is A-2d, $(R^2)_n$ is 6-Br and G is CH. |
| 1178 | A is A-2d, $(R^2)_n$ is 6-Me and G is CH. |
| 1179 | A is A-2d, $(R^2)_n$ is 6-CF$_3$ and G is CH. |
| 1180 | A is A-2d, $(R^2)_n$ is 6-MeO and G is CH. |
| 1181 | A is A-2d, $(R^2)_n$ is 6-CN and G is CH. |
| 1182 | A is A-2d, $(R^2)_n$ is 6-F and G is C—F. |
| 1183 | A is A-2d, $(R^2)_n$ is 6-Cl and G is C—Cl. |
| 1184 | A is A-2d, $(R^2)_n$ is 6-Br and G is C—Br. |
| 1185 | A is A-2d, $(R^2)_n$ is 6-Me and G is C—Me. |
| 1186 | A is A-2d, $(R^2)_n$ is 6-CF$_3$ and G is C—CF$_3$. |
| 1187 | A is A-2d, $(R^2)_n$ is 6-MeO and G is C—OMe. |
| 1188 | A is A-2d, $(R^2)_n$ is H and G is N. |
| 1189 | A is A-2d, $(R^2)_n$ is 3-F and G is N. |
| 1190 | A is A-2d, $(R^2)_n$ is 3,5-di-F and G is N. |
| 1191 | A is A-2d, $(R^2)_n$ is 3-Cl and G is N. |
| 1192 | A is A-2d, $(R^2)_n$ is 3,5-di-Cl and G is N. |
| 1193 | A is A-2d, $(R^2)_n$ is 3-Br and G is N. |
| 1194 | A is A-2d, $(R^2)_n$ is 3,5-di-Br and G is N. |
| 1195 | A is A-2d, $(R^2)_n$ is 3-Me and G is N. |
| 1196 | A is A-2d, $(R^2)_n$ is 3,5-di-Me and G is N. |
| 1197 | A is A-2d, $(R^2)_n$ is 3-CF$_3$ and G is N. |
| 1198 | A is A-2d, $(R^2)_n$ is 3,5-di-CF$_3$ and G is N. |
| 1199 | A is A-2d, $(R^2)_n$ is 3-MeO and G is N. |
| 1200 | A is A-2d, $(R^2)_n$ is 3,5-di-MeO and G is N. |
| 1201 | A is A-2d, $(R^2)_n$ is 3-CN and G is N. |
| 1202 | A is A-2d, $(R^2)_n$ is 3,5-di-CN and G is N. |
| 1203 | A is A-2d, $(R^2)_n$ is 3,6-di-F and G is N. |
| 1204 | A is A-2d, $(R^2)_n$ is 3,6-di-Cl and G is N. |
| 1205 | A is A-2d, $(R^2)_n$ is 3,6-di-Br and G is N. |
| 1206 | A is A-2d, $(R^2)_n$ is 3,6-di-Me and G is N. |
| 1207 | A is A-2d, $(R^2)_n$ is 3,6-di-CF$_3$ and G is N. |
| 1208 | A is A-2d, $(R^2)_n$ is 3,6-di-MeO and G is N. |
| 1209 | A is A-2d, $(R^2)_n$ is 3,6-di-CN and G is N. |
| 1210 | A is A-2d, $(R^2)_n$ is 6-F and G is N. |
| 1211 | A is A-2d, $(R^2)_n$ is 6-Cl and G is N. |
| 1212 | A is A-2d, $(R^2)_n$ is 6-Br and G is N. |
| 1213 | A is A-2d, $(R^2)_n$ is 6-Me and G is N. |
| 1214 | A is A-2d, $(R^2)_n$ is 6-CF$_3$ and G is N. |
| 1215 | A is A-2d, $(R^2)_n$ is 6-MeO and G is N. |
| 1216 | A is A-2d, $(R^2)_n$ is 6-CN and G is N. |
| 1217 | A is A-2e, $(R^2)_n$ is H and G is CH. |
| 1218 | A is A-2e, $(R^2)_n$ is 3-F and G is CH. |
| 1219 | A is A-2e, $(R^2)_n$ is 3,5-di-F and G is CH. |
| 1220 | A is A-2e, $(R^2)_n$ is 3-Cl and G is CH. |
| 1221 | A is A-2e, $(R^2)_n$ is 3,5-di-Cl and G is CH. |
| 1222 | A is A-2e, $(R^2)_n$ is 3-Br and G is CH. |
| 1223 | A is A-2e, $(R^2)_n$ is 3,5-di-Br and G is CH. |
| 1224 | A is A-2e, $(R^2)_n$ is 3-Me and G is CH. |
| 1225 | A is A-2e, $(R^2)_n$ is 3,5-di-Me and G is CH. |
| 1226 | A is A-2e, $(R^2)_n$ is 3-CF$_3$ and G is CH. |
| 1227 | A is A-2e, $(R^2)_n$ is 3,5-di-CF$_3$ and G is CH. |
| 1228 | A is A-2e, $(R^2)_n$ is 3-MeO and G is CH. |
| 1229 | A is A-2e, $(R^2)_n$ is 3,5-di-MeO and G is CH. |
| 1230 | A is A-2e, $(R^2)_n$ is 3-CN and G is CH. |
| 1231 | A is A-2e, $(R^2)_n$ is 3,5-di-CN and G is CH. |
| 1232 | A is A-2e, $(R^2)_n$ is 3,6-di-F and G is CH. |
| 1233 | A is A-2e, $(R^2)_n$ is 3,6-di-Cl and G is CH. |
| 1234 | A is A-2e, $(R^2)_n$ is 3,6-di-Br and G is CH. |
| 1235 | A is A-2e, $(R^2)_n$ is 3,6-di-Me and G is CH. |
| 1236 | A is A-2e, $(R^2)_n$ is 3,6-di-CF$_3$ and G is CH. |
| 1237 | A is A-2e, $(R^2)_n$ is 3,6-di-MeO and G is CH. |
| 1238 | A is A-2e, $(R^2)_n$ is 3,6-di-CN and G is CH. |
| 1239 | A is A-2e, $(R^2)_n$ is 6-F and G is CH. |
| 1240 | A is A-2e, $(R^2)_n$ is 6-Cl and G is CH. |
| 1241 | A is A-2e, $(R^2)_n$ is 6-Br and G is CH. |
| 1242 | A is A-2e, $(R^2)_n$ is 6-Me and G is CH. |
| 1243 | A is A-2e, $(R^2)_n$ is 6-CF$_3$ and G is CH. |
| 1244 | A is A-2e, $(R^2)_n$ is 6-MeO and G is CH. |
| 1245 | A is A-2e, $(R^2)_n$ is 6-CN and G is CH. |
| 1246 | A is A-2e, $(R^2)_n$ is 6-F and G is C—F. |
| 1247 | A is A-2e, $(R^2)_n$ is 6-Cl and G is C—Cl. |
| 1248 | A is A-2e, $(R^2)_n$ is 6-Br and G is C—Br. |
| 1249 | A is A-2e, $(R^2)_n$ is 6-Me and G is C—Me. |
| 1250 | A is A-2e, $(R^2)_n$ is 6-CF$_3$ and G is C—CF$_3$. |
| 1251 | A is A-2e, $(R^2)_n$ is 6-MeO and G is C—OMe. |
| 1252 | A is A-2e, $(R^2)_n$ is H and G is N. |
| 1253 | A is A-2e, $(R^2)_n$ is 3-F and G is N. |
| 1254 | A is A-2e, $(R^2)_n$ is 3,5-di-F and G is N. |
| 1255 | A is A-2e, $(R^2)_n$ is 3-Cl and G is N. |
| 1256 | A is A-2e, $(R^2)_n$ is 3,5-di-Cl and G is N. |
| 1257 | A is A-2e, $(R^2)_n$ is 3-Br and G is N. |
| 1258 | A is A-2e, $(R^2)_n$ is 3,5-di-Br and G is N. |
| 1259 | A is A-2e, $(R^2)_n$ is 3-Me and G is N. |
| 1260 | A is A-2e, $(R^2)_n$ is 3,5-di-Me and G is N. |
| 1261 | A is A-2e, $(R^2)_n$ is 3-CF$_3$ and G is N. |
| 1262 | A is A-2e, $(R^2)_n$ is 3,5-di-CF$_3$ and G is N. |
| 1263 | A is A-2e, $(R^2)_n$ is 3-MeO and G is N. |
| 1264 | A is A-2e, $(R^2)_n$ is 3,5-di-MeO and G is N. |
| 1265 | A is A-2e, $(R^2)_n$ is 3-CN and G is N. |
| 1266 | A is A-2e, $(R^2)_n$ is 3,5-di-CN and G is N. |
| 1267 | A is A-2e, $(R^2)_n$ is 3,6-di-F and G is N. |
| 1268 | A is A-2e, $(R^2)_n$ is 3,6-di-Cl and G is N. |
| 1269 | A is A-2e, $(R^2)_n$ is 3,6-di-Br and G is N. |

TABLES 2-1728-continued

| Table | Row Heading |
|---|---|
| 1270 | A is A-2e, $(R^2)_n$ is 3,6-di-Me and G is N. |
| 1271 | A is A-2e, $(R^2)_n$ is 3,6-di-CF$_3$ and G is N. |
| 1272 | A is A-2e, $(R^2)_n$ is 3,6-di-MeO and G is N. |
| 1273 | A is A-2e, $(R^2)_n$ is 3,6-di-CN and G is N. |
| 1274 | A is A-2e, $(R^2)_n$ is 6-F and G is N. |
| 1275 | A is A-2e, $(R^2)_n$ is 6-Cl and G is N. |
| 1276 | A is A-2e, $(R^2)_n$ is 6-Br and G is N. |
| 1277 | A is A-2e, $(R^2)_n$ is 6-Me and G is N. |
| 1278 | A is A-2e, $(R^2)_n$ is 6-CF$_3$ and G is N. |
| 1279 | A is A-2e, $(R^2)_n$ is 6-MeO and G is N. |
| 1280 | A is A-2e, $(R^2)_n$ is 6-CN and G is N. |
| 1281 | A is A-3a, $(R^2)_n$ is H and G is CH. |
| 1282 | A is A-3a, $(R^2)_n$ is 3-F and G is CH. |
| 1283 | A is A-3a, $(R^2)_n$ is 3,5-di-F and G is CH. |
| 1284 | A is A-3a, $(R^2)_n$ is 3-Cl and G is CH. |
| 1285 | A is A-3a, $(R^2)_n$ is 3,5-di-Cl and G is CH. |
| 1286 | A is A-3a, $(R^2)_n$ is 3-Br and G is CH. |
| 1287 | A is A-3a, $(R^2)_n$ is 3,5-di-Br and G is CH. |
| 1288 | A is A-3a, $(R^2)_n$ is 3-Me and G is CH. |
| 1289 | A is A-3a, $(R^2)_n$ is 3,5-di-Me and G is CH. |
| 1290 | A is A-3a, $(R^2)_n$ is 3-CF$_3$ and G is CH. |
| 1291 | A is A-3a, $(R^2)_n$ is 3,5-di-CF$_3$ and G is CH. |
| 1292 | A is A-3a, $(R^2)_n$ is 3-MeO and G is CH. |
| 1293 | A is A-3a, $(R^2)_n$ is 3,5-di-MeO and G is CH. |
| 1294 | A is A-3a, $(R^2)_n$ is 3-CN and G is CH. |
| 1295 | A is A-3a, $(R^2)_n$ is 3,5-di-CN and G is CH. |
| 1296 | A is A-3a, $(R^2)_n$ is 3,6-di-F and G is CH. |
| 1297 | A is A-3a, $(R^2)_n$ is 3,6-di-Cl and G is CH. |
| 1298 | A is A-3a, $(R^2)_n$ is 3,6-di-Br and G is CH. |
| 1299 | A is A-3a, $(R^2)_n$ is 3,6-di-Me and G is CH. |
| 1300 | A is A-3a, $(R^2)_n$ is 3,6-di-CF$_3$ and G is CH. |
| 1301 | A is A-3a, $(R^2)_n$ is 3,6-di-MeO and G is CH. |
| 1302 | A is A-3a, $(R^2)_n$ is 3,6-di-CN and G is CH. |
| 1303 | A is A-3a, $(R^2)_n$ is 6-F and G is CH. |
| 1304 | A is A-3a, $(R^2)_n$ is 6-Cl and G is CH. |
| 1305 | A is A-3a, $(R^2)_n$ is 6-Br and G is CH. |
| 1306 | A is A-3a, $(R^2)_n$ is 6-Me and G is CH. |
| 1307 | A is A-3a, $(R^2)_n$ is 6-CF$_3$ and G is CH. |
| 1308 | A is A-3a, $(R^2)_n$ is 6-MeO and G is CH. |
| 1309 | A is A-3a, $(R^2)_n$ is 6-CN and G is CH. |
| 1310 | A is A-3a, $(R^2)_n$ is 6-F and G is C—F. |
| 1311 | A is A-3a, $(R^2)_n$ is 6-Cl and G is C—Cl. |
| 1312 | A is A-3a, $(R^2)_n$ is 6-Br and G is C—Br. |
| 1313 | A is A-3a, $(R^2)_n$ is 6-Me and G is C—Me. |
| 1314 | A is A-3a, $(R^2)_n$ is 6-CF$_3$ and G is C—CF$_3$. |
| 1315 | A is A-3a, $(R^2)_n$ is 6-MeO and G is C—OMe. |
| 1316 | A is A-3a, $(R^2)_n$ is H and G is N. |
| 1317 | A is A-3a, $(R^2)_n$ is 3-F and G is N. |
| 1318 | A is A-3a, $(R^2)_n$ is 3,5-di-F and G is N. |
| 1319 | A is A-3a, $(R^2)_n$ is 3-Cl and G is N. |
| 1320 | A is A-3a, $(R^2)_n$ is 3,5-di-Cl and G is N. |
| 1321 | A is A-3a, $(R^2)_n$ is 3-Br and G is N. |
| 1322 | A is A-3a, $(R^2)_n$ is 3,5-di-Br and G is N. |
| 1323 | A is A-3a, $(R^2)_n$ is 3-Me and G is N. |
| 1324 | A is A-3a, $(R^2)_n$ is 3,5-di-Me and G is N. |
| 1325 | A is A-3a, $(R^2)_n$ is 3-CF$_3$ and G is N. |
| 1326 | A is A-3a, $(R^2)_n$ is 3,5-di-CF$_3$ and G is N. |
| 1327 | A is A-3a, $(R^2)_n$ is 3-MeO and G is N. |
| 1328 | A is A-3a, $(R^2)_n$ is 3,5-di-MeO and G is N. |
| 1329 | A is A-3a, $(R^2)_n$ is 3-CN and G is N. |
| 1330 | A is A-3a, $(R^2)_n$ is 3,5-di-CN and G is N. |
| 1331 | A is A-3a, $(R^2)_n$ is 3,6-di-F and G is N. |
| 1332 | A is A-3a, $(R^2)_n$ is 3,6-di-Cl and G is N. |
| 1333 | A is A-3a, $(R^2)_n$ is 3,6-di-Br and G is N. |
| 1334 | A is A-3a, $(R^2)_n$ is 3,6-di-Me and G is N. |
| 1335 | A is A-3a, $(R^2)_n$ is 3,6-di-CF$_3$ and G is N. |
| 1336 | A is A-3a, $(R^2)_n$ is 3,6-di-MeO and G is N. |
| 1337 | A is A-3a, $(R^2)_n$ is 3,6-di-CN and G is N. |
| 1338 | A is A-3a, $(R^2)_n$ is 6-F and G is N. |
| 1339 | A is A-3a, $(R^2)_n$ is 6-Cl and G is N. |
| 1340 | A is A-3a, $(R^2)_n$ is 6-Br and G is N. |
| 1341 | A is A-3a, $(R^2)_n$ is 6-Me and G is N. |
| 1342 | A is A-3a, $(R^2)_n$ is 6-CF$_3$ and G is N. |
| 1343 | A is A-3a, $(R^2)_n$ is 6-MeO and G is N. |
| 1344 | A is A-3a, $(R^2)_n$ is 6-CN and G is N. |
| 1345 | A is A-3b, $(R^2)_n$ is H and G is CH. |
| 1346 | A is A-3b, $(R^2)_n$ is 3-F and G is CH. |
| 1347 | A is A-3b, $(R^2)_n$ is 3,5-di-F and G is CH. |
| 1348 | A is A-3b, $(R^2)_n$ is 3-Cl and G is CH. |
| 1349 | A is A-3b, $(R^2)_n$ is 3,5-di-Cl and G is CH. |
| 1350 | A is A-3b, $(R^2)_n$ is 3-Br and G is CH. |
| 1351 | A is A-3b, $(R^2)_n$ is 3,5-di-Br and G is CH. |
| 1352 | A is A-3b, $(R^2)_n$ is 3-Me and G is CH. |
| 1353 | A is A-3b, $(R^2)_n$ is 3,5-di-Me and G is CH. |
| 1354 | A is A-3b, $(R^2)_n$ is 3-CF$_3$ and G is CH. |
| 1355 | A is A-3b, $(R^2)_n$ is 3,5-di-CF$_3$ and G is CH. |
| 1356 | A is A-3b, $(R^2)_n$ is 3-MeO and G is CH. |
| 1357 | A is A-3b, $(R^2)_n$ is 3,5-di-MeO and G is CH. |
| 1358 | A is A-3b, $(R^2)_n$ is 3-CN and G is CH. |
| 1359 | A is A-3b, $(R^2)_n$ is 3,5-di-CN and G is CH. |
| 1360 | A is A-3b, $(R^2)_n$ is 3,6-di-F and G is CH. |
| 1361 | A is A-3b, $(R^2)_n$ is 3,6-di-Cl and G is CH. |
| 1362 | A is A-3b, $(R^2)_n$ is 3,6-di-Br and G is CH. |
| 1363 | A is A-3b, $(R^2)_n$ is 3,6-di-Me and G is CH. |
| 1364 | A is A-3b, $(R^2)_n$ is 3,6-di-CF$_3$ and G is CH. |
| 1365 | A is A-3b, $(R^2)_n$ is 3,6-di-MeO and G is CH. |
| 1366 | A is A-3b, $(R^2)_n$ is 3,6-di-CN and G is CH. |
| 1367 | A is A-3b, $(R^2)_n$ is 6-F and G is CH. |
| 1368 | A is A-3b, $(R^2)_n$ is 6-Cl and G is CH. |
| 1369 | A is A-3b, $(R^2)_n$ is 6-Br and G is CH. |
| 1370 | A is A-3b, $(R^2)_n$ is 6-Me and G is CH. |
| 1371 | A is A-3b, $(R^2)_n$ is 6-CF$_3$ and G is CH. |
| 1372 | A is A-3b, $(R^2)_n$ is 6-MeO and G is CH. |
| 1373 | A is A-3b, $(R^2)_n$ is 6-CN and G is CH. |
| 1374 | A is A-3b, $(R^2)_n$ is 6-F and G is C—F. |
| 1375 | A is A-3b, $(R^2)_n$ is 6-Cl and G is C—Cl. |
| 1376 | A is A-3b, $(R^2)_n$ is 6-Br and G is C—Br. |
| 1377 | A is A-3b, $(R^2)_n$ is 6-Me and G is C—Me. |
| 1378 | A is A-3b, $(R^2)_n$ is 6-CF$_3$ and G is C—CF$_3$. |
| 1379 | A is A-3b, $(R^2)_n$ is 6-MeO and G is C—OMe. |
| 1380 | A is A-3b, $(R^2)_n$ is H and G is N. |
| 1381 | A is A-3b, $(R^2)_n$ is 3-F and G is N. |
| 1382 | A is A-3b, $(R^2)_n$ is 3,5-di-F and G is N. |
| 1383 | A is A-3b, $(R^2)_n$ is 3-Cl and G is N. |
| 1384 | A is A-3b, $(R^2)_n$ is 3,5-di-Cl and G is N. |
| 1385 | A is A-3b, $(R^2)_n$ is 3-Br and G is N. |
| 1386 | A is A-3b, $(R^2)_n$ is 3,5-di-Br and G is N. |
| 1387 | A is A-3b, $(R^2)_n$ is 3-Me and G is N. |
| 1388 | A is A-3b, $(R^2)_n$ is 3,5-di-Me and G is N. |
| 1389 | A is A-3b, $(R^2)_n$ is 3-CF$_3$ and G is N. |
| 1390 | A is A-3b, $(R^2)_n$ is 3,5-di-CF$_3$ and G is N. |
| 1391 | A is A-3b, $(R^2)_n$ is 3-MeO and G is N. |
| 1392 | A is A-3b, $(R^2)_n$ is 3,5-di-MeO and G is N. |
| 1393 | A is A-3b, $(R^2)_n$ is 3-CN and G is N. |
| 1394 | A is A-3b, $(R^2)_n$ is 3,5-di-CN and G is N. |
| 1395 | A is A-3b, $(R^2)_n$ is 3,6-di-F and G is N. |
| 1396 | A is A-3b, $(R^2)_n$ is 3,6-di-Cl and G is N. |
| 1397 | A is A-3b, $(R^2)_n$ is 3,6-di-Br and G is N. |
| 1398 | A is A-3b, $(R^2)_n$ is 3,6-di-Me and G is N. |
| 1399 | A is A-3b, $(R^2)_n$ is 3,6-di-CF$_3$ and G is N. |
| 1400 | A is A-3b, $(R^2)_n$ is 3,6-di-MeO and G is N. |
| 1401 | A is A-3b, $(R^2)_n$ is 3,6-di-CN and G is N. |
| 1402 | A is A-3b, $(R^2)_n$ is 6-F and G is N. |
| 1403 | A is A-3b, $(R^2)_n$ is 6-Cl and G is N. |
| 1404 | A is A-3b, $(R^2)_n$ is 6-Br and G is N. |
| 1405 | A is A-3b, $(R^2)_n$ is 6-Me and G is N. |
| 1406 | A is A-3b, $(R^2)_n$ is 6-CF$_3$ and G is N. |
| 1407 | A is A-3b, $(R^2)_n$ is 6-MeO and G is N. |
| 1408 | A is A-3b, $(R^2)_n$ is 6-CN and G is N. |
| 1409 | A is A-3c, $(R^2)_n$ is H and G is CH. |
| 1410 | A is A-3c, $(R^2)_n$ is 3-F and G is CH. |
| 1411 | A is A-3c, $(R^2)_n$ is 3,5-di-F and G is CH. |
| 1412 | A is A-3c, $(R^2)_n$ is 3-Cl and G is CH. |
| 1413 | A is A-3c, $(R^2)_n$ is 3,5-di-Cl and G is CH. |
| 1414 | A is A-3c, $(R^2)_n$ is 3-Br and G is CH. |
| 1415 | A is A-3c, $(R^2)_n$ is 3,5-di-Br and G is CH. |
| 1416 | A is A-3c, $(R^2)_n$ is 3-Me and G is CH. |
| 1417 | A is A-3c, $(R^2)_n$ is 3,5-di-Me and G is CH. |
| 1418 | A is A-3c, $(R^2)_n$ is 3-CF$_3$ and G is CH. |
| 1419 | A is A-3c, $(R^2)_n$ is 3,5-di-CF$_3$ and G is CH. |
| 1420 | A is A-3c, $(R^2)_n$ is 3-MeO and G is CH. |
| 1421 | A is A-3c, $(R^2)_n$ is 3,5-di-MeO and G is CH. |
| 1422 | A is A-3c, $(R^2)_n$ is 3-CN and G is CH. |
| 1423 | A is A-3c, $(R^2)_n$ is 3,5-di-CN and G is CH. |
| 1424 | A is A-3c, $(R^2)_n$ is 3,6-di-F and G is CH. |
| 1425 | A is A-3c, $(R^2)_n$ is 3,6-di-Cl and G is CH. |

TABLES 2-1728-continued

| Table | Row Heading |
|---|---|
| 1426 | A is A-3c, $(R^2)_n$ is 3,6-di-Br and G is CH. |
| 1427 | A is A-3c, $(R^2)_n$ is 3,6-di-Me and G is CH. |
| 1428 | A is A-3c, $(R^2)_n$ is 3,6-di-CF$_3$ and G is CH. |
| 1429 | A is A-3c, $(R^2)_n$ is 3,6-di-MeO and G is CH. |
| 1430 | A is A-3c, $(R^2)_n$ is 3,6-di-CN and G is CH. |
| 1431 | A is A-3c, $(R^2)_n$ is 6-F and G is CH. |
| 1432 | A is A-3c, $(R^2)_n$ is 6-Cl and G is CH. |
| 1433 | A is A-3c, $(R^2)_n$ is 6-Br and G is CH. |
| 1434 | A is A-3c, $(R^2)_n$ is 6-Me and G is CH. |
| 1435 | A is A-3c, $(R^2)_n$ is 6-CF$_3$ and G is CH. |
| 1436 | A is A-3c, $(R^2)_n$ is 6-MeO and G is CH. |
| 1437 | A is A-3c, $(R^2)_n$ is 6-CN and G is CH. |
| 1438 | A is A-3c, $(R^2)_n$ is 6-F and G is C—F. |
| 1439 | A is A-3c, $(R^2)_n$ is 6-Cl and G is C—Cl. |
| 1440 | A is A-3c, $(R^2)_n$ is 6-Br and G is C—Br. |
| 1441 | A is A-3c, $(R^2)_n$ is 6-Me and G is C—Me. |
| 1442 | A is A-3c, $(R^2)_n$ is 6-CF$_3$ and G is C—CF$_3$. |
| 1443 | A is A-3c, $(R^2)_n$ is 6-MeO and G is C—OMe. |
| 1444 | A is A-3c, $(R^2)_n$ is H and G is N. |
| 1445 | A is A-3c, $(R^2)_n$ is 3-F and G is N. |
| 1446 | A is A-3c, $(R^2)_n$ is 3,5-di-F and G is N. |
| 1447 | A is A-3c, $(R^2)_n$ is 3-Cl and G is N. |
| 1448 | A is A-3c, $(R^2)_n$ is 3,5-di-Cl and G is N. |
| 1449 | A is A-3c, $(R^2)_n$ is 3-Br and G is N. |
| 1450 | A is A-3c, $(R^2)_n$ is 3,5-di-Br and G is N. |
| 1451 | A is A-3c, $(R^2)_n$ is 3-Me and G is N. |
| 1452 | A is A-3c, $(R^2)_n$ is 3,5-di-Me and G is N. |
| 1453 | A is A-3c, $(R^2)_n$ is 3-CF$_3$ and G is N. |
| 1454 | A is A-3c, $(R^2)_n$ is 3,5-di-CF$_3$ and G is N. |
| 1455 | A is A-3c, $(R^2)_n$ is 3-MeO and G is N. |
| 1456 | A is A-3c, $(R^2)_n$ is 3,5-di-MeO and G is N. |
| 1457 | A is A-3c, $(R^2)_n$ is 3-CN and G is N. |
| 1458 | A is A-3c, $(R^2)_n$ is 3,5-di-CN and G is N. |
| 1459 | A is A-3c, $(R^2)_n$ is 3,6-di-F and G is N. |
| 1460 | A is A-3c, $(R^2)_n$ is 3,6-di-Cl and G is N. |
| 1461 | A is A-3c, $(R^2)_n$ is 3,6-di-Br and G is N. |
| 1462 | A is A-3c, $(R^2)_n$ is 3,6-di-Me and G is N. |
| 1463 | A is A-3c, $(R^2)_n$ is 3,6-di-CF$_3$ and G is N. |
| 1464 | A is A-3c, $(R^2)_n$ is 3,6-di-MeO and G is N. |
| 1465 | A is A-3c, $(R^2)_n$ is 3,6-di-CN and G is N. |
| 1466 | A is A-3c, $(R^2)_n$ is 6-F and G is N. |
| 1467 | A is A-3c, $(R^2)_n$ is 6-Cl and G is N. |
| 1468 | A is A-3c, $(R^2)_n$ is 6-Br and G is N. |
| 1469 | A is A-3c, $(R^2)_n$ is 6-Me and G is N. |
| 1470 | A is A-3c, $(R^2)_n$ is 6-CF$_3$ and G is N. |
| 1471 | A is A-3c, $(R^2)_n$ is 6-MeO and G is N. |
| 1472 | A is A-3c, $(R^2)_n$ is 6-CN and G is N. |
| 1473 | A is A-4a, $(R^2)_n$ is H and G is CH. |
| 1474 | A is A-4a, $(R^2)_n$ is 3-F and G is CH. |
| 1475 | A is A-4a, $(R^2)_n$ is 3,5-di-F and G is CH. |
| 1476 | A is A-4a, $(R^2)_n$ is 3-Cl and G is CH. |
| 1477 | A is A-4a, $(R^2)_n$ is 3,5-di-Cl and G is CH. |
| 1478 | A is A-4a, $(R^2)_n$ is 3-Br and G is CH. |
| 1479 | A is A-4a, $(R^2)_n$ is 3,5-di-Br and G is CH. |
| 1480 | A is A-4a, $(R^2)_n$ is 3-Me and G is CH. |
| 1481 | A is A-4a, $(R^2)_n$ is 3,5-di-Me and G is CH. |
| 1482 | A is A-4a, $(R^2)_n$ is 3-CF$_3$ and G is CH. |
| 1483 | A is A-4a, $(R^2)_n$ is 3,5-di-CF$_3$ and G is CH. |
| 1484 | A is A-4a, $(R^2)_n$ is 3-MeO and G is CH. |
| 1485 | A is A-4a, $(R^2)_n$ is 3,5-di-MeO and G is CH. |
| 1486 | A is A-4a, $(R^2)_n$ is 3-CN and G is CH. |
| 1487 | A is A-4a, $(R^2)_n$ is 3,5-di-CN and G is CH. |
| 1488 | A is A-4a, $(R^2)_n$ is 3,6-di-F and G is CH. |
| 1489 | A is A-4a, $(R^2)_n$ is 3,6-di-Cl and G is CH. |
| 1490 | A is A-4a, $(R^2)_n$ is 3,6-di-Br and G is CH. |
| 1491 | A is A-4a, $(R^2)_n$ is 3,6-di-Me and G is CH. |
| 1492 | A is A-4a, $(R^2)_n$ is 3,6-di-CF$_3$ and G is CH. |
| 1493 | A is A-4a, $(R^2)_n$ is 3,6-di-MeO and G is CH. |
| 1494 | A is A-4a, $(R^2)_n$ is 3,6-di-CN and G is CH. |
| 1495 | A is A-4a, $(R^2)_n$ is 6-F and G is CH. |
| 1496 | A is A-4a, $(R^2)_n$ is 6-Cl and G is CH. |
| 1497 | A is A-4a, $(R^2)_n$ is 6-Br and G is CH. |
| 1498 | A is A-4a, $(R^2)_n$ is 6-Me and G is CH. |
| 1499 | A is A-4a, $(R^2)_n$ is 6-CF$_3$ and G is CH. |
| 1500 | A is A-4a, $(R^2)_n$ is 6-MeO and G is CH. |
| 1501 | A is A-4a, $(R^2)_n$ is 6-CN and G is CH. |
| 1502 | A is A-4a, $(R^2)_n$ is 6-F and G is C—F. |
| 1503 | A is A-4a, $(R^2)_n$ is 6-Cl and G is C—Cl. |
| 1504 | A is A-4a, $(R^2)_n$ is 6-Br and G is C—Br. |
| 1505 | A is A-4a, $(R^2)_n$ is 6-Me and G is C—Me. |
| 1506 | A is A-4a, $(R^2)_n$ is 6-CF$_3$ and G is C—CF$_3$. |
| 1507 | A is A-4a, $(R^2)_n$ is 6-MeO and G is C—OMe. |
| 1508 | A is A-4a, $(R^2)_n$ is H and G is N. |
| 1509 | A is A-4a, $(R^2)_n$ is 3-F and G is N. |
| 1510 | A is A-4a, $(R^2)_n$ is 3,5-di-F and G is N. |
| 1511 | A is A-4a, $(R^2)_n$ is 3-Cl and G is N. |
| 1512 | A is A-4a, $(R^2)_n$ is 3,5-di-Cl and G is N. |
| 1513 | A is A-4a, $(R^2)_n$ is 3-Br and G is N. |
| 1514 | A is A-4a, $(R^2)_n$ is 3,5-di-Br and G is N. |
| 1515 | A is A-4a, $(R^2)_n$ is 3-Me and G is N. |
| 1516 | A is A-4a, $(R^2)_n$ is 3,5-di-Me and G is N. |
| 1517 | A is A-4a, $(R^2)_n$ is 3-CF$_3$ and G is N. |
| 1518 | A is A-4a, $(R^2)_n$ is 3,5-di-CF$_3$ and G is N. |
| 1519 | A is A-4a, $(R^2)_n$ is 3-MeO and G is N. |
| 1520 | A is A-4a, $(R^2)_n$ is 3,5-di-MeO and G is N. |
| 1521 | A is A-4a, $(R^2)_n$ is 3-CN and G is N. |
| 1522 | A is A-4a, $(R^2)_n$ is 3,5-di-CN and G is N. |
| 1523 | A is A-4a, $(R^2)_n$ is 3,6-di-F and G is N. |
| 1524 | A is A-4a, $(R^2)_n$ is 3,6-di-Cl and G is N. |
| 1525 | A is A-4a, $(R^2)_n$ is 3,6-di-Br and G is N. |
| 1526 | A is A-4a, $(R^2)_n$ is 3,6-di-Me and G is N. |
| 1527 | A is A-4a, $(R^2)_n$ is 3,6-di-CF$_3$ and G is N. |
| 1528 | A is A-4a, $(R^2)_n$ is 3,6-di-MeO and G is N. |
| 1529 | A is A-4a, $(R^2)_n$ is 3,6-di-CN and G is N. |
| 1530 | A is A-4a, $(R^2)_n$ is 6-F and G is N. |
| 1531 | A is A-4a, $(R^2)_n$ is 6-Cl and G is N. |
| 1532 | A is A-4a, $(R^2)_n$ is 6-Br and G is N. |
| 1533 | A is A-4a, $(R^2)_n$ is 6-Me and G is N. |
| 1534 | A is A-4a, $(R^2)_n$ is 6-CF$_3$ and G is N. |
| 1535 | A is A-4a, $(R^2)_n$ is 6-MeO and G is N. |
| 1536 | A is A-4a, $(R^2)_n$ is 6-CN and G is N. |
| 1537 | A is A-4b, $(R^2)_n$ is H and G is CH. |
| 1538 | A is A-4b, $(R^2)_n$ is 3-F and G is CH. |
| 1539 | A is A-4b, $(R^2)_n$ is 3,5-di-F and G is CH. |
| 1540 | A is A-4b, $(R^2)_n$ is 3-Cl and G is CH. |
| 1541 | A is A-4b, $(R^2)_n$ is 3,5-di-Cl and G is CH. |
| 1542 | A is A-4b, $(R^2)_n$ is 3-Br and G is CH. |
| 1543 | A is A-4b, $(R^2)_n$ is 3,5-di-Br and G is CH. |
| 1544 | A is A-4b, $(R^2)_n$ is 3-Me and G is CH. |
| 1545 | A is A-4b, $(R^2)_n$ is 3,5-di-Me and G is CH. |
| 1546 | A is A-4b, $(R^2)_n$ is 3-CF$_3$ and G is CH. |
| 1547 | A is A-4b, $(R^2)_n$ is 3,5-di-CF$_3$ and G is CH. |
| 1548 | A is A-4b, $(R^2)_n$ is 3-MeO and G is CH. |
| 1549 | A is A-4b, $(R^2)_n$ is 3,5-di-MeO and G is CH. |
| 1550 | A is A-4b, $(R^2)_n$ is 3-CN and G is CH. |
| 1551 | A is A-4b, $(R^2)_n$ is 3,5-di-CN and G is CH. |
| 1552 | A is A-4b, $(R^2)_n$ is 3,6-di-F and G is CH. |
| 1553 | A is A-4b, $(R^2)_n$ is 3,6-di-Cl and G is CH. |
| 1554 | A is A-4b, $(R^2)_n$ is 3,6-di-Br and G is CH. |
| 1555 | A is A-4b, $(R^2)_n$ is 3,6-di-Me and G is CH. |
| 1556 | A is A-4b, $(R^2)_n$ is 3,6-di-CF$_3$ and G is CH. |
| 1557 | A is A-4b, $(R^2)_n$ is 3,6-di-MeO and G is CH. |
| 1558 | A is A-4b, $(R^2)_n$ is 3,6-di-CN and G is CH. |
| 1559 | A is A-4b, $(R^2)_n$ is 6-F and G is CH. |
| 1560 | A is A-4b, $(R^2)_n$ is 6-Cl and G is CH. |
| 1561 | A is A-4b, $(R^2)_n$ is 6-Br and G is CH. |
| 1562 | A is A-4b, $(R^2)_n$ is 6-Me and G is CH. |
| 1563 | A is A-4b, $(R^2)_n$ is 6-CF$_3$ and G is CH. |
| 1564 | A is A-4b, $(R^2)_n$ is 6-MeO and G is CH. |
| 1565 | A is A-4b, $(R^2)_n$ is 6-CN and G is CH. |
| 1566 | A is A-4b, $(R^2)_n$ is 6-F and G is C—F. |
| 1567 | A is A-4b, $(R^2)_n$ is 6-Cl and G is C—Cl. |
| 1568 | A is A-4b, $(R^2)_n$ is 6-Br and G is C—Br. |
| 1569 | A is A-4b, $(R^2)_n$ is 6-Me and G is C—Me. |
| 1570 | A is A-4b, $(R^2)_n$ is 6-CF$_3$ and G is C—CF$_3$. |
| 1571 | A is A-4b, $(R^2)_n$ is 6-MeO and G is C—OMe. |
| 1572 | A is A-4b, $(R^2)_n$ is H and G is N. |
| 1573 | A is A-4b, $(R^2)_n$ is 3-F and G is N. |
| 1574 | A is A-4b, $(R^2)_n$ is 3,5-di-F and G is N. |
| 1575 | A is A-4b, $(R^2)_n$ is 3-Cl and G is N. |
| 1576 | A is A-4b, $(R^2)_n$ is 3,5-di-Cl and G is N. |
| 1577 | A is A-4b, $(R^2)_n$ is 3-Br and G is N. |
| 1578 | A is A-4b, $(R^2)_n$ is 3,5-di-Br and G is N. |
| 1579 | A is A-4b, $(R^2)_n$ is 3-Me and G is N. |
| 1580 | A is A-4b, $(R^2)_n$ is 3,5-di-Me and G is N. |
| 1581 | A is A-4b, $(R^2)_n$ is 3-CF$_3$ and G is N. |

TABLES 2-1728-continued

| Table | Row Heading |
|---|---|
| 1582 | A is A-4b, $(R^2)_n$ is 3,5-di-CF$_3$ and G is N. |
| 1583 | A is A-4b, $(R^2)_n$ is 3-MeO and G is N. |
| 1584 | A is A-4b, $(R^2)_n$ is 3,5-di-MeO and G is N. |
| 1585 | A is A-4b, $(R^2)_n$ is 3-CN and G is N. |
| 1586 | A is A-4b, $(R^2)_n$ is 3,5-di-CN and G is N. |
| 1587 | A is A-4b, $(R^2)_n$ is 3,6-di-F and G is N. |
| 1588 | A is A-4b, $(R^2)_n$ is 3,6-di-Cl and G is N. |
| 1589 | A is A-4b, $(R^2)_n$ is 3,6-di-Br and G is N. |
| 1590 | A is A-4b, $(R^2)_n$ is 3,6-di-Me and G is N. |
| 1591 | A is A-4b, $(R^2)_n$ is 3,6-di-CF$_3$ and G is N. |
| 1592 | A is A-4b, $(R^2)_n$ is 3,6-di-MeO and G is N. |
| 1593 | A is A-4b, $(R^2)_n$ is 3,6-di-CN and G is N. |
| 1594 | A is A-4b, $(R^2)_n$ is 6-F and G is N. |
| 1595 | A is A-4b, $(R^2)_n$ is 6-Cl and G is N. |
| 1596 | A is A-4b, $(R^2)_n$ is 6-Br and G is N. |
| 1597 | A is A-4b, $(R^2)_n$ is 6-Me and G is N. |
| 1598 | A is A-4b, $(R^2)_n$ is 6-CF$_3$ and G is N. |
| 1599 | A is A-4b, $(R^2)_n$ is 6-MeO and G is N. |
| 1600 | A is A-4b, $(R^2)_n$ is 6-CN and G is N. |
| 1601 | A is A-4c, $(R^2)_n$ is H and G is CH. |
| 1602 | A is A-4c, $(R^2)_n$ is 3-F and G is CH. |
| 1603 | A is A-4c, $(R^2)_n$ is 3,5-di-F and G is CH. |
| 1604 | A is A-4c, $(R^2)_n$ is 3-Cl and G is CH. |
| 1605 | A is A-4c, $(R^2)_n$ is 3,5-di-Cl and G is CH. |
| 1606 | A is A-4c, $(R^2)_n$ is 3-Br and G is CH. |
| 1607 | A is A-4c, $(R^2)_n$ is 3,5-di-Br and G is CH. |
| 1608 | A is A-4c, $(R^2)_n$ is 3-Me and G is CH. |
| 1609 | A is A-4c, $(R^2)_n$ is 3,5-di-Me and G is CH. |
| 1610 | A is A-4c, $(R^2)_n$ is 3-CF$_3$ and G is CH. |
| 1611 | A is A-4c, $(R^2)_n$ is 3,5-di-CF$_3$ and G is CH. |
| 1612 | A is A-4c, $(R^2)_n$ is 3-MeO and G is CH. |
| 1613 | A is A-4c, $(R^2)_n$ is 3,5-di-MeO and G is CH. |
| 1614 | A is A-4c, $(R^2)_n$ is 3-CN and G is CH. |
| 1615 | A is A-4c, $(R^2)_n$ is 3,5-di-CN and G is CH. |
| 1616 | A is A-4c, $(R^2)_n$ is 3,6-di-F and G is CH. |
| 1617 | A is A-4c, $(R^2)_n$ is 3,6-di-Cl and G is CH. |
| 1618 | A is A-4c, $(R^2)_n$ is 3,6-di-Br and G is CH. |
| 1619 | A is A-4c, $(R^2)_n$ is 3,6-di-Me and G is CH. |
| 1620 | A is A-4c, $(R^2)_n$ is 3,6-di-CF$_3$ and G is CH. |
| 1621 | A is A-4c, $(R^2)_n$ is 3,6-di-MeO and G is CH. |
| 1622 | A is A-4c, $(R^2)_n$ is 3,6-di-CN and G is CH. |
| 1623 | A is A-4c, $(R^2)_n$ is 6-F and G is CH. |
| 1624 | A is A-4c, $(R^2)_n$ is 6-Cl and G is CH. |
| 1625 | A is A-4c, $(R^2)_n$ is 6-Br and G is CH. |
| 1626 | A is A-4c, $(R^2)_n$ is 6-Me and G is CH. |
| 1627 | A is A-4c, $(R^2)_n$ is 6-CF$_3$ and G is CH. |
| 1628 | A is A-4c, $(R^2)_n$ is 6-MeO and G is CH. |
| 1629 | A is A-4c, $(R^2)_n$ is 6-CN and G is CH. |
| 1630 | A is A-4c, $(R^2)_n$ is 6-F and G is C—F. |
| 1631 | A is A-4c, $(R^2)_n$ is 6-Cl and G is C—Cl. |
| 1632 | A is A-4c, $(R^2)_n$ is 6-Br and G is C—Br. |
| 1633 | A is A-4c, $(R^2)_n$ is 6-Me and G is C—Me. |
| 1634 | A is A-4c, $(R^2)_n$ is 6-CF$_3$ and G is C—CF$_3$. |
| 1635 | A is A-4c, $(R^2)_n$ is 6-MeO and G is C—OMe. |
| 1636 | A is A-4c, $(R^2)_n$ is H and G is N. |
| 1637 | A is A-4c, $(R^2)_n$ is 3-F and G is N. |
| 1638 | A is A-4c, $(R^2)_n$ is 3,5-di-F and G is N. |
| 1639 | A is A-4c, $(R^2)_n$ is 3-Cl and G is N. |
| 1640 | A is A-4c, $(R^2)_n$ is 3,5-di-Cl and G is N. |
| 1641 | A is A-4c, $(R^2)_n$ is 3-Br and G is N. |
| 1642 | A is A-4c, $(R^2)_n$ is 3,5-di-Br and G is N. |
| 1643 | A is A-4c, $(R^2)_n$ is 3-Me and G is N. |
| 1644 | A is A-4c, $(R^2)_n$ is 3,5-di-Me and G is N. |
| 1645 | A is A-4c, $(R^2)_n$ is 3-CF$_3$ and G is N. |
| 1646 | A is A-4c, $(R^2)_n$ is 3,5-di-CF$_3$ and G is N. |
| 1647 | A is A-4c, $(R^2)_n$ is 3-MeO and G is N. |
| 1648 | A is A-4c, $(R^2)_n$ is 3,5-di-MeO and G is N. |
| 1649 | A is A-4c, $(R^2)_n$ is 3-CN and G is N. |
| 1650 | A is A-4c, $(R^2)_n$ is 3,5-di-CN and G is N. |
| 1651 | A is A-4c, $(R^2)_n$ is 3,6-di-F and G is N. |
| 1652 | A is A-4c, $(R^2)_n$ is 3,6-di-Cl and G is N. |
| 1653 | A is A-4c, $(R^2)_n$ is 3,6-di-Br and G is N. |
| 1654 | A is A-4c, $(R^2)_n$ is 3,6-di-Me and G is N. |
| 1655 | A is A-4c, $(R^2)_n$ is 3,6-di-CF$_3$ and G is N. |
| 1656 | A is A-4c, $(R^2)_n$ is 3,6-di-MeO and G is N. |
| 1657 | A is A-4c, $(R^2)_n$ is 3,6-di-CN and G is N. |
| 1658 | A is A-4c, $(R^2)_n$ is 6-F and G is N. |
| 1659 | A is A-4c, $(R^2)_n$ is 6-Cl and G is N. |
| 1660 | A is A-4c, $(R^2)_n$ is 6-Br and G is N. |
| 1661 | A is A-4c, $(R^2)_n$ is 6-Me and G is N. |
| 1662 | A is A-4c, $(R^2)_n$ is 6-CF$_3$ and G is N. |
| 1663 | A is A-4c, $(R^2)_n$ is 6-MeO and G is N. |
| 1664 | A is A-4c, $(R^2)_n$ is 6-CN and G is N. |
| 1665 | A is A-4d, $(R^2)_n$ is H and G is CH. |
| 1666 | A is A-4d, $(R^2)_n$ is 3-F and G is CH. |
| 1667 | A is A-4d, $(R^2)_n$ is 3,5-di-F and G is CH. |
| 1668 | A is A-4d, $(R^2)_n$ is 3-Cl and G is CH. |
| 1669 | A is A-4d, $(R^2)_n$ is 3,5-di-Cl and G is CH. |
| 1670 | A is A-4d, $(R^2)_n$ is 3-Br and G is CH. |
| 1671 | A is A-4d, $(R^2)_n$ is 3,5-di-Br and G is CH. |
| 1672 | A is A-4d, $(R^2)_n$ is 3-Me and G is CH. |
| 1673 | A is A-4d, $(R^2)_n$ is 3,5-di-Me and G is CH. |
| 1674 | A is A-4d, $(R^2)_n$ is 3-CF$_3$ and G is CH. |
| 1675 | A is A-4d, $(R^2)_n$ is 3,5-di-CF$_3$ and G is CH. |
| 1676 | A is A-4d, $(R^2)_n$ is 3-MeO and G is CH. |
| 1677 | A is A-4d, $(R^2)_n$ is 3,5-di-MeO and G is CH. |
| 1678 | A is A-4d, $(R^2)_n$ is 3-CN and G is CH. |
| 1679 | A is A-4d, $(R^2)_n$ is 3,5-di-CN and G is CH. |
| 1680 | A is A-4d, $(R^2)_n$ is 3,6-di-F and G is CH. |
| 1681 | A is A-4d, $(R^2)_n$ is 3,6-di-Cl and G is CH. |
| 1682 | A is A-4d, $(R^2)_n$ is 3,6-di-Br and G is CH. |
| 1683 | A is A-4d, $(R^2)_n$ is 3,6-di-Me and G is CH. |
| 1684 | A is A-4d, $(R^2)_n$ is 3,6-di-CF$_3$ and G is CH. |
| 1685 | A is A-4d, $(R^2)_n$ is 3,6-di-MeO and G is CH. |
| 1686 | A is A-4d, $(R^2)_n$ is 3,6-di-CN and G is CH. |
| 1687 | A is A-4d, $(R^2)_n$ is 6-F and G is CH. |
| 1688 | A is A-4d, $(R^2)_n$ is 6-Cl and G is CH. |
| 1689 | A is A-4d, $(R^2)_n$ is 6-Br and G is CH. |
| 1690 | A is A-4d, $(R^2)_n$ is 6-Me and G is CH. |
| 1691 | A is A-4d, $(R^2)_n$ is 6-CF$_3$ and G is CH. |
| 1692 | A is A-4d, $(R^2)_n$ is 6-MeO and G is CH. |
| 1693 | A is A-4d, $(R^2)_n$ is 6-CN and G is CH. |
| 1694 | A is A-4d, $(R^2)_n$ is 6-F and G is C—F. |
| 1695 | A is A-4d, $(R^2)_n$ is 6-Cl and G is C—Cl. |
| 1696 | A is A-4d, $(R^2)_n$ is 6-Br and G is C—Br. |
| 1697 | A is A-4d, $(R^2)_n$ is 6-Me and G is C—Me. |
| 1698 | A is A-4d, $(R^2)_n$ is 6-CF$_3$ and G is C—CF$_3$. |
| 1699 | A is A-4d, $(R^2)_n$ is 6-MeO and G is C—OMe. |
| 1700 | A is A-4d, $(R^2)_n$ is H and G is N. |
| 1701 | A is A-4d, $(R^2)_n$ is 3-F and G is N. |
| 1702 | A is A-4d, $(R^2)_n$ is 3,5-di-F and G is N. |
| 1703 | A is A-4d, $(R^2)_n$ is 3-Cl and G is N. |
| 1704 | A is A-4d, $(R^2)_n$ is 3,5-di-Cl and G is N. |
| 1705 | A is A-4d, $(R^2)_n$ is 3-Br and G is N. |
| 1706 | A is A-4d, $(R^2)_n$ is 3,5-di-Br and G is N. |
| 1707 | A is A-4d, $(R^2)_n$ is 3-Me and G is N. |
| 1708 | A is A-4d, $(R^2)_n$ is 3,5-di-Me and G is N. |
| 1709 | A is A-4d, $(R^2)_n$ is 3-CF$_3$ and G is N. |
| 1710 | A is A-4d, $(R^2)_n$ is 3,5-di-CF$_3$ and G is N. |
| 1711 | A is A-4d, $(R^2)_n$ is 3-MeO and G is N. |
| 1712 | A is A-4d, $(R^2)_n$ is 3,5-di-MeO and G is N. |
| 1713 | A is A-4d, $(R^2)_n$ is 3-CN and G is N. |
| 1714 | A is A-4d, $(R^2)_n$ is 3,5-di-CN and G is N. |
| 1715 | A is A-4d, $(R^2)_n$ is 3,6-di-F and G is N. |
| 1716 | A is A-4d, $(R^2)_n$ is 3,6-di-Cl and G is N. |
| 1717 | A is A-4d, $(R^2)_n$ is 3,6-di-Br and G is N. |
| 1718 | A is A-4d, $(R^2)_n$ is 3,6-di-Me and G is N. |
| 1719 | A is A-4d, $(R^2)_n$ is 3,6-di-CF$_3$ and G is N. |
| 1720 | A is A-4d, $(R^2)_n$ is 3,6-di-MeO and G is N. |
| 1721 | A is A-4d, $(R^2)_n$ is 3,6-di-CN and G is N. |
| 1722 | A is A-4d, $(R^2)_n$ is 6-F and G is N. |
| 1723 | A is A-4d, $(R^2)_n$ is 6-Cl and G is N. |
| 1724 | A is A-4d, $(R^2)_n$ is 6-Br and G is N. |
| 1725 | A is A-4d, $(R^2)_n$ is 6-Me and G is N. |
| 1726 | A is A-4d, $(R^2)_n$ is 6-CF$_3$ and G is N. |
| 1727 | A is A-4d, $(R^2)_n$ is 6-MeO and G is N. |
| 1728 | A is A-4d, $(R^2)_n$ is 6-CN and G is N. |

TABLE 1729

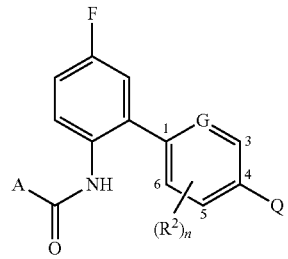

A is A-1a, (R²)ₙ is H, and G is CH.

| Q | Q | Q |
|---|---|---|
| 3-CF₃—1H-pyrazol-1-yl | 3-Me—1H-pyrazol-1-yl | 3-F—1H-pyrazol-1-yl |
| 3-Br—1H-pyrazol-1-yl | 4-CF₃—1H-pyrazol-1-yl | 4-Me—1H-pyrazol-1-yl |
| 4-F—1H-pyrazol-1-yl | 4-Br—1H-pyrazol-1-yl | 5-CF₃—1H-pyrazol-1-yl |
| 5-Me—1H-pyrazol-1-yl | 5-F—1H-pyrazol-1-yl | 5-Br—1H-pyrazol-1-yl |
| 3-CHF₂—1H-pyrazol-1-yl | 3-Et—1H-pyrazol-1-yl | 3-Cl—1H-pyrazol-1-yl |
| 3-I—1H-pyrazol-1-yl | 4-CHF₂—1H-pyrazol-1-yl | 4-Et—1H-pyrazol-1-yl |
| 4-Cl—1H-pyrazol-1-yl | 4-I—1H-pyrazol-1-yl | 5-CHF₂—1H-pyrazol-1-yl |
| 5-Et—1H-pyrazol-1-yl | 5-Cl—1H-pyrazol-1-yl | 3-I—1H-pyrazol-1-yl |
| 3-MeO—1H-pyrazol-1-yl | 3-CN—1H-pyrazol-1-yl | 3-CF₃O—1H-pyrazol-1-yl |
| 3-CHF₂O—1H-pyrazol-1-yl | 4-MeO—1H-pyrazol-1-yl | 4-CN—1H-pyrazol-1-yl |
| 4-CF₃O—1H-pyrazol-1-yl | 4-CHF₂O—1H-pyrazol-1-yl | 5-CF₃O—1H-pyrazol-1-yl |
| 5-CN—1H-pyrazol-1-yl | 5-CF₃O—1H-pyrazol-1-yl | 5-CHF₂O—1H-pyrazol-1-yl |
| 3-MeO(O=)C—1H-pyrazol-1-yl | 3-Ph—1H-pyrazol-1-yl | 3,5-di-Me—1H-pyrazol-1-yl |
| 3,5-di-F—1H-pyrazol-1-yl | 4-MeO(O=)C—1H-pyrazol-1-yl | 4-Ph—1H-pyrazol-1-yl |
| 3,5-di-CF₃—1H-pyrazol-1-yl | 3,5-di-Cl—1H-pyrazol-1-yl | 5-MeO(O=)C—1H-pyrazol-1-yl |
| 5-Ph—1H-pyrazol-1-yl | 3,5-di-CHF₂—1H-pyrazol-1-yl | 3,5-di-Br—1H-pyrazol-1-yl |
| 3-CF₃-5-Me-1H-pyrazol-1-yl | 3,4-di-Me—1H-pyrazol-1-yl | 3,4-di-CF₃—1H-pyrazol-1-yl |
| 3,4-di-Br—1H-pyrazol-1-yl | 3,4-di-Cl—1H-pyrazol-1-yl | 1H-pyrazol-1-yl |
| 3-Me—1H-[1,2,4]triazol-1-yl | 3-CF₃—1H-[1,2,4]triazol-1-yl | 3-CHF₂—1H-[1,2,4]triazol-1-yl |
| 3-F—1H-[1,2,4]triazol-1-yl | 3-Cl—1H-[1,2,4]triazol-1-yl | 3-Br—1H-[1,2,4]triazol-1-yl |
| 3,5-di-Me—1H-[1,2,4]triazol-1-yl | 3,5-di-CF₃—1H-[1,2,4]triazol-1-yl | 3,5-di-CHF₂—1H-[1,2,4]triazol-1-yl |
| 3,5-di-Cl—H-[1,2,4]triazol-1-yl | 3,5-di-Br—1H-[1,2,4]triazol-1-yl | 3-Ph—1H-[1,2,4]triazol-1-yl |
| 1H-[1,2,4]triazol-1-yl | 4-Me—2H-[1,2,3]triazol-2-yl | 4-CF₃—2H-[1,2,3]triazol-2-yl |
| 4-CHF₂—2H-[1,2,3]triazol-2-yl | 4-F—2H-[1,2,3]triazol-2-yl | 4-Cl—2H-[1,2,3]triazol-2-yl |
| 4-Br—2H-[1,2,3]triazol-2-yl | 4-Ph—2H-[1,2,3]triazol-2-yl | 4,5-di-Me—2H-[1,2,3]triazol-2-yl |
| 4,5-di-CF₃—2H-[1,2,3]triazol-2-yl | 4,5-di-Cl—2H-[1,2,3]triazol-2-yl | 4,5-di-Br—2H-[1,2,3]triazol-2-yl |
| 2H-[1,2,3]triazol-2-yl | 4-Me—1H-[1,2,3]triazol-1-yl | 4-CF₃—1H-[1,2,3]triazol-1-yl |
| 4-CHF₂—1H-[1,2,3]triazol-1-yl | 4-F—1H-[1,2,3]triazol-1-yl | 4-Cl—1H-[1,2,3]triazol-1-yl |
| 4-Br—1H-[1,2,3]triazol-1-yl | 4-Ph—1H-[1,2,3]triazol-1-yl | 1H-[1,2,3]triazol-1-yl |
| 3-Me—1H-pyrrol-1-yl | 3-CF₃—1H-pyrrol-1-yl | 3-CHF₂—1H-pyrrol-1-yl |
| 3,4-di-Me—1H-pyrrol-1-yl | 2,4-di-Me—1H-pyrrol-1-yl | 3,4-di-CF₃—1H-pyrrol-1-yl |
| 2,4-di-CF₃—1H-pyrrol-1-yl | 3,4-di-Br—1H-pyrrol-1-yl | 3,4-di-Cl—1H-pyrrol-1-yl |
| 1H-pyrrol-1-yl | 1-Me—1H-pyrazol-3-yl | 1-CF₃—1H-pyrazol-3-yl |
| 1-Et—1H-pyrazol-3-yl | 1-i-Pr—1H-pyrazol-3-yl | 1-(F₃CCH₂)—1H-pyrazol-3-yl |
| 1-Ph—1H-pyrazol-3-yl | 1,4-di-Me—1H-pyrazol-3-yl | 1-Me-4-CF₃—1H-pyrazol-3-yl |
| 1-Me—1H-pyrazol-4-yl | 1-CF₃—1H-pyrazol-4-yl | 1-Et—1H-pyrazol-4-yl |
| 1-i-Pr—1H-pyrazol-4-yl | 1-(F₃CCH₂)—1H-pyrazol-4-yl | 1-Ph—1H-pyrazol-4-yl |
| 1,3-di-Me—1H-pyrazol-4-yl | 1-Me-3-CF₃—1H-pyrazol-4-yl | 3-Me-1-CF₃—1H-pyrazol-4-yl |
| 1-Me—1H-[1,2,4]triazol-3-yl | 1-CF₃—1H-[1,2,4]triazol-3-yl | 1-Et—1H-[1,2,4]triazol-3-yl |
| 1-i-Pr—1H-[1,2,4]triazol-3-yl | 1-Ph—1H-[1,2,4]triazol-3-yl | 5-Ph-4,5-dihydro-isoxazol-3-yl |
| 5-CF₃-2,4-dihydro-3-oxopyrazol-1-yl | 5-Me-2,4-dihydro-3-oxopyrazol-1-yl | |

The present disclosure also includes Tables 1730 through 2304, each of which is constructed the same as Table 1729 above, except that the row heading in Table 1729 (i.e. "A is A-1a, (R²)ₙ is H, and G is CH.") is replaced with the respective row heading shown below. For example, in Table 1730 the row heading is "A is A-1a, (R²)ₙ is 3-F, and G is CH." and Q is as defined in Table 1 above. Thus, the first entry in Table 1730 specifically discloses N-[3',6-difluoro-4'-[3-(trifluoromethyl)-1H-pyrazol-1-yl][1,1'-biphenyl]-2-yl]-2-(trifluoromethyl)benzamide. Tables 1731 through 2304 are constructed similarly.

TABLES 1730-2304

| Table | Row Heading |
|---|---|
| 1730 | A is A-1a, (R²)ₙ is 3-F and G is CH. |
| 1731 | A is A-1a, (R²)ₙ is 3,5-di-F and G is CH. |
| 1732 | A is A-1a, (R²)ₙ is 3-Cl and G is CH. |
| 1733 | A is A-1a, (R²)ₙ is 3,5-di-Cl and G is CH. |
| 1734 | A is A-1a, (R²)ₙ is 3-Br and G is CH. |
| 1735 | A is A-1a, (R²)ₙ is 3,5-di-Br and G is CH. |
| 1736 | A is A-1a, (R²)ₙ is 3-Me and G is CH. |
| 1737 | A is A-1a, (R²)ₙ is 3,5-di-Me and G is CH. |
| 1738 | A is A-1a, (R²)ₙ is 3-CF₃ and G is CH. |
| 1739 | A is A-1a, (R²)ₙ is 3,5-di-CF₃ and G is CH. |

TABLES 1730-2304-continued

| Table | Row Heading |
|---|---|
| 1740 | A is A-1a, $(R^2)_n$ is 3-MeO and G is CH. |
| 1741 | A is A-1a, $(R^2)_n$ is 3,5-di-MeO and G is CH. |
| 1742 | A is A-1a, $(R^2)_n$ is 3-CN and G is CH. |
| 1743 | A is A-1a, $(R^2)_n$ is 3,5-di-CN and G is CH. |
| 1744 | A is A-1a, $(R^2)_n$ is 3,6-di-F and G is CH. |
| 1745 | A is A-1a, $(R^2)_n$ is 3,6-di-Cl and G is CH. |
| 1746 | A is A-1a, $(R^2)_n$ is 3,6-di-Br and G is CH. |
| 1747 | A is A-1a, $(R^2)_n$ is 3,6-di-Me and G is CH. |
| 1748 | A is A-1a, $(R^2)_n$ is 3,6-di-CF$_3$ and G is CH. |
| 1749 | A is A-1a, $(R^2)_n$ is 3,6-di-MeO and G is CH. |
| 1750 | A is A-1a, $(R^2)_n$ is 3,6-di-CN and G is CH. |
| 1751 | A is A-1a, $(R^2)_n$ is 6-F and G is CH. |
| 1752 | A is A-1a, $(R^2)_n$ is 6-Cl and G is CH. |
| 1753 | A is A-1a, $(R^2)_n$ is 6-Br and G is CH. |
| 1754 | A is A-1a, $(R^2)_n$ is 6-Me and G is CH. |
| 1755 | A is A-1a, $(R^2)_n$ is 6-CF$_3$ and G is CH. |
| 1756 | A is A-1a, $(R^2)_n$ is 6-MeO and G is CH. |
| 1757 | A is A-1a, $(R^2)_n$ is 6-CN and G is CH. |
| 1758 | A is A-1a, $(R^2)_n$ is 6-F and G is C—F. |
| 1759 | A is A-1a, $(R^2)_n$ is 6-Cl and G is C—Cl. |
| 1760 | A is A-1a, $(R^2)_n$ is 6-Br and G is C—Br. |
| 1761 | A is A-1a, $(R^2)_n$ is 6-Me and G is C—Me. |
| 1762 | A is A-1a, $(R^2)_n$ is 6-CF$_3$ and G is C—CF$_3$. |
| 1763 | A is A-1a, $(R^2)_n$ is 6-MeO and G is C—OMe. |
| 1764 | A is A-1a, $(R^2)_n$ is H and G is N. |
| 1765 | A is A-1a, $(R^2)_n$ is 3-F and G is N. |
| 1766 | A is A-1a, $(R^2)_n$ is 3,5-di-F and G is N. |
| 1767 | A is A-1a, $(R^2)_n$ is 3-Cl and G is N. |
| 1768 | A is A-1a, $(R^2)_n$ is 3,5-di-Cl and G is N. |
| 1769 | A is A-1a, $(R^2)_n$ is 3-Br and G is N. |
| 1770 | A is A-1a, $(R^2)_n$ is 3,5-di-Br and G is N. |
| 1771 | A is A-1a, $(R^2)_n$ is 3-Me and G is N. |
| 1772 | A is A-1a, $(R^2)_n$ is 3,5-di-Me and G is N. |
| 1773 | A is A-1a, $(R^2)_n$ is 3-CF$_3$ and G is N. |
| 1774 | A is A-1a, $(R^2)_n$ is 3,5-di-CF$_3$ and G is N. |
| 1775 | A is A-1a, $(R^2)_n$ is 3-MeO and G is N. |
| 1776 | A is A-1a, $(R^2)_n$ is 3,5-di-MeO and G is N. |
| 1777 | A is A-1a, $(R^2)_n$ is 3-CN and G is N. |
| 1778 | A is A-1a, $(R^2)_n$ is 3,5-di-CN and G is N. |
| 1779 | A is A-1a, $(R^2)_n$ is 3,6-di-F and G is N. |
| 1780 | A is A-1a, $(R^2)_n$ is 3,6-di-Cl and G is N. |
| 1781 | A is A-1a, $(R^2)_n$ is 3,6-di-Br and G is N. |
| 1782 | A is A-1a, $(R^2)_n$ is 3,6-di-Me and G is N. |
| 1783 | A is A-1a, $(R^2)_n$ is 3,6-di-CF$_3$ and G is N. |
| 1784 | A is A-1a, $(R^2)_n$ is 3,6-di-MeO and G is N. |
| 1785 | A is A-1a, $(R^2)_n$ is 3,6-di-CN and G is N. |
| 1786 | A is A-1a, $(R^2)_n$ is 6-F and G is N. |
| 1787 | A is A-1a, $(R^2)_n$ is 6-Cl and G is N. |
| 1788 | A is A-1a, $(R^2)_n$ is 6-Br and G is N. |
| 1789 | A is A-1a, $(R^2)_n$ is 6-Me and G is N. |
| 1790 | A is A-1a, $(R^2)_n$ is 6-CF$_3$ and G is N. |
| 1791 | A is A-1a, $(R^2)_n$ is 6-MeO and G is N. |
| 1792 | A is A-1a, $(R^2)_n$ is 6-CN and G is N. |
| 1793 | A is A-1b, $(R^2)_n$ is H and G is CH. |
| 1794 | A is A-1b, $(R^2)_n$ is 3-F and G is CH. |
| 1795 | A is A-1b, $(R^2)_n$ is 3,5-di-F and G is CH. |
| 1796 | A is A-1b, $(R^2)_n$ is 3-Cl and G is CH. |
| 1797 | A is A-1b, $(R^2)_n$ is 3,5-di-Cl and G is CH. |
| 1798 | A is A-1b, $(R^2)_n$ is 3-Br and G is CH. |
| 1799 | A is A-1b, $(R^2)_n$ is 3,5-di-Br and G is CH. |
| 1800 | A is A-1b, $(R^2)_n$ is 3-Me and G is CH. |
| 1801 | A is A-1b, $(R^2)_n$ is 3,5-di-Me and G is CH. |
| 1802 | A is A-1b, $(R^2)_n$ is 3-CF$_3$ and G is CH. |
| 1803 | A is A-1b, $(R^2)_n$ is 3,5-di-CF$_3$ and G is CH. |
| 1804 | A is A-1b, $(R^2)_n$ is 3-MeO and G is CH. |
| 1805 | A is A-1b, $(R^2)_n$ is 3,5-di-MeO and G is CH. |
| 1806 | A is A-1b, $(R^2)_n$ is 3-CN and G is CH. |
| 1807 | A is A-1b, $(R^2)_n$ is 3,5-di-CN and G is CH. |
| 1808 | A is A-1b, $(R^2)_n$ is 3,6-di-F and G is CH. |
| 1809 | A is A-1b, $(R^2)_n$ is 3,6-di-Cl and G is CH. |
| 1810 | A is A-1b, $(R^2)_n$ is 3,6-di-Br and G is CH. |
| 1811 | A is A-1b, $(R^2)_n$ is 3,6-di-Me and G is CH. |
| 1812 | A is A-1b, $(R^2)_n$ is 3,6-di-CF$_3$ and G is CH. |
| 1813 | A is A-1b, $(R^2)_n$ is 3,6-di-MeO and G is CH. |
| 1814 | A is A-1b, $(R^2)_n$ is 3,6-di-CN and G is CH. |
| 1815 | A is A-1b, $(R^2)_n$ is 6-F and G is CH. |
| 1816 | A is A-1b, $(R^2)_n$ is 6-Cl and G is CH. |
| 1817 | A is A-1b, $(R^2)_n$ is 6-Br and G is CH. |
| 1818 | A is A-1b, $(R^2)_n$ is 6-Me and G is CH. |
| 1819 | A is A-1b, $(R^2)_n$ is 6-CF$_3$ and G is CH. |
| 1820 | A is A-1b, $(R^2)_n$ is 6-MeO and G is CH. |
| 1821 | A is A-1b, $(R^2)_n$ is 6-CN and G is CH. |
| 1822 | A is A-1b, $(R^2)_n$ is 6-F and G is C—F. |
| 1823 | A is A-1b, $(R^2)_n$ is 6-Cl and G is C—Cl. |
| 1824 | A is A-1b, $(R^2)_n$ is 6-Br and G is C—Br. |
| 1825 | A is A-1b, $(R^2)_n$ is 6-Me and G is C—Me. |
| 1826 | A is A-1b, $(R^2)_n$ is 6-CF$_3$ and G is C—CF$_3$. |
| 1827 | A is A-1b, $(R^2)_n$ is 6-MeO and G is C—OMe. |
| 1828 | A is A-1b, $(R^2)_n$ is H and G is N. |
| 1829 | A is A-1b, $(R^2)_n$ is 3-F and G is N. |
| 1830 | A is A-1b, $(R^2)_n$ is 3,5-di-F and G is N. |
| 1831 | A is A-1b, $(R^2)_n$ is 3-Cl and G is N. |
| 1832 | A is A-1b, $(R^2)_n$ is 3,5-di-Cl and G is N. |
| 1833 | A is A-1b, $(R^2)_n$ is 3-Br and G is N. |
| 1834 | A is A-1b, $(R^2)_n$ is 3,5-di-Br and G is N. |
| 1835 | A is A-1b, $(R^2)_n$ is 3-Me and G is N. |
| 1836 | A is A-1b, $(R^2)_n$ is 3,5-di-Me and G is N. |
| 1837 | A is A-1b, $(R^2)_n$ is 3-CF$_3$ and G is N. |
| 1838 | A is A-1b, $(R^2)_n$ is 3,5-di-CF$_3$ and G is N. |
| 1839 | A is A-1b, $(R^2)_n$ is 3-MeO and G is N. |
| 1840 | A is A-1b, $(R^2)_n$ is 3,5-di-MeO and G is N. |
| 1841 | A is A-1b, $(R^2)_n$ is 3-CN and G is N. |
| 1842 | A is A-1b, $(R^2)_n$ is 3,5-di-CN and G is N. |
| 1843 | A is A-1b, $(R^2)_n$ is 3,6-di-F and G is N. |
| 1844 | A is A-1b, $(R^2)_n$ is 3,6-di-Cl and G is N. |
| 1845 | A is A-1b, $(R^2)_n$ is 3,6-di-Br and G is N. |
| 1846 | A is A-1b, $(R^2)_n$ is 3,6-di-Me and G is N. |
| 1847 | A is A-1b, $(R^2)_n$ is 3,6-di-CF$_3$ and G is N. |
| 1848 | A is A-1b, $(R^2)_n$ is 3,6-di-MeO and G is N. |
| 1849 | A is A-1b, $(R^2)_n$ is 3,6-di-CN and G is N. |
| 1850 | A is A-1b, $(R^2)_n$ is 6-F and G is N. |
| 1851 | A is A-1b, $(R^2)_n$ is 6-Cl and G is N. |
| 1852 | A is A-1b, $(R^2)_n$ is 6-Br and G is N. |
| 1853 | A is A-1b, $(R^2)_n$ is 6-Me and G is N. |
| 1854 | A is A-1b, $(R^2)_n$ is 6-CF$_3$ and G is N. |
| 1855 | A is A-1b, $(R^2)_n$ is 6-MeO and G is N. |
| 1856 | A is A-1b, $(R^2)_n$ is 6-CN and G is N. |
| 1857 | A is A-1c, $(R^2)_n$ is H and G is CH. |
| 1858 | A is A-1c, $(R^2)_n$ is 3-F and G is CH. |
| 1859 | A is A-1c, $(R^2)_n$ is 3,5-di-F and G is CH. |
| 1860 | A is A-1c, $(R^2)_n$ is 3-Cl and G is CH. |
| 1861 | A is A-1c, $(R^2)_n$ is 3,5-di-Cl and G is CH. |
| 1862 | A is A-1c, $(R^2)_n$ is 3-Br and G is CH. |
| 1863 | A is A-1c, $(R^2)_n$ is 3,5-di-Br and G is CH. |
| 1864 | A is A-1c, $(R^2)_n$ is 3-Me and G is CH. |
| 1865 | A is A-1c, $(R^2)_n$ is 3,5-di-Me and G is CH. |
| 1866 | A is A-1c, $(R^2)_n$ is 3-CF$_3$ and G is CH. |
| 1867 | A is A-1c, $(R^2)_n$ is 3,5-di-CF$_3$ and G is CH. |
| 1868 | A is A-1c, $(R^2)_n$ is 3-MeO and G is CH. |
| 1869 | A is A-1c, $(R^2)_n$ is 3,5-di-MeO and G is CH. |
| 1870 | A is A-1c, $(R^2)_n$ is 3-CN and G is CH. |
| 1871 | A is A-1c, $(R^2)_n$ is 3,5-di-CN and G is CH. |
| 1872 | A is A-1c, $(R^2)_n$ is 3,6-di-F and G is CH. |
| 1873 | A is A-1c, $(R^2)_n$ is 3,6-di-Cl and G is CH. |
| 1874 | A is A-1c, $(R^2)_n$ is 3,6-di-Br and G is CH. |
| 1875 | A is A-1c, $(R^2)_n$ is 3,6-di-Me and G is CH. |
| 1876 | A is A-1c, $(R^2)_n$ is 3,6-di-CF$_3$ and G is CH. |
| 1877 | A is A-1c, $(R^2)_n$ is 3,6-di-MeO and G is CH. |
| 1878 | A is A-1c, $(R^2)_n$ is 3,6-di-CN and G is CH. |
| 1879 | A is A-1c, $(R^2)_n$ is 6-F and G is CH. |
| 1880 | A is A-1c, $(R^2)_n$ is 6-Cl and G is CH. |
| 1881 | A is A-1c, $(R^2)_n$ is 6-Br and G is CH. |
| 1882 | A is A-1c, $(R^2)_n$ is 6-Me and G is CH. |
| 1883 | A is A-1c, $(R^2)_n$ is 6-CF$_3$ and G is CH. |

TABLES 1730-2304-continued

| Table | Row Heading |
|---|---|
| 1884 | A is A-1c, $(R^2)_n$ is 6-MeO and G is CH. |
| 1885 | A is A-1c, $(R^2)_n$ is 6-CN and G is CH. |
| 1886 | A is A-1c, $(R^2)_n$ is 6-F and G is C—F. |
| 1887 | A is A-1c, $(R^2)_n$ is 6-Cl and G is C—Cl. |
| 1888 | A is A-1c, $(R^2)_n$ is 6-Br and G is C—Br. |
| 1889 | A is A-1c, $(R^2)_n$ is 6-Me and G is C—Me. |
| 1890 | A is A-1c, $(R^2)_n$ is 6-CF$_3$ and G is C—CF$_3$. |
| 1891 | A is A-1c, $(R^2)_n$ is 6-MeO and G is C—OMe. |
| 1892 | A is A-1c, $(R^2)_n$ is H and G is N. |
| 1893 | A is A-1c, $(R^2)_n$ is 3-F and G is N. |
| 1894 | A is A-1c, $(R^2)_n$ is 3,5-di-F and G is N. |
| 1895 | A is A-1c, $(R^2)_n$ is 3-Cl and G is N. |
| 1896 | A is A-1c, $(R^2)_n$ is 3,5-di-Cl and G is N. |
| 1897 | A is A-1c, $(R^2)_n$ is 3-Br and G is N. |
| 1898 | A is A-1c, $(R^2)_n$ is 3,5-di-Br and G is N. |
| 1899 | A is A-1c, $(R^2)_n$ is 3-Me and G is N. |
| 1900 | A is A-1c, $(R^2)_n$ is 3,5-di-Me and G is N. |
| 1901 | A is A-1c, $(R^2)_n$ is 3-CF$_3$ and G is N. |
| 1902 | A is A-1c, $(R^2)_n$ is 3,5-di-CF$_3$ and G is N. |
| 1903 | A is A-1c, $(R^2)_n$ is 3-MeO and G is N. |
| 1904 | A is A-1c, $(R^2)_n$ is 3,5-di-MeO and G is N. |
| 1905 | A is A-1c, $(R^2)_n$ is 3-CN and G is N. |
| 1906 | A is A-1c, $(R^2)_n$ is 3,5-di-CN and G is N. |
| 1907 | A is A-1c, $(R^2)_n$ is 3,6-di-F and G is N. |
| 1908 | A is A-1c, $(R^2)_n$ is 3,6-di-Cl and G is N. |
| 1909 | A is A-1c, $(R^2)_n$ is 3,6-di-Br and G is N. |
| 1910 | A is A-1c, $(R^2)_n$ is 3,6-di-Me and G is N. |
| 1911 | A is A-1c, $(R^2)_n$ is 3,6-di-CF$_3$ and G is N. |
| 1912 | A is A-1c, $(R^2)_n$ is 3,6-di-MeO and G is N. |
| 1913 | A is A-1c, $(R^2)_n$ is 3,6-di-CN and G is N. |
| 1914 | A is A-1c, $(R^2)_n$ is 6-F and G is N. |
| 1915 | A is A-1c, $(R^2)_n$ is 6-Cl and G is N. |
| 1916 | A is A-1c, $(R^2)_n$ is 6-Br and G is N. |
| 1917 | A is A-1c, $(R^2)_n$ is 6-Me and G is N. |
| 1918 | A is A-1c, $(R^2)_n$ is 6-CF$_3$ and G is N. |
| 1919 | A is A-1c, $(R^2)_n$ is 6-MeO and G is N. |
| 1920 | A is A-1c, $(R^2)_n$ is 6-CN and G is N. |
| 1921 | A is A-1d, $(R^2)_n$ is H and G is CH. |
| 1922 | A is A-1d, $(R^2)_n$ is 3-F and G is CH. |
| 1923 | A is A-1d, $(R^2)_n$ is 3,5-di-F and G is CH. |
| 1924 | A is A-1d, $(R^2)_n$ is 3-Cl and G is CH. |
| 1925 | A is A-1d, $(R^2)_n$ is 3,5-di-Cl and G is CH. |
| 1926 | A is A-1d, $(R^2)_n$ is 3-Br and G is CH. |
| 1927 | A is A-1d, $(R^2)_n$ is 3,5-di-Br and G is CH. |
| 1928 | A is A-1d, $(R^2)_n$ is 3-Me and G is CH. |
| 1929 | A is A-1d, $(R^2)_n$ is 3,5-di-Me and G is CH. |
| 1930 | A is A-1d, $(R^2)_n$ is 3-CF$_3$ and G is CH. |
| 1931 | A is A-1d, $(R^2)_n$ is 3,5-di-CF$_3$ and G is CH. |
| 1932 | A is A-1d, $(R^2)_n$ is 3-MeO and G is CH. |
| 1933 | A is A-1d, $(R^2)_n$ is 3,5-di-MeO and G is CH. |
| 1934 | A is A-1d, $(R^2)_n$ is 3-CN and G is CH. |
| 1935 | A is A-1d, $(R^2)_n$ is 3,5-di-CN and G is CH. |
| 1936 | A is A-1d, $(R^2)_n$ is 3,6-di-F and G is CH. |
| 1937 | A is A-1d, $(R^2)_n$ is 3,6-di-Cl and G is CH. |
| 1938 | A is A-1d, $(R^2)_n$ is 3,6-di-Br and G is CH. |
| 1939 | A is A-1d, $(R^2)_n$ is 3,6-di-Me and G is CH. |
| 1940 | A is A-1d, $(R^2)_n$ is 3,6-di-CF$_3$ and G is CH. |
| 1941 | A is A-1d, $(R^2)_n$ is 3,6-di-MeO and G is CH. |
| 1942 | A is A-1d, $(R^2)_n$ is 3,6-di-CN and G is CH. |
| 1943 | A is A-1d, $(R^2)_n$ is 6-F and G is CH. |
| 1944 | A is A-1d, $(R^2)_n$ is 6-Cl and G is CH. |
| 1945 | A is A-1d, $(R^2)_n$ is 6-Br and G is CH. |
| 1946 | A is A-1d, $(R^2)_n$ is 6-Me and G is CH. |
| 1947 | A is A-1d, $(R^2)_n$ is 6-CF$_3$ and G is CH. |
| 1948 | A is A-1d, $(R^2)_n$ is 6-MeO and G is CH. |
| 1949 | A is A-1d, $(R^2)_n$ is 6-CN and G is CH. |
| 1950 | A is A-1d, $(R^2)_n$ is 6-F and G is C—F. |
| 1951 | A is A-1d, $(R^2)_n$ is 6-Cl and G is C—Cl. |
| 1952 | A is A-1d, $(R^2)_n$ is 6-Br and G is C—Br. |
| 1953 | A is A-1d, $(R^2)_n$ is 6-Me and G is C—Me. |
| 1954 | A is A-1d, $(R^2)_n$ is 6-CF$_3$ and G is C—CF$_3$. |
| 1955 | A is A-1d, $(R^2)_n$ is 6-MeO and G is C—OMe. |
| 1956 | A is A-1d, $(R^2)_n$ is H and G is N. |
| 1957 | A is A-1d, $(R^2)_n$ is 3-F and G is N. |
| 1958 | A is A-1d, $(R^2)_n$ is 3,5-di-F and G is N. |
| 1959 | A is A-1d, $(R^2)_n$ is 3-Cl and G is N. |
| 1960 | A is A-1d, $(R^2)_n$ is 3,5-di-Cl and G is N. |
| 1961 | A is A-1d, $(R^2)_n$ is 3-Br and G is N. |
| 1962 | A is A-1d, $(R^2)_n$ is 3,5-di-Br and G is N. |
| 1963 | A is A-1d, $(R^2)_n$ is 3-Me and G is N. |
| 1964 | A is A-1d, $(R^2)_n$ is 3,5-di-Me and G is N. |
| 1965 | A is A-1d, $(R^2)_n$ is 3-CF$_3$ and G is N. |
| 1966 | A is A-1d, $(R^2)_n$ is 3,5-di-CF$_3$ and G is N. |
| 1967 | A is A-1d, $(R^2)_n$ is 3-MeO and G is N. |
| 1968 | A is A-1d, $(R^2)_n$ is 3,5-di-MeO and G is N. |
| 1969 | A is A-1d, $(R^2)_n$ is 3-CN and G is N. |
| 1970 | A is A-1d, $(R^2)_n$ is 3,5-di-CN and G is N. |
| 1971 | A is A-1d, $(R^2)_n$ is 3,6-di-F and G is N. |
| 1972 | A is A-1d, $(R^2)_n$ is 3,6-di-Cl and G is N. |
| 1973 | A is A-1d, $(R^2)_n$ is 3,6-di-Br and G is N. |
| 1974 | A is A-1d, $(R^2)_n$ is 3,6-di-Me and G is N. |
| 1975 | A is A-1d, $(R^2)_n$ is 3,6-di-CF$_3$ and G is N. |
| 1976 | A is A-1d, $(R^2)_n$ is 3,6-di-MeO and G is N. |
| 1977 | A is A-1d, $(R^2)_n$ is 3,6-di-CN and G is N. |
| 1978 | A is A-1d, $(R^2)_n$ is 6-F and G is N. |
| 1979 | A is A-1d, $(R^2)_n$ is 6-Cl and G is N. |
| 1980 | A is A-1d, $(R^2)_n$ is 6-Br and G is N. |
| 1981 | A is A-1d, $(R^2)_n$ is 6-Me and G is N. |
| 1982 | A is A-1d, $(R^2)_n$ is 6-CF$_3$ and G is N. |
| 1983 | A is A-1d, $(R^2)_n$ is 6-MeO and G is N. |
| 1984 | A is A-1d, $(R^2)_n$ is 6-CN and G is N. |
| 1985 | A is A-1e, $(R^2)_n$ is H and G is CH. |
| 1986 | A is A-1e, $(R^2)_n$ is 3-F and G is CH. |
| 1987 | A is A-1e, $(R^2)_n$ is 3,5-di-F and G is CH. |
| 1988 | A is A-1e, $(R^2)_n$ is 3-Cl and G is CH. |
| 1989 | A is A-1e, $(R^2)_n$ is 3,5-di-Cl and G is CH. |
| 1990 | A is A-1e, $(R^2)_n$ is 3-Br and G is CH. |
| 1991 | A is A-1e, $(R^2)_n$ is 3,5-di-Br and G is CH. |
| 1992 | A is A-1e, $(R^2)_n$ is 3-Me and G is CH. |
| 1993 | A is A-1e, $(R^2)_n$ is 3,5-di-Me and G is CH. |
| 1994 | A is A-1e, $(R^2)_n$ is 3-CF$_3$ and G is CH. |
| 1995 | A is A-1e, $(R^2)_n$ is 3,5-di-CF$_3$ and G is CH. |
| 1996 | A is A-1e, $(R^2)_n$ is 3-MeO and G is CH. |
| 1997 | A is A-1e, $(R^2)_n$ is 3,5-di-MeO and G is CH. |
| 1998 | A is A-1e, $(R^2)_n$ is 3-CN and G is CH. |
| 1999 | A is A-1e, $(R^2)_n$ is 3,5-di-CN and G is CH. |
| 2000 | A is A-1e, $(R^2)_n$ is 3,6-di-F and G is CH. |
| 2001 | A is A-1e, $(R^2)_n$ is 3,6-di-Cl and G is CH. |
| 2002 | A is A-1e, $(R^2)_n$ is 3,6-di-Br and G is CH. |
| 2003 | A is A-1e, $(R^2)_n$ is 3,6-di-Me and G is CH. |
| 2004 | A is A-1e, $(R^2)_n$ is 3,6-di-CF$_3$ and G is CH. |
| 2005 | A is A-1e, $(R^2)_n$ is 3,6-di-MeO and G is CH. |
| 2006 | A is A-1e, $(R^2)_n$ is 3,6-di-CN and G is CH. |
| 2007 | A is A-1e, $(R^2)_n$ is 6-F and G is CH. |
| 2008 | A is A-1e, $(R^2)_n$ is 6-Cl and G is CH. |
| 2009 | A is A-1e, $(R^2)_n$ is 6-Br and G is CH. |
| 2010 | A is A-1e, $(R^2)_n$ is 6-Me and G is CH. |
| 2011 | A is A-1e, $(R^2)_n$ is 6-CF$_3$ and G is CH. |
| 2012 | A is A-1e, $(R^2)_n$ is 6-MeO and G is CH. |
| 2013 | A is A-1e, $(R^2)_n$ is 6-CN and G is CH. |
| 2014 | A is A-1e, $(R^2)_n$ is 6-F and G is C—F. |
| 2015 | A is A-1e, $(R^2)_n$ is 6-Cl and G is C—Cl. |
| 2016 | A is A-1e, $(R^2)_n$ is 6-Br and G is C—Br. |
| 2017 | A is A-1e, $(R^2)_n$ is 6-Me and G is C—Me. |
| 2018 | A is A-1e, $(R^2)_n$ is 6-CF$_3$ and G is C—CF$_3$. |
| 2019 | A is A-1e, $(R^2)_n$ is 6-MeO and G is C—OMe. |
| 2020 | A is A-1e, $(R^2)_n$ is H and G is N. |
| 2021 | A is A-1e, $(R^2)_n$ is 3-F and G is N. |
| 2022 | A is A-1e, $(R^2)_n$ is 3,5-di-F and G is N. |
| 2023 | A is A-1e, $(R^2)_n$ is 3-Cl and G is N. |
| 2024 | A is A-1e, $(R^2)_n$ is 3,5-di-Cl and G is N. |
| 2025 | A is A-1e, $(R^2)_n$ is 3-Br and G is N. |
| 2026 | A is A-1e, $(R^2)_n$ is 3,5-di-Br and G is N. |
| 2027 | A is A-1e, $(R^2)_n$ is 3-Me and G is N. |
| 2028 | A is A-1e, $(R^2)_n$ is 3,5-di-Me and G is N. |
| 2029 | A is A-1e, $(R^2)_n$ is 3-CF$_3$ and G is N. |
| 2030 | A is A-1e, $(R^2)_n$ is 3,5-di-CF$_3$ and G is N. |
| 2031 | A is A-1e, $(R^2)_n$ is 3-MeO and G is N. |

TABLES 1730-2304-continued

| Table | Row Heading |
|---|---|
| 2032 | A is A-1e, $(R^2)_n$ is 3,5-di-MeO and G is N. |
| 2033 | A is A-1e, $(R^2)_n$ is 3-CN and G is N. |
| 2034 | A is A-1e, $(R^2)_n$ is 3,5-di-CN and G is N. |
| 2035 | A is A-1e, $(R^2)_n$ is 3,6-di-F and G is N. |
| 2036 | A is A-1e, $(R^2)_n$ is 3,6-di-Cl and G is N. |
| 2037 | A is A-1e, $(R^2)_n$ is 3,6-di-Br and G is N. |
| 2038 | A is A-1e, $(R^2)_n$ is 3,6-di-Me and G is N. |
| 2039 | A is A-1e, $(R^2)_n$ is 3,6-di-CF$_3$ and G is N. |
| 2040 | A is A-1e, $(R^2)_n$ is 3,6-di-MeO and G is N. |
| 2041 | A is A-1e, $(R^2)_n$ is 3,6-di-CN and G is N. |
| 2042 | A is A-1e, $(R^2)_n$ is 6-F and G is N. |
| 2043 | A is A-1e, $(R^2)_n$ is 6-Cl and G is N. |
| 2044 | A is A-1e, $(R^2)_n$ is 6-Br and G is N. |
| 2045 | A is A-1e, $(R^2)_n$ is 6-Me and G is N. |
| 2046 | A is A-1e, $(R^2)_n$ is 6-CF$_3$ and G is N. |
| 2047 | A is A-1e, $(R^2)_n$ is 6-MeO and G is N. |
| 2048 | A is A-1e, $(R^2)_n$ is 6-CN and G is N. |
| 2049 | A is A-1f, $(R^2)_n$ is H and G is CH. |
| 2050 | A is A-1f, $(R^2)_n$ is 3-F and G is CH. |
| 2051 | A is A-1f, $(R^2)_n$ is 3,5-di-F and G is CH. |
| 2052 | A is A-1f, $(R^2)_n$ is 3-Cl and G is CH. |
| 2053 | A is A-1f, $(R^2)_n$ is 3,5-di-Cl and G is CH. |
| 2054 | A is A-1f, $(R^2)_n$ is 3-Br and G is CH. |
| 2055 | A is A-1f, $(R^2)_n$ is 3,5-di-Br and G is CH. |
| 2056 | A is A-1f, $(R^2)_n$ is 3-Me and G is CH. |
| 2057 | A is A-1f, $(R^2)_n$ is 3,5-di-Me and G is CH. |
| 2058 | A is A-1f, $(R^2)_n$ is 3-CF$_3$ and G is CH. |
| 2059 | A is A-1f, $(R^2)_n$ is 3,5-di-CF$_3$ and G is CH. |
| 2060 | A is A-1f, $(R^2)_n$ is 3-MeO and G is CH. |
| 2061 | A is A-1f, $(R^2)_n$ is 3,5-di-MeO and G is CH. |
| 2062 | A is A-1f, $(R^2)_n$ is 3-CN and G is CH. |
| 2063 | A is A-1f, $(R^2)_n$ is 3,5-di-CN and G is CH. |
| 2064 | A is A-1f, $(R^2)_n$ is 3,6-di-F and G is CH. |
| 2065 | A is A-1f, $(R^2)_n$ is 3,6-di-Cl and G is CH. |
| 2066 | A is A-1f, $(R^2)_n$ is 3,6-di-Br and G is CH. |
| 2067 | A is A-1f, $(R^2)_n$ is 3,6-di-Me and G is CH. |
| 2068 | A is A-1f, $(R^2)_n$ is 3,6-di-CF$_3$ and G is CH. |
| 2069 | A is A-1f, $(R^2)_n$ is 3,6-di-MeO and G is CH. |
| 2070 | A is A-1f, $(R^2)_n$ is 3,6-di-CN and G is CH. |
| 2071 | A is A-1f, $(R^2)_n$ is 6-F and G is CH. |
| 2072 | A is A-1f, $(R^2)_n$ is 6-Cl and G is CH. |
| 2073 | A is A-1f, $(R^2)_n$ is 6-Br and G is CH. |
| 2074 | A is A-1f, $(R^2)_n$ is 6-Me and G is CH. |
| 2075 | A is A-1f, $(R^2)_n$ is 6-CF$_3$ and G is CH. |
| 2076 | A is A-1f, $(R^2)_n$ is 6-MeO and G is CH. |
| 2077 | A is A-1f, $(R^2)_n$ is 6-CN and G is CH. |
| 2078 | A is A-1f, $(R^2)_n$ is 6-F and G is C—F. |
| 2079 | A is A-1f, $(R^2)_n$ is 6-Cl and G is C—Cl. |
| 2080 | A is A-1f, $(R^2)_n$ is 6-Br and G is C—Br. |
| 2081 | A is A-1f, $(R^2)_n$ is 6-Me and G is C—Me. |
| 2082 | A is A-1f, $(R^2)_n$ is 6-CF$_3$ and G is C—CF$_3$. |
| 2083 | A is A-1f, $(R^2)_n$ is 6-MeO and G is C—OMe. |
| 2084 | A is A-1f, $(R^2)_n$ is H and G is N. |
| 2085 | A is A-1f, $(R^2)_n$ is 3-F and G is N. |
| 2086 | A is A-1f, $(R^2)_n$ is 3,5-di-F and G is N. |
| 2087 | A is A-1f, $(R^2)_n$ is 3-Cl and G is N. |
| 2088 | A is A-1f, $(R^2)_n$ is 3,5-di-Cl and G is N. |
| 2089 | A is A-1f, $(R^2)_n$ is 3-Br and G is N. |
| 2090 | A is A-1f, $(R^2)_n$ is 3,5-di-Br and G is N. |
| 2091 | A is A-1f, $(R^2)_n$ is 3-Me and G is N. |
| 2092 | A is A-1f, $(R^2)_n$ is 3,5-di-Me and G is N. |
| 2093 | A is A-1f, $(R^2)_n$ is 3-CF$_3$ and G is N. |
| 2094 | A is A-1f, $(R^2)_n$ is 3,5-di-CF$_3$ and G is N. |
| 2095 | A is A-1f, $(R^2)_n$ is 3-MeO and G is N. |
| 2096 | A is A-1f, $(R^2)_n$ is 3,5-di-MeO and G is N. |
| 2097 | A is A-1f, $(R^2)_n$ is 3-CN and G is N. |
| 2098 | A is A-1f, $(R^2)_n$ is 3,5-di-CN and G is N. |
| 2099 | A is A-1f, $(R^2)_n$ is 3,6-di-F and G is N. |
| 2100 | A is A-1f, $(R^2)_n$ is 3,6-di-Cl and G is N. |
| 2101 | A is A-1f, $(R^2)_n$ is 3,6-di-Br and G is N. |
| 2102 | A is A-1f, $(R^2)_n$ is 3,6-di-Me and G is N. |
| 2103 | A is A-1f, $(R^2)_n$ is 3,6-di-CF$_3$ and G is N. |
| 2104 | A is A-1f, $(R^2)_n$ is 3,6-di-MeO and G is N. |
| 2105 | A is A-1f, $(R^2)_n$ is 3,6-di-CN and G is N. |
| 2106 | A is A-1f, $(R^2)_n$ is 6-F and G is N. |
| 2107 | A is A-1f, $(R^2)_n$ is 6-Cl and G is N. |
| 2108 | A is A-1f, $(R^2)_n$ is 6-Br and G is N. |
| 2109 | A is A-1f, $(R^2)_n$ is 6-Me and G is N. |
| 2110 | A is A-1f, $(R^2)_n$ is 6-CF$_3$ and G is N. |
| 2111 | A is A-1f, $(R^2)_n$ is 6-MeO and G is N. |
| 2112 | A is A-1f, $(R^2)_n$ is 6-CN and G is N. |
| 2113 | A is A-2a, $(R^2)_n$ is H and G is CH. |
| 2114 | A is A-2a, $(R^2)_n$ is 3-F and G is CH. |
| 2115 | A is A-2a, $(R^2)_n$ is 3,5-di-F and G is CH. |
| 2116 | A is A-2a, $(R^2)_n$ is 3-Cl and G is CH. |
| 2117 | A is A-2a, $(R^2)_n$ is 3,5-di-Cl and G is CH. |
| 2118 | A is A-2a, $(R^2)_n$ is 3-Br and G is CH. |
| 2119 | A is A-2a, $(R^2)_n$ is 3,5-di-Br and G is CH. |
| 2120 | A is A-2a, $(R^2)_n$ is 3-Me and G is CH. |
| 2121 | A is A-2a, $(R^2)_n$ is 3,5-di-Me and G is CH. |
| 2122 | A is A-2a, $(R^2)_n$ is 3-CF$_3$ and G is CH. |
| 2123 | A is A-2a, $(R^2)_n$ is 3,5-di-CF$_3$ and G is CH. |
| 2124 | A is A-2a, $(R^2)_n$ is 3-MeO and G is CH. |
| 2125 | A is A-2a, $(R^2)_n$ is 3,5-di-MeO and G is CH. |
| 2126 | A is A-2a, $(R^2)_n$ is 3-CN and G is CH. |
| 2127 | A is A-2a, $(R^2)_n$ is 3,5-di-CN and G is CH. |
| 2128 | A is A-2a, $(R^2)_n$ is 3,6-di-F and G is CH. |
| 2129 | A is A-2a, $(R^2)_n$ is 3,6-di-Cl and G is CH. |
| 2130 | A is A-2a, $(R^2)_n$ is 3,6-di-Br and G is CH. |
| 2131 | A is A-2a, $(R^2)_n$ is 3,6-di-Me and G is CH. |
| 2132 | A is A-2a, $(R^2)_n$ is 3,6-di-CF$_3$ and G is CH. |
| 2133 | A is A-2a, $(R^2)_n$ is 3,6-di-MeO and G is CH. |
| 2134 | A is A-2a, $(R^2)_n$ is 3,6-di-CN and G is CH. |
| 2135 | A is A-2a, $(R^2)_n$ is 6-F and G is CH. |
| 2136 | A is A-2a, $(R^2)_n$ is 6-Cl and G is CH. |
| 2137 | A is A-2a, $(R^2)_n$ is 6-Br and G is CH. |
| 2138 | A is A-2a, $(R^2)_n$ is 6-Me and G is CH. |
| 2139 | A is A-2a, $(R^2)_n$ is 6-CF$_3$ and G is CH. |
| 2140 | A is A-2a, $(R^2)_n$ is 6-MeO and G is CH. |
| 2141 | A is A-2a, $(R^2)_n$ is 6-CN and G is CH. |
| 2142 | A is A-2a, $(R^2)_n$ is 6-F and G is C—F. |
| 2143 | A is A-2a, $(R^2)_n$ is 6-Cl and G is C—Cl. |
| 2144 | A is A-2a, $(R^2)_n$ is 6-Br and G is C—Br. |
| 2145 | A is A-2a, $(R^2)_n$ is 6-Me and G is C—Me. |
| 2146 | A is A-2a, $(R^2)_n$ is 6-CF$_3$ and G is C—CF$_3$. |
| 2147 | A is A-2a, $(R^2)_n$ is 6-MeO and G is C—OMe. |
| 2148 | A is A-2a, $(R^2)_n$ is H and G is N. |
| 2149 | A is A-2a, $(R^2)_n$ is 3-F and G is N. |
| 2150 | A is A-2a, $(R^2)_n$ is 3,5-di-F and G is N. |
| 2151 | A is A-2a, $(R^2)_n$ is 3-Cl and G is N. |
| 2152 | A is A-2a, $(R^2)_n$ is 3,5-di-Cl and G is N. |
| 2153 | A is A-2a, $(R^2)_n$ is 3-Br and G is N. |
| 2154 | A is A-2a, $(R^2)_n$ is 3,5-di-Br and G is N. |
| 2155 | A is A-2a, $(R^2)_n$ is 3-Me and G is N. |
| 2156 | A is A-2a, $(R^2)_n$ is 3,5-di-Me and G is N. |
| 2157 | A is A-2a, $(R^2)_n$ is 3-CF$_3$ and G is N. |
| 2158 | A is A-2a, $(R^2)_n$ is 3,5-di-CF$_3$ and G is N. |
| 2159 | A is A-2a, $(R^2)_n$ is 3-MeO and G is N. |
| 2160 | A is A-2a, $(R^2)_n$ is 3,5-di-MeO and G is N. |
| 2161 | A is A-2a, $(R^2)_n$ is 3-CN and G is N. |
| 2162 | A is A-2a, $(R^2)_n$ is 3,5-di-CN and G is N. |
| 2163 | A is A-2a, $(R^2)_n$ is 3,6-di-F and G is N. |
| 2164 | A is A-2a, $(R^2)_n$ is 3,6-di-Cl and G is N. |
| 2165 | A is A-2a, $(R^2)_n$ is 3,6-di-Br and G is N. |
| 2166 | A is A-2a, $(R^2)_n$ is 3,6-di-Me and G is N. |
| 2167 | A is A-2a, $(R^2)_n$ is 3,6-di-CF$_3$ and G is N. |
| 2168 | A is A-2a, $(R^2)_n$ is 3,6-di-MeO and G is N. |
| 2169 | A is A-2a, $(R^2)_n$ is 3,6-di-CN and G is N. |
| 2170 | A is A-2a, $(R^2)_n$ is 6-F and G is N. |
| 2171 | A is A-2a, $(R^2)_n$ is 6-Cl and G is N. |
| 2172 | A is A-2a, $(R^2)_n$ is 6-Br and G is N. |
| 2173 | A is A-2a, $(R^2)_n$ is 6-Me and G is N. |
| 2174 | A is A-2a, $(R^2)_n$ is 6-CF$_3$ and G is N. |
| 2175 | A is A-2a, $(R^2)_n$ is 6-MeO and G is N. |
| 2176 | A is A-2a, $(R^2)_n$ is 6-CN and G is N. |
| 2177 | A is A-2b, $(R^2)_n$ is H and G is CH. |
| 2178 | A is A-2b, $(R^2)_n$ is 3-F and G is CH. |
| 2179 | A is A-2b, $(R^2)_n$ is 3,5-di-F and G is CH. |
| 2180 | A is A-2b, $(R^2)_n$ is 3-Cl and G is CH. |
| 2181 | A is A-2b, $(R^2)_n$ is 3,5-di-Cl and G is CH. |
| 2182 | A is A-2b, $(R^2)_n$ is 3-Br and G is CH. |
| 2183 | A is A-2b, $(R^2)_n$ is 3,5-di-Br and G is CH. |
| 2184 | A is A-2b, $(R^2)_n$ is 3-Me and G is CH. |
| 2185 | A is A-2b, $(R^2)_n$ is 3,5-di-Me and G is CH. |
| 2186 | A is A-2b, $(R^2)_n$ is 3-CF$_3$ and G is CH. |
| 2187 | A is A-2b, $(R^2)_n$ is 3,5-di-CF$_3$ and G is CH. |

TABLES 1730-2304-continued

| Table | Row Heading |
|---|---|
| 2188 | A is A-2b, $(R^2)_n$ is 3-MeO and G is CH. |
| 2189 | A is A-2b, $(R^2)_n$ is 3,5-di-MeO and G is CH. |
| 2190 | A is A-2b, $(R^2)_n$ is 3-CN and G is CH. |
| 2191 | A is A-2b, $(R^2)_n$ is 3,5-di-CN and G is CH. |
| 2192 | A is A-2b, $(R^2)_n$ is 3,6-di-F and G is CH. |
| 2193 | A is A-2b, $(R^2)_n$ is 3,6-di-Cl and G is CH. |
| 2194 | A is A-2b, $(R^2)_n$ is 3,6-di-Br and G is CH. |
| 2195 | A is A-2b, $(R^2)_n$ is 3,6-di-Me and G is CH. |
| 2196 | A is A-2b, $(R^2)_n$ is 3,6-di-CF$_3$ and G is CH. |
| 2197 | A is A-2b, $(R^2)_n$ is 3,6-di-MeO and G is CH. |
| 2198 | A is A-2b, $(R^2)_n$ is 3,6-di-CN and G is CH. |
| 2199 | A is A-2b, $(R^2)_n$ is 6-F and G is CH. |
| 2200 | A is A-2b, $(R^2)_n$ is 6-Cl and G is CH. |
| 2201 | A is A-2b, $(R^2)_n$ is 6-Br and G is CH. |
| 2202 | A is A-2b, $(R^2)_n$ is 6-Me and G is CH. |
| 2203 | A is A-2b, $(R^2)_n$ is 6-CF$_3$ and G is CH. |
| 2204 | A is A-2b, $(R^2)_n$ is 6-MeO and G is CH. |
| 2205 | A is A-2b, $(R^2)_n$ is 6-CN and G is CH. |
| 2206 | A is A-2b, $(R^2)_n$ is 6-F and G is C—F. |
| 2207 | A is A-2b, $(R^2)_n$ is 6-Cl and G is C—Cl. |
| 2208 | A is A-2b, $(R^2)_n$ is 6-Br and G is C—Br. |
| 2209 | A is A-2b, $(R^2)_n$ is 6-Me and G is C—Me. |
| 2210 | A is A-2b, $(R^2)_n$ is 6-CF$_3$ and G is C—CF$_3$. |
| 2211 | A is A-2b, $(R^2)_n$ is 6-MeO and G is C—OMe. |
| 2212 | A is A-2b, $(R^2)_n$ is H and G is N. |
| 2213 | A is A-2b, $(R^2)_n$ is 3-F and G is N. |
| 2214 | A is A-2b, $(R^2)_n$ is 3,5-di-F and G is N. |
| 2215 | A is A-2b, $(R^2)_n$ is 3-Cl and G is N. |
| 2216 | A is A-2b, $(R^2)_n$ is 3,5-di-Cl and G is N. |
| 2217 | A is A-2b, $(R^2)_n$ is 3-Br and G is N. |
| 2218 | A is A-2b, $(R^2)_n$ is 3,5-di-Br and G is N. |
| 2219 | A is A-2b, $(R^2)_n$ is 3-Me and G is N. |
| 2220 | A is A-2b, $(R^2)_n$ is 3,5-di-Me and G is N. |
| 2221 | A is A-2b, $(R^2)_n$ is 3-CF$_3$ and G is N. |
| 2222 | A is A-2b, $(R^2)_n$ is 3,5-di-CF$_3$ and G is N. |
| 2223 | A is A-2b, $(R^2)_n$ is 3-MeO and G is N. |
| 2224 | A is A-2b, $(R^2)_n$ is 3,5-di-MeO and G is N. |
| 2225 | A is A-2b, $(R^2)_n$ is 3-CN and G is N. |
| 2226 | A is A-2b, $(R^2)_n$ is 3,5-di-CN and G is N. |
| 2227 | A is A-2b, $(R^2)_n$ is 3,6-di-F and G is N. |
| 2228 | A is A-2b, $(R^2)_n$ is 3,6-di-Cl and G is N. |
| 2229 | A is A-2b, $(R^2)_n$ is 3,6-di-Br and G is N. |
| 2230 | A is A-2b, $(R^2)_n$ is 3,6-di-Me and G is N. |
| 2231 | A is A-2b, $(R^2)_n$ is 3,6-di-CF$_3$ and G is N. |
| 2232 | A is A-2b, $(R^2)_n$ is 3,6-di-MeO and G is N. |
| 2233 | A is A-2b, $(R^2)_n$ is 3,6-di-CN and G is N. |
| 2234 | A is A-2b, $(R^2)_n$ is 6-F and G is N. |
| 2235 | A is A-2b, $(R^2)_n$ is 6-Cl and G is N. |
| 2236 | A is A-2b, $(R^2)_n$ is 6-Br and G is N. |
| 2237 | A is A-2b, $(R^2)_n$ is 6-Me and G is N. |
| 2238 | A is A-2b, $(R^2)_n$ is 6-CF$_3$ and G is N. |
| 2239 | A is A-2b, $(R^2)_n$ is 6-MeO and G is N. |
| 2240 | A is A-2b, $(R^2)_n$ is 6-CN and G is N. |
| 2241 | A is A-2c, $(R^2)_n$ is H and G is CH. |
| 2242 | A is A-2c, $(R^2)_n$ is 3-F and G is CH. |
| 2243 | A is A-2c, $(R^2)_n$ is 3,5-di-F and G is CH. |
| 2244 | A is A-2c, $(R^2)_n$ is 3-Cl and G is CH. |
| 2245 | A is A-2c, $(R^2)_n$ is 3,5-di-Cl and G is CH. |
| 2246 | A is A-2c, $(R^2)_n$ is 3-Br and G is CH. |
| 2247 | A is A-2c, $(R^2)_n$ is 3,5-di-Br and G is CH. |
| 2248 | A is A-2c, $(R^2)_n$ is 3-Me and G is CH. |
| 2249 | A is A-2c, $(R^2)_n$ is 3,5-di-Me and G is CH. |
| 2250 | A is A-2c, $(R^2)_n$ is 3-CF$_3$ and G is CH. |
| 2251 | A is A-2c, $(R^2)_n$ is 3,5-di-CF$_3$ and G is CH. |
| 2252 | A is A-2c, $(R^2)_n$ is 3-MeO and G is CH. |
| 2253 | A is A-2c, $(R^2)_n$ is 3,5-di-MeO and G is CH. |
| 2254 | A is A-2c, $(R^2)_n$ is 3-CN and G is CH. |
| 2255 | A is A-2c, $(R^2)_n$ is 3,5-di-CN and G is CH. |
| 2256 | A is A-2c, $(R^2)_n$ is 3,6-di-F and G is CH. |
| 2257 | A is A-2c, $(R^2)_n$ is 3,6-di-Cl and G is CH. |
| 2258 | A is A-2c, $(R^2)_n$ is 3,6-di-Br and G is CH. |
| 2259 | A is A-2c, $(R^2)_n$ is 3,6-di-Me and G is CH. |
| 2260 | A is A-2c, $(R^2)_n$ is 3,6-di-CF$_3$ and G is CH. |
| 2261 | A is A-2c, $(R^2)_n$ is 3,6-di-MeO and G is CH. |
| 2262 | A is A-2c, $(R^2)_n$ is 3,6-di-CN and G is CH. |
| 2263 | A is A-2c, $(R^2)_n$ is 6-F and G is CH. |
| 2264 | A is A-2c, $(R^2)_n$ is 6-Cl and G is CH. |
| 2265 | A is A-2c, $(R^2)_n$ is 6-Br and G is CH. |
| 2266 | A is A-2c, $(R^2)_n$ is 6-Me and G is CH. |
| 2267 | A is A-2c, $(R^2)_n$ is 6-CF$_3$ and G is CH. |
| 2268 | A is A-2c, $(R^2)_n$ is 6-MeO and G is CH. |
| 2269 | A is A-2c, $(R^2)_n$ is 6-CN and G is CH. |
| 2270 | A is A-2c, $(R^2)_n$ is 6-F and G is C—F. |
| 2271 | A is A-2c, $(R^2)_n$ is 6-Cl and G is C—Cl. |
| 2272 | A is A-2c, $(R^2)_n$ is 6-Br and G is C—Br. |
| 2273 | A is A-2c, $(R^2)_n$ is 6-Me and G is C—Me. |
| 2274 | A is A-2c, $(R^2)_n$ is 6-CF$_3$ and G is C—CF$_3$. |
| 2275 | A is A-2c, $(R^2)_n$ is 6-MeO and G is C—OMe. |
| 2276 | A is A-2c, $(R^2)_n$ is H and G is N. |
| 2277 | A is A-2c, $(R^2)_n$ is 3-F and G is N. |
| 2278 | A is A-2c, $(R^2)_n$ is 3,5-di-F and G is N. |
| 2279 | A is A-2c, $(R^2)_n$ is 3-Cl and G is N. |
| 2280 | A is A-2c, $(R^2)_n$ is 3,5-di-Cl and G is N. |
| 2281 | A is A-2c, $(R^2)_n$ is 3-Br and G is N. |
| 2282 | A is A-2c, $(R^2)_n$ is 3,5-di-Br and G is N. |
| 2283 | A is A-2c, $(R^2)_n$ is 3-Me and G is N. |
| 2284 | A is A-2c, $(R^2)_n$ is 3,5-di-Me and G is N. |
| 2285 | A is A-2c, $(R^2)_n$ is 3-CF$_3$ and G is N. |
| 2286 | A is A-2c, $(R^2)_n$ is 3,5-di-CF$_3$ and G is N. |
| 2287 | A is A-2c, $(R^2)_n$ is 3-MeO and G is N. |
| 2288 | A is A-2c, $(R^2)_n$ is 3,5-di-MeO and G is N. |
| 2289 | A is A-2c, $(R^2)_n$ is 3-CN and G is N. |
| 2290 | A is A-2c, $(R^2)_n$ is 3,5-di-CN and G is N. |
| 2291 | A is A-2c, $(R^2)_n$ is 3,6-di-F and G is N. |
| 2292 | A is A-2c, $(R^2)_n$ is 3,6-di-Cl and G is N. |
| 2293 | A is A-2c, $(R^2)_n$ is 3,6-di-Br and G is N. |
| 2294 | A is A-2c, $(R^2)_n$ is 3,6-di-Me and G is N. |
| 2295 | A is A-2c, $(R^2)_n$ is 3,6-di-CF$_3$ and G is N. |
| 2296 | A is A-2c, $(R^2)_n$ is 3,6-di-MeO and G is N. |
| 2297 | A is A-2c, $(R^2)_n$ is 3,6-di-CN and G is N. |
| 2298 | A is A-2c, $(R^2)_n$ is 6-F and G is N. |
| 2299 | A is A-2c, $(R^2)_n$ is 6-Cl and G is N. |
| 2300 | A is A-2c, $(R^2)_n$ is 6-Br and G is N. |
| 2301 | A is A-2c, $(R^2)_n$ is 6-Me and G is N. |
| 2302 | A is A-2c, $(R^2)_n$ is 6-CF$_3$ and G is N. |
| 2303 | A is A-2c, $(R^2)_n$ is 6-MeO and G is N. |
| 2304 | A is A-2c, $(R^2)_n$ is 6-CN and G is N. |

TABLE 2305

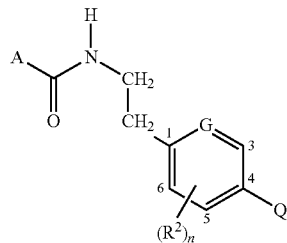

A is A-1a, $(R^2)_n$ is H, and G is CH.

| Q | Q | Q |
|---|---|---|
| 3-CF$_3$—1H-pyrazol-1-yl | 3-Me—1H-pyrazol-1-yl | 3-F—1H-pyrazol-1-yl |
| 3-Br—1H-pyrazol-1-yl | 4-CF$_3$—1H-pyrazol-1-yl | 4-Me—1H-pyrazol-1-yl |
| 4-F—1H-pyrazol-1-yl | 4-Br—1H-pyrazol-1-yl | 5-CF$_3$—1H-pyrazol-1-yl |
| 5-Me—1H-pyrazol-1-yl | 5-F—1H-pyrazol-1-yl | 5-Br—1H-pyrazol-1-yl |
| 3-CHF$_2$—1H-pyrazol-1-yl | 3-Et—1H-pyrazol-1-yl | 3-Cl—1H-pyrazol-1-yl |
| 3-I—1H-pyrazol-1-yl | 4-CHF$_2$—1H-pyrazol-1-yl | 4-Et—1H-pyrazol-1-yl |
| 4-Cl—1H-pyrazol-1-yl | 4-I—1H-pyrazol-1-yl | 5-CHF$_2$—1H-pyrazol-1-yl |
| 5-Et—1H-pyrazol-1-yl | 5-Cl—1H-pyrazol-1-yl | 5-I—1H-pyrazol-1-yl |
| 3-MeO—1H-pyrazol-1-yl | 3-CN—1H-pyrazol-1-yl | 3-CF$_3$O—1H-pyrazol-1-yl |
| 3-CHF$_2$O—1H-pyrazol-1-yl | 4-MeO—1H-pyrazol-1-yl | 4-CN—1H-pyrazol-1-yl |
| 4-CF$_3$O—1H-pyrazol-1-yl | 4-CHF$_2$O—1H-pyrazol-1-yl | 5-CF$_3$O—1H-pyrazol-1-yl |
| 5-CN—1H-pyrazol-1-yl | 5-CF$_3$O—1H-pyrazol-1-yl | 5-CHF$_2$O—1H-pyrazol-1-yl |
| 3-MeO(O=)C—1H-pyrazol-1-yl | 3-Ph—1H-pyrazol-1-yl | 3,5-di-Me—1H-pyrazol-1-yl |
| 3,5-di-F—1H-pyrazol-1-yl | 4-MeO(O=)C—1H-pyrazol-1-yl | 4-Ph—1H-pyrazol-1-yl |
| 3,5-di-CF$_3$—1H-pyrazol-1-yl | 3,5-di-Cl—1H-pyrazol-1-yl | 5-MeO(O=)C—1H-pyrazol-1-yl |
| 5-Ph—1H-pyrazol-1-yl | 3,5-di-CHF$_2$—1H-pyrazol-1-yl | 3,5-di-Br—1H-pyrazol-1-yl |
| 3-CF$_3$-5-Me-1H-pyrazol-1-yl | 3,4-di-Me—1H-pyrazol-1-yl | 3,4-di-CF$_3$—1H-pyrazol-1-yl |
| 3,4-di-Br—1H-pyrazol-1-yl | 3,4-di-Cl—1H-pyrazol-1-yl | 1H-pyrazol-1-yl |
| 3-Me—1H-[1,2,4]triazol-1-yl | 3-CF$_3$—1H-[1,2,4]triazol-1-yl | 3-CHF$_2$—1H-[1,2,4]triazol-1-yl |
| 3-F—1H-[1,2,4]triazol-1-yl | 3-Cl—1H-[1,2,4]triazol-1-yl | 3-Br—1H-[1,2,4]triazol-1-yl |
| 3,5-di-Me—1H-[1,2,4]triazol-1-yl | 3,5-di-CF$_3$—1H-[1,2,4]triazol-1-yl | 3,5-di-CHF$_2$—1H-[1,2,4]triazol-1-yl |
| 3,5-di-Cl—1H-[1,2,4]triazol-1-yl | 3,5-di-Br—1H-[1,2,4]triazol-1-yl | 3-Ph—1H-[1,2,4]triazol-1-yl |
| 1H-[1,2,4]triazol-1-yl | 4-Me—2H-[1,2,3]triazol-2-yl | 4-CF$_3$—2H-[1,2,3]triazol-2-yl |
| 4-CHF$_2$—2H-[1,2,3]triazol-2-yl | 4-F—2H-[1,2,3]triazol-2-yl | 4-Cl—2H-[1,2,3]triazol-2-yl |
| 4-Br—2H-[1,2,3]triazol-2-yl | 4-Ph—2H-[1,2,3]triazol-2-yl | 4,5-di-Me—2H-[1,2,3]triazol-2-yl |
| 4,5-di-CF$_3$—2H-[1,2,3]triazol-2-yl | 4,5-di-Cl—2H-[1,2,3]triazol-2-yl | 4,5-di-Br—2H-[1,2,3]triazol-2-yl |
| 2H-[1,2,3]triazol-2-yl | 4-Me—1H-[1,2,3]triazol-1-yl | 4-CF$_3$—1H-[1,2,3]triazol-1-yl |
| 4-CHF$_2$—1H-[1,2,3]triazol-1-yl | 4-F—1H-[1,2,3]triazol-1-yl | 4-Cl—1H-[1,2,3]triazol-1-yl |
| 4-Br—1H-[1,2,3]triazol-1-yl | 4-Ph—1H-[1,2,3]triazol-1-yl | 1H-[1,2,3]triazol-1-yl |
| 3-Me—1H-pyrrol-1-yl | 3-CF$_3$—1H-pyrrol-1-yl | 3-CHF$_2$—1H-pyrrol-1-yl |
| 3,4-di-Me—1H-pyrrol-1-yl | 2,4-di-Me—1H-pyrrol-1-yl | 3,4-di-CF$_3$—1H-pyrrol-1-yl |
| 2,4-di-CF$_3$—1H-pyrrol-1-yl | 3,4-di-Br—1H-pyrrol-1-yl | 3,4-di-Cl—1H-pyrrol-1-yl |
| 1H-pyrrol-1-yl | 1-Me—1H-pyrazol-3-yl | 1-CF$_3$—1H-pyrazol-3-yl |
| 1-Et—1H-pyrazol-3-yl | 1-i-Pr—1H-pyrazol-3-yl | 1-(F$_3$CCH$_2$)—1H-pyrazol-3-yl |
| 1-Ph—1H-pyrazol-3-yl | 1,4-di-Me—1H-pyrazol-3-yl | 1-Me-4-CF$_3$—1H-pyrazol-3-yl |
| 1-Me—1H-pyrazol-4-yl | 1-CF$_3$—1H-pyrazol-4-yl | 1-Et—1H-pyrazol-4-yl |
| 1-i-Pr—1H-pyrazol-4-yl | 1-(F$_3$CCH$_2$)—1H-pyrazol-4-yl | 1-Ph—1H-pyrazol-4-yl |
| 1,3-di-Me—1H-pyrazol-4-yl | 1-Me-3-CF$_3$—1H-pyrazol-4-yl | 3-Me-1-CF$_3$—1H-pyrazol-4-yl |
| 1-Me—1H-[1,2,4]triazol-3-yl | 1-CF$_3$—1H-[1,2,4]triazol-3-yl | 1-Et—1H-[1,2,4]triazol-3-yl |
| 1-i-Pr—1H-[1,2,4]triazol-3-yl | 1-Ph—1H-[1,2,4]triazol-3-yl | 5-Ph-4,5-dihydro-isoxazol-3-yl |
| 5-CF$_3$-2,4-dihydro-3-oxopyrazol-1-yl | 5-Me-2,4-dihydro-3-oxopyrazol-1-yl | |

The present disclosure also includes Tables 2306 through 4032, each of which is constructed the same as Table 2305 above, except that the row heading in Table 2305 (i.e. "A is A-1a, $(R^2)_n$ is H, and G is CH.") is replaced with the respective row heading shown below. For example, in Table 2306 the row heading is "A is A-1a, $(R^2)_n$ is 3-F, and G is CH." and Q is as defined in Table 1 above. Thus, the first entry in Table 2306 specifically discloses N-[2-[3-fluoro-4-[3-(trifluoromethyl)-1H-pyrazol-1-yl]phenyl]ethyl]-2-(trifluoromethyl)benzamide. Tables 2307 through 4032 are constructed similarly.

TABLES 2306-4032

| Table | Row Heading |
|---|---|
| 2306 | A is A-1a, $(R^2)_n$ is 3-F and G is CH. |
| 2307 | A is A-1a, $(R^2)_n$ is 3,5-di-F and G is CH. |
| 2308 | A is A-1a, $(R^2)_n$ is 3-Cl and G is CH. |
| 2309 | A is A-1a, $(R^2)_n$ is 3,5-di-Cl and G is CH. |
| 2310 | A is A-1a, $(R^2)_n$ is 3-Br and G is CH. |
| 2311 | A is A-1a, $(R^2)_n$ is 3,5-di-Br and G is CH. |
| 2312 | A is A-1a, $(R^2)_n$ is 3-Me and G is CH. |
| 2313 | A is A-1a, $(R^2)_n$ is 3,5-di-Me and G is CH. |
| 2314 | A is A-1a, $(R^2)_n$ is 3-CF$_3$ and G is CH. |
| 2315 | A is A-1a, $(R^2)_n$ is 3,5-di-CF$_3$ and G is CH. |
| 2316 | A is A-1a, $(R^2)_n$ is 3-MeO and G is CH. |
| 2317 | A is A-1a, $(R^2)_n$ is 3,5-di-MeO and G is CH. |

TABLES 2306-4032-continued

| Table | Row Heading |
|---|---|
| 2318 | A is A-1a, $(R^2)_n$ is 3-CN and G is CH. |
| 2319 | A is A-1a, $(R^2)_n$ is 3,5-di-CN and G is CH. |
| 2320 | A is A-1a, $(R^2)_n$ is 3,6-di-F and G is CH. |
| 2321 | A is A-1a, $(R^2)_n$ is 3,6-di-Cl and G is CH. |
| 2322 | A is A-1a, $(R^2)_n$ is 3,6-di-Br and G is CH. |
| 2323 | A is A-1a, $(R^2)_n$ is 3,6-di-Me G is CH. |
| 2324 | A is A-1a, $(R^2)_n$ is 3,6-di-$CF_3$ and G is CH. |
| 2325 | A is A-1a, $(R^2)_n$ is 3,6-di-MeO G is CH. |
| 2326 | A is A-1a, $(R^2)_n$ is 3,6-di-CN and G is CH. |
| 2327 | A is A-1a, $(R^2)_n$ is 6-F and G is CH. |
| 2328 | A is A-1a, $(R^2)_n$ is 6-Cl and G is CH. |
| 2329 | A is A-1a, $(R^2)_n$ is 6-Br and G is CH. |
| 2330 | A is A-1a, $(R^2)_n$ is 6-Me and G is CH. |
| 2331 | A is A-1a, $(R^2)_n$ is 6-$CF_3$ and G is CH. |
| 2332 | A is A-1a, $(R^2)_n$ is 6-MeO and G is CH. |
| 2333 | A is A-1a, $(R^2)_n$ is 6-CN and G is CH. |
| 2334 | A is A-1a, $(R^2)_n$ is 6-F and G is C—F. |
| 2335 | A is A-1a, $(R^2)_n$ is 6-Cl and G is C—Cl. |
| 2336 | A is A-1a, $(R^2)_n$ is 6-Br and G is C—Br. |
| 2337 | A is A-1a, $(R^2)_n$ is 6-Me and G is C—Me. |
| 2338 | A is A-1a, $(R^2)_n$ is 6-$CF_3$ and G is C—$CF_3$. |
| 2339 | A is A-1a, $(R^2)_n$ is 6-MeO and G is C—OMe. |
| 2340 | A is A-1a, $(R^2)_n$ is H and G is N. |
| 2341 | A is A-1a, $(R^2)_n$ is 3-F and G is N. |
| 2342 | A is A-1a, $(R^2)_n$ is 3,5-di-F and G is N. |
| 2343 | A is A-1a, $(R^2)_n$ is 3-Cl and G is N. |
| 2344 | A is A-1a, $(R^2)_n$ is 3,5-di-Cl and G is N. |
| 2345 | A is A-1a, $(R^2)_n$ is 3-Br and G is N. |
| 2346 | A is A-1a, $(R^2)_n$ is 3,5-di-Br and G is N. |
| 2347 | A is A-1a, $(R^2)_n$ is 3-Me and G is N. |
| 2348 | A is A-1a, $(R^2)_n$ is 3,5-di-Me and G is N. |
| 2349 | A is A-1a, $(R^2)_n$ is 3-$CF_3$ and G is N. |
| 2350 | A is A-1a, $(R^2)_n$ is 3,5-di-$CF_3$ and G is N. |
| 2351 | A is A-1a, $(R^2)_n$ is 3-MeO and G is N. |
| 2352 | A is A-1a, $(R^2)_n$ is 3,5-di-MeO and G is N. |
| 2353 | A is A-1a, $(R^2)_n$ is 3-CN and G is N. |
| 2354 | A is A-1a, $(R^2)_n$ is 3,5-di-CN and G is N. |
| 2355 | A is A-1a, $(R^2)_n$ is 3,6-di-F and G is N. |
| 2356 | A is A-1a, $(R^2)_n$ is 3,6-di-Cl and G is N. |
| 2357 | A is A-1a, $(R^2)_n$ is 3,6-di-Br and G is N. |
| 2358 | A is A-1a, $(R^2)_n$ is 3,6-di-Me and G is N. |
| 2359 | A is A-1a, $(R^2)_n$ is 3,6-di-$CF_3$ and G is N. |
| 2360 | A is A-1a, $(R^2)_n$ is 3,6-di-MeO and G is N. |
| 2361 | A is A-1a, $(R^2)_n$ is 3,6-di-CN and G is N. |
| 2362 | A is A-1a, $(R^2)_n$ is 6-F and G is N. |
| 2363 | A is A-1a, $(R^2)_n$ is 6-Cl and G is N. |
| 2364 | A is A-1a, $(R^2)_n$ is 6-Br and G is N. |
| 2365 | A is A-1a, $(R^2)_n$ is 6-Me and G is N. |
| 2366 | A is A-1a, $(R^2)_n$ is 6-$CF_3$ and G is N. |
| 2367 | A is A-1a, $(R^2)_n$ is 6-MeO and G is N. |
| 2368 | A is A-1a, $(R^2)_n$ is 6-CN and G is N. |
| 2369 | A is A-1b, $(R^2)_n$ is H and G is CH. |
| 2370 | A is A-1b, $(R^2)_n$ is 3-F and G is CH. |
| 2371 | A is A-1b, $(R^2)_n$ is 3,5-di-F and G is CH. |
| 2372 | A is A-1b, $(R^2)_n$ is 3-Cl and G is CH. |
| 2373 | A is A-1b, $(R^2)_n$ is 3,5-di-Cl and G is CH. |
| 2374 | A is A-1b, $(R^2)_n$ is 3-Br and G is CH. |
| 2375 | A is A-1b, $(R^2)_n$ is 3,5-di-Br and G is CH. |
| 2376 | A is A-1b, $(R^2)_n$ is 3-Me and G is CH. |
| 2377 | A is A-1b, $(R^2)_n$ is 3,5-di-Me and G is CH. |
| 2378 | A is A-1b, $(R^2)_n$ is 3-$CF_3$ and G is CH. |
| 2379 | A is A-1b, $(R^2)_n$ is 3,5-di-$CF_3$ and G is CH. |
| 2380 | A is A-1b, $(R^2)_n$ is 3-MeO and G is CH. |
| 2381 | A is A-1b, $(R^2)_n$ is 3,5-di-MeO and G is CH. |
| 2382 | A is A-1b, $(R^2)_n$ is 3-CN and G is CH. |
| 2383 | A is A-1b, $(R^2)_n$ is 3,5-di-CN and G is CH. |
| 2384 | A is A-1b, $(R^2)_n$ is 3,6-di-F and G is CH. |
| 2385 | A is A-1b, $(R^2)_n$ is 3,6-di-Cl and G is CH. |
| 2386 | A is A-1b, $(R^2)_n$ is 3,6-di-Br and G is CH. |
| 2387 | A is A-1b, $(R^2)_n$ is 3,6-di-Me and G is CH. |
| 2388 | A is A-1b, $(R^2)_n$ is 3,6-di-$CF_3$ and G is CH. |
| 2389 | A is A-1b, $(R^2)_n$ is 3,6-di-MeO and G is CH. |
| 2390 | A is A-1b, $(R^2)_n$ is 3,6-di-CN and G is CH. |
| 2391 | A is A-1b, $(R^2)_n$ is 6-F and G is CH. |
| 2392 | A is A-1b, $(R^2)_n$ is 6-Cl and G is CH. |
| 2393 | A is A-1b, $(R^2)_n$ is 6-Br and G is CH. |
| 2394 | A is A-1b, $(R^2)_n$ is 6-Me and G is CH. |
| 2395 | A is A-1b, $(R^2)_n$ is 6-$CF_3$ and G is CH. |
| 2396 | A is A-1b, $(R^2)_n$ is 6-MeO and G is CH. |
| 2397 | A is A-1b, $(R^2)_n$ is 6-CN and G is CH. |
| 2398 | A is A-1b, $(R^2)_n$ is 6-F and G is C—F. |
| 2399 | A is A-1b, $(R^2)_n$ is 6-Cl and G is C—Cl. |
| 2400 | A is A-1b, $(R^2)_n$ is 6-Br and G is C—Br. |
| 2401 | A is A-1b, $(R^2)_n$ is 6-Me and G is C—Me. |
| 2402 | A is A-1b, $(R^2)_n$ is 6-$CF_3$ and G is C—$CF_3$. |
| 2403 | A is A-1b, $(R^2)_n$ is 6-MeO and G is C—OMe. |
| 2404 | A is A-1b, $(R^2)_n$ is H and G is N. |
| 2405 | A is A-1b, $(R^2)_n$ is 3-F and G is N. |
| 2406 | A is A-1b, $(R^2)_n$ is 3,5-di-F and G is N. |
| 2407 | A is A-1b, $(R^2)_n$ is 3-Cl and G is N. |
| 2408 | A is A-1b, $(R^2)_n$ is 3,5-di-Cl and G is N. |
| 2409 | A is A-1b, $(R^2)_n$ is 3-Br and G is N. |
| 2410 | A is A-1b, $(R^2)_n$ is 3,5-di-Br and G is N. |
| 2411 | A is A-1b, $(R^2)_n$ is 3-Me and G is N. |
| 2412 | A is A-1b, $(R^2)_n$ is 3,5-di-Me and G is N. |
| 2413 | A is A-1b, $(R^2)_n$ is 3-$CF_3$ and G is N. |
| 2414 | A is A-1b, $(R^2)_n$ is 3,5-di-$CF_3$ and G is N. |
| 2415 | A is A-1b, $(R^2)_n$ is 3-MeO and G is N. |
| 2416 | A is A-1b, $(R^2)_n$ is 3,5-di-MeO and G is N. |
| 2417 | A is A-1b, $(R^2)_n$ is 3-CN and G is N. |
| 2418 | A is A-1b, $(R^2)_n$ is 3,5-di-CN and G is N. |
| 2419 | A is A-1b, $(R^2)_n$ is 3,6-di-F and G is N. |
| 2420 | A is A-1b, $(R^2)_n$ is 3,6-di-Cl and G is N. |
| 2421 | A is A-1b, $(R^2)_n$ is 3,6-di-Br and G is N. |
| 2422 | A is A-1b, $(R^2)_n$ is 3,6-di-Me and G is N. |
| 2423 | A is A-1b, $(R^2)_n$ is 3,6-di-$CF_3$ and G is N. |
| 2424 | A is A-1b, $(R^2)_n$ is 3,6-di-MeO and G is N. |
| 2425 | A is A-1b, $(R^2)_n$ is 3,6-di-CN and G is N. |
| 2426 | A is A-1b, $(R^2)_n$ is 6-F and G is N. |
| 2427 | A is A-1b, $(R^2)_n$ is 6-Cl and G is N. |
| 2428 | A is A-1b, $(R^2)_n$ is 6-Br and G is N. |
| 2429 | A is A-1b, $(R^2)_n$ is 6-Me and G is N. |
| 2430 | A is A-1b, $(R^2)_n$ is 6-$CF_3$ and G is N. |
| 2431 | A is A-1b, $(R^2)_n$ is 6-MeO and G is N. |
| 2432 | A is A-1b, $(R^2)_n$ is 6-CN and G is N. |
| 2433 | A is A-1c, $(R^2)_n$ is H and G is CH. |
| 2434 | A is A-1c, $(R^2)_n$ is 3-F and G is CH. |
| 2435 | A is A-1c, $(R^2)_n$ is 3,5-di-F and G is CH. |
| 2436 | A is A-1c, $(R^2)_n$ is 3-Cl and G is CH. |
| 2437 | A is A-1c, $(R^2)_n$ is 3,5-di-Cl and G is CH. |
| 2438 | A is A-1c, $(R^2)_n$ is 3-Br and G is CH. |
| 2439 | A is A-1c, $(R^2)_n$ is 3,5-di-Br and G is CH. |
| 2440 | A is A-1c, $(R^2)_n$ is 3-Me and G is CH. |
| 2441 | A is A-1c, $(R^2)_n$ is 3,5-di-Me and G is CH. |
| 2442 | A is A-1c, $(R^2)_n$ is 3-$CF_3$ and G is CH. |
| 2443 | A is A-1c, $(R^2)_n$ is 3,5-di-$CF_3$ and G is CH. |
| 2444 | A is A-1c, $(R^2)_n$ is 3-MeO and G is CH. |
| 2445 | A is A-1c, $(R^2)_n$ is 3,5-di-MeO and G is CH. |
| 2446 | A is A-1c, $(R^2)_n$ is 3-CN and G is CH. |
| 2447 | A is A-1c, $(R^2)_n$ is 3,5-di-CN and G is CH. |
| 2448 | A is A-1c, $(R^2)_n$ is 3,6-di-F and G is CH. |
| 2449 | A is A-1c, $(R^2)_n$ is 3,6-di-Cl and G is CH. |
| 2450 | A is A-1c, $(R^2)_n$ is 3,6-di-Br and G is CH. |
| 2451 | A is A-1c, $(R^2)_n$ is 3,6-di-Me and G is CH. |
| 2452 | A is A-1c, $(R^2)_n$ is 3,6-di-$CF_3$ and G is CH. |
| 2453 | A is A-1c, $(R^2)_n$ is 3,6-di-MeO and G is CH. |
| 2454 | A is A-1c, $(R^2)_n$ is 3,6-di-CN and G is CH. |
| 2455 | A is A-1c, $(R^2)_n$ is 6-F and G is CH. |
| 2456 | A is A-1c, $(R^2)_n$ is 6-Cl and G is CH. |
| 2457 | A is A-1c, $(R^2)_n$ is 6-Br and G is CH. |
| 2458 | A is A-1c, $(R^2)_n$ is 6-Me and G is CH. |
| 2459 | A is A-1c, $(R^2)_n$ is 6-$CF_3$ and G is CH. |
| 2460 | A is A-1c, $(R^2)_n$ is 6-MeO and G is CH. |
| 2461 | A is A-1c, $(R^2)_n$ is 6-CN and G is CH. |
| 2462 | A is A-1c, $(R^2)_n$ is 6-F and G is C—F. |
| 2463 | A is A-1c, $(R^2)_n$ is 6-Cl and G is C—Cl. |
| 2464 | A is A-1c, $(R^2)_n$ is 6-Br and G is C—Br. |
| 2465 | A is A-1c, $(R^2)_n$ is 6-Me and G is C—Me. |
| 2466 | A is A-1c, $(R^2)_n$ is 6-$CF_3$ and G is C—$CF_3$. |
| 2467 | A is A-1c, $(R^2)_n$ is 6-MeO and G is C—OMe. |
| 2468 | A is A-1c, $(R^2)_n$ is H and G is N. |
| 2469 | A is A-1c, $(R^2)_n$ is 3-F and G is N. |
| 2470 | A is A-1c, $(R^2)_n$ is 3,5-di-F and G is N. |
| 2471 | A is A-1c, $(R^2)_n$ is 3-Cl and G is N. |
| 2472 | A is A-1c, $(R^2)_n$ is 3,5-di-Cl and G is N. |
| 2473 | A is A-1c, $(R^2)_n$ is 3-Br and G is N. |

TABLES 2306-4032-continued

| Table | Row Heading |
|---|---|
| 2474 | A is A-1c, $(R^2)_n$ is 3,5-di-Br and G is N. |
| 2475 | A is A-1c, $(R^2)_n$ is 3-Me and G is N. |
| 2476 | A is A-1c, $(R^2)_n$ is 3,5-di-Me and G is N. |
| 2477 | A is A-1c, $(R^2)_n$ is 3-CF$_3$ and G is N. |
| 2478 | A is A-1c, $(R^2)_n$ is 3,5-di-CF$_3$ and G is N. |
| 2479 | A is A-1c, $(R^2)_n$ is 3-MeO and G is N. |
| 2480 | A is A-1c, $(R^2)_n$ is 3,5-di-MeO and G is N. |
| 2481 | A is A-1c, $(R^2)_n$ is 3-CN and G is N. |
| 2482 | A is A-1c, $(R^2)_n$ is 3,5-di-CN and G is N. |
| 2483 | A is A-1c, $(R^2)_n$ is 3,6-di-F and G is N. |
| 2484 | A is A-1c, $(R^2)_n$ is 3,6-di-Cl and G is N. |
| 2485 | A is A-1c, $(R^2)_n$ is 3,6-di-Br and G is N. |
| 2486 | A is A-1c, $(R^2)_n$ is 3,6-di-Me and G is N. |
| 2487 | A is A-1c, $(R^2)_n$ is 3,6-di-CF$_3$ and G is N. |
| 2488 | A is A-1c, $(R^2)_n$ is 3,6-di-MeO and G is N. |
| 2489 | A is A-1c, $(R^2)_n$ is 3,6-di-CN and G is N. |
| 2490 | A is A-1c, $(R^2)_n$ is 6-F and G is N. |
| 2491 | A is A-1c, $(R^2)_n$ is 6-Cl and G is N. |
| 2492 | A is A-1c, $(R^2)_n$ is 6-Br and G is N. |
| 2493 | A is A-1c, $(R^2)_n$ is 6-Me and G is N. |
| 2494 | A is A-1c, $(R^2)_n$ is 6-CF$_3$ and G is N. |
| 2495 | A is A-1c, $(R^2)_n$ is 6-MeO and G is N. |
| 2496 | A is A-1c, $(R^2)_n$ is 6-CN and G is N. |
| 2497 | A is A-1d, $(R^2)_n$ is H and G is CH. |
| 2498 | A is A-1d, $(R^2)_n$ is 3-F and G is CH. |
| 2499 | A is A-1d, $(R^2)_n$ is 3,5-di-F and G is CH. |
| 2500 | A is A-1d, $(R^2)_n$ is 3-Cl and G is CH. |
| 2501 | A is A-1d, $(R^2)_n$ is 3,5-di-Cl and G is CH. |
| 2502 | A is A-1d, $(R^2)_n$ is 3-Br and G is CH. |
| 2503 | A is A-1d, $(R^2)_n$ is 3,5-di-Br and G is CH. |
| 2504 | A is A-1d, $(R^2)_n$ is 3-Me and G is CH. |
| 2505 | A is A-1d, $(R^2)_n$ is 3,5-di-Me and G is CH. |
| 2506 | A is A-1d, $(R^2)_n$ is 3-CF$_3$ and G is CH. |
| 2507 | A is A-1d, $(R^2)_n$ is 3,5-di-CF$_3$ and G is CH. |
| 2508 | A is A-1d, $(R^2)_n$ is 3-MeO and G is CH. |
| 2509 | A is A-1d, $(R^2)_n$ is 3,5-di-MeO and G is CH. |
| 2510 | A is A-1d, $(R^2)_n$ is 3-CN and G is CH. |
| 2511 | A is A-1d, $(R^2)_n$ is 3,5-di-CN and G is CH. |
| 2512 | A is A-1d, $(R^2)_n$ is 3,6-di-F and G is CH. |
| 2513 | A is A-1d, $(R^2)_n$ is 3,6-di-Cl and G is CH. |
| 2514 | A is A-1d, $(R^2)_n$ is 3,6-di-Br and G is CH. |
| 2515 | A is A-1d, $(R^2)_n$ is 3,6-di-Me and G is CH. |
| 2516 | A is A-1d, $(R^2)_n$ is 3,6-di-CF$_3$ and G is CH. |
| 2517 | A is A-1d, $(R^2)_n$ is 3,6-di-MeO and G is CH. |
| 2518 | A is A-1d, $(R^2)_n$ is 3,6-di-CN and G is CH. |
| 2519 | A is A-1d, $(R^2)_n$ is 6-F and G is CH. |
| 2520 | A is A-1d, $(R^2)_n$ is 6-Cl and G is CH. |
| 2521 | A is A-1d, $(R^2)_n$ is 6-Br and G is CH. |
| 2522 | A is A-1d, $(R^2)_n$ is 6-Me and G is CH. |
| 2523 | A is A-1d, $(R^2)_n$ is 6-CF$_3$ and G is CH. |
| 2524 | A is A-1d, $(R^2)_n$ is 6-MeO and G is CH. |
| 2525 | A is A-1d, $(R^2)_n$ is 6-CN and G is CH. |
| 2526 | A is A-1d, $(R^2)_n$ is 6-F and G is C—F. |
| 2527 | A is A-1d, $(R^2)_n$ is 6-Cl and G is C—Cl. |
| 2528 | A is A-1d, $(R^2)_n$ is 6-Br and G is C—Br. |
| 2529 | A is A-1d, $(R^2)_n$ is 6-Me and G is C—Me. |
| 2530 | A is A-1d, $(R^2)_n$ is 6-CF$_3$ and G is C—CF$_3$. |
| 2531 | A is A-1d, $(R^2)_n$ is 6-MeO and G is C—OMe. |
| 2532 | A is A-1d, $(R^2)_n$ is H and G is N. |
| 2533 | A is A-1d, $(R^2)_n$ is 3-F and G is N. |
| 2534 | A is A-1d, $(R^2)_n$ is 3,5-di-F and G is N. |
| 2535 | A is A-1d, $(R^2)_n$ is 3-Cl and G is N. |
| 2536 | A is A-1d, $(R^2)_n$ is 3,5-di-Cl and G is N. |
| 2537 | A is A-1d, $(R^2)_n$ is 3-Br and G is N. |
| 2538 | A is A-1d, $(R^2)_n$ is 3,5-di-Br and G is N. |
| 2539 | A is A-1d, $(R^2)_n$ is 3-Me and G is N. |
| 2540 | A is A-1d, $(R^2)_n$ is 3,5-di-Me and G is N. |
| 2541 | A is A-1d, $(R^2)_n$ is 3-CF$_3$ and G is N. |
| 2542 | A is A-1d, $(R^2)_n$ is 3,5-di-CF$_3$ and G is N. |
| 2543 | A is A-1d, $(R^2)_n$ is 3-MeO and G is N. |
| 2544 | A is A-1d, $(R^2)_n$ is 3,5-di-MeO and G is N. |
| 2545 | A is A-1d, $(R^2)_n$ is 3-CN and G is N. |
| 2546 | A is A-1d, $(R^2)_n$ is 3,5-di-CN and G is N. |
| 2547 | A is A-1d, $(R^2)_n$ is 3,6-di-F and G is N. |
| 2548 | A is A-1d, $(R^2)_n$ is 3,6-di-Cl and G is N. |
| 2549 | A is A-1d, $(R^2)_n$ is 3,6-di-Br and G is N. |
| 2550 | A is A-1d, $(R^2)_n$ is 3,6-di-Me and G is N. |
| 2551 | A is A-1d, $(R^2)_n$ is 3,6-di-CF$_3$ and G is N. |
| 2552 | A is A-1d, $(R^2)_n$ is 3,6-di-MeO and G is N. |
| 2553 | A is A-1d, $(R^2)_n$ is 3,6-di-CN and G is N. |
| 2554 | A is A-1d, $(R^2)_n$ is 6-F and G is N. |
| 2555 | A is A-1d, $(R^2)_n$ is 6-Cl and G is N. |
| 2556 | A is A-1d, $(R^2)_n$ is 6-Br and G is N. |
| 2557 | A is A-1d, $(R^2)_n$ is 6-Me and G is N. |
| 2558 | A is A-1d, $(R^2)_n$ is 6-CF$_3$ and G is N. |
| 2559 | A is A-1d, $(R^2)_n$ is 6-MeO and G is N. |
| 2560 | A is A-1d, $(R^2)_n$ is 6-CN and G is N. |
| 2561 | A is A-1e, $(R^2)_n$ is H and G is CH. |
| 2562 | A is A-1e, $(R^2)_n$ is 3-F and G is CH. |
| 2563 | A is A-1e, $(R^2)_n$ is 3,5-di-F and G is CH. |
| 2564 | A is A-1e, $(R^2)_n$ is 3-Cl and G is CH. |
| 2565 | A is A-1e, $(R^2)_n$ is 3,5-di-Cl and G is CH. |
| 2566 | A is A-1e, $(R^2)_n$ is 3-Br and G is CH. |
| 2567 | A is A-1e, $(R^2)_n$ is 3,5-di-Br and G is CH. |
| 2568 | A is A-1e, $(R^2)_n$ is 3-Me and G is CH. |
| 2569 | A is A-1e, $(R^2)_n$ is 3,5-di-Me and G is CH. |
| 2570 | A is A-1e, $(R^2)_n$ is 3-CF$_3$ and G is CH. |
| 2571 | A is A-1e, $(R^2)_n$ is 3,5-di-CF$_3$ and G is CH. |
| 2572 | A is A-1e, $(R^2)_n$ is 3-MeO and G is CH. |
| 2573 | A is A-1e, $(R^2)_n$ is 3,5-di-MeO and G is CH. |
| 2574 | A is A-1e, $(R^2)_n$ is 3-CN and G is CH. |
| 2575 | A is A-1e, $(R^2)_n$ is 3,5-di-CN and G is CH. |
| 2576 | A is A-1e, $(R^2)_n$ is 3,6-di-F and G is CH. |
| 2577 | A is A-1e, $(R^2)_n$ is 3,6-di-Cl and G is CH. |
| 2578 | A is A-1e, $(R^2)_n$ is 3,6-di-Br and G is CH. |
| 2579 | A is A-1e, $(R^2)_n$ is 3,6-di-Me and G is CH. |
| 2580 | A is A-1e, $(R^2)_n$ is 3,6-di-CF$_3$ and G is CH. |
| 2581 | A is A-1e, $(R^2)_n$ is 3,6-di-MeO and G is CH. |
| 2582 | A is A-1e, $(R^2)_n$ is 3,6-di-CN and G is CH. |
| 2583 | A is A-1e, $(R^2)_n$ is 6-F and G is CH. |
| 2584 | A is A-1e, $(R^2)_n$ is 6-Cl and G is CH. |
| 2585 | A is A-1e, $(R^2)_n$ is 6-Br and G is CH. |
| 2586 | A is A-1e, $(R^2)_n$ is 6-Me and G is CH. |
| 2587 | A is A-1e, $(R^2)_n$ is 6-CF$_3$ and G is CH. |
| 2588 | A is A-1e, $(R^2)_n$ is 6-MeO and G is CH. |
| 2589 | A is A-1e, $(R^2)_n$ is 6-CN and G is CH. |
| 2590 | A is A-1e, $(R^2)_n$ is 6-F and G is C—F. |
| 2591 | A is A-1e, $(R^2)_n$ is 6-Cl and G is C—Cl. |
| 2592 | A is A-1e, $(R^2)_n$ is 6-Br and G is C—Br. |
| 2593 | A is A-1e, $(R^2)_n$ is 6-Me and G is C—Me. |
| 2594 | A is A-1e, $(R^2)_n$ is 6-CF$_3$ and G is C—CF$_3$. |
| 2595 | A is A-1e, $(R^2)_n$ is 6-MeO and G is C—OMe. |
| 2596 | A is A-1e, $(R^2)_n$ is H and G is N. |
| 2597 | A is A-1e, $(R^2)_n$ is 3-F and G is N. |
| 2598 | A is A-1e, $(R^2)_n$ is 3,5-di-F and G is N. |
| 2599 | A is A-1e, $(R^2)_n$ is 3-Cl and G is N. |
| 2600 | A is A-1e, $(R^2)_n$ is 3,5-di-Cl and G is N. |
| 2601 | A is A-1e, $(R^2)_n$ is 3-Br and G is N. |
| 2602 | A is A-1e, $(R^2)_n$ is 3,5-di-Br and G is N. |
| 2603 | A is A-1e, $(R^2)_n$ is 3-Me and G is N. |
| 2604 | A is A-1e, $(R^2)_n$ is 3,5-di-Me and G is N. |
| 2605 | A is A-1e, $(R^2)_n$ is 3-CF$_3$ and G is N. |
| 2606 | A is A-1e, $(R^2)_n$ is 3,5-di-CF$_3$ and G is N. |
| 2607 | A is A-1e, $(R^2)_n$ is 3-MeO and G is N. |
| 2608 | A is A-1e, $(R^2)_n$ is 3,5-di-MeO and G is N. |
| 2609 | A is A-1e, $(R^2)_n$ is 3-CN and G is N. |
| 2610 | A is A-1e, $(R^2)_n$ is 3,5-di-CN and G is N. |
| 2611 | A is A-1e, $(R^2)_n$ is 3,6-di-F and G is N. |
| 2612 | A is A-1e, $(R^2)_n$ is 3,6-di-Cl and G is N. |
| 2613 | A is A-1e, $(R^2)_n$ is 3,6-di-Br and G is N. |
| 2614 | A is A-1e, $(R^2)_n$ is 3,6-di-Me and G is N. |
| 2615 | A is A-1e, $(R^2)_n$ is 3,6-di-CF$_3$ and G is N. |
| 2616 | A is A-1e, $(R^2)_n$ is 3,6-di-MeO and G is N. |
| 2617 | A is A-1e, $(R^2)_n$ is 3,6-di-CN and G is N. |
| 2618 | A is A-1e, $(R^2)_n$ is 6-F and G is N. |
| 2619 | A is A-1e, $(R^2)_n$ is 6-Cl and G is N. |
| 2620 | A is A-1e, $(R^2)_n$ is 6-Br and G is N. |
| 2621 | A is A-1e, $(R^2)_n$ is 6-Me and G is N. |
| 2622 | A is A-1e, $(R^2)_n$ is 6-CF$_3$ and G is N. |
| 2623 | A is A-1e, $(R^2)_n$ is 6-MeO and G is N. |
| 2624 | A is A-1e, $(R^2)_n$ is 6-CN and G is N. |
| 2625 | A is A-1f, $(R^2)_n$ is H and G is CH. |
| 2626 | A is A-1f, $(R^2)_n$ is 3-F and G is CH. |
| 2627 | A is A-1f, $(R^2)_n$ is 3,5-di-F and G is CH. |
| 2628 | A is A-1f, $(R^2)_n$ is 3-Cl and G is CH. |
| 2629 | A is A-1f, $(R^2)_n$ is 3,5-di-Cl and G is CH. |

TABLES 2306-4032-continued

| Table | Row Heading |
|---|---|
| 2630 | A is A-1f, $(R^2)_n$ is 3-Br and G is CH. |
| 2631 | A is A-1f, $(R^2)_n$ is 3,5-di-Br and G is CH. |
| 2632 | A is A-1f, $(R^2)_n$ is 3-Me and G is CH. |
| 2633 | A is A-1f, $(R^2)_n$ is 3,5-di-Me and G is CH. |
| 2634 | A is A-1f, $(R^2)_n$ is 3-CF$_3$ and G is CH. |
| 2635 | A is A-1f, $(R^2)_n$ is 3,5-di-CF$_3$ and G is CH. |
| 2636 | A is A-1f, $(R^2)_n$ is 3-MeO and G is CH. |
| 2637 | A is A-1f, $(R^2)_n$ is 3,5-di-MeO and G is CH. |
| 2638 | A is A-1f, $(R^2)_n$ is 3-CN and G is CH. |
| 2639 | A is A-1f, $(R^2)_n$ is 3,5-di-CN and G is CH. |
| 2640 | A is A-1f, $(R^2)_n$ is 3,6-di-F and G is CH. |
| 2641 | A is A-1f, $(R^2)_n$ is 3,6-di-Cl and G is CH. |
| 2642 | A is A-1f, $(R^2)_n$ is 3,6-di-Br and G is CH. |
| 2643 | A is A-1f, $(R^2)_n$ is 3,6-di-Me and G is CH. |
| 2644 | A is A-1f, $(R^2)_n$ is 3,6-di-CF$_3$ and G is CH. |
| 2645 | A is A-1f, $(R^2)_n$ is 3,6-di-MeO and G is CH. |
| 2646 | A is A-1f, $(R^2)_n$ is 3,6-di-CN and G is CH. |
| 2647 | A is A-1f, $(R^2)_n$ is 6-F and G is CH. |
| 2648 | A is A-1f, $(R^2)_n$ is 6-Cl and G is CH. |
| 2649 | A is A-1f, $(R^2)_n$ is 6-Br and G is CH. |
| 2650 | A is A-1f, $(R^2)_n$ is 6-Me and G is CH. |
| 2651 | A is A-1f, $(R^2)_n$ is 6-CF$_3$ and G is CH. |
| 2652 | A is A-1f, $(R^2)_n$ is 6-MeO and G is CH. |
| 2653 | A is A-1f, $(R^2)_n$ is 6-CN and G is CH. |
| 2654 | A is A-1f, $(R^2)_n$ is 6-F and G is C—F. |
| 2655 | A is A-1f, $(R^2)_n$ is 6-Cl and G is C—Cl. |
| 2656 | A is A-1f, $(R^2)_n$ is 6-Br and G is C—Br. |
| 2657 | A is A-1f, $(R^2)_n$ is 6-Me and G is C—Me. |
| 2658 | A is A-1f, $(R^2)_n$ is 6-CF$_3$ and G is C—CF$_3$. |
| 2659 | A is A-1f, $(R^2)_n$ is 6-MeO and G is C—OMe. |
| 2660 | A is A-1f, $(R^2)_n$ is H and G is N. |
| 2661 | A is A-1f, $(R^2)_n$ is 3-F and G is N. |
| 2662 | A is A-1f, $(R^2)_n$ is 3,5-di-F and G is N. |
| 2663 | A is A-1f, $(R^2)_n$ is 3-Cl and G is N. |
| 2664 | A is A-1f, $(R^2)_n$ is 3,5-di-Cl and G is N. |
| 2665 | A is A-1f, $(R^2)_n$ is 3-Br and G is N. |
| 2666 | A is A-1f, $(R^2)_n$ is 3,5-di-Br and G is N. |
| 2667 | A is A-1f, $(R^2)_n$ is 3-Me and G is N. |
| 2668 | A is A-1f, $(R^2)_n$ is 3,5-di-Me and G is N. |
| 2669 | A is A-1f, $(R^2)_n$ is 3-CF$_3$ and G is N. |
| 2670 | A is A-1f, $(R^2)_n$ is 3,5-di-CF$_3$ and G is N. |
| 2671 | A is A-1f, $(R^2)_n$ is 3-MeO and G is N. |
| 2672 | A is A-1f, $(R^2)_n$ is 3,5-di-MeO and G is N. |
| 2673 | A is A-1f, $(R^2)_n$ is 3-CN and G is N. |
| 2674 | A is A-1f, $(R^2)_n$ is 3,5-di-CN and G is N. |
| 2675 | A is A-1f, $(R^2)_n$ is 3,6-di-F and G is N. |
| 2676 | A is A-1f, $(R^2)_n$ is 3,6-di-Cl and G is N. |
| 2677 | A is A-1f, $(R^2)_n$ is 3,6-di-Br and G is N. |
| 2678 | A is A-1f, $(R^2)_n$ is 3,6-di-Me and G is N. |
| 2679 | A is A-1f, $(R^2)_n$ is 3,6-di-CF$_3$ and G is N. |
| 2680 | A is A-1f, $(R^2)_n$ is 3,6-di-MeO and G is N. |
| 2681 | A is A-1f, $(R^2)_n$ is 3,6-di-CN and G is N. |
| 2682 | A is A-1f, $(R^2)_n$ is 6-F and G is N. |
| 2683 | A is A-1f, $(R^2)_n$ is 6-Cl and G is N. |
| 2684 | A is A-1f, $(R^2)_n$ is 6-Br and G is N. |
| 2685 | A is A-1f, $(R^2)_n$ is 6-Me and G is N. |
| 2686 | A is A-1f, $(R^2)_n$ is 6-CF$_3$ and G is N. |
| 2687 | A is A-1f, $(R^2)_n$ is 6-MeO and G is N. |
| 2688 | A is A-1f, $(R^2)_n$ is 6-CN and G is N. |
| 2689 | A is A-1g, $(R^2)_n$ is H and G is CH. |
| 2690 | A is A-1g, $(R^2)_n$ is 3-F and G is CH. |
| 2691 | A is A-1g, $(R^2)_n$ is 3,5-di-F and G is CH. |
| 2692 | A is A-1g, $(R^2)_n$ is 3-Cl and G is CH. |
| 2693 | A is A-1g, $(R^2)_n$ is 3,5-di-Cl and G is CH. |
| 2694 | A is A-1g, $(R^2)_n$ is 3-Br and G is CH. |
| 2695 | A is A-1g, $(R^2)_n$ is 3,5-di-Br and G is CH. |
| 2696 | A is A-1g, $(R^2)_n$ is 3-Me and G is CH. |
| 2697 | A is A-1g, $(R^2)_n$ is 3,5-di-Me and G is CH. |
| 2698 | A is A-1g, $(R^2)_n$ is 3-CF$_3$ and G is CH. |
| 2699 | A is A-1g, $(R^2)_n$ is 3,5-di-CF$_3$ and G is CH. |
| 2700 | A is A-1g, $(R^2)_n$ is 3-MeO and G is CH. |
| 2701 | A is A-1g, $(R^2)_n$ is 3,5-di-MeO and G is CH. |
| 2702 | A is A-1g, $(R^2)_n$ is 3-CN and G is CH. |
| 2703 | A is A-1g, $(R^2)_n$ is 3,5-di-CN and G is CH. |
| 2704 | A is A-1g, $(R^2)_n$ is 3,6-di-F and G is CH. |
| 2705 | A is A-1g, $(R^2)_n$ is 3,6-di-Cl and G is CH. |
| 2706 | A is A-1g, $(R^2)_n$ is 3,6-di-Br and G is CH. |
| 2707 | A is A-1g, $(R^2)_n$ is 3,6-di-Me and G is CH. |
| 2708 | A is A-1g, $(R^2)_n$ is 3,6-di-CF$_3$ and G is CH. |
| 2709 | A is A-1g, $(R^2)_n$ is 3,6-di-MeO and G is CH. |
| 2710 | A is A-1g, $(R^2)_n$ is 3,6-di-CN and G is CH. |
| 2711 | A is A-1g, $(R^2)_n$ is 6-F and G is CH. |
| 2712 | A is A-1g, $(R^2)_n$ is 6-Cl and G is CH. |
| 2713 | A is A-1g, $(R^2)_n$ is 6-Br and G is CH. |
| 2714 | A is A-1g, $(R^2)_n$ is 6-Me and G is CH. |
| 2715 | A is A-1g, $(R^2)_n$ is 6-CF$_3$ and G is CH. |
| 2716 | A is A-1g, $(R^2)_n$ is 6-MeO and G is CH. |
| 2717 | A is A-1g, $(R^2)_n$ is 6-CN and G is CH. |
| 2718 | A is A-1g, $(R^2)_n$ is 6-F and G is C—F. |
| 2719 | A is A-1g, $(R^2)_n$ is 6-Cl and G is C—Cl. |
| 2720 | A is A-1g, $(R^2)_n$ is 6-Br and G is C—Br. |
| 2721 | A is A-1g, $(R^2)_n$ is 6-Me and G is C—Me. |
| 2722 | A is A-1g, $(R^2)_n$ is 6-CF$_3$ and G is C—CF$_3$. |
| 2723 | A is A-1g, $(R^2)_n$ is 6-MeO and G is C—OMe. |
| 2724 | A is A-1g, $(R^2)_n$ is H and G is N. |
| 2725 | A is A-1g, $(R^2)_n$ is 3-F and G is N. |
| 2726 | A is A-1g, $(R^2)_n$ is 3,5-di-F and G is N. |
| 2727 | A is A-1g, $(R^2)_n$ is 3-Cl and G is N. |
| 2728 | A is A-1g, $(R^2)_n$ is 3,5-di-Cl and G is N. |
| 2729 | A is A-1g, $(R^2)_n$ is 3-Br and G is N. |
| 2730 | A is A-1g, $(R^2)_n$ is 3,5-di-Br and G is N. |
| 2731 | A is A-1g, $(R^2)_n$ is 3-Me and G is N. |
| 2732 | A is A-1g, $(R^2)_n$ is 3,5-di-Me and G is N. |
| 2733 | A is A-1g, $(R^2)_n$ is 3-CF$_3$ and G is N. |
| 2734 | A is A-1g, $(R^2)_n$ is 3,5-di-CF$_3$ and G is N. |
| 2735 | A is A-1g, $(R^2)_n$ is 3-MeO and G is N. |
| 2736 | A is A-1g, $(R^2)_n$ is 3,5-di-MeO and G is N. |
| 2737 | A is A-1g, $(R^2)_n$ is 3-CN and G is N. |
| 2738 | A is A-1g, $(R^2)_n$ is 3,5-di-CN and G is N. |
| 2739 | A is A-1g, $(R^2)_n$ is 3,6-di-F and G is N. |
| 2740 | A is A-1g, $(R^2)_n$ is 3,6-di-Cl and G is N. |
| 2741 | A is A-1g, $(R^2)_n$ is 3,6-di-Br and G is N. |
| 2742 | A is A-1g, $(R^2)_n$ is 3,6-di-Me and G is N. |
| 2743 | A is A-1g, $(R^2)_n$ is 3,6-di-CF$_3$ and G is N. |
| 2744 | A is A-1g, $(R^2)_n$ is 3,6-di-MeO and G is N. |
| 2745 | A is A-1g, $(R^2)_n$ is 3,6-di-CN and G is N. |
| 2746 | A is A-1g, $(R^2)_n$ is 6-F and G is N. |
| 2747 | A is A-1g, $(R^2)_n$ is 6-Cl and G is N. |
| 2748 | A is A-1g, $(R^2)_n$ is 6-Br and G is N. |
| 2749 | A is A-1g, $(R^2)_n$ is 6-Me and G is N. |
| 2750 | A is A-1g, $(R^2)_n$ is 6-CF$_3$ and G is N. |
| 2751 | A is A-1g, $(R^2)_n$ is 6-MeO and G is N. |
| 2752 | A is A-1g, $(R^2)_n$ is 6-CN and G is N. |
| 2753 | A is A-1h, $(R^2)_n$ is H and G is CH. |
| 2754 | A is A-1h, $(R^2)_n$ is 3-F and G is CH. |
| 2755 | A is A-1h, $(R^2)_n$ is 3,5-di-F and G is CH. |
| 2756 | A is A-1h, $(R^2)_n$ is 3-Cl and G is CH. |
| 2757 | A is A-1h, $(R^2)_n$ is 3,5-di-Cl and G is CH. |
| 2758 | A is A-1h, $(R^2)_n$ is 3-Br and G is CH. |
| 2759 | A is A-1h, $(R^2)_n$ is 3,5-di-Br and G is CH. |
| 2760 | A is A-1h, $(R^2)_n$ is 3-Me and G is CH. |
| 2761 | A is A-1h, $(R^2)_n$ is 3,5-di-Me and G is CH. |
| 2762 | A is A-1h, $(R^2)_n$ is 3-CF$_3$ and G is CH. |
| 2763 | A is A-1h, $(R^2)_n$ is 3,5-di-CF$_3$ and G is CH. |
| 2764 | A is A-1h, $(R^2)_n$ is 3-MeO and G is CH. |
| 2765 | A is A-1h, $(R^2)_n$ is 3,5-di-MeO and G is CH. |
| 2766 | A is A-1h, $(R^2)_n$ is 3-CN and G is CH. |
| 2767 | A is A-1h, $(R^2)_n$ is 3,5-di-CN and G is CH. |
| 2768 | A is A-1h, $(R^2)_n$ is 3,6-di-F and G is CH. |
| 2769 | A is A-1h, $(R^2)_n$ is 3,6-di-Cl and G is CH. |
| 2770 | A is A-1h, $(R^2)_n$ is 3,6-di-Br and G is CH. |
| 2771 | A is A-1h, $(R^2)_n$ is 3,6-di-Me and G is CH. |
| 2772 | A is A-1h, $(R^2)_n$ is 3,6-di-CF$_3$ and G is CH. |
| 2773 | A is A-1h, $(R^2)_n$ is 3,6-di-MeO and G is CH. |
| 2774 | A is A-1h, $(R^2)_n$ is 3,6-di-CN and G is CH. |
| 2775 | A is A-1h, $(R^2)_n$ is 6-F and G is CH. |
| 2776 | A is A-1h, $(R^2)_n$ is 6-Cl and G is CH. |
| 2777 | A is A-1h, $(R^2)_n$ is 6-Br and G is CH. |
| 2778 | A is A-1h, $(R^2)_n$ is 6-Me and G is CH. |
| 2779 | A is A-1h, $(R^2)_n$ is 6-CF$_3$ and G is CH. |
| 2780 | A is A-1h, $(R^2)_n$ is 6-MeO and G is CH. |
| 2781 | A is A-1h, $(R^2)_n$ is 6-CN and G is CH. |
| 2782 | A is A-1h, $(R^2)_n$ is 6-F and G is C—F. |
| 2783 | A is A-1h, $(R^2)_n$ is 6-Cl and G is C—Cl. |
| 2784 | A is A-1h, $(R^2)_n$ is 6-Br and G is C—Br. |
| 2785 | A is A-1h, $(R^2)_n$ is 6-Me and G is C—Me. |

TABLES 2306-4032-continued

| Table | Row Heading |
|---|---|
| 2786 | A is A-1h, $(R^2)_n$ is 6-CF$_3$ and G is C—CF$_3$. |
| 2787 | A is A-1h, $(R^2)_n$ is 6-MeO and G is C—OMe. |
| 2788 | A is A-1h, $(R^2)_n$ is H and G is N. |
| 2789 | A is A-1h, $(R^2)_n$ is 3-F and G is N. |
| 2790 | A is A-1h, $(R^2)_n$ is 3,5-di-F and G is N. |
| 2791 | A is A-1h, $(R^2)_n$ is 3-Cl and G is N. |
| 2792 | A is A-1h, $(R^2)_n$ is 3,5-di-Cl and G is N. |
| 2793 | A is A-1h, $(R^2)_n$ is 3-Br and G is N. |
| 2794 | A is A-1h, $(R^2)_n$ is 3,5-di-Br and G is N. |
| 2795 | A is A-1h, $(R^2)_n$ is 3-Me and G is N. |
| 2796 | A is A-1h, $(R^2)_n$ is 3,5-di-Me and G is N. |
| 2797 | A is A-1h, $(R^2)_n$ is 3-CF$_3$ and G is N. |
| 2798 | A is A-1h, $(R^2)_n$ is 3,5-di-CF$_3$ and G is N. |
| 2799 | A is A-1h, $(R^2)_n$ is 3-MeO and G is N. |
| 2800 | A is A-1h, $(R^2)_n$ is 3,5-di-MeO and G is N. |
| 2801 | A is A-1h, $(R^2)_n$ is 3-CN and G is N. |
| 2802 | A is A-1h, $(R^2)_n$ is 3,5-di-CN and G is N. |
| 2803 | A is A-1h, $(R^2)_n$ is 3,6-di-F and G is N. |
| 2804 | A is A-1h, $(R^2)_n$ is 3,6-di-Cl and G is N. |
| 2805 | A is A-1h, $(R^2)_n$ is 3,6-di-Br and G is N. |
| 2806 | A is A-1h, $(R^2)_n$ is 3,6-di-Me and G is N. |
| 2807 | A is A-1h, $(R^2)_n$ is 3,6-di-CF$_3$ and G is N. |
| 2808 | A is A-1h, $(R^2)_n$ is 3,6-di-MeO and G is N. |
| 2809 | A is A-1h, $(R^2)_n$ is 3,6-di-CN and G is N. |
| 2810 | A is A-1h, $(R^2)_n$ is 6-F and G is N. |
| 2811 | A is A-1h, $(R^2)_n$ is 6-Cl and G is N. |
| 2812 | A is A-1h, $(R^2)_n$ is 6-Br and G is N. |
| 2813 | A is A-1h, $(R^2)_n$ is 6-Me and G is N. |
| 2814 | A is A-1h, $(R^2)_n$ is 6-CF$_3$ and G is N. |
| 2815 | A is A-1h, $(R^2)_n$ is 6-MeO and G is N. |
| 2816 | A is A-1h, $(R^2)_n$ is 6-CN and G is N. |
| 2817 | A is A-1i, $(R^2)_n$ is H and G is CH. |
| 2818 | A is A-1i, $(R^2)_n$ is 3-F and G is CH. |
| 2819 | A is A-1i, $(R^2)_n$ is 3,5-di-F and G is CH. |
| 2820 | A is A-1i, $(R^2)_n$ is 3-Cl and G is CH. |
| 2821 | A is A-1i, $(R^2)_n$ is 3,5-di-Cl and G is CH. |
| 2822 | A is A-1i, $(R^2)_n$ is 3-Br and G is CH. |
| 2823 | A is A-1i, $(R^2)_n$ is 3,5-di-Br and G is CH. |
| 2824 | A is A-1i, $(R^2)_n$ is 3-Me and G is CH. |
| 2825 | A is A-1i, $(R^2)_n$ is 3,5-di-Me and G is CH. |
| 2826 | A is A-1i, $(R^2)_n$ is 3-CF$_3$ and G is CH. |
| 2827 | A is A-1i, $(R^2)_n$ is 3,5-di-CF$_3$ and G is CH. |
| 2828 | A is A-1i, $(R^2)_n$ is 3-MeO and G is CH. |
| 2829 | A is A-1i, $(R^2)_n$ is 3,5-di-MeO and G is CH. |
| 2830 | A is A-1i, $(R^2)_n$ is 3-CN and G is CH. |
| 2831 | A is A-1i, $(R^2)_n$ is 3,5-di-CN and G is CH. |
| 2832 | A is A-1i, $(R^2)_n$ is 3,6-di-F and G is CH. |
| 2833 | A is A-1i, $(R^2)_n$ is 3,6-di-Cl and G is CH. |
| 2834 | A is A-1i, $(R^2)_n$ is 3,6-di-Br and G is CH. |
| 2835 | A is A-1i, $(R^2)_n$ is 3,6-di-Me and G is CH. |
| 2836 | A is A-1i, $(R^2)_n$ is 3,6-di-CF$_3$ and G is CH. |
| 2837 | A is A-1i, $(R^2)_n$ is 3,6-di-MeO and G is CH. |
| 2838 | A is A-1i, $(R^2)_n$ is 3,6-di-CN and G is CH. |
| 2839 | A is A-1i, $(R^2)_n$ is 6-F and G is CH. |
| 2840 | A is A-1i, $(R^2)_n$ is 6-Cl and G is CH. |
| 2841 | A is A-1i, $(R^2)_n$ is 6-Br and G is CH. |
| 2842 | A is A-1i, $(R^2)_n$ is 6-Me and G is CH. |
| 2843 | A is A-1i, $(R^2)_n$ is 6-CF$_3$ and G is CH. |
| 2844 | A is A-1i, $(R^2)_n$ is 6-MeO and G is CH. |
| 2845 | A is A-1i, $(R^2)_n$ is 6-CN and G is CH. |
| 2846 | A is A-1i, $(R^2)_n$ is 6-F and G is C—F. |
| 2847 | A is A-1i, $(R^2)_n$ is 6-Cl and G is C—Cl. |
| 2848 | A is A-1i, $(R^2)_n$ is 6-Br and G is C—Br. |
| 2849 | A is A-1i, $(R^2)_n$ is 6-Me and G is C—Me. |
| 2850 | A is A-1i, $(R^2)_n$ is 6-CF$_3$ and G is C—CF$_3$. |
| 2851 | A is A-1i, $(R^2)_n$ is 6-MeO and G is C—OMe. |
| 2852 | A is A-1i, $(R^2)_n$ is H and G is N. |
| 2853 | A is A-1i, $(R^2)_n$ is 3-F and G is N. |
| 2854 | A is A-1i, $(R^2)_n$ is 3,5-di-F and G is N. |
| 2855 | A is A-1i, $(R^2)_n$ is 3-Cl and G is N. |
| 2856 | A is A-1i, $(R^2)_n$ is 3,5-di-Cl and G is N. |
| 2857 | A is A-1i, $(R^2)_n$ is 3-Br and G is N. |
| 2858 | A is A-1i, $(R^2)_n$ is 3,5-di-Br and G is N. |
| 2859 | A is A-1i, $(R^2)_n$ is 3-Me and G is N. |
| 2860 | A is A-1i, $(R^2)_n$ is 3,5-di-Me and G is N. |
| 2861 | A is A-1i, $(R^2)_n$ is 3-CF$_3$ and G is N. |
| 2862 | A is A-1i, $(R^2)_n$ is 3,5-di-CF$_3$ and G is N. |
| 2863 | A is A-1i, $(R^2)_n$ is 3-MeO and G is N. |
| 2864 | A is A-1i, $(R^2)_n$ is 3,5-di-MeO and G is N. |
| 2865 | A is A-1i, $(R^2)_n$ is 3-CN and G is N. |
| 2866 | A is A-1i, $(R^2)_n$ is 3,5-di-CN and G is N. |
| 2867 | A is A-1i, $(R^2)_n$ is 3,6-di-F and G is N. |
| 2868 | A is A-1i, $(R^2)_n$ is 3,6-di-Cl and G is N. |
| 2869 | A is A-1i, $(R^2)_n$ is 3,6-di-Br and G is N. |
| 2870 | A is A-1i, $(R^2)_n$ is 3,6-di-Me and G is N. |
| 2871 | A is A-1i, $(R^2)_n$ is 3,6-di-CF$_3$ and G is N. |
| 2872 | A is A-1i, $(R^2)_n$ is 3,6-di-MeO and G is N. |
| 2873 | A is A-1i, $(R^2)_n$ is 3,6-di-CN and G is N. |
| 2874 | A is A-1i, $(R^2)_n$ is 6-F and G is N. |
| 2875 | A is A-1i, $(R^2)_n$ is 6-Cl and G is N. |
| 2876 | A is A-1i, $(R^2)_n$ is 6-Br and G is N. |
| 2877 | A is A-1i, $(R^2)_n$ is 6-Me and G is N. |
| 2878 | A is A-1i, $(R^2)_n$ is 6-CF$_3$ and G is N. |
| 2879 | A is A-1i, $(R^2)_n$ is 6-MeO and G is N. |
| 2880 | A is A-1i, $(R^2)_n$ is 6-CN and G is N. |
| 2881 | A is A-1j, $(R^2)_n$ is H and G is CH. |
| 2882 | A is A-1j, $(R^2)_n$ is 3-F and G is CH. |
| 2883 | A is A-1j, $(R^2)_n$ is 3,5-di-F and G is CH. |
| 2884 | A is A-1j, $(R^2)_n$ is 3-Cl and G is CH. |
| 2885 | A is A-1j, $(R^2)_n$ is 3,5-di-Cl and G is CH. |
| 2886 | A is A-1j, $(R^2)_n$ is 3-Br and G is CH. |
| 2887 | A is A-1j, $(R^2)_n$ is 3,5-di-Br and G is CH. |
| 2888 | A is A-1j, $(R^2)_n$ is 3-Me and G is CH. |
| 2889 | A is A-1j, $(R^2)_n$ is 3,5-di-Me and G is CH. |
| 2890 | A is A-1j, $(R^2)_n$ is 3-CF$_3$ and G is CH. |
| 2891 | A is A-1j, $(R^2)_n$ is 3,5-di-CF$_3$ and G is CH. |
| 2892 | A is A-1j, $(R^2)_n$ is 3-MeO and G is CH. |
| 2893 | A is A-1j, $(R^2)_n$ is 3,5-di-MeO and G is CH. |
| 2894 | A is A-1j, $(R^2)_n$ is 3-CN and G is CH. |
| 2895 | A is A-1j, $(R^2)_n$ is 3,5-di-CN and G is CH. |
| 2896 | A is A-1j, $(R^2)_n$ is 3,6-di-F and G is CH. |
| 2897 | A is A-1j, $(R^2)_n$ is 3,6-di-Cl and G is CH. |
| 2898 | A is A-1j, $(R^2)_n$ is 3,6-di-Br and G is CH. |
| 2899 | A is A-1j, $(R^2)_n$ is 3,6-di-Me and G is CH. |
| 2900 | A is A-1j, $(R^2)_n$ is 3,6-di-CF$_3$ and G is CH. |
| 2901 | A is A-1j, $(R^2)_n$ is 3,6-di-MeO and G is CH. |
| 2902 | A is A-1j, $(R^2)_n$ is 3,6-di-CN and G is CH. |
| 2903 | A is A-1j, $(R^2)_n$ is 6-F and G is CH. |
| 2904 | A is A-1j, $(R^2)_n$ is 6-Cl and G is CH. |
| 2905 | A is A-1j, $(R^2)_n$ is 6-Br and G is CH. |
| 2906 | A is A-1j, $(R^2)_n$ is 6-Me and G is CH. |
| 2907 | A is A-1j, $(R^2)_n$ is 6-CF$_3$ and G is CH. |
| 2908 | A is A-1j, $(R^2)_n$ is 6-MeO and G is CH. |
| 2909 | A is A-1j, $(R^2)_n$ is 6-CN and G is CH. |
| 2910 | A is A-1j, $(R^2)_n$ is 6-F and G is C—F. |
| 2911 | A is A-1j, $(R^2)_n$ is 6-Cl and G is C—Cl. |
| 2912 | A is A-1j, $(R^2)_n$ is 6-Br and G is C—Br. |
| 2913 | A is A-1j, $(R^2)_n$ is 6-Me and G is C—Me. |
| 2914 | A is A-1j, $(R^2)_n$ is 6-CF$_3$ and G is C—CF$_3$. |
| 2915 | A is A-1j, $(R^2)_n$ is 6-MeO and G is C—OMe. |
| 2916 | A is A-1j, $(R^2)_n$ is H and G is N. |
| 2917 | A is A-1j, $(R^2)_n$ is 3-F and G is N. |
| 2918 | A is A-1j, $(R^2)_n$ is 3,5-di-F and G is N. |
| 2919 | A is A-1j, $(R^2)_n$ is 3-Cl and G is N. |
| 2920 | A is A-1j, $(R^2)_n$ is 3,5-di-Cl and G is N. |
| 2921 | A is A-1j, $(R^2)_n$ is 3-Br and G is N. |
| 2922 | A is A-1j, $(R^2)_n$ is 3,5-di-Br and G is N. |
| 2923 | A is A-1j, $(R^2)_n$ is 3-Me and G is N. |
| 2924 | A is A-1j, $(R^2)_n$ is 3,5-di-Me and G is N. |
| 2925 | A is A-1j, $(R^2)_n$ is 3-CF$_3$ and G is N. |
| 2926 | A is A-1j, $(R^2)_n$ is 3,5-di-CF$_3$ and G is N. |
| 2927 | A is A-1j, $(R^2)_n$ is 3-MeO and G is N. |
| 2928 | A is A-1j, $(R^2)_n$ is 3,5-di-MeO and G is N. |
| 2929 | A is A-1j, $(R^2)_n$ is 3-CN and G is N. |
| 2930 | A is A-1j, $(R^2)_n$ is 3,5-di-CN and G is N. |
| 2931 | A is A-1j, $(R^2)_n$ is 3,6-di-F and G is N. |
| 2932 | A is A-1j, $(R^2)_n$ is 3,6-di-Cl and G is N. |
| 2933 | A is A-1j, $(R^2)_n$ is 3,6-di-Br and G is N. |
| 2934 | A is A-1j, $(R^2)_n$ is 3,6-di-Me and G is N. |
| 2935 | A is A-1j, $(R^2)_n$ is 3,6-di-CF$_3$ and G is N. |
| 2936 | A is A-1j, $(R^2)_n$ is 3,6-di-MeO and G is N. |
| 2937 | A is A-1j, $(R^2)_n$ is 3,6-di-CN and G is N. |
| 2938 | A is A-1j, $(R^2)_n$ is 6-F and G is N. |
| 2939 | A is A-1j, $(R^2)_n$ is 6-Cl and G is N. |
| 2940 | A is A-1j, $(R^2)_n$ is 6-Br and G is N. |
| 2941 | A is A-1j, $(R^2)_n$ is 6-Me and G is N. |

TABLES 2306-4032-continued

| Table | Row Heading |
|---|---|
| 2942 | A is A-1j, $(R^2)_n$ is 6-CF$_3$ and G is N. |
| 2943 | A is A-1j, $(R^2)_n$ is 6-MeO and G is N. |
| 2944 | A is A-1j, $(R^2)_n$ is 6-CN and G is N. |
| 2945 | A is A-1k, $(R^2)_n$ is H and G is CH. |
| 2946 | A is A-1k, $(R^2)_n$ is 3-F and G is CH. |
| 2947 | A is A-1k, $(R^2)_n$ is 3,5-di-F and G is CH. |
| 2948 | A is A-1k, $(R^2)_n$ is 3-Cl and G is CH. |
| 2949 | A is A-1k, $(R^2)_n$ is 3,5-di-Cl and G is CH. |
| 2950 | A is A-1k, $(R^2)_n$ is 3-Br and G is CH. |
| 2951 | A is A-1k, $(R^2)_n$ is 3,5-di-Br and G is CH. |
| 2952 | A is A-1k, $(R^2)_n$ is 3-Me and G is CH. |
| 2953 | A is A-1k, $(R^2)_n$ is 3,5-di-Me and G is CH. |
| 2954 | A is A-1k, $(R^2)_n$ is 3-CF$_3$ and G is CH. |
| 2955 | A is A-1k, $(R^2)_n$ is 3,5-di-CF$_3$ and G is CH. |
| 2956 | A is A-1k, $(R^2)_n$ is 3-MeO and G is CH. |
| 2957 | A is A-1k, $(R^2)_n$ is 3,5-di-MeO and G is CH. |
| 2958 | A is A-1k, $(R^2)_n$ is 3-CN and G is CH. |
| 2959 | A is A-1k, $(R^2)_n$ is 3,5-di-CN and G is CH. |
| 2960 | A is A-1k, $(R^2)_n$ is 3,6-di-F and G is CH. |
| 2961 | A is A-1k, $(R^2)_n$ is 3,6-di-Cl and G is CH. |
| 2962 | A is A-1k, $(R^2)_n$ is 3,6-di-Br and G is CH. |
| 2963 | A is A-1k, $(R^2)_n$ is 3,6-di-Me and G is CH. |
| 2964 | A is A-1k, $(R^2)_n$ is 3,6-di-CF$_3$ and G is CH. |
| 2965 | A is A-1k, $(R^2)_n$ is 3,6-di-MeO and G is CH. |
| 2966 | A is A-1k, $(R^2)_n$ is 3,6-di-CN and G is CH. |
| 2967 | A is A-1k, $(R^2)_n$ is 6-F and G is CH. |
| 2968 | A is A-1k, $(R^2)_n$ is 6-Cl and G is CH. |
| 2969 | A is A-1k, $(R^2)_n$ is 6-Br and G is CH. |
| 2970 | A is A-1k, $(R^2)_n$ is 6-Me and G is CH. |
| 2971 | A is A-1k, $(R^2)_n$ is 6-CF$_3$ and G is CH. |
| 2972 | A is A-1k, $(R^2)_n$ is 6-MeO and G is CH. |
| 2973 | A is A-1k, $(R^2)_n$ is 6-CN and G is CH. |
| 2974 | A is A-1k, $(R^2)_n$ is 6-F and G is C—F. |
| 2975 | A is A-1k, $(R^2)_n$ is 6-Cl and G is C—Cl. |
| 2976 | A is A-1k, $(R^2)_n$ is 6-Br and G is C—Br. |
| 2977 | A is A-1k, $(R^2)_n$ is 6-Me and G is C—Me. |
| 2978 | A is A-1k, $(R^2)_n$ is 6-CF$_3$ and G is C—CF$_3$. |
| 2979 | A is A-1k, $(R^2)_n$ is 6-MeO and G is C—OMe. |
| 2980 | A is A-1k, $(R^2)_n$ is H and G is N. |
| 2981 | A is A-1k, $(R^2)_n$ is 3-F and G is N. |
| 2982 | A is A-1k, $(R^2)_n$ is 3,5-di-F and G is N. |
| 2983 | A is A-1k, $(R^2)_n$ is 3-Cl and G is N. |
| 2984 | A is A-1k, $(R^2)_n$ is 3,5-di-Cl and G is N. |
| 2985 | A is A-1k, $(R^2)_n$ is 3-Br and G is N. |
| 2986 | A is A-1k, $(R^2)_n$ is 3,5-di-Br and G is N. |
| 2987 | A is A-1k, $(R^2)_n$ is 3-Me and G is N. |
| 2988 | A is A-1k, $(R^2)_n$ is 3,5-di-Me and G is N. |
| 2989 | A is A-1k, $(R^2)_n$ is 3-CF$_3$ and G is N. |
| 2990 | A is A-1k, $(R^2)_n$ is 3,5-di-CF$_3$ and G is N. |
| 2991 | A is A-1k, $(R^2)_n$ is 3-MeO and G is N. |
| 2992 | A is A-1k, $(R^2)_n$ is 3,5-di-MeO and G is N. |
| 2993 | A is A-1k, $(R^2)_n$ is 3-CN and G is N. |
| 2994 | A is A-1k, $(R^2)_n$ is 3,5-di-CN and G is N. |
| 2995 | A is A-1k, $(R^2)_n$ is 3,6-di-F and G is N. |
| 2996 | A is A-1k, $(R^2)_n$ is 3,6-di-Cl and G is N. |
| 2997 | A is A-1k, $(R^2)_n$ is 3,6-di-Br and G is N. |
| 2998 | A is A-1k, $(R^2)_n$ is 3,6-di-Me and G is N. |
| 2999 | A is A-1k, $(R^2)_n$ is 3,6-di-CF$_3$ and G is N. |
| 3000 | A is A-1k, $(R^2)_n$ is 3,6-di-MeO and G is N. |
| 3001 | A is A-1k, $(R^2)_n$ is 3,6-di-CN and G is N. |
| 3002 | A is A-1k, $(R^2)_n$ is 6-F and G is N. |
| 3003 | A is A-1k, $(R^2)_n$ is 6-Cl and G is N. |
| 3004 | A is A-1k, $(R^2)_n$ is 6-Br and G is N. |
| 3005 | A is A-1k, $(R^2)_n$ is 6-Me and G is N. |
| 3006 | A is A-1k, $(R^2)_n$ is 6-CF$_3$ and G is N. |
| 3007 | A is A-1k, $(R^2)_n$ is 6-MeO and G is N. |
| 3008 | A is A-1k, $(R^2)_n$ is 6-CN and G is N. |
| 3009 | A is A-1l, $(R^2)_n$ is H and G is CH. |
| 3010 | A is A-1l, $(R^2)_n$ is 3-F and G is CH. |
| 3011 | A is A-1l, $(R^2)_n$ is 3,5-di-F and G is CH. |
| 3012 | A is A-1l, $(R^2)_n$ is 3-Cl and G is CH. |
| 3013 | A is A-1l, $(R^2)_n$ is 3,5-di-Cl and G is CH. |
| 3014 | A is A-1l, $(R^2)_n$ is 3-Br and G is CH. |
| 3015 | A is A-1l, $(R^2)_n$ is 3,5-di-Br and G is CH. |
| 3016 | A is A-1l, $(R^2)_n$ is 3-Me and G is CH. |
| 3017 | A is A-1l, $(R^2)_n$ is 3,5-di-Me and G is CH. |
| 3018 | A is A-1l, $(R^2)_n$ is 3-CF$_3$ and G is CH. |
| 3019 | A is A-1l, $(R^2)_n$ is 3,5-di-CF$_3$ and G is CH. |
| 3020 | A is A-1l, $(R^2)_n$ is 3-MeO and G is CH. |
| 3021 | A is A-1l, $(R^2)_n$ is 3,5-di-MeO and G is CH. |
| 3022 | A is A-1l, $(R^2)_n$ is 3-CN and G is CH. |
| 3023 | A is A-1l, $(R^2)_n$ is 3,5-di-CN and G is CH. |
| 3024 | A is A-1l, $(R^2)_n$ is 3,6-di-F and G is CH. |
| 3025 | A is A-1l, $(R^2)_n$ is 3,6-di-Cl and G is CH. |
| 3026 | A is A-1l, $(R^2)_n$ is 3,6-di-Br and G is CH. |
| 3027 | A is A-1l, $(R^2)_n$ is 3,6-di-Me and G is CH. |
| 3028 | A is A-1l, $(R^2)_n$ is 3,6-di-CF$_3$ and G is CH. |
| 3029 | A is A-1l, $(R^2)_n$ is 3,6-di-MeO and G is CH. |
| 3030 | A is A-1l, $(R^2)_n$ is 3,6-di-CN and G is CH. |
| 3031 | A is A-1l, $(R^2)_n$ is 6-F and G is CH. |
| 3032 | A is A-1l, $(R^2)_n$ is 6-Cl and G is CH. |
| 3033 | A is A-1l, $(R^2)_n$ is 6-Br and G is CH. |
| 3034 | A is A-1l, $(R^2)_n$ is 6-Me and G is CH. |
| 3035 | A is A-1l, $(R^2)_n$ is 6-CF$_3$ and G is CH. |
| 3036 | A is A-1l, $(R^2)_n$ is 6-MeO and G is CH. |
| 3037 | A is A-1l, $(R^2)_n$ is 6-CN and G is CH. |
| 3038 | A is A-1l, $(R^2)_n$ is 6-F and G is C—F. |
| 3039 | A is A-1l, $(R^2)_n$ is 6-Cl and G is C—Cl. |
| 3040 | A is A-1l, $(R^2)_n$ is 6-Br and G is C—Br. |
| 3041 | A is A-1l, $(R^2)_n$ is 6-Me and G is C—Me. |
| 3042 | A is A-1l, $(R^2)_n$ is 6-CF$_3$ and G is C—CF$_3$. |
| 3043 | A is A-1l, $(R^2)_n$ is 6-MeO and G is C—OMe. |
| 3044 | A is A-1l, $(R^2)_n$ is H and G is N. |
| 3045 | A is A-1l, $(R^2)_n$ is 3-F and G is N. |
| 3046 | A is A-1l, $(R^2)_n$ is 3,5-di-F and G is N. |
| 3047 | A is A-1l, $(R^2)_n$ is 3-Cl and G is N. |
| 3048 | A is A-1l, $(R^2)_n$ is 3,5-di-Cl and G is N. |
| 3049 | A is A-1l, $(R^2)_n$ is 3-Br and G is N. |
| 3050 | A is A-1l, $(R^2)_n$ is 3,5-di-Br and G is N. |
| 3051 | A is A-1l, $(R^2)_n$ is 3-Me and G is N. |
| 3052 | A is A-1l, $(R^2)_n$ is 3,5-di-Me and G is N. |
| 3053 | A is A-1l, $(R^2)_n$ is 3-CF$_3$ and G is N. |
| 3054 | A is A-1l, $(R^2)_n$ is 3,5-di-CF$_3$ and G is N. |
| 3055 | A is A-1l, $(R^2)_n$ is 3-MeO and G is N. |
| 3056 | A is A-1l, $(R^2)_n$ is 3,5-di-MeO and G is N. |
| 3057 | A is A-1l, $(R^2)_n$ is 3-CN and G is N. |
| 3058 | A is A-1l, $(R^2)_n$ is 3,5-di-CN and G is N. |
| 3059 | A is A-1l, $(R^2)_n$ is 3,6-di-F and G is N. |
| 3060 | A is A-1l, $(R^2)_n$ is 3,6-di-Cl and G is N. |
| 3061 | A is A-1l, $(R^2)_n$ is 3,6-di-Br and G is N. |
| 3062 | A is A-1l, $(R^2)_n$ is 3,6-di-Me and G is N. |
| 3063 | A is A-1l, $(R^2)_n$ is 3,6-di-CF$_3$ and G is N. |
| 3064 | A is A-1l, $(R^2)_n$ is 3,6-di-MeO and G is N. |
| 3065 | A is A-1l, $(R^2)_n$ is 3,6-di-CN and G is N. |
| 3066 | A is A-1l, $(R^2)_n$ is 6-F and G is N. |
| 3067 | A is A-1l, $(R^2)_n$ is 6-Cl and G is N. |
| 3068 | A is A-1l, $(R^2)_n$ is 6-Br and G is N. |
| 3069 | A is A-1l, $(R^2)_n$ is 6-Me and G is N. |
| 3070 | A is A-1l, $(R^2)_n$ is 6-CF$_3$ and G is N. |
| 3071 | A is A-1l, $(R^2)_n$ is 6-MeO and G is N. |
| 3072 | A is A-1l, $(R^2)_n$ is 6-CN and G is N. |
| 3073 | A is A-1m, $(R^2)_n$ is H and G is CH. |
| 3074 | A is A-1m, $(R^2)_n$ is 3-F and G is CH. |
| 3075 | A is A-1m, $(R^2)_n$ is 3,5-di-F and G is CH. |
| 3076 | A is A-1m, $(R^2)_n$ is 3-Cl and G is CH. |
| 3077 | A is A-1m, $(R^2)_n$ is 3,5-di-Cl and G is CH. |
| 3078 | A is A-1m, $(R^2)_n$ is 3-Br and G is CH. |
| 3079 | A is A-1m, $(R^2)_n$ is 3,5-di-Br and G is CH. |
| 3080 | A is A-1m, $(R^2)_n$ is 3-Me and G is CH. |
| 3081 | A is A-1m, $(R^2)_n$ is 3,5-di-Me and G is CH. |
| 3082 | A is A-1m, $(R^2)_n$ is 3-CF$_3$ and G is CH. |
| 3083 | A is A-1m, $(R^2)_n$ is 3,5-di-CF$_3$ and G is CH. |
| 3084 | A is A-1m, $(R^2)_n$ is 3-MeO and G is CH. |
| 3085 | A is A-1m, $(R^2)_n$ is 3,5-di-MeO and G is CH. |
| 3086 | A is A-1m, $(R^2)_n$ is 3-CN and G is CH. |
| 3087 | A is A-1m, $(R^2)_n$ is 3,5-di-CN and G is CH. |
| 3088 | A is A-1m, $(R^2)_n$ is 3,6-di-F and G is CH. |
| 3089 | A is A-1m, $(R^2)_n$ is 3,6-di-Cl and G is CH. |
| 3090 | A is A-1m, $(R^2)_n$ is 3,6-di-Br and G is CH. |
| 3091 | A is A-1m, $(R^2)_n$ is 3,6-di-Me and G is CH. |
| 3092 | A is A-1m, $(R^2)_n$ is 3,6-di-CF$_3$ and G is CH. |
| 3093 | A is A-1m, $(R^2)_n$ is 3,6-di-MeO and G is CH. |
| 3094 | A is A-1m, $(R^2)_n$ is 3,6-di-CN and G is CH. |
| 3095 | A is A-1m, $(R^2)_n$ is 6-F and G is CH. |
| 3096 | A is A-1m, $(R^2)_n$ is 6-Cl and G is CH. |
| 3097 | A is A-1m, $(R^2)_n$ is 6-Br and G is CH. |

TABLES 2306-4032-continued

| Table | Row Heading |
|---|---|
| 3098 | A is A-1m, $(R^2)_n$ is 6-Me and G is CH. |
| 3099 | A is A-1m, $(R^2)_n$ is 6-CF$_3$ and G is CH. |
| 3100 | A is A-1m, $(R^2)_n$ is 6-MeO and G is CH. |
| 3101 | A is A-1m, $(R^2)_n$ is 6-CN and G is CH. |
| 3102 | A is A-1m, $(R^2)_n$ is 6-F and G is C—F. |
| 3103 | A is A-1m, $(R^2)_n$ is 6-Cl and G is C—Cl. |
| 3104 | A is A-1m, $(R^2)_n$ is 6-Br and G is C—Br. |
| 3105 | A is A-1m, $(R^2)_n$ is 6-Me and G is C—Me. |
| 3106 | A is A-1m, $(R^2)_n$ is 6-CF$_3$ and G is C—CF$_3$. |
| 3107 | A is A-1m, $(R^2)_n$ is 6-MeO and G is C—OMe. |
| 3108 | A is A-1m, $(R^2)_n$ is H and G is N. |
| 3109 | A is A-1m, $(R^2)_n$ is 3-F and G is N. |
| 3110 | A is A-1m, $(R^2)_n$ is 3,5-di-F and G is N. |
| 3111 | A is A-1m, $(R^2)_n$ is 3-Cl and G is N. |
| 3112 | A is A-1m, $(R^2)_n$ is 3,5-di-Cl and G is N. |
| 3113 | A is A-1m, $(R^2)_n$ is 3-Br and G is N. |
| 3114 | A is A-1m, $(R^2)_n$ is 3,5-di-Br and G is N. |
| 3115 | A is A-1m, $(R^2)_n$ is 3-Me and G is N. |
| 3116 | A is A-1m, $(R^2)_n$ is 3,5-di-Me and G is N. |
| 3117 | A is A-1m, $(R^2)_n$ is 3-CF$_3$ and G is N. |
| 3118 | A is A-1m, $(R^2)_n$ is 3,5-di-CF$_3$ and G is N. |
| 3119 | A is A-1m, $(R^2)_n$ is 3-MeO and G is N. |
| 3120 | A is A-1m, $(R^2)_n$ is 3,5-di-MeO and G is N. |
| 3121 | A is A-1m, $(R^2)_n$ is 3-CN and G is N. |
| 3122 | A is A-1m, $(R^2)_n$ is 3,5-di-CN and G is N. |
| 3123 | A is A-1m, $(R^2)_n$ is 3,6-di-F and G is N. |
| 3124 | A is A-1m, $(R^2)_n$ is 3,6-di-Cl and G is N. |
| 3125 | A is A-1m, $(R^2)_n$ is 3,6-di-Br and G is N. |
| 3126 | A is A-1m, $(R^2)_n$ is 3,6-di-Me and G is N. |
| 3127 | A is A-1m, $(R^2)_n$ is 3,6-di-CF$_3$ and G is N. |
| 3128 | A is A-1m, $(R^2)_n$ is 3,6-di-MeO and G is N. |
| 3129 | A is A-1m, $(R^2)_n$ is 3,6-di-CN and G is N. |
| 3130 | A is A-1m, $(R^2)_n$ is 6-F and G is N. |
| 3131 | A is A-1m, $(R^2)_n$ is 6-Cl and G is N. |
| 3132 | A is A-1m, $(R^2)_n$ is 6-Br and G is N. |
| 3133 | A is A-1m, $(R^2)_n$ is 6-Me and G is N. |
| 3134 | A is A-1m, $(R^2)_n$ is 6-CF$_3$ and G is N. |
| 3135 | A is A-1m, $(R^2)_n$ is 6-MeO and G is N. |
| 3136 | A is A-1m, $(R^2)_n$ is 6-CN and G is N. |
| 3137 | A is A-1n, $(R^2)_n$ is H and G is CH. |
| 3138 | A is A-1n, $(R^2)_n$ is 3-F and G is CH. |
| 3139 | A is A-1n, $(R^2)_n$ is 3,5-di-F and G is CH. |
| 3140 | A is A-1n, $(R^2)_n$ is 3-Cl and G is CH. |
| 3141 | A is A-1n, $(R^2)_n$ is 3,5-di-Cl and G is CH. |
| 3142 | A is A-1n, $(R^2)_n$ is 3-Br and G is CH. |
| 3143 | A is A-1n, $(R^2)_n$ is 3,5-di-Br and G is CH. |
| 3144 | A is A-1n, $(R^2)_n$ is 3-Me and G is CH. |
| 3145 | A is A-1n, $(R^2)_n$ is 3,5-di-Me and G is CH. |
| 3146 | A is A-1n, $(R^2)_n$ is 3-CF$_3$ and G is CH. |
| 3147 | A is A-1n, $(R^2)_n$ is 3,5-di-CF$_3$ and G is CH. |
| 3148 | A is A-1n, $(R^2)_n$ is 3-MeO and G is CH. |
| 3149 | A is A-1n, $(R^2)_n$ is 3,5-di-MeO and G is CH. |
| 3150 | A is A-1n, $(R^2)_n$ is 3-CN and G is CH. |
| 3151 | A is A-1n, $(R^2)_n$ is 3,5-di-CN and G is CH. |
| 3152 | A is A-1n, $(R^2)_n$ is 3,6-di-F and G is CH. |
| 3153 | A is A-1n, $(R^2)_n$ is 3,6-di-Cl and G is CH. |
| 3154 | A is A-1n, $(R^2)_n$ is 3,6-di-Br and G is CH. |
| 3155 | A is A-1n, $(R^2)_n$ is 3,6-di-Me and G is CH. |
| 3156 | A is A-1n, $(R^2)_n$ is 3,6-di-CF$_3$ and G is CH. |
| 3157 | A is A-1n, $(R^2)_n$ is 3,6-di-MeO and G is CH. |
| 3158 | A is A-1n, $(R^2)_n$ is 3,6-di-CN and G is CH. |
| 3159 | A is A-1n, $(R^2)_n$ is 6-F and G is CH. |
| 3160 | A is A-1n, $(R^2)_n$ is 6-Cl and G is CH. |
| 3161 | A is A-1n, $(R^2)_n$ is 6-Br and G is CH. |
| 3162 | A is A-1n, $(R^2)_n$ is 6-Me and G is CH. |
| 3163 | A is A-1n, $(R^2)_n$ is 6-CF$_3$ and G is CH. |
| 3164 | A is A-1n, $(R^2)_n$ is 6-MeO and G is CH. |
| 3165 | A is A-1n, $(R^2)_n$ is 6-CN and G is CH. |
| 3166 | A is A-1n, $(R^2)_n$ is 6-F and G is C—F. |
| 3167 | A is A-1n, $(R^2)_n$ is 6-Cl and G is C—Cl. |
| 3168 | A is A-1n, $(R^2)_n$ is 6-Br and G is C—Br. |
| 3169 | A is A-1n, $(R^2)_n$ is 6-Me and G is C—Me. |
| 3170 | A is A-1n, $(R^2)_n$ is 6-CF$_3$ and G is C—CF$_3$. |
| 3171 | A is A-1n, $(R^2)_n$ is 6-MeO and G is C—OMe. |
| 3172 | A is A-1n, $(R^2)_n$ is H and G is N. |
| 3173 | A is A-1n, $(R^2)_n$ is 3-F and G is N. |
| 3174 | A is A-1n, $(R^2)_n$ is 3,5-di-F and G is N. |
| 3175 | A is A-1n, $(R^2)_n$ is 3-Cl and G is N. |
| 3176 | A is A-1n, $(R^2)_n$ is 3,5-di-Cl and G is N. |
| 3177 | A is A-1n, $(R^2)_n$ is 3-Br and G is N. |
| 3178 | A is A-1n, $(R^2)_n$ is 3,5-di-Br and G is N. |
| 3179 | A is A-1n, $(R^2)_n$ is 3-Me and G is N. |
| 3180 | A is A-1n, $(R^2)_n$ is 3,5-di-Me and G is N. |
| 3181 | A is A-1n, $(R^2)_n$ is 3-CF$_3$ and G is N. |
| 3182 | A is A-1n, $(R^2)_n$ is 3,5-di-CF$_3$ and G is N. |
| 3183 | A is A-1n, $(R^2)_n$ is 3-MeO and G is N. |
| 3184 | A is A-1n, $(R^2)_n$ is 3,5-di-MeO and G is N. |
| 3185 | A is A-1n, $(R^2)_n$ is 3-CN and G is N. |
| 3186 | A is A-1n, $(R^2)_n$ is 3,5-di-CN and G is N. |
| 3187 | A is A-1n, $(R^2)_n$ is 3,6-di-F and G is N. |
| 3188 | A is A-1n, $(R^2)_n$ is 3,6-di-Cl and G is N. |
| 3189 | A is A-1n, $(R^2)_n$ is 3,6-di-Br and G is N. |
| 3190 | A is A-1n, $(R^2)_n$ is 3,6-di-Me and G is N. |
| 3191 | A is A-1n, $(R^2)_n$ is 3,6-di-CF$_3$ and G is N. |
| 3192 | A is A-1n, $(R^2)_n$ is 3,6-di-MeO and G is N. |
| 3193 | A is A-1n, $(R^2)_n$ is 3,6-di-CN and G is N. |
| 3194 | A is A-1n, $(R^2)_n$ is 6-F and G is N. |
| 3195 | A is A-1n, $(R^2)_n$ is 6-Cl and G is N. |
| 3196 | A is A-1n, $(R^2)_n$ is 6-Br and G is N. |
| 3197 | A is A-1n, $(R^2)_n$ is 6-Me and G is N. |
| 3198 | A is A-1n, $(R^2)_n$ is 6-CF$_3$ and G is N. |
| 3199 | A is A-1n, $(R^2)_n$ is 6-MeO and G is N. |
| 3200 | A is A-1n, $(R^2)_n$ is 6-CN and G is N. |
| 3201 | A is A-1p, $(R^2)_n$ is H and G is CH. |
| 3202 | A is A-1p, $(R^2)_n$ is 3-F and G is CH. |
| 3203 | A is A-1p, $(R^2)_n$ is 3,5-di-F and G is CH. |
| 3204 | A is A-1p, $(R^2)_n$ is 3-Cl and G is CH. |
| 3205 | A is A-1p, $(R^2)_n$ is 3,5-di-Cl and G is CH. |
| 3206 | A is A-1p, $(R^2)_n$ is 3-Br and G is CH. |
| 3207 | A is A-1p, $(R^2)_n$ is 3,5-di-Br and G is CH. |
| 3208 | A is A-1p, $(R^2)_n$ is 3-Me and G is CH. |
| 3209 | A is A-1p, $(R^2)_n$ is 3,5-di-Me and G is CH. |
| 3210 | A is A-1p, $(R^2)_n$ is 3-CF$_3$ and G is CH. |
| 3211 | A is A-1p, $(R^2)_n$ is 3,5-di-CF$_3$ and G is CH. |
| 3212 | A is A-1p, $(R^2)_n$ is 3-MeO and G is CH. |
| 3213 | A is A-1p, $(R^2)_n$ is 3,5-di-MeO and G is CH. |
| 3214 | A is A-1p, $(R^2)_n$ is 3-CN and G is CH. |
| 3215 | A is A-1p, $(R^2)_n$ is 3,5-di-CN and G is CH. |
| 3216 | A is A-1p, $(R^2)_n$ is 3,6-di-F and G is CH. |
| 3217 | A is A-1p, $(R^2)_n$ is 3,6-di-Cl and G is CH. |
| 3218 | A is A-1p, $(R^2)_n$ is 3,6-di-Br and G is CH. |
| 3219 | A is A-1p, $(R^2)_n$ is 3,6-di-Me and G is CH. |
| 3220 | A is A-1p, $(R^2)_n$ is 3,6-di-CF$_3$ and G is CH. |
| 3221 | A is A-1p, $(R^2)_n$ is 3,6-di-MeO and G is CH. |
| 3222 | A is A-1p, $(R^2)_n$ is 3,6-di-CN and G is CH. |
| 3223 | A is A-1p, $(R^2)_n$ is 6-F and G is CH. |
| 3224 | A is A-1p, $(R^2)_n$ is 6-Cl and G is CH. |
| 3225 | A is A-1p, $(R^2)_n$ is 6-Br and G is CH. |
| 3226 | A is A-1p, $(R^2)_n$ is 6-Me and G is CH. |
| 3227 | A is A-1p, $(R^2)_n$ is 6-CF$_3$ and G is CH. |
| 3228 | A is A-1p, $(R^2)_n$ is 6-MeO and G is CH. |
| 3229 | A is A-1p, $(R^2)_n$ is 6-CN and G is CH. |
| 3230 | A is A-1p, $(R^2)_n$ is 6-F and G is C—F. |
| 3231 | A is A-1p, $(R^2)_n$ is 6-Cl and G is C—Cl. |
| 3232 | A is A-1p, $(R^2)_n$ is 6-Br and G is C—Br. |
| 3233 | A is A-1p, $(R^2)_n$ is 6-Me and G is C—Me. |
| 3234 | A is A-1p, $(R^2)_n$ is 6-CF$_3$ and G is C—CF$_3$. |
| 3235 | A is A-1p, $(R^2)_n$ is 6-MeO and G is C—OMe. |
| 3236 | A is A-1p, $(R^2)_n$ is H and G is N. |
| 3237 | A is A-1p, $(R^2)_n$ is 3-F and G is N. |
| 3238 | A is A-1p, $(R^2)_n$ is 3,5-di-F and G is N. |
| 3239 | A is A-1p, $(R^2)_n$ is 3-Cl and G is N. |
| 3240 | A is A-1p, $(R^2)_n$ is 3,5-di-Cl and G is N. |
| 3241 | A is A-1p, $(R^2)_n$ is 3-Br and G is N. |
| 3242 | A is A-1p, $(R^2)_n$ is 3,5-di-Br and G is N. |
| 3243 | A is A-1p, $(R^2)_n$ is 3-Me and G is N. |
| 3244 | A is A-1p, $(R^2)_n$ is 3,5-di-Me and G is N. |
| 3245 | A is A-1p, $(R^2)_n$ is 3-CF$_3$ and G is N. |
| 3246 | A is A-1p, $(R^2)_n$ is 3,5-di-CF$_3$ and G is N. |
| 3247 | A is A-1p, $(R^2)_n$ is 3-MeO and G is N. |
| 3248 | A is A-1p, $(R^2)_n$ is 3,5-di-MeO and G is N. |
| 3249 | A is A-1p, $(R^2)_n$ is 3-CN and G is N. |
| 3250 | A is A-1p, $(R^2)_n$ is 3,5-di-CN and G is N. |
| 3251 | A is A-1p, $(R^2)_n$ is 3,6-di-F and G is N. |
| 3252 | A is A-1p, $(R^2)_n$ is 3,6-di-Cl and G is N. |
| 3253 | A is A-1p, $(R^2)_n$ is 3,6-di-Br and G is N. |

TABLES 2306-4032-continued

| Table | Row Heading |
|---|---|
| 3254 | A is A-1p, $(R^2)_n$ is 3,6-di-Me and G is N. |
| 3255 | A is A-1p, $(R^2)_n$ is 3,6-di-CF$_3$ and G is N. |
| 3256 | A is A-1p, $(R^2)_n$ is 3,6-di-MeO and G is N. |
| 3257 | A is A-1p, $(R^2)_n$ is 3,6-di-CN and G is N. |
| 3258 | A is A-1p, $(R^2)_n$ is 6-F and G is N. |
| 3259 | A is A-1p, $(R^2)_n$ is 6-Cl and G is N. |
| 3260 | A is A-1p, $(R^2)_n$ is 6-Br and G is N. |
| 3261 | A is A-1p, $(R^2)_n$ is 6-Me and G is N. |
| 3262 | A is A-1p, $(R^2)_n$ is 6-CF$_3$ and G is N. |
| 3263 | A is A-1p, $(R^2)_n$ is 6-MeO and G is N. |
| 3264 | A is A-1p, $(R^2)_n$ is 6-CN and G is N. |
| 3265 | A is A-2a, $(R^2)_n$ is H and G is CH. |
| 3266 | A is A-2a, $(R^2)_n$ is 3-F and G is CH. |
| 3267 | A is A-2a, $(R^2)_n$ is 3,5-di-F and G is CH. |
| 3268 | A is A-2a, $(R^2)_n$ is 3-Cl and G is CH. |
| 3269 | A is A-2a, $(R^2)_n$ is 3,5-di-Cl and G is CH. |
| 3270 | A is A-2a, $(R^2)_n$ is 3-Br and G is CH. |
| 3271 | A is A-2a, $(R^2)_n$ is 3,5-di-Br and G is CH. |
| 3272 | A is A-2a, $(R^2)_n$ is 3-Me and G is CH. |
| 3273 | A is A-2a, $(R^2)_n$ is 3,5-di-Me and G is CH. |
| 3274 | A is A-2a, $(R^2)_n$ is 3-CF$_3$ and G is CH. |
| 3275 | A is A-2a, $(R^2)_n$ is 3,5-di-CF$_3$ and G is CH. |
| 3276 | A is A-2a, $(R^2)_n$ is 3-MeO and G is CH. |
| 3277 | A is A-2a, $(R^2)_n$ is 3,5-di-MeO and G is CH. |
| 3278 | A is A-2a, $(R^2)_n$ is 3-CN and G is CH. |
| 3279 | A is A-2a, $(R^2)_n$ is 3,5-di-CN and G is CH. |
| 3280 | A is A-2a, $(R^2)_n$ is 3,6-di-F and G is CH. |
| 3281 | A is A-2a, $(R^2)_n$ is 3,6-di-Cl and G is CH. |
| 3282 | A is A-2a, $(R^2)_n$ is 3,6-di-Br and G is CH. |
| 3283 | A is A-2a, $(R^2)_n$ is 3,6-di-Me and G is CH. |
| 3284 | A is A-2a, $(R^2)_n$ is 3,6-di-CF$_3$ and G is CH. |
| 3285 | A is A-2a, $(R^2)_n$ is 3,6-di-MeO and G is CH. |
| 3286 | A is A-2a, $(R^2)_n$ is 3,6-di-CN and G is CH. |
| 3287 | A is A-2a, $(R^2)_n$ is 6-F and G is CH. |
| 3288 | A is A-2a, $(R^2)_n$ is 6-Cl and G is CH. |
| 3289 | A is A-2a, $(R^2)_n$ is 6-Br and G is CH. |
| 3290 | A is A-2a, $(R^2)_n$ is 6-Me and G is CH. |
| 3291 | A is A-2a, $(R^2)_n$ is 6-CF$_3$ and G is CH. |
| 3292 | A is A-2a, $(R^2)_n$ is 6-MeO and G is CH. |
| 3293 | A is A-2a, $(R^2)_n$ is 6-CN and G is CH. |
| 3294 | A is A-2a, $(R^2)_n$ is 6-F and G is C—F. |
| 3295 | A is A-2a, $(R^2)_n$ is 6-Cl and G is C—Cl. |
| 3296 | A is A-2a, $(R^2)_n$ is 6-Br and G is C—Br. |
| 3297 | A is A-2a, $(R^2)_n$ is 6-Me and G is C—Me. |
| 3298 | A is A-2a, $(R^2)_n$ is 6-CF$_3$ and G is C—CF$_3$. |
| 3299 | A is A-2a, $(R^2)_n$ is 6-MeO and G is C—OMe. |
| 3300 | A is A-2a, $(R^2)_n$ is H and G is N. |
| 3301 | A is A-2a, $(R^2)_n$ is 3-F and G is N. |
| 3302 | A is A-2a, $(R^2)_n$ is 3,5-di-F and G is N. |
| 3303 | A is A-2a, $(R^2)_n$ is 3-Cl and G is N. |
| 3304 | A is A-2a, $(R^2)_n$ is 3,5-di-Cl and G is N. |
| 3305 | A is A-2a, $(R^2)_n$ is 3-Br and G is N. |
| 3306 | A is A-2a, $(R^2)_n$ is 3,5-di-Br and G is N. |
| 3307 | A is A-2a, $(R^2)_n$ is 3-Me and G is N. |
| 3308 | A is A-2a, $(R^2)_n$ is 3,5-di-Me and G is N. |
| 3309 | A is A-2a, $(R^2)_n$ is 3-CF$_3$ and G is N. |
| 3310 | A is A-2a, $(R^2)_n$ is 3,5-di-CF$_3$ and G is N. |
| 3311 | A is A-2a, $(R^2)_n$ is 3-MeO and G is N. |
| 3312 | A is A-2a, $(R^2)_n$ is 3,5-di-MeO and G is N. |
| 3313 | A is A-2a, $(R^2)_n$ is 3-CN and G is N. |
| 3314 | A is A-2a, $(R^2)_n$ is 3,5-di-CN and G is N. |
| 3315 | A is A-2a, $(R^2)_n$ is 3,6-di-F and G is N. |
| 3316 | A is A-2a, $(R^2)_n$ is 3,6-di-Cl and G is N. |
| 3317 | A is A-2a, $(R^2)_n$ is 3,6-di-Br and G is N. |
| 3318 | A is A-2a, $(R^2)_n$ is 3,6-di-Me and G is N. |
| 3319 | A is A-2a, $(R^2)_n$ is 3,6-di-CF$_3$ and G is N. |
| 3320 | A is A-2a, $(R^2)_n$ is 3,6-di-MeO and G is N. |
| 3321 | A is A-2a, $(R^2)_n$ is 3,6-di-CN and G is N. |
| 3322 | A is A-2a, $(R^2)_n$ is 6-F and G is N. |
| 3323 | A is A-2a, $(R^2)_n$ is 6-Cl and G is N. |
| 3324 | A is A-2a, $(R^2)_n$ is 6-Br and G is N. |
| 3325 | A is A-2a, $(R^2)_n$ is 6-Me and G is N. |
| 3326 | A is A-2a, $(R^2)_n$ is 6-CF$_3$ and G is N. |
| 3327 | A is A-2a, $(R^2)_n$ is 6-MeO and G is N. |
| 3328 | A is A-2a, $(R^2)_n$ is 6-CN and G is N. |
| 3329 | A is A-2b, $(R^2)_n$ is H and G is CH. |
| 3330 | A is A-2b, $(R^2)_n$ is 3-F and G is CH. |
| 3331 | A is A-2b, $(R^2)_n$ is 3,5-di-F and G is CH. |
| 3332 | A is A-2b, $(R^2)_n$ is 3-Cl and G is CH. |
| 3333 | A is A-2b, $(R^2)_n$ is 3,5-di-Cl and G is CH. |
| 3334 | A is A-2b, $(R^2)_n$ is 3-Br and G is CH. |
| 3335 | A is A-2b, $(R^2)_n$ is 3,5-di-Br and G is CH. |
| 3336 | A is A-2b, $(R^2)_n$ is 3-Me and G is CH. |
| 3337 | A is A-2b, $(R^2)_n$ is 3,5-di-Me and G is CH. |
| 3338 | A is A-2b, $(R^2)_n$ is 3-CF$_3$ and G is CH. |
| 3339 | A is A-2b, $(R^2)_n$ is 3,5-di-CF$_3$ and G is CH. |
| 3340 | A is A-2b, $(R^2)_n$ is 3-MeO and G is CH. |
| 3341 | A is A-2b, $(R^2)_n$ is 3,5-di-MeO and G is CH. |
| 3342 | A is A-2b, $(R^2)_n$ is 3-CN and G is CH. |
| 3343 | A is A-2b, $(R^2)_n$ is 3,5-di-CN and G is CH. |
| 3344 | A is A-2b, $(R^2)_n$ is 3,6-di-F and G is CH. |
| 3345 | A is A-2b, $(R^2)_n$ is 3,6-di-Cl and G is CH. |
| 3346 | A is A-2b, $(R^2)_n$ is 3,6-di-Br and G is CH. |
| 3347 | A is A-2b, $(R^2)_n$ is 3,6-di-Me and G is CH. |
| 3348 | A is A-2b, $(R^2)_n$ is 3,6-di-CF$_3$ and G is CH. |
| 3349 | A is A-2b, $(R^2)_n$ is 3,6-di-MeO and G is CH. |
| 3350 | A is A-2b, $(R^2)_n$ is 3,6-di-CN and G is CH. |
| 3351 | A is A-2b, $(R^2)_n$ is 6-F and G is CH. |
| 3352 | A is A-2b, $(R^2)_n$ is 6-Cl and G is CH. |
| 3353 | A is A-2b, $(R^2)_n$ is 6-Br and G is CH. |
| 3354 | A is A-2b, $(R^2)_n$ is 6-Me and G is CH. |
| 3355 | A is A-2b, $(R^2)_n$ is 6-CF$_3$ and G is CH. |
| 3356 | A is A-2b, $(R^2)_n$ is 6-MeO and G is CH. |
| 3357 | A is A-2b, $(R^2)_n$ is 6-CN and G is CH. |
| 3358 | A is A-2b, $(R^2)_n$ is 6-F and G is C—F. |
| 3359 | A is A-2b, $(R^2)_n$ is 6-Cl and G is C—Cl. |
| 3360 | A is A-2b, $(R^2)_n$ is 6-Br and G is C—Br. |
| 3361 | A is A-2b, $(R^2)_n$ is 6-Me and G is C—Me. |
| 3362 | A is A-2b, $(R^2)_n$ is 6-CF$_3$ and G is C—CF$_3$. |
| 3363 | A is A-2b, $(R^2)_n$ is 6-MeO and G is C—OMe. |
| 3364 | A is A-2b, $(R^2)_n$ is H and G is N. |
| 3365 | A is A-2b, $(R^2)_n$ is 3-F and G is N. |
| 3366 | A is A-2b, $(R^2)_n$ is 3,5-di-F and G is N. |
| 3367 | A is A-2b, $(R^2)_n$ is 3-Cl and G is N. |
| 3368 | A is A-2b, $(R^2)_n$ is 3,5-di-Cl and G is N. |
| 3369 | A is A-2b, $(R^2)_n$ is 3-Br and G is N. |
| 3370 | A is A-2b, $(R^2)_n$ is 3,5-di-Br and G is N. |
| 3371 | A is A-2b, $(R^2)_n$ is 3-Me and G is N. |
| 3372 | A is A-2b, $(R^2)_n$ is 3,5-di-Me and G is N. |
| 3373 | A is A-2b, $(R^2)_n$ is 3-CF$_3$ and G is N. |
| 3374 | A is A-2b, $(R^2)_n$ is 3,5-di-CF$_3$ and G is N. |
| 3375 | A is A-2b, $(R^2)_n$ is 3-MeO and G is N. |
| 3376 | A is A-2b, $(R^2)_n$ is 3,5-di-MeO and G is N. |
| 3377 | A is A-2b, $(R^2)_n$ is 3-CN and G is N. |
| 3378 | A is A-2b, $(R^2)_n$ is 3,5-di-CN and G is N. |
| 3379 | A is A-2b, $(R^2)_n$ is 3,6-di-F and G is N. |
| 3380 | A is A-2b, $(R^2)_n$ is 3,6-di-Cl and G is N. |
| 3381 | A is A-2b, $(R^2)_n$ is 3,6-di-Br and G is N. |
| 3382 | A is A-2b, $(R^2)_n$ is 3,6-di-Me and G is N. |
| 3383 | A is A-2b, $(R^2)_n$ is 3,6-di-CF$_3$ and G is N. |
| 3384 | A is A-2b, $(R^2)_n$ is 3,6-di-MeO and G is N. |
| 3385 | A is A-2b, $(R^2)_n$ is 3,6-di-CN and G is N. |
| 3386 | A is A-2b, $(R^2)_n$ is 6-F and G is N. |
| 3387 | A is A-2b, $(R^2)_n$ is 6-Cl and G is N. |
| 3388 | A is A-2b, $(R^2)_n$ is 6-Br and G is N. |
| 3389 | A is A-2b, $(R^2)_n$ is 6-Me and G is N. |
| 3390 | A is A-2b, $(R^2)_n$ is 6-CF$_3$ and G is N. |
| 3391 | A is A-2b, $(R^2)_n$ is 6-MeO and G is N. |
| 3392 | A is A-2b, $(R^2)_n$ is 6-CN and G is N. |
| 3393 | A is A-2c, $(R^2)_n$ is H and G is CH. |
| 3394 | A is A-2c, $(R^2)_n$ is 3-F and G is CH. |
| 3395 | A is A-2c, $(R^2)_n$ is 3,5-di-F and G is CH. |
| 3396 | A is A-2c, $(R^2)_n$ is 3-Cl and G is CH. |
| 3397 | A is A-2c, $(R^2)_n$ is 3,5-di-Cl and G is CH. |
| 3398 | A is A-2c, $(R^2)_n$ is 3-Br and G is CH. |
| 3399 | A is A-2c, $(R^2)_n$ is 3,5-di-Br and G is CH. |
| 3400 | A is A-2c, $(R^2)_n$ is 3-Me and G is CH. |
| 3401 | A is A-2c, $(R^2)_n$ is 3,5-di-Me and G is CH. |
| 3402 | A is A-2c, $(R^2)_n$ is 3-CF$_3$ and G is CH. |
| 3403 | A is A-2c, $(R^2)_n$ is 3,5-di-CF$_3$ and G is CH. |
| 3404 | A is A-2c, $(R^2)_n$ is 3-MeO and G is CH. |
| 3405 | A is A-2c, $(R^2)_n$ is 3,5-di-MeO and G is CH. |
| 3406 | A is A-2c, $(R^2)_n$ is 3-CN and G is CH. |
| 3407 | A is A-2c, $(R^2)_n$ is 3,5-di-CN and G is CH. |
| 3408 | A is A-2c, $(R^2)_n$ is 3,6-di-F and G is CH. |
| 3409 | A is A-2c, $(R^2)_n$ is 3,6-di-Cl and G is CH. |

TABLES 2306-4032-continued

| Table | Row Heading |
|---|---|
| 3410 | A is A-2c, $(R^2)_n$ is 3,6-di-Br and G is CH. |
| 3411 | A is A-2c, $(R^2)_n$ is 3,6-di-Me and G is CH. |
| 3412 | A is A-2c, $(R^2)_n$ is 3,6-di-CF$_3$ and G is CH. |
| 3413 | A is A-2c, $(R^2)_n$ is 3,6-di-MeO and G is CH. |
| 3414 | A is A-2c, $(R^2)_n$ is 3,6-di-CN and G is CH. |
| 3415 | A is A-2c, $(R^2)_n$ is 6-F and G is CH. |
| 3416 | A is A-2c, $(R^2)_n$ is 6-Cl and G is CH. |
| 3417 | A is A-2c, $(R^2)_n$ is 6-Br and G is CH. |
| 3418 | A is A-2c, $(R^2)_n$ is 6-Me and G is CH. |
| 3419 | A is A-2c, $(R^2)_n$ is 6-CF$_3$ and G is CH. |
| 3420 | A is A-2c, $(R^2)_n$ is 6-MeO and G is CH. |
| 3421 | A is A-2c, $(R^2)_n$ is 6-CN and G is CH. |
| 3422 | A is A-2c, $(R^2)_n$ is 6-F and G is C—F. |
| 3423 | A is A-2c, $(R^2)_n$ is 6-Cl and G is C—Cl. |
| 3424 | A is A-2c, $(R^2)_n$ is 6-Br and G is C—Br. |
| 3425 | A is A-2c, $(R^2)_n$ is 6-Me and G is C—Me. |
| 3426 | A is A-2c, $(R^2)_n$ is 6-CF$_3$ and G is C—CF$_3$. |
| 3427 | A is A-2c, $(R^2)_n$ is 6-MeO and G is C—OMe. |
| 3428 | A is A-2c, $(R^2)_n$ is H and G is N. |
| 3429 | A is A-2c, $(R^2)_n$ is 3-F and G is N. |
| 3430 | A is A-2c, $(R^2)_n$ is 3,5-di-F and G is N. |
| 3431 | A is A-2c, $(R^2)_n$ is 3-Cl and G is N. |
| 3432 | A is A-2c, $(R^2)_n$ is 3,5-di-Cl and G is N. |
| 3433 | A is A-2c, $(R^2)_n$ is 3-Br and G is N. |
| 3434 | A is A-2c, $(R^2)_n$ is 3,5-di-Br and G is N. |
| 3435 | A is A-2c, $(R^2)_n$ is 3-Me and G is N. |
| 3436 | A is A-2c, $(R^2)_n$ is 3,5-di-Me and G is N. |
| 3437 | A is A-2c, $(R^2)_n$ is 3-CF$_3$ and G is N. |
| 3438 | A is A-2c, $(R^2)_n$ is 3,5-di-CF$_3$ and G is N. |
| 3439 | A is A-2c, $(R^2)_n$ is 3-MeO and G is N. |
| 3440 | A is A-2c, $(R^2)_n$ is 3,5-di-MeO and G is N. |
| 3441 | A is A-2c, $(R^2)_n$ is 3-CN and G is N. |
| 3442 | A is A-2c, $(R^2)_n$ is 3,5-di-CN and G is N. |
| 3443 | A is A-2c, $(R^2)_n$ is 3,6-di-F and G is N. |
| 3444 | A is A-2c, $(R^2)_n$ is 3,6-di-Cl and G is N. |
| 3445 | A is A-2c, $(R^2)_n$ is 3,6-di-Br and G is N. |
| 3446 | A is A-2c, $(R^2)_n$ is 3,6-di-Me and G is N. |
| 3447 | A is A-2c, $(R^2)_n$ is 3,6-di-CF$_3$ and G is N. |
| 3448 | A is A-2c, $(R^2)_n$ is 3,6-di-MeO and G is N. |
| 3449 | A is A-2c, $(R^2)_n$ is 3,6-di-CN and G is N. |
| 3450 | A is A-2c, $(R^2)_n$ is 6-F and G is N. |
| 3451 | A is A-2c, $(R^2)_n$ is 6-Cl and G is N. |
| 3452 | A is A-2c, $(R^2)_n$ is 6-Br and G is N. |
| 3453 | A is A-2c, $(R^2)_n$ is 6-Me and G is N. |
| 3454 | A is A-2c, $(R^2)_n$ is 6-CF$_3$ and G is N. |
| 3455 | A is A-2c, $(R^2)_n$ is 6-MeO and G is N. |
| 3456 | A is A-2c, $(R^2)_n$ is 6-CN and G is N. |
| 3457 | A is A-2d, $(R^2)_n$ is H and G is CH. |
| 3458 | A is A-2d, $(R^2)_n$ is 3-F and G is CH. |
| 3459 | A is A-2d, $(R^2)_n$ is 3,5-di-F and G is CH. |
| 3460 | A is A-2d, $(R^2)_n$ is 3-Cl and G is CH. |
| 3461 | A is A-2d, $(R^2)_n$ is 3,5-di-Cl and G is CH. |
| 3462 | A is A-2d, $(R^2)_n$ is 3-Br and G is CH. |
| 3463 | A is A-2d, $(R^2)_n$ is 3,5-di-Br and G is CH. |
| 3464 | A is A-2d, $(R^2)_n$ is 3-Me and G is CH. |
| 3465 | A is A-2d, $(R^2)_n$ is 3,5-di-Me and G is CH. |
| 3466 | A is A-2d, $(R^2)_n$ is 3-CF$_3$ and G is CH. |
| 3467 | A is A-2d, $(R^2)_n$ is 3,5-di-CF$_3$ and G is CH. |
| 3468 | A is A-2d, $(R^2)_n$ is 3-MeO and G is CH. |
| 3469 | A is A-2d, $(R^2)_n$ is 3,5-di-MeO and G is CH. |
| 3470 | A is A-2d, $(R^2)_n$ is 3-CN and G is CH. |
| 3471 | A is A-2d, $(R^2)_n$ is 3,5-di-CN and G is CH. |
| 3472 | A is A-2d, $(R^2)_n$ is 3,6-di-F and G is CH. |
| 3473 | A is A-2d, $(R^2)_n$ is 3,6-di-Cl and G is CH. |
| 3474 | A is A-2d, $(R^2)_n$ is 3,6-di-Br and G is CH. |
| 3475 | A is A-2d, $(R^2)_n$ is 3,6-di-Me and G is CH. |
| 3476 | A is A-2d, $(R^2)_n$ is 3,6-di-CF$_3$ and G is CH. |
| 3477 | A is A-2d, $(R^2)_n$ is 3,6-di-MeO and G is CH. |
| 3478 | A is A-2d, $(R^2)_n$ is 3,6-di-CN and G is CH. |
| 3479 | A is A-2d, $(R^2)_n$ is 6-F and G is CH. |
| 3480 | A is A-2d, $(R^2)_n$ is 6-Cl and G is CH. |
| 3481 | A is A-2d, $(R^2)_n$ is 6-Br and G is CH. |
| 3482 | A is A-2d, $(R^2)_n$ is 6-Me and G is CH. |
| 3483 | A is A-2d, $(R^2)_n$ is 6-CF$_3$ and G is CH. |
| 3484 | A is A-2d, $(R^2)_n$ is 6-MeO and G is CH. |
| 3485 | A is A-2d, $(R^2)_n$ is 6-CN and G is CH. |
| 3486 | A is A-2d, $(R^2)_n$ is 6-F and G is C—F. |
| 3487 | A is A-2d, $(R^2)_n$ is 6-Cl and G is C—Cl. |
| 3488 | A is A-2d, $(R^2)_n$ is 6-Br and G is C—Br. |
| 3489 | A is A-2d, $(R^2)_n$ is 6-Me and G is C—Me. |
| 3490 | A is A-2d, $(R^2)_n$ is 6-CF$_3$ and G is C—CF$_3$. |
| 3491 | A is A-2d, $(R^2)_n$ is 6-MeO and G is C—OMe. |
| 3492 | A is A-2d, $(R^2)_n$ is H and G is N. |
| 3493 | A is A-2d, $(R^2)_n$ is 3-F and G is N. |
| 3494 | A is A-2d, $(R^2)_n$ is 3,5-di-F and G is N. |
| 3495 | A is A-2d, $(R^2)_n$ is 3-Cl and G is N. |
| 3496 | A is A-2d, $(R^2)_n$ is 3,5-di-Cl and G is N. |
| 3497 | A is A-2d, $(R^2)_n$ is 3-Br and G is N. |
| 3498 | A is A-2d, $(R^2)_n$ is 3,5-di-Br and G is N. |
| 3499 | A is A-2d, $(R^2)_n$ is 3-Me and G is N. |
| 3500 | A is A-2d, $(R^2)_n$ is 3,5-di-Me and G is N. |
| 3501 | A is A-2d, $(R^2)_n$ is 3-CF$_3$ and G is N. |
| 3502 | A is A-2d, $(R^2)_n$ is 3,5-di-CF$_3$ and G is N. |
| 3503 | A is A-2d, $(R^2)_n$ is 3-MeO and G is N. |
| 3504 | A is A-2d, $(R^2)_n$ is 3,5-di-MeO and G is N. |
| 3505 | A is A-2d, $(R^2)_n$ is 3-CN and G is N. |
| 3506 | A is A-2d, $(R^2)_n$ is 3,5-di-CN and G is N. |
| 3507 | A is A-2d, $(R^2)_n$ is 3,6-di-F and G is N. |
| 3508 | A is A-2d, $(R^2)_n$ is 3,6-di-Cl and G is N. |
| 3509 | A is A-2d, $(R^2)_n$ is 3,6-di-Br and G is N. |
| 3510 | A is A-2d, $(R^2)_n$ is 3,6-di-Me and G is N. |
| 3511 | A is A-2d, $(R^2)_n$ is 3,6-di-CF$_3$ and G is N. |
| 3512 | A is A-2d, $(R^2)_n$ is 3,6-di-MeO and G is N. |
| 3513 | A is A-2d, $(R^2)_n$ is 3,6-di-CN and G is N. |
| 3514 | A is A-2d, $(R^2)_n$ is 6-F and G is N. |
| 3515 | A is A-2d, $(R^2)_n$ is 6-Cl and G is N. |
| 3516 | A is A-2d, $(R^2)_n$ is 6-Br and G is N. |
| 3517 | A is A-2d, $(R^2)_n$ is 6-Me and G is N. |
| 3518 | A is A-2d, $(R^2)_n$ is 6-CF$_3$ and G is N. |
| 3519 | A is A-2d, $(R^2)_n$ is 6-MeO and G is N. |
| 3520 | A is A-2d, $(R^2)_n$ is 6-CN and G is N. |
| 3521 | A is A-2e, $(R^2)_n$ is H and G is CH. |
| 3522 | A is A-2e, $(R^2)_n$ is 3-F and G is CH. |
| 3523 | A is A-2e, $(R^2)_n$ is 3,5-di-F and G is CH. |
| 3524 | A is A-2e, $(R^2)_n$ is 3-Cl and G is CH. |
| 3525 | A is A-2e, $(R^2)_n$ is 3,5-di-Cl and G is CH. |
| 3526 | A is A-2e, $(R^2)_n$ is 3-Br and G is CH. |
| 3527 | A is A-2e, $(R^2)_n$ is 3,5-di-Br and G is CH. |
| 3528 | A is A-2e, $(R^2)_n$ is 3-Me and G is CH. |
| 3529 | A is A-2e, $(R^2)_n$ is 3,5-di-Me and G is CH. |
| 3530 | A is A-2e, $(R^2)_n$ is 3-CF$_3$ and G is CH. |
| 3531 | A is A-2e, $(R^2)_n$ is 3,5-di-CF$_3$ and G is CH. |
| 3532 | A is A-2e, $(R^2)_n$ is 3-MeO and G is CH. |
| 3533 | A is A-2e, $(R^2)_n$ is 3,5-di-MeO and G is CH. |
| 3534 | A is A-2e, $(R^2)_n$ is 3-CN and G is CH. |
| 3535 | A is A-2e, $(R^2)_n$ is 3,5-di-CN and G is CH. |
| 3536 | A is A-2e, $(R^2)_n$ is 3,6-di-F and G is CH. |
| 3537 | A is A-2e, $(R^2)_n$ is 3,6-di-Cl and G is CH. |
| 3538 | A is A-2e, $(R^2)_n$ is 3,6-di-Br and G is CH. |
| 3539 | A is A-2e, $(R^2)_n$ is 3,6-di-Me and G is CH. |
| 3540 | A is A-2e, $(R^2)_n$ is 3,6-di-CF$_3$ and G is CH. |
| 3541 | A is A-2e, $(R^2)_n$ is 3,6-di-MeO and G is CH. |
| 3542 | A is A-2e, $(R^2)_n$ is 3,6-di-CN and G is CH. |
| 3543 | A is A-2e, $(R^2)_n$ is 6-F and G is CH. |
| 3544 | A is A-2e, $(R^2)_n$ is 6-Cl and G is CH. |
| 3545 | A is A-2e, $(R^2)_n$ is 6-Br and G is CH. |
| 3546 | A is A-2e, $(R^2)_n$ is 6-Me and G is CH. |
| 3547 | A is A-2e, $(R^2)_n$ is 6-CF$_3$ and G is CH. |
| 3548 | A is A-2e, $(R^2)_n$ is 6-MeO and G is CH. |
| 3549 | A is A-2e, $(R^2)_n$ is 6-CN and G is CH. |
| 3550 | A is A-2e, $(R^2)_n$ is 6-F and G is C—F. |
| 3551 | A is A-2e, $(R^2)_n$ is 6-Cl and G is C—Cl. |
| 3552 | A is A-2e, $(R^2)_n$ is 6-Br and G is C—Br. |
| 3553 | A is A-2e, $(R^2)_n$ is 6-Me and G is C—Me. |
| 3554 | A is A-2e, $(R^2)_n$ is 6-CF$_3$ and G is C—CF$_3$. |
| 3555 | A is A-2e, $(R^2)_n$ is 6-MeO and G is C—OMe. |
| 3556 | A is A-2e, $(R^2)_n$ is H and G is N. |
| 3557 | A is A-2e, $(R^2)_n$ is 3-F and G is N. |
| 3558 | A is A-2e, $(R^2)_n$ is 3,5-di-F and G is N. |
| 3559 | A is A-2e, $(R^2)_n$ is 3-Cl and G is N. |
| 3560 | A is A-2e, $(R^2)_n$ is 3,5-di-Cl and G is N. |
| 3561 | A is A-2e, $(R^2)_n$ is 3-Br and G is N. |
| 3562 | A is A-2e, $(R^2)_n$ is 3,5-di-Br and G is N. |
| 3563 | A is A-2e, $(R^2)_n$ is 3-Me and G is N. |
| 3564 | A is A-2e, $(R^2)_n$ is 3,5-di-Me and G is N. |
| 3565 | A is A-2e, $(R^2)_n$ is 3-CF$_3$ and G is N. |

TABLES 2306-4032-continued

| Table | Row Heading |
|---|---|
| 3566 | A is A-2e, $(R^2)_n$ is 3,5-di-CF$_3$ and G is N. |
| 3567 | A is A-2e, $(R^2)_n$ is 3-MeO and G is N. |
| 3568 | A is A-2e, $(R^2)_n$ is 3,5-di-MeO and G is N. |
| 3569 | A is A-2e, $(R^2)_n$ is 3-CN and G is N. |
| 3570 | A is A-2e, $(R^2)_n$ is 3,5-di-CN and G is N. |
| 3571 | A is A-2e, $(R^2)_n$ is 3,6-di-F and G is N. |
| 3572 | A is A-2e, $(R^2)_n$ is 3,6-di-Cl and G is N. |
| 3573 | A is A-2e, $(R^2)_n$ is 3,6-di-Br and G is N. |
| 3574 | A is A-2e, $(R^2)_n$ is 3,6-di-Me and G is N. |
| 3575 | A is A-2e, $(R^2)_n$ is 3,6-di-CF$_3$ and G is N. |
| 3576 | A is A-2e, $(R^2)_n$ is 3,6-di-MeO and G is N. |
| 3577 | A is A-2e, $(R^2)_n$ is 3,6-di-CN and G is N. |
| 3578 | A is A-2e, $(R^2)_n$ is 6-F and G is N. |
| 3579 | A is A-2e, $(R^2)_n$ is 6-Cl and G is N. |
| 3580 | A is A-2e, $(R^2)_n$ is 6-Br and G is N. |
| 3581 | A is A-2e, $(R^2)_n$ is 6-Me and G is N. |
| 3582 | A is A-2e, $(R^2)_n$ is 6-CF$_3$ and G is N. |
| 3583 | A is A-2e, $(R^2)_n$ is 6-MeO and G is N. |
| 3584 | A is A-2e, $(R^2)_n$ is 6-CN and G is N. |
| 3585 | A is A-3a, $(R^2)_n$ is H and G is CH. |
| 3586 | A is A-3a, $(R^2)_n$ is 3-F and G is CH. |
| 3587 | A is A-3a, $(R^2)_n$ is 3,5-di-F and G is CH. |
| 3588 | A is A-3a, $(R^2)_n$ is 3-Cl and G is CH. |
| 3589 | A is A-3a, $(R^2)_n$ is 3,5-di-Cl and G is CH. |
| 3590 | A is A-3a, $(R^2)_n$ is 3-Br and G is CH. |
| 3591 | A is A-3a, $(R^2)_n$ is 3,5-di-Br and G is CH. |
| 3592 | A is A-3a, $(R^2)_n$ is 3-Me and G is CH. |
| 3593 | A is A-3a, $(R^2)_n$ is 3,5-di-Me and G is CH. |
| 3594 | A is A-3a, $(R^2)_n$ is 3-CF$_3$ and G is CH. |
| 3595 | A is A-3a, $(R^2)_n$ is 3,5-di-CF$_3$ and G is CH. |
| 3596 | A is A-3a, $(R^2)_n$ is 3-MeO and G is CH. |
| 3597 | A is A-3a, $(R^2)_n$ is 3,5-di-MeO and G is CH. |
| 3598 | A is A-3a, $(R^2)_n$ is 3-CN and G is CH. |
| 3599 | A is A-3a, $(R^2)_n$ is 3,5-di-CN and G is CH. |
| 3600 | A is A-3a, $(R^2)_n$ is 3,6-di-F and G is CH. |
| 3601 | A is A-3a, $(R^2)_n$ is 3,6-di-Cl and G is CH. |
| 3602 | A is A-3a, $(R^2)_n$ is 3,6-di-Br and G is CH. |
| 3603 | A is A-3a, $(R^2)_n$ is 3,6-di-Me and G is CH. |
| 3604 | A is A-3a, $(R^2)_n$ is 3,6-di-CF$_3$ and G is CH. |
| 3605 | A is A-3a, $(R^2)_n$ is 3,6-di-MeO and G is CH. |
| 3606 | A is A-3a, $(R^2)_n$ is 3,6-di-CN and G is CH. |
| 3607 | A is A-3a, $(R^2)_n$ is 6-F and G is CH. |
| 3608 | A is A-3a, $(R^2)_n$ is 6-Cl and G is CH. |
| 3609 | A is A-3a, $(R^2)_n$ is 6-Br and G is CH. |
| 3610 | A is A-3a, $(R^2)_n$ is 6-Me and G is CH. |
| 3611 | A is A-3a, $(R^2)_n$ is 6-CF$_3$ and G is CH. |
| 3612 | A is A-3a, $(R^2)_n$ is 6-MeO and G is CH. |
| 3613 | A is A-3a, $(R^2)_n$ is 6-CN and G is CH. |
| 3614 | A is A-3a, $(R^2)_n$ is 6-F and G is C—F. |
| 3615 | A is A-3a, $(R^2)_n$ is 6-Cl and G is C—Cl. |
| 3616 | A is A-3a, $(R^2)_n$ is 6-Br and G is C—Br. |
| 3617 | A is A-3a, $(R^2)_n$ is 6-Me and G is C—Me. |
| 3618 | A is A-3a, $(R^2)_n$ is 6-CF$_3$ and G is C—CF$_3$. |
| 3619 | A is A-3a, $(R^2)_n$ is 6-MeO and G is C—OMe. |
| 3620 | A is A-3a, $(R^2)_n$ is H and G is N. |
| 3621 | A is A-3a, $(R^2)_n$ is 3-F and G is N. |
| 3622 | A is A-3a, $(R^2)_n$ is 3,5-di-F and G is N. |
| 3623 | A is A-3a, $(R^2)_n$ is 3-Cl and G is N. |
| 3624 | A is A-3a, $(R^2)_n$ is 3,5-di-Cl and G is N. |
| 3625 | A is A-3a, $(R^2)_n$ is 3-Br and G is N. |
| 3626 | A is A-3a, $(R^2)_n$ is 3,5-di-Br and G is N. |
| 3627 | A is A-3a, $(R^2)_n$ is 3-Me and G is N. |
| 3628 | A is A-3a, $(R^2)_n$ is 3,5-di-Me and G is N. |
| 3629 | A is A-3a, $(R^2)_n$ is 3-CF$_3$ and G is N. |
| 3630 | A is A-3a, $(R^2)_n$ is 3,5-di-CF$_3$ and G is N. |
| 3631 | A is A-3a, $(R^2)_n$ is 3-MeO and G is N. |
| 3632 | A is A-3a, $(R^2)_n$ is 3,5-di-MeO and G is N. |
| 3633 | A is A-3a, $(R^2)_n$ is 3-CN and G is N. |
| 3634 | A is A-3a, $(R^2)_n$ is 3,5-di-CN and G is N. |
| 3635 | A is A-3a, $(R^2)_n$ is 3,6-di-F and G is N. |
| 3636 | A is A-3a, $(R^2)_n$ is 3,6-di-Cl and G is N. |
| 3637 | A is A-3a, $(R^2)_n$ is 3,6-di-Br and G is N. |
| 3638 | A is A-3a, $(R^2)_n$ is 3,6-di-Me and G is N. |
| 3639 | A is A-3a, $(R^2)_n$ is 3,6-di-CF$_3$ and G is N. |
| 3640 | A is A-3a, $(R^2)_n$ is 3,6-di-MeO and G is N. |
| 3641 | A is A-3a, $(R^2)_n$ is 3,6-di-CN and G is N. |
| 3642 | A is A-3a, $(R^2)_n$ is 6-F and G is N. |
| 3643 | A is A-3a, $(R^2)_n$ is 6-Cl and G is N. |
| 3644 | A is A-3a, $(R^2)_n$ is 6-Br and G is N. |
| 3645 | A is A-3a, $(R^2)_n$ is 6-Me and G is N. |
| 3646 | A is A-3a, $(R^2)_n$ is 6-CF$_3$ and G is N. |
| 3647 | A is A-3a, $(R^2)_n$ is 6-MeO and G is N. |
| 3648 | A is A-3a, $(R^2)_n$ is 6-CN and G is N. |
| 3649 | A is A-3b, $(R^2)_n$ is H and G is CH. |
| 3650 | A is A-3b, $(R^2)_n$ is 3-F and G is CH. |
| 3651 | A is A-3b, $(R^2)_n$ is 3,5-di-F and G is CH. |
| 3652 | A is A-3b, $(R^2)_n$ is 3-Cl and G is CH. |
| 3653 | A is A-3b, $(R^2)_n$ is 3,5-di-Cl and G is CH. |
| 3654 | A is A-3b, $(R^2)_n$ is 3-Br and G is CH. |
| 3655 | A is A-3b, $(R^2)_n$ is 3,5-di-Br and G is CH. |
| 3656 | A is A-3b, $(R^2)_n$ is 3-Me and G is CH. |
| 3657 | A is A-3b, $(R^2)_n$ is 3,5-di-Me and G is CH. |
| 3658 | A is A-3b, $(R^2)_n$ is 3-CF$_3$ and G is CH. |
| 3659 | A is A-3b, $(R^2)_n$ is 3,5-di-CF$_3$ and G is CH. |
| 3660 | A is A-3b, $(R^2)_n$ is 3-MeO and G is CH. |
| 3661 | A is A-3b, $(R^2)_n$ is 3,5-di-MeO and G is CH. |
| 3662 | A is A-3b, $(R^2)_n$ is 3-CN and G is CH. |
| 3663 | A is A-3b, $(R^2)_n$ is 3,5-di-CN and G is CH. |
| 3664 | A is A-3b, $(R^2)_n$ is 3,6-di-F and G is CH. |
| 3665 | A is A-3b, $(R^2)_n$ is 3,6-di-Cl and G is CH. |
| 3666 | A is A-3b, $(R^2)_n$ is 3,6-di-Br and G is CH. |
| 3667 | A is A-3b, $(R^2)_n$ is 3,6-di-Me and G is CH. |
| 3668 | A is A-3b, $(R^2)_n$ is 3,6-di-CF$_3$ and G is CH. |
| 3669 | A is A-3b, $(R^2)_n$ is 3,6-di-MeO and G is CH. |
| 3670 | A is A-3b, $(R^2)_n$ is 3,6-di-CN and G is CH. |
| 3671 | A is A-3b, $(R^2)_n$ is 6-F and G is CH. |
| 3672 | A is A-3b, $(R^2)_n$ is 6-Cl and G is CH. |
| 3673 | A is A-3b, $(R^2)_n$ is 6-Br and G is CH. |
| 3674 | A is A-3b, $(R^2)_n$ is 6-Me and G is CH. |
| 3675 | A is A-3b, $(R^2)_n$ is 6-CF$_3$ and G is CH. |
| 3676 | A is A-3b, $(R^2)_n$ is 6-MeO and G is CH. |
| 3677 | A is A-3b, $(R^2)_n$ is 6-CN and G is CH. |
| 3678 | A is A-3b, $(R^2)_n$ is 6-F and G is C—F. |
| 3679 | A is A-3b, $(R^2)_n$ is 6-Cl and G is C—Cl. |
| 3680 | A is A-3b, $(R^2)_n$ is 6-Br and G is C—Br. |
| 3681 | A is A-3b, $(R^2)_n$ is 6-Me and G is C—Me. |
| 3682 | A is A-3b, $(R^2)_n$ is 6-CF$_3$ and G is C—CF$_3$. |
| 3683 | A is A-3b, $(R^2)_n$ is 6-MeO and G is C—OMe. |
| 3684 | A is A-3b, $(R^2)_n$ is H and G is N. |
| 3685 | A is A-3b, $(R^2)_n$ is 3-F and G is N. |
| 3686 | A is A-3b, $(R^2)_n$ is 3,5-di-F and G is N. |
| 3687 | A is A-3b, $(R^2)_n$ is 3-Cl and G is N. |
| 3688 | A is A-3b, $(R^2)_n$ is 3,5-di-Cl and G is N. |
| 3689 | A is A-3b, $(R^2)_n$ is 3-Br and G is N. |
| 3690 | A is A-3b, $(R^2)_n$ is 3,5-di-Br and G is N. |
| 3691 | A is A-3b, $(R^2)_n$ is 3-Me and G is N. |
| 3692 | A is A-3b, $(R^2)_n$ is 3,5-di-Me and G is N. |
| 3693 | A is A-3b, $(R^2)_n$ is 3-CF$_3$ and G is N. |
| 3694 | A is A-3b, $(R^2)_n$ is 3,5-di-CF$_3$ and G is N. |
| 3695 | A is A-3b, $(R^2)_n$ is 3-MeO and G is N. |
| 3696 | A is A-3b, $(R^2)_n$ is 3,5-di-MeO and G is N. |
| 3697 | A is A-3b, $(R^2)_n$ is 3-CN and G is N. |
| 3698 | A is A-3b, $(R^2)_n$ is 3,5-di-CN and G is N. |
| 3699 | A is A-3b, $(R^2)_n$ is 3,6-di-F and G is N. |
| 3700 | A is A-3b, $(R^2)_n$ is 3,6-di-Cl and G is N. |
| 3701 | A is A-3b, $(R^2)_n$ is 3,6-di-Br and G is N. |
| 3702 | A is A-3b, $(R^2)_n$ is 3,6-di-Me and G is N. |
| 3703 | A is A-3b, $(R^2)_n$ is 3,6-di-CF$_3$ and G is N. |
| 3704 | A is A-3b, $(R^2)_n$ is 3,6-di-MeO and G is N. |
| 3705 | A is A-3b, $(R^2)_n$ is 3,6-di-CN and G is N. |
| 3706 | A is A-3b, $(R^2)_n$ is 6-F and G is N. |
| 3707 | A is A-3b, $(R^2)_n$ is 6-Cl and G is N. |
| 3708 | A is A-3b, $(R^2)_n$ is 6-Br and G is N. |
| 3709 | A is A-3b, $(R^2)_n$ is 6-Me and G is N. |
| 3710 | A is A-3b, $(R^2)_n$ is 6-CF$_3$ and G is N. |
| 3711 | A is A-3b, $(R^2)_n$ is 6-MeO and G is N. |
| 3712 | A is A-3b, $(R^2)_n$ is 6-CN and G is N. |
| 3713 | A is A-3c, $(R^2)_n$ is H and G is CH. |
| 3714 | A is A-3c, $(R^2)_n$ is 3-F and G is CH. |
| 3715 | A is A-3c, $(R^2)_n$ is 3,5-di-F and G is CH. |
| 3716 | A is A-3c, $(R^2)_n$ is 3-Cl and G is CH. |
| 3717 | A is A-3c, $(R^2)_n$ is 3,5-di-Cl and G is CH. |
| 3718 | A is A-3c, $(R^2)_n$ is 3-Br and G is CH. |
| 3719 | A is A-3c, $(R^2)_n$ is 3,5-di-Br and G is CH. |
| 3720 | A is A-3c, $(R^2)_n$ is 3-Me and G is CH. |
| 3721 | A is A-3c, $(R^2)_n$ is 3,5-di-Me and G is CH. |

TABLES 2306-4032-continued

| Table | Row Heading |
|---|---|
| 3722 | A is A-3c, $(R^2)_n$ is 3-CF$_3$ and G is CH. |
| 3723 | A is A-3c, $(R^2)_n$ is 3,5-di-CF$_3$ and G is CH. |
| 3724 | A is A-3c, $(R^2)_n$ is 3-MeO and G is CH. |
| 3725 | A is A-3c, $(R^2)_n$ is 3,5-di-MeO and G is CH. |
| 3726 | A is A-3c, $(R^2)_n$ is 3-CN and G is CH. |
| 3727 | A is A-3c, $(R^2)_n$ is 3,5-di-CN and G is CH. |
| 3728 | A is A-3c, $(R^2)_n$ is 3,6-di-F and G is CH. |
| 3729 | A is A-3c, $(R^2)_n$ is 3,6-di-Cl and G is CH. |
| 3730 | A is A-3c, $(R^2)_n$ is 3,6-di-Br and G is CH. |
| 3731 | A is A-3c, $(R^2)_n$ is 3,6-di-Me and G is CH. |
| 3732 | A is A-3c, $(R^2)_n$ is 3,6-di-CF$_3$ and G is CH. |
| 3733 | A is A-3c, $(R^2)_n$ is 3,6-di-MeO and G is CH. |
| 3734 | A is A-3c, $(R^2)_n$ is 3,6-di-CN and G is CH. |
| 3735 | A is A-3c, $(R^2)_n$ is 6-F and G is CH. |
| 3736 | A is A-3c, $(R^2)_n$ is 6-Cl and G is CH. |
| 3737 | A is A-3c, $(R^2)_n$ is 6-Br and G is CH. |
| 3738 | A is A-3c, $(R^2)_n$ is 6-Me and G is CH. |
| 3739 | A is A-3c, $(R^2)_n$ is 6-CF$_3$ and G is CH. |
| 3740 | A is A-3c, $(R^2)_n$ is 6-MeO and G is CH. |
| 3741 | A is A-3c, $(R^2)_n$ is 6-CN and G is CH. |
| 3742 | A is A-3c, $(R^2)_n$ is 6-F and G is C—F. |
| 3743 | A is A-3c, $(R^2)_n$ is 6-Cl and G is C—Cl. |
| 3744 | A is A-3c, $(R^2)_n$ is 6-Br and G is C—Br. |
| 3745 | A is A-3c, $(R^2)_n$ is 6-Me and G is C—Me. |
| 3746 | A is A-3c, $(R^2)_n$ is 6-CF$_3$ and G is C—CF$_3$. |
| 3747 | A is A-3c, $(R^2)_n$ is 6-MeO and G is C—OMe. |
| 3748 | A is A-3c, $(R^2)_n$ is H and G is N. |
| 3749 | A is A-3c, $(R^2)_n$ is 3-F and G is N. |
| 3750 | A is A-3c, $(R^2)_n$ is 3,5-di-F and G is N. |
| 3751 | A is A-3c, $(R^2)_n$ is 3-Cl and G is N. |
| 3752 | A is A-3c, $(R^2)_n$ is 3,5-di-Cl and G is N. |
| 3753 | A is A-3c, $(R^2)_n$ is 3-Br and G is N. |
| 3754 | A is A-3c, $(R^2)_n$ is 3,5-di-Br and G is N. |
| 3755 | A is A-3c, $(R^2)_n$ is 3-Me and G is N. |
| 3756 | A is A-3c, $(R^2)_n$ is 3,5-di-Me and G is N. |
| 3757 | A is A-3c, $(R^2)_n$ is 3-CF$_3$ and G is N. |
| 3758 | A is A-3c, $(R^2)_n$ is 3,5-di-CF$_3$ and G is N. |
| 3759 | A is A-3c, $(R^2)_n$ is 3-MeO and G is N. |
| 3760 | A is A-3c, $(R^2)_n$ is 3,5-di-MeO and G is N. |
| 3761 | A is A-3c, $(R^2)_n$ is 3-CN and G is N. |
| 3762 | A is A-3c, $(R^2)_n$ is 3,5-di-CN and G is N. |
| 3763 | A is A-3c, $(R^2)_n$ is 3,6-di-F and G is N. |
| 3764 | A is A-3c, $(R^2)_n$ is 3,6-di-Cl and G is N. |
| 3765 | A is A-3c, $(R^2)_n$ is 3,6-di-Br and G is N. |
| 3766 | A is A-3c, $(R^2)_n$ is 3,6-di-Me and G is N. |
| 3767 | A is A-3c, $(R^2)_n$ is 3,6-di-CF$_3$ and G is N. |
| 3768 | A is A-3c, $(R^2)_n$ is 3,6-di-MeO and G is N. |
| 3769 | A is A-3c, $(R^2)_n$ is 3,6-di-CN and G is N. |
| 3770 | A is A-3c, $(R^2)_n$ is 6-F and G is N. |
| 3771 | A is A-3c, $(R^2)_n$ is 6-Cl and G is N. |
| 3772 | A is A-3c, $(R^2)_n$ is 6-Br and G is N. |
| 3773 | A is A-3c, $(R^2)_n$ is 6-Me and G is N. |
| 3774 | A is A-3c, $(R^2)_n$ is 6-CF$_3$ and G is N. |
| 3775 | A is A-3c, $(R^2)_n$ is 6-MeO and G is N. |
| 3776 | A is A-3c, $(R^2)_n$ is 6-CN and G is N. |
| 3777 | A is A-4a, $(R^2)_n$ is H and G is CH. |
| 3778 | A is A-4a, $(R^2)_n$ is 3-F and G is CH. |
| 3779 | A is A-4a, $(R^2)_n$ is 3,5-di-F and G is CH. |
| 3780 | A is A-4a, $(R^2)_n$ is 3-Cl and G is CH. |
| 3781 | A is A-4a, $(R^2)_n$ is 3,5-di-Cl and G is CH. |
| 3782 | A is A-4a, $(R^2)_n$ is 3-Br and G is CH. |
| 3783 | A is A-4a, $(R^2)_n$ is 3,5-di-Br and G is CH. |
| 3784 | A is A-4a, $(R^2)_n$ is 3-Me and G is CH. |
| 3785 | A is A-4a, $(R^2)_n$ is 3,5-di-Me and G is CH. |
| 3786 | A is A-4a, $(R^2)_n$ is 3-CF$_3$ and G is CH. |
| 3787 | A is A-4a, $(R^2)_n$ is 3,5-di-CF$_3$ and G is CH. |
| 3788 | A is A-4a, $(R^2)_n$ is 3-MeO and G is CH. |
| 3789 | A is A-4a, $(R^2)_n$ is 3,5-di-MeO and G is CH. |
| 3790 | A is A-4a, $(R^2)_n$ is 3-CN and G is CH. |
| 3791 | A is A-4a, $(R^2)_n$ is 3,5-di-CN and G is CH. |
| 3792 | A is A-4a, $(R^2)_n$ is 3,6-di-F and G is CH. |
| 3793 | A is A-4a, $(R^2)_n$ is 3,6-di-Cl and G is CH. |
| 3794 | A is A-4a, $(R^2)_n$ is 3,6-di-Br and G is CH. |
| 3795 | A is A-4a, $(R^2)_n$ is 3,6-di-Me and G is CH. |
| 3796 | A is A-4a, $(R^2)_n$ is 3,6-di-CF$_3$ and G is CH. |
| 3797 | A is A-4a, $(R^2)_n$ is 3,6-di-MeO and G is CH. |
| 3798 | A is A-4a, $(R^2)_n$ is 3,6-di-CN and G is CH. |
| 3799 | A is A-4a, $(R^2)_n$ is 6-F and G is CH. |
| 3800 | A is A-4a, $(R^2)_n$ is 6-Cl and G is CH. |
| 3801 | A is A-4a, $(R^2)_n$ is 6-Br and G is CH. |
| 3802 | A is A-4a, $(R^2)_n$ is 6-Me and G is CH. |
| 3803 | A is A-4a, $(R^2)_n$ is 6-CF$_3$ and G is CH. |
| 3804 | A is A-4a, $(R^2)_n$ is 6-MeO and G is CH. |
| 3805 | A is A-4a, $(R^2)_n$ is 6-CN and G is CH. |
| 3806 | A is A-4a, $(R^2)_n$ is 6-F and G is C—F. |
| 3807 | A is A-4a, $(R^2)_n$ is 6-Cl and G is C—Cl. |
| 3808 | A is A-4a, $(R^2)_n$ is 6-Br and G is C—Br. |
| 3809 | A is A-4a, $(R^2)_n$ is 6-Me and G is C—Me. |
| 3810 | A is A-4a, $(R^2)_n$ is 6-CF$_3$ and G is C—CF$_3$. |
| 3811 | A is A-4a, $(R^2)_n$ is 6-MeO and G is C—OMe. |
| 3812 | A is A-4a, $(R^2)_n$ is H and G is N. |
| 3813 | A is A-4a, $(R^2)_n$ is 3-F and G is N. |
| 3814 | A is A-4a, $(R^2)_n$ is 3,5-di-F and G is N. |
| 3815 | A is A-4a, $(R^2)_n$ is 3-Cl and G is N. |
| 3816 | A is A-4a, $(R^2)_n$ is 3,5-di-Cl and G is N. |
| 3817 | A is A-4a, $(R^2)_n$ is 3-Br and G is N. |
| 3818 | A is A-4a, $(R^2)_n$ is 3,5-di-Br and G is N. |
| 3819 | A is A-4a, $(R^2)_n$ is 3-Me and G is N. |
| 3820 | A is A-4a, $(R^2)_n$ is 3,5-di-Me and G is N. |
| 3821 | A is A-4a, $(R^2)_n$ is 3-CF$_3$ and G is N. |
| 3822 | A is A-4a, $(R^2)_n$ is 3,5-di-CF$_3$ and G is N. |
| 3823 | A is A-4a, $(R^2)_n$ is 3-MeO and G is N. |
| 3824 | A is A-4a, $(R^2)_n$ is 3,5-di-MeO and G is N. |
| 3825 | A is A-4a, $(R^2)_n$ is 3-CN and G is N. |
| 3826 | A is A-4a, $(R^2)_n$ is 3,5-di-CN and G is N. |
| 3827 | A is A-4a, $(R^2)_n$ is 3,6-di-F and G is N. |
| 3828 | A is A-4a, $(R^2)_n$ is 3,6-di-Cl and G is N. |
| 3829 | A is A-4a, $(R^2)_n$ is 3,6-di-Br and G is N. |
| 3830 | A is A-4a, $(R^2)_n$ is 3,6-di-Me and G is N. |
| 3831 | A is A-4a, $(R^2)_n$ is 3,6-di-CF$_3$ and G is N. |
| 3832 | A is A-4a, $(R^2)_n$ is 3,6-di-MeO and G is N. |
| 3833 | A is A-4a, $(R^2)_n$ is 3,6-di-CN and G is N. |
| 3834 | A is A-4a, $(R^2)_n$ is 6-F and G is N. |
| 3835 | A is A-4a, $(R^2)_n$ is 6-Cl and G is N. |
| 3836 | A is A-4a, $(R^2)_n$ is 6-Br and G is N. |
| 3837 | A is A-4a, $(R^2)_n$ is 6-Me and G is N. |
| 3838 | A is A-4a, $(R^2)_n$ is 6-CF$_3$ and G is N. |
| 3839 | A is A-4a, $(R^2)_n$ is 6-MeO and G is N. |
| 3840 | A is A-4a, $(R^2)_n$ is 6-CN and G is N. |
| 3841 | A is A-4b, $(R^2)_n$ is H and G is CH. |
| 3842 | A is A-4b, $(R^2)_n$ is 3-F and G is CH. |
| 3843 | A is A-4b, $(R^2)_n$ is 3,5-di-F and G is CH. |
| 3844 | A is A-4b, $(R^2)_n$ is 3-Cl and G is CH. |
| 3845 | A is A-4b, $(R^2)_n$ is 3,5-di-Cl and G is CH. |
| 3846 | A is A-4b, $(R^2)_n$ is 3-Br and G is CH. |
| 3847 | A is A-4b, $(R^2)_n$ is 3,5-di-Br and G is CH. |
| 3848 | A is A-4b, $(R^2)_n$ is 3-Me and G is CH. |
| 3849 | A is A-4b, $(R^2)_n$ is 3,5-di-Me and G is CH. |
| 3850 | A is A-4b, $(R^2)_n$ is 3-CF$_3$ and G is CH. |
| 3851 | A is A-4b, $(R^2)_n$ is 3,5-di-CF$_3$ and G is CH. |
| 3852 | A is A-4b, $(R^2)_n$ is 3-MeO and G is CH. |
| 3853 | A is A-4b, $(R^2)_n$ is 3,5-di-MeO and G is CH. |
| 3854 | A is A-4b, $(R^2)_n$ is 3-CN and G is CH. |
| 3855 | A is A-4b, $(R^2)_n$ is 3,5-di-CN and G is CH. |
| 3856 | A is A-4b, $(R^2)_n$ is 3,6-di-F and G is CH. |
| 3857 | A is A-4b, $(R^2)_n$ is 3,6-di-Cl and G is CH. |
| 3858 | A is A-4b, $(R^2)_n$ is 3,6-di-Br and G is CH. |
| 3859 | A is A-4b, $(R^2)_n$ is 3,6-di-Me and G is CH. |
| 3860 | A is A-4b, $(R^2)_n$ is 3,6-di-CF$_3$ and G is CH. |
| 3861 | A is A-4b, $(R^2)_n$ is 3,6-di-MeO and G is CH. |
| 3862 | A is A-4b, $(R^2)_n$ is 3,6-di-CN and G is CH. |
| 3863 | A is A-4b, $(R^2)_n$ is 6-F and G is CH. |
| 3864 | A is A-4b, $(R^2)_n$ is 6-Cl and G is CH. |
| 3865 | A is A-4b, $(R^2)_n$ is 6-Br and G is CH. |
| 3866 | A is A-4b, $(R^2)_n$ is 6-Me and G is CH. |
| 3867 | A is A-4b, $(R^2)_n$ is 6-CF$_3$ and G is CH. |
| 3868 | A is A-4b, $(R^2)_n$ is 6-MeO and G is CH. |
| 3869 | A is A-4b, $(R^2)_n$ is 6-CN and G is CH. |
| 3870 | A is A-4b, $(R^2)_n$ is 6-F and G is C—F. |
| 3871 | A is A-4b, $(R^2)_n$ is 6-Cl and G is C—Cl. |
| 3872 | A is A-4b, $(R^2)_n$ is 6-Br and G is C—Br. |
| 3873 | A is A-4b, $(R^2)_n$ is 6-Me and G is C—Me. |
| 3874 | A is A-4b, $(R^2)_n$ is 6-CF$_3$ and G is C—CF$_3$. |
| 3875 | A is A-4b, $(R^2)_n$ is 6-MeO and G is C—OMe. |
| 3876 | A is A-4b, $(R^2)_n$ is H and G is N. |
| 3877 | A is A-4b, $(R^2)_n$ is 3-F and G is N. |

TABLES 2306-4032-continued

| Table | Row Heading |
|---|---|
| 3878 | A is A-4b, $(R^2)_n$ is 3,5-di-F and G is N. |
| 3879 | A is A-4b, $(R^2)_n$ is 3-Cl and G is N. |
| 3880 | A is A-4b, $(R^2)_n$ is 3,5-di-Cl and G is N. |
| 3881 | A is A-4b, $(R^2)_n$ is 3-Br and G is N. |
| 3882 | A is A-4b, $(R^2)_n$ is 3,5-di-Br and G is N. |
| 3883 | A is A-4b, $(R^2)_n$ is 3-Me and G is N. |
| 3884 | A is A-4b, $(R^2)_n$ is 3,5-di-Me and G is N. |
| 3885 | A is A-4b, $(R^2)_n$ is 3-CF$_3$ and G is N. |
| 3886 | A is A-4b, $(R^2)_n$ is 3,5-di-CF$_3$ and G is N. |
| 3887 | A is A-4b, $(R^2)_n$ is 3-MeO and G is N. |
| 3888 | A is A-4b, $(R^2)_n$ is 3,5-di-MeO and G is N. |
| 3889 | A is A-4b, $(R^2)_n$ is 3-CN and G is N. |
| 3890 | A is A-4b, $(R^2)_n$ is 3,5-di-CN and G is N. |
| 3891 | A is A-4b, $(R^2)_n$ is 3,6-di-F and G is N. |
| 3892 | A is A-4b, $(R^2)_n$ is 3,6-di-Cl and G is N. |
| 3893 | A is A-4b, $(R^2)_n$ is 3,6-di-Br and G is N. |
| 3894 | A is A-4b, $(R^2)_n$ is 3,6-di-Me and G is N. |
| 3895 | A is A-4b, $(R^2)_n$ is 3,6-di-CF$_3$ and G is N. |
| 3896 | A is A-4b, $(R^2)_n$ is 3,6-di-MeO and G is N. |
| 3897 | A is A-4b, $(R^2)_n$ is 3,6-di-CN and G is N. |
| 3898 | A is A-4b, $(R^2)_n$ is 6-F and G is N. |
| 3899 | A is A-4b, $(R^2)_n$ is 6-Cl and G is N. |
| 3900 | A is A-4b, $(R^2)_n$ is 6-Br and G is N. |
| 3901 | A is A-4b, $(R^2)_n$ is 6-Me and G is N. |
| 3902 | A is A-4b, $(R^2)_n$ is 6-CF$_3$ and G is N. |
| 3903 | A is A-4b, $(R^2)_n$ is 6-MeO and G is N. |
| 3904 | A is A-4b, $(R^2)_n$ is 6-CN and G is N. |
| 3905 | A is A-4c, $(R^2)_n$ is H and G is CH. |
| 3906 | A is A-4c, $(R^2)_n$ is 3-F and G is CH. |
| 3907 | A is A-4c, $(R^2)_n$ is 3,5-di-F and G is CH. |
| 3908 | A is A-4c, $(R^2)_n$ is 3-Cl and G is CH. |
| 3909 | A is A-4c, $(R^2)_n$ is 3,5-di-Cl and G is CH. |
| 3910 | A is A-4c, $(R^2)_n$ is 3-Br and G is CH. |
| 3911 | A is A-4c, $(R^2)_n$ is 3,5-di-Br and G is CH. |
| 3912 | A is A-4c, $(R^2)_n$ is 3-Me and G is CH. |
| 3913 | A is A-4c, $(R^2)_n$ is 3,5-di-Me and G is CH. |
| 3914 | A is A-4c, $(R^2)_n$ is 3-CF$_3$ and G is CH. |
| 3915 | A is A-4c, $(R^2)_n$ is 3,5-di-CF$_3$ and G is CH. |
| 3916 | A is A-4c, $(R^2)_n$ is 3-MeO and G is CH. |
| 3917 | A is A-4c, $(R^2)_n$ is 3,5-di-MeO and G is CH. |
| 3918 | A is A-4c, $(R^2)_n$ is 3-CN and G is CH. |
| 3919 | A is A-4c, $(R^2)_n$ is 3,5-di-CN and G is CH. |
| 3920 | A is A-4c, $(R^2)_n$ is 3,6-di-F and G is CH. |
| 3921 | A is A-4c, $(R^2)_n$ is 3,6-di-Cl and G is CH. |
| 3922 | A is A-4c, $(R^2)_n$ is 3,6-di-Br and G is CH. |
| 3923 | A is A-4c, $(R^2)_n$ is 3,6-di-Me and G is CH. |
| 3924 | A is A-4c, $(R^2)_n$ is 3,6-di-CF$_3$ and G is CH. |
| 3925 | A is A-4c, $(R^2)_n$ is 3,6-di-MeO and G is CH. |
| 3926 | A is A-4c, $(R^2)_n$ is 3,6-di-CN and G is CH. |
| 3927 | A is A-4c, $(R^2)_n$ is 6-F and G is CH. |
| 3928 | A is A-4c, $(R^2)_n$ is 6-Cl and G is CH. |
| 3929 | A is A-4c, $(R^2)_n$ is 6-Br and G is CH. |
| 3930 | A is A-4c, $(R^2)_n$ is 6-Me and G is CH. |
| 3931 | A is A-4c, $(R^2)_n$ is 6-CF$_3$ and G is CH. |
| 3932 | A is A-4c, $(R^2)_n$ is 6-MeO and G is CH. |
| 3933 | A is A-4c, $(R^2)_n$ is 6-CN and G is CH. |
| 3934 | A is A-4c, $(R^2)_n$ is 6-F and G is C—F. |
| 3935 | A is A-4c, $(R^2)_n$ is 6-Cl and G is C—Cl. |
| 3936 | A is A-4c, $(R^2)_n$ is 6-Br and G is C—Br. |
| 3937 | A is A-4c, $(R^2)_n$ is 6-Me and G is C—Me. |
| 3938 | A is A-4c, $(R^2)_n$ is 6-CF$_3$ and G is C—CF$_3$. |
| 3939 | A is A-4c, $(R^2)_n$ is 6-MeO and G is C—OMe. |
| 3940 | A is A-4c, $(R^2)_n$ is H and G is N. |
| 3941 | A is A-4c, $(R^2)_n$ is 3-F and G is N. |
| 3942 | A is A-4c, $(R^2)_n$ is 3,5-di-F and G is N. |
| 3943 | A is A-4c, $(R^2)_n$ is 3-Cl and G is N. |
| 3944 | A is A-4c, $(R^2)_n$ is 3,5-di-Cl and G is N. |
| 3945 | A is A-4c, $(R^2)_n$ is 3-Br and G is N. |
| 3946 | A is A-4c, $(R^2)_n$ is 3,5-di-Br and G is N. |
| 3947 | A is A-4c, $(R^2)_n$ is 3-Me and G is N. |
| 3948 | A is A-4c, $(R^2)_n$ is 3,5-di-Me and G is N. |
| 3949 | A is A-4c, $(R^2)_n$ is 3-CF$_3$ and G is N. |
| 3950 | A is A-4c, $(R^2)_n$ is 3,5-di-CF$_3$ and G is N. |
| 3951 | A is A-4c, $(R^2)_n$ is 3-MeO and G is N. |
| 3952 | A is A-4c, $(R^2)_n$ is 3,5-di-MeO and G is N. |
| 3953 | A is A-4c, $(R^2)_n$ is 3-CN and G is N. |
| 3954 | A is A-4c, $(R^2)_n$ is 3,5-di-CN and G is N. |
| 3955 | A is A-4c, $(R^2)_n$ is 3,6-di-F and G is N. |
| 3956 | A is A-4c, $(R^2)_n$ is 3,6-di-Cl and G is N. |
| 3957 | A is A-4c, $(R^2)_n$ is 3,6-di-Br and G is N. |
| 3958 | A is A-4c, $(R^2)_n$ is 3,6-di-Me and G is N. |
| 3959 | A is A-4c, $(R^2)_n$ is 3,6-di-CF$_3$ and G is N. |
| 3960 | A is A-4c, $(R^2)_n$ is 3,6-di-MeO and G is N. |
| 3961 | A is A-4c, $(R^2)_n$ is 3,6-di-CN and G is N. |
| 3962 | A is A-4c, $(R^2)_n$ is 6-F and G is N. |
| 3963 | A is A-4c, $(R^2)_n$ is 6-Cl and G is N. |
| 3964 | A is A-4c, $(R^2)_n$ is 6-Br and G is N. |
| 3965 | A is A-4c, $(R^2)_n$ is 6-Me and G is N. |
| 3966 | A is A-4c, $(R^2)_n$ is 6-CF$_3$ and G is N. |
| 3967 | A is A-4c, $(R^2)_n$ is 6-MeO and G is N. |
| 3968 | A is A-4c, $(R^2)_n$ is 6-CN and G is N. |
| 3969 | A is A-4d, $(R^2)_n$ is H and G is CH. |
| 3970 | A is A-4d, $(R^2)_n$ is 3-F and G is CH. |
| 3971 | A is A-4d, $(R^2)_n$ is 3,5-di-F and G is CH. |
| 3972 | A is A-4d, $(R^2)_n$ is 3-Cl and G is CH. |
| 3973 | A is A-4d, $(R^2)_n$ is 3,5-di-Cl and G is CH. |
| 3974 | A is A-4d, $(R^2)_n$ is 3-Br and G is CH. |
| 3975 | A is A-4d, $(R^2)_n$ is 3,5-di-Br and G is CH. |
| 3976 | A is A-4d, $(R^2)_n$ is 3-Me and G is CH. |
| 3977 | A is A-4d, $(R^2)_n$ is 3,5-di-Me and G is CH. |
| 3978 | A is A-4d, $(R^2)_n$ is 3-CF$_3$ and G is CH. |
| 3979 | A is A-4d, $(R^2)_n$ is 3,5-di-CF$_3$ and G is CH. |
| 3980 | A is A-4d, $(R^2)_n$ is 3-MeO and G is CH. |
| 3981 | A is A-4d, $(R^2)_n$ is 3,5-di-MeO and G is CH. |
| 3982 | A is A-4d, $(R^2)_n$ is 3-CN and G is CH. |
| 3983 | A is A-4d, $(R^2)_n$ is 3,5-di-CN and G is CH. |
| 3984 | A is A-4d, $(R^2)_n$ is 3,6-di-F and G is CH. |
| 3985 | A is A-4d, $(R^2)_n$ is 3,6-di-Cl and G is CH. |
| 3986 | A is A-4d, $(R^2)_n$ is 3,6-di-Br and G is CH. |
| 3987 | A is A-4d, $(R^2)_n$ is 3,6-di-Me and G is CH. |
| 3988 | A is A-4d, $(R^2)_n$ is 3,6-di-CF$_3$ and G is CH. |
| 3989 | A is A-4d, $(R^2)_n$ is 3,6-di-MeO and G is CH. |
| 3990 | A is A-4d, $(R^2)_n$ is 3,6-di-CN and G is CH. |
| 3991 | A is A-4d, $(R^2)_n$ is 6-F and G is CH. |
| 3992 | A is A-4d, $(R^2)_n$ is 6-Cl and G is CH. |
| 3993 | A is A-4d, $(R^2)_n$ is 6-Br and G is CH. |
| 3994 | A is A-4d, $(R^2)_n$ is 6-Me and G is CH. |
| 3995 | A is A-4d, $(R^2)_n$ is 6-CF$_3$ and G is CH. |
| 3996 | A is A-4d, $(R^2)_n$ is 6-MeO and G is CH. |
| 3997 | A is A-4d, $(R^2)_n$ is 6-CN and G is CH. |
| 3998 | A is A-4d, $(R^2)_n$ is 6-F and G is C—F. |
| 3999 | A is A-4d, $(R^2)_n$ is 6-Cl and G is C—Cl. |
| 4000 | A is A-4d, $(R^2)_n$ is 6-Br and G is C—Br. |
| 4001 | A is A-4d, $(R^2)_n$ is 6-Me and G is C—Me. |
| 4002 | A is A-4d, $(R^2)_n$ is 6-CF$_3$ and G is C—CF$_3$. |
| 4003 | A is A-4d, $(R^2)_n$ is 6-MeO and G is C—OMe. |
| 4004 | A is A-4d, $(R^2)_n$ is H and G is N. |
| 4005 | A is A-4d, $(R^2)_n$ is 3-F and G is N. |
| 4006 | A is A-4d, $(R^2)_n$ is 3,5-di-F and G is N. |
| 4007 | A is A-4d, $(R^2)_n$ is 3-Cl and G is N. |
| 4008 | A is A-4d, $(R^2)_n$ is 3,5-di-Cl and G is N. |
| 4009 | A is A-4d, $(R^2)_n$ is 3-Br and G is N. |
| 4010 | A is A-4d, $(R^2)_n$ is 3,5-di-Br and G is N. |
| 4011 | A is A-4d, $(R^2)_n$ is 3-Me and G is N. |
| 4012 | A is A-4d, $(R^2)_n$ is 3,5-di-Me and G is N. |
| 4013 | A is A-4d, $(R^2)_n$ is 3-CF$_3$ and G is N. |
| 4014 | A is A-4d, $(R^2)_n$ is 3,5-di-CF$_3$ and G is N. |
| 4015 | A is A-4d, $(R^2)_n$ is 3-MeO and G is N. |
| 4016 | A is A-4d, $(R^2)_n$ is 3,5-di-MeO and G is N. |
| 4017 | A is A-4d, $(R^2)_n$ is 3-CN and G is N. |
| 4018 | A is A-4d, $(R^2)_n$ is 3,5-di-CN and G is N. |
| 4019 | A is A-4d, $(R^2)_n$ is 3,6-di-F and G is N. |
| 4020 | A is A-4d, $(R^2)_n$ is 3,6-di-Cl and G is N. |
| 4021 | A is A-4d, $(R^2)_n$ is 3,6-di-Br and G is N. |
| 4022 | A is A-4d, $(R^2)_n$ is 3,6-di-Me and G is N. |
| 4023 | A is A-4d, $(R^2)_n$ is 3,6-di-CF$_3$ and G is N. |
| 4024 | A is A-4d, $(R^2)_n$ is 3,6-di-MeO and G is N. |
| 4025 | A is A-4d, $(R^2)_n$ is 3,6-di-CN and G is N. |
| 4026 | A is A-4d, $(R^2)_n$ is 6-F and G is N. |
| 4027 | A is A-4d, $(R^2)_n$ is 6-Cl and G is N. |
| 4028 | A is A-4d, $(R^2)_n$ is 6-Br and G is N. |
| 4029 | A is A-4d, $(R^2)_n$ is 6-Me and G is N. |
| 4030 | A is A-4d, $(R^2)_n$ is 6-CF$_3$ and G is N. |
| 4031 | A is A-4d, $(R^2)_n$ is 6-MeO and G is N. |
| 4032 | A is A-4d, $(R^2)_n$ is 6-CN and G is N. |

TABLE 4033

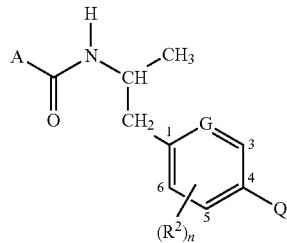

A is A-1a, $(R^2)_n$ is H, and G is CH.

| Q | Q | Q |
|---|---|---|
| 3-CF$_3$—1H-pyrazol-1-yl | 3-Me—1H-pyrazol-1-yl | 3-F—1H-pyrazol-1-yl |
| 3-Br—1H-pyrazol-1-yl | 4-CF$_3$—1H-pyrazol-1-yl | 4-Me—1H-pyrazol-1-yl |
| 4-F—1H-pyrazol-1-yl | 4-Br—1H-pyrazol-1-yl | 5-CF$_3$—1H-pyrazol-1-yl |
| 5-Me—1H-pyrazol-1-yl | 5-F—1H-pyrazol-1-yl | 5-Br—1H-pyrazol-1-yl |
| 3-CHF$_2$—1H-pyrazol-1-yl | 3-Et—1H-pyrazol-1-yl | 3-Cl—1H-pyrazol-1-yl |
| 3-I—1H-pyrazol-1-yl | 4-CHF$_2$—1H-pyrazol-1-yl | 4-Et—1H-pyrazol-1-yl |
| 4-Cl—1H-pyrazol-1-yl | 4-I—1H-pyrazol-1-yl | 5-CHF$_2$—1H-pyrazol-1-yl |
| 5-Et—1H-pyrazol-1-yl | 5-Cl—1H-pyrazol-1-yl | 5-I—1H-pyrazol-1-yl |
| 3-MeO—1H-pyrazol-1-yl | 3-CN—1H-pyrazol-1-yl | 3-CF$_3$O—1H-pyrazol-1-yl |
| 3-CHF$_2$O—1H-pyrazol-1-yl | 4-MeO—1H-pyrazol-1-yl | 4-CN—1H-pyrazol-1-yl |
| 4-CF$_3$O—1H-pyrazol-1-yl | 4-CHF$_2$O—1H-pyrazol-1-yl | 5-CF$_3$O—1H-pyrazol-1-yl |
| 5-CN—1H-pyrazol-1-yl | 5-CF$_3$O—1H-pyrazol-1-yl | 5-CHF$_2$O—1H-pyrazol-1-yl |
| 3-MeO(O=)C—1H-pyrazol-1-yl | 3-Ph—1H-pyrazol-1-yl | 3,5-di-Me—1H-pyrazol-1-yl |
| 3,5-di-F—1H-pyrazol-1-yl | 4-MeO(O=)C—1H-pyrazol-1-yl | 4-Ph—1H-pyrazol-1-yl |
| 3,5-di-CF$_3$—1H-pyrazol-1-yl | 3,5-di-Cl—1H-pyrazol-1-yl | 5-MeO(O=)C—1H-pyrazol-1-yl |
| 5-Ph—1H-pyrazol-1-yl | 3,5-di-CHF$_2$—1H-pyrazol-1-yl | 3,5-di-Br—1H-pyrazol-1-yl |
| 3-CF$_3$-5-Me1H-pyrazol-1-yl | 3,4-di-Me—1H-pyrazol-1-yl | 3,4-di-CF$_3$—1H-pyrazol-1-yl |
| 3,4-di-Br—1H-pyrazol-1-yl | 3,4-di-Cl—1H-pyrazol-1-yl | 1H-pyrazol-1-yl |
| 3-Me—1H-[1,2,4]triazol-1-yl | 3-CF$_3$—1H-[1,2,4]triazol-1-yl | 3-CHF$_2$—1H-[1,2,4]triazol-1-yl |
| 3-F—1H-[1,2,4]triazol-1-yl | 3-Cl—1H-[1,2,4]triazol-1-yl | 3-Br—1H-[1,2,4]triazol-1-yl |
| 3,5-di-Me—1H-[1,2,4]triazol-1-yl | 3,5-di-CF$_3$—1H-[1,2,4]triazol-1-yl | 3,5-di-CHF$_2$—1H-[1,2,4]triazol-1-yl |
| 3,5-di-Cl—1H-[1,2,4]triazol-1-yl | 3,5-di-Br—1H-[1,2,4]triazol-1-yl | 3-Ph—1H-[1,2,4]triazol-1-yl |
| 1H-[1,2,4]triazol-1-yl | 4-Me—2H-[1,2,3]triazol-2-yl | 4-CF$_3$—2H-[1,2,3]triazol-2-yl |
| 4-CHF$_2$—2H-[1,2,3]triazol-2-yl | 4-F—2H-[1,2,3]triazol-2-yl | 4-Cl—2H-[1,2,3]triazol-2-yl |
| 4-Br—2H-[1,2,3]triazol-2-yl | 4-Ph—2H-[1,2,3]triazol-2-yl | 4,5-di-Me—2H-[1,2,3]triazol-2-yl |
| 4,5-di-CF$_3$—2H-[1,2,3]triazol-2-yl | 4,5-di-Cl—2H-[1,2,3]triazol-2-yl | 4,5-di-Br—2H-[1,2,3]triazol-2-yl |
| 2H-[1,2,3]triazol-2-yl | 4-Me—1H-[1,2,3]triazol-1-yl | 4-CF$_3$—1H-[1,2,3]triazol-1-yl |
| 4-CHF$_2$—1H-[1,2,3]triazol-1-yl | 4-F—1H-[1,2,3]triazol-1-yl | 4-Cl—1H-[1,2,3]triazol-1-yl |
| 4-Br—1H-[1,2,3]triazol-1-yl | 4-Ph—1H-[1,2,3]triazol-1-yl | 1H-[1,2,3]triazol-1-yl |
| 3-Me—1H-pyrrol-1-yl | 3-CF$_3$—1H-pyrrol-1-yl | 3-CHF$_2$—1H-pyrrol-1-yl |
| 3,4-di-Me—1H-pyrrol-1-yl | 2,4-di-Me—1H-pyrrol-1-yl | 3,4-di-CF$_3$—1H-pyrrol-1-yl |
| 2,4-di-CF$_3$—1H-pyrrol-1-yl | 3,4-di-Br—1H-pyrrol-1-yl | 3,4-di-Cl—1H-pyrrol-1-yl |
| 1H-pyrrol-1-yl | 1-Me—1H-pyrazol-3-yl | 1-CF$_3$—1H-pyrazol-3-yl |
| 1-Et—1H-pyrazol-3-yl | 1-i-Pr—1H-pyrazol-3-yl | 1-(F$_3$CCH$_2$)—1H-pyrazol-3-yl |
| 1-Ph—1H-pyrazol-3-yl | 1,4-di-Me—1H-pyrazol-3-yl | 1-Me-4-CF$_3$—1H-pyrazol-3-yl |
| 1-Me—1H-pyrazol-4-yl | 1-CF$_3$—1H-pyrazol-4-yl | 1-Et—1H-pyrazol-4-yl |
| 1-i-Pr—1H-pyrazol-4-yl | 1-(F$_3$CCH$_2$)—1H-pyrazol-4-yl | 1-Ph—1H-pyrazol-4-yl |
| 1,3-di-Me—1H-pyrazol-4-yl | 1-Me-3-CF$_3$—1H-pyrazol-4-yl | 3-Me-1-CF$_3$—1H-pyrazol-4-yl |
| 1-Me—1H-[1,2,4]triazol-3-yl | 1-CF$_3$—1H-[1,2,4]triazol-3-yl | 1-Et—1H-[1,2,4]triazol-3-yl |
| 1-i-Pr—1H-[1,2,4]triazol-3-yl | 1-Ph—1H-[1,2,4]triazol-3-yl | 5-Ph-4,5-dihydro-isoxazol-3-yl |
| 5-CF$_3$-2,4-dihydro-3-oxopyrazol-1-yl | 5-Me-2,4-dihydro-3-oxopyrazol-1-yl | |

The present disclosure also includes Tables 4034 through 5760 each of which is constructed the same as Table 4033 above, except that the row heading in Table 4033 (i.e. "A is A-1a, $(R^2)_n$ is H, and G is CH.") is replaced with the respective row heading shown below. For example, in Table 4034 the row heading is "A is A-1a, $(R^2)_n$ is 3-F, and G is CH." and Q is as defined in Table 1 above. Thus, the first entry in Table 4034 specifically discloses N-[2-[3-fluoro-4-[3-(trifluoromethyl)-1H-pyrazol-1-yl]phenyl]-1-methylethyl]-2-(trifluoromethyl)benzamide. Tables 4035 through 5760 are constructed similarly.

TABLES 4034-5760

| Table | Row Heading |
|---|---|
| 4034 | A is A-1a, $(R^2)_n$ is 3-F and G is CH. |
| 4035 | A is A-1a, $(R^2)_n$ is 3,5-di-F and G is CH. |
| 4036 | A is A-1a, $(R^2)_n$ is 3-Cl and G is CH. |
| 4037 | A is A-1a, $(R^2)_n$ is 3,5-di-Cl and G is CH. |
| 4038 | A is A-1a, $(R^2)_n$ is 3-Br and G is CH. |
| 4039 | A is A-1a, $(R^2)_n$ is 3,5-di-Br and G is CH. |
| 4040 | A is A-1a, $(R^2)_n$ is 3-Me and G is CH. |
| 4041 | A is A-1a, $(R^2)_n$ is 3,5-di-Me and G is CH. |
| 4042 | A is A-1a, $(R^2)_n$ is 3-CF$_3$ and G is CH. |
| 4043 | A is A-1a, $(R^2)_n$ is 3,5-di-CF$_3$ and G is CH. |
| 4044 | A is A-1a, $(R^2)_n$ is 3-MeO and G is CH. |

TABLES 4034-5760-continued

| Table | Row Heading |
|---|---|
| 4045 | A is A-1a, $(R^2)_n$ is 3,5-di-MeO and G is CH. |
| 4046 | A is A-1a, $(R^2)_n$ is 3-CN and G is CH. |
| 4047 | A is A-1a, $(R^2)_n$ is 3,5-di-CN and G is CH. |
| 4048 | A is A-1a, $(R^2)_n$ is 3,6-di-F and G is CH. |
| 4049 | A is A-1a, $(R^2)_n$ is 3,6-di-Cl and G is CH. |
| 4050 | A is A-1a, $(R^2)_n$ is 3,6-di-Br and G is CH. |
| 4051 | A is A-1a, $(R^2)_n$ is 3,6-di-Me and G is CH. |
| 4052 | A is A-1a, $(R^2)_n$ is 3,6-di-CF$_3$ and G is CH. |
| 4053 | A is A-1a, $(R^2)_n$ is 3,6-di-MeO and G is CH. |
| 4054 | A is A-1a, $(R^2)_n$ is 3,6-di-CN and G is CH. |
| 4055 | A is A-1a, $(R^2)_n$ is 6-F and G is CH. |
| 4056 | A is A-1a, $(R^2)_n$ is 6-Cl and G is CH. |
| 4057 | A is A-1a, $(R^2)_n$ is 6-Br and G is CH. |
| 4058 | A is A-1a, $(R^2)_n$ is 6-Me and G is CH. |
| 4059 | A is A-1a, $(R^2)_n$ is 6-CF$_3$ and G is CH. |
| 4060 | A is A-1a, $(R^2)_n$ is 6-MeO and G is CH. |
| 4061 | A is A-1a, $(R^2)_n$ is 6-CN and G is CH. |
| 4062 | A is A-1a, $(R^2)_n$ is 6-F and G is C—F. |
| 4063 | A is A-1a, $(R^2)_n$ is 6-Cl and G is C—Cl. |
| 4064 | A is A-1a, $(R^2)_n$ is 6-Br and G is C—Br. |
| 4065 | A is A-1a, $(R^2)_n$ is 6-Me and G is C—Me. |
| 4066 | A is A-1a, $(R^2)_n$ is 6-CF$_3$ and G is C—CF$_3$. |
| 4067 | A is A-1a, $(R^2)_n$ is 6-MeO and G is C—OMe. |
| 4068 | A is A-1a, $(R^2)_n$ is H and G is N. |
| 4069 | A is A-1a, $(R^2)_n$ is 3-F and G is N. |
| 4070 | A is A-1a, $(R^2)_n$ is 3,5-di-F and G is N. |
| 4071 | A is A-1a, $(R^2)_n$ is 3-Cl and G is N. |
| 4072 | A is A-1a, $(R^2)_n$ is 3,5-di-Cl and G is N. |
| 4073 | A is A-1a, $(R^2)_n$ is 3-Br and G is N. |
| 4074 | A is A-1a, $(R^2)_n$ is 3,5-di-Br and G is N. |
| 4075 | A is A-1a, $(R^2)_n$ is 3-Me and G is N. |
| 4076 | A is A-1a, $(R^2)_n$ is 3,5-di-Me and G is N. |
| 4077 | A is A-1a, $(R^2)_n$ is 3-CF$_3$ and G is N. |
| 4078 | A is A-1a, $(R^2)_n$ is 3,5-di-CF$_3$ and G is N. |
| 4079 | A is A-1a, $(R^2)_n$ is 3-MeO and G is N. |
| 4080 | A is A-1a, $(R^2)_n$ is 3,5-di-MeO and G is N. |
| 4081 | A is A-1a, $(R^2)_n$ is 3-CN and G is N. |
| 4082 | A is A-1a, $(R^2)_n$ is 3,5-di-CN and G is N. |
| 4083 | A is A-1a, $(R^2)_n$ is 3,6-di-F and G is N. |
| 4084 | A is A-1a, $(R^2)_n$ is 3,6-di-Cl and G is N. |
| 4085 | A is A-1a, $(R^2)_n$ is 3,6-di-Br and G is N. |
| 4086 | A is A-1a, $(R^2)_n$ is 3,6-di-Me and G is N. |
| 4087 | A is A-1a, $(R^2)_n$ is 3,6-di-CF$_3$ and G is N. |
| 4088 | A is A-1a, $(R^2)_n$ is 3,6-di-MeO and G is N. |
| 4089 | A is A-1a, $(R^2)_n$ is 3,6-di-CN and G is N. |
| 4090 | A is A-1a, $(R^2)_n$ is 6-F and G is N. |
| 4091 | A is A-1a, $(R^2)_n$ is 6-Cl and G is N. |
| 4092 | A is A-1a, $(R^2)_n$ is 6-Br and G is N. |
| 4093 | A is A-1a, $(R^2)_n$ is 6-Me and G is N. |
| 4094 | A is A-1a, $(R^2)_n$ is 6-CF$_3$ and G is N. |
| 4095 | A is A-1a, $(R^2)_n$ is 6-MeO and G is N. |
| 4096 | A is A-1a, $(R^2)_n$ is 6-CN and G is N. |
| 4097 | A is A-1b, $(R^2)_n$ is H and G is CH. |
| 4098 | A is A-1b, $(R^2)_n$ is 3-F and G is CH. |
| 4099 | A is A-1b, $(R^2)_n$ is 3,5-di-F and G is CH. |
| 4100 | A is A-1b, $(R^2)_n$ is 3-Cl and G is CH. |
| 4101 | A is A-1b, $(R^2)_n$ is 3,5-di-Cl and G is CH. |
| 4102 | A is A-1b, $(R^2)_n$ is 3-Br and G is CH. |
| 4103 | A is A-1b, $(R^2)_n$ is 3,5-di-Br and G is CH. |
| 4104 | A is A-1b, $(R^2)_n$ is 3-Me and G is CH. |
| 4105 | A is A-1b, $(R^2)_n$ is 3,5-di-Me and G is CH. |
| 4106 | A is A-1b, $(R^2)_n$ is 3-CF$_3$ and G is CH. |
| 4107 | A is A-1b, $(R^2)_n$ is 3,5-di-CF$_3$ and G is CH. |
| 4108 | A is A-1b, $(R^2)_n$ is 3-MeO and G is CH. |
| 4109 | A is A-1b, $(R^2)_n$ is 3,5-di-MeO and G is CH. |
| 4110 | A is A-1b, $(R^2)_n$ is 3-CN and G is CH. |
| 4111 | A is A-1b, $(R^2)_n$ is 3,5-di-CN and G is CH. |
| 4112 | A is A-1b, $(R^2)_n$ is 3,6-di-F and G is CH. |
| 4113 | A is A-1b, $(R^2)_n$ is 3,6-di-Cl and G is CH. |
| 4114 | A is A-1b, $(R^2)_n$ is 3,6-di-Br and G is CH. |
| 4115 | A is A-1b, $(R^2)_n$ is 3,6-di-Me and G is CH. |
| 4116 | A is A-1b, $(R^2)_n$ is 3,6-di-CF$_3$ and G is CH. |
| 4117 | A is A-1b, $(R^2)_n$ is 3,6-di-MeO and G is CH. |
| 4118 | A is A-1b, $(R^2)_n$ is 3,6-di-CN and G is CH. |
| 4119 | A is A-1b, $(R^2)_n$ is 6-F and G is CH. |
| 4120 | A is A-1b, $(R^2)_n$ is 6-Cl and G is CH. |
| 4121 | A is A-1b, $(R^2)_n$ is 6-Br and G is CH. |
| 4122 | A is A-1b, $(R^2)_n$ is 6-Me and G is CH. |
| 4123 | A is A-1b, $(R^2)_n$ is 6-CF$_3$ and G is CH. |
| 4124 | A is A-1b, $(R^2)_n$ is 6-MeO and G is CH. |
| 4125 | A is A-1b, $(R^2)_n$ is 6-CN and G is CH. |
| 4126 | A is A-1b, $(R^2)_n$ is 6-F and G is C—F. |
| 4127 | A is A-1b, $(R^2)_n$ is 6-Cl and G is C—Cl. |
| 4128 | A is A-1b, $(R^2)_n$ is 6-Br and G is C—Br. |
| 4129 | A is A-1b, $(R^2)_n$ is 6-Me and G is C—Me. |
| 4130 | A is A-1b, $(R^2)_n$ is 6-CF$_3$ and G is C—CF$_3$. |
| 4131 | A is A-1b, $(R^2)_n$ is 6-MeO and G is C—OMe. |
| 4132 | A is A-1b, $(R^2)_n$ is H and G is N. |
| 4133 | A is A-1b, $(R^2)_n$ is 3-F and G is N. |
| 4134 | A is A-1b, $(R^2)_n$ is 3,5-di-F and G is N. |
| 4135 | A is A-1b, $(R^2)_n$ is 3-Cl and G is N. |
| 4136 | A is A-1b, $(R^2)_n$ is 3,5-di-Cl and G is N. |
| 4137 | A is A-1b, $(R^2)_n$ is 3-Br and G is N. |
| 4138 | A is A-1b, $(R^2)_n$ is 3,5-di-Br and G is N. |
| 4139 | A is A-1b, $(R^2)_n$ is 3-Me and G is N. |
| 4140 | A is A-1b, $(R^2)_n$ is 3,5-di-Me and G is N. |
| 4141 | A is A-1b, $(R^2)_n$ is 3-CF$_3$ and G is N. |
| 4142 | A is A-1b, $(R^2)_n$ is 3,5-di-CF$_3$ and G is N. |
| 4143 | A is A-1b, $(R^2)_n$ is 3-MeO and G is N. |
| 4144 | A is A-1b, $(R^2)_n$ is 3,5-di-MeO and G is N. |
| 4145 | A is A-1b, $(R^2)_n$ is 3-CN and G is N. |
| 4146 | A is A-1b, $(R^2)_n$ is 3,5-di-CN and G is N. |
| 4147 | A is A-1b, $(R^2)_n$ is 3,6-di-F and G is N. |
| 4148 | A is A-1b, $(R^2)_n$ is 3,6-di-Cl and G is N. |
| 4149 | A is A-1b, $(R^2)_n$ is 3,6-di-Br and G is N. |
| 4150 | A is A-1b, $(R^2)_n$ is 3,6-di-Me and G is N. |
| 4151 | A is A-1b, $(R^2)_n$ is 3,6-di-CF$_3$ and G is N. |
| 4152 | A is A-1b, $(R^2)_n$ is 3,6-di-MeO and G is N. |
| 4153 | A is A-1b, $(R^2)_n$ is 3,6-di-CN and G is N. |
| 4154 | A is A-1b, $(R^2)_n$ is 6-F and G is N. |
| 4155 | A is A-1b, $(R^2)_n$ is 6-Cl and G is N. |
| 4156 | A is A-1b, $(R^2)_n$ is 6-Br and G is N. |
| 4157 | A is A-1b, $(R^2)_n$ is 6-Me and G is N. |
| 4158 | A is A-1b, $(R^2)_n$ is 6-CF$_3$ and G is N. |
| 4159 | A is A-1b, $(R^2)_n$ is 6-MeO and G is N. |
| 4160 | A is A-1b, $(R^2)_n$ is 6-CN and G is N. |
| 4161 | A is A-1c, $(R^2)_n$ is H and G is CH. |
| 4162 | A is A-1c, $(R^2)_n$ is 3-F and G is CH. |
| 4163 | A is A-1c, $(R^2)_n$ is 3,5-di-F and G is CH. |
| 4164 | A is A-1c, $(R^2)_n$ is 3-Cl and G is CH. |
| 4165 | A is A-1c, $(R^2)_n$ is 3,5-di-Cl and G is CH. |
| 4166 | A is A-1c, $(R^2)_n$ is 3-Br and G is CH. |
| 4167 | A is A-1c, $(R^2)_n$ is 3,5-di-Br and G is CH. |
| 4168 | A is A-1c, $(R^2)_n$ is 3-Me and G is CH. |
| 4169 | A is A-1c, $(R^2)_n$ is 3,5-di-Me and G is CH. |
| 4170 | A is A-1c, $(R^2)_n$ is 3-CF$_3$ and G is CH. |
| 4171 | A is A-1c, $(R^2)_n$ is 3,5-di-CF$_3$ and G is CH. |
| 4172 | A is A-1c, $(R^2)_n$ is 3-MeO and G is CH. |
| 4173 | A is A-1c, $(R^2)_n$ is 3,5-di-MeO and G is CH. |
| 4174 | A is A-1c, $(R^2)_n$ is 3-CN and G is CH. |
| 4175 | A is A-1c, $(R^2)_n$ is 3,5-di-CN and G is CH. |
| 4176 | A is A-1c, $(R^2)_n$ is 3,6-di-F and G is CH. |
| 4177 | A is A-1c, $(R^2)_n$ is 3,6-di-Cl and G is CH. |
| 4178 | A is A-1c, $(R^2)_n$ is 3,6-di-Br and G is CH. |
| 4179 | A is A-1c, $(R^2)_n$ is 3,6-di-Me and G is CH. |
| 4180 | A is A-1c, $(R^2)_n$ is 3,6-di-CF$_3$ and G is CH. |
| 4181 | A is A-1c, $(R^2)_n$ is 3,6-di-MeO and G is CH. |
| 4182 | A is A-1c, $(R^2)_n$ is 3,6-di-CN and G is CH. |
| 4183 | A is A-1c, $(R^2)_n$ is 6-F and G is CH. |
| 4184 | A is A-1c, $(R^2)_n$ is 6-Cl and G is CH. |
| 4185 | A is A-1c, $(R^2)_n$ is 6-Br and G is CH. |
| 4186 | A is A-1c, $(R^2)_n$ is 6-Me and G is CH. |
| 4187 | A is A-1c, $(R^2)_n$ is 6-CF$_3$ and G is CH. |
| 4188 | A is A-1c, $(R^2)_n$ is 6-MeO and G is CH. |
| 4189 | A is A-1c, $(R^2)_n$ is 6-CN and G is CH. |
| 4190 | A is A-1c, $(R^2)_n$ is 6-F and G is C—F. |
| 4191 | A is A-1c, $(R^2)_n$ is 6-Cl and G is C—Cl. |
| 4192 | A is A-1c, $(R^2)_n$ is 6-Br and G is C—Br. |
| 4193 | A is A-1c, $(R^2)_n$ is 6-Me and G is C—Me. |
| 4194 | A is A-1c, $(R^2)_n$ is 6-CF$_3$ and G is C—CF$_3$. |
| 4195 | A is A-1c, $(R^2)_n$ is 6-MeO and G is C—OMe. |
| 4196 | A is A-1c, $(R^2)_n$ is H and G is N. |
| 4197 | A is A-1c, $(R^2)_n$ is 3-F and G is N. |
| 4198 | A is A-1c, $(R^2)_n$ is 3,5-di-F and G is N. |
| 4199 | A is A-1c, $(R^2)_n$ is 3-Cl and G is N. |
| 4200 | A is A-1c, $(R^2)_n$ is 3,5-di-Cl and G is N. |

TABLES 4034-5760-continued

| Table | Row Heading |
|---|---|
| 4201 | A is A-1c, $(R^2)_n$ is 3-Br and G is N. |
| 4202 | A is A-1c, $(R^2)_n$ is 3,5-di-Br and G is N. |
| 4203 | A is A-1c, $(R^2)_n$ is 3-Me and G is N. |
| 4204 | A is A-1c, $(R^2)_n$ is 3,5-di-Me and G is N. |
| 4205 | A is A-1c, $(R^2)_n$ is 3-$CF_3$ and G is N. |
| 4206 | A is A-1c, $(R^2)_n$ is 3,5-di-$CF_3$ and G is N. |
| 4207 | A is A-1c, $(R^2)_n$ is 3-MeO and G is N. |
| 4208 | A is A-1c, $(R^2)_n$ is 3,5-di-MeO and G is N. |
| 4209 | A is A-1c, $(R^2)_n$ is 3-CN and G is N. |
| 4210 | A is A-1c, $(R^2)_n$ is 3,5-di-CN and G is N. |
| 4211 | A is A-1c, $(R^2)_n$ is 3,6-di-F and G is N. |
| 4212 | A is A-1c, $(R^2)_n$ is 3,6-di-Cl and G is N. |
| 4213 | A is A-1c, $(R^2)_n$ is 3,6-di-Br and G is N. |
| 4214 | A is A-1c, $(R^2)_n$ is 3,6-di-Me and G is N. |
| 4215 | A is A-1c, $(R^2)_n$ is 3,6-di-$CF_3$ and G is N. |
| 4216 | A is A-1c, $(R^2)_n$ is 3,6-di-MeO and G is N. |
| 4217 | A is A-1c, $(R^2)_n$ is 3,6-di-CN and G is N. |
| 4218 | A is A-1c, $(R^2)_n$ is 6-F and G is N. |
| 4219 | A is A-1c, $(R^2)_n$ is 6-Cl and G is N. |
| 4220 | A is A-1c, $(R^2)_n$ is 6-Br and G is N. |
| 4221 | A is A-1c, $(R^2)_n$ is 6-Me and G is N. |
| 4222 | A is A-1c, $(R^2)_n$ is 6-$CF_3$ and G is N. |
| 4223 | A is A-1c, $(R^2)_n$ is 6-MeO and G is N. |
| 4224 | A is A-1c, $(R^2)_n$ is 6-CN and G is N. |
| 4225 | A is A-1d, $(R^2)_n$ is H and G is CH. |
| 4226 | A is A-1d, $(R^2)_n$ is 3-F and G is CH. |
| 4227 | A is A-1d, $(R^2)_n$ is 3,5-di-F and G is CH. |
| 4228 | A is A-1d, $(R^2)_n$ is 3-Cl and G is CH. |
| 4229 | A is A-1d, $(R^2)_n$ is 3,5-di-Cl and G is CH. |
| 4230 | A is A-1d, $(R^2)_n$ is 3-Br and G is CH. |
| 4231 | A is A-1d, $(R^2)_n$ is 3,5-di-Br and G is CH. |
| 4232 | A is A-1d, $(R^2)_n$ is 3-Me and G is CH. |
| 4233 | A is A-1d, $(R^2)_n$ is 3,5-di-Me and G is CH. |
| 4234 | A is A-1d, $(R^2)_n$ is 3-$CF_3$ and G is CH. |
| 4235 | A is A-1d, $(R^2)_n$ is 3,5-di-$CF_3$ and G is CH. |
| 4236 | A is A-1d, $(R^2)_n$ is 3-MeO and G is CH. |
| 4237 | A is A-1d, $(R^2)_n$ is 3,5-di-MeO and G is CH. |
| 4238 | A is A-1d, $(R^2)_n$ is 3-CN and G is CH. |
| 4239 | A is A-1d, $(R^2)_n$ is 3,5-di-CN and G is CH. |
| 4240 | A is A-1d, $(R^2)_n$ is 3,6-di-F and G is CH. |
| 4241 | A is A-1d, $(R^2)_n$ is 3,6-di-Cl and G is CH. |
| 4242 | A is A-1d, $(R^2)_n$ is 3,6-di-Br and G is CH. |
| 4243 | A is A-1d, $(R^2)_n$ is 3,6-di-Me and G is CH. |
| 4244 | A is A-1d, $(R^2)_n$ is 3,6-di-$CF_3$ and G is CH. |
| 4245 | A is A-1d, $(R^2)_n$ is 3,6-di-MeO and G is CH. |
| 4246 | A is A-1d, $(R^2)_n$ is 3,6-di-CN and G is CH. |
| 4247 | A is A-1d, $(R^2)_n$ is 6-F and G is CH. |
| 4248 | A is A-1d, $(R^2)_n$ is 6-Cl and G is CH. |
| 4249 | A is A-1d, $(R^2)_n$ is 6-Br and G is CH. |
| 4250 | A is A-1d, $(R^2)_n$ is 6-Me and G is CH. |
| 4251 | A is A-1d, $(R^2)_n$ is 6-$CF_3$ and G is CH. |
| 4252 | A is A-1d, $(R^2)_n$ is 6-MeO and G is CH. |
| 4253 | A is A-1d, $(R^2)_n$ is 6-CN and G is CH. |
| 4254 | A is A-1d, $(R^2)_n$ is 6-F and G is C—F. |
| 4255 | A is A-1d, $(R^2)_n$ is 6-Cl and G is C—Cl. |
| 4256 | A is A-1d, $(R^2)_n$ is 6-Br and G is C—Br. |
| 4257 | A is A-1d, $(R^2)_n$ is 6-Me and G is C—Me. |
| 4258 | A is A-1d, $(R^2)_n$ is 6-$CF_3$ and G is C—$CF_3$. |
| 4259 | A is A-1d, $(R^2)_n$ is 6-MeO and G is C—OMe. |
| 4260 | A is A-1d, $(R^2)_n$ is H and G is N. |
| 4261 | A is A-1d, $(R^2)_n$ is 3-F and G is N. |
| 4262 | A is A-1d, $(R^2)_n$ is 3,5-di-F and G is N. |
| 4263 | A is A-1d, $(R^2)_n$ is 3-Cl and G is N. |
| 4264 | A is A-1d, $(R^2)_n$ is 3,5-di-Cl and G is N. |
| 4265 | A is A-1d, $(R^2)_n$ is 3-Br and G is N. |
| 4266 | A is A-1d, $(R^2)_n$ is 3,5-di-Br and G is N. |
| 4267 | A is A-1d, $(R^2)_n$ is 3-Me and G is N. |
| 4268 | A is A-1d, $(R^2)_n$ is 3,5-di-Me and G is N. |
| 4269 | A is A-1d, $(R^2)_n$ is 3-$CF_3$ and G is N. |
| 4270 | A is A-1d, $(R^2)_n$ is 3,5-di-$CF_3$ and G is N. |
| 4271 | A is A-1d, $(R^2)_n$ is 3-MeO and G is N. |
| 4272 | A is A-1d, $(R^2)_n$ is 3,5-di-MeO and G is N. |
| 4273 | A is A-1d, $(R^2)_n$ is 3-CN and G is N. |
| 4274 | A is A-1d, $(R^2)_n$ is 3,5-di-CN and G is N. |
| 4275 | A is A-1d, $(R^2)_n$ is 3,6-di-F and G is N. |
| 4276 | A is A-1d, $(R^2)_n$ is 3,6-di-Cl and G is N. |
| 4277 | A is A-1d, $(R^2)_n$ is 3,6-di-Br and G is N. |
| 4278 | A is A-1d, $(R^2)_n$ is 3,6-di-Me and G is N. |
| 4279 | A is A-1d, $(R^2)_n$ is 3,6-di-$CF_3$ and G is N. |
| 4280 | A is A-1d, $(R^2)_n$ is 3,6-di-MeO and G is N. |
| 4281 | A is A-1d, $(R^2)_n$ is 3,6-di-CN and G is N. |
| 4282 | A is A-1d, $(R^2)_n$ is 6-F and G is N. |
| 4283 | A is A-1d, $(R^2)_n$ is 6-Cl and G is N. |
| 4284 | A is A-1d, $(R^2)_n$ is 6-Br and G is N. |
| 4285 | A is A-1d, $(R^2)_n$ is 6-Me and G is N. |
| 4286 | A is A-1d, $(R^2)_n$ is 6-$CF_3$ and G is N. |
| 4287 | A is A-1d, $(R^2)_n$ is 6-MeO and G is N. |
| 4288 | A is A-1d, $(R^2)_n$ is 6-CN and G is N. |
| 4289 | A is A-1e, $(R^2)_n$ is H and G is CH. |
| 4290 | A is A-1e, $(R^2)_n$ is 3-F and G is CH. |
| 4291 | A is A-1e, $(R^2)_n$ is 3,5-di-F and G is CH. |
| 4292 | A is A-1e, $(R^2)_n$ is 3-Cl and G is CH. |
| 4293 | A is A-1e, $(R^2)_n$ is 3,5-di-Cl and G is CH. |
| 4294 | A is A-1e, $(R^2)_n$ is 3-Br and G is CH. |
| 4295 | A is A-1e, $(R^2)_n$ is 3,5-di-Br and G is CH. |
| 4296 | A is A-1e, $(R^2)_n$ is 3-Me and G is CH. |
| 4297 | A is A-1e, $(R^2)_n$ is 3,5-di-Me and G is CH. |
| 4298 | A is A-1e, $(R^2)_n$ is 3-$CF_3$ and G is CH. |
| 4299 | A is A-1e, $(R^2)_n$ is 3,5-di-$CF_3$ and G is CH. |
| 4300 | A is A-1e, $(R^2)_n$ is 3-MeO and G is CH. |
| 4301 | A is A-1e, $(R^2)_n$ is 3,5-di-MeO and G is CH. |
| 4302 | A is A-1e, $(R^2)_n$ is 3-CN and G is CH. |
| 4303 | A is A-1e, $(R^2)_n$ is 3,5-di-CN and G is CH. |
| 4304 | A is A-1e, $(R^2)_n$ is 3,6-di-F and G is CH. |
| 4305 | A is A-1e, $(R^2)_n$ is 3,6-di-Cl and G is CH. |
| 4306 | A is A-1e, $(R^2)_n$ is 3,6-di-Br and G is CH. |
| 4307 | A is A-1e, $(R^2)_n$ is 3,6-di-Me and G is CH. |
| 4308 | A is A-1e, $(R^2)_n$ is 3,6-di-$CF_3$ and G is CH. |
| 4309 | A is A-1e, $(R^2)_n$ is 3,6-di-MeO and G is CH. |
| 4310 | A is A-1e, $(R^2)_n$ is 3,6-di-CN and G is CH. |
| 4311 | A is A-1e, $(R^2)_n$ is 6-F and G is CH. |
| 4312 | A is A-1e, $(R^2)_n$ is 6-Cl and G is CH. |
| 4313 | A is A-1e, $(R^2)_n$ is 6-Br and G is CH. |
| 4314 | A is A-1e, $(R^2)_n$ is 6-Me and G is CH. |
| 4315 | A is A-1e, $(R^2)_n$ is 6-$CF_3$ and G is CH. |
| 4316 | A is A-1e, $(R^2)_n$ is 6-MeO and G is CH. |
| 4317 | A is A-1e, $(R^2)_n$ is 6-CN and G is CH. |
| 4318 | A is A-1e, $(R^2)_n$ is 6-F and G is C—F. |
| 4319 | A is A-1e, $(R^2)_n$ is 6-Cl and G is C—Cl. |
| 4320 | A is A-1e, $(R^2)_n$ is 6-Br and G is C—Br. |
| 4321 | A is A-1e, $(R^2)_n$ is 6-Me and G is C—Me. |
| 4322 | A is A-1e, $(R^2)_n$ is 6-$CF_3$ and G is C—$CF_3$. |
| 4323 | A is A-1e, $(R^2)_n$ is 6-MeO and G is C—OMe. |
| 4324 | A is A-1e, $(R^2)_n$ is H and G is N. |
| 4325 | A is A-1e, $(R^2)_n$ is 3-F and G is N. |
| 4326 | A is A-1e, $(R^2)_n$ is 3,5-di-F and G is N. |
| 4327 | A is A-1e, $(R^2)_n$ is 3-Cl and G is N. |
| 4328 | A is A-1e, $(R^2)_n$ is 3,5-di-Cl and G is N. |
| 4329 | A is A-1e, $(R^2)_n$ is 3-Br and G is N. |
| 4330 | A is A-1e, $(R^2)_n$ is 3,5-di-Br and G is N. |
| 4331 | A is A-1e, $(R^2)_n$ is 3-Me and G is N. |
| 4332 | A is A-1e, $(R^2)_n$ is 3,5-di-Me and G is N. |
| 4333 | A is A-1e, $(R^2)_n$ is 3-$CF_3$ and G is N. |
| 4334 | A is A-1e, $(R^2)_n$ is 3,5-di-$CF_3$ and G is N. |
| 4335 | A is A-1e, $(R^2)_n$ is 3-MeO and G is N. |
| 4336 | A is A-1e, $(R^2)_n$ is 3,5-di-MeO and G is N. |
| 4337 | A is A-1e, $(R^2)_n$ is 3-CN and G is N. |
| 4338 | A is A-1e, $(R^2)_n$ is 3,5-di-CN and G is N. |
| 4339 | A is A-1e, $(R^2)_n$ is 3,6-di-F and G is N. |
| 4340 | A is A-1e, $(R^2)_n$ is 3,6-di-Cl and G is N. |
| 4341 | A is A-1e, $(R^2)_n$ is 3,6-di-Br and G is N. |
| 4342 | A is A-1e, $(R^2)_n$ is 3,6-di-Me and G is N. |
| 4343 | A is A-1e, $(R^2)_n$ is 3,6-di-$CF_3$ and G is N. |
| 4344 | A is A-1e, $(R^2)_n$ is 3,6-di-MeO and G is N. |
| 4345 | A is A-1e, $(R^2)_n$ is 3,6-di-CN and G is N. |
| 4346 | A is A-1e, $(R^2)_n$ is 6-F and G is N. |
| 4347 | A is A-1e, $(R^2)_n$ is 6-Cl and G is N. |
| 4348 | A is A-1e, $(R^2)_n$ is 6-Br and G is N. |
| 4349 | A is A-1e, $(R^2)_n$ is 6-Me and G is N. |
| 4350 | A is A-1e, $(R^2)_n$ is 6-$CF_3$ and G is N. |
| 4351 | A is A-1e, $(R^2)_n$ is 6-MeO and G is N. |
| 4352 | A is A-1e, $(R^2)_n$ is 6-CN and G is N. |
| 4353 | A is A-1f, $(R^2)_n$ is H and G is CH. |
| 4354 | A is A-1f, $(R^2)_n$ is 3-F and G is CH. |
| 4355 | A is A-1f, $(R^2)_n$ is 3,5-di-F and G is CH. |
| 4356 | A is A-1f, $(R^2)_n$ is 3-Cl and G is CH. |

TABLES 4034-5760-continued

| Table | Row Heading |
|---|---|
| 4357 | A is A-1f, $(R^2)_n$ is 3,5-di-Cl and G is CH. |
| 4358 | A is A-1f, $(R^2)_n$ is 3-Br and G is CH. |
| 4359 | A is A-1f, $(R^2)_n$ is 3,5-di-Br and G is CH. |
| 4360 | A is A-1f, $(R^2)_n$ is 3-Me and G is CH. |
| 4361 | A is A-1f, $(R^2)_n$ is 3,5-di-Me and G is CH. |
| 4362 | A is A-1f, $(R^2)_n$ is 3-CF$_3$ and G is CH. |
| 4363 | A is A-1f, $(R^2)_n$ is 3,5-di-CF$_3$ and G is CH. |
| 4364 | A is A-1f, $(R^2)_n$ is 3-MeO and G is CH. |
| 4365 | A is A-1f, $(R^2)_n$ is 3,5-di-MeO and G is CH. |
| 4366 | A is A-1f, $(R^2)_n$ is 3-CN and G is CH. |
| 4367 | A is A-1f, $(R^2)_n$ is 3,5-di-CN and G is CH. |
| 4368 | A is A-1f, $(R^2)_n$ is 3,6-di-F and G is CH. |
| 4369 | A is A-1f, $(R^2)_n$ is 3,6-di-Cl and G is CH. |
| 4370 | A is A-1f, $(R^2)_n$ is 3,6-di-Br and G is CH. |
| 4371 | A is A-1f, $(R^2)_n$ is 3,6-di-Me and G is CH. |
| 4372 | A is A-1f, $(R^2)_n$ is 3,6-di-CF$_3$ and G is CH. |
| 4373 | A is A-1f, $(R^2)_n$ is 3,6-di-MeO and G is CH. |
| 4374 | A is A-1f, $(R^2)_n$ is 3,6-di-CN and G is CH. |
| 4375 | A is A-1f, $(R^2)_n$ is 6-F and G is CH. |
| 4376 | A is A-1f, $(R^2)_n$ is 6-Cl and G is CH. |
| 4377 | A is A-1f, $(R^2)_n$ is 6-Br and G is CH. |
| 4378 | A is A-1f, $(R^2)_n$ is 6-Me and G is CH. |
| 4379 | A is A-1f, $(R^2)_n$ is 6-CF$_3$ and G is CH. |
| 4380 | A is A-1f, $(R^2)_n$ is 6-MeO and G is CH. |
| 4381 | A is A-1f, $(R^2)_n$ is 6-CN and G is CH. |
| 4382 | A is A-1f, $(R^2)_n$ is 6-F and G is C—F. |
| 4383 | A is A-1f, $(R^2)_n$ is 6-Cl and G is C—Cl. |
| 4384 | A is A-1f, $(R^2)_n$ is 6-Br and G is C—Br. |
| 4385 | A is A-1f, $(R^2)_n$ is 6-Me and G is C—Me. |
| 4386 | A is A-1f, $(R^2)_n$ is 6-CF$_3$ and G is C—CF$_3$. |
| 4387 | A is A-1f, $(R^2)_n$ is 6-MeO and G is C—OMe. |
| 4388 | A is A-1f, $(R^2)_n$ is H and G is N. |
| 4389 | A is A-1f, $(R^2)_n$ is 3-F and G is N. |
| 4390 | A is A-1f, $(R^2)_n$ is 3,5-di-F and G is N. |
| 4391 | A is A-1f, $(R^2)_n$ is 3-Cl and G is N. |
| 4392 | A is A-1f, $(R^2)_n$ is 3,5-di-Cl and G is N. |
| 4393 | A is A-1f, $(R^2)_n$ is 3-Br and G is N. |
| 4394 | A is A-1f, $(R^2)_n$ is 3,5-di-Br and G is N. |
| 4395 | A is A-1f, $(R^2)_n$ is 3-Me and G is N. |
| 4396 | A is A-1f, $(R^2)_n$ is 3,5-di-Me and G is N. |
| 4397 | A is A-1f, $(R^2)_n$ is 3-CF$_3$ and G is N. |
| 4398 | A is A-1f, $(R^2)_n$ is 3,5-di-CF$_3$ and G is N. |
| 4399 | A is A-1f, $(R^2)_n$ is 3-MeO and G is N. |
| 4400 | A is A-1f, $(R^2)_n$ is 3,5-di-MeO and G is N. |
| 4401 | A is A-1f, $(R^2)_n$ is 3-CN and G is N. |
| 4402 | A is A-1f, $(R^2)_n$ is 3,5-di-CN and G is N. |
| 4403 | A is A-1f, $(R^2)_n$ is 3,6-di-F and G is N. |
| 4404 | A is A-1f, $(R^2)_n$ is 3,6-di-Cl and G is N. |
| 4405 | A is A-1f, $(R^2)_n$ is 3,6-di-Br and G is N. |
| 4406 | A is A-1f, $(R^2)_n$ is 3,6-di-Me and G is N. |
| 4407 | A is A-1f, $(R^2)_n$ is 3,6-di-CF$_3$ and G is N. |
| 4408 | A is A-1f, $(R^2)_n$ is 3,6-di-MeO and G is N. |
| 4409 | A is A-1f, $(R^2)_n$ is 3,6-di-CN and G is N. |
| 4410 | A is A-1f, $(R^2)_n$ is 6-F and G is N. |
| 4411 | A is A-1f, $(R^2)_n$ is 6-Cl and G is N. |
| 4412 | A is A-1f, $(R^2)_n$ is 6-Br and G is N. |
| 4413 | A is A-1f, $(R^2)_n$ is 6-Me and G is N. |
| 4414 | A is A-1f, $(R^2)_n$ is 6-CF$_3$ and G is N. |
| 4415 | A is A-1f, $(R^2)_n$ is 6-MeO and G is N. |
| 4416 | A is A-1f, $(R^2)_n$ is 6-CN and G is N. |
| 4417 | A is A-1g, $(R^2)_n$ is H and G is CH. |
| 4418 | A is A-1g, $(R^2)_n$ is 3-F and G is CH. |
| 4419 | A is A-1g, $(R^2)_n$ is 3,5-di-F and G is CH. |
| 4420 | A is A-1g, $(R^2)_n$ is 3-Cl and G is CH. |
| 4421 | A is A-1g, $(R^2)_n$ is 3,5-di-Cl and G is CH. |
| 4422 | A is A-1g, $(R^2)_n$ is 3-Br and G is CH. |
| 4423 | A is A-1g, $(R^2)_n$ is 3,5-di-Br and G is CH. |
| 4424 | A is A-1g, $(R^2)_n$ is 3-Me and G is CH. |
| 4425 | A is A-1g, $(R^2)_n$ is 3,5-di-Me and G is CH. |
| 4426 | A is A-1g, $(R^2)_n$ is 3-CF$_3$ and G is CH. |
| 4427 | A is A-1g, $(R^2)_n$ is 3,5-di-CF$_3$ and G is CH. |
| 4428 | A is A-1g, $(R^2)_n$ is 3-MeO and G is CH. |
| 4429 | A is A-1g, $(R^2)_n$ is 3,5-di-MeO and G is CH. |
| 4430 | A is A-1g, $(R^2)_n$ is 3-CN and G is CH. |
| 4431 | A is A-1g, $(R^2)_n$ is 3,5-di-CN and G is CH. |
| 4432 | A is A-1g, $(R^2)_n$ is 3,6-di-F and G is CH. |
| 4433 | A is A-1g, $(R^2)_n$ is 3,6-di-Cl and G is CH. |
| 4434 | A is A-1g, $(R^2)_n$ is 3,6-di-Br and G is CH. |
| 4435 | A is A-1g, $(R^2)_n$ is 3,6-di-Me and G is CH. |
| 4436 | A is A-1g, $(R^2)_n$ is 3,6-di-CF$_3$ and G is CH. |
| 4437 | A is A-1g, $(R^2)_n$ is 3,6-di-MeO and G is CH. |
| 4438 | A is A-1g, $(R^2)_n$ is 3,6-di-CN and G is CH. |
| 4439 | A is A-1g, $(R^2)_n$ is 6-F and G is CH. |
| 4440 | A is A-1g, $(R^2)_n$ is 6-Cl and G is CH. |
| 4441 | A is A-1g, $(R^2)_n$ is 6-Br and G is CH. |
| 4442 | A is A-1g, $(R^2)_n$ is 6-Me and G is CH. |
| 4443 | A is A-1g, $(R^2)_n$ is 6-CF$_3$ and G is CH. |
| 4444 | A is A-1g, $(R^2)_n$ is 6-MeO and G is CH. |
| 4445 | A is A-1g, $(R^2)_n$ is 6-CN and G is CH. |
| 4446 | A is A-1g, $(R^2)_n$ is 6-F and G is C—F. |
| 4447 | A is A-1g, $(R^2)_n$ is 6-Cl and G is C—Cl. |
| 4448 | A is A-1g, $(R^2)_n$ is 6-Br and G is C—Br. |
| 4449 | A is A-1g, $(R^2)_n$ is 6-Me and G is C—Me. |
| 4450 | A is A-1g, $(R^2)_n$ is 6-CF$_3$ and G is C—CF$_3$. |
| 4451 | A is A-1g, $(R^2)_n$ is 6-MeO and G is C—OMe. |
| 4452 | A is A-1g, $(R^2)_n$ is H and G is N. |
| 4453 | A is A-1g, $(R^2)_n$ is 3-F and G is N. |
| 4454 | A is A-1g, $(R^2)_n$ is 3,5-di-F and G is N. |
| 4455 | A is A-1g, $(R^2)_n$ is 3-Cl and G is N. |
| 4456 | A is A-1g, $(R^2)_n$ is 3,5-di-Cl and G is N. |
| 4457 | A is A-1g, $(R^2)_n$ is 3-Br and G is N. |
| 4458 | A is A-1g, $(R^2)_n$ is 3,5-di-Br and G is N. |
| 4459 | A is A-1g, $(R^2)_n$ is 3-Me and G is N. |
| 4460 | A is A-1g, $(R^2)_n$ is 3,5-di-Me and G is N. |
| 4461 | A is A-1g, $(R^2)_n$ is 3-CF$_3$ and G is N. |
| 4462 | A is A-1g, $(R^2)_n$ is 3,5-di-CF$_3$ and G is N. |
| 4463 | A is A-1g, $(R^2)_n$ is 3-MeO and G is N. |
| 4464 | A is A-1g, $(R^2)_n$ is 3,5-di-MeO and G is N. |
| 4465 | A is A-1g, $(R^2)_n$ is 3-CN and G is N. |
| 4466 | A is A-1g, $(R^2)_n$ is 3,5-di-CN and G is N. |
| 4467 | A is A-1g, $(R^2)_n$ is 3,6-di-F and G is N. |
| 4468 | A is A-1g, $(R^2)_n$ is 3,6-di-Cl and G is N. |
| 4469 | A is A-1g, $(R^2)_n$ is 3,6-di-Br and G is N. |
| 4470 | A is A-1g, $(R^2)_n$ is 3,6-di-Me and G is N. |
| 4471 | A is A-1g, $(R^2)_n$ is 3,6-di-CF$_3$ and G is N. |
| 4472 | A is A-1g, $(R^2)_n$ is 3,6-di-MeO and G is N. |
| 4473 | A is A-1g, $(R^2)_n$ is 3,6-di-CN and G is N. |
| 4474 | A is A-1g, $(R^2)_n$ is 6-F and G is N. |
| 4475 | A is A-1g, $(R^2)_n$ is 6-Cl and G is N. |
| 4476 | A is A-1g, $(R^2)_n$ is 6-Br and G is N. |
| 4477 | A is A-1g, $(R^2)_n$ is 6-Me and G is N. |
| 4478 | A is A-1g, $(R^2)_n$ is 6-CF$_3$ and G is N. |
| 4479 | A is A-1g, $(R^2)_n$ is 6-MeO and G is N. |
| 4480 | A is A-1g, $(R^2)_n$ is 6-CN and G is N. |
| 4481 | A is A-1h, $(R^2)_n$ is H and G is CH. |
| 4482 | A is A-1h, $(R^2)_n$ is 3-F and G is CH. |
| 4483 | A is A-1h, $(R^2)_n$ is 3,5-di-F and G is CH. |
| 4484 | A is A-1h, $(R^2)_n$ is 3-Cl and G is CH. |
| 4485 | A is A-1h, $(R^2)_n$ is 3,5-di-Cl and G is CH. |
| 4486 | A is A-1h, $(R^2)_n$ is 3-Br and G is CH. |
| 4487 | A is A-1h, $(R^2)_n$ is 3,5-di-Br and G is CH. |
| 4488 | A is A-1h, $(R^2)_n$ is 3-Me and G is CH. |
| 4489 | A is A-1h, $(R^2)_n$ is 3,5-di-Me and G is CH. |
| 4490 | A is A-1h, $(R^2)_n$ is 3-CF$_3$ and G is CH. |
| 4491 | A is A-1h, $(R^2)_n$ is 3,5-di-CF$_3$ and G is CH. |
| 4492 | A is A-1h, $(R^2)_n$ is 3-MeO and G is CH. |
| 4493 | A is A-1h, $(R^2)_n$ is 3,5-di-MeO and G is CH. |
| 4494 | A is A-1h, $(R^2)_n$ is 3-CN and G is CH. |
| 4495 | A is A-1h, $(R^2)_n$ is 3,5-di-CN and G is CH. |
| 4496 | A is A-1h, $(R^2)_n$ is 3,6-di-F and G is CH. |
| 4497 | A is A-1h, $(R^2)_n$ is 3,6-di-Cl and G is CH. |
| 4498 | A is A-1h, $(R^2)_n$ is 3,6-di-Br and G is CH. |
| 4499 | A is A-1h, $(R^2)_n$ is 3,6-di-Me and G is CH. |
| 4500 | A is A-1h, $(R^2)_n$ is 3,6-di-CF$_3$ and G is CH. |
| 4501 | A is A-1h, $(R^2)_n$ is 3,6-di-MeO and G is CH. |
| 4502 | A is A-1h, $(R^2)_n$ is 3,6-di-CN and G is CH. |
| 4503 | A is A-1h, $(R^2)_n$ is 6-F and G is CH. |
| 4504 | A is A-1h, $(R^2)_n$ is 6-Cl and G is CH. |
| 4505 | A is A-1h, $(R^2)_n$ is 6-Br and G is CH. |
| 4506 | A is A-1h, $(R^2)_n$ is 6-Me and G is CH. |
| 4507 | A is A-1h, $(R^2)_n$ is 6-CF$_3$ and G is CH. |
| 4508 | A is A-1h, $(R^2)_n$ is 6-MeO and G is CH. |
| 4509 | A is A-1h, $(R^2)_n$ is 6-CN and G is CH. |
| 4510 | A is A-1h, $(R^2)_n$ is 6-F and G is C—F. |
| 4511 | A is A-1h, $(R^2)_n$ is 6-Cl and G is C—Cl. |
| 4512 | A is A-1h, $(R^2)_n$ is 6-Br and G is C—Br. |

TABLES 4034-5760-continued

| Table | Row Heading |
|---|---|
| 4513 | A is A-1h, $(R^2)_n$ is 6-Me and G is C—Me. |
| 4514 | A is A-1h, $(R^2)_n$ is 6-$CF_3$ and G is C—$CF_3$. |
| 4515 | A is A-1h, $(R^2)_n$ is 6-MeO and G is C—OMe. |
| 4516 | A is A-1h, $(R^2)_n$ is H and G is N. |
| 4517 | A is A-1h, $(R^2)_n$ is 3-F and G is N. |
| 4518 | A is A-1h, $(R^2)_n$ is 3,5-di-F and G is N. |
| 4519 | A is A-1h, $(R^2)_n$ is 3-Cl and G is N. |
| 4520 | A is A-1h, $(R^2)_n$ is 3,5-di-Cl and G is N. |
| 4521 | A is A-1h, $(R^2)_n$ is 3-Br and G is N. |
| 4522 | A is A-1h, $(R^2)_n$ is 3,5-di-Br and G is N. |
| 4523 | A is A-1h, $(R^2)_n$ is 3-Me and G is N. |
| 4524 | A is A-1h, $(R^2)_n$ is 3,5-di-Me and G is N. |
| 4525 | A is A-1h, $(R^2)_n$ is 3-$CF_3$ and G is N. |
| 4526 | A is A-1h, $(R^2)_n$ is 3,5-di-$CF_3$ and G is N. |
| 4527 | A is A-1h, $(R^2)_n$ is 3-MeO and G is N. |
| 4528 | A is A-1h, $(R^2)_n$ is 3,5-di-MeO and G is N. |
| 4529 | A is A-1h, $(R^2)_n$ is 3-CN and G is N. |
| 4530 | A is A-1h, $(R^2)_n$ is 3,5-di-CN and G is N. |
| 4531 | A is A-1h, $(R^2)_n$ is 3,6-di-F and G is N. |
| 4532 | A is A-1h, $(R^2)_n$ is 3,6-di-Cl and G is N. |
| 4533 | A is A-1h, $(R^2)_n$ is 3,6-di-Br and G is N. |
| 4534 | A is A-1h, $(R^2)_n$ is 3,6-di-Me and G is N. |
| 4535 | A is A-1h, $(R^2)_n$ is 3,6-di-$CF_3$ and G is N. |
| 4536 | A is A-1h, $(R^2)_n$ is 3,6-di-MeO and G is N. |
| 4537 | A is A-1h, $(R^2)_n$ is 3,6-di-CN and G is N. |
| 4538 | A is A-1h, $(R^2)_n$ is 6-F and G is N. |
| 4539 | A is A-1h, $(R^2)_n$ is 6-Cl and G is N. |
| 4540 | A is A-1h, $(R^2)_n$ is 6-Br and G is N. |
| 4541 | A is A-1h, $(R^2)_n$ is 6-Me and G is N. |
| 4542 | A is A-1h, $(R^2)_n$ is 6-$CF_3$ and G is N. |
| 4543 | A is A-1h, $(R^2)_n$ is 6-MeO and G is N. |
| 4544 | A is A-1h, $(R^2)_n$ is 6-CN and G is N. |
| 4545 | A is A-1i, $(R^2)_n$ is H and G is CH. |
| 4546 | A is A-1i, $(R^2)_n$ is 3-F and G is CH. |
| 4547 | A is A-1i, $(R^2)_n$ is 3,5-di-F and G is CH. |
| 4548 | A is A-1i, $(R^2)_n$ is 3-Cl and G is CH. |
| 4549 | A is A-1i, $(R^2)_n$ is 3,5-di-Cl and G is CH. |
| 4550 | A is A-1i, $(R^2)_n$ is 3-Br and G is CH. |
| 4551 | A is A-1i, $(R^2)_n$ is 3,5-di-Br and G is CH. |
| 4552 | A is A-1i, $(R^2)_n$ is 3-Me and G is CH. |
| 4553 | A is A-1i, $(R^2)_n$ is 3,5-di-Me and G is CH. |
| 4554 | A is A-1i, $(R^2)_n$ is 3-$CF_3$ and G is CH. |
| 4555 | A is A-1i, $(R^2)_n$ is 3,5-di-$CF_3$ and G is CH. |
| 4556 | A is A-1i, $(R^2)_n$ is 3-MeO and G is CH. |
| 4557 | A is A-1i, $(R^2)_n$ is 3,5-di-MeO and G is CH. |
| 4558 | A is A-1i, $(R^2)_n$ is 3-CN and G is CH. |
| 4559 | A is A-1i, $(R^2)_n$ is 3,5-di-CN and G is CH. |
| 4560 | A is A-1i, $(R^2)_n$ is 3,6-di-F and G is CH. |
| 4561 | A is A-1i, $(R^2)_n$ is 3,6-di-Cl and G is CH. |
| 4562 | A is A-1i, $(R^2)_n$ is 3,6-di-Br and G is CH. |
| 4563 | A is A-1i, $(R^2)_n$ is 3,6-di-Me and G is CH. |
| 4564 | A is A-1i, $(R^2)_n$ is 3,6-di-$CF_3$ and G is CH. |
| 4565 | A is A-1i, $(R^2)_n$ is 3,6-di-MeO and G is CH. |
| 4566 | A is A-1i, $(R^2)_n$ is 3,6-di-CN and G is CH. |
| 4567 | A is A-1i, $(R^2)_n$ is 6-F and G is CH. |
| 4568 | A is A-1i, $(R^2)_n$ is 6-Cl and G is CH. |
| 4569 | A is A-1i, $(R^2)_n$ is 6-Br and G is CH. |
| 4570 | A is A-1i, $(R^2)_n$ is 6-Me and G is CH. |
| 4571 | A is A-1i, $(R^2)_n$ is 6-$CF_3$ and G is CH. |
| 4572 | A is A-1i, $(R^2)_n$ is 6-MeO and G is CH. |
| 4573 | A is A-1i, $(R^2)_n$ is 6-CN and G is CH. |
| 4574 | A is A-1i, $(R^2)_n$ is 6-F and G is C—F. |
| 4575 | A is A-1i, $(R^2)_n$ is 6-Cl and G is C—Cl. |
| 4576 | A is A-1i, $(R^2)_n$ is 6-Br and G is C—Br. |
| 4577 | A is A-1i, $(R^2)_n$ is 6-Me and G is C—Me. |
| 4578 | A is A-1i, $(R^2)_n$ is 6-$CF_3$ and G is C—$CF_3$. |
| 4579 | A is A-1i, $(R^2)_n$ is 6-MeO and G is C—OMe. |
| 4580 | A is A-1i, $(R^2)_n$ is H and G is N. |
| 4581 | A is A-1i, $(R^2)_n$ is 3-F and G is N. |
| 4582 | A is A-1i, $(R^2)_n$ is 3,5-di-F and G is N. |
| 4583 | A is A-1i, $(R^2)_n$ is 3-Cl and G is N. |
| 4584 | A is A-1i, $(R^2)_n$ is 3,5-di-Cl and G is N. |
| 4585 | A is A-1i, $(R^2)_n$ is 3-Br and G is N. |
| 4586 | A is A-1i, $(R^2)_n$ is 3,5-di-Br and G is N. |
| 4587 | A is A-1i, $(R^2)_n$ is 3-Me and G is N. |
| 4588 | A is A-1i, $(R^2)_n$ is 3,5-di-Me and G is N. |
| 4589 | A is A-1i, $(R^2)_n$ is 3-$CF_3$ and G is N. |
| 4590 | A is A-1i, $(R^2)_n$ is 3,5-di-$CF_3$ and G is N. |
| 4591 | A is A-1i, $(R^2)_n$ is 3-MeO and G is N. |
| 4592 | A is A-1i, $(R^2)_n$ is 3,5-di-MeO and G is N. |
| 4593 | A is A-1i, $(R^2)_n$ is 3-CN and G is N. |
| 4594 | A is A-1i, $(R^2)_n$ is 3,5-di-CN and G is N. |
| 4595 | A is A-1i, $(R^2)_n$ is 3,6-di-F and G is N. |
| 4596 | A is A-1i, $(R^2)_n$ is 3,6-di-Cl and G is N. |
| 4597 | A is A-1i, $(R^2)_n$ is 3,6-di-Br and G is N. |
| 4598 | A is A-1i, $(R^2)_n$ is 3,6-di-Me and G is N. |
| 4599 | A is A-1i, $(R^2)_n$ is 3,6-di-$CF_3$ and G is N. |
| 4600 | A is A-1i, $(R^2)_n$ is 3,6-di-MeO and G is N. |
| 4601 | A is A-1i, $(R^2)_n$ is 3,6-di-CN and G is N. |
| 4602 | A is A-1i, $(R^2)_n$ is 6-F and G is N. |
| 4603 | A is A-1i, $(R^2)_n$ is 6-Cl and G is N. |
| 4604 | A is A-1i, $(R^2)_n$ is 6-Br and G is N. |
| 4605 | A is A-1i, $(R^2)_n$ is 6-Me and G is N. |
| 4606 | A is A-1i, $(R^2)_n$ is 6-$CF_3$ and G is N. |
| 4607 | A is A-1i, $(R^2)_n$ is 6-MeO and G is N. |
| 4608 | A is A-1i, $(R^2)_n$ is 6-CN and G is N. |
| 4609 | A is A-1j, $(R^2)_n$ is H and G is CH. |
| 4610 | A is A-1j, $(R^2)_n$ is 3-F and G is CH. |
| 4611 | A is A-1j, $(R^2)_n$ is 3,5-di-F and G is CH. |
| 4612 | A is A-1j, $(R^2)_n$ is 3-Cl and G is CH. |
| 4613 | A is A-1j, $(R^2)_n$ is 3,5-di-Cl and G is CH. |
| 4614 | A is A-1j, $(R^2)_n$ is 3-Br and G is CH. |
| 4615 | A is A-1j, $(R^2)_n$ is 3,5-di-Br and G is CH. |
| 4616 | A is A-1j, $(R^2)_n$ is 3-Me and G is CH. |
| 4617 | A is A-1j, $(R^2)_n$ is 3,5-di-Me and G is CH. |
| 4618 | A is A-1j, $(R^2)_n$ is 3-$CF_3$ and G is CH. |
| 4619 | A is A-1j, $(R^2)_n$ is 3,5-di-$CF_3$ and G is CH. |
| 4620 | A is A-1j, $(R^2)_n$ is 3-MeO and G is CH. |
| 4621 | A is A-1j, $(R^2)_n$ is 3,5-di-MeO and G is CH. |
| 4622 | A is A-1j, $(R^2)_n$ is 3-CN and G is CH. |
| 4623 | A is A-1j, $(R^2)_n$ is 3,5-di-CN and G is CH. |
| 4624 | A is A-1j, $(R^2)_n$ is 3,6-di-F and G is CH. |
| 4625 | A is A-1j, $(R^2)_n$ is 3,6-di-Cl and G is CH. |
| 4626 | A is A-1j, $(R^2)_n$ is 3,6-di-Br and G is CH. |
| 4627 | A is A-1j, $(R^2)_n$ is 3,6-di-Me and G is CH. |
| 4628 | A is A-1j, $(R^2)_n$ is 3,6-di-$CF_3$ and G is CH. |
| 4629 | A is A-1j, $(R^2)_n$ is 3,6-di-MeO and G is CH. |
| 4630 | A is A-1j, $(R^2)_n$ is 3,6-di-CN and G is CH. |
| 4631 | A is A-1j, $(R^2)_n$ is 6-F and G is CH. |
| 4632 | A is A-1j, $(R^2)_n$ is 6-Cl and G is CH. |
| 4633 | A is A-1j, $(R^2)_n$ is 6-Br and G is CH. |
| 4634 | A is A-1j, $(R^2)_n$ is 6-Me and G is CH. |
| 4635 | A is A-1j, $(R^2)_n$ is 6-$CF_3$ and G is CH. |
| 4636 | A is A-1j, $(R^2)_n$ is 6-MeO and G is CH. |
| 4637 | A is A-1j, $(R^2)_n$ is 6-CN and G is CH. |
| 4638 | A is A-1j, $(R^2)_n$ is 6-F and G is C—F. |
| 4639 | A is A-1j, $(R^2)_n$ is 6-Cl and G is C—Cl. |
| 4640 | A is A-1j, $(R^2)_n$ is 6-Br and G is C—Br. |
| 4641 | A is A-1j, $(R^2)_n$ is 6-Me and G is C—Me. |
| 4642 | A is A-1j, $(R^2)_n$ is 6-$CF_3$ and G is C—$CF_3$. |
| 4643 | A is A-1j, $(R^2)_n$ is 6-MeO and G is C—OMe. |
| 4644 | A is A-1j, $(R^2)_n$ is H and G is N. |
| 4645 | A is A-1j, $(R^2)_n$ is 3-F and G is N. |
| 4646 | A is A-1j, $(R^2)_n$ is 3,5-di-F and G is N. |
| 4647 | A is A-1j, $(R^2)_n$ is 3-Cl and G is N. |
| 4648 | A is A-1j, $(R^2)_n$ is 3,5-di-Cl and G is N. |
| 4649 | A is A-1j, $(R^2)_n$ is 3-Br and G is N. |
| 4650 | A is A-1j, $(R^2)_n$ is 3,5-di-Br and G is N. |
| 4651 | A is A-1j, $(R^2)_n$ is 3-Me and G is N. |
| 4652 | A is A-1j, $(R^2)_n$ is 3,5-di-Me and G is N. |
| 4653 | A is A-1j, $(R^2)_n$ is 3-$CF_3$ and G is N. |
| 4654 | A is A-1j, $(R^2)_n$ is 3,5-di-$CF_3$ and G is N. |
| 4655 | A is A-1j, $(R^2)_n$ is 3-MeO and G is N. |
| 4656 | A is A-1j, $(R^2)_n$ is 3,5-di-MeO and G is N. |
| 4657 | A is A-1j, $(R^2)_n$ is 3-CN and G is N. |
| 4658 | A is A-1j, $(R^2)_n$ is 3,5-di-CN and G is N. |
| 4659 | A is A-1j, $(R^2)_n$ is 3,6-di-F and G is N. |
| 4660 | A is A-1j, $(R^2)_n$ is 3,6-di-Cl and G is N. |
| 4661 | A is A-1j, $(R^2)_n$ is 3,6-di-Br and G is N. |
| 4662 | A is A-1j, $(R^2)_n$ is 3,6-di-Me and G is N. |
| 4663 | A is A-1j, $(R^2)_n$ is 3,6-di-$CF_3$ and G is N. |
| 4664 | A is A-1j, $(R^2)_n$ is 3,6-di-MeO and G is N. |
| 4665 | A is A-1j, $(R^2)_n$ is 3,6-di-CN and G is N. |
| 4666 | A is A-1j, $(R^2)_n$ is 6-F and G is N. |
| 4667 | A is A-1j, $(R^2)_n$ is 6-Cl and G is N. |
| 4668 | A is A-1j, $(R^2)_n$ is 6-Br and G is N. |

TABLES 4034-5760-continued

| Table | Row Heading |
|---|---|
| 4669 | A is A-1j, $(R^2)_n$ is 6-Me and G is N. |
| 4670 | A is A-1j, $(R^2)_n$ is 6-CF$_3$ and G is N. |
| 4671 | A is A-1j, $(R^2)_n$ is 6-MeO and G is N. |
| 4672 | A is A-1j, $(R^2)_n$ is 6-CN and G is N. |
| 4673 | A is A-1k, $(R^2)_n$ is H and G is CH. |
| 4674 | A is A-1k, $(R^2)_n$ is 3-F and G is CH. |
| 4675 | A is A-1k, $(R^2)_n$ is 3,5-di-F and G is CH. |
| 4676 | A is A-1k, $(R^2)_n$ is 3-Cl and G is CH. |
| 4677 | A is A-1k, $(R^2)_n$ is 3,5-di-Cl and G is CH. |
| 4678 | A is A-1k, $(R^2)_n$ is 3-Br and G is CH. |
| 4679 | A is A-1k, $(R^2)_n$ is 3,5-di-Br and G is CH. |
| 4680 | A is A-1k, $(R^2)_n$ is 3-Me and G is CH. |
| 4681 | A is A-1k, $(R^2)_n$ is 3,5-di-Me and G is CH. |
| 4682 | A is A-1k, $(R^2)_n$ is 3-CF$_3$ and G is CH. |
| 4683 | A is A-1k, $(R^2)_n$ is 3,5-di-CF$_3$ and G is CH. |
| 4684 | A is A-1k, $(R^2)_n$ is 3-MeO and G is CH. |
| 4685 | A is A-1k, $(R^2)_n$ is 3,5-di-MeO and G is CH. |
| 4686 | A is A-1k, $(R^2)_n$ is 3-CN and G is CH. |
| 4687 | A is A-1k, $(R^2)_n$ is 3,5-di-CN and G is CH. |
| 4688 | A is A-1k, $(R^2)_n$ is 3,6-di-F and G is CH. |
| 4689 | A is A-1k, $(R^2)_n$ is 3,6-di-Cl and G is CH. |
| 4690 | A is A-1k, $(R^2)_n$ is 3,6-di-Br and G is CH. |
| 4691 | A is A-1k, $(R^2)_n$ is 3,6-di-Me and G is CH. |
| 4692 | A is A-1k, $(R^2)_n$ is 3,6-di-CF$_3$ and G is CH. |
| 4693 | A is A-1k, $(R^2)_n$ is 3,6-di-MeO and G is CH. |
| 4694 | A is A-1k, $(R^2)_n$ is 3,6-di-CN and G is CH. |
| 4695 | A is A-1k, $(R^2)_n$ is 6-F and G is CH. |
| 4696 | A is A-1k, $(R^2)_n$ is 6-Cl and G is CH. |
| 4697 | A is A-1k, $(R^2)_n$ is 6-Br and G is CH. |
| 4698 | A is A-1k, $(R^2)_n$ is 6-Me and G is CH. |
| 4699 | A is A-1k, $(R^2)_n$ is 6-CF$_3$ and G is CH. |
| 4700 | A is A-1k, $(R^2)_n$ is 6-MeO and G is CH. |
| 4701 | A is A-1k, $(R^2)_n$ is 6-CN and G is CH. |
| 4702 | A is A-1k, $(R^2)_n$ is 6-F and G is C—F. |
| 4703 | A is A-1k, $(R^2)_n$ is 6-Cl and G is C—Cl. |
| 4704 | A is A-1k, $(R^2)_n$ is 6-Br and G is C—Br. |
| 4705 | A is A-1k, $(R^2)_n$ is 6-Me and G is C—Me. |
| 4706 | A is A-1k, $(R^2)_n$ is 6-CF$_3$ and G is C—CF$_3$. |
| 4707 | A is A-1k, $(R^2)_n$ is 6-MeO and G is C—OMe. |
| 4708 | A is A-1k, $(R^2)_n$ is H and G is N. |
| 4709 | A is A-1k, $(R^2)_n$ is 3-F and G is N. |
| 4710 | A is A-1k, $(R^2)_n$ is 3,5-di-F and G is N. |
| 4711 | A is A-1k, $(R^2)_n$ is 3-Cl and G is N. |
| 4712 | A is A-1k, $(R^2)_n$ is 3,5-di-Cl and G is N. |
| 4713 | A is A-1k, $(R^2)_n$ is 3-Br and G is N. |
| 4714 | A is A-1k, $(R^2)_n$ is 3,5-di-Br and G is N. |
| 4715 | A is A-1k, $(R^2)_n$ is 3-Me and G is N. |
| 4716 | A is A-1k, $(R^2)_n$ is 3,5-di-Me and G is N. |
| 4717 | A is A-1k, $(R^2)_n$ is 3-CF$_3$ and G is N. |
| 4718 | A is A-1k, $(R^2)_n$ is 3,5-di-CF$_3$ and G is N. |
| 4719 | A is A-1k, $(R^2)_n$ is 3-MeO and G is N. |
| 4720 | A is A-1k, $(R^2)_n$ is 3,5-di-MeO and G is N. |
| 4721 | A is A-1k, $(R^2)_n$ is 3-CN and G is N. |
| 4722 | A is A-1k, $(R^2)_n$ is 3,5-di-CN and G is N. |
| 4723 | A is A-1k, $(R^2)_n$ is 3,6-di-F and G is N. |
| 4724 | A is A-1k, $(R^2)_n$ is 3,6-di-Cl and G is N. |
| 4725 | A is A-1k, $(R^2)_n$ is 3,6-di-Br and G is N. |
| 4726 | A is A-1k, $(R^2)_n$ is 3,6-di-Me and G is N. |
| 4727 | A is A-1k, $(R^2)_n$ is 3,6-di-CF$_3$ and G is N. |
| 4728 | A is A-1k, $(R^2)_n$ is 3,6-di-MeO and G is N. |
| 4729 | A is A-1k, $(R^2)_n$ is 3,6-di-CN and G is N. |
| 4730 | A is A-1k, $(R^2)_n$ is 6-F and G is N. |
| 4731 | A is A-1k, $(R^2)_n$ is 6-Cl and G is N. |
| 4732 | A is A-1k, $(R^2)_n$ is 6-Br and G is N. |
| 4733 | A is A-1k, $(R^2)_n$ is 6-Me and G is N. |
| 4734 | A is A-1k, $(R^2)_n$ is 6-CF$_3$ and G is N. |
| 4735 | A is A-1k, $(R^2)_n$ is 6-MeO and G is N. |
| 4736 | A is A-1k, $(R^2)_n$ is 6-CN and G is N. |
| 4737 | A is A-1l, $(R^2)_n$ is H and G is CH. |
| 4738 | A is A-1l, $(R^2)_n$ is 3-F and G is CH. |
| 4739 | A is A-1l, $(R^2)_n$ is 3,5-di-F and G is CH. |
| 4740 | A is A-1l, $(R^2)_n$ is 3-Cl and G is CH. |
| 4741 | A is A-1l, $(R^2)_n$ is 3,5-di-Cl and G is CH. |
| 4742 | A is A-1l, $(R^2)_n$ is 3-Br and G is CH. |
| 4743 | A is A-1l, $(R^2)_n$ is 3,5-di-Br and G is CH. |
| 4744 | A is A-1l, $(R^2)_n$ is 3-Me and G is CH. |
| 4745 | A is A-1l, $(R^2)_n$ is 3,5-di-Me and G is CH. |
| 4746 | A is A-1l, $(R^2)_n$ is 3-CF$_3$ and G is CH. |
| 4747 | A is A-1l, $(R^2)_n$ is 3,5-di-CF$_3$ and G is CH. |
| 4748 | A is A-1l, $(R^2)_n$ is 3-MeO and G is CH. |
| 4749 | A is A-1l, $(R^2)_n$ is 3,5-di-MeO and G is CH. |
| 4750 | A is A-1l, $(R^2)_n$ is 3-CN and G is CH. |
| 4751 | A is A-1l, $(R^2)_n$ is 3,5-di-CN and G is CH. |
| 4752 | A is A-1l, $(R^2)_n$ is 3,6-di-F and G is CH. |
| 4753 | A is A-1l, $(R^2)_n$ is 3,6-di-Cl and G is CH. |
| 4754 | A is A-1l, $(R^2)_n$ is 3,6-di-Br and G is CH. |
| 4755 | A is A-1l, $(R^2)_n$ is 3,6-di-Me and G is CH. |
| 4756 | A is A-1l, $(R^2)_n$ is 3,6-di-CF$_3$ and G is CH. |
| 4757 | A is A-1l, $(R^2)_n$ is 3,6-di-MeO and G is CH. |
| 4758 | A is A-1l, $(R^2)_n$ is 3,6-di-CN and G is CH. |
| 4759 | A is A-1l, $(R^2)_n$ is 6-F and G is CH. |
| 4760 | A is A-1l, $(R^2)_n$ is 6-Cl and G is CH. |
| 4761 | A is A-1l, $(R^2)_n$ is 6-Br and G is CH. |
| 4762 | A is A-1l, $(R^2)_n$ is 6-Me and G is CH. |
| 4763 | A is A-1l, $(R^2)_n$ is 6-CF$_3$ and G is CH. |
| 4764 | A is A-1l, $(R^2)_n$ is 6-MeO and G is CH. |
| 4765 | A is A-1l, $(R^2)_n$ is 6-CN and G is CH. |
| 4766 | A is A-1l, $(R^2)_n$ is 6-F and G is C—F. |
| 4767 | A is A-1l, $(R^2)_n$ is 6-Cl and G is C—Cl. |
| 4768 | A is A-1l, $(R^2)_n$ is 6-Br and G is C—Br. |
| 4769 | A is A-1l, $(R^2)_n$ is 6-Me and G is C—Me. |
| 4770 | A is A-1l, $(R^2)_n$ is 6-CF$_3$ and G is C—CF$_3$. |
| 4771 | A is A-1l, $(R^2)_n$ is 6-MeO and G is C—OMe. |
| 4772 | A is A-1l, $(R^2)_n$ is H and G is N. |
| 4773 | A is A-1l, $(R^2)_n$ is 3-F and G is N. |
| 4774 | A is A-1l, $(R^2)_n$ is 3,5-di-F and G is N. |
| 4775 | A is A-1l, $(R^2)_n$ is 3-Cl and G is N. |
| 4776 | A is A-1l, $(R^2)_n$ is 3,5-di-Cl and G is N. |
| 4777 | A is A-1l, $(R^2)_n$ is 3-Br and G is N. |
| 4778 | A is A-1l, $(R^2)_n$ is 3,5-di-Br and G is N. |
| 4779 | A is A-1l, $(R^2)_n$ is 3-Me and G is N. |
| 4780 | A is A-1l, $(R^2)_n$ is 3,5-di-Me and G is N. |
| 4781 | A is A-1l, $(R^2)_n$ is 3-CF$_3$ and G is N. |
| 4782 | A is A-1l, $(R^2)_n$ is 3,5-di-CF$_3$ and G is N. |
| 4783 | A is A-1l, $(R^2)_n$ is 3-MeO and G is N. |
| 4784 | A is A-1l, $(R^2)_n$ is 3,5-di-MeO and G is N. |
| 4785 | A is A-1l, $(R^2)_n$ is 3-CN and G is N. |
| 4786 | A is A-1l, $(R^2)_n$ is 3,5-di-CN and G is N. |
| 4787 | A is A-1l, $(R^2)_n$ is 3,6-di-F and G is N. |
| 4788 | A is A-1l, $(R^2)_n$ is 3,6-di-Cl and G is N. |
| 4789 | A is A-1l, $(R^2)_n$ is 3,6-di-Br and G is N. |
| 4790 | A is A-1l, $(R^2)_n$ is 3,6-di-Me and G is N. |
| 4791 | A is A-1l, $(R^2)_n$ is 3,6-di-CF$_3$ and G is N. |
| 4792 | A is A-1l, $(R^2)_n$ is 3,6-di-MeO and G is N. |
| 4793 | A is A-1l, $(R^2)_n$ is 3,6-di-CN and G is N. |
| 4794 | A is A-1l, $(R^2)_n$ is 6-F and G is N. |
| 4795 | A is A-1l, $(R^2)_n$ is 6-Cl and G is N. |
| 4796 | A is A-1l, $(R^2)_n$ is 6-Br and G is N. |
| 4797 | A is A-1l, $(R^2)_n$ is 6-Me and G is N. |
| 4798 | A is A-1l, $(R^2)_n$ is 6-CF$_3$ and G is N. |
| 4799 | A is A-1l, $(R^2)_n$ is 6-MeO and G is N. |
| 4800 | A is A-1l, $(R^2)_n$ is 6-CN and G is N. |
| 4801 | A is A-1m, $(R^2)_n$ is H and G is CH. |
| 4802 | A is A-1m, $(R^2)_n$ is 3-F and G is CH. |
| 4803 | A is A-1m, $(R^2)_n$ is 3,5-di-F and G is CH. |
| 4804 | A is A-1m, $(R^2)_n$ is 3-Cl and G is CH. |
| 4805 | A is A-1m, $(R^2)_n$ is 3,5-di-Cl and G is CH. |
| 4806 | A is A-1m, $(R^2)_n$ is 3-Br and G is CH. |
| 4807 | A is A-1m, $(R^2)_n$ is 3,5-di-Br and G is CH. |
| 4808 | A is A-1m, $(R^2)_n$ is 3-Me and G is CH. |
| 4809 | A is A-1m, $(R^2)_n$ is 3,5-di-Me and G is CH. |
| 4810 | A is A-1m, $(R^2)_n$ is 3-CF$_3$ and G is CH. |
| 4811 | A is A-1m, $(R^2)_n$ is 3,5-di-CF$_3$ and G is CH. |
| 4812 | A is A-1m, $(R^2)_n$ is 3-MeO and G is CH. |
| 4813 | A is A-1m, $(R^2)_n$ is 3,5-di-MeO and G is CH. |
| 4814 | A is A-1m, $(R^2)_n$ is 3-CN and G is CH. |
| 4815 | A is A-1m, $(R^2)_n$ is 3,5-di-CN and G is CH. |
| 4816 | A is A-1m, $(R^2)_n$ is 3,6-di-F and G is CH. |
| 4817 | A is A-1m, $(R^2)_n$ is 3,6-di-Cl and G is CH. |
| 4818 | A is A-1m, $(R^2)_n$ is 3,6-di-Br and G is CH. |
| 4819 | A is A-1m, $(R^2)_n$ is 3,6-di-Me and G is CH. |
| 4820 | A is A-1m, $(R^2)_n$ is 3,6-di-CF$_3$ and G is CH. |
| 4821 | A is A-1m, $(R^2)_n$ is 3,6-di-MeO and G is CH. |
| 4822 | A is A-1m, $(R^2)_n$ is 3,6-di-CN and G is CH. |
| 4823 | A is A-1m, $(R^2)_n$ is 6-F and G is CH. |
| 4824 | A is A-1m, $(R^2)_n$ is 6-Cl and G is CH. |

TABLES 4034-5760-continued

| Table | Row Heading |
|---|---|
| 4825 | A is A-1m, (R²)ₙ is 6-Br and G is CH. |
| 4826 | A is A-1m, (R²)ₙ is 6-Me and G is CH. |
| 4827 | A is A-1m, (R²)ₙ is 6-CF₃ and G is CH. |
| 4828 | A is A-1m, (R²)ₙ is 6-MeO and G is CH. |
| 4829 | A is A-1m, (R²)ₙ is 6-CN and G is CH. |
| 4830 | A is A-1m, (R²)ₙ is 6-F and G is C—F. |
| 4831 | A is A-1m, (R²)ₙ is 6-Cl and G is C—Cl. |
| 4832 | A is A-1m, (R²)ₙ is 6-Br and G is C—Br. |
| 4833 | A is A-1m, (R²)ₙ is 6-Me and G is C—Me. |
| 4834 | A is A-1m, (R²)ₙ is 6-CF₃ and G is C—CF₃. |
| 4835 | A is A-1m, (R²)ₙ is 6-MeO and G is C—OMe. |
| 4836 | A is A-1m, (R²)ₙ is H and G is N. |
| 4837 | A is A-1m, (R²)ₙ is 3-F and G is N. |
| 4838 | A is A-1m, (R²)ₙ is 3,5-di-F and G is N. |
| 4839 | A is A-1m, (R²)ₙ is 3-Cl and G is N. |
| 4840 | A is A-1m, (R²)ₙ is 3,5-di-Cl and G is N. |
| 4841 | A is A-1m, (R²)ₙ is 3-Br and G is N. |
| 4842 | A is A-1m, (R²)ₙ is 3,5-di-Br and G is N. |
| 4843 | A is A-1m, (R²)ₙ is 3-Me and G is N. |
| 4844 | A is A-1m, (R²)ₙ is 3,5-di-Me and G is N. |
| 4845 | A is A-1m, (R²)ₙ is 3-CF₃ and G is N. |
| 4846 | A is A-1m, (R²)ₙ is 3,5-di-CF₃ and G is N. |
| 4847 | A is A-1m, (R²)ₙ is 3-MeO and G is N. |
| 4848 | A is A-1m, (R²)ₙ is 3,5-di-MeO and G is N. |
| 4849 | A is A-1m, (R²)ₙ is 3-CN and G is N. |
| 4850 | A is A-1m, (R²)ₙ is 3,5-di-CN and G is N. |
| 4851 | A is A-1m, (R²)ₙ is 3,6-di-F and G is N. |
| 4852 | A is A-1m, (R²)ₙ is 3,6-di-Cl and G is N. |
| 4853 | A is A-1m, (R²)ₙ is 3,6-di-Br and G is N. |
| 4854 | A is A-1m, (R²)ₙ is 3,6-di-Me and G is N. |
| 4855 | A is A-1m, (R²)ₙ is 3,6-di-CF₃ and G is N. |
| 4856 | A is A-1m, (R²)ₙ is 3,6-di-MeO and G is N. |
| 4857 | A is A-1m, (R²)ₙ is 3,6-di-CN and G is N. |
| 4858 | A is A-1m, (R²)ₙ is 6-F and G is N. |
| 4859 | A is A-1m, (R²)ₙ is 6-Cl and G is N. |
| 4860 | A is A-1m, (R²)ₙ is 6-Br and G is N. |
| 4861 | A is A-1m, (R²)ₙ is 6-Me and G is N. |
| 4862 | A is A-1m, (R²)ₙ is 6-CF₃ and G is N. |
| 4863 | A is A-1m, (R²)ₙ is 6-MeO and G is N. |
| 4864 | A is A-1m, (R²)ₙ is 6-CN and G is N. |
| 4865 | A is A-1n, (R²)ₙ is H and G is CH. |
| 4866 | A is A-1n, (R²)ₙ is 3-F and G is CH. |
| 4867 | A is A-1n, (R²)ₙ is 3,5-di-F and G is CH. |
| 4868 | A is A-1n, (R²)ₙ is 3-Cl and G is CH. |
| 4869 | A is A-1n, (R²)ₙ is 3,5-di-Cl and G is CH. |
| 4870 | A is A-1n, (R²)ₙ is 3-Br and G is CH. |
| 4871 | A is A-1n, (R²)ₙ is 3,5-di-Br and G is CH. |
| 4872 | A is A-1n, (R²)ₙ is 3-Me and G is CH. |
| 4873 | A is A-1n, (R²)ₙ is 3,5-di-Me and G is CH. |
| 4874 | A is A-1n, (R²)ₙ is 3-CF₃ and G is CH. |
| 4875 | A is A-1n, (R²)ₙ is 3,5-di-CF₃ and G is CH. |
| 4876 | A is A-1n, (R²)ₙ is 3-MeO and G is CH. |
| 4877 | A is A-1n, (R²)ₙ is 3,5-di-MeO and G is CH. |
| 4878 | A is A-1n, (R²)ₙ is 3-CN and G is CH. |
| 4879 | A is A-1n, (R²)ₙ is 3,5-di-CN and G is CH. |
| 4880 | A is A-1n, (R²)ₙ is 3,6-di-F and G is CH. |
| 4881 | A is A-1n, (R²)ₙ is 3,6-di-Cl and G is CH. |
| 4882 | A is A-1n, (R²)ₙ is 3,6-di-Br and G is CH. |
| 4883 | A is A-1n, (R²)ₙ is 3,6-di-Me and G is CH. |
| 4884 | A is A-1n, (R²)ₙ is 3,6-di-CF₃ and G is CH. |
| 4885 | A is A-1n, (R²)ₙ is 3,6-di-MeO and G is CH. |
| 4886 | A is A-1n, (R²)ₙ is 3,6-di-CN and G is CH. |
| 4887 | A is A-1n, (R²)ₙ is 6-F and G is CH. |
| 4888 | A is A-1n, (R²)ₙ is 6-Cl and G is CH. |
| 4889 | A is A-1n, (R²)ₙ is 6-Br and G is CH. |
| 4890 | A is A-1n, (R²)ₙ is 6-Me and G is CH. |
| 4891 | A is A-1n, (R²)ₙ is 6-CF₃ and G is CH. |
| 4892 | A is A-1n, (R²)ₙ is 6-MeO and G is CH. |
| 4893 | A is A-1n, (R²)ₙ is 6-CN and G is CH. |
| 4894 | A is A-1n, (R²)ₙ is 6-F and G is C—F. |
| 4895 | A is A-1n, (R²)ₙ is 6-Cl and G is C—Cl. |
| 4896 | A is A-1n, (R²)ₙ is 6-Br and G is C—Br. |
| 4897 | A is A-1n, (R²)ₙ is 6-Me and G is C—Me. |
| 4898 | A is A-1n, (R²)ₙ is 6-CF₃ and G is C—CF₃. |
| 4899 | A is A-1n, (R²)ₙ is 6-MeO and G is C—OMe. |
| 4900 | A is A-1n, (R²)ₙ is H and G is N. |
| 4901 | A is A-1n, (R²)ₙ is 3-F and G is N. |
| 4902 | A is A-1n, (R²)ₙ is 3,5-di-F and G is N. |
| 4903 | A is A-1n, (R²)ₙ is 3-Cl and G is N. |
| 4904 | A is A-1n, (R²)ₙ is 3,5-di-Cl and G is N. |
| 4905 | A is A-1n, (R²)ₙ is 3-Br and G is N. |
| 4906 | A is A-1n, (R²)ₙ is 3,5-di-Br and G is N. |
| 4907 | A is A-1n, (R²)ₙ is 3-Me and G is N. |
| 4908 | A is A-1n, (R²)ₙ is 3,5-di-Me and G is N. |
| 4909 | A is A-1n, (R²)ₙ is 3-CF₃ and G is N. |
| 4910 | A is A-1n, (R²)ₙ is 3,5-di-CF₃ and G is N. |
| 4911 | A is A-1n, (R²)ₙ is 3-MeO and G is N. |
| 4912 | A is A-1n, (R²)ₙ is 3,5-di-MeO and G is N. |
| 4913 | A is A-1n, (R²)ₙ is 3-CN and G is N. |
| 4914 | A is A-1n, (R²)ₙ is 3,5-di-CN and G is N. |
| 4915 | A is A-1n, (R²)ₙ is 3,6-di-F and G is N. |
| 4916 | A is A-1n, (R²)ₙ is 3,6-di-Cl and G is N. |
| 4917 | A is A-1n, (R²)ₙ is 3,6-di-Br and G is N. |
| 4918 | A is A-1n, (R²)ₙ is 3,6-di-Me and G is N. |
| 4919 | A is A-1n, (R²)ₙ is 3,6-di-CF₃ and G is N. |
| 4920 | A is A-1n, (R²)ₙ is 3,6-di-MeO and G is N. |
| 4921 | A is A-1n, (R²)ₙ is 3,6-di-CN and G is N. |
| 4922 | A is A-1n, (R²)ₙ is 6-F and G is N. |
| 4923 | A is A-1n, (R²)ₙ is 6-Cl and G is N. |
| 4924 | A is A-1n, (R²)ₙ is 6-Br and G is N. |
| 4925 | A is A-1n, (R²)ₙ is 6-Me and G is N. |
| 4926 | A is A-1n, (R²)ₙ is 6-CF₃ and G is N. |
| 4927 | A is A-1n, (R²)ₙ is 6-MeO and G is N. |
| 4928 | A is A-1n, (R²)ₙ is 6-CN and G is N. |
| 4929 | A is A-1p, (R²)ₙ is H and G is CH. |
| 4930 | A is A-1p, (R²)ₙ is 3-F and G is CH. |
| 4931 | A is A-1p, (R²)ₙ is 3,5-di-F and G is CH. |
| 4932 | A is A-1p, (R²)ₙ is 3-Cl and G is CH. |
| 4933 | A is A-1p, (R²)ₙ is 3,5-di-Cl and G is CH. |
| 4934 | A is A-1p, (R²)ₙ is 3-Br and G is CH. |
| 4935 | A is A-1p, (R²)ₙ is 3,5-di-Br and G is CH. |
| 4936 | A is A-1p, (R²)ₙ is 3-Me and G is CH. |
| 4937 | A is A-1p, (R²)ₙ is 3,5-di-Me and G is CH. |
| 4938 | A is A-1p, (R²)ₙ is 3-CF₃ and G is CH. |
| 4939 | A is A-1p, (R²)ₙ is 3,5-di-CF₃ and G is CH. |
| 4940 | A is A-1p, (R²)ₙ is 3-MeO and G is CH. |
| 4941 | A is A-1p, (R²)ₙ is 3,5-di-MeO and G is CH. |
| 4942 | A is A-1p, (R²)ₙ is 3-CN and G is CH. |
| 4943 | A is A-1p, (R²)ₙ is 3,5-di-CN and G is CH. |
| 4944 | A is A-1p, (R²)ₙ is 3,6-di-F and G is CH. |
| 4945 | A is A-1p, (R²)ₙ is 3,6-di-Cl and G is CH. |
| 4946 | A is A-1p, (R²)ₙ is 3,6-di-Br and G is CH. |
| 4947 | A is A-1p, (R²)ₙ is 3,6-di-Me and G is CH. |
| 4948 | A is A-1p, (R²)ₙ is 3,6-di-CF₃ and G is CH. |
| 4949 | A is A-1p, (R²)ₙ is 3,6-di-MeO and G is CH. |
| 4950 | A is A-1p, (R²)ₙ is 3,6-di-CN and G is CH. |
| 4951 | A is A-1p, (R²)ₙ is 6-F and G is CH. |
| 4952 | A is A-1p, (R²)ₙ is 6-Cl and G is CH. |
| 4953 | A is A-1p, (R²)ₙ is 6-Br and G is CH. |
| 4954 | A is A-1p, (R²)ₙ is 6-Me and G is CH. |
| 4955 | A is A-1p, (R²)ₙ is 6-CF₃ and G is CH. |
| 4956 | A is A-1p, (R²)ₙ is 6-MeO and G is CH. |
| 4957 | A is A-1p, (R²)ₙ is 6-CN and G is CH. |
| 4958 | A is A-1p, (R²)ₙ is 6-F and G is C—F. |
| 4959 | A is A-1p, (R²)ₙ is 6-Cl and G is C—Cl. |
| 4960 | A is A-1p, (R²)ₙ is 6-Br and G is C—Br. |
| 4961 | A is A-1p, (R²)ₙ is 6-Me and G is C—Me. |
| 4962 | A is A-1p, (R²)ₙ is 6-CF₃ and G is C—CF₃. |
| 4963 | A is A-1p, (R²)ₙ is 6-MeO and G is C—OMe. |
| 4964 | A is A-1p, (R²)ₙ is H and G is N. |
| 4965 | A is A-1p, (R²)ₙ is 3-F and G is N. |
| 4966 | A is A-1p, (R²)ₙ is 3,5-di-F and G is N. |
| 4967 | A is A-1p, (R²)ₙ is 3-Cl and G is N. |
| 4968 | A is A-1p, (R²)ₙ is 3,5-di-Cl and G is N. |
| 4969 | A is A-1p, (R²)ₙ is 3-Br and G is N. |
| 4970 | A is A-1p, (R²)ₙ is 3,5-di-Br and G is N. |
| 4971 | A is A-1p, (R²)ₙ is 3-Me and G is N. |
| 4972 | A is A-1p, (R²)ₙ is 3,5-di-Me and G is N. |
| 4973 | A is A-1p, (R²)ₙ is 3-CF₃ and G is N. |
| 4974 | A is A-1p, (R²)ₙ is 3,5-di-CF₃ and G is N. |
| 4975 | A is A-1p, (R²)ₙ is 3-MeO and G is N. |
| 4976 | A is A-1p, (R²)ₙ is 3,5-di-MeO and G is N. |
| 4977 | A is A-1p, (R²)ₙ is 3-CN and G is N. |
| 4978 | A is A-1p, (R²)ₙ is 3,5-di-CN and G is N. |
| 4979 | A is A-1p, (R²)ₙ is 3,6-di-F and G is N. |
| 4980 | A is A-1p, (R²)ₙ is 3,6-di-Cl and G is N. |

TABLES 4034-5760-continued

| Table | Row Heading |
|---|---|
| 4981 | A is A-1p, $(R^2)_n$ is 3,6-di-Br and G is N. |
| 4982 | A is A-1p, $(R^2)_n$ is 3,6-di-Me and G is N. |
| 4983 | A is A-1p, $(R^2)_n$ is 3,6-di-CF$_3$ and G is N. |
| 4984 | A is A-1p, $(R^2)_n$ is 3,6-di-MeO and G is N. |
| 4985 | A is A-1p, $(R^2)_n$ is 3,6-di-CN and G is N. |
| 4986 | A is A-1p, $(R^2)_n$ is 6-F and G is N. |
| 4987 | A is A-1p, $(R^2)_n$ is 6-Cl and G is N. |
| 4988 | A is A-1p, $(R^2)_n$ is 6-Br and G is N. |
| 4989 | A is A-1p, $(R^2)_n$ is 6-Me and G is N. |
| 4990 | A is A-1p, $(R^2)_n$ is 6-CF$_3$ and G is N. |
| 4991 | A is A-1p, $(R^2)_n$ is 6-MeO and G is N. |
| 4992 | A is A-1p, $(R^2)_n$ is 6-CN and G is N. |
| 4993 | A is A-2a, $(R^2)_n$ is H and G is CH. |
| 4994 | A is A-2a, $(R^2)_n$ is 3-F and G is CH. |
| 4995 | A is A-2a, $(R^2)_n$ is 3,5-di-F and G is CH. |
| 4996 | A is A-2a, $(R^2)_n$ is 3-Cl and G is CH. |
| 4997 | A is A-2a, $(R^2)_n$ is 3,5-di-Cl and G is CH. |
| 4998 | A is A-2a, $(R^2)_n$ is 3-Br and G is CH. |
| 4999 | A is A-2a, $(R^2)_n$ is 3,5-di-Br and G is CH. |
| 5000 | A is A-2a, $(R^2)_n$ is 3-Me and G is CH. |
| 5001 | A is A-2a, $(R^2)_n$ is 3,5-di-Me and G is CH. |
| 5002 | A is A-2a, $(R^2)_n$ is 3-CF$_3$ and G is CH. |
| 5003 | A is A-2a, $(R^2)_n$ is 3,5-di-CF$_3$ and G is CH. |
| 5004 | A is A-2a, $(R^2)_n$ is 3-MeO and G is CH. |
| 5005 | A is A-2a, $(R^2)_n$ is 3,5-di-MeO and G is CH. |
| 5006 | A is A-2a, $(R^2)_n$ is 3-CN and G is CH. |
| 5007 | A is A-2a, $(R^2)_n$ is 3,5-di-CN and G is CH. |
| 5008 | A is A-2a, $(R^2)_n$ is 3,6-di-F and G is CH. |
| 5009 | A is A-2a, $(R^2)_n$ is 3,6-di-Cl and G is CH. |
| 5010 | A is A-2a, $(R^2)_n$ is 3,6-di-Br and G is CH. |
| 5011 | A is A-2a, $(R^2)_n$ is 3,6-di-Me and G is CH. |
| 5012 | A is A-2a, $(R^2)_n$ is 3,6-di-CF$_3$ and G is CH. |
| 5013 | A is A-2a, $(R^2)_n$ is 3,6-di-MeO and G is CH. |
| 5014 | A is A-2a, $(R^2)_n$ is 3,6-di-CN and G is CH. |
| 5015 | A is A-2a, $(R^2)_n$ is 6-F and G is CH. |
| 5016 | A is A-2a, $(R^2)_n$ is 6-Cl and G is CH. |
| 5017 | A is A-2a, $(R^2)_n$ is 6-Br and G is CH. |
| 5018 | A is A-2a, $(R^2)_n$ is 6-Me and G is CH. |
| 5019 | A is A-2a, $(R^2)_n$ is 6-CF$_3$ and G is CH. |
| 5020 | A is A-2a, $(R^2)_n$ is 6-MeO and G is CH. |
| 5021 | A is A-2a, $(R^2)_n$ is 6-CN and G is CH. |
| 5022 | A is A-2a, $(R^2)_n$ is 6-F and G is C—F. |
| 5023 | A is A-2a, $(R^2)_n$ is 6-Cl and G is C—Cl. |
| 5024 | A is A-2a, $(R^2)_n$ is 6-Br and G is C—Br. |
| 5025 | A is A-2a, $(R^2)_n$ is 6-Me and G is C—Me. |
| 5026 | A is A-2a, $(R^2)_n$ is 6-CF$_3$ and G is C—CF$_3$. |
| 5027 | A is A-2a, $(R^2)_n$ is 6-MeO and G is C—OMe. |
| 5028 | A is A-2a, $(R^2)_n$ is H and G is N. |
| 5029 | A is A-2a, $(R^2)_n$ is 3-F and G is N. |
| 5030 | A is A-2a, $(R^2)_n$ is 3,5-di-F and G is N. |
| 5031 | A is A-2a, $(R^2)_n$ is 3-Cl and G is N. |
| 5032 | A is A-2a, $(R^2)_n$ is 3,5-di-Cl and G is N. |
| 5033 | A is A-2a, $(R^2)_n$ is 3-Br and G is N. |
| 5034 | A is A-2a, $(R^2)_n$ is 3,5-di-Br and G is N. |
| 5035 | A is A-2a, $(R^2)_n$ is 3-Me and G is N. |
| 5036 | A is A-2a, $(R^2)_n$ is 3,5-di-Me and G is N. |
| 5037 | A is A-2a, $(R^2)_n$ is 3-CF$_3$ and G is N. |
| 5038 | A is A-2a, $(R^2)_n$ is 3,5-di-CF$_3$ and G is N. |
| 5039 | A is A-2a, $(R^2)_n$ is 3-MeO and G is N. |
| 5040 | A is A-2a, $(R^2)_n$ is 3,5-di-MeO and G is N. |
| 5041 | A is A-2a, $(R^2)_n$ is 3-CN and G is N. |
| 5042 | A is A-2a, $(R^2)_n$ is 3,5-di-CN and G is N. |
| 5043 | A is A-2a, $(R^2)_n$ is 3,6-di-F and G is N. |
| 5044 | A is A-2a, $(R^2)_n$ is 3,6-di-Cl and G is N. |
| 5045 | A is A-2a, $(R^2)_n$ is 3,6-di-Br and G is N. |
| 5046 | A is A-2a, $(R^2)_n$ is 3,6-di-Me and G is N. |
| 5047 | A is A-2a, $(R^2)_n$ is 3,6-di-CF$_3$ and G is N. |
| 5048 | A is A-2a, $(R^2)_n$ is 3,6-di-MeO and G is N. |
| 5049 | A is A-2a, $(R^2)_n$ is 3,6-di-CN and G is N. |
| 5050 | A is A-2a, $(R^2)_n$ is 6-F and G is N. |
| 5051 | A is A-2a, $(R^2)_n$ is 6-Cl and G is N. |
| 5052 | A is A-2a, $(R^2)_n$ is 6-Br and G is N. |
| 5053 | A is A-2a, $(R^2)_n$ is 6-Me and G is N. |
| 5054 | A is A-2a, $(R^2)_n$ is 6-CF$_3$ and G is N. |
| 5055 | A is A-2a, $(R^2)_n$ is 6-MeO and G is N. |
| 5056 | A is A-2a, $(R^2)_n$ is 6-CN and G is N. |
| 5057 | A is A-2b, $(R^2)_n$ is H and G is CH. |
| 5058 | A is A-2b, $(R^2)_n$ is 3-F and G is CH. |
| 5059 | A is A-2b, $(R^2)_n$ is 3,5-di-F and G is CH. |
| 5060 | A is A-2b, $(R^2)_n$ is 3-Cl and G is CH. |
| 5061 | A is A-2b, $(R^2)_n$ is 3,5-di-Cl and G is CH. |
| 5062 | A is A-2b, $(R^2)_n$ is 3-Br and G is CH. |
| 5063 | A is A-2b, $(R^2)_n$ is 3,5-di-Br and G is CH. |
| 5064 | A is A-2b, $(R^2)_n$ is 3-Me and G is CH. |
| 5065 | A is A-2b, $(R^2)_n$ is 3,5-di-Me and G is CH. |
| 5066 | A is A-2b, $(R^2)_n$ is 3-CF$_3$ and G is CH. |
| 5067 | A is A-2b, $(R^2)_n$ is 3,5-di-CF$_3$ and G is CH. |
| 5068 | A is A-2b, $(R^2)_n$ is 3-MeO and G is CH. |
| 5069 | A is A-2b, $(R^2)_n$ is 3,5-di-MeO and G is CH. |
| 5070 | A is A-2b, $(R^2)_n$ is 3-CN and G is CH. |
| 5071 | A is A-2b, $(R^2)_n$ is 3,5-di-CN and G is CH. |
| 5072 | A is A-2b, $(R^2)_n$ is 3,6-di-F and G is CH. |
| 5073 | A is A-2b, $(R^2)_n$ is 3,6-di-Cl and G is CH. |
| 5074 | A is A-2b, $(R^2)_n$ is 3,6-di-Br and G is CH. |
| 5075 | A is A-2b, $(R^2)_n$ is 3,6-di-Me and G is CH. |
| 5076 | A is A-2b, $(R^2)_n$ is 3,6-di-CF$_3$ and G is CH. |
| 5077 | A is A-2b, $(R^2)_n$ is 3,6-di-MeO and G is CH. |
| 5078 | A is A-2b, $(R^2)_n$ is 3,6-di-CN and G is CH. |
| 5079 | A is A-2b, $(R^2)_n$ is 6-F and G is CH. |
| 5080 | A is A-2b, $(R^2)_n$ is 6-Cl and G is CH. |
| 5081 | A is A-2b, $(R^2)_n$ is 6-Br and G is CH. |
| 5082 | A is A-2b, $(R^2)_n$ is 6-Me and G is CH. |
| 5083 | A is A-2b, $(R^2)_n$ is 6-CF$_3$ and G is CH. |
| 5084 | A is A-2b, $(R^2)_n$ is 6-MeO and G is CH. |
| 5085 | A is A-2b, $(R^2)_n$ is 6-CN and G is CH. |
| 5086 | A is A-2b, $(R^2)_n$ is 6-F and G is C—F. |
| 5087 | A is A-2b, $(R^2)_n$ is 6-Cl and G is C—Cl. |
| 5088 | A is A-2b, $(R^2)_n$ is 6-Br and G is C—Br. |
| 5089 | A is A-2b, $(R^2)_n$ is 6-Me and G is C—Me. |
| 5090 | A is A-2b, $(R^2)_n$ is 6-CF$_3$ and G is C—CF$_3$. |
| 5091 | A is A-2b, $(R^2)_n$ is 6-MeO and G is C—OMe. |
| 5092 | A is A-2b, $(R^2)_n$ is H and G is N. |
| 5093 | A is A-2b, $(R^2)_n$ is 3-F and G is N. |
| 5094 | A is A-2b, $(R^2)_n$ is 3,5-di-F and G is N. |
| 5095 | A is A-2b, $(R^2)_n$ is 3-Cl and G is N. |
| 5096 | A is A-2b, $(R^2)_n$ is 3,5-di-Cl and G is N. |
| 5097 | A is A-2b, $(R^2)_n$ is 3-Br and G is N. |
| 5098 | A is A-2b, $(R^2)_n$ is 3,5-di-Br and G is N. |
| 5099 | A is A-2b, $(R^2)_n$ is 3-Me and G is N. |
| 5100 | A is A-2b, $(R^2)_n$ is 3,5-di-Me and G is N. |
| 5101 | A is A-2b, $(R^2)_n$ is 3-CF$_3$ and G is N. |
| 5102 | A is A-2b, $(R^2)_n$ is 3,5-di-CF$_3$ and G is N. |
| 5103 | A is A-2b, $(R^2)_n$ is 3-MeO and G is N. |
| 5104 | A is A-2b, $(R^2)_n$ is 3,5-di-MeO and G is N. |
| 5105 | A is A-2b, $(R^2)_n$ is 3-CN and G is N. |
| 5106 | A is A-2b, $(R^2)_n$ is 3,5-di-CN and G is N. |
| 5107 | A is A-2b, $(R^2)_n$ is 3,6-di-F and G is N. |
| 5108 | A is A-2b, $(R^2)_n$ is 3,6-di-Cl and G is N. |
| 5109 | A is A-2b, $(R^2)_n$ is 3,6-di-Br and G is N. |
| 5110 | A is A-2b, $(R^2)_n$ is 3,6-di-Me and G is N. |
| 5111 | A is A-2b, $(R^2)_n$ is 3,6-di-CF$_3$ and G is N. |
| 5112 | A is A-2b, $(R^2)_n$ is 3,6-di-MeO and G is N. |
| 5113 | A is A-2b, $(R^2)_n$ is 3,6-di-CN and G is N. |
| 5114 | A is A-2b, $(R^2)_n$ is 6-F and G is N. |
| 5115 | A is A-2b, $(R^2)_n$ is 6-Cl and G is N. |
| 5116 | A is A-2b, $(R^2)_n$ is 6-Br and G is N. |
| 5117 | A is A-2b, $(R^2)_n$ is 6-Me and G is N. |
| 5118 | A is A-2b, $(R^2)_n$ is 6-CF$_3$ and G is N. |
| 5119 | A is A-2b, $(R^2)_n$ is 6-MeO and G is N. |
| 5120 | A is A-2b, $(R^2)_n$ is 6-CN and G is N. |
| 5121 | A is A-2c, $(R^2)_n$ is H and G is CH. |
| 5122 | A is A-2c, $(R^2)_n$ is 3-F and G is CH. |
| 5123 | A is A-2c, $(R^2)_n$ is 3,5-di-F and G is CH. |
| 5124 | A is A-2c, $(R^2)_n$ is 3-Cl and G is CH. |
| 5125 | A is A-2c, $(R^2)_n$ is 3,5-di-Cl and G is CH. |
| 5126 | A is A-2c, $(R^2)_n$ is 3-Br and G is CH. |
| 5127 | A is A-2c, $(R^2)_n$ is 3,5-di-Br and G is CH. |
| 5128 | A is A-2c, $(R^2)_n$ is 3-Me and G is CH. |
| 5129 | A is A-2c, $(R^2)_n$ is 3,5-di-Me and G is CH. |
| 5130 | A is A-2c, $(R^2)_n$ is 3-CF$_3$ and G is CH. |
| 5131 | A is A-2c, $(R^2)_n$ is 3,5-di-CF$_3$ and G is CH. |
| 5132 | A is A-2c, $(R^2)_n$ is 3-MeO and G is CH. |
| 5133 | A is A-2c, $(R^2)_n$ is 3,5-di-MeO and G is CH. |
| 5134 | A is A-2c, $(R^2)_n$ is 3-CN and G is CH. |
| 5135 | A is A-2c, $(R^2)_n$ is 3,5-di-CN and G is CH. |
| 5136 | A is A-2c, $(R^2)_n$ is 3,6-di-F and G is CH. |

TABLES 4034-5760-continued

| Table | Row Heading |
|---|---|
| 5137 | A is A-2c, $(R^2)_n$ is 3,6-di-Cl and G is CH. |
| 5138 | A is A-2c, $(R^2)_n$ is 3,6-di-Br and G is CH. |
| 5139 | A is A-2c, $(R^2)_n$ is 3,6-di-Me and G is CH. |
| 5140 | A is A-2c, $(R^2)_n$ is 3,6-di-$CF_3$ and G is CH. |
| 5141 | A is A-2c, $(R^2)_n$ is 3,6-di-MeO and G is CH. |
| 5142 | A is A-2c, $(R^2)_n$ is 3,6-di-CN and G is CH. |
| 5143 | A is A-2c, $(R^2)_n$ is 6-F and G is CH. |
| 5144 | A is A-2c, $(R^2)_n$ is 6-Cl and G is CH. |
| 5145 | A is A-2c, $(R^2)_n$ is 6-Br and G is CH. |
| 5146 | A is A-2c, $(R^2)_n$ is 6-Me and G is CH. |
| 5147 | A is A-2c, $(R^2)_n$ is 6-$CF_3$ and G is CH. |
| 5148 | A is A-2c, $(R^2)_n$ is 6-MeO and G is CH. |
| 5149 | A is A-2c, $(R^2)_n$ is 6-CN and G is CH. |
| 5150 | A is A-2c, $(R^2)_n$ is 6-F and G is C—F. |
| 5151 | A is A-2c, $(R^2)_n$ is 6-Cl and G is C—Cl. |
| 5152 | A is A-2c, $(R^2)_n$ is 6-Br and G is C—Br. |
| 5153 | A is A-2c, $(R^2)_n$ is 6-Me and G is C—Me. |
| 5154 | A is A-2c, $(R^2)_n$ is 6-$CF_3$ and G is C—$CF_3$. |
| 5155 | A is A-2c, $(R^2)_n$ is 6-MeO and G is C—OMe. |
| 5156 | A is A-2c, $(R^2)_n$ is H and G is N. |
| 5157 | A is A-2c, $(R^2)_n$ is 3-F and G is N. |
| 5158 | A is A-2c, $(R^2)_n$ is 3,5-di-F and G is N. |
| 5159 | A is A-2c, $(R^2)_n$ is 3-Cl and G is N. |
| 5160 | A is A-2c, $(R^2)_n$ is 3,5-di-Cl and G is N. |
| 5161 | A is A-2c, $(R^2)_n$ is 3-Br and G is N. |
| 5162 | A is A-2c, $(R^2)_n$ is 3,5-di-Br and G is N. |
| 5163 | A is A-2c, $(R^2)_n$ is 3-Me and G is N. |
| 5164 | A is A-2c, $(R^2)_n$ is 3,5-di-Me and G is N. |
| 5165 | A is A-2c, $(R^2)_n$ is 3-$CF_3$ and G is N. |
| 5166 | A is A-2c, $(R^2)_n$ is 3,5-di-$CF_3$ and G is N. |
| 5167 | A is A-2c, $(R^2)_n$ is 3-MeO and G is N. |
| 5168 | A is A-2c, $(R^2)_n$ is 3,5-di-MeO and G is N. |
| 5169 | A is A-2c, $(R^2)_n$ is 3-CN and G is N. |
| 5170 | A is A-2c, $(R^2)_n$ is 3,5-di-CN and G is N. |
| 5171 | A is A-2c, $(R^2)_n$ is 3,6-di-F and G is N. |
| 5172 | A is A-2c, $(R^2)_n$ is 3,6-di-Cl and G is N. |
| 5173 | A is A-2c, $(R^2)_n$ is 3,6-di-Br and G is N. |
| 5174 | A is A-2c, $(R^2)_n$ is 3,6-di-Me and G is N. |
| 5175 | A is A-2c, $(R^2)_n$ is 3,6-di-$CF_3$ and G is N. |
| 5176 | A is A-2c, $(R^2)_n$ is 3,6-di-MeO and G is N. |
| 5177 | A is A-2c, $(R^2)_n$ is 3,6-di-CN and G is N. |
| 5178 | A is A-2c, $(R^2)_n$ is 6-F and G is N. |
| 5179 | A is A-2c, $(R^2)_n$ is 6-Cl and G is N. |
| 5180 | A is A-2c, $(R^2)_n$ is 6-Br and G is N. |
| 5181 | A is A-2c, $(R^2)_n$ is 6-Me and G is N. |
| 5182 | A is A-2c, $(R^2)_n$ is 6-$CF_3$ and G is N. |
| 5183 | A is A-2c, $(R^2)_n$ is 6-MeO and G is N. |
| 5184 | A is A-2c, $(R^2)_n$ is 6-CN and G is N. |
| 5185 | A is A-2d, $(R^2)_n$ is H and G is CH. |
| 5186 | A is A-2d, $(R^2)_n$ is 3-F and G is CH. |
| 5187 | A is A-2d, $(R^2)_n$ is 3,5-di-F and G is CH. |
| 5188 | A is A-2d, $(R^2)_n$ is 3-Cl and G is CH. |
| 5189 | A is A-2d, $(R^2)_n$ is 3,5-di-Cl and G is CH. |
| 5190 | A is A-2d, $(R^2)_n$ is 3-Br and G is CH. |
| 5191 | A is A-2d, $(R^2)_n$ is 3,5-di-Br and G is CH. |
| 5192 | A is A-2d, $(R^2)_n$ is 3-Me and G is CH. |
| 5193 | A is A-2d, $(R^2)_n$ is 3,5-di-Me and G is CH. |
| 5194 | A is A-2d, $(R^2)_n$ is 3-$CF_3$ and G is CH. |
| 5195 | A is A-2d, $(R^2)_n$ is 3,5-di-$CF_3$ and G is CH. |
| 5196 | A is A-2d, $(R^2)_n$ is 3-MeO and G is CH. |
| 5197 | A is A-2d, $(R^2)_n$ is 3,5-di-MeO and G is CH. |
| 5198 | A is A-2d, $(R^2)_n$ is 3-CN and G is CH. |
| 5199 | A is A-2d, $(R^2)_n$ is 3,5-di-CN and G is CH. |
| 5200 | A is A-2d, $(R^2)_n$ is 3,6-di-F and G is CH. |
| 5201 | A is A-2d, $(R^2)_n$ is 3,6-di-Cl and G is CH. |
| 5202 | A is A-2d, $(R^2)_n$ is 3,6-di-Br and G is CH. |
| 5203 | A is A-2d, $(R^2)_n$ is 3,6-di-Me and G is CH. |
| 5204 | A is A-2d, $(R^2)_n$ is 3,6-di-$CF_3$ and G is CH. |
| 5205 | A is A-2d, $(R^2)_n$ is 3,6-di-MeO and G is CH. |
| 5206 | A is A-2d, $(R^2)_n$ is 3,6-di-CN and G is CH. |
| 5207 | A is A-2d, $(R^2)_n$ is 6-F and G is CH. |
| 5208 | A is A-2d, $(R^2)_n$ is 6-Cl and G is CH. |
| 5209 | A is A-2d, $(R^2)_n$ is 6-Br and G is CH. |
| 5210 | A is A-2d, $(R^2)_n$ is 6-Me and G is CH. |
| 5211 | A is A-2d, $(R^2)_n$ is 6-$CF_3$ and G is CH. |
| 5212 | A is A-2d, $(R^2)_n$ is 6-MeO and G is CH. |
| 5213 | A is A-2d, $(R^2)_n$ is 6-CN and G is CH. |
| 5214 | A is A-2d, $(R^2)_n$ is 6-F and G is C—F. |
| 5215 | A is A-2d, $(R^2)_n$ is 6-Cl and G is C—Cl. |
| 5216 | A is A-2d, $(R^2)_n$ is 6-Br and G is C—Br. |
| 5217 | A is A-2d, $(R^2)_n$ is 6-Me and G is C—Me. |
| 5218 | A is A-2d, $(R^2)_n$ is 6-$CF_3$ and G is C—$CF_3$. |
| 5219 | A is A-2d, $(R^2)_n$ is 6-MeO and G is C—OMe. |
| 5220 | A is A-2d, $(R^2)_n$ is H and G is N. |
| 5221 | A is A-2d, $(R^2)_n$ is 3-F and G is N. |
| 5222 | A is A-2d, $(R^2)_n$ is 3,5-di-F and G is N. |
| 5223 | A is A-2d, $(R^2)_n$ is 3-Cl and G is N. |
| 5224 | A is A-2d, $(R^2)_n$ is 3,5-di-Cl and G is N. |
| 5225 | A is A-2d, $(R^2)_n$ is 3-Br and G is N. |
| 5226 | A is A-2d, $(R^2)_n$ is 3,5-di-Br and G is N. |
| 5227 | A is A-2d, $(R^2)_n$ is 3-Me and G is N. |
| 5228 | A is A-2d, $(R^2)_n$ is 3,5-di-Me and G is N. |
| 5229 | A is A-2d, $(R^2)_n$ is 3-$CF_3$ and G is N. |
| 5230 | A is A-2d, $(R^2)_n$ is 3,5-di-$CF_3$ and G is N. |
| 5231 | A is A-2d, $(R^2)_n$ is 3-MeO and G is N. |
| 5232 | A is A-2d, $(R^2)_n$ is 3,5-di-MeO and G is N. |
| 5233 | A is A-2d, $(R^2)_n$ is 3-CN and G is N. |
| 5234 | A is A-2d, $(R^2)_n$ is 3,5-di-CN and G is N. |
| 5235 | A is A-2d, $(R^2)_n$ is 3,6-di-F and G is N. |
| 5236 | A is A-2d, $(R^2)_n$ is 3,6-di-Cl and G is N. |
| 5237 | A is A-2d, $(R^2)_n$ is 3,6-di-Br and G is N. |
| 5238 | A is A-2d, $(R^2)_n$ is 3,6-di-Me and G is N. |
| 5239 | A is A-2d, $(R^2)_n$ is 3,6-di-$CF_3$ and G is N. |
| 5240 | A is A-2d, $(R^2)_n$ is 3,6-di-MeO and G is N. |
| 5241 | A is A-2d, $(R^2)_n$ is 3,6-di-CN and G is N. |
| 5242 | A is A-2d, $(R^2)_n$ is 6-F and G is N. |
| 5243 | A is A-2d, $(R^2)_n$ is 6-Cl and G is N. |
| 5244 | A is A-2d, $(R^2)_n$ is 6-Br and G is N. |
| 5245 | A is A-2d, $(R^2)_n$ is 6-Me and G is N. |
| 5246 | A is A-2d, $(R^2)_n$ is 6-$CF_3$ and G is N. |
| 5247 | A is A-2d, $(R^2)_n$ is 6-MeO and G is N. |
| 5248 | A is A-2d, $(R^2)_n$ is 6-CN and G is N. |
| 5249 | A is A-2e, $(R^2)_n$ is H and G is CH. |
| 5250 | A is A-2e, $(R^2)_n$ is 3-F and G is CH. |
| 5251 | A is A-2e, $(R^2)_n$ is 3,5-di-F and G is CH. |
| 5252 | A is A-2e, $(R^2)_n$ is 3-Cl and G is CH. |
| 5253 | A is A-2e, $(R^2)_n$ is 3,5-di-Cl and G is CH. |
| 5254 | A is A-2e, $(R^2)_n$ is 3-Br and G is CH. |
| 5255 | A is A-2e, $(R^2)_n$ is 3,5-di-Br and G is CH. |
| 5256 | A is A-2e, $(R^2)_n$ is 3-Me and G is CH. |
| 5257 | A is A-2e, $(R^2)_n$ is 3,5-di-Me and G is CH. |
| 5258 | A is A-2e, $(R^2)_n$ is 3-$CF_3$ and G is CH. |
| 5259 | A is A-2e, $(R^2)_n$ is 3,5-di-$CF_3$ and G is CH. |
| 5260 | A is A-2e, $(R^2)_n$ is 3-MeO and G is CH. |
| 5261 | A is A-2e, $(R^2)_n$ is 3,5-di-MeO and G is CH. |
| 5262 | A is A-2e, $(R^2)_n$ is 3-CN and G is CH. |
| 5263 | A is A-2e, $(R^2)_n$ is 3,5-di-CN and G is CH. |
| 5264 | A is A-2e, $(R^2)_n$ is 3,6-di-F and G is CH. |
| 5265 | A is A-2e, $(R^2)_n$ is 3,6-di-Cl and G is CH. |
| 5266 | A is A-2e, $(R^2)_n$ is 3,6-di-Br and G is CH. |
| 5267 | A is A-2e, $(R^2)_n$ is 3,6-di-Me and G is CH. |
| 5268 | A is A-2e, $(R^2)_n$ is 3,6-di-$CF_3$ and G is CH. |
| 5269 | A is A-2e, $(R^2)_n$ is 3,6-di-MeO and G is CH. |
| 5270 | A is A-2e, $(R^2)_n$ is 3,6-di-CN and G is CH. |
| 5271 | A is A-2e, $(R^2)_n$ is 6-F and G is CH. |
| 5272 | A is A-2e, $(R^2)_n$ is 6-Cl and G is CH. |
| 5273 | A is A-2e, $(R^2)_n$ is 6-Br and G is CH. |
| 5274 | A is A-2e, $(R^2)_n$ is 6-Me and G is CH. |
| 5275 | A is A-2e, $(R^2)_n$ is 6-$CF_3$ and G is CH. |
| 5276 | A is A-2e, $(R^2)_n$ is 6-MeO and G is CH. |
| 5277 | A is A-2e, $(R^2)_n$ is 6-CN and G is CH. |
| 5278 | A is A-2e, $(R^2)_n$ is 6-F and G is C—F. |
| 5279 | A is A-2e, $(R^2)_n$ is 6-Cl and G is C—Cl. |
| 5280 | A is A-2e, $(R^2)_n$ is 6-Br and G is C—Br. |
| 5281 | A is A-2e, $(R^2)_n$ is 6-Me and G is C—Me. |
| 5282 | A is A-2e, $(R^2)_n$ is 6-$CF_3$ and G is C—$CF_3$. |
| 5283 | A is A-2e, $(R^2)_n$ is 6-MeO and G is C—OMe. |
| 5284 | A is A-2e, $(R^2)_n$ is H and G is N. |
| 5285 | A is A-2e, $(R^2)_n$ is 3-F and G is N. |
| 5286 | A is A-2e, $(R^2)_n$ is 3,5-di-F and G is N. |
| 5287 | A is A-2e, $(R^2)_n$ is 3-Cl and G is N. |
| 5288 | A is A-2e, $(R^2)_n$ is 3,5-di-Cl and G is N. |
| 5289 | A is A-2e, $(R^2)_n$ is 3-Br and G is N. |
| 5290 | A is A-2e, $(R^2)_n$ is 3,5-di-Br and G is N. |
| 5291 | A is A-2e, $(R^2)_n$ is 3-Me and G is N. |
| 5292 | A is A-2e, $(R^2)_n$ is 3,5-di-Me and G is N. |

TABLES 4034-5760-continued

| Table | Row Heading |
|---|---|
| 5293 | A is A-2e, $(R^2)_n$ is 3-$CF_3$ and G is N. |
| 5294 | A is A-2e, $(R^2)_n$ is 3,5-di-$CF_3$ and G is N. |
| 5295 | A is A-2e, $(R^2)_n$ is 3-MeO and G is N. |
| 5296 | A is A-2e, $(R^2)_n$ is 3,5-di-MeO and G is N. |
| 5297 | A is A-2e, $(R^2)_n$ is 3-CN and G is N. |
| 5298 | A is A-2e, $(R^2)_n$ is 3,5-di-CN and G is N. |
| 5299 | A is A-2e, $(R^2)_n$ is 3,6-di-F and G is N. |
| 5300 | A is A-2e, $(R^2)_n$ is 3,6-di-Cl and G is N. |
| 5301 | A is A-2e, $(R^2)_n$ is 3,6-di-Br and G is N. |
| 5302 | A is A-2e, $(R^2)_n$ is 3,6-di-Me and G is N. |
| 5303 | A is A-2e, $(R^2)_n$ is 3,6-di-$CF_3$ and G is N. |
| 5304 | A is A-2e, $(R^2)_n$ is 3,6-di-MeO and G is N. |
| 5305 | A is A-2e, $(R^2)_n$ is 3,6-di-CN and G is N. |
| 5306 | A is A-2e, $(R^2)_n$ is 6-F and G is N. |
| 5307 | A is A-2e, $(R^2)_n$ is 6-Cl and G is N. |
| 5308 | A is A-2e, $(R^2)_n$ is 6-Br and G is N. |
| 5309 | A is A-2e, $(R^2)_n$ is 6-Me and G is N. |
| 5310 | A is A-2e, $(R^2)_n$ is 6-$CF_3$ and G is N. |
| 5311 | A is A-2e, $(R^2)_n$ is 6-MeO and G is N. |
| 5312 | A is A-2e, $(R^2)_n$ is 6-CN and G is N. |
| 5313 | A is A-3a, $(R^2)_n$ is H and G is CH. |
| 5314 | A is A-3a, $(R^2)_n$ is 3-F and G is CH. |
| 5315 | A is A-3a, $(R^2)_n$ is 3,5-di-F and G is CH. |
| 5316 | A is A-3a, $(R^2)_n$ is 3-Cl and G is CH. |
| 5317 | A is A-3a, $(R^2)_n$ is 3,5-di-Cl and G is CH. |
| 5318 | A is A-3a, $(R^2)_n$ is 3-Br and G is CH. |
| 5319 | A is A-3a, $(R^2)_n$ is 3,5-di-Br and G is CH. |
| 5320 | A is A-3a, $(R^2)_n$ is 3-Me and G is CH. |
| 5321 | A is A-3a, $(R^2)_n$ is 3,5-di-Me and G is CH. |
| 5322 | A is A-3a, $(R^2)_n$ is 3-$CF_3$ and G is CH. |
| 5323 | A is A-3a, $(R^2)_n$ is 3,5-di-$CF_3$ and G is CH. |
| 5324 | A is A-3a, $(R^2)_n$ is 3-MeO and G is CH. |
| 5325 | A is A-3a, $(R^2)_n$ is 3,5-di-MeO and G is CH. |
| 5326 | A is A-3a, $(R^2)_n$ is 3-CN and G is CH. |
| 5327 | A is A-3a, $(R^2)_n$ is 3,5-di-CN and G is CH. |
| 5328 | A is A-3a, $(R^2)_n$ is 3,6-di-F and G is CH. |
| 5329 | A is A-3a, $(R^2)_n$ is 3,6-di-Cl and G is CH. |
| 5330 | A is A-3a, $(R^2)_n$ is 3,6-di-Br and G is CH. |
| 5331 | A is A-3a, $(R^2)_n$ is 3,6-di-Me and G is CH. |
| 5332 | A is A-3a, $(R^2)_n$ is 3,6-di-$CF_3$ and G is CH. |
| 5333 | A is A-3a, $(R^2)_n$ is 3,6-di-MeO and G is CH. |
| 5334 | A is A-3a, $(R^2)_n$ is 3,6-di-CN and G is CH. |
| 5335 | A is A-3a, $(R^2)_n$ is 6-F and G is CH. |
| 5336 | A is A-3a, $(R^2)_n$ is 6-Cl and G is CH. |
| 5337 | A is A-3a, $(R^2)_n$ is 6-Br and G is CH. |
| 5338 | A is A-3a, $(R^2)_n$ is 6-Me and G is CH. |
| 5339 | A is A-3a, $(R^2)_n$ is 6-$CF_3$ and G is CH. |
| 5340 | A is A-3a, $(R^2)_n$ is 6-MeO and G is CH. |
| 5341 | A is A-3a, $(R^2)_n$ is 6-CN and G is CH. |
| 5342 | A is A-3a, $(R^2)_n$ is 6-F and G is C—F. |
| 5343 | A is A-3a, $(R^2)_n$ is 6-Cl and G is C—Cl. |
| 5344 | A is A-3a, $(R^2)_n$ is 6-Br and G is C—Br. |
| 5345 | A is A-3a, $(R^2)_n$ is 6-Me and G is C—Me. |
| 5346 | A is A-3a, $(R^2)_n$ is 6-$CF_3$ and G is C—$CF_3$. |
| 5347 | A is A-3a, $(R^2)_n$ is 6-MeO and G is C—OMe. |
| 5348 | A is A-3a, $(R^2)_n$ is H and G is N. |
| 5349 | A is A-3a, $(R^2)_n$ is 3-F and G is N. |
| 5350 | A is A-3a, $(R^2)_n$ is 3,5-di-F and G is N. |
| 5351 | A is A-3a, $(R^2)_n$ is 3-Cl and G is N. |
| 5352 | A is A-3a, $(R^2)_n$ is 3,5-di-Cl and G is N. |
| 5353 | A is A-3a, $(R^2)_n$ is 3-Br and G is N. |
| 5354 | A is A-3a, $(R^2)_n$ is 3,5-di-Br and G is N. |
| 5355 | A is A-3a, $(R^2)_n$ is 3-Me and G is N. |
| 5356 | A is A-3a, $(R^2)_n$ is 3,5-di-Me and G is N. |
| 5357 | A is A-3a, $(R^2)_n$ is 3-$CF_3$ and G is N. |
| 5358 | A is A-3a, $(R^2)_n$ is 3,5-di-$CF_3$ and G is N. |
| 5359 | A is A-3a, $(R^2)_n$ is 3-MeO and G is N. |
| 5360 | A is A-3a, $(R^2)_n$ is 3,5-di-MeO and G is N. |
| 5361 | A is A-3a, $(R^2)_n$ is 3-CN and G is N. |
| 5362 | A is A-3a, $(R^2)_n$ is 3,5-di-CN and G is N. |
| 5363 | A is A-3a, $(R^2)_n$ is 3,6-di-F and G is N. |
| 5364 | A is A-3a, $(R^2)_n$ is 3,6-di-Cl and G is N. |
| 5365 | A is A-3a, $(R^2)_n$ is 3,6-di-Br and G is N. |
| 5366 | A is A-3a, $(R^2)_n$ is 3,6-di-Me and G is N. |
| 5367 | A is A-3a, $(R^2)_n$ is 3,6-di-$CF_3$ and G is N. |
| 5368 | A is A-3a, $(R^2)_n$ is 3,6-di-MeO and G is N. |
| 5369 | A is A-3a, $(R^2)_n$ is 3,6-di-CN and G is N. |
| 5370 | A is A-3a, $(R^2)_n$ is 6-F and G is N. |
| 5371 | A is A-3a, $(R^2)_n$ is 6-Cl and G is N. |
| 5372 | A is A-3a, $(R^2)_n$ is 6-Br and G is N. |
| 5373 | A is A-3a, $(R^2)_n$ is 6-Me and G is N. |
| 5374 | A is A-3a, $(R^2)_n$ is 6-$CF_3$ and G is N. |
| 5375 | A is A-3a, $(R^2)_n$ is 6-MeO and G is N. |
| 5376 | A is A-3a, $(R^2)_n$ is 6-CN and G is N. |
| 5377 | A is A-3b, $(R^2)_n$ is H and G is CH. |
| 5378 | A is A-3b, $(R^2)_n$ is 3-F and G is CH. |
| 5379 | A is A-3b, $(R^2)_n$ is 3,5-di-F and G is CH. |
| 5380 | A is A-3b, $(R^2)_n$ is 3-Cl and G is CH. |
| 5381 | A is A-3b, $(R^2)_n$ is 3,5-di-Cl and G is CH. |
| 5382 | A is A-3b, $(R^2)_n$ is 3-Br and G is CH. |
| 5383 | A is A-3b, $(R^2)_n$ is 3,5-di-Br and G is CH. |
| 5384 | A is A-3b, $(R^2)_n$ is 3-Me and G is CH. |
| 5385 | A is A-3b, $(R^2)_n$ is 3,5-di-Me and G is CH. |
| 5386 | A is A-3b, $(R^2)_n$ is 3-$CF_3$ and G is CH. |
| 5387 | A is A-3b, $(R^2)_n$ is 3,5-di-$CF_3$ and G is CH. |
| 5388 | A is A-3b, $(R^2)_n$ is 3-MeO and G is CH. |
| 5389 | A is A-3b, $(R^2)_n$ is 3,5-di-MeO and G is CH. |
| 5390 | A is A-3b, $(R^2)_n$ is 3-CN and G is CH. |
| 5391 | A is A-3b, $(R^2)_n$ is 3,5-di-CN and G is CH. |
| 5392 | A is A-3b, $(R^2)_n$ is 3,6-di-F and G is CH. |
| 5393 | A is A-3b, $(R^2)_n$ is 3,6-di-Cl and G is CH. |
| 5394 | A is A-3b, $(R^2)_n$ is 3,6-di-Br and G is CH. |
| 5395 | A is A-3b, $(R^2)_n$ is 3,6-di-Me and G is CH. |
| 5396 | A is A-3b, $(R^2)_n$ is 3,6-di-$CF_3$ and G is CH. |
| 5397 | A is A-3b, $(R^2)_n$ is 3,6-di-MeO and G is CH. |
| 5398 | A is A-3b, $(R^2)_n$ is 3,6-di-CN and G is CH. |
| 5399 | A is A-3b, $(R^2)_n$ is 6-F and G is CH. |
| 5400 | A is A-3b, $(R^2)_n$ is 6-Cl and G is CH. |
| 5401 | A is A-3b, $(R^2)_n$ is 6-Br and G is CH. |
| 5402 | A is A-3b, $(R^2)_n$ is 6-Me and G is CH. |
| 5403 | A is A-3b, $(R^2)_n$ is 6-$CF_3$ and G is CH. |
| 5404 | A is A-3b, $(R^2)_n$ is 6-MeO and G is CH. |
| 5405 | A is A-3b, $(R^2)_n$ is 6-CN and G is CH. |
| 5406 | A is A-3b, $(R^2)_n$ is 6-F and G is C—F. |
| 5407 | A is A-3b, $(R^2)_n$ is 6-Cl and G is C—Cl. |
| 5408 | A is A-3b, $(R^2)_n$ is 6-Br and G is C—Br. |
| 5409 | A is A-3b, $(R^2)_n$ is 6-Me and G is C—Me. |
| 5410 | A is A-3b, $(R^2)_n$ is 6-$CF_3$ and G is C—$CF_3$. |
| 5411 | A is A-3b, $(R^2)_n$ is 6-MeO and G is C—OMe. |
| 5412 | A is A-3b, $(R^2)_n$ is H and G is N. |
| 5413 | A is A-3b, $(R^2)_n$ is 3-F and G is N. |
| 5414 | A is A-3b, $(R^2)_n$ is 3,5-di-F and G is N. |
| 5415 | A is A-3b, $(R^2)_n$ is 3-Cl and G is N. |
| 5416 | A is A-3b, $(R^2)_n$ is 3,5-di-Cl and G is N. |
| 5417 | A is A-3b, $(R^2)_n$ is 3-Br and G is N. |
| 5418 | A is A-3b, $(R^2)_n$ is 3,5-di-Br and G is N. |
| 5419 | A is A-3b, $(R^2)_n$ is 3-Me and G is N. |
| 5420 | A is A-3b, $(R^2)_n$ is 3,5-di-Me and G is N. |
| 5421 | A is A-3b, $(R^2)_n$ is 3-$CF_3$ and G is N. |
| 5422 | A is A-3b, $(R^2)_n$ is 3,5-di-$CF_3$ and G is N. |
| 5423 | A is A-3b, $(R^2)_n$ is 3-MeO and G is N. |
| 5424 | A is A-3b, $(R^2)_n$ is 3,5-di-MeO and G is N. |
| 5425 | A is A-3b, $(R^2)_n$ is 3-CN and G is N. |
| 5426 | A is A-3b, $(R^2)_n$ is 3,5-di-CN and G is N. |
| 5427 | A is A-3b, $(R^2)_n$ is 3,6-di-F and G is N. |
| 5428 | A is A-3b, $(R^2)_n$ is 3,6-di-Cl and G is N. |
| 5429 | A is A-3b, $(R^2)_n$ is 3,6-di-Br and G is N. |
| 5430 | A is A-3b, $(R^2)_n$ is 3,6-di-Me and G is N. |
| 5431 | A is A-3b, $(R^2)_n$ is 3,6-di-$CF_3$ and G is N. |
| 5432 | A is A-3b, $(R^2)_n$ is 3,6-di-MeO and G is N. |
| 5433 | A is A-3b, $(R^2)_n$ is 3,6-di-CN and G is N. |
| 5434 | A is A-3b, $(R^2)_n$ is 6-F and G is N. |
| 5435 | A is A-3b, $(R^2)_n$ is 6-Cl and G is N. |
| 5436 | A is A-3b, $(R^2)_n$ is 6-Br and G is N. |
| 5437 | A is A-3b, $(R^2)_n$ is 6-Me and G is N. |
| 5438 | A is A-3b, $(R^2)_n$ is 6-$CF_3$ and G is N. |
| 5439 | A is A-3b, $(R^2)_n$ is 6-MeO and G is N. |
| 5440 | A is A-3b, $(R^2)_n$ is 6-CN and G is N. |
| 5441 | A is A-3c, $(R^2)_n$ is H and G is CH. |
| 5442 | A is A-3c, $(R^2)_n$ is 3-F and G is CH. |
| 5443 | A is A-3c, $(R^2)_n$ is 3,5-di-F and G is CH. |
| 5444 | A is A-3c, $(R^2)_n$ is 3-Cl and G is CH. |
| 5445 | A is A-3c, $(R^2)_n$ is 3,5-di-Cl and G is CH. |
| 5446 | A is A-3c, $(R^2)_n$ is 3-Br and G is CH. |
| 5447 | A is A-3c, $(R^2)_n$ is 3,5-di-Br and G is CH. |
| 5448 | A is A-3c, $(R^2)_n$ is 3-Me and G is CH. |

TABLES 4034-5760-continued

| Table | Row Heading |
|---|---|
| 5449 | A is A-3c, $(R^2)_n$ is 3,5-di-Me and G is CH. |
| 5450 | A is A-3c, $(R^2)_n$ is 3-CF$_3$ and G is CH. |
| 5451 | A is A-3c, $(R^2)_n$ is 3,5-di-CF$_3$ and G is CH. |
| 5452 | A is A-3c, $(R^2)_n$ is 3-MeO and G is CH. |
| 5453 | A is A-3c, $(R^2)_n$ is 3,5-di-MeO and G is CH. |
| 5454 | A is A-3c, $(R^2)_n$ is 3-CN and G is CH. |
| 5455 | A is A-3c, $(R^2)_n$ is 3,5-di-CN and G is CH. |
| 5456 | A is A-3c, $(R^2)_n$ is 3,6-di-F and G is CH. |
| 5457 | A is A-3c, $(R^2)_n$ is 3,6-di-Cl and G is CH. |
| 5458 | A is A-3c, $(R^2)_n$ is 3,6-di-Br and G is CH. |
| 5459 | A is A-3c, $(R^2)_n$ is 3,6-di-Me and G is CH. |
| 5460 | A is A-3c, $(R^2)_n$ is 3,6-di-CF$_3$ and G is CH. |
| 5461 | A is A-3c, $(R^2)_n$ is 3,6-di-MeO and G is CH. |
| 5462 | A is A-3c, $(R^2)_n$ is 3,6-di-CN and G is CH. |
| 5463 | A is A-3c, $(R^2)_n$ is 6-F and G is CH. |
| 5464 | A is A-3c, $(R^2)_n$ is 6-Cl and G is CH. |
| 5465 | A is A-3c, $(R^2)_n$ is 6-Br and G is CH. |
| 5466 | A is A-3c, $(R^2)_n$ is 6-Me and G is CH. |
| 5467 | A is A-3c, $(R^2)_n$ is 6-CF$_3$ and G is CH. |
| 5468 | A is A-3c, $(R^2)_n$ is 6-MeO and G is CH. |
| 5469 | A is A-3c, $(R^2)_n$ is 6-CN and G is CH. |
| 5470 | A is A-3c, $(R^2)_n$ is 6-F and G is C—F. |
| 5471 | A is A-3c, $(R^2)_n$ is 6-Cl and G is C—Cl. |
| 5472 | A is A-3c, $(R^2)_n$ is 6-Br and G is C—Br. |
| 5473 | A is A-3c, $(R^2)_n$ is 6-Me and G is C—Me. |
| 5474 | A is A-3c, $(R^2)_n$ is 6-CF$_3$ and G is C—CF$_3$. |
| 5475 | A is A-3c, $(R^2)_n$ is 6-MeO and G is C—OMe. |
| 5476 | A is A-3c, $(R^2)_n$ is H and G is N. |
| 5477 | A is A-3c, $(R^2)_n$ is 3-F and G is N. |
| 5478 | A is A-3c, $(R^2)_n$ is 3,5-di-F and G is N. |
| 5479 | A is A-3c, $(R^2)_n$ is 3-Cl and G is N. |
| 5480 | A is A-3c, $(R^2)_n$ is 3,5-di-Cl and G is N. |
| 5481 | A is A-3c, $(R^2)_n$ is 3-Br and G is N. |
| 5482 | A is A-3c, $(R^2)_n$ is 3,5-di-Br and G is N. |
| 5483 | A is A-3c, $(R^2)_n$ is 3-Me and G is N. |
| 5484 | A is A-3c, $(R^2)_n$ is 3,5-di-Me and G is N. |
| 5485 | A is A-3c, $(R^2)_n$ is 3-CF$_3$ and G is N. |
| 5486 | A is A-3c, $(R^2)_n$ is 3,5-di-CF$_3$ and G is N. |
| 5487 | A is A-3c, $(R^2)_n$ is 3-MeO and G is N. |
| 5488 | A is A-3c, $(R^2)_n$ is 3,5-di-MeO and G is N. |
| 5489 | A is A-3c, $(R^2)_n$ is 3-CN and G is N. |
| 5490 | A is A-3c, $(R^2)_n$ is 3,5-di-CN and G is N. |
| 5491 | A is A-3c, $(R^2)_n$ is 3,6-di-F and G is N. |
| 5492 | A is A-3c, $(R^2)_n$ is 3,6-di-Cl and G is N. |
| 5493 | A is A-3c, $(R^2)_n$ is 3,6-di-Br and G is N. |
| 5494 | A is A-3c, $(R^2)_n$ is 3,6-di-Me and G is N. |
| 5495 | A is A-3c, $(R^2)_n$ is 3,6-di-CF$_3$ and G is N. |
| 5496 | A is A-3c, $(R^2)_n$ is 3,6-di-MeO and G is N. |
| 5497 | A is A-3c, $(R^2)_n$ is 3,6-di-CN and G is N. |
| 5498 | A is A-3c, $(R^2)_n$ is 6-F and G is N. |
| 5499 | A is A-3c, $(R^2)_n$ is 6-Cl and G is N. |
| 5500 | A is A-3c, $(R^2)_n$ is 6-Br and G is N. |
| 5501 | A is A-3c, $(R^2)_n$ is 6-Me and G is N. |
| 5502 | A is A-3c, $(R^2)_n$ is 6-CF$_3$ and G is N. |
| 5503 | A is A-3c, $(R^2)_n$ is 6-MeO and G is N. |
| 5504 | A is A-3c, $(R^2)_n$ is 6-CN and G is N. |
| 5505 | A is A-4a, $(R^2)_n$ is H and G is CH. |
| 5506 | A is A-4a, $(R^2)_n$ is 3-F and G is CH. |
| 5507 | A is A-4a, $(R^2)_n$ is 3,5-di-F and G is CH. |
| 5508 | A is A-4a, $(R^2)_n$ is 3-Cl and G is CH. |
| 5509 | A is A-4a, $(R^2)_n$ is 3,5-di-Cl and G is CH. |
| 5510 | A is A-4a, $(R^2)_n$ is 3-Br and G is CH. |
| 5511 | A is A-4a, $(R^2)_n$ is 3,5-di-Br and G is CH. |
| 5512 | A is A-4a, $(R^2)_n$ is 3-Me and G is CH. |
| 5513 | A is A-4a, $(R^2)_n$ is 3,5-di-Me and G is CH. |
| 5514 | A is A-4a, $(R^2)_n$ is 3-CF$_3$ and G is CH. |
| 5515 | A is A-4a, $(R^2)_n$ is 3,5-di-CF$_3$ and G is CH. |
| 5516 | A is A-4a, $(R^2)_n$ is 3-MeO and G is CH. |
| 5517 | A is A-4a, $(R^2)_n$ is 3,5-di-MeO and G is CH. |
| 5518 | A is A-4a, $(R^2)_n$ is 3-CN and G is CH. |
| 5519 | A is A-4a, $(R^2)_n$ is 3,5-di-CN and G is CH. |
| 5520 | A is A-4a, $(R^2)_n$ is 3,6-di-F and G is CH. |
| 5521 | A is A-4a, $(R^2)_n$ is 3,6-di-Cl and G is CH. |
| 5522 | A is A-4a, $(R^2)_n$ is 3,6-di-Br and G is CH. |
| 5523 | A is A-4a, $(R^2)_n$ is 3,6-di-Me and G is CH. |
| 5524 | A is A-4a, $(R^2)_n$ is 3,6-di-CF$_3$ and G is CH. |
| 5525 | A is A-4a, $(R^2)_n$ is 3,6-di-MeO and G is CH. |
| 5526 | A is A-4a, $(R^2)_n$ is 3,6-di-CN and G is CH. |
| 5527 | A is A-4a, $(R^2)_n$ is 6-F and G is CH. |
| 5528 | A is A-4a, $(R^2)_n$ is 6-Cl and G is CH. |
| 5529 | A is A-4a, $(R^2)_n$ is 6-Br and G is CH. |
| 5530 | A is A-4a, $(R^2)_n$ is 6-Me and G is CH. |
| 5531 | A is A-4a, $(R^2)_n$ is 6-CF$_3$ and G is CH. |
| 5532 | A is A-4a, $(R^2)_n$ is 6-MeO and G is CH. |
| 5533 | A is A-4a, $(R^2)_n$ is 6-CN and G is CH. |
| 5534 | A is A-4a, $(R^2)_n$ is 6-F and G is C—F. |
| 5535 | A is A-4a, $(R^2)_n$ is 6-Cl and G is C—Cl. |
| 5536 | A is A-4a, $(R^2)_n$ is 6-Br and G is C—Br. |
| 5537 | A is A-4a, $(R^2)_n$ is 6-Me and G is C—Me. |
| 5538 | A is A-4a, $(R^2)_n$ is 6-CF$_3$ and G is C—CF$_3$. |
| 5539 | A is A-4a, $(R^2)_n$ is 6-MeO and G is C—OMe. |
| 5540 | A is A-4a, $(R^2)_n$ is H and G is N. |
| 5541 | A is A-4a, $(R^2)_n$ is 3-F and G is N. |
| 5542 | A is A-4a, $(R^2)_n$ is 3,5-di-F and G is N. |
| 5543 | A is A-4a, $(R^2)_n$ is 3-Cl and G is N. |
| 5544 | A is A-4a, $(R^2)_n$ is 3,5-di-Cl and G is N. |
| 5545 | A is A-4a, $(R^2)_n$ is 3-Br and G is N. |
| 5546 | A is A-4a, $(R^2)_n$ is 3,5-di-Br and G is N. |
| 5547 | A is A-4a, $(R^2)_n$ is 3-Me and G is N. |
| 5548 | A is A-4a, $(R^2)_n$ is 3,5-di-Me and G is N. |
| 5549 | A is A-4a, $(R^2)_n$ is 3-CF$_3$ and G is N. |
| 5550 | A is A-4a, $(R^2)_n$ is 3,5-di-CF$_3$ and G is N. |
| 5551 | A is A-4a, $(R^2)_n$ is 3-MeO and G is N. |
| 5552 | A is A-4a, $(R^2)_n$ is 3,5-di-MeO and G is N. |
| 5553 | A is A-4a, $(R^2)_n$ is 3-CN and G is N. |
| 5554 | A is A-4a, $(R^2)_n$ is 3,5-di-CN and G is N. |
| 5555 | A is A-4a, $(R^2)_n$ is 3,6-di-F and G is N. |
| 5556 | A is A-4a, $(R^2)_n$ is 3,6-di-Cl and G is N. |
| 5557 | A is A-4a, $(R^2)_n$ is 3,6-di-Br and G is N. |
| 5558 | A is A-4a, $(R^2)_n$ is 3,6-di-Me and G is N. |
| 5559 | A is A-4a, $(R^2)_n$ is 3,6-di-CF$_3$ and G is N. |
| 5560 | A is A-4a, $(R^2)_n$ is 3,6-di-MeO and G is N. |
| 5561 | A is A-4a, $(R^2)_n$ is 3,6-di-CN and G is N. |
| 5562 | A is A-4a, $(R^2)_n$ is 6-F and G is N. |
| 5563 | A is A-4a, $(R^2)_n$ is 6-Cl and G is N. |
| 5564 | A is A-4a, $(R^2)_n$ is 6-Br and G is N. |
| 5565 | A is A-4a, $(R^2)_n$ is 6-Me and G is N. |
| 5566 | A is A-4a, $(R^2)_n$ is 6-CF$_3$ and G is N. |
| 5567 | A is A-4a, $(R^2)_n$ is 6-MeO and G is N. |
| 5568 | A is A-4a, $(R^2)_n$ is 6-CN and G is N. |
| 5569 | A is A-4b, $(R^2)_n$ is H and G is CH. |
| 5570 | A is A-4b, $(R^2)_n$ is 3-F and G is CH. |
| 5571 | A is A-4b, $(R^2)_n$ is 3,5-di-F and G is CH. |
| 5572 | A is A-4b, $(R^2)_n$ is 3-Cl and G is CH. |
| 5573 | A is A-4b, $(R^2)_n$ is 3,5-di-Cl and G is CH. |
| 5574 | A is A-4b, $(R^2)_n$ is 3-Br and G is CH. |
| 5575 | A is A-4b, $(R^2)_n$ is 3,5-di-Br and G is CH. |
| 5576 | A is A-4b, $(R^2)_n$ is 3-Me and G is CH. |
| 5577 | A is A-4b, $(R^2)_n$ is 3,5-di-Me and G is CH. |
| 5578 | A is A-4b, $(R^2)_n$ is 3-CF$_3$ and G is CH. |
| 5579 | A is A-4b, $(R^2)_n$ is 3,5-di-CF$_3$ and G is CH. |
| 5580 | A is A-4b, $(R^2)_n$ is 3-MeO and G is CH. |
| 5581 | A is A-4b, $(R^2)_n$ is 3,5-di-MeO and G is CH. |
| 5582 | A is A-4b, $(R^2)_n$ is 3-CN and G is CH. |
| 5583 | A is A-4b, $(R^2)_n$ is 3,5-di-CN and G is CH. |
| 5584 | A is A-4b, $(R^2)_n$ is 3,6-di-F and G is CH. |
| 5585 | A is A-4b, $(R^2)_n$ is 3,6-di-Cl and G is CH. |
| 5586 | A is A-4b, $(R^2)_n$ is 3,6-di-Br and G is CH. |
| 5587 | A is A-4b, $(R^2)_n$ is 3,6-di-Me and G is CH. |
| 5588 | A is A-4b, $(R^2)_n$ is 3,6-di-CF$_3$ and G is CH. |
| 5589 | A is A-4b, $(R^2)_n$ is 3,6-di-MeO and G is CH. |
| 5590 | A is A-4b, $(R^2)_n$ is 3,6-di-CN and G is CH. |
| 5591 | A is A-4b, $(R^2)_n$ is 6-F and G is CH. |
| 5592 | A is A-4b, $(R^2)_n$ is 6-Cl and G is CH. |
| 5593 | A is A-4b, $(R^2)_n$ is 6-Br and G is CH. |
| 5594 | A is A-4b, $(R^2)_n$ is 6-Me and G is CH. |
| 5595 | A is A-4b, $(R^2)_n$ is 6-CF$_3$ and G is CH. |
| 5596 | A is A-4b, $(R^2)_n$ is 6-MeO and G is CH. |
| 5597 | A is A-4b, $(R^2)_n$ is 6-CN and G is CH. |
| 5598 | A is A-4b, $(R^2)_n$ is 6-F and G is C—F. |
| 5599 | A is A-4b, $(R^2)_n$ is 6-Cl and G is C—Cl. |
| 5600 | A is A-4b, $(R^2)_n$ is 6-Br and G is C—Br. |
| 5601 | A is A-4b, $(R^2)_n$ is 6-Me and G is C—Me. |
| 5602 | A is A-4b, $(R^2)_n$ is 6-CF$_3$ and G is C—CF$_3$. |
| 5603 | A is A-4b, $(R^2)_n$ is 6-MeO and G is C—OMe. |
| 5604 | A is A-4b, $(R^2)_n$ is H and G is N. |

TABLES 4034-5760-continued

| Table | Row Heading |
|---|---|
| 5605 | A is A-4b, $(R^2)_n$ is 3-F and G is N. |
| 5606 | A is A-4b, $(R^2)_n$ is 3,5-di-F and G is N. |
| 5607 | A is A-4b, $(R^2)_n$ is 3-Cl and G is N. |
| 5608 | A is A-4b, $(R^2)_n$ is 3,5-di-Cl and G is N. |
| 5609 | A is A-4b, $(R^2)_n$ is 3-Br and G is N. |
| 5610 | A is A-4b, $(R^2)_n$ is 3,5-di-Br and G is N. |
| 5611 | A is A-4b, $(R^2)_n$ is 3-Me and G is N. |
| 5612 | A is A-4b, $(R^2)_n$ is 3,5-di-Me and G is N. |
| 5613 | A is A-4b, $(R^2)_n$ is 3-$CF_3$ and G is N. |
| 5614 | A is A-4b, $(R^2)_n$ is 3,5-di-$CF_3$ and G is N. |
| 5615 | A is A-4b, $(R^2)_n$ is 3-MeO and G is N. |
| 5616 | A is A-4b, $(R^2)_n$ is 3,5-di-MeO and G is N. |
| 5617 | A is A-4b, $(R^2)_n$ is 3-CN and G is N. |
| 5618 | A is A-4b, $(R^2)_n$ is 3,5-di-CN and G is N. |
| 5619 | A is A-4b, $(R^2)_n$ is 3,6-di-F and G is N. |
| 5620 | A is A-4b, $(R^2)_n$ is 3,6-di-Cl and G is N. |
| 5621 | A is A-4b, $(R^2)_n$ is 3,6-di-Br and G is N. |
| 5622 | A is A-4b, $(R^2)_n$ is 3,6-di-Me and G is N. |
| 5623 | A is A-4b, $(R^2)_n$ is 3,6-di-$CF_3$ and G is N. |
| 5624 | A is A-4b, $(R^2)_n$ is 3,6-di-MeO and G is N. |
| 5625 | A is A-4b, $(R^2)_n$ is 3,6-di-CN and G is N. |
| 5626 | A is A-4b, $(R^2)_n$ is 6-F and G is N. |
| 5627 | A is A-4b, $(R^2)_n$ is 6-Cl and G is N. |
| 5628 | A is A-4b, $(R^2)_n$ is 6-Br and G is N. |
| 5629 | A is A-4b, $(R^2)_n$ is 6-Me and G is N. |
| 5630 | A is A-4b, $(R^2)_n$ is 6-$CF_3$ and G is N. |
| 5631 | A is A-4b, $(R^2)_n$ is 6-MeO and G is N. |
| 5632 | A is A-4b, $(R^2)_n$ is 6-CN and G is N. |
| 5633 | A is A-4c, $(R^2)_n$ is H and G is CH. |
| 5634 | A is A-4c, $(R^2)_n$ is 3-F and G is CH. |
| 5635 | A is A-4c, $(R^2)_n$ is 3,5-di-F and G is CH. |
| 5636 | A is A-4c, $(R^2)_n$ is 3-Cl and G is CH. |
| 5637 | A is A-4c, $(R^2)_n$ is 3,5-di-Cl and G is CH. |
| 5638 | A is A-4c, $(R^2)_n$ is 3-Br and G is CH. |
| 5639 | A is A-4c, $(R^2)_n$ is 3,5-di-Br and G is CH. |
| 5640 | A is A-4c, $(R^2)_n$ is 3-Me and G is CH. |
| 5641 | A is A-4c, $(R^2)_n$ is 3,5-di-Me and G is CH. |
| 5642 | A is A-4c, $(R^2)_n$ is 3-$CF_3$ and G is CH. |
| 5643 | A is A-4c, $(R^2)_n$ is 3,5-di-$CF_3$ and G is CH. |
| 5644 | A is A-4c, $(R^2)_n$ is 3-MeO and G is CH. |
| 5645 | A is A-4c, $(R^2)_n$ is 3,5-di-MeO and G is CH. |
| 5646 | A is A-4c, $(R^2)_n$ is 3-CN and G is CH. |
| 5647 | A is A-4c, $(R^2)_n$ is 3,5-di-CN and G is CH. |
| 5648 | A is A-4c, $(R^2)_n$ is 3,6-di-F and G is CH. |
| 5649 | A is A-4c, $(R^2)_n$ is 3,6-di-Cl and G is CH. |
| 5650 | A is A-4c, $(R^2)_n$ is 3,6-di-Br and G is CH. |
| 5651 | A is A-4c, $(R^2)_n$ is 3,6-di-Me and G is CH. |
| 5652 | A is A-4c, $(R^2)_n$ is 3,6-di-$CF_3$ and G is CH. |
| 5653 | A is A-4c, $(R^2)_n$ is 3,6-di-MeO and G is CH. |
| 5654 | A is A-4c, $(R^2)_n$ is 3,6-di-CN and G is CH. |
| 5655 | A is A-4c, $(R^2)_n$ is 6-F and G is CH. |
| 5656 | A is A-4c, $(R^2)_n$ is 6-Cl and G is CH. |
| 5657 | A is A-4c, $(R^2)_n$ is 6-Br and G is CH. |
| 5658 | A is A-4c, $(R^2)_n$ is 6-Me and G is CH. |
| 5659 | A is A-4c, $(R^2)_n$ is 6-$CF_3$ and G is CH. |
| 5660 | A is A-4c, $(R^2)_n$ is 6-MeO and G is CH. |
| 5661 | A is A-4c, $(R^2)_n$ is 6-CN and G is CH. |
| 5662 | A is A-4c, $(R^2)_n$ is 6-F and G is C—F. |
| 5663 | A is A-4c, $(R^2)_n$ is 6-Cl and G is C—Cl. |
| 5664 | A is A-4c, $(R^2)_n$ is 6-Br and G is C—Br. |
| 5665 | A is A-4c, $(R^2)_n$ is 6-Me and G is C—Me. |
| 5666 | A is A-4c, $(R^2)_n$ is 6-$CF_3$ and G is C—$CF_3$. |
| 5667 | A is A-4c, $(R^2)_n$ is 6-MeO and G is C—OMe. |
| 5668 | A is A-4c, $(R^2)_n$ is H and G is N. |
| 5669 | A is A-4c, $(R^2)_n$ is 3-F and G is N. |
| 5670 | A is A-4c, $(R^2)_n$ is 3,5-di-F and G is N. |
| 5671 | A is A-4c, $(R^2)_n$ is 3-Cl and G is N. |
| 5672 | A is A-4c, $(R^2)_n$ is 3,5-di-Cl and G is N. |
| 5673 | A is A-4c, $(R^2)_n$ is 3-Br and G is N. |
| 5674 | A is A-4c, $(R^2)_n$ is 3,5-di-Br and G is N. |
| 5675 | A is A-4c, $(R^2)_n$ is 3-Me and G is N. |
| 5676 | A is A-4c, $(R^2)_n$ is 3,5-di-Me and G is N. |
| 5677 | A is A-4c, $(R^2)_n$ is 3-$CF_3$ and G is N. |
| 5678 | A is A-4c, $(R^2)_n$ is 3,5-di-$CF_3$ and G is N. |
| 5679 | A is A-4c, $(R^2)_n$ is 3-MeO and G is N. |
| 5680 | A is A-4c, $(R^2)_n$ is 3,5-di-MeO and G is N. |
| 5681 | A is A-4c, $(R^2)_n$ is 3-CN and G is N. |
| 5682 | A is A-4c, $(R^2)_n$ is 3,5-di-CN and G is N. |
| 5683 | A is A-4c, $(R^2)_n$ is 3,6-di-F and G is N. |
| 5684 | A is A-4c, $(R^2)_n$ is 3,6-di-Cl and G is N. |
| 5685 | A is A-4c, $(R^2)_n$ is 3,6-di-Br and G is N. |
| 5686 | A is A-4c, $(R^2)_n$ is 3,6-di-Me and G is N. |
| 5687 | A is A-4c, $(R^2)_n$ is 3,6-di-$CF_3$ and G is N. |
| 5688 | A is A-4c, $(R^2)_n$ is 3,6-di-MeO and G is N. |
| 5689 | A is A-4c, $(R^2)_n$ is 3,6-di-CN and G is N. |
| 5690 | A is A-4c, $(R^2)_n$ is 6-F and G is N. |
| 5691 | A is A-4c, $(R^2)_n$ is 6-Cl and G is N. |
| 5692 | A is A-4c, $(R^2)_n$ is 6-Br and G is N. |
| 5693 | A is A-4c, $(R^2)_n$ is 6-Me and G is N. |
| 5694 | A is A-4c, $(R^2)_n$ is 6-$CF_3$ and G is N. |
| 5695 | A is A-4c, $(R^2)_n$ is 6-MeO and G is N. |
| 5696 | A is A-4c, $(R^2)_n$ is 6-CN and G is N. |
| 5697 | A is A-4d, $(R^2)_n$ is H and G is CH. |
| 5698 | A is A-4d, $(R^2)_n$ is 3-F and G is CH. |
| 5699 | A is A-4d, $(R^2)_n$ is 3,5-di-F and G is CH. |
| 5700 | A is A-4d, $(R^2)_n$ is 3-Cl and G is CH. |
| 5701 | A is A-4d, $(R^2)_n$ is 3,5-di-Cl and G is CH. |
| 5702 | A is A-4d, $(R^2)_n$ is 3-Br and G is CH. |
| 5703 | A is A-4d, $(R^2)_n$ is 3,5-di-Br and G is CH. |
| 5704 | A is A-4d, $(R^2)_n$ is 3-Me and G is CH. |
| 5705 | A is A-4d, $(R^2)_n$ is 3,5-di-Me and G is CH. |
| 5706 | A is A-4d, $(R^2)_n$ is 3-$CF_3$ and G is CH. |
| 5707 | A is A-4d, $(R^2)_n$ is 3,5-di-$CF_3$ and G is CH. |
| 5708 | A is A-4d, $(R^2)_n$ is 3-MeO and G is CH. |
| 5709 | A is A-4d, $(R^2)_n$ is 3,5-di-MeO and G is CH. |
| 5710 | A is A-4d, $(R^2)_n$ is 3-CN and G is CH. |
| 5711 | A is A-4d, $(R^2)_n$ is 3,5-di-CN and G is CH. |
| 5712 | A is A-4d, $(R^2)_n$ is 3,6-di-F and G is CH. |
| 5713 | A is A-4d, $(R^2)_n$ is 3,6-di-Cl and G is CH. |
| 5714 | A is A-4d, $(R^2)_n$ is 3,6-di-Br and G is CH. |
| 5715 | A is A-4d, $(R^2)_n$ is 3,6-di-Me and G is CH. |
| 5716 | A is A-4d, $(R^2)_n$ is 3,6-di-$CF_3$ and G is CH. |
| 5717 | A is A-4d, $(R^2)_n$ is 3,6-di-MeO and G is CH. |
| 5718 | A is A-4d, $(R^2)_n$ is 3,6-di-CN and G is CH. |
| 5719 | A is A-4d, $(R^2)_n$ is 6-F and G is CH. |
| 5720 | A is A-4d, $(R^2)_n$ is 6-Cl and G is CH. |
| 5721 | A is A-4d, $(R^2)_n$ is 6-Br and G is CH. |
| 5722 | A is A-4d, $(R^2)_n$ is 6-Me and G is CH. |
| 5723 | A is A-4d, $(R^2)_n$ is 6-$CF_3$ and G is CH. |
| 5724 | A is A-4d, $(R^2)_n$ is 6-MeO and G is CH. |
| 5725 | A is A-4d, $(R^2)_n$ is 6-CN and G is CH. |
| 5726 | A is A-4d, $(R^2)_n$ is 6-F and G is C—F. |
| 5727 | A is A-4d, $(R^2)_n$ is 6-Cl and G is C—Cl. |
| 5728 | A is A-4d, $(R^2)_n$ is 6-Br and G is C—Br. |
| 5729 | A is A-4d, $(R^2)_n$ is 6-Me and G is C—Me. |
| 5730 | A is A-4d, $(R^2)_n$ is 6-$CF_3$ and G is C—$CF_3$. |
| 5731 | A is A-4d, $(R^2)_n$ is 6-MeO and G is C—OMe. |
| 5732 | A is A-4d, $(R^2)_n$ is H and G is N. |
| 5733 | A is A-4d, $(R^2)_n$ is 3-F and G is N. |
| 5734 | A is A-4d, $(R^2)_n$ is 3,5-di-F and G is N. |
| 5735 | A is A-4d, $(R^2)_n$ is 3-Cl and G is N. |
| 5736 | A is A-4d, $(R^2)_n$ is 3,5-di-Cl and G is N. |
| 5737 | A is A-4d, $(R^2)_n$ is 3-Br and G is N. |
| 5738 | A is A-4d, $(R^2)_n$ is 3,5-di-Br and G is N. |
| 5739 | A is A-4d, $(R^2)_n$ is 3-Me and G is N. |
| 5740 | A is A-4d, $(R^2)_n$ is 3,5-di-Me and G is N. |
| 5741 | A is A-4d, $(R^2)_n$ is 3-$CF_3$ and G is N. |
| 5742 | A is A-4d, $(R^2)_n$ is 3,5-di-$CF_3$ and G is N. |
| 5743 | A is A-4d, $(R^2)_n$ is 3-MeO and G is N. |
| 5744 | A is A-4d, $(R^2)_n$ is 3,5-di-MeO and G is N. |
| 5745 | A is A-4d, $(R^2)_n$ is 3-CN and G is N. |
| 5746 | A is A-4d, $(R^2)_n$ is 3,5-di-CN and G is N. |
| 5747 | A is A-4d, $(R^2)_n$ is 3,6-di-F and G is N. |
| 5748 | A is A-4d, $(R^2)_n$ is 3,6-di-Cl and G is N. |
| 5749 | A is A-4d, $(R^2)_n$ is 3,6-di-Br and G is N. |
| 5750 | A is A-4d, $(R^2)_n$ is 3,6-di-Me and G is N. |
| 5751 | A is A-4d, $(R^2)_n$ is 3,6-di-$CF_3$ and G is N. |
| 5752 | A is A-4d, $(R^2)_n$ is 3,6-di-MeO and G is N. |
| 5753 | A is A-4d, $(R^2)_n$ is 3,6-di-CN and G is N. |
| 5754 | A is A-4d, $(R^2)_n$ is 6-F and G is N. |
| 5755 | A is A-4d, $(R^2)_n$ is 6-Cl and G is N. |
| 5756 | A is A-4d, $(R^2)_n$ is 6-Br and G is N. |
| 5757 | A is A-4d, $(R^2)_n$ is 6-Me and G is N. |
| 5758 | A is A-4d, $(R^2)_n$ is 6-$CF_3$ and G is N. |

TABLES 4034-5760-continued

| Table | Row Heading |
|---|---|
| 5759 | A is A-4d, $(R^2)_n$ is 6-MeO and G is N. |
| 5760 | A is A-4d, $(R^2)_n$ is 6-CN and G is N. |

TABLE 5761

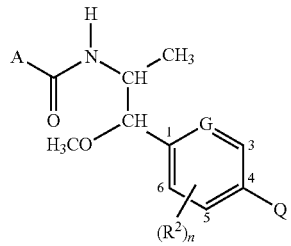

A is A-1a, $(R^2)_n$ is H, and G is CH.

| Q | Q | Q |
|---|---|---|
| 3-CF₃—1H-pyrazol-1-yl | 3-Me—1H-pyrazol-1-yl | 3-F—1H-pyrazol-1-yl |
| 3-Br—1H-pyrazol-1-yl | 4-CF₃—1H-pyrazol-1-yl | 4-Me—1H-pyrazol-1-yl |
| 4-F—1H-pyrazol-1-yl | 4-Br—1H-pyrazol-1-yl | 5-CF₃—1H-pyrazol-1-yl |
| 5-Me—1H-pyrazol-1-yl | 5-F—1H-pyrazol-1-yl | 5-Br—1H-pyrazol-1-yl |
| 3-CHF₂—1H-pyrazol-1-yl | 3-Et—1H-pyrazol-1-yl | 3-Cl—1H-pyrazol-1-yl |
| 3-I—1H-pyrazol-1-yl | 4-CHF₂—1H-pyrazol-1-yl | 4-Et—1H-pyrazol-1-yl |
| 4-Cl—1H-pyrazol-1-yl | 4-I—1H-pyrazol-1-yl | 5-CHF₂—1H-pyrazol-1-yl |
| 5-Et—1H-pyrazol-1-yl | 5-Cl—1H-pyrazol-1-yl | 3-I—1H-pyrazol-1-yl |
| 3-MeO—1H-pyrazol-1-yl | 3-CN—1H-pyrazol-1-yl | 3-CF₃O—1H-pyrazol-1-yl |
| 3-CHF₂O—1H-pyrazol-1-yl | 4-MeO—1H-pyrazol-1-yl | 4-CN—1H-pyrazol-1-yl |
| 4-CF₃O—1H-pyrazol-1-yl | 4-CHF₂O—1H-pyrazol-1-yl | 5-CF₃O—1H-pyrazol-1-yl |
| 5-CN—1H-pyrazol-1-yl | 5-CF₃O—1H-pyrazol-1-yl | 5-CHF₂O—1H-pyrazol-1-yl |
| 3-MeO(O═)C—1H-pyrazol-1-yl | 3-Ph—1H-pyrazol-1-yl | 3,5-di-Me—1H-pyrazol-1-yl |
| 3,5-di-F—1H-pyrazol-1-yl | 4-MeO(O═)C—1H-pyrazol-1-yl | 4-Ph—1H-pyrazol-1-yl |
| 3,5-di-CF₃—1H-pyrazol-1-yl | 3,5-di-Cl—1H-pyrazol-1-yl | 5-MeO(O═)C—1H-pyrazol-1-yl |
| 5-Ph—1H-pyrazol-1-yl | 3,5-di-CHF₂—1H-pyrazol-1-yl | 3,5-di-Br—1H-pyrazol-1-yl |
| 3-CF₃-5-Me-1H-pyrazol-1-yl | 3,4-di-Me—1H-pyrazol-1-yl | 3,4-di-CF₃—1H-pyrazol-1-yl |
| 3,4-di-Br—1H-pyrazol-1-yl | 3,4-di-Cl—1H-pyrazol-1-yl | 1H-pyrazol-1-yl |
| 3-Me—1H-[1,2,4]triazol-1-yl | 3-CF₃—1H-[1,2,4]triazol-1-yl | 3-CHF₂—1H-[1,2,4]triazol-1-yl |
| 3-F—1H-[1,2,4]triazol-1-yl | 3-Cl—1H-[1,2,4]triazol-1-yl | 3-Br—1H-[1,2,4]triazol-1-yl |
| 3,5-di-Me—1H-[1,2,4]triazol-1-yl | 3,5-di-CF₃—1H-[1,2,4]triazol-1-yl | 3,5-di-CHF₂—1H-[1,2,4]triazol-1-yl |
| 3,5-di-Cl—H-[1,2,4]triazol-1-yl | 3,5-di-Br—1H-[1,2,4]triazol-1-yl | 3-Ph—1H-[1,2,4]triazol-1-yl |
| 1H-[1,2,4]triazol-1-yl | 4-Me—2H-[1,2,3]triazol-2-yl | 4-CF₃—2H-[1,2,3]triazol-2-yl |
| 4-CHF₂—2H-[1,2,3]triazol-2-yl | 4-F—2H-[1,2,3]triazol-2-yl | 4-Cl—2H-[1,2,3]triazol-2-yl |
| 4-Br—2H-[1,2,3]triazol-2-yl | 4-Ph—2H-[1,2,3]triazol-2-yl | 4,5-di-Me—2H-[1,2,3]triazol-2-yl |
| 4,5-di-CF₃—2H-[1,2,3]triazol-2-yl | 4,5-di-Cl—2H-[1,2,3]triazol-2-yl | 4,5-di-Br—2H-[1,2,3]triazol-2-yl |
| 2H-[1,2,3]triazol-2-yl | 4-Me—1H-[1,2,3]triazol-1-yl | 4-CF₃—1H-[1,2,3]triazol-1-yl |
| 4-CHF₂—1H-[1,2,3]triazol-1-yl | 4-F—1H-[1,2,3]triazol-1-yl | 4-Cl—1H-[1,2,3]triazol-1-yl |
| 4-Br—1H-[1,2,3]triazol-1-yl | 4-Ph—1H-[1,2,3]triazol-1-yl | 1H-[1,2,3]triazol-1-yl |
| 3-Me—1H-pyrrol-1-yl | 3-CF₃—1H-pyrrol-1-yl | 3-CHF₂—1H-pyrrol-1-yl |
| 3,4-di-Me—1H-pyrrol-1-yl | 2,4-di-Me—1H-pyrrol-1-yl | 3,4-di-CF₃—1H-pyrrol-1-yl |
| 2,4-di-CF₃—1H-pyrrol-1-yl | 3,4-di-Br—1H-pyrrol-1-yl | 3,4-di-Cl—1H-pyrrol-1-yl |
| 1H-pyrrol-1-yl | 1-Me—1H-pyrazol-3-yl | 1-CF₃—1H-pyrazol-3-yl |
| 1-Et—1H-pyrazol-3-yl | 1-i-Pr—1H-pyrazol-3-yl | 1-(F₃CCH₂)—1H-pyrazol-3-yl |
| 1-Ph—1H-pyrazol-3-yl | 1,4-di-Me—1H-pyrazol-3-yl | 1-Me-4-CF₃—1H-pyrazol-3-yl |
| 1-Me—1H-pyrazol-4-yl | 1-CF₃—1H-pyrazol-4-yl | 1-Et—1H-pyrazol-4-yl |
| 1-i-Pr—1H-pyrazol-4-yl | 1-(F₃CCH₂)—1H-pyrazol-4-yl | 1-Ph—1H-pyrazol-4-yl |
| 1,3-di-Me—1H-pyrazol-4-yl | 1-Me-3-CF₃—1H-pyrazol-4-yl | 3-Me-1-CF₃—1H-pyrazol-4-yl |
| 1-Me—1H-[1,2,4]triazol-3-yl | 1-CF₃—1H-[1,2,4]triazol-3-yl | 1-Et—1H-[1,2,4]triazol-3-yl |
| 1-i-Pr—1H-[1,2,4]triazol-3-yl | 1-Ph—1H-[1,2,4]triazol-3-yl | 5-Ph-4,5-dihydro-isoxazol-3-yl |
| 5-CF₃-2,4-dihydro-3-oxopyrazol-1-yl | 5-Me-2,4-dihydro-3-oxopyrazol-1-yl | |

The present disclosure also includes Tables 5762 through 6336 each of which is constructed the same as Table 5761 above, except that the row heading in Table 5761 (i.e. "A is A-1a, $(R^2)_n$ is H, and G is CH.") is replaced with the respective row heading shown below. For example, in Table 5762 the row heading is "A is A-1a, $(R^2)_n$ is 3-F, and G is CH." and Q is as defined in Table 5761 above. Thus, the first entry in Table 5762 specifically discloses N-[2-[3-fluoro-4-[3-(trifluoromethyl)-1H-pyrazol-1-yl]phenyl]-2-methoxy-1-methylethyl]-2-(trifluoromethyl)benzamide. Tables 5763 through 6336 are constructed similarly.

TABLES 5762-6336

| Table | Row Heading |
|---|---|
| 5762 | A is A-1a, $(R^2)_n$ is 3-F and G is CH. |
| 5763 | A is A-1a, $(R^2)_n$ is 3,5-di-F and G is CH. |

TABLES 5762-6336-continued

| Table | Row Heading |
|---|---|
| 5764 | A is A-1a, $(R^2)_n$ is 3-Cl and G is CH. |
| 5765 | A is A-1a, $(R^2)_n$ is 3,5-di-Cl and G is CH. |
| 5766 | A is A-1a, $(R^2)_n$ is 3-Br and G is CH. |
| 5767 | A is A-1a, $(R^2)_n$ is 3,5-di-Br and G is CH. |
| 5768 | A is A-1a, $(R^2)_n$ is 3-Me and G is CH. |
| 5769 | A is A-1a, $(R^2)_n$ is 3,5-di-Me and G is CH. |
| 5770 | A is A-1a, $(R^2)_n$ is 3-CF$_3$ and G is CH. |
| 5771 | A is A-1a, $(R^2)_n$ is 3,5-di-CF$_3$ and G is CH. |
| 5772 | A is A-1a, $(R^2)_n$ is 3-MeO and G is CH. |
| 5773 | A is A-1a, $(R^2)_n$ is 3,5-di-MeO and G is CH. |
| 5774 | A is A-1a, $(R^2)_n$ is 3-CN and G is CH. |
| 5775 | A is A-1a, $(R^2)_n$ is 3,5-di-CN and G is CH. |
| 5776 | A is A-1a, $(R^2)_n$ is 3,6-di-F and G is CH. |
| 5777 | A is A-1a, $(R^2)_n$ is 3,6-di-Cl and G is CH. |
| 5778 | A is A-1a, $(R^2)_n$ is 3,6-di-Br and G is CH. |
| 5779 | A is A-1a, $(R^2)_n$ is 3,6-di-Me and G is CH. |
| 5780 | A is A-1a, $(R^2)_n$ is 3,6-di-CF$_3$ and G is CH. |
| 5781 | A is A-1a, $(R^2)_n$ is 3,6-di-MeO and G is CH. |
| 5782 | A is A-1a, $(R^2)_n$ is 3,6-di-CN and G is CH. |
| 5783 | A is A-1a, $(R^2)_n$ is 6-F and G is CH. |
| 5784 | A is A-1a, $(R^2)_n$ is 6-Cl and G is CH. |
| 5785 | A is A-1a, $(R^2)_n$ is 6-Br and G is CH. |
| 5786 | A is A-1a, $(R^2)_n$ is 6-Me and G is CH. |
| 5787 | A is A-1a, $(R^2)_n$ is 6-CF$_3$ and G is CH. |
| 5788 | A is A-1a, $(R^2)_n$ is 6-MeO and G is CH. |
| 5789 | A is A-1a, $(R^2)_n$ is 6-CN and G is CH. |
| 5790 | A is A-1a, $(R^2)_n$ is 6-F and G is C—F. |
| 5791 | A is A-1a, $(R^2)_n$ is 6-Cl and G is C—Cl. |
| 5792 | A is A-1a, $(R^2)_n$ is 6-Br and G is C—Br. |
| 5793 | A is A-1a, $(R^2)_n$ is 6-Me and G is C—Me. |
| 5794 | A is A-1a, $(R^2)_n$ is 6-CF$_3$ and G is C—CF$_3$. |
| 5795 | A is A-1a, $(R^2)_n$ is 6-MeO and G is C—OMe. |
| 5796 | A is A-1a, $(R^2)_n$ is H and G is N. |
| 5797 | A is A-1a, $(R^2)_n$ is 3-F and G is N. |
| 5798 | A is A-1a, $(R^2)_n$ is 3,5-di-F and G is N. |
| 5799 | A is A-1a, $(R^2)_n$ is 3-Cl and G is N. |
| 5800 | A is A-1a, $(R^2)_n$ is 3,5-di-Cl and G is N. |
| 5801 | A is A-1a, $(R^2)_n$ is 3-Br and G is N. |
| 5802 | A is A-1a, $(R^2)_n$ is 3,5-di-Br and G is N. |
| 5803 | A is A-1a, $(R^2)_n$ is 3-Me and G is N. |
| 5804 | A is A-1a, $(R^2)_n$ is 3,5-di-Me and G is N. |
| 5805 | A is A-1a, $(R^2)_n$ is 3-CF$_3$ and G is N. |
| 5806 | A is A-1a, $(R^2)_n$ is 3,5-di-CF$_3$ and G is N. |
| 5807 | A is A-1a, $(R^2)_n$ is 3-MeO and G is N. |
| 5808 | A is A-1a, $(R^2)_n$ is 3,5-di-MeO and G is N. |
| 5809 | A is A-1a, $(R^2)_n$ is 3-CN and G is N. |
| 5810 | A is A-1a, $(R^2)_n$ is 3,5-di-CN and G is N. |
| 5811 | A is A-1a, $(R^2)_n$ is 3,6-di-F and G is N. |
| 5812 | A is A-1a, $(R^2)_n$ is 3,6-di-Cl and G is N. |
| 5813 | A is A-1a, $(R^2)_n$ is 3,6-di-Br and G is N. |
| 5814 | A is A-1a, $(R^2)_n$ is 3,6-di-Me and G is N. |
| 5815 | A is A-1a, $(R^2)_n$ is 3,6-di-CF$_3$ and G is N. |
| 5816 | A is A-1a, $(R^2)_n$ is 3,6-di-MeO and G is N. |
| 5817 | A is A-1a, $(R^2)_n$ is 3,6-di-CN and G is N. |
| 5818 | A is A-1a, $(R^2)_n$ is 6-F and G is N. |
| 5819 | A is A-1a, $(R^2)_n$ is 6-Cl and G is N. |
| 5820 | A is A-1a, $(R^2)_n$ is 6-Br and G is N. |
| 5821 | A is A-1a, $(R^2)_n$ is 6-Me and G is N. |
| 5822 | A is A-1a, $(R^2)_n$ is 6-CF$_3$ and G is N. |
| 5823 | A is A-1a, $(R^2)_n$ is 6-MeO and G is N. |
| 5824 | A is A-1a, $(R^2)_n$ is 6-CN and G is N. |
| 5825 | A is A-1b, $(R^2)_n$ is H and G is CH. |
| 5826 | A is A-1b, $(R^2)_n$ is 3-F and G is CH. |
| 5827 | A is A-1b, $(R^2)_n$ is 3,5-di-F and G is CH. |
| 5828 | A is A-1b, $(R^2)_n$ is 3-Cl and G is CH. |
| 5829 | A is A-1b, $(R^2)_n$ is 3,5-di-Cl and G is CH. |
| 5830 | A is A-1b, $(R^2)_n$ is 3-Br and G is CH. |
| 5831 | A is A-1b, $(R^2)_n$ is 3,5-di-Br and G is CH. |
| 5832 | A is A-1b, $(R^2)_n$ is 3-Me and G is CH. |
| 5833 | A is A-1b, $(R^2)_n$ is 3,5-di-Me and G is CH. |
| 5834 | A is A-1b, $(R^2)_n$ is 3-CF$_3$ and G is CH. |
| 5835 | A is A-1b, $(R^2)_n$ is 3,5-di-CF$_3$ and G is CH. |
| 5836 | A is A-1b, $(R^2)_n$ is 3-MeO and G is CH. |
| 5837 | A is A-1b, $(R^2)_n$ is 3,5-di-MeO and G is CH. |
| 5838 | A is A-1b, $(R^2)_n$ is 3-CN and G is CH. |
| 5839 | A is A-1b, $(R^2)_n$ is 3,5-di-CN and G is CH. |
| 5840 | A is A-1b, $(R^2)_n$ is 3,6-di-F and G is CH. |
| 5841 | A is A-1b, $(R^2)_n$ is 3,6-di-Cl and G is CH. |
| 5842 | A is A-1b, $(R^2)_n$ is 3,6-di-Br and G is CH. |
| 5843 | A is A-1b, $(R^2)_n$ is 3,6-di-Me and G is CH. |
| 5844 | A is A-1b, $(R^2)_n$ is 3,6-di-CF$_3$ and G is CH. |
| 5845 | A is A-1b, $(R^2)_n$ is 3,6-di-MeO and G is CH. |
| 5846 | A is A-1b, $(R^2)_n$ is 3,6-di-CN and G is CH. |
| 5847 | A is A-1b, $(R^2)_n$ is 6-F and G is CH. |
| 5848 | A is A-1b, $(R^2)_n$ is 6-Cl and G is CH. |
| 5849 | A is A-1b, $(R^2)_n$ is 6-Br and G is CH. |
| 5850 | A is A-1b, $(R^2)_n$ is 6-Me and G is CH. |
| 5851 | A is A-1b, $(R^2)_n$ is 6-CF$_3$ and G is CH. |
| 5852 | A is A-1b, $(R^2)_n$ is 6-MeO and G is CH. |
| 5853 | A is A-1b, $(R^2)_n$ is 6-CN and G is CH. |
| 5854 | A is A-1b, $(R^2)_n$ is 6-F and G is C—F. |
| 5855 | A is A-1b, $(R^2)_n$ is 6-Cl and G is C—Cl. |
| 5856 | A is A-1b, $(R^2)_n$ is 6-Br and G is C—Br. |
| 5857 | A is A-1b, $(R^2)_n$ is 6-Me and G is C—Me. |
| 5858 | A is A-1b, $(R^2)_n$ is 6-CF$_3$ and G is C—CF$_3$. |
| 5859 | A is A-1b, $(R^2)_n$ is 6-MeO and G is C—OMe. |
| 5860 | A is A-1b, $(R^2)_n$ is H and G is N. |
| 5861 | A is A-1b, $(R^2)_n$ is 3-F and G is N. |
| 5862 | A is A-1b, $(R^2)_n$ is 3,5-di-F and G is N. |
| 5863 | A is A-1b, $(R^2)_n$ is 3-Cl and G is N. |
| 5864 | A is A-1b, $(R^2)_n$ is 3,5-di-Cl and G is N. |
| 5865 | A is A-1b, $(R^2)_n$ is 3-Br and G is N. |
| 5866 | A is A-1b, $(R^2)_n$ is 3,5-di-Br and G is N. |
| 5867 | A is A-1b, $(R^2)_n$ is 3-Me and G is N. |
| 5868 | A is A-1b, $(R^2)_n$ is 3,5-di-Me and G is N. |
| 5869 | A is A-1b, $(R^2)_n$ is 3-CF$_3$ and G is N. |
| 5870 | A is A-1b, $(R^2)_n$ is 3,5-di-CF$_3$ and G is N. |
| 5871 | A is A-1b, $(R^2)_n$ is 3-MeO and G is N. |
| 5872 | A is A-1b, $(R^2)_n$ is 3,5-di-MeO and G is N. |
| 5873 | A is A-1b, $(R^2)_n$ is 3-CN and G is N. |
| 5874 | A is A-1b, $(R^2)_n$ is 3,5-di-CN and G is N. |
| 5875 | A is A-1b, $(R^2)_n$ is 3,6-di-F and G is N. |
| 5876 | A is A-1b, $(R^2)_n$ is 3,6-di-Cl and G is N. |
| 5877 | A is A-1b, $(R^2)_n$ is 3,6-di-Br and G is N. |
| 5878 | A is A-1b, $(R^2)_n$ is 3,6-di-Me and G is N. |
| 5879 | A is A-1b, $(R^2)_n$ is 3,6-di-CF$_3$ and G is N. |
| 5880 | A is A-1b, $(R^2)_n$ is 3,6-di-MeO and G is N. |
| 5881 | A is A-1b, $(R^2)_n$ is 3,6-di-CN and G is N. |
| 5882 | A is A-1b, $(R^2)_n$ is 6-F and G is N. |
| 5883 | A is A-1b, $(R^2)_n$ is 6-Cl and G is N. |
| 5884 | A is A-1b, $(R^2)_n$ is 6-Br and G is N. |
| 5885 | A is A-1b, $(R^2)_n$ is 6-Me and G is N. |
| 5886 | A is A-1b, $(R^2)_n$ is 6-CF$_3$ and G is N. |
| 5887 | A is A-1b, $(R^2)_n$ is 6-MeO and G is N. |
| 5888 | A is A-1b, $(R^2)_n$ is 6-CN and G is N. |
| 5889 | A is A-1c, $(R^2)_n$ is H and G is CH. |
| 5890 | A is A-1c, $(R^2)_n$ is 3-F and G is CH. |
| 5891 | A is A-1c, $(R^2)_n$ is 3,5-di-F and G is CH. |
| 5892 | A is A-1c, $(R^2)_n$ is 3-Cl and G is CH. |
| 5893 | A is A-1c, $(R^2)_n$ is 3,5-di-Cl and G is CH. |
| 5894 | A is A-1c, $(R^2)_n$ is 3-Br and G is CH. |
| 5895 | A is A-1c, $(R^2)_n$ is 3,5-di-Br and G is CH. |
| 5896 | A is A-1c, $(R^2)_n$ is 3-Me and G is CH. |
| 5897 | A is A-1c, $(R^2)_n$ is 3,5-di-Me and G is CH. |
| 5898 | A is A-1c, $(R^2)_n$ is 3-CF$_3$ and G is CH. |
| 5899 | A is A-1c, $(R^2)_n$ is 3,5-di-CF$_3$ and G is CH. |
| 5900 | A is A-1c, $(R^2)_n$ is 3-MeO and G is CH. |
| 5901 | A is A-1c, $(R^2)_n$ is 3,5-di-MeO and G is CH. |
| 5902 | A is A-1c, $(R^2)_n$ is 3-CN and G is CH. |
| 5903 | A is A-1c, $(R^2)_n$ is 3,5-di-CN and G is CH. |
| 5904 | A is A-1c, $(R^2)_n$ is 3,6-di-F and G is CH. |
| 5905 | A is A-1c, $(R^2)_n$ is 3,6-di-Cl and G is CH. |
| 5906 | A is A-1c, $(R^2)_n$ is 3,6-di-Br and G is CH. |
| 5907 | A is A-1c, $(R^2)_n$ is 3,6-di-Me and G is CH. |
| 5908 | A is A-1c, $(R^2)_n$ is 3,6-di-CF$_3$ and G is CH. |
| 5909 | A is A-1c, $(R^2)_n$ is 3,6-di-MeO and G is CH. |
| 5910 | A is A-1c, $(R^2)_n$ is 3,6-di-CN and G is CH. |
| 5911 | A is A-1c, $(R^2)_n$ is 6-F and G is CH. |
| 5912 | A is A-1c, $(R^2)_n$ is 6-Cl and G is CH. |
| 5913 | A is A-1c, $(R^2)_n$ is 6-Br and G is CH. |
| 5914 | A is A-1c, $(R^2)_n$ is 6-Me and G is CH. |
| 5915 | A is A-1c, $(R^2)_n$ is 6-CF$_3$ and G is CH. |
| 5916 | A is A-1c, $(R^2)_n$ is 6-MeO and G is CH. |
| 5917 | A is A-1c, $(R^2)_n$ is 6-CN and G is CH. |
| 5918 | A is A-1c, $(R^2)_n$ is 6-F and G is C—F. |
| 5919 | A is A-1c, $(R^2)_n$ is 6-Cl and G is C—Cl. |

TABLES 5762-6336-continued

| Table | Row Heading |
|---|---|
| 5920 | A is A-1c, $(R^2)_n$ is 6-Br and G is C—Br. |
| 5921 | A is A-1c, $(R^2)_n$ is 6-Me and G is C—Me. |
| 5922 | A is A-1c, $(R^2)_n$ is 6-CF$_3$ and G is C—CF$_3$. |
| 5923 | A is A-1c, $(R^2)_n$ is 6-MeO and G is C—OMe. |
| 5924 | A is A-1c, $(R^2)_n$ is H and G is N. |
| 5925 | A is A-1c, $(R^2)_n$ is 3-F and G is N. |
| 5926 | A is A-1c, $(R^2)_n$ is 3,5-di-F and G is N. |
| 5927 | A is A-1c, $(R^2)_n$ is 3-Cl and G is N. |
| 5928 | A is A-1c, $(R^2)_n$ is 3,5-di-Cl and G is N. |
| 5929 | A is A-1c, $(R^2)_n$ is 3-Br and G is N. |
| 5930 | A is A-1c, $(R^2)_n$ is 3,5-di-Br and G is N. |
| 5931 | A is A-1c, $(R^2)_n$ is 3-Me and G is N. |
| 5932 | A is A-1c, $(R^2)_n$ is 3,5-di-Me and G is N. |
| 5933 | A is A-1c, $(R^2)_n$ is 3-CF$_3$ and G is N. |
| 5934 | A is A-1c, $(R^2)_n$ is 3,5-di-CF$_3$ and G is N. |
| 5935 | A is A-1c, $(R^2)_n$ is 3-MeO and G is N. |
| 5936 | A is A-1c, $(R^2)_n$ is 3,5-di-MeO and G is N. |
| 5937 | A is A-1c, $(R^2)_n$ is 3-CN and G is N. |
| 5938 | A is A-1c, $(R^2)_n$ is 3,5-di-CN and G is N. |
| 5939 | A is A-1c, $(R^2)_n$ is 3,6-di-F and G is N. |
| 5940 | A is A-1c, $(R^2)_n$ is 3,6-di-Cl and G is N. |
| 5941 | A is A-1c, $(R^2)_n$ is 3,6-di-Br and G is N. |
| 5942 | A is A-1c, $(R^2)_n$ is 3,6-di-Me and G is N. |
| 5943 | A is A-1c, $(R^2)_n$ is 3,6-di-CF$_3$ and G is N. |
| 5944 | A is A-1c, $(R^2)_n$ is 3,6-di-MeO and G is N. |
| 5945 | A is A-1c, $(R^2)_n$ is 3,6-di-CN and G is N. |
| 5946 | A is A-1c, $(R^2)_n$ is 6-F and G is N. |
| 5947 | A is A-1c, $(R^2)_n$ is 6-Cl and G is N. |
| 5948 | A is A-1c, $(R^2)_n$ is 6-Br and G is N. |
| 5949 | A is A-1c, $(R^2)_n$ is 6-Me and G is N. |
| 5950 | A is A-1c, $(R^2)_n$ is 6-CF$_3$ and G is N. |
| 5951 | A is A-1c, $(R^2)_n$ is 6-MeO and G is N. |
| 5952 | A is A-1c, $(R^2)_n$ is 6-CN and G is N. |
| 5953 | A is A-1d, $(R^2)_n$ is H and G is CH. |
| 5954 | A is A-1d, $(R^2)_n$ is 3-F and G is CH. |
| 5955 | A is A-1d, $(R^2)_n$ is 3,5-di-F and G is CH. |
| 5956 | A is A-1d, $(R^2)_n$ is 3-Cl and G is CH. |
| 5957 | A is A-1d, $(R^2)_n$ is 3,5-di-Cl and G is CH. |
| 5958 | A is A-1d, $(R^2)_n$ is 3-Br and G is CH. |
| 5959 | A is A-1d, $(R^2)_n$ is 3,5-di-Br and G is CH. |
| 5960 | A is A-1d, $(R^2)_n$ is 3-Me and G is CH. |
| 5961 | A is A-1d, $(R^2)_n$ is 3,5-di-Me and G is CH. |
| 5962 | A is A-1d, $(R^2)_n$ is 3-CF$_3$ and G is CH. |
| 5963 | A is A-1d, $(R^2)_n$ is 3,5-di-CF$_3$ and G is CH. |
| 5964 | A is A-1d, $(R^2)_n$ is 3-MeO and G is CH. |
| 5965 | A is A-1d, $(R^2)_n$ is 3,5-di-MeO and G is CH. |
| 5966 | A is A-1d, $(R^2)_n$ is 3-CN and G is CH. |
| 5967 | A is A-1d, $(R^2)_n$ is 3,5-di-CN and G is CH. |
| 5968 | A is A-1d, $(R^2)_n$ is 3,6-di-F and G is CH. |
| 5969 | A is A-1d, $(R^2)_n$ is 3,6-di-Cl and G is CH. |
| 5970 | A is A-1d, $(R^2)_n$ is 3,6-di-Br and G is CH. |
| 5971 | A is A-1d, $(R^2)_n$ is 3,6-di-Me and G is CH. |
| 5972 | A is A-1d, $(R^2)_n$ is 3,6-di-CF$_3$ and G is CH. |
| 5973 | A is A-1d, $(R^2)_n$ is 3,6-di-MeO and G is CH. |
| 5974 | A is A-1d, $(R^2)_n$ is 3,6-di-CN and G is CH. |
| 5975 | A is A-1d, $(R^2)_n$ is 6-F and G is CH. |
| 5976 | A is A-1d, $(R^2)_n$ is 6-Cl and G is CH. |
| 5977 | A is A-1d, $(R^2)_n$ is 6-Br and G is CH. |
| 5978 | A is A-1d, $(R^2)_n$ is 6-Me and G is CH. |
| 5979 | A is A-1d, $(R^2)_n$ is 6-CF$_3$ and G is CH. |
| 5980 | A is A-1d, $(R^2)_n$ is 6-MeO and G is CH. |
| 5981 | A is A-1d, $(R^2)_n$ is 6-CN and G is CH. |
| 5982 | A is A-1d, $(R^2)_n$ is 6-F and G is C—F. |
| 5983 | A is A-1d, $(R^2)_n$ is 6-Cl and G is C—Cl. |
| 5984 | A is A-1d, $(R^2)_n$ is 6-Br and G is C—Br. |
| 5985 | A is A-1d, $(R^2)_n$ is 6-Me and G is C—Me. |
| 5986 | A is A-1d, $(R^2)_n$ is 6-CF$_3$ and G is C—CF$_3$. |
| 5987 | A is A-1d, $(R^2)_n$ is 6-MeO and G is C—OMe. |
| 5988 | A is A-1d, $(R^2)_n$ is H and G is N. |
| 5989 | A is A-1d, $(R^2)_n$ is 3-F and G is N. |
| 5990 | A is A-1d, $(R^2)_n$ is 3,5-di-F and G is N. |
| 5991 | A is A-1d, $(R^2)_n$ is 3-Cl and G is N. |
| 5992 | A is A-1d, $(R^2)_n$ is 3,5-di-Cl and G is N. |
| 5993 | A is A-1d, $(R^2)_n$ is 3-Br and G is N. |
| 5994 | A is A-1d, $(R^2)_n$ is 3,5-di-Br and G is N. |
| 5995 | A is A-1d, $(R^2)_n$ is 3-Me and G is N. |
| 5996 | A is A-1d, $(R^2)_n$ is 3,5-di-Me and G is N. |
| 5997 | A is A-1d, $(R^2)_n$ is 3-CF$_3$ and G is N. |
| 5998 | A is A-1d, $(R^2)_n$ is 3,5-di-CF$_3$ and G is N. |
| 5999 | A is A-1d, $(R^2)_n$ is 3-MeO and G is N. |
| 6000 | A is A-1d, $(R^2)_n$ is 3,5-di-MeO and G is N. |
| 6001 | A is A-1d, $(R^2)_n$ is 3-CN and G is N. |
| 6002 | A is A-1d, $(R^2)_n$ is 3,5-di-CN and G is N. |
| 6003 | A is A-1d, $(R^2)_n$ is 3,6-di-F and G is N. |
| 6004 | A is A-1d, $(R^2)_n$ is 3,6-di-Cl and G is N. |
| 6005 | A is A-1d, $(R^2)_n$ is 3,6-di-Br and G is N. |
| 6006 | A is A-1d, $(R^2)_n$ is 3,6-di-Me and G is N. |
| 6007 | A is A-1d, $(R^2)_n$ is 3,6-di-CF$_3$ and G is N. |
| 6008 | A is A-1d, $(R^2)_n$ is 3,6-di-MeO and G is N. |
| 6009 | A is A-1d, $(R^2)_n$ is 3,6-di-CN and G is N. |
| 6010 | A is A-1d, $(R^2)_n$ is 6-F and G is N. |
| 6011 | A is A-1d, $(R^2)_n$ is 6-Cl and G is N. |
| 6012 | A is A-1d, $(R^2)_n$ is 6-Br and G is N. |
| 6013 | A is A-1d, $(R^2)_n$ is 6-Me and G is N. |
| 6014 | A is A-1d, $(R^2)_n$ is 6-CF$_3$ and G is N. |
| 6015 | A is A-1d, $(R^2)_n$ is 6-MeO and G is N. |
| 6016 | A is A-1d, $(R^2)_n$ is 6-CN and G is N. |
| 6017 | A is A-1e, $(R^2)_n$ is H and G is CH. |
| 6018 | A is A-1e, $(R^2)_n$ is 3-F and G is CH. |
| 6019 | A is A-1e, $(R^2)_n$ is 3,5-di-F and G is CH. |
| 6020 | A is A-1e, $(R^2)_n$ is 3-Cl and G is CH. |
| 6021 | A is A-1e, $(R^2)_n$ is 3,5-di-Cl and G is CH. |
| 6022 | A is A-1e, $(R^2)_n$ is 3-Br and G is CH. |
| 6023 | A is A-1e, $(R^2)_n$ is 3,5-di-Br and G is CH. |
| 6024 | A is A-1e, $(R^2)_n$ is 3-Me and G is CH. |
| 6025 | A is A-1e, $(R^2)_n$ is 3,5-di-Me and G is CH. |
| 6026 | A is A-1e, $(R^2)_n$ is 3-CF$_3$ and G is CH. |
| 6027 | A is A-1e, $(R^2)_n$ is 3,5-di-CF$_3$ and G is CH. |
| 6028 | A is A-1e, $(R^2)_n$ is 3-MeO and G is CH. |
| 6029 | A is A-1e, $(R^2)_n$ is 3,5-di-MeO and G is CH. |
| 6030 | A is A-1e, $(R^2)_n$ is 3-CN and G is CH. |
| 6031 | A is A-1e, $(R^2)_n$ is 3,5-di-CN and G is CH. |
| 6032 | A is A-1e, $(R^2)_n$ is 3,6-di-F and G is CH. |
| 6033 | A is A-1e, $(R^2)_n$ is 3,6-di-Cl and G is CH. |
| 6034 | A is A-1e, $(R^2)_n$ is 3,6-di-Br and G is CH. |
| 6035 | A is A-1e, $(R^2)_n$ is 3,6-di-Me and G is CH. |
| 6036 | A is A-1e, $(R^2)_n$ is 3,6-di-CF$_3$ and G is CH. |
| 6037 | A is A-1e, $(R^2)_n$ is 3,6-di-MeO and G is CH. |
| 6038 | A is A-1e, $(R^2)_n$ is 3,6-di-CN and G is CH. |
| 6039 | A is A-1e, $(R^2)_n$ is 6-F and G is CH. |
| 6040 | A is A-1e, $(R^2)_n$ is 6-Cl and G is CH. |
| 6041 | A is A-1e, $(R^2)_n$ is 6-Br and G is CH. |
| 6042 | A is A-1e, $(R^2)_n$ is 6-Me and G is CH. |
| 6043 | A is A-1e, $(R^2)_n$ is 6-CF$_3$ and G is CH. |
| 6044 | A is A-1e, $(R^2)_n$ is 6-MeO and G is CH. |
| 6045 | A is A-1e, $(R^2)_n$ is 6-CN and G is CH. |
| 6046 | A is A-1e, $(R^2)_n$ is 6-F and G is C—F. |
| 6047 | A is A-1e, $(R^2)_n$ is 6-Cl and G is C—Cl. |
| 6048 | A is A-1e, $(R^2)_n$ is 6-Br and G is C—Br. |
| 6049 | A is A-1e, $(R^2)_n$ is 6-Me and G is C—Me. |
| 6050 | A is A-1e, $(R^2)_n$ is 6-CF$_3$ and G is C—CF$_3$. |
| 6051 | A is A-1e, $(R^2)_n$ is 6-MeO and G is C—OMe. |
| 6052 | A is A-1e, $(R^2)_n$ is H and G is N. |
| 6053 | A is A-1e, $(R^2)_n$ is 3-F and G is N. |
| 6054 | A is A-1e, $(R^2)_n$ is 3,5-di-F and G is N. |
| 6055 | A is A-1e, $(R^2)_n$ is 3-Cl and G is N. |
| 6056 | A is A-1e, $(R^2)_n$ is 3,5-di-Cl and G is N. |
| 6057 | A is A-1e, $(R^2)_n$ is 3-Br and G is N. |
| 6058 | A is A-1e, $(R^2)_n$ is 3,5-di-Br and G is N. |
| 6059 | A is A-1e, $(R^2)_n$ is 3-Me and G is N. |
| 6060 | A is A-1e, $(R^2)_n$ is 3,5-di-Me and G is N. |
| 6061 | A is A-1e, $(R^2)_n$ is 3-CF$_3$ and G is N. |
| 6062 | A is A-1e, $(R^2)_n$ is 3,5-di-CF$_3$ and G is N. |
| 6063 | A is A-1e, $(R^2)_n$ is 3-MeO and G is N. |
| 6064 | A is A-1e, $(R^2)_n$ is 3,5-di-MeO and G is N. |
| 6065 | A is A-1e, $(R^2)_n$ is 3-CN and G is N. |
| 6066 | A is A-1e, $(R^2)_n$ is 3,5-di-CN and G is N. |
| 6067 | A is A-1e, $(R^2)_n$ is 3,6-di-F and G is N. |
| 6068 | A is A-1e, $(R^2)_n$ is 3,6-di-Cl and G is N. |
| 6069 | A is A-1e, $(R^2)_n$ is 3,6-di-Br and G is N. |
| 6070 | A is A-1e, $(R^2)_n$ is 3,6-di-Me and G is N. |
| 6071 | A is A-1e, $(R^2)_n$ is 3,6-di-CF$_3$ and G is N. |
| 6072 | A is A-1e, $(R^2)_n$ is 3,6-di-MeO and G is N. |
| 6073 | A is A-1e, $(R^2)_n$ is 3,6-di-CN and G is N. |
| 6074 | A is A-1e, $(R^2)_n$ is 6-F and G is N. |
| 6075 | A is A-1e, $(R^2)_n$ is 6-Cl and G is N. |

TABLES 5762-6336-continued

| Table | Row Heading |
|---|---|
| 6076 | A is A-1e, $(R^2)_n$ is 6-Br and G is N. |
| 6077 | A is A-1e, $(R^2)_n$ is 6-Me and G is N. |
| 6078 | A is A-1e, $(R^2)_n$ is 6-CF$_3$ and G is N. |
| 6079 | A is A-1e, $(R^2)_n$ is 6-MeO and G is N. |
| 6080 | A is A-1e, $(R^2)_n$ is 6-CN and G is N. |
| 6081 | A is A-1f, $(R^2)_n$ is H and G is CH. |
| 6082 | A is A-1f, $(R^2)_n$ is 3-F and G is CH. |
| 6083 | A is A-1f, $(R^2)_n$ is 3,5-di-F and G is CH. |
| 6084 | A is A-1f, $(R^2)_n$ is 3-Cl and G is CH. |
| 6085 | A is A-1f, $(R^2)_n$ is 3,5-di-Cl and G is CH. |
| 6086 | A is A-1f, $(R^2)_n$ is 3-Br and G is CH. |
| 6087 | A is A-1f, $(R^2)_n$ is 3,5-di-Br and G is CH. |
| 6088 | A is A-1f, $(R^2)_n$ is 3-Me and G is CH. |
| 6089 | A is A-1f, $(R^2)_n$ is 3,5-di-Me and G is CH. |
| 6090 | A is A-1f, $(R^2)_n$ is 3-CF$_3$ and G is CH. |
| 6091 | A is A-1f, $(R^2)_n$ is 3,5-di-CF$_3$ and G is CH. |
| 6092 | A is A-1f, $(R^2)_n$ is 3-MeO and G is CH. |
| 6093 | A is A-1f, $(R^2)_n$ is 3,5-di-MeO and G is CH. |
| 6094 | A is A-1f, $(R^2)_n$ is 3-CN and G is CH. |
| 6095 | A is A-1f, $(R^2)_n$ is 3,5-di-CN and G is CH. |
| 6096 | A is A-1f, $(R^2)_n$ is 3,6-di-F and G is CH. |
| 6097 | A is A-1f, $(R^2)_n$ is 3,6-di-Cl and G is CH. |
| 6098 | A is A-1f, $(R^2)_n$ is 3,6-di-Br and G is CH. |
| 6099 | A is A-1f, $(R^2)_n$ is 3,6-di-Me and G is CH. |
| 6100 | A is A-1f, $(R^2)_n$ is 3,6-di-CF$_3$ and G is CH. |
| 6101 | A is A-1f, $(R^2)_n$ is 3,6-di-MeO and G is CH. |
| 6102 | A is A-1f, $(R^2)_n$ is 3,6-di-CN and G is CH. |
| 6103 | A is A-1f, $(R^2)_n$ is 6-F and G is CH. |
| 6104 | A is A-1f, $(R^2)_n$ is 6-Cl and G is CH. |
| 6105 | A is A-1f, $(R^2)_n$ is 6-Br and G is CH. |
| 6106 | A is A-1f, $(R^2)_n$ is 6-Me and G is CH. |
| 6107 | A is A-1f, $(R^2)_n$ is 6-CF$_3$ and G is CH. |
| 6108 | A is A-1f, $(R^2)_n$ is 6-MeO and G is CH. |
| 6109 | A is A-1f, $(R^2)_n$ is 6-CN and G is CH. |
| 6110 | A is A-1f, $(R^2)_n$ is 6-F and G is C—F. |
| 6111 | A is A-1f, $(R^2)_n$ is 6-Cl and G is C—Cl. |
| 6112 | A is A-1f, $(R^2)_n$ is 6-Br and G is C—Br. |
| 6113 | A is A-1f, $(R^2)_n$ is 6-Me and G is C—Me. |
| 6114 | A is A-1f, $(R^2)_n$ is 6-CF$_3$ and G is C—CF$_3$. |
| 6115 | A is A-1f, $(R^2)_n$ is 6-MeO and G is C—OMe. |
| 6116 | A is A-1f, $(R^2)_n$ is H and G is N. |
| 6117 | A is A-1f, $(R^2)_n$ is 3-F and G is N. |
| 6118 | A is A-1f, $(R^2)_n$ is 3,5-di-F and G is N. |
| 6119 | A is A-1f, $(R^2)_n$ is 3-Cl and G is N. |
| 6120 | A is A-1f, $(R^2)_n$ is 3,5-di-Cl and G is N. |
| 6121 | A is A-1f, $(R^2)_n$ is 3-Br and G is N. |
| 6122 | A is A-1f, $(R^2)_n$ is 3,5-di-Br and G is N. |
| 6123 | A is A-1f, $(R^2)_n$ is 3-Me and G is N. |
| 6124 | A is A-1f, $(R^2)_n$ is 3,5-di-Me and G is N. |
| 6125 | A is A-1f, $(R^2)_n$ is 3-CF$_3$ and G is N. |
| 6126 | A is A-1f, $(R^2)_n$ is 3,5-di-CF$_3$ and G is N. |
| 6127 | A is A-1f, $(R^2)_n$ is 3-MeO and G is N. |
| 6128 | A is A-1f, $(R^2)_n$ is 3,5-di-MeO and G is N. |
| 6129 | A is A-1f, $(R^2)_n$ is 3-CN and G is N. |
| 6130 | A is A-1f, $(R^2)_n$ is 3,5-di-CN and G is N. |
| 6131 | A is A-1f, $(R^2)_n$ is 3,6-di-F and G is N. |
| 6132 | A is A-1f, $(R^2)_n$ is 3,6-di-Cl and G is N. |
| 6133 | A is A-1f, $(R^2)_n$ is 3,6-di-Br and G is N. |
| 6134 | A is A-1f, $(R^2)_n$ is 3,6-di-Me and G is N. |
| 6135 | A is A-1f, $(R^2)_n$ is 3,6-di-CF$_3$ and G is N. |
| 6136 | A is A-1f, $(R^2)_n$ is 3,6-di-MeO and G is N. |
| 6137 | A is A-1f, $(R^2)_n$ is 3,6-di-CN and G is N. |
| 6138 | A is A-1f, $(R^2)_n$ is 6-F and G is N. |
| 6139 | A is A-1f, $(R^2)_n$ is 6-Cl and G is N. |
| 6140 | A is A-1f, $(R^2)_n$ is 6-Br and G is N. |
| 6141 | A is A-1f, $(R^2)_n$ is 6-Me and G is N. |
| 6142 | A is A-1f, $(R^2)_n$ is 6-CF$_3$ and G is N. |
| 6143 | A is A-1f, $(R^2)_n$ is 6-MeO and G is N. |
| 6144 | A is A-1f, $(R^2)_n$ is 6-CN and G is N. |
| 6145 | A is A-2a, $(R^2)_n$ is H and G is CH. |
| 6146 | A is A-2a, $(R^2)_n$ is 3-F and G is CH. |
| 6147 | A is A-2a, $(R^2)_n$ is 3,5-di-F and G is CH. |
| 6148 | A is A-2a, $(R^2)_n$ is 3-Cl and G is CH. |
| 6149 | A is A-2a, $(R^2)_n$ is 3,5-di-Cl and G is CH. |
| 6150 | A is A-2a, $(R^2)_n$ is 3-Br and G is CH. |
| 6151 | A is A-2a, $(R^2)_n$ is 3,5-di-Br and G is CH. |
| 6152 | A is A-2a, $(R^2)_n$ is 3-Me and G is CH. |
| 6153 | A is A-2a, $(R^2)_n$ is 3,5-di-Me and G is CH. |
| 6154 | A is A-2a, $(R^2)_n$ is 3-CF$_3$ and G is CH. |
| 6155 | A is A-2a, $(R^2)_n$ is 3,5-di-CF$_3$ and G is CH. |
| 6156 | A is A-2a, $(R^2)_n$ is 3-MeO and G is CH. |
| 6157 | A is A-2a, $(R^2)_n$ is 3,5-di-MeO and G is CH. |
| 6158 | A is A-2a, $(R^2)_n$ is 3-CN and G is CH. |
| 6159 | A is A-2a, $(R^2)_n$ is 3,5-di-CN and G is CH. |
| 6160 | A is A-2a, $(R^2)_n$ is 3,6-di-F and G is CH. |
| 6161 | A is A-2a, $(R^2)_n$ is 3,6-di-Cl and G is CH. |
| 6162 | A is A-2a, $(R^2)_n$ is 3,6-di-Br and G is CH. |
| 6163 | A is A-2a, $(R^2)_n$ is 3,6-di-Me and G is CH. |
| 6164 | A is A-2a, $(R^2)_n$ is 3,6-di-CF$_3$ and G is CH. |
| 6165 | A is A-2a, $(R^2)_n$ is 3,6-di-MeO and G is CH. |
| 6166 | A is A-2a, $(R^2)_n$ is 3,6-di-CN and G is CH. |
| 6167 | A is A-2a, $(R^2)_n$ is 6-F and G is CH. |
| 6168 | A is A-2a, $(R^2)_n$ is 6-Cl and G is CH. |
| 6169 | A is A-2a, $(R^2)_n$ is 6-Br and G is CH. |
| 6170 | A is A-2a, $(R^2)_n$ is 6-Me and G is CH. |
| 6171 | A is A-2a, $(R^2)_n$ is 6-CF$_3$ and G is CH. |
| 6172 | A is A-2a, $(R^2)_n$ is 6-MeO and G is CH. |
| 6173 | A is A-2a, $(R^2)_n$ is 6-CN and G is CH. |
| 6174 | A is A-2a, $(R^2)_n$ is 6-F and G is C—F. |
| 6175 | A is A-2a, $(R^2)_n$ is 6-Cl and G is C—Cl. |
| 6176 | A is A-2a, $(R^2)_n$ is 6-Br and G is C—Br. |
| 6177 | A is A-2a, $(R^2)_n$ is 6-Me and G is C—Me. |
| 6178 | A is A-2a, $(R^2)_n$ is 6-CF$_3$ and G is C—CF$_3$. |
| 6179 | A is A-2a, $(R^2)_n$ is 6-MeO and G is C—OMe. |
| 6180 | A is A-2a, $(R^2)_n$ is H and G is N. |
| 6181 | A is A-2a, $(R^2)_n$ is 3-F and G is N. |
| 6182 | A is A-2a, $(R^2)_n$ is 3,5-di-F and G is N. |
| 6183 | A is A-2a, $(R^2)_n$ is 3-Cl and G is N. |
| 6184 | A is A-2a, $(R^2)_n$ is 3,5-di-Cl and G is N. |
| 6185 | A is A-2a, $(R^2)_n$ is 3-Br and G is N. |
| 6186 | A is A-2a, $(R^2)_n$ is 3,5-di-Br and G is N. |
| 6187 | A is A-2a, $(R^2)_n$ is 3-Me and G is N. |
| 6188 | A is A-2a, $(R^2)_n$ is 3,5-di-Me and G is N. |
| 6189 | A is A-2a, $(R^2)_n$ is 3-CF$_3$ and G is N. |
| 6190 | A is A-2a, $(R^2)_n$ is 3,5-di-CF$_3$ and G is N. |
| 6191 | A is A-2a, $(R^2)_n$ is 3-MeO and G is N. |
| 6192 | A is A-2a, $(R^2)_n$ is 3,5-di-MeO and G is N. |
| 6193 | A is A-2a, $(R^2)_n$ is 3-CN and G is N. |
| 6194 | A is A-2a, $(R^2)_n$ is 3,5-di-CN and G is N. |
| 6195 | A is A-2a, $(R^2)_n$ is 3,6-di-F and G is N. |
| 6196 | A is A-2a, $(R^2)_n$ is 3,6-di-Cl and G is N. |
| 6197 | A is A-2a, $(R^2)_n$ is 3,6-di-Br and G is N. |
| 6198 | A is A-2a, $(R^2)_n$ is 3,6-di-Me and G is N. |
| 6199 | A is A-2a, $(R^2)_n$ is 3,6-di-CF$_3$ and G is N. |
| 6200 | A is A-2a, $(R^2)_n$ is 3,6-di-MeO and G is N. |
| 6201 | A is A-2a, $(R^2)_n$ is 3,6-di-CN and G is N. |
| 6202 | A is A-2a, $(R^2)_n$ is 6-F and G is N. |
| 6203 | A is A-2a, $(R^2)_n$ is 6-Cl and G is N. |
| 6204 | A is A-2a, $(R^2)_n$ is 6-Br and G is N. |
| 6205 | A is A-2a, $(R^2)_n$ is 6-Me and G is N. |
| 6206 | A is A-2a, $(R^2)_n$ is 6-CF$_3$ and G is N. |
| 6207 | A is A-2a, $(R^2)_n$ is 6-MeO and G is N. |
| 6208 | A is A-2a, $(R^2)_n$ is 6-CN and G is N. |
| 6209 | A is A-2b, $(R^2)_n$ is H and G is CH. |
| 6210 | A is A-2b, $(R^2)_n$ is 3-F and G is CH. |
| 6211 | A is A-2b, $(R^2)_n$ is 3,5-di-F and G is CH. |
| 6212 | A is A-2b, $(R^2)_n$ is 3-Cl and G is CH. |
| 6213 | A is A-2b, $(R^2)_n$ is 3,5-di-Cl and G is CH. |
| 6214 | A is A-2b, $(R^2)_n$ is 3-Br and G is CH. |
| 6215 | A is A-2b, $(R^2)_n$ is 3,5-di-Br and G is CH. |
| 6216 | A is A-2b, $(R^2)_n$ is 3-Me and G is CH. |
| 6217 | A is A-2b, $(R^2)_n$ is 3,5-di-Me and G is CH. |
| 6218 | A is A-2b, $(R^2)_n$ is 3-CF$_3$ and G is CH. |
| 6219 | A is A-2b, $(R^2)_n$ is 3,5-di-CF$_3$ and G is CH. |
| 6220 | A is A-2b, $(R^2)_n$ is 3-MeO and G is CH. |
| 6221 | A is A-2b, $(R^2)_n$ is 3,5-di-MeO and G is CH. |
| 6222 | A is A-2b, $(R^2)_n$ is 3-CN and G is CH. |
| 6223 | A is A-2b, $(R^2)_n$ is 3,5-di-CN and G is CH. |
| 6224 | A is A-2b, $(R^2)_n$ is 3,6-di-F and G is CH. |
| 6225 | A is A-2b, $(R^2)_n$ is 3,6-di-Cl and G is CH. |
| 6226 | A is A-2b, $(R^2)_n$ is 3,6-di-Br and G is CH. |
| 6227 | A is A-2b, $(R^2)_n$ is 3,6-di-Me and G is CH. |
| 6228 | A is A-2b, $(R^2)_n$ is 3,6-di-CF$_3$ and G is CH. |
| 6229 | A is A-2b, $(R^2)_n$ is 3,6-di-MeO and G is CH. |
| 6230 | A is A-2b, $(R^2)_n$ is 3,6-di-CN and G is CH. |
| 6231 | A is A-2b, $(R^2)_n$ is 6-F and G is CH. |

TABLES 5762-6336-continued

| Table | Row Heading |
|---|---|
| 6232 | A is A-2b, (R²)ₙ is 6-Cl and G is CH. |
| 6233 | A is A-2b, (R²)ₙ is 6-Br and G is CH. |
| 6234 | A is A-2b, (R²)ₙ is 6-Me and G is CH. |
| 6235 | A is A-2b, (R²)ₙ is 6-CF₃ and G is CH. |
| 6236 | A is A-2b, (R²)ₙ is 6-MeO and G is CH. |
| 6237 | A is A-2b, (R²)ₙ is 6-CN and G is CH. |
| 6238 | A is A-2b, (R²)ₙ is 6-F and G is C—F. |
| 6239 | A is A-2b, (R²)ₙ is 6-Cl and G is C—Cl. |
| 6240 | A is A-2b, (R²)ₙ is 6-Br and G is C—Br. |
| 6241 | A is A-2b, (R²)ₙ is 6-Me and G is C—Me. |
| 6242 | A is A-2b, (R²)ₙ is 6-CF₃ and G is C—CF₃. |
| 6243 | A is A-2b, (R²)ₙ is 6-MeO and G is C—OMe. |
| 6244 | A is A-2b, (R²)ₙ is H and G is N. |
| 6245 | A is A-2b, (R²)ₙ is 3-F and G is N. |
| 6246 | A is A-2b, (R²)ₙ is 3,5-di-F and G is N. |
| 6247 | A is A-2b, (R²)ₙ is 3-Cl and G is N. |
| 6248 | A is A-2b, (R²)ₙ is 3,5-di-Cl and G is N. |
| 6249 | A is A-2b, (R²)ₙ is 3-Br and G is N. |
| 6250 | A is A-2b, (R²)ₙ is 3,5-di-Br and G is N. |
| 6251 | A is A-2b, (R²)ₙ is 3-Me and G is N. |
| 6252 | A is A-2b, (R²)ₙ is 3,5-di-Me and G is N. |
| 6253 | A is A-2b, (R²)ₙ is 3-CF₃ and G is N. |
| 6254 | A is A-2b, (R²)ₙ is 3,5-di-CF₃ and G is N. |
| 6255 | A is A-2b, (R²)ₙ is 3-MeO and G is N. |
| 6256 | A is A-2b, (R²)ₙ is 3,5-di-MeO and G is N. |
| 6257 | A is A-2b, (R²)ₙ is 3-CN and G is N. |
| 6258 | A is A-2b, (R²)ₙ is 3,5-di-CN and G is N. |
| 6259 | A is A-2b, (R²)ₙ is 3,6-di-F and G is N. |
| 6260 | A is A-2b, (R²)ₙ is 3,6-di-Cl and G is N. |
| 6261 | A is A-2b, (R²)ₙ is 3,6-di-Br and G is N. |
| 6262 | A is A-2b, (R²)ₙ is 3,6-di-Me and G is N. |
| 6263 | A is A-2b, (R²)ₙ is 3,6-di-CF₃ and G is N. |
| 6264 | A is A-2b, (R²)ₙ is 3,6-di-MeO and G is N. |
| 6265 | A is A-2b, (R²)ₙ is 3,6-di-CN and G is N. |
| 6266 | A is A-2b, (R²)ₙ is 6-F and G is N. |
| 6267 | A is A-2b, (R²)ₙ is 6-Cl and G is N. |
| 6268 | A is A-2b, (R²)ₙ is 6-Br and G is N. |
| 6269 | A is A-2b, (R²)ₙ is 6-Me and G is N. |
| 6270 | A is A-2b, (R²)ₙ is 6-CF₃ and G is N. |
| 6271 | A is A-2b, (R²)ₙ is 6-MeO and G is N. |
| 6272 | A is A-2b, (R²)ₙ is 6-CN and G is N. |
| 6273 | A is A-2c, (R²)ₙ is H and G is CH. |
| 6274 | A is A-2c, (R²)ₙ is 3-F and G is CH. |
| 6275 | A is A-2c, (R²)ₙ is 3,5-di-F and G is CH. |
| 6276 | A is A-2c, (R²)ₙ is 3-Cl and G is CH. |
| 6277 | A is A-2c, (R²)ₙ is 3,5-di-Cl and G is CH. |
| 6278 | A is A-2c, (R²)ₙ is 3-Br and G is CH. |
| 6279 | A is A-2c, (R²)ₙ is 3,5-di-Br and G is CH. |
| 6280 | A is A-2c, (R²)ₙ is 3-Me and G is CH. |
| 6281 | A is A-2c, (R²)ₙ is 3,5-di-Me and G is CH. |
| 6282 | A is A-2c, (R²)ₙ is 3-CF₃ and G is CH. |
| 6283 | A is A-2c, (R²)ₙ is 3,5-di-CF₃ and G is CH. |
| 6284 | A is A-2c, (R²)ₙ is 3-MeO and G is CH. |
| 6285 | A is A-2c, (R²)ₙ is 3,5-di-MeO and G is CH. |
| 6286 | A is A-2c, (R²)ₙ is 3-CN and G is CH. |
| 6287 | A is A-2c, (R²)ₙ is 3,5-di-CN and G is CH. |
| 6288 | A is A-2c, (R²)ₙ is 3,6-di-F and G is CH. |
| 6289 | A is A-2c, (R²)ₙ is 3,6-di-Cl and G is CH. |
| 6290 | A is A-2c, (R²)ₙ is 3,6-di-Br and G is CH. |
| 6291 | A is A-2c, (R²)ₙ is 3,6-di-Me and G is CH. |
| 6292 | A is A-2c, (R²)ₙ is 3,6-di-CF₃ and G is CH. |
| 6293 | A is A-2c, (R²)ₙ is 3,6-di-MeO and G is CH. |
| 6294 | A is A-2c, (R²)ₙ is 3,6-di-CN and G is CH. |
| 6295 | A is A-2c, (R²)ₙ is 6-F and G is CH. |
| 6296 | A is A-2c, (R²)ₙ is 6-Cl and G is CH. |
| 6297 | A is A-2c, (R²)ₙ is 6-Br and G is CH. |
| 6298 | A is A-2c, (R²)ₙ is 6-Me and G is CH. |
| 6299 | A is A-2c, (R²)ₙ is 6-CF₃ and G is CH. |
| 6300 | A is A-2c, (R²)ₙ is 6-MeO and G is CH. |
| 6301 | A is A-2c, (R²)ₙ is 6-CN and G is CH. |
| 6302 | A is A-2c, (R²)ₙ is 6-F and G is C—F. |
| 6303 | A is A-2c, (R²)ₙ is 6-Cl and G is C—Cl. |
| 6304 | A is A-2c, (R²)ₙ is 6-Br and G is C—Br. |
| 6305 | A is A-2c, (R²)ₙ is 6-Me and G is C—Me. |
| 6306 | A is A-2c, (R²)ₙ is 6-CF₃ and G is C—CF₃. |
| 6307 | A is A-2c, (R²)ₙ is 6-MeO and G is C—OMe. |
| 6308 | A is A-2c, (R²)ₙ is H and G is N. |
| 6309 | A is A-2c, (R²)ₙ is 3-F and G is N. |
| 6310 | A is A-2c, (R²)ₙ is 3,5-di-F and G is N. |
| 6311 | A is A-2c, (R²)ₙ is 3-Cl and G is N. |
| 6312 | A is A-2c, (R²)ₙ is 3,5-di-Cl and G is N. |
| 6313 | A is A-2c, (R²)ₙ is 3-Br and G is N. |
| 6314 | A is A-2c, (R²)ₙ is 3,5-di-Br and G is N. |
| 6315 | A is A-2c, (R²)ₙ is 3-Me and G is N. |
| 6316 | A is A-2c, (R²)ₙ is 3,5-di-Me and G is N. |
| 6317 | A is A-2c, (R²)ₙ is 3-CF₃ and G is N. |
| 6318 | A is A-2c, (R²)ₙ is 3,5-di-CF₃ and G is N. |
| 6319 | A is A-2c, (R²)ₙ is 3-MeO and G is N. |
| 6320 | A is A-2c, (R²)ₙ is 3,5-di-MeO and G is N. |
| 6321 | A is A-2c, (R²)ₙ is 3-CN and G is N. |
| 6322 | A is A-2c, (R²)ₙ is 3,5-di-CN and G is N. |
| 6323 | A is A-2c, (R²)ₙ is 3,6-di-F and G is N. |
| 6324 | A is A-2c, (R²)ₙ is 3,6-di-Cl and G is N. |
| 6325 | A is A-2c, (R²)ₙ is 3,6-di-Br and G is N. |
| 6326 | A is A-2c, (R²)ₙ is 3,6-di-Me and G is N. |
| 6327 | A is A-2c, (R²)ₙ is 3,6-di-CF₃ and G is N. |
| 6328 | A is A-2c, (R²)ₙ is 3,6-di-MeO and G is N. |
| 6329 | A is A-2c, (R²)ₙ is 3,6-di-CN and G is N. |
| 6330 | A is A-2c, (R²)ₙ is 6-F and G is N. |
| 6331 | A is A-2c, (R²)ₙ is 6-Cl and G is N. |
| 6332 | A is A-2c, (R²)ₙ is 6-Br and G is N. |
| 6333 | A is A-2c, (R²)ₙ is 6-Me and G is N. |
| 6334 | A is A-2c, (R²)ₙ is 6-CF₃ and G is N. |
| 6335 | A is A-2c, (R²)ₙ is 6-MeO and G is N. |
| 6336 | A is A-2c, (R²)ₙ is 6-CN and G is N. |

TABLE 6337

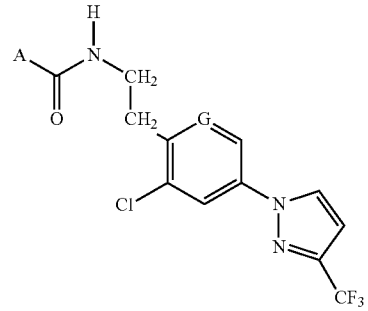

| A | G |
|---|---|
| A-1a | CH |
| A-1b | CH |
| A-1c | CH |
| A-1d | CH |
| A-1e | CH |
| A-1f | CH |
| A-1g | CH |
| A-1h | CH |
| A-1i | CH |
| A-1j | CH |
| A-1k | CH |
| A-1l | CH |
| A-1m | CH |
| A-1n | CH |
| A-1o | CH |
| A-1p | CH |
| A-1q | CH |
| A-1r | CH |
| A-1s | CH |
| A-1t | CH |
| A-2a | CH |
| A-2b | CH |
| A-2c | CH |
| A-2d | CH |
| A-2e | CH |
| A-3a | CH |
| A-3b | CH |

TABLE 6337-continued

| A | G |
|---|---|
| A-3c | CH |
| A-4a | CH |
| A-4b | CH |
| A-4c | CH |
| A-4d | CH |
| A-5a | CH |
| A-6a | CH |
| A-6b | CH |
| A-7a | CH |
| A-7b | CH |
| A-8a | CH |
| A-8b | CH |
| A-8c | CH |
| A-1a | N |
| A-1b | N |
| A-1c | N |
| A-1d | N |
| A-1e | N |
| A-1f | N |
| A-1g | N |
| A-1h | N |
| A-1i | N |
| A-1j | N |
| A-1k | N |
| A-1l | N |
| A-1m | N |
| A-1n | N |
| A-1o | N |
| A-1p | N |
| A-1q | N |
| A-1r | N |
| A-1s | N |
| A-1t | N |
| A-2a | N |
| A-2b | N |
| A-2c | N |
| A-2d | N |
| A-2e | N |
| A-3a | N |
| A-3b | N |
| A-3c | N |
| A-4a | N |
| A-4b | N |
| A-4c | N |
| A-4d | N |
| A-5a | N |
| A-6a | N |
| A-6b | N |
| A-7a | N |
| A-7b | N |
| A-8a | N |
| A-8b | N |
| A-8c | N |

TABLE 6338

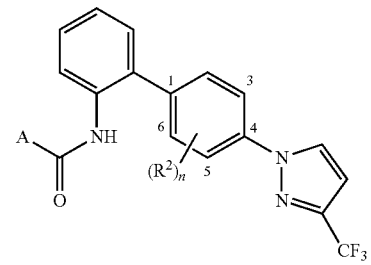

| A | $(R^2)_n$ |
|---|---|
| A-1a | 3-F |
| A-1b | 3-F |
| A-1c | 3-F |
| A-1d | 3-F |
| A-1e | 3-F |
| A-1f | 3-F |
| A-1g | 3-F |
| A-1h | 3-F |
| A-1i | 3-F |
| A-1j | 3-F |
| A-1k | 3-F |
| A-1l | 3-F |
| A-1m | 3-F |
| A-1n | 3-F |
| A-1o | 3-F |
| A-1p | 3-F |
| A-1q | 3-F |
| A-1r | 3-F |
| A-1s | 3-F |
| A-1t | 3-F |
| A-2a | 3-F |
| A-2b | 3-F |
| A-2c | 3-F |
| A-2d | 3-F |
| A-2e | 3-F |
| A-3a | 3-F |
| A-3b | 3-F |
| A-3c | 3-F |
| A-4a | 3-F |
| A-4b | 3-F |
| A-4c | 3-F |
| A-4d | 3-F |
| A-5a | 3-F |
| A-6a | 3-F |
| A-6b | 3-F |
| A-7a | 3-F |
| A-7b | 3-F |
| A-8a | 3-F |
| A-8b | 3-F |
| A-8c | 3-F |
| A-1a | 3,5-di-F |
| A-1b | 3,5-di-F |
| A-1c | 3,5-di-F |
| A-1d | 3,5-di-F |
| A-1e | 3,5-di-F |
| A-1f | 3,5-di-F |
| A-1g | 3,5-di-F |
| A-1h | 3,5-di-F |
| A-1i | 3,5-di-F |
| A-1j | 3,5-di-F |
| A-1k | 3,5-di-F |
| A-1l | 3,5-di-F |
| A-1m | 3,5-di-F |
| A-1n | 3,5-di-F |
| A-1o | 3,5-di-F |
| A-1p | 3,5-di-F |
| A-1q | 3,5-di-F |
| A-1r | 3,5-di-F |
| A-1s | 3,5-di-F |
| A-1t | 3,5-di-F |
| A-2a | 3,5-di-F |
| A-2b | 3,5-di-F |
| A-2c | 3,5-di-F |
| A-2d | 3,5-di-F |

TABLE 6338-continued

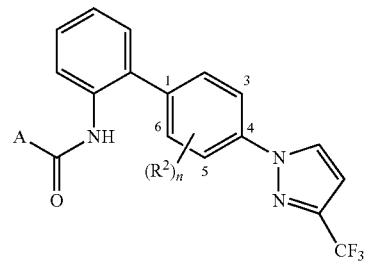

| A | $(R^2)_n$ |
|---|---|
| A-2e | 3,5-di-F |
| A-3a | 3,5-di-F |
| A-3b | 3,5-di-F |
| A-3c | 3,5-di-F |
| A-4a | 3,5-di-F |
| A-4b | 3,5-di-F |
| A-4c | 3,5-di-F |
| A-4d | 3,5-di-F |
| A-5a | 3,5-di-F |
| A-6a | 3,5-di-F |
| A-6b | 3,5-di-F |
| A-7a | 3,5-di-F |
| A-7b | 3,5-di-F |
| A-8a | 3,5-di-F |
| A-8b | 3,5-di-F |
| A-8c | 3,5-di-F |

Formulation/Utility

A compound of Formula 1 of this invention (including N-oxides and salts thereof) will generally be used as a fungicidal active ingredient in a composition, i.e. formulation, with at least one additional component selected from the group consisting of surfactants, solid diluents and liquid diluents, which serve as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., Handbook of Insecticide Dust Diluents and Carriers, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such as polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 m can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No.

3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables 1-6. Without further elaboration, it is believed that one skilled in the art using the preceding description can utilize the present invention to its fullest extent. The following Examples are, therefore, to be constructed as merely illustrative, and not limiting of the disclosure in any way whatsoever. Percentages are by weight except where otherwise indicated.

Example A

| High Strength Concentrate | |
|---|---|
| Compound 1 | 98.5% |
| silica aerogel | 0.5% |
| synthetic amorphous fine silica | 1.0% |

Example B

| Wettable Powder | |
|---|---|
| Compound 40 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| Compound 172 | 10.0% |
| attapulgite granules (low volatile matter, 0.71/0.30 mm; U.S.S. No. 25-50 sieves) | 90.0% |

Example D

| Extruded Pellet | |
|---|---|
| Compound 173 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
|---|---|
| Compound 85 | 10.0% |
| polyoxyethylene sorbitol hexoleate | 20.0% |
| $C_6$-$C_{10}$ fatty acid methyl ester | 70.0% |

Example F

| Microemulsion | |
|---|---|
| Compound 1 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Seed Treatment | |
|---|---|
| Compound 85 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Water-soluble and water-dispersible formulations are typically diluted with water to form aqueous compositions before application. Aqueous compositions for direct applications to the plant or portion thereof (e.g., spray tank compositions) typically at least about 1 ppm or more (e.g., from 1 ppm to 100 ppm) of the compound(s) of this invention.

The compounds of this invention are useful as plant disease control agents. The present invention therefore further comprises a method for controlling plant diseases caused by fungal plant pathogens comprising applying to the plant or portion thereof to be protected, or to the plant seed to be protected, an effective amount of a compound of the invention or a fungicidal composition containing said compound. The compounds and/or compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, turf, vegetable, field, cereal, and fruit crops. These pathogens include: Oomycetes, including *Phytophthora* pathogens such as *Phytophthora infestans*, *Phytophthora megasperma*, *Phytophthora parasitica*, *Phytophthora cinnamomi* and *Phytophthora capsici*, *Pythium* pathogens such as *Pythium aphanidermatum*, and pathogens in the Peronosporaceae family such as *Plasmopara viticola*, *Peronospora* spp. (including *Peronospora tabacina* and *Peronospora parasitica*), *Pseudoperonospora* spp. (including *Pseudoperonospora cubensis*) and *Bremia lactucae*; Ascomycetes, including *Alternaria* pathogens such as *Alternaria solani* and *Alternaria brassicae*, *Guignardia* pathogens such as *Guignardia bidwell*, *Venturia* pathogens such as *Venturia inaequalis*, *Septoria* pathogens such as *Septoria nodorum* and *Septoria tritici*, powdery mildew pathogens such as *Blumeria* spp. (including *Blumeria graminis*) and *Erysiphe* spp. (including *Erysiphe polygoni*), *Uncinula necatur*, *Sphaerothecafuliginea*, *Podosphaera leucotricha* and *Pseudocercosporella herpotrichoides*, *Botrytis* pathogens such as *Botrytis cinerea*, *Monilinia fructicola*, *Sclerotinia* pathogens such as *Sclerotinia sclerotiorum*, *Sclerotinia minor*, *Magnaporthe grisea*, and *Phomopsis viticola*, *Helminthosporium* pathogens such as *Helminthosporium tritici repentis* and *Pyrenophora teres*, anthracnose pathogens such as *Glomerella* or *Colletotrichum* spp. (such as *Colletotrichum graminicola* and *Colletotrichum orbiculare*), and *Gaeumannomyces graminis*; Basidiomycetes, including rust diseases caused by *Puccinia* spp. (such as *Puccinia recondita*, *Puccinia striiformis*, *Puccinia hordei*, *Puccinia graminis* and *Puccinia arachidis*), *Hemileia vastatrix* and *Phakopsora pachyrhizi*; other pathogens including *Rutstroemia floccosum* (also known as *Sclerontina homoeocarpa*); *Rhizoctonia* spp. (such as *Rhizoctonia solani* and *Rhizoctonia oryzae*); *Fusarium* pathogens such as *Fusarium roseum*, *Fusarium graminearum* and *Fusarium oxysporum*; *Verticillium dahliae*; *Sclerotium rolfsii*; *Rynchosporium secalis*; *Cercosporidium personatum*, *Cercospora arachidicola* and *Cercospora beticola*; *Rhizopus* spp. (such as *Rhizopus stolonifer*); *Aspergillus* spp. (such as *Aspergillus flavus* and *Aspergillus parasiticus*); and other genera and species closely related to these pathogens. In addition to their fungicidal activity, the compositions or combinations also have activity against bacteria such as *Erwinia amylovora*, *Xanthomonas campestris*, *Pseudomonas syringae*, and other related species. By controlling harmful microorganisms, the compounds of the invention are useful for improving (i.e. increasing) the ratio of beneficial to harmful microorganisms in contact with crop plants or their propagules (e.g., seeds, corms, bulbs, tubers, cuttings) or in the agronomic environment of the crop plants or their propagules.

Furthermore, the compounds of this invention are useful in treating postharvest diseases of fruits and vegetables caused by fungi and bacteria. These infections can occur before, during and after harvest. For example, infections can occur before harvest and then remain dormant until some point during ripening (e.g., host begins tissue changes in such a way that infection can progress); also infections can arise from surface wounds created by mechanical or insect injury. In this respect, the compounds of this invention can reduce losses (i.e. losses resulting from quantity and quality) due to postharvest diseases which may occur at any time from harvest to consumption. Treatment of postharvest diseases with compounds of the invention can increase the period of time during which perishable edible plant parts (e.g., fruits, seeds, foliage, stems, bulbs. tubers) can be stored refrigerated or un-refrigerated after harvest, and remain edible and free from noticeable or harmful degradation or contamination by fungi or other microorganisms. Treatment of edible plant parts before or after harvest with compounds of the invention can also decrease the formation of toxic metabolites of fungi or other microorganisms, for example mycotoxins such as aflatoxins.

The compounds of the invention are believed to provide protection from fungal plant pathogens by inhibiting Complex II (succinate dehydrogenase) fungal respiration by disrupting a key enzyme in the Krebs Cycle (TCA cycle) named succinate dehydrogenase (SDH). SDH is composed of four nuclear-encoded polypeptides, identified as SDHA, SDHB, SDHC and SDHD. Inhibiting respiration prevents the fungus from making ATP, and thus inhibits growth and reproduction. At the molecular level, carboxamides inhibit ubiquinone reduction by binding to the ubiquinone binding site ($Q_p$ site) formed by subunits SDHB, SDHC and SDHD in the SDH enzyme. The Fungicide Resistance Action Committee (FRAC) has identified chemical compounds having this fungicidal mode of action as "SDHIs" as an abbreviation for succinate dehydrogenase inhibitors and categorized them with FRAC Code 7.

A variety of mutations in subunits SDHB, SDHC and SDHD forming the ubiquinone binding site are now known to cause resistance to SDHIs. FRAC has published on their website a "List of fungal species with resistance reports towards SDHI fungicides and mutations in the succinate dehydrogenates gene (updated March 2012)" (http://frac.info/frac/work/List%20of%20SDHI%20resistant%20species.pdf available as of 28 Jun. 2012), which includes both mutants produced in the laboratory through artificial mutagenesis and naturally occurring mutants found in the field showing resistance to SDHIs. Scalliet et al., "Mutagenesis and Functional Studies with Succinate Dehydrogenase Inhibitors in the Wheat Pathogen *Mycosphaerella graminicola*", *PLoS ONE*, 2012, 7 (4), 1-20 (published in Adobe Acrobat file format as journal.pone.0035429.pdf and available through http://www.plosone.org/article/info%3Adoi%2F10.1371%2Fjournal.pone.0035429 on 28 Jun. 2012) describes additional mutants of *Mycosphaerella graminicola*. These publications disclose fungal pathogens having known resistant mutants include *Alternaria alternata* (SDHB: H277Y, H277R; SDHC: H134R; SDHD: D123E, H133R), *Aspergillus oryzae* (SDHB: H249Y, H249L, H249N; SDHC: T90I; SDHD: D124E), *Botrytis cinearea* (SDHB: P225L, P225T, P225F, H272Y, H272R, H272L, N230I; SDHD: H132R), *Botrytis elliptica* (SDHB: H272Y, H272R), *Corynespora cassiicola* (SDHB: H287Y, H287R; SDHC: S73P, SDHD: S89P), *Didymella bryoniae* (SDHB: H277R, H277Y), *Mycosphaerella graminicola* (SDHB: S218F, P220T, P220L, S221P, N225H, N225I, R265P, H267L, H267N, H267R, H267Q, H267Y, 1269V, N271K; SDHC: T79I, S83G, A84V, A84I, L85P, N86K, R87C, V88D, H145R, H152R; SDHD: D129E, D129G, D129S, D129T, H139E), *Podosphaera xanthii* (SDHB: H[???]Y), *Sclerotinia sclerotiorum* (SDHD: H132R), *Ustilago maydis* (SDHB: H257L), *Stemphylium botryose* (SDHB: P225L, H272Y, H272R) and *Ustilago maydis* (SDHB: H257L), wherein the left letter identifies the amino acid in the prevalent wild-type enzyme subunit, the number specifies the amino acid location in the subunit, and the right letter identifies the amino acid in the mutant subunit (the amino acids are identified by standard single letter codes; see for example http://www.bio.davidson.edu/Biology/aatable.html, accessed 28 Jun. 2012). Because the metabolism of other fungal pathogens, such as *Septoria tritici*, also involve succinate dehydrogenase, SDHI-resistant mutants are possible for them as well.

Remarkably, compounds of the present invention, particularly wherein when G is N or $R^{2a}$ is H, then the ring comprising G is substituted with at least one instance of $R^2$, retain sufficient activity against mutant fungal pathogens highly resistant to other SDHIs, so that the present compounds remain agronomically useful for protecting plants against the mutant as well as wild-type pathogens. The improved efficacy of the present compounds compared to other SDHI fungicides for controlling plant disease caused by the SDHI-resistant fungal pathogens can be determined by simple plant disease control testing, for example tests similar to Tests A-H disclosed herein, but using SDHI-resistant instead of wild-type fungal pathogens.

Compounds of Formula 1, particularly wherein L is —$C(R^{12a})R^{12b}$—$C(R^{13a})R^{13b}$— not only have activity against organisms, i.e. pathogens, causing fungal disease but also activity against nematodes feeding on plants (i.e. phytophagous nematodes). Among these compounds, compounds wherein A is A-1 are of particular note for controlling phytophagous nematodes. Phytophagous nematodes live and feed on the surface (i.e. ectoparasitic) or inside (i.e. endoparasitic) of plant parts (e.g., foliage, fruit, stems, roots or seeds) and thereby damage growing and stored agronomic crops, forestry, greenhouse crops, ornamentals and nursery crops. Examples of phytophagous nematodes include both classes Adenophorea and Secernentea of the Phylum Nematoda, including economically important members of the orders Enoplida, Dorylaimida, Rhabditida, Strongylida, Ascarida, Oxyurida, Spirurida, Tylenchida and Aphelenchida, such as but not limited to economically important agricultural pests such as root-knot nematodes of the genus *Meloidogyne*, cyst nematodes of the genus *Heterodera* and *Globodera*, lesion nematodes of the genus *Pratylenchus*, reniform nematodes of the genus *Rotylenchulus*, burrowing nematodes of the genus *Radopholus*, sting nematodes of the genus *Belonolaimus*, spiral nematodes of the genus *Helicotylenchus* and *Scutellonema*, citrus nematodes of the genus *Tylenchulus*, stubby root nematodes of the genus *Trichodorus* and *Paratrichodorus*, needle nematodes of the genus *Longidorus*, lance nematodes of the genus *Hoplolaimus*, and stem nematodes of the genus *Ditylenchus*. Of note is use of compounds of this invention for controlling southern root-knot nematode (*Meloidogyne incognita*). Those skilled in the art will appreciate that not all compounds are equally effective against all growth stages of all nematodes.

Treatment with compounds of Formula 1, particularly wherein L is —$C(R^{12a})R^{12b}$—$C(R^{13a})R^{13b}$—, may also prevent or cure infections of parasitic nematodes in animals and humans (e.g., vascular or digestive systems or other tissues). Examples of parasitic nematodes afflicting the health of animals and humans include economically important roundworms such as *Strongylus vulgaris* in horses, *Toxocara canis* in dogs, *Haemonchus contortus* in sheep, *Dirofilaria immitis* in dogs and *Ascaris lumbricoides* in humans.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to seeds to protect the seeds and seedlings developing from the seeds. The compounds can also be applied through irrigation water to treat plants.

Accordingly, this aspect of the present invention can also be described as a method for protecting a plant or plant seed from diseases caused by fungal pathogens comprising applying a fungicidally effective amount of a compound of Formula 1, an N-oxide, or salt thereof to the plant (or portion thereof) or plant seed (directly or through the environment (e.g., growing medium) of the plant or plant seed).

Control of postharvest pathogens which infect the produce before harvest is typically accomplished by field application of a compound of this invention, and in cases where infection occurs after harvest the compounds can be applied to the harvested crop as dips, sprays, fumigants, treated wraps and box liners.

Control of phytophagous nematodes using a compound of the invention is ordinarily accomplished by methods of application similar to those described for plant disease control.

Rates of application for these compounds (i.e. a fungicidally effective amount or a nematocidally effective amount) can be influenced by factors such as the plant diseases or nematodes to be controlled, the plant species to be protected, ambient moisture and temperature and should be determined under actual use conditions. One skilled in the art can easily determine through simple experimentation the fungicidally effective amount necessary for the desired level of plant disease control, or the nematocidally effective amount necessary for the desired level of phytophagous nematode control. Control of plant diseases caused by fungal pathogens may require higher application rates when at least one mutation is present causing resistance to SDHIs, but nevertheless application rates often remain economically acceptable to agronomic practice. Foliage can normally be protected when treated at a rate of from less than about 1 g/ha to about 5,000 g/ha of active ingredient. Seed and seedlings can normally be protected when seed is treated at a rate of from about 0.1 to about 10 g per kilogram of seed.

Compounds of this invention can also be mixed with one or more other biologically active compounds or agents including fungicides, insecticides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Thus the present invention also pertains to a composition comprising a compound of Formula 1 (in a fungicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

As mentioned in the Summary of the Invention, one aspect of the present invention is a fungicidal composition comprising (i.e. a mixture or combination of) a compound of Formula 1, an N-oxide, or a salt thereof (i.e. component a), and at least one other fungicide (i.e. component b). Of note is such a combination where the other fungicidal active ingredient has different site of action from the compound of Formula 1. In certain instances, a combination with at least one other fungicidal active ingredient having a similar spectrum of control but a different site of action will be particularly advantageous for resistance management. Thus, a composition of the present invention can further comprise a fungicidally effective amount of at least one additional fungicidal active ingredient having a similar spectrum of control but a different site of action.

Of particular note is a composition which in addition to the Formula 1 compound of component (a), includes as component (b) at least one fungicidal compound selected from the group consisting of the classes (b1) methyl benzimidazole carbamate (MBC) fungicides; (b2) dicarboximide fungicides; (b3) demethylation inhibitor (DMI) fungicides; (b4) phenylamide fungicides; (b5) amine/morpholine fungicides; (b6) phospholipid biosynthesis inhibitor fungicides; (b7) carboxamide fungicides; (b8) hydroxy(2-amino-)pyrimidine fungicides; (b9) anilinopyrimidine fungicides; (b10) N-phenyl carbamate fungicides; (b11) quinone outside inhibitor (QoI) fungicides; (b12) phenylpyrrole fungicides; (b13) quinoline fungicides; (b14) lipid peroxidation inhibitor fungicides; (b15) melanin biosynthesis inhibitors-reductase (MBI-R) fungicides; (b16) melanin biosynthesis inhibitors-dehydratase (MBI-D) fungicides; (b17) hydroxyanilide fungicides; (b18) squalene-epoxidase inhibitor fungicides; (b19) polyoxin fungicides; (b20) phenylurea fungicides; (b21) quinone inside inhibitor (QiI) fungicides; (b22) benzamide fungicides; (b23) enopyranuronic acid antibiotic fungicides; (b24) hexopyranosyl antibiotic fungicides; (b25) glucopyranosyl antibiotic: protein synthesis fungicides; (b26) glucopyranosyl antibiotic: trehalase and inositol biosynthesis fungicides; (b27) cyanoacetamideoxime fungicides; (b28) carbamate fungicides; (b29) oxidative phosphorylation uncoupling fungicides; (b30) organo tin fungicides; (b31) carboxylic acid fungicides; (b32) heteroaromatic fungicides; (b33) phosphonate fungicides; (b34) phthalamic acid fungicides; (b35) benzotriazine fungicides; (b36) benzene-sulfonamide fungicides; (b37) pyridazinone fungicides; (b38) thiophene-carboxamide fungicides; (b39) pyrimidinamide fungicides; (b40) carboxylic acid amide (CAA) fungicides; (b41) tetracycline antibiotic fungicides; (b42) thiocarbamate fungicides; (b43) benzamide fungicides; (b44) host plant defense induction fungicides; (b45) multi-site contact activity fungicides; (b46) fungicides other than fungicides of classes (b1) through (b45); and salts of compounds of classes (b1) through (b46).

Further descriptions of these classes of fungicidal compounds are provided below.

(b1) "Methyl benzimidazole carbamate (MBC) fungicides" (FRAC (Fungicide Resistance Action Committee) code 1) inhibit mitosis by binding to β-tubulin during microtubule assembly. Inhibition of microtubule assembly can disrupt cell division, transport within the cell and cell structure. Methyl benzimidazole carbamate fungicides include benzimidazole and thiophanate fungicides. The benzimidazoles include benomyl, carbendazim, fuberidazole and thiabendazole. The thiophanates include thiophanate and thiophanate-methyl.

(b2) "Dicarboximide fungicides" (FRAC code 2) are proposed to inhibit a lipid peroxidation in fungi through interference with NADH cytochrome c reductase. Examples include chlozolinate, iprodione, procymidone and vinclozolin.

(b3) "Demethylation inhibitor (DMI) fungicides" (FRAC code 3) inhibit C14-demethylase, which plays a role in sterol production. Sterols, such as ergosterol, are needed for membrane structure and function, making them essential for the development of functional cell walls. Therefore, exposure to these fungicides results in abnormal growth and eventually death of sensitive fungi. DMI fungicides are divided between several chemical classes: azoles (including triazoles and imidazoles), pyrimidines, piperazines and pyridines. The triazoles include azaconazole, bitertanol, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole, rel-1-[[(2R,3S)-3-(2-chlorophenyl)-2-(2,4-difluorophenyl)-2-oxiranyl]methyl]-1H-1,2,4-triazole, rel-2-[[(2R,3S)-3-(2-chlorophenyl)-2-(2,4-difluorophenyl)-2-oxiranyl]-methyl]-1,2-dihydro-3H-1,2,4-triazole-3-thione, and rel-1-[[(2R,3S)-3-(2-chlorophenyl)-2-(2,4-difluorophenyl)-2-oxiranyl]methyl]-5-(2-propen-1-ylthio)-1H-1,2,4-triazole. The imidazoles include clotrimazole, econazole, imazalil, isoconazole, miconazole, oxpoconazole, prochloraz, pefurazoate and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag New York, 1995, 205-258.

(b4) "Phenylamide fungicides" (FRAC code 4) are specific inhibitors of RNA polymerase in Oomycete fungi. Sensitive fungi exposed to these fungicides show a reduced capacity to incorporate uridine into rRNA. Growth and development in sensitive fungi is prevented by exposure to this class of fungicide. Phenylamide fungicides include acylalanine, oxazolidinone and butyrolactone fungicides. The acylalanines include benalaxyl, benalaxyl-M, furalaxyl, metalaxyl and metalaxyl-M (also known as mefenoxam). The oxazolidinones include oxadixyl. The butyrolactones include ofurace.

(b5) "Amine/morpholine fungicides" (FRAC code 5) inhibit two target sites within the sterol biosynthetic pathway, $\Delta^8 \to \Delta^7$ isomerase and $\Delta^{14}$ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholine, piperidine and spiroketal-amine fungicides. The morpholines include aldimorph, dodemorph, fenpropimorph, tridemorph and trimorphamide. The piperidines include fenpropidin and piperalin. The spiroketal-amines include spiroxamine.

(b6) "Phospholipid biosynthesis inhibitor fungicides" (FRAC code 6) inhibit growth of fungi by affecting phospholipid biosynthesis. Phospholipid biosynthesis fungicides include phosphorothiolate and dithiolane fungicides. The phosphorothiolates include edifenphos, iprobenfos and pyrazophos. The dithiolanes include isoprothiolane.

(b7) "Carboxamide fungicides" (FRAC code 7) inhibit Complex II (succinate dehydrogenase) fungal respiration by disrupting a key enzyme in the Krebs Cycle (TCA cycle) named succinate dehydrogenase. Inhibiting respiration prevents the fungus from making ATP, and thus inhibits growth and reproduction. Carboxamide fungicides include benzamide, furan carboxamide, oxathiin carboxamide, thiazole carboxamide, pyrazole carboxamide, pyridine carboxamide and thiophene carboxamide fungicides. The benzamides include benodanil, flutolanil and mepronil. The furan carboxamides include fenfuram. The oxathiin carboxamides include carboxin and oxycarboxin. The thiazole carboxamides include thifluzamide. The pyrazole carboxamides include bixafen, furametpyr, isopyrazam, fluxapyroxad, penthiopyrad, sedaxane, N-[2-(1S,2R)-[1,1'-bicyclopropyl]-2-ylphenyl]-3-(difluoromethyl)-1-methyl-1H-pyrazole-4-carboxamide and penflufen (N-[2-(1,3-dimethylbutyl)phenyl]-5-fluoro-1,3-dimethyl-1H-pyrazole-4-carboxamide). The pyridine carboxamides include boscalid. The thiophene carboxamides include isofetamid.

(b8) "Hydroxy(2-amino-)pyrimidine fungicides" (FRAC code 8) inhibit nucleic acid synthesis by interfering with adenosine deaminase. Examples include bupirimate, dimethirimol and ethirimol.

(b9) "Anilinopyrimidine fungicides" (FRAC code 9) are proposed to inhibit biosynthesis of the amino acid methionine and to disrupt the secretion of hydrolytic enzymes that lyse plant cells during infection. Examples include cyprodinil, mepanipyrim and pyrimethanil.

(b10) "N-Phenyl carbamate fungicides" (FRAC code 10) inhibit mitosis by binding to β-tubulin and disrupting microtubule assembly. Inhibition of microtubule assembly can disrupt cell division, transport within the cell and cell structure. Examples include diethofencarb.

(b11) "Quinone outside inhibitor (QoI) fungicides" (FRAC code 11) inhibit Complex III mitochondrial respiration in fungi by affecting ubiquinol oxidase. Oxidation of ubiquinol is blocked at the "quinone outside" ($Q_O$) site of the cytochrome $bc_1$ complex, which is located in the inner mitochondrial membrane of fungi. Inhibiting mitochondrial respiration prevents normal fungal growth and development. Quinone outside inhibitor fungicides include methoxyacrylate, methoxycarbamate, oximinoacetate, oximinoacetamide and dihydrodioxazine fungicides (collectively also known as strobilurin fungicides), and oxazolidinedione, imidazolinone and benzylcarbamate fungicides. The methoxyacrylates include azoxystrobin, enestroburin (SYP-Z071) and picoxystrobin. The methoxycarbamates include pyraclostrobin and pyrametostrobin. The oximinoacetates include kresoxim-methyl, pyraoxystrobin and trifloxystrobin. The oximinoacetamides include dimoxystrobin, metominostrobin, orysastrobin and α-[methoxyimino]-N-methyl-2-[[[1-[3-(trifluoromethyl)phenyl]ethoxy]imino]methyl]benzeneacetamide. The dihydrodioxazines include fluoxastrobin. The oxazolidinediones include famoxadone. The imidazolinones include fenamidone. The benzylcarbamates include pyribencarb.

(b12) "Phenylpyrrole fungicides" (FRAC code 12) inhibit a MAP protein kinase associated with osmotic signal transduction in fungi. Fenpiclonil and fludioxonil are examples of this fungicide class.

(b13) "Quinoline fungicides" (FRAC code 13) are proposed to inhibit signal transduction by affecting G-proteins in early cell signaling. They have been shown to interfere with germination and/or appressorium formation in fungi that cause powdery mildew diseases. Quinoxyfen is an example of this class of fungicide.

(b14) "Lipid peroxidation inhibitor fungicides" (FRAC code 14) are proposed to inhibit lipid peroxidation which affects membrane synthesis in fungi. Members of this class, such as etridiazole, may also affect other biological processes such as respiration and melanin biosynthesis. Lipid peroxidation fungicides include aromatic carbon and 1,2,4-thiadiazole fungicides. The aromatic carbon fungicides include biphenyl, chloroneb, dicloran, quintozene, tecnazene and tolclofos-methyl. The 1,2,4-thiadiazoles include etridiazole.

(b15) "Melanin biosynthesis inhibitors-reductase (MBI-R) fungicides" (FRAC code 16.1) inhibit the naphthal reduction step in melanin biosynthesis. Melanin is required for host plant infection by some fungi. Melanin biosynthesis inhibitors-reductase fungicides include isobenzofuranone, pyrroloquinolinone and triazolobenzothiazole fungicides. The isobenzofuranones include fthalide. The pyrroloquinolinones include pyroquilon. The triazolobenzothiazoles include tricyclazole.

(b16) "Melanin biosynthesis inhibitors-dehydratase (MBI-D) fungicides" (FRAC code 16.2) inhibit scytalone dehydratase in melanin biosynthesis. Melanin in required for host plant infection by some fungi. Melanin biosynthesis inhibitors-dehydratase fungicides include cyclopropanecarboxamide, carboxamide and propionamide fungicides. The cyclopropanecarboxamides include carpropamid. The carboxamides include diclocymet. The propionamides include fenoxanil.

(b17) "Hydroxyanilide fungicides (FRAC code 17) inhibit C4-demethylase which plays a role in sterol production. Examples include fenhexamid.

(b18) "Squalene-epoxidase inhibitor fungicides" (FRAC code 18) inhibit squalene-epoxidase in ergosterol biosynthesis pathway. Sterols such as ergosterol are needed for membrane structure and function, making them essential for the development of functional cell walls. Therefore exposure to these fungicides results in abnormal growth and eventually death of sensitive fungi. Squalene-epoxidase inhibitor fungicides include thiocarbamate and allylamine fungicides. The thiocarbamates include pyributicarb. The allylamines include naftifine and terbinafine.

(b19) "Polyoxin fungicides" (FRAC code 19) inhibit chitin synthase. Examples include polyoxin.

(b20) "Phenylurea fungicides" (FRAC code 20) are proposed to affect cell division. Examples include pencycuron.

(b21) "Quinone inside inhibitor (QiI) fungicides" (FRAC code 21) inhibit Complex III mitochondrial respiration in fungi by affecting ubiquinol reductase. Reduction of ubiquinol is blocked at the "quinone inside" ($Q_i$) site of the cytochrome $bc_1$ complex, which is located in the inner mitochondrial membrane of fungi. Inhibiting mitochondrial respiration prevents normal fungal growth and development. Quinone inside inhibitor fungicides include cyanoimidazole and sulfamoyltriazole fungicides. The cyanoimidazoles include cyazofamid. The sulfamoyltriazoles include amisulbrom.

(b22) "Benzamide fungicides" (FRAC code 22) inhibit mitosis by binding to β-tubulin and disrupting microtubule assembly. Inhibition of microtubule assembly can disrupt cell division, transport within the cell and cell structure. Examples include zoxamide.

(b23) "Enopyranuronic acid antibiotic fungicides" (FRAC code 23) inhibit growth of fungi by affecting protein biosynthesis. Examples include blasticidin-S.

(b24) "Hexopyranosyl antibiotic fungicides" (FRAC code 24) inhibit growth of fungi by affecting protein biosynthesis. Examples include kasugamycin.

(b25) "Glucopyranosyl antibiotic: protein synthesis fungicides" (FRAC code 25) inhibit growth of fungi by affecting protein biosynthesis. Examples include streptomycin.

(b26) "Glucopyranosyl antibiotic: trehalase and inositol biosynthesis fungicides" (FRAC code 26) inhibit trehalase in inositol biosynthesis pathway. Examples include validamycin.

(b27) "Cyanoacetamideoxime fungicides (FRAC code 27) include cymoxanil.

(b28) "Carbamate fungicides" (FRAC code 28) are considered multi-site inhibitors of fungal growth. They are proposed to interfere with the synthesis of fatty acids in cell membranes, which then disrupts cell membrane permeability. Propamacarb, iodocarb, and prothiocarb are examples of this fungicide class.

(b29) "Oxidative phosphorylation uncoupling fungicides" (FRAC code 29) inhibit fungal respiration by uncoupling oxidative phosphorylation. Inhibiting respiration prevents normal fungal growth and development. This class includes 2,6-dinitroanilines such as fluazinam, pyrimidonehydrazones such as ferimzone and dinitrophenyl crotonates such as dinocap, meptyldinocap and binapacryl.

(b30) "Organo tin fungicides" (FRAC code 30) inhibit adenosine triphosphate (ATP) synthase in oxidative phosphorylation pathway. Examples include fentin acetate, fentin chloride and fentin hydroxide.

(b31) "Carboxylic acid fungicides" (FRAC code 31) inhibit growth of fungi by affecting deoxyribonucleic acid (DNA) topoisomerase type II (gyrase). Examples include oxolinic acid.

(b32) "Heteroaromatic fungicides" (Fungicide Resistance Action Committee (FRAC) code 32) are proposed to affect DNA/ribonucleic acid (RNA) synthesis. Heteroaromatic fungicides include isoxazoles and isothiazolones. The isoxazoles include hymexazole and the isothiazolones include octhilinone.

(b33) "Phosphonate fungicides" (FRAC code 33) include phosphorous acid and its various salts, including fosetyl-aluminum.

(b34) "Phthalamic acid fungicides" (FRAC code 34) include teclofthalam.

(b35) "Benzotriazine fungicides" (FRAC code 35) include triazoxide.

(b36) "Benzene-sulfonamide fungicides" (FRAC code 36) include flusulfamide.

(b37) "Pyridazinone fungicides" (FRAC code 37) include diclomezine.

(b38) "Thiophene-carboxamide fungicides" (FRAC code 38) are proposed to affect ATP production. Examples include silthiofam.

(b39) "Pyrimidinamide fungicides" (FRAC code 39) inhibit growth of fungi by affecting phospholipid biosynthesis and include diflumetorim.

(b40) "Carboxylic acid amide (CAA) fungicides" (FRAC code 40) are proposed to inhibit phospholipid biosynthesis and cell wall deposition. Inhibition of these processes prevents growth and leads to death of the target fungus. Carboxylic acid amide fungicides include cinnamic acid amide, valinamide and other carbamate, and mandelic acid amide fungicides. The cinnamic acid amides include dimethomorph and flumorph. The valinamide and other carbamates include benthiavalicarb, benthiavalicarb-isopropyl, iprovalicarb, tolprocarb and valifenalate (valiphenal). The mandelic acid amides include mandipropamid, N-[2-[4-[[3-(4-chlorophenyl)-2-propyn-1-yl]oxy]-3-methoxyphenyl]ethyl]-3-methyl-2-[(methylsulfonyl)amino]butanamide and N-[2-[4-[[3-(4-chlorophenyl)-2-propyn-1-yl]oxy]-3-methoxyphenyl]ethyl]-3-methyl-2-[(ethylsulfonyl)amino]butanamide.

(b41) "Tetracycline antibiotic fungicides" (FRAC code 41) inhibit growth of fungi by affecting complex 1 nicotinamide adenine dinucleotide (NADH) oxidoreductase. Examples include oxytetracycline.

(b42) "Thiocarbamate fungicides" (FRAC code 42) include methasulfocarb.

(b43) "Benzamide fungicides" (FRAC code 43) inhibit growth of fungi by delocalization of spectrin-like proteins. Examples include acylpicolide fungicides such as fluopicolide and fluopyram.

(b44) "Host plant defense induction fungicides" (FRAC code P) induce host plant defense mechanisms. Host plant defense induction fungicides include benzothiadiazoles, benzisothiazole and thiadiazole-carboxamide fungicides. The benzothiadiazoles include acibenzolar-S-methyl. The benzisothiazoles include probenazole. The thiadiazole-carboxamides include tiadinil and isotianil.

(b45) "Multi-site contact fungicides" inhibit fungal growth through multiple sites of action and have contact/preventive activity. This class of fungicides includes: (b45.1) "copper fungicides" (FRAC code M1)", (b45.2) "sulfur fungicides" (FRAC code M2), (b45.3) "dithiocarbamate fungicides" (FRAC code M3), (b45.4) "phthalimide fungicides" (FRAC code M4), (b45.5) "chloronitrile fungicides" (FRAC code M5), (b45.6) "sulfamide fungicides" (FRAC code M6), (b45.7) "guanidine fungicides" (FRAC code M7), (b45.8) "triazine fungicides" (FRAC code M8) and (b45.9) "quinone fungicides" (FRAC code M9). "Copper fungicides" are inorganic compounds containing copper, typically in the copper (II) oxidation state; examples include copper oxychloride, copper sulfate and copper hydroxide, including compositions such as Bordeaux mixture (tribasic copper sulfate). "Sulfur fungicides" are inorganic chemicals containing rings or chains of sulfur atoms; examples include elemental sulfur. "Dithiocarbamate fungicides" contain a dithiocarbamate molecular moiety; examples include mancozeb, metiram, propineb, ferbam, maneb, thiram, zineb and ziram. "Phthalimide fungicides" contain a phthalimide molecular moiety; examples include folpet, captan and captafol. "Chloronitrile fungicides" contain an aromatic ring substituted with chloro and cyano; examples include chlorothalonil. "Sulfamide fungicides" include dichlofluanid and tolyfluanid. "Guanidine fungicides" include dodine, guazatine, iminoctadine albesilate and iminoctadine triacetate. "Triazine fungicides" include anilazine. "Quinone fungicides" include dithianon.

(b46) "Fungicides other than fungicides of classes (b1) through (b45)" include certain fungicides whose mode of action may be unknown. These include: (b46.1) "thiazole carboxamide fungicides" (FRAC code U5), (b46.2) "phenyl-acetamide fungicides" (FRAC code U6), (b46.3) "quinazolinone fungicides" (FRAC code U7), (b46.4) "benzophenone fungicides" (FRAC code U8) and (b46.5) "triazolopyrimidine fungicides". The thiazole carboxamides include ethaboxam. The phenyl-acetamides include cyflufenamid and N-[[(cyclopropylmethoxy)amino][6-(difluoromethoxy)-2,3-difluorophenyl]-methylene]-benzeneacetamide. The quinazolinones include proquinazid. The benzophenones include metrafenone. The triazolopyrimidines include ametoctradin. The (b46) class also includes bethoxazin, neoasozin (ferric methanearsonate), pyriofenone, pyrrolnitrin, quinomethionate, tebufloquin, 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, N-[2-[4-[[3-(4-chlorophenyl)-2-propyn-1-yl]oxy]-3-methoxyphenyl]ethyl]-3-methyl-2-[(methylsulfonyl)-amino]butanamide, N-[2-[4-[[3-(4-chlorophenyl)-2-propyn-1-yl]oxy]-3-methoxyphenyl]-ethyl]-3-methyl-2-[(ethylsulfonyl)amino]butanamide, (2Z)-2-[[2-fluoro-5-(trifluoromethyl)-phenyl]thio]-2-[3-(2-methoxyphenyl)-2-thiazolidinylidene]acetonitrile (flutianil), 3-[5-(4-chlorophenyl)-2,3-dimethyl-3-isoxazolidinyl]pyridine, 4-fluorophenyl N-[1-[[[1-(4-cyanophenyl)ethyl]sulfonyl]methyl]propyl]carbamate, 5-chloro-6-(2,4,6-trifluorophenyl)-7-(4-methylpiperidin-1-yl)[1,2,4]triazolo[1,5-a]pyrimidine, N-(4-chloro-2-nitrophenyl)-N-ethyl-4-methylbenzenesulfonamide, N-[[(cyclopropylmethoxy)amino][6-(difluoromethoxy)-2,3-difluorophenyl]methylene]benzeneacetamide, N-[4-[4- chloro-3-(trifluoromethyl)-phenoxy]-2,5-dimethylphenyl]-N-ethyl-N-methylmethanimidamide, S-2-propen-1-yl 5-amino-2,3-dihydro-2-(1-methylethyl)-4-(2-methylphenyl)-3-oxo-1H-pyrazole-1-carbothioate (fenpyrazamine), N-[4-[[3-[(4-chlorophenyl)methyl]-1,2,4-thiadiazol-5-yl]oxy]-2,5-dimethylphenyl]-N-ethyl-N-methyl-methanimidamide, 1,1-dimethylethyl N-[6-[[[[(1-methyl-1H-tetrazol-5-yl)phenylmethylene]amino]oxy]methyl]-2-pyridinyl] carbamate, 3-butyn-1-yl N-[6-[[[[(1-methyl-1H-tetrazol-5-yl)phenylmethylene]amino]oxy]methyl]-2-pyridinyl]-carbamate, 2,6-dimethyl-1H,5H-[1,4]dithiino[2,3-c:5,6-c']dipyrrole-1,3,5,7(2H,6H)-tetrone, 5-fluoro-2-[(4-methylphenyl)methoxy]-4-pyrimidinamine and 5-fluoro-2-[(4-fluoro-phenyl)methoxy]-4-pyrimidinamine.

Therefore of note is a mixture (i.e. composition) comprising as component (a) a compound of Formula 1 (or an N-oxide or salt thereof) and as component (b) at least one fungicidal compound selected from the group consisting of the aforedescribed classes (b1) through (b46). Also of note are embodiments wherein component (b) comprises at least one fungicide from each of two different groups selected from (b1) through (b46). Also of note is a composition comprising said mixture (in fungicidally effective amount) and further comprising at least one additional component selected from the group consisting of surfactants, solid diluents and liquid diluents. Of particular note is a mixture (i.e. composition) comprising a compound of Formula 1 and at least one fungicidal compound selected from the group of specific compounds listed above in connection with classes (b1) through (b46). Also of particular note is a composition comprising said mixture (in fungicidally effective amount) and further comprising at least one additional surfactant selected from the group consisting of surfactants, solid diluents and liquid diluents.

Examples of component (b) fungicides include acibenzolar-S-methyl, aldimorph, ametoctradin, amisulbrom, anilazine, azaconazole, azoxystrobin, benalaxyl (including benalaxyl-M), benodanil, benomyl, benthiavalicarb (including benthiavalicarb-isopropyl), benzovindiflupyr, bethoxazin, binapacryl, biphenyl, bitertanol, bixafen, blasticidin-S, boscalid, bromuconazole, bupirimate, buthiobate, captafol, captan, carbendazim, carboxin, carpropamid, chloroneb, chlorothalonil, chlozolinate, clotrimazole, copper hydroxide, copper oxychloride, copper sulfate, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole (including diniconazole-M), dinocap, dithianon, dithiolanes, dodemorph, dodine, econazole, edifenphos, enestroburin, epoxiconazole, etaconazole, ethaboxam, ethirimol, etridiazole, etridiazole, famoxadone, fenarimol, fenamidone, fenbuconazole, fenfuram, fenhexamid, fenoxanil, fenpiclonil, fenpropidin, fenpropimorph, fenpyrazamine, fentin acetate, fentin chloride, fentin hydroxide, ferbam, ferimzone, fluazinam, fludioxonil, flumorph, fluopicolide, fluopyram, fluoxastrobin, fluquinconazole, flusilazole, flusulfamide, flutianil, flutolanil, flutriafol, fluxapyroxad, folpet, fthalide, fuberidazole, furalaxyl, furametpyr, guazatine, hexaconazole, hymexazole, imazalil, imibenconazole, iminoctadine albesilate, iminoctadine triacetate, iodocarb, ipconazole, iprobenfos, iprodione, iprovalicarb, isoconazole, isofetamid, isoprothiolane, isopyrazam, isotianil, kasugamycin, kresoxim-methyl, mancozeb, maneb, mepanipyrim, mepronil, meptyldinocap, metalaxyl (including metalaxyl-M/mefenoxam), metconazole, methasulfocarb, metiram, metominostrobin, metrafenone, miconazole, myclobutanil, naftifine, neo-asozin, nuarimol, octhilinone, ofurace, orysastrobin, oxadixyl, oxolinic acid, oxpoconazole, oxycarboxin, oxytetracycline, pefurazoate, penconazole, pencycuron, penflufen, penthiopyrad, phosphorous acid (including salts thereof, e.g., fosetyl-aluminum), picoxystrobin, piperalin, polyoxin, probenazole, prochloraz, procymidone, propamacarb, propiconazole, propineb, proquinazid, prothiocarb, prothioconazole, pyraclostrobin, pyrametostrobin, pyraoxystrobin, pyrazophos, pyribencarb, pyributicarb, pyrifenox, pyrimethanil, pyriofenone, pyroquilon, pyrrolnitrin, quinconazole, quinomethionate, quinoxyfen, quintozene, silthiofam, simeconazole, spiroxamine, streptomycin, sulfur, tebuconazole, tebufloquin, tebufloquin, teclofthalam, tecnazene, terbinafine, tetraconazole, thiabendazole, thifluzamide, thiophanate, thiophanate-methyl, thiram, tiadinil, tolclofos-methyl, tolprocarb, tolyfluanid, triadimefon, triadimenol, triarimol, triticonazole, triazoxide, tribasic copper sulfate, tricyclazole, tridemorph, trifloxystrobin, triflumizole, triforine, trimorphamide, uniconazole, validamycin, valifenalate, valiphenal, vinclozolin, zineb, ziram, zoxamide, 1,1-dimethylethyl N-[6-[[[[(1-methyl-1H-tetrazol-5-yl)phenylmethylene]amino]oxy]methyl]-2-pyridinyl]carbamate, 1-[4-[4-[5-(2,6-difluoro-phenyl)-4,5-dihydro-3-isoxazolyl]-2-thiazolyl]-1-piperidinyl]-2-[5-methyl-3-(trifluoro-methyl)-1H-pyrazol-1-yl]ethanone, 2,6-dimethyl-1H,5H-[1,4]dithiino[2,3-c:5,6-c']dipyrrole-1,3,5,7(2H,6H)-tetrone, 2-[(2,5-dimethylphenoxy)methyl]-α-methoxy-N-benzeneacetamide, 3-[5-(4-chlorophenyl)-2,3-dimethyl-3-isoxazolidinyl]pyridine, 3-butyn-1-yl N-[6-[[[[(1-methyl-1H-tetrazol-5-yl)phenylmethylene]amino]oxy]methyl]-2-pyridinyl]carbamate, 4-fluorophenyl N-[1-[[[1-(4-cyanophenyl)ethyl]sulfonyl]methyl]propyl]carbamate, 5-chloro-6-(2,4,6-trifluorophenyl)-7-(4-methylpiperidin-1-yl)[1,2,4]triazolo[1,5-a]pyrimidine, 5-fluoro-2-[(4-fluorophenyl)methoxy]-4-pyrimidinamine, 5-fluoro-2-[(4-methylphenyl)-methoxy]-4-pyrimidinamine, N-(4-chloro-2-nitrophenyl)-N-ethyl-4-methylbenzenesulfonamide, N-[[(cyclopropylmethoxy)amino][6-(difluoromethoxy)-2,3-difluorophenyl]-methylene]benzeneacetamide, N-[[(cyclopropylmethoxy)amino][6-(difluoromethoxy)-2,3-difluorophenyl]-methylene] benzeneacetamide, N-[2-(1S,2R)-[1,1'-bicyclopropyl]-2-ylphenyl]-3-(difluoromethyl)-1-methyl-1H-pyrazole-4-carboxamide, N-[2-[4-[[3-(4-chlorophenyl)-2-propyn-1-yl]oxy]-3-methoxyphenyl]ethyl]-3-methyl-2-[(methylsulfonyl)amino]-butanamide, N-[2-[4-[[3-(4-chlorophenyl)-2-propyn-1-yl]oxy]-3-methoxyphenyl]ethyl]-3-methyl-2-[(ethylsulfonyl)amino]butanamide, N-[2-[4-[[3-(4-chlorophenyl)-2-propyn-1-yl]oxy]-3-methoxyphenyl]ethyl]-3-methyl-2-[(methylsulfonyl)amino]butanamide and N-[2-[4-[[3-(4-chlorophenyl)-2-propyn-1-yl]oxy]-3-methoxyphenyl]ethyl]-3-methyl-2-[(ethylsulfonyl)amino]butanamide, N-[4-[[3-[(4-chlorophenyl)methyl]-1,2,4-thiadiazol-5-yl]oxy]-2,5-dimethylphenyl]-N-ethyl-N-methyl-methanimidamide, N-[4-[4-chloro-3-(trifluoro-methyl)phenoxy]-2,5-dimethylphenyl]-N-ethyl-N-methylmethanimidamide, α-[methoxyimino]-N-methyl-2-[[[1-[3-(trifluoromethyl)phenyl]ethoxy]imino]methyl] benzeneacetamide, rel-1-[[(2R,3S)-3-(2-chlorophenyl)-2-(2,4-difluorophenyl)-2-oxiranyl]methyl]-1H-1,2,4-triazole, rel-2-[[(2R,3S)-3-(2-chlorophenyl)-2-(2,4-difluorophenyl)-2-oxiranyl]methyl]-1,2-dihydro-3H-1,2,4-triazole-3-thione, and rel-1-[[(2R,3S)-3-(2-chlorophenyl)-2-(2,4-difluorophenyl)-2-oxiranyl]methyl]-5-(2-propen-1-ylthio)-1H-1,2,4-triazole.

Of note are combinations of compounds of Formula 1 (or an N-oxide or salt thereof) (i.e. Component (a) in compositions) with azoxystrobin, kresoxim-methyl, trifloxystrobin, pyraclostrobin, picoxystrobin, pyrametostrobin, pyraoxystrobin, dimoxystrobin, metominostrobin/fenominostrobin, carbendazim, chlorothalonil, quinoxyfen, metrafenone, cyflufenamid, fenpropidine, fenpropimorph, bromuconazole, cyproconazole, difenoconazole, epoxiconazole, fenbuconazole, flusilazole, fluxapyroxad, hexaconazole, ipconazole, metconazole, penconazole, propiconazole, proquinazid, prothioconazole, pyriofenone, tebuconazole, triticonazole, famoxadone, prochloraz, penthiopyrad and boscalid (nicobifen) (i.e. as Component (b) in compositions).

Preferred for better control of plant diseases caused by fungal plant pathogens (e.g., lower use rate or broader spectrum of plant pathogens controlled) or resistance management are mixtures of a compound of this invention with a fungicide selected from the group: azoxystrobin, kresoxim-methyl, trifloxystrobin, pyraclostrobin, picoxystrobin, pyrametostrobin, pyraoxystrobin, dimoxystrobin, metominostrobin/fenominostrobin, quinoxyfen, metrafenone, cyflufenamid, fenpropidine, fenpropimorph, cyproconazole, epoxiconazole, flusilazole, metconazole, propiconazole, proquinazid, prothioconazole, pyriofenone, tebuconazole, triticonazole, famoxadone and penthiopyrad.

Examples of other biologically active compounds or agents with which compounds of this invention can be formulated are: insecticides such as abamectin, acephate, acetamiprid, acrinathrin, amidoflumet (S-1955), avermectin, azadirachtin, azinphos-methyl, bifenthrin, bifenazate, buprofezin, carbofuran, cartap, chlorantraniliprole, chlorfenapyr, chlorfluazuron, chlorpyrifos, chlorpyrifos-methyl, chromafenozide, clothianidin, cyantraniliprole (3-bromo-1-(3-chloro-2-pyridinyl)-N-[4-cyano-2-methyl-6-[(methylamino)carbonyl]phenyl]-1H-pyrazole-5-carboxamide), cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, meperfluthrin, metaflumizone, metaldehyde, methamidophos, methidathion, methomyl, methoprene, methoxychlor, methoxyfenozide, metofluthrin, milbemycin oxime, monocrotophos, nicotine, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen (BSN 2060), spirotetramat, sulfoxaflor, sulprofos, tebufenozide, teflubenzuron, tefluthrin, terbufos, tetrachlorvinphos, tetramethylfluthrin, thiacloprid, thiamethoxam, thiodicarb, thiosultap-sodium, tolfenpyrad, tralomethrin, triazamate, trichlorfon and triflumuron; and biological agents including entomopathogenic bacteria, such as *Bacillus thuringiensis* subsp. *aizawai*, *Bacillus thuringiensis* subsp. *kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

Compounds of this invention and compositions thereof can be applied to plants genetically transformed to express proteins toxic to invertebrate pests (such as *Bacillus thuringiensis* delta-endotoxins). The effect of the exogenously applied fungicidal compounds of this invention may be synergistic with the expressed toxin proteins.

General references for agricultural protectants (i.e. insecticides, fungicides, nematocides, acaricides, herbicides and biological agents) include *The Pesticide Manual, 13th Edition*, C. D. S. Tomlin, Ed., British Crop Protection Council, Farnham, Surrey, U.K., 2003 and *The BioPesticide Manual, 2nd Edition*, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of diseases controlled beyond the spectrum controlled by the compound of Formula 1 alone.

In certain instances, combinations of a compound of this invention with other biologically active (particularly fungicidal) compounds or agents (i.e. active ingredients) can result in a greater-than-additive (i.e. synergistic) effect. Reducing the quantity of active ingredients released in the environment while ensuring effective pest control is always desirable. When synergism of fungicidal active ingredients occurs at application rates giving agronomically satisfactory levels of fungal control, such combinations can be advantageous for reducing crop production cost and decreasing environmental load.

Also in certain instances, combinations of a compound of the invention with other biologically active compounds or agents can result in a less-than-additive (i.e. safening) effect on organisms beneficial to the agronomic environment. For example, a compound of the invention may safen a herbicide on crop plants or protect a beneficial insect species (e.g., insect predators, pollinators such as bees) from an insecticide.

Of note is a combination of a compound of Formula 1 with at least one other fungicidal active ingredient. Of particular note is such a combination where the other fungicidal active ingredient has different site of action from the compound of Formula 1. In certain instances, a combination with at least one other fungicidal active ingredient having a similar spectrum of control but a different site of action will be particularly advantageous for resistance management. Thus, a composition of the present invention can further comprise a fungicidally effective amount of at least one additional fungicidal active ingredient having a similar spectrum of control but a different site of action.

Of particular note are compositions which in addition to compound of Formula 1 include at least one compound selected from the group consisting of (1) alkylenebis(dithiocarbamate) fungicides; (2) cymoxanil; (3) phenylamide fungicides; (4) proquinazid (6-iodo-3-propyl-2-propyloxy-4 (3H)-quinazolinone); (5) chlorothalonil; (6) carboxamides acting at complex II of the fungal mitochondrial respiratory electron transfer site; (7) quinoxyfen; (8) metrafenone; (9) cyflufenamid; (10) cyprodinil; (11) copper compounds; (12) phthalimide fungicides; (13) fosetyl-aluminum; (14) benzimidazole fungicides; (15) cyazofamid; (16) fluazinam; (17) iprovalicarb; (18) propamocarb; (19) validomycin; (20) dichlorophenyl dicarboximide fungicides; (21) zoxamide; (22) fluopicolide; (23) mandipropamid; (24) carboxylic acid amides acting on phospholipid biosynthesis and cell wall deposition; (25) dimethomorph; (26) non-DMI sterol biosynthesis inhibitors; (27) inhibitors of demethylase in sterol biosynthesis; (28) bc$_1$ complex fungicides; and salts of compounds of (1) through (28).

Further descriptions of classes of fungicidal compounds are provided below.

Sterol biosynthesis inhibitors (group (27)) control fungi by inhibiting enzymes in the sterol biosynthesis pathway. Demethylase-inhibiting fungicides have a common site of action within the fungal sterol biosynthesis pathway, involving inhibition of demethylation at position 14 of lanosterol or 24-methylene dihydrolanosterol, which are precursors to sterols in fungi. Compounds acting at this site are often referred to as demethylase inhibitors, DMI fungicides, or DMIs. The demethylase enzyme is sometimes referred to by other names in the biochemical literature, including cytochrome P-450 (14DM). The demethylase enzyme is described in, for example, *J. Biol. Chem.* 1992, 267, 13175-79 and references cited therein. DMI fungicides are divided between several chemical classes: azoles (including triazoles and imidazoles), pyrimidines, piperazines and pyridines. The triazoles include azaconazole, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole and uniconazole. The imidazoles include clotrimazole, econazole, imazalil, isoconazole, miconazole, oxpoconazole, prochloraz and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

bc$_1$ Complex Fungicides (group 28) have a fungicidal mode of action which inhibits the bc$_1$ complex in the mitochondrial respiration chain. The bc$_1$ complex is sometimes referred to by other names in the biochemical literature, including complex III of the electron transfer chain, and ubihydroquinone:cytochrome c oxidoreductase. This complex is uniquely identified by Enzyme Commission number EC1.10.2.2. The bc$_1$ complex is described in, for example, *J. Biol. Chem.* 1989, 264, 14543-48; *Methods Enzymol.* 1986, 126, 253-71; and references cited therein. Strobilurin fungicides such as azoxystrobin, dimoxystrobin, enestroburin (SYP-Z071), fluoxastrobin, kresoxim-methyl, metominostrobin, orysastrobin, picoxystrobin, pyraclostrobin, pyrametostrobin, pyraoxystrobin and trifloxystrobin are known to have this mode of action (H. Sauter et al., *Angew. Chem. Int. Ed.* 1999, 38, 1328-1349). Other fungicidal compounds that inhibit the bc$_1$ complex in the mitochondrial respiration chain include famoxadone and fenamidone.

Alkylenebis(dithiocarbamate)s (group (1)) include compounds such as mancozeb, maneb, propineb and zineb. Phenylamides (group (3)) include compounds such as metalaxyl, benalaxyl, furalaxyl and oxadixyl. Carboxamides (group (6)) include compounds such as boscalid, carboxin, fenfuram, flutolanil, furametpyr, mepronil, oxycarboxin, thifluzamide, penthiopyrad and N-[2-(1,3-dimethylbutyl)phenyl]-5-fluoro-1,3-dimethyl-1H-pyrazole-4-carboxamide (PCT Patent Publication WO 2003/010149), and are known to inhibit mitochondrial function by disrupting complex II (succinate dehydrogenase) in the respiratory electron transport chain. Copper compounds (group (11)) include compounds such as copper oxychloride, copper sulfate and copper hydroxide, including compositions such as Bordeaux mixture (tribasic copper sulfate). Phthalimides (group (12)) include compounds such as folpet and captan. Benzimidazole fungicides (group (14)) include benomyl and carbendazim. Dichlorophenyl dicarboximide fungicides (group (20)) include chlozolinate, dichlozoline, iprodione, isovaledione, myclozolin, procymidone and vinclozolin.

Non-DMI sterol biosynthesis inhibitors (group (26)) include morpholine and piperidine fungicides. The morpholines and piperidines are sterol biosynthesis inhibitors that have been shown to inhibit steps in the sterol biosynthesis pathway at a point later than the inhibitions achieved by the DMI sterol biosynthesis (group (27)). The morpholines include aldimorph, dodemorph, fenpropimorph, tridemorph and trimorphamide. The piperidines include fenpropidin.

Of further note are combinations of compounds of Formula 1 with azoxystrobin, kresoxim-methyl, trifloxystrobin, pyraclostrobin, picoxystrobin, dimoxystrobin, metominostrobin/fenominostrobin, carbendazim, chlorothalonil, quinoxyfen, metrafenone, cyflufenamid, fenpropidine, fenpropimorph, bromuconazole, cyproconazole, difenoconazole, epoxiconazole, fenbuconazole, flusilazole, hexaconazole, ipconazole, metconazole, penconazole, propiconazole, proquinazid, prothioconazole, tebuconazole, triticonazole, famoxadone, prochloraz, penthiopyrad and boscalid (nicobifen).

The following Tests demonstrate the control efficacy of compounds of this invention on specific pathogens. The pathogen control protection afforded by the compounds is not limited, however, to these species. See Index Tables 1-6 for compound descriptions. See Index Table 7 for $^1$H NMR data. See Index Table 8 for melting point data. The following abbreviations are used in the Index Tables which follow: Me is methyl, Et is ethyl, c-Pr is cyclopropyl, i-Pr is isopropyl, Ph is phenyl, OMe or MeO is methoxy, OEt or EtO is ethoxy and CN is cyano. The structures of individual "A" substituents in the Index Tables are depicted in Exhibit 4. The abbreviation "Ex." stands for "Example" and is followed by a number indicating in which example the compound is prepared. A dash "—" in the $(R^2)_n$ column means that n is 0, and hydrogen atoms instead of $R^2$ substituents are bonded to the available ring atoms. Similarly, a dash "—" in the $(R^{31})_p$ column means that p is 0, and hydrogen atoms instead of $R^{31}$ substituents are bonded to the available ring atoms. Mass spectra are reported as the molecular weight of the highest isotopic abundance parent ion (M+1) formed by addition of H$^+$ (molecular weight of 1) to the molecule, or (M−1) formed by the loss of H$^+$ (molecular weight of 1) from the molecule, observed by using an liquid chromatography coupled to a mass spectrometer (MS) using either atmospheric pressure chemical ionization (AP$^+$) or electrospray ionization (ESI$^+$), where "amu" stands for atomic mass units.

INDEX TABLE 1

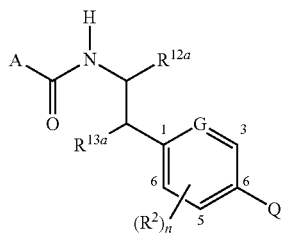

| Cmpd No. | A | R$^{12a}$ | R$^{13a}$ | G | (R$^2$)$_n$ | Q | M + 1 | M − 1 |
|---|---|---|---|---|---|---|---|---|
| 1 | A-1f | Me | H | C—Cl | — | 3-CF$_3$-1H-pyrazol-1-yl | ** | |
| 2 | A-1l | Me | H | C—Cl | — | 3-CF$_3$-1H-pyrazol-1-yl | 477 | |
| 3 | A-1l | H | H | C—H | — | 3-CF$_3$-1H-pyrazol-1-yl | 429 | |
| 4 | A-1d | H | H | C—H | — | 3-CF$_3$-1H-pyrazol-1-yl | 429 | |
| 5 (Ex. 3) | A-1a | H | H | C—H | — | 3-CF$_3$-1H-pyrazol-1-yl | *** | |
| 6 | A-1j | H | H | C—H | — | 3-CF$_3$-1H-pyrazol-1-yl | 395 | |
| 7 | A-1f | Me | H | C—H | — | 3-CF$_3$-1H-pyrazol-1-yl | | 408 |
| 8 | A-1a | Me | H | C—H | — | 3-CF$_3$-1H-pyrazol-1-yl | 442 | |
| 9 | A-1l | Me | H | C—H | — | 3-CF$_3$-1H-pyrazol-1-yl | | 441 |
| 10 | A-1j | Me | H | C—H | — | 3-CF$_3$-1H-pyrazol-1-yl | | 407 |
| 11 | A-1f | Et | H | C—H | — | 3-CF$_3$-1H-pyrazol-1-yl | 425 | |
| 12 | A-1f | Et | H | C—Cl | — | 3-CF$_3$-1H-pyrazol-1-yl | 460 | |
| 13 | A-1l | Et | H | C—Cl | — | 3-CF$_3$-1H-pyrazol-1-yl | | 489 |
| 14 | A-1l | Et | H | C—Me | — | 3-CF$_3$-1H-pyrazol-1-yl | | 469 |
| 15 | A-1f | Et | H | C—Me | — | 3-CF$_3$-1H-pyrazol-1-yl | | 436 |
| 16 | A-1f | Me | H | C—Br | — | 3-CF$_3$-1H-pyrazol-1-yl | 490 | |
| 17 | A-1j | Me | H | C—Br | — | 3-CF$_3$-1H-pyrazol-1-yl | 489 | |
| 18 | A-1d | Me | H | C—Br | — | 3-CF$_3$-1H-pyrazol-1-yl | | 520 |
| 19 | A-1a | Me | H | C—Br | — | 3-CF$_3$-1H-pyrazol-1-yl | 522 | |
| 20 | A-1j | Et | H | C—Cl | — | 3-CF$_3$-1H-pyrazol-1-yl | | 455 |
| 21 | A-1a | Et | H | C—Cl | — | 3-CF$_3$-1H-pyrazol-1-yl | | 488 |
| 22 | A-1d | Et | H | C—Cl | — | 3-CF$_3$-1H-pyrazol-1-yl | | 489 |
| 23 | A-1d | Et | H | C—Me | — | 3-CF$_3$-1H-pyrazol-1-yl | | 469 |
| 24 | A-1a | Et | H | C—Me | — | 3-CF$_3$-1H-pyrazol-1-yl | 470 | |
| 25 | A-1j | Et | H | C—Me | — | 3-CF$_3$-1H-pyrazol-1-yl | | 435 |
| 26 | A-1l | Me | H | C—Br | — | 3-CF$_3$-1H-pyrazol-1-yl | 523 | |
| 27 | A-1h | H | H | C—H | — | 3-CF$_3$-1H-pyrazol-1-yl | 430 | |
| 28 | A-1a | H | H | C—H | — | 3-CF$_3$-1H-pyrazol-1-yl | 428 | |
| 29 | A-1f | Me | H | C—Cl | — | 4-CF$_3$-1H-imidazol-1-yl | | 443 |
| 30 | A-1n | Et | H | C—H | — | 3-CF$_3$-1H-pyrazol-1-yl | 515 | |
| 31 | A-1h | Me | H | C—Cl | — | 3-CF$_3$-1H-pyrazol-1-yl | 478 | |
| 32 | A-1d | Me | H | C—Cl | — | 3-CF$_3$-1H-pyrazol-1-yl | 477 | |
| 33 | A-1h | Me | H | C—Br | — | 3-CF$_3$-1H-pyrazol-1-yl | 523 | |
| 34 | A-1h | Me | H | C—H | — | 3-CF$_3$-1H-pyrazol-1-yl | 444 | |
| 35 | A-1d | Me | H | C—H | — | 3-CF$_3$-1H-pyrazol-1-yl | 443 | |
| 36 | A-1h | H | H | C—Cl | — | 3-CF$_3$-1H-pyrazol-1-yl | | 462 |
| 37 | A-1f | H | H | C—Cl | — | 3-CF$_3$-1H-pyrazol-1-yl | 432 | |
| 38 | A-1j | H | H | C—Cl | — | 3-CF$_3$-1H-pyrazol-1-yl | 430 | |
| 39 | A-1l | H | H | C—Cl | — | 3-CF$_3$-1H-pyrazol-1-yl | 464 | |
| 40 (Ex. 5) | A-1d | H | H | C—Cl | — | 3-CF$_3$-1H-pyrazol-1-yl | *** | |
| 41 | A-1f | Me | H | C—Br | 6-Br | 3-CF$_3$-1H-pyrazol-1-yl | 568 | |
| 42 | A-1h | Me | H | C—Br | 6-Br | 3-CF$_3$-1H-pyrazol-1-yl | 602 | |
| 43 | A-1j | Me | H | C—CF$_3$ | — | 3-CF$_3$-1H-pyrazol-1-yl | 477 | |
| 44 | A-1a | Me | H | C—CF$_3$ | — | 3-CF$_3$-1H-pyrazol-1-yl | | 508 |
| 45 | A-1l | Me | H | C—CF$_3$ | — | 3-CF$_3$-1H-pyrazol-1-yl | 511 | |
| 46 | A-1h | Me | H | C—CF$_3$ | — | 3-CF$_3$-1H-pyrazol-1-yl | 513 | |
| 47 | A-1f | Me | H | C—CF$_3$ | — | 3-CF$_3$-1H-pyrazol-1-yl | 478 | |
| 48 | A-1d | Me | H | C—CF$_3$ | — | 3-CF$_3$-1H-pyrazol-1-yl | 512 | |
| 49 | A-1j | Me | H | C—OMe | — | 3-CF$_3$-1H-pyrazol-1-yl | 440 | |
| 50 | A-1h | Me | H | C—OMe | — | 3-CF$_3$-1H-pyrazol-1-yl | | 472 |
| 51 | A-1d | Me | H | C—OMe | — | 3-CF$_3$-1H-pyrazol-1-yl | 474 | |
| 52 | A-1f | Me | H | C—OMe | — | 3-CF$_3$-1H-pyrazol-1-yl | 441 | |
| 53 | A-1f | Me | H | C—Cl | — | 3-Cl-1H-pyrazol-1-yl | 412 | |
| 54 | A-1h | Me | H | C—Cl | — | 3-Cl-1H-pyrazol-1-yl | 444 | |
| 55 | A-1f | Me | H | C—Cl | — | 3-Br-1H-pyrazol-1-yl | 456 | |
| 56 | A-1h | Me | H | C—Cl | — | 3-Br-1H-pyrazol-1-yl | 490 | |
| 57 | A-1h | Me | H | C—Cl | — | 3-CF$_3$-1H-[1,2,4]triazol-1-yl | 479 | |
| 58 | A-1f | Me | H | C—Cl | — | 3-CF$_3$-1H-[1,2,4]triazol-1-yl | 445 | |
| 59 | A-1o | H | H | C—Cl | — | 3-CF$_3$-1H-pyrazol-1-yl | 411 | |
| 60 | A-1b | H | H | C—Cl | — | 3-CF$_3$-1H-pyrazol-1-yl | 431 | |
| 61[b] | A-1h | Me | MeO | C—Cl | — | 3-CF$_3$-1H-pyrazol-1-yl | ** | |
| 62[c] | A-1h | Me | MeO | C—Cl | — | 3-CF$_3$-1H-pyrazol-1-yl | ** | |
| 63[d] | A-1h | Me | MeO | C—Cl | — | 3-CF$_3$-1H-pyrazol-1-yl | ** | |
| 64 | A-1l | Et | H | C—H | — | 3-CF$_3$-1H-pyrazol-1-yl | | 455 |

INDEX TABLE 1

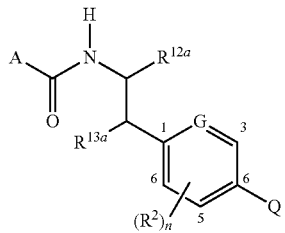

| Cmpd No. | A | R$^{12a}$ | R$^{13a}$ | G | (R$^2$)$_n$ | Q | M + 1 | M − 1 |
|---|---|---|---|---|---|---|---|---|
| 65 | A-1j | Et | H | C—H | — | 3-CF$_3$-1H-pyrazol-1-yl | | 421 |
| 66 | A-1d | Et | H | C—H | — | 3-CF$_3$-1H-pyrazol-1-yl | | 455 |
| 67 | A-1a | Et | H | C—H | — | 3-CF$_3$-1H-pyrazol-1-yl | | 454 |
| 68 | A-1f | Me | H | C—Me | — | 3-CF$_3$-1H-pyrazol-1-yl | | 422 |
| 69 | A-1j | Me | H | C—Me | — | 3-CF$_3$-1H-pyrazol-1-yl | | 421 |
| 70 | A-1l | Me | H | C—Me | — | 3-CF$_3$-1H-pyrazol-1-yl | | 455 |
| 71 | A-1a | Me | H | C—Me | — | 3-CF$_3$-1H-pyrazol-1-yl | | 454 |
| 72 | A-1d | Me | H | C—Me | 6-Me | 3-CF$_3$-1H-pyrazol-1-yl | ** | |
| 73 | A-1l | Me | H | C—Me | 6-Me | 3-CF$_3$-1H-pyrazol-1-yl | ** | |
| 74 | A-1h | Me | H | C—Me | 6-Me | 3-CF$_3$-1H-pyrazol-1-yl | ** | |
| 75 | A-1j | Me | H | C—Cl | 6-Cl | 3-CF$_3$-1H-pyrazol-1-yl | ** | |
| 76 | A-1f | Me | H | C—Cl | 6-Cl | 3-CF$_3$-1H-pyrazol-1-yl | ** | |
| 77 | A-1a | Me | H | C—Me | 6-Me | 3-CF$_3$-1H-pyrazol-1-yl | ** | |
| 78 | A-1f | Me | H | C—Me | 6-Me | 3-CF$_3$-1H-pyrazol-1-yl | ** | |
| 79 | A-1j | Me | H | C—Me | 6-Me | 3-CF$_3$-1H-pyrazol-1-yl | ** | |
| 80 | A-1a | Me | H | C—Cl | 6-Cl | 3-CF$_3$-1H-pyrazol-1-yl | ** | |
| 81 | A-1d | Me | H | C—Cl | 6-Cl | 3-CF$_3$-1H-pyrazol-1-yl | ** | |
| 82 | A-1l | Me | H | C—Cl | 6-Cl | 3-CF$_3$-1H-pyrazol-1-yl | ** | |
| 83 | A-1h | Me | H | C—Cl | 6-Cl | 3-CF$_3$-1H-pyrazol-1-yl | ** | |
| 84 | A-1c | H | H | C—Cl | — | 3-CF$_3$-1H-pyrazol-1-yl | 475 | |
| 85 (Ex. 4) | A-1a | H | H | N | 6-Cl | 3-CF$_3$-1H-pyrazol-1-yl | *** | |
| 86 | A-1d | H | Me | C—Cl | — | 3-CF$_3$-1H-pyrazol-1-yl | | 475 |
| 87 | A-4a | H | H | C—Cl | — | 3-CF$_3$-1H-pyrazol-1-yl | | 412 |
| 88 | A-1d | H | MeO | C—Cl | — | 3-CF$_3$-1H-pyrazol-1-yl | | 491 |
| 89 | A-1j | H | H | N | 6-Cl | 3-CF$_3$-1H-pyrazol-1-yl | ** | |
| 90 | A-1f | H | H | N | 6-Cl | 3-CF$_3$-1H-pyrazol-1-yl | ** | |
| 91 | A-1h | H | H | N | 6-Cl | 3-CF$_3$-1H-pyrazol-1-yl | ** | |
| 92 | A-1l | H | H | N | 6-Cl | 3-CF$_3$-1H-pyrazol-1-yl | ** | |
| 93 | A-1d | H | H | N | 6-Cl | 3-CF$_3$-1H-pyrazol-1-yl | ** | |
| 94 | A-3a | H | H | C—Cl | — | 3-CF$_3$-1H-pyrazol-1-yl | 429 | |
| 95 | A-3c | H | H | C—Cl | — | 3-CF$_3$-1H-pyrazol-1-yl | 483 | |
| 96 | A-1d | H | H | C—Cl | — | 3-Me, 4-Br-1H-pyrazol-1-yl | 488 | |
| 97 | A-1d | H | H | C—Cl | — | 3-CF$_3$, 4-Br-1H-pyrazol-1-yl | | 540 |
| 98 | A-1h | Me | MeO | C—Cl | — | 4-Cl-1H-pyrazol-1-yl | 472 | |
| 99 | A-1h | Me | MeO | C—Cl | — | 3-Br-1H-pyrazol-1-yl | 518 | |
| 100 | A-1h | Me | MeO | C—Cl | — | 3-Cl-1H-pyrazol-1-yl | 472 | |
| 101 | A-1h | Me | MeO | C—Cl | — | 3-Me-1H-pyrazol-1-yl | 452 | |
| 102 | A-1h | Me | MeO | C—Cl | — | 3-Ph-1H-pyrazol-1-yl | 514 | |
| 103 | A-1h | Me | MeO | C—Cl | — | 4-Br-1H-pyrazol-1-yl | 518 | |
| 104 | A-1h | Me | MeO | C—Cl | — | 4-Me-1H-pyrazol-1-yl | 452 | |
| 105 | A-1h | Me | MeO | C—Cl | — | 3,4-di-Me-1H-pyrazol-1-yl | 466 | |
| 106 | A-1h | Me | MeO | C—Cl | — | 3,5-di-Me-1H-pyrazol-1-yl | 466 | |
| 107 | A-2b | Me | MeO | C—Cl | — | 3-Br-1H-pyrazol-1-yl | 502 | |
| 108 | A-2b | Me | MeO | C—Cl | — | 3-Cl-1H-pyrazol-1-yl | 456 | |
| 109 | A-2b | Me | MeO | C—Cl | — | 3-Me-1H-pyrazol-1-yl | 436 | |
| 110 | A-2b | Me | MeO | C—Cl | — | 3-Ph-1H-pyrazol-1-yl | 498 | |
| 111 | A-2b | Me | MeO | C—Cl | — | 4-Cl-1H-pyrazol-1-yl | 456 | |
| 112 | A-2b | Me | MeO | C—Cl | — | 4-Br-1H-pyrazol-1-yl | 502 | |
| 113 | A-2b | Me | MeO | C—Cl | — | 4-Me-1H-pyrazol-1-yl | 436 | |
| 114 | A-2b | Me | MeO | C—Cl | — | 3,4-di-Me-1H-pyrazol-1-yl | 450 | |
| 115 | A-2b | Me | MeO | C—Cl | — | 3,5-di-Me-1H-pyrazol-1-yl | 452 | |
| 116 | A-1d | Me | MeO | C—Cl | — | 3-Br-1H-pyrazol-1-yl | | 517 |
| 117 | A-1d | Me | MeO | C—Cl | — | 3-Ph-1H-pyrazol-1-yl | 515 | |
| 118 | A-1d | Me | MeO | C—Cl | — | 4-Cl-1H-pyrazol-1-yl | 497 | |
| 119 | A-1d | Me | MeO | C—Cl | — | 4-Br-1H-pyrazol-1-yl | 541 | |
| 120 | A-1d | Me | MeO | C—Cl | — | 4-Me-1H-pyrazol-1-yl | 475 | |
| 121 | A-1d | Me | MeO | C—Cl | — | 3,4-di-Me-1H-pyrazol-1-yl | 489 | |
| 122 | A-1a | H | H | C—Cl | — | 3-CF$_3$-1H-pyrazol-1-yl | 462 | |
| 123 | A-2b | H | H | C—H | — | 3-CF$_3$-1H-pyrazol-1-yl | 414 | |
| 124 | A-2c | H | H | C—H | — | 3-CF$_3$-1H-pyrazol-1-yl | 466 | |
| 125 | A-3a | H | H | C—H | — | 3-CF$_3$-1H-pyrazol-1-yl | 395 | |
| 126 | A-1a | H | H | C—H | — | 3-Me-1H-pyrazol-1-yl | 374 | |
| 127 | A-1a | H | H | C—H | — | 1H-pyrazol-1-yl | 360 | |

INDEX TABLE 1

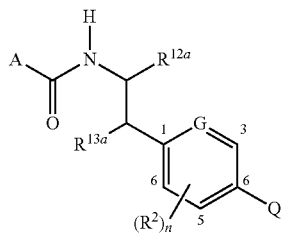

| Cmpd No. | A | R[12a] | R[13a] | G | (R[2])[n] | Q | M + 1 | M − 1 |
|---|---|---|---|---|---|---|---|---|
| 128 | A-1f | H | H | C—H | — | 3-CF$_3$-1H-pyrazol-1-yl | 396 | |
| 129 | A-1a | H | H | C—H | — | 3-Br-1H-pyrazol-1-yl | 440 | |
| 130 | A-1q | H | H | C—H | — | 3-CF$_3$-1H-pyrazol-1-yl | 394 | |
| 131 | A-1p | H | H | C—H | — | 3-CF$_3$-1H-pyrazol-1-yl | 438 | |
| 132 | A-1r | H | H | C—H | — | 3-CF$_3$-1H-pyrazol-1-yl | 378 | |
| 133 | A-1n | H | H | C—H | — | 3-CF$_3$-1H-pyrazol-1-yl | 486 | |
| 134 | A-1s | H | H | C—H | — | 3-CF$_3$-1H-pyrazol-1-yl | 374 | |
| 135 | A-1a | Me | H | C—Cl | — | 3-CF$_3$-1H-pyrazol-1-yl | ** | |
| 136 | A-1t | H | H | C—H | — | 3-CF$_3$-1H-pyrazol-1-yl | 388 | |
| 137 | A-1j | Me | H | C—Cl | — | 3-CF$_3$-1H-pyrazol-1-yl | ** | |
| 138[c] | A-1d | Me | MeO | C—Cl | — | 3-Br-1H-pyrazol-1-yl | | 517 |
| 139[d] | A-1d | Me | MeO | C—Cl | — | 3-Br-1H-pyrazol-1-yl | | 517 |
| 140[c] | A-1d | Me | MeO | C—Cl | — | 3-Cl-1H-pyrazol-1-yl | * | |
| 141[d] | A-1d | Me | MeO | C—Cl | — | 3-Cl-1H-pyrazol-1-yl | * | |
| 142[c] | A-1d | Me | MeO | C—Cl | — | 3-Me-1H-pyrazol-1-yl | * | |
| 143[d] | A-1d | Me | MeO | C—Cl | — | 3-Me-1H-pyrazol-1-yl | * | |
| 144 | A-1b | H | H | C—H | 3,5-di-F | 3-CF$_3$-1H-pyrazol-1-yl | | 463 |
| 145 | A-1d | H | H | C—H | 3,5-di-F | 3-CF$_3$-1H-pyrazol-1-yl | | 429 |
| 146 | A-1d | Me | H | C—Cl | — | 1-i-Pr-1H-pyrazol-4-yl | 451 | |
| 147 | A-1b | Me | H | C—Cl | — | 1-i-Pr-1H-pyrazol-4-yl | 418 | |
| 269 | A-1h | Me | H | C—Cl | — | 4-Br-1H-pyrazol-1-yl | 490 | |
| 270 | A-1h | Me | H | C—Cl | — | 4-Cl-1H-pyrazol-1-yl | 444 | |
| 271 | A-1h | Me | H | C—Cl | — | 3-Br-1H-[1,2,4]triazol-1-yl | 491 | |
| 272 | A-2b | Me | H | C—Cl | — | 4-Br-1H-pyrazol-1-yl | 474 | |
| 273 | A-2b | Me | H | C—Cl | — | 4-Cl-1H-pyrazol-1-yl | 428 | |
| 274 | A-2b | Me | H | C—Cl | — | 3-Br-1H-[1,2,4]triazol-1-yl | 475 | |
| 275 | A-1d | Me | H | C—Cl | — | 4-Br-1H-pyrazol-1-yl | 489 | |
| 276 | A-1d | Me | H | C—Cl | — | 4-Cl-1H-pyrazol-1-yl | 443 | |
| 277 | A-1d | Me | H | C—Cl | — | 3-Br-1H-[1,2,4]triazol-1-yl | 490 | |
| 278[b] | A-1d | Me | MeO | C—Cl | — | 3-CF$_3$-1H-pyrazol-1-yl | 507 | |
| 279[b] | A-2b | Me | MeO | C—Cl | — | 3-CF$_3$-1H-pyrazol-1-yl | 492 | |
| 280[b] | A-1f | Me | MeO | C—Cl | — | 3-CF$_3$-1H-pyrazol-1-yl | 476 | |
| 281 | A-1d | H | MeO | C—Br | — | 3-CF$_3$-1H-pyrazol-1-yl | 537 | |
| 282 | A-1d | H | MeO | C—Br | — | 3-Br-1H-pyrazol-1-yl | ** | |
| 283 | A-1d | H | MeO | C—Br | — | 4-Br-1H-pyrazol-1-yl | ** | |
| 284 | A-1d | H | MeO | C—Br | — | 4-Cl-1H-pyrazol-1-yl | ** | |
| 285 | A-1d | H | MeO | C—Br | — | 3-Me-5-CF$_3$-1H-pyrazol-1-yl | * | |
| 286 | A-1d | H | MeO | C—Br | — | 3,5-di-CF$_3$-1H-pyrazol-1-yl | ** | |
| 287 | A-2b | H | MeO | C—Br | — | 3-CF$_3$-1H-pyrazol-1-yl | 524 | |
| 288 | A-2b | H | MeO | C—Br | — | 3-Br-1H-pyrazol-1-yl | * | |
| 289 | A-2b | H | MeO | C—Br | — | 4-Br-1H-pyrazol-1-yl | * | |
| 290 | A-2b | H | MeO | C—Br | — | 4-Cl-1H-pyrazol-1-yl | ** | |
| 291 | A-2b | H | MeO | C—Br | — | 3-Me-5-CF$_3$-1H-pyrazol-1-yl | ** | |
| 292 | A-2b | H | MeO | C—Br | — | 3,5-di-CF$_3$-1H-pyrazol-1-yl | * | |
| 293 | A-1f | H | MeO | C—Br | — | 3-CF$_3$-1H-pyrazol-1-yl | ** | |
| 294 | A-1f | H | MeO | C—Br | — | 3-Br-1H-pyrazol-1-yl | ** | |
| 295 | A-1f | H | MeO | C—Br | — | 4-Br-1H-pyrazol-1-yl | ** | |
| 296 | A-1f | H | MeO | C—Br | — | 4-Cl-1H-pyrazol-1-yl | ** | |
| 297 | A-1f | H | MeO | C—Br | — | 3-Me-5-CF$_3$-1H-pyrazol-1-yl | ** | |
| 298 | A-1f | H | MeO | C—Br | — | 3,5-di-CF$_3$-1H-pyrazol-1-yl | ** | |
| 299 | A-1a | H | H | N | 6-Cl | 4-Br-1H-pyrazol-1-yl | ** | |
| 300 | A-1a | H | H | N | 6-Cl | 1H-pyrazol-1-yl | ** | |
| 301 | A-1a | H | H | N | 6-Cl | 4-Cl-1H-pyrazol-1-yl | ** | |
| 302 | A-1a | H | H | N | 6-Cl | 3-Me-1H-pyrazol-1-yl | ** | |
| 303 | A-1a | H | H | N | 6-Cl | 3-Ph-1H-pyrazol-1-yl | ** | |
| 304 | A-1a | H | H | N | 6-Cl | 3-Br-1H-pyrazol-1-yl | ** | |
| 338[b] | A-1h | Me | MeO | C—Cl | — | 4-Cl-1H-pyrazol-1-yl | | 472 |
| 339[b] | A-2b | Me | MeO | C—Cl | — | 3-Me-1H-pyrazol-1-yl | | 436 |
| 340 | A-2b | H | H | C—CN | — | 3-CF$_3$-1H-pyrazol-1-yl | ** | |
| 341 | A-1d | H | H | C—CN | — | 3-CF$_3$-1H-pyrazol-1-yl | ** | |
| 342 | A-1a | H | H | C—Br | — | 3-CF$_3$-1H-pyrazol-1-yl | ** | |
| 343 | A-1a | H | H | C—CN | — | 3-CF$_3$-1H-pyrazol-1-yl | ** | |
| 344 | A-2b | Me | H | C—Cl | — | 3-Ph-1H-pyrazol-1-yl | 470 | |

INDEX TABLE 1

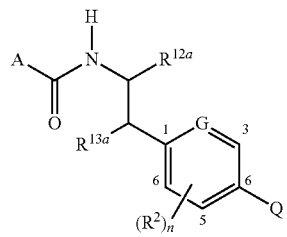

| Cmpd No. | A | $R^{12a}$ | $R^{13a}$ | G | $(R^2)_n$ | Q | M + 1 | M − 1 |
|---|---|---|---|---|---|---|---|---|

*$^1$H NMR data found in Index Table 7
**MP data found in Index Table 8
***MS, $^1$H NMR or MP data found in the Synthesis Examples
[b]Mixture of racemic syn and anti diastereomers
[c]Racemic anti diastereomer
[d]Racemic syn diastereomer

INDEX TABLE 2

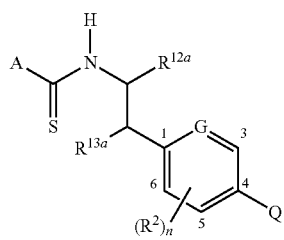

| Cmpd No. | A | $R^{12a}$ | $R^{13a}$ | G | $(R^2)_n$ | Q | M + 1 | M − 1 |
|---|---|---|---|---|---|---|---|---|
| 313[e] | A-1d | H | H | C—Cl | — | 3-CF$_3$-1H-pyrazol-1-yl | 478 | |

[e]Prepared compound may contain in a small amount of Compound No. 40 as an impurity.

INDEX TABLE 3

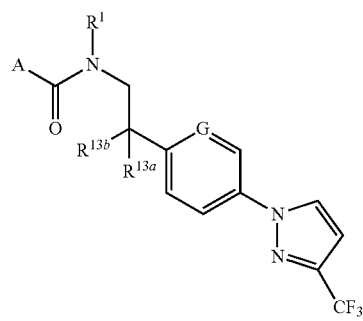

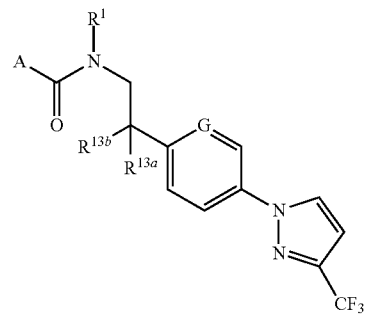

| Cmpd No. | A | $R^1$ | $R^{13a}$ | $R^{13b}$ | G | M + 1 | M − 1 |
|---|---|---|---|---|---|---|---|
| 148 | A-1f | c-Pr | H | H | C—H | * | |
| 149 | A-1h | c-Pr | H | H | C—H | * | |
| 150 (Ex. 6) | A-1d | H | F | F | C—Cl | *** | |
| 304 | A-1d | H | —CH$_2$CH$_2$— | | C—Cl | 487 | |
| 306 | A-1b | H | —CH$_2$CH$_2$— | | C—Cl | 453 | |
| 307 | A-1f | H | —CH$_2$CH$_2$— | | C—Cl | 455 | |
| 308 | A-2a | H | —CH$_2$CH$_2$— | | C—Cl | 490 | |
| 309 | A-1d | H | —CH$_2$CH$_2$CH$_2$CH$_2$— | | C—Cl | 515 | |
| 310 | A-1f | H | —CH$_2$CH$_2$CH$_2$CH$_2$— | | C—Cl | 482 | |
| 311 | A-2b | H | —CH$_2$CH$_2$CH$_2$CH$_2$— | | C—Cl | 500 | |
| 312 | A-1d | H | —CH$_2$CH$_2$— | | C—F | 471 | |

*$^1$H NMR data found in Index Table 7
***MS, $^1$H NMR or MP data found in the Synthesis Examples

INDEX TABLE 4

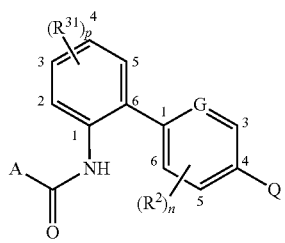

| Cmpd No. | A | $(R^{31})_p$ | G | $(R^2)_n$ | Q | M + 1 | M − 1 |
|---|---|---|---|---|---|---|---|
| 151 | A-1f | — | C—H | — | 3-CF$_3$-1H-pyrazol-1-yl | 445 | |
| 152 | A-2a | — | C—H | — | 3-CF$_3$-1H-pyrazol-1-yl | | 478 |
| 153 | A-1a | — | C—H | — | 3-CF$_3$-1H-pyrazol-1-yl | | 474 |
| 154 | A-1n | — | C—H | — | 3-CF$_3$-1H-pyrazol-1-yl | 534 | |
| 155 | A-1j | — | C—H | — | 3-CF$_3$-1H-pyrazol-1-yl | 444 | |
| 156 | A-1h | — | C—H | — | 3-CF$_3$-1H-pyrazol-1-yl | | 476 |
| 157 | A-1h | 3-F | C—H | — | 3-CF$_3$-1H-pyrazol-1-yl | | 494 |
| 158 | A-1j | 3-F | C—H | — | 3-CF$_3$-1H-pyrazol-1-yl | | 459 |
| 159 | A-1h | 4-Me | C—H | — | 3-CF$_3$-1H-pyrazol-1-yl | 492 | |
| 160 | A-1j | 4-Me | C—H | — | 3-CF$_3$-1H-pyrazol-1-yl | 458 | |
| 161 | A-1f | — | C—H | — | 3-Cl-1H-pyrazol-1-yl | | * |
| 162 | A-1h | — | C—H | — | 3-Cl-1H-pyrazol-1-yl | 444 | |
| 163 | A-1h | 4-Cl | C—H | — | 3-CF$_3$-1H-pyrazol-1-yl | | 510 |
| 164 | A-1j | 4-Cl | C—H | — | 3-CF$_3$-1H-pyrazol-1-yl | | 476 |
| 165 | A-1l | 4-Cl | C—H | — | 3-CF$_3$-1H-pyrazol-1-yl | 511 | |
| 166 | A-1f | — | C—H | 3-F | 3-CF$_3$-1H-pyrazol-1-yl | 462 | |
| 167 | A-1h | — | C—H | 3-F | 3-CF$_3$-1H-pyrazol-1-yl | 496 | |
| 168 | A-1h | — | C—H | 3,5-di-F | 3-CF$_3$-1H-pyrazol-1-yl | 514 | |
| 169 | A-1f | — | C—H | 3,5-di-F | 3-CF$_3$-1H-pyrazol-1-yl | 480 | |
| 170 (Ex. 1) | A-1j | — | C—H | 3,5-di-F | 3-CF$_3$-1H-pyrazol-1-yl | *** | |
| 171 | A-1l | — | C—H | 3,5-di-F | 3-CF$_3$-1H-pyrazol-1-yl | 513 | |
| 172 | A-1d | — | C—H | 3,5-di-F | 3-CF$_3$-1H-pyrazol-1-yl | 513 | |
| 173 | A-2b | — | C—H | 3,5-di-F | 3-CF$_3$-1H-pyrazol-1-yl | 498 | |
| 174 | A-1f | — | C—H | — | 4-Cl-1H-pyrazol-1-yl | 410 | |
| 175 | A-1h | — | C—H | — | 4-Cl-1H-pyrazol-1-yl | 444 | |
| 176 | A-1b | — | C—H | — | 4-Cl-1H-pyrazol-1-yl | 409 | |
| 177 | A-1a | — | C—H | — | 4-Cl-1H-pyrazol-1-yl | 442 | |
| 178 | A-4a | — | C—H | — | 4-Cl-1H-pyrazol-1-yl | 394 | |
| 179 | A-1j | — | C—H | 3-F | 3-CF$_3$-1H-pyrazol-1-yl | 461 | |
| 180 | A-1l | — | C—H | 3-F | 3-CF$_3$-1H-pyrazol-1-yl | 495 | |
| 181 | A-1d | — | C—H | 3-F | 3-CF$_3$-1H-pyrazol-1-yl | 495 | |
| 182 | A-2b | — | C—H | 3-F | 3-CF$_3$-1H-pyrazol-1-yl | 481 | |
| 183 | A-1h | — | C—H | — | 1H-pyrazol-1-yl | 410 | |
| 184 | A-1h | — | C—H | — | 5-Cl-1H-pyrazol-1-yl | 444 | |
| 185 | A-4c | — | C—H | — | 3-CF$_3$-1H-pyrazol-1-yl | 448 | |
| 186 | A-4d | — | C—H | — | 1H-pyrazol-1-yl | 426 | |
| 187 | A-1a | — | C—H | — | 1H-pyrazol-1-yl | 408 | |
| 188 | A-4a | — | C—H | — | 3-CF$_3$-1H-pyrazol-1-yl | 428 | |
| 189 | A-1d | — | C—H | — | 3-Cl-1H-pyrazol-1-yl | 443 | |
| 190 | A-1l | — | C—H | — | 3-Cl-1H-pyrazol-1-yl | 443 | |
| 191 | A-4a | — | C—H | — | 3-Cl-1H-pyrazol-1-yl | 394 | |
| 192 | A-4d | — | C—H | — | 3-CF$_3$-1H-pyrazol-1-yl | 494 | |
| 193 | A-3c | — | C—H | — | 3-CF$_3$-1H-pyrazol-1-yl | 497 | |
| 194 | A-3b | — | C—H | — | 3-CF$_3$-1H-pyrazol-1-yl | 483 | |
| 195 | A-3a | — | C—H | — | 3-CF$_3$-1H-pyrazol-1-yl | 443 | |
| 196 | A-4b | — | C—H | — | 3-CF$_3$-1H-pyrazol-1-yl | 482 | |
| 197 | A-1h | — | C—H | — | 2H-[1,2,3]triazol-2-yl | 411 | |
| 198 | A-1d | — | C—H | — | 3-CF$_3$-1H-pyrazol-1-yl | | 475 |
| 199 | A-1b | — | C—H | — | 3-CF$_3$-1H-pyrazol-1-yl | | 441 |
| 200 | A-2b | — | C—H | 3,5-di-F | 3-Br-1H-pyrazol-1-yl | 510 | |
| 201 | A-2b | — | C—H | 3,5-di-F | 4-Br-1H-pyrazol-1-yl | 510 | |
| 202 | A-2b | — | C—H | 3,5-di-F | 3-Me-1H-pyrazol-1-yl | 444 | |
| 203 | A-2b | — | C—H | 3,5-di-F | 4-Me-1H-pyrazol-1-yl | 444 | |
| 204 | A-2b | — | C—H | 3,5-di-F | 3,5-di-Me-1H-pyrazol-1-yl | 458 | |
| 205 | A-2b | — | C—H | 3,5-di-F | 3,5-di-CF$_3$-1H-pyrazol-1-yl | 566 | |
| 206 | A-2b | — | C—H | 3,5-di-F | 3-Ph-1H-pyrazol-1-yl | 506 | |
| 207 | A-2b | — | C—H | 3,5-di-F | 1H-pyrazol-1-yl | 430 | |
| 208 | A-2b | — | C—H | 3,5-di-F | 1H-[1,2,4]triazol-1-yl | 431 | |
| 209 | A-2b | — | C—H | 3,5-di-F | 3-Br-1H-[1,2,4]triazol-1-yl | 511 | |
| 210 | A-2b | — | C—H | 3,5-di-F | 4-Cl-1H-pyrazol-1-yl | 464 | |
| 211 | A-2b | — | C—H | 3,5-di-F | 3-Cl-1H-pyrazol-1-yl | | 462 |
| 212 | A-1h | — | C—H | 3,5-di-F | 3-Br-1H-pyrazol-1-yl | 526 | |
| 213 | A-1h | — | C—H | 3,5-di-F | 4-Br-1H-pyrazol-1-yl | 526 | |
| 214 | A-1h | — | C—H | 3,5-di-F | 3-Me-1H-pyrazol-1-yl | 460 | |

INDEX TABLE 4

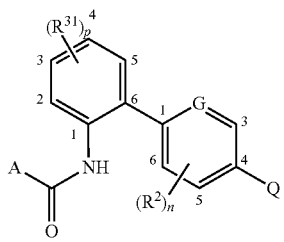

| Cmpd No. | A | $(R^{31})_p$ | G | $(R^2)_n$ | Q | M + 1 | M − 1 |
|---|---|---|---|---|---|---|---|
| 215 | A-1h | — | C—H | 3,5-di-F | 4-Me-1H-pyrazol-1-yl | 460 | |
| 216 | A-1h | — | C—H | 3,5-di-F | 3,5-di-Me-1H-pyrazol-1-yl | 474 | |
| 217 | A-1h | — | C—H | 3,5-di-F | 3,5-di-CF$_3$-1H-pyrazol-1-yl | 582 | |
| 218 | A-1h | — | C—H | 3,5-di-F | 3-Ph-1H-pyrazol-1-yl | 522 | |
| 219 | A-1h | — | C—H | 3,5-di-F | 1H-pyrazol-1-yl | 446 | |
| 220 | A-1h | — | C—H | 3,5-di-F | 1H-[1,2,4]triazol-1-yl | 446 | |
| 221 | A-1h | — | C—H | 3,5-di-F | 3-Br-1H-[1,2,4]triazol-1-yl | 527 | |
| 222 | A-1h | — | C—H | 3,5-di-F | 4-Cl-1H-pyrazol-1-yl | 480 | |
| 223 | A-1h | — | C—H | 3,5-di-F | 3-Cl-1H-pyrazol-1-yl | | 478 |
| 224 | A-1d | — | C—F | 3-F | 3-CF$_3$-1H-pyrazol-1-yl | | 511 |
| 225 | A-1d | — | C—H | — | 5-Cl-1H-pyrazol-1-yl | 443 | |
| 226 | A-1d | — | C—H | — | 2H-[1,2,3]triazol-2-yl | 410 | |
| 227 | A-1d | — | C—F | 5-F | 3-CF$_3$-1H-pyrazol-1-yl | 513 | |
| 228 | A-2b | — | C—H | — | 1,4-di-Me-1H-pyrazol-3-yl | 422 | |
| 229 | A-2b | — | C—H | — | 4-Me-1-(CF$_3$CH$_2$)-1H-pyrazol-3-yl | 490 | |
| 230 | A-1d | — | C—H | — | 1-i-Pr-1H-pyrazol-4-yl | 451 | |
| 231 | A-2b | — | C—H | — | 1-Me-1H-[1,2,4]triazol-3-yl | 409 | |
| 232 (Ex. 2) | A-2b | — | C—H | 3,5-di-F | 1-Me-1H-pyrazol-3-yl | 444 | |
| 233 | A-2b | — | C—H | 3,5-di-F | 1-(CF$_3$CH$_2$)-1H-pyrazol-3-yl | 512 | |
| 234 | A-1d | — | C—H | — | 4-Me-1-(CF$_3$CH$_2$)-1H-pyrazol-3-yl | 505 | |
| 235 | A-1d | — | C—H | — | 1,4-di-Me-1H-pyrazol-3-yl | 537 | |
| 236 | A-1d | — | C—F | — | 3-CF$_3$-1H-pyrazol-1-yl | | 493 |
| 237 | A-1d | — | C—H | 3,5-di-F | 3-Br-1H-pyrazol-1-yl | 525 | |
| 238 | A-1d | — | C—H | 3,5-di-F | 4-Br-1H-pyrazol-1-yl | 525 | |
| 239 | A-1d | — | C—H | 3,5-di-F | 3-Me-1H-pyrazol-1-yl | 459 | |
| 240 | A-1d | — | C—H | 3,5-di-F | 4-Me-1H-pyrazol-1-yl | 459 | |
| 241 | A-1d | — | C—H | 3,5-di-F | 3,5-di-Me-1H-pyrazol-1-yl | 473 | |
| 242 | A-1d | — | C—H | 3,5-di-F | 3,5-di-CF$_3$-1H-pyrazol-1-yl | 581 | |
| 243 | A-1d | — | C—H | 3,5-di-F | 3-Ph-1H-pyrazol-1-yl | 521 | |
| 244 | A-1d | — | C—H | 3,5-di-F | 1H-pyrazol-1-yl | 445 | |
| 245 | A-1d | — | C—H | 3,5-di-F | 1H-[1,2,4]triazol-1-yl | 446 | |
| 246 | A-1d | — | C—H | 3,5-di-F | 3-Br-1H-[1,2,4]triazol-1-yl | 526 | |
| 247 | A-1d | — | C—H | 3,5-di-F | 4-Cl-1H-pyrazol-1-yl | 479 | |
| 248 | A-1d | — | C—H | 3,5-di-F | 3-Cl-1H-pyrazol-1-yl | 479 | |
| 249 | A-1d | — | C—H | — | 1-Me-1H-[1,2,4]triazol-3-yl | 424 | |
| 250 | A-1d | — | C—H | — | 1-(CF$_3$CH$_2$)-1H-[1,2,4]triazol-3-yl | 492 | |
| 251 | A-1d | — | C—H | 3,5-di-F | 1-Me-1H-pyrazol-3-yl | 459 | |
| 252 | A-1d | — | C—H | — | 5-Me-2,4-dihydro-3-oxopyrazol-1-yl | 439 | |
| 253 | A-2b | — | C—H | — | 1-(CF$_3$CH$_2$)-1H-[1,2,4]triazol-3-yl | 477 | |
| 254 | A-1d | — | C—H | 3,5-di-F | 1-(CF$_3$CH$_2$)-1H-pyrazol-1-yl | 527 | |
| 255 | A-1d | 4-F | C—H | 3,5-di-F | 3-CF$_3$-1H-pyrazol-1-yl | 531 | |
| 256 | A-2b | 4-F | C—H | 3,5-di-F | 3-CF$_3$-1H-pyrazol-1-yl | 516 | |
| 257 | A-2b | — | C—H | — | 1,3-di-Me-1H-pyrazol-4-yl | 422 | |
| 258 | A-1d | — | C—H | — | 5-CF$_3$-2,4-dihydro-3-oxopyrazol-1-yl | 493 | |
| 259 | A-1d | — | C—H | 3,5-di-F | 5-Ph-4,5-dihydro-isoxazol-3-yl | 524 | |
| 260 | A-1d | 4-Me | C—H | — | 3-CF$_3$-1H-pyrazol-1-yl | 492 | |
| 261 | A-1d | — | C—H | 3-CN | 3-Br-1H-pyrazol-1-yl | 513 | |
| 262 | A-1d | — | C—H | 3-CN | 3-Me-1H-pyrazol-1-yl | 448 | |
| 263 | A-1d | — | C—H | 3-CN | 3-CF$_3$-1H-pyrazol-1-yl | 502 | |
| 264 | A-1d | — | C—H | 3-CN | 4-Cl-1H-pyrazol-1-yl | 468 | |
| 265 | A-1d | — | C—H | 3-CN | 4-Br-1H-pyrazol-1-yl | 513 | |
| 266 | A-1d | — | C—H | 3-CN | 3-(3,5-di-MeO—Ph)-1H-pyrazol-1-yl | 570 | |
| 267 | A-1d | — | C—H | 3-CN | 3-(2-F—Ph)-1H-pyrazol-1-yl | 528 | |
| 268 | A-1d | — | C—H | 3,5-di-F | 3-CHF$_2$-1H-pyrazol-1-y | 495 | |
| 315 | A-1h | — | C—H | 3,5-di-Me | 5-CF$_3$-1H-pyrazol-1-yl | ** | |
| 316 | A-1d | — | C—H | 3-Cl-5-F | 3-CF$_3$-1H-pyrazol-1-yl | ** | |
| 317 | A-1h | — | C—H | 3-Cl-5-F | 3-CF$_3$-1H-pyrazol-1-yl | ** | |
| 318 | A-2b | — | C—H | 3-Cl-5-F | 3-CF$_3$-1H-pyrazol-1-yl | ** | |
| 319 | A-2b | — | C—H | 3,5-di-Me | 3-CF$_3$-1H-pyrazol-1-yl | ** | |
| 320 | A-1h | — | C—H | 3,5-di-Cl | 3-CF$_3$-1H-pyrazol-1-yl | ** | |
| 321 | A-1d | — | C—H | 3-F-5-Me | 3-CF$_3$-1H-pyrazol-1-yl | ** | |
| 322 | A-1d | — | C—H | 3-Br-5-F | 3-CF$_3$-1H-pyrazol-1-yl | ** | |

INDEX TABLE 4

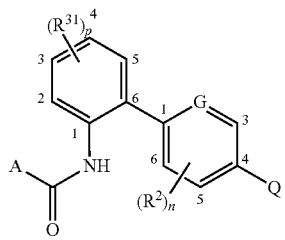

| Cmpd No. | A | $(R^{31})_p$ | G | $(R^2)_n$ | Q | M + 1 | M − 1 |
|---|---|---|---|---|---|---|---|
| 323 | A-1h | — | C—H | 3,5-di-Me | 3-CF$_3$-1H-pyrazol-1-yl | ** | |
| 324 | A-1d | — | C—H | 3-Cl-5-Me | 3-CF$_3$-1H-pyrazol-1-yl | ** | |
| 325 | A-1h | — | C—H | 3-Cl-5-Me | 3-CF$_3$-1H-pyrazol-1-yl | ** | |
| 326 | A-1d | — | C—H | — | 3-Me-1H-pyrrol-1-yl | 422 | |
| 327 | A-2b | — | C—H | 3-Cl-5-Me | 3-CF$_3$-1H-pyrazol-1-yl | ** | |
| 328 | A-1d | — | C—H | 3,5-di-Cl | 3-CF$_3$-1H-pyrazol-1-yl | ** | |
| 329 | A-1l | — | C—H | 3,5-di-Cl | 3-CF$_3$-1H-pyrazol-1-yl | ** | |
| 330 | A-1d | — | C—H | — | 1H-pyrrol-1-yl | 408 | |
| 331 | A-1d | — | C—H | 3,5-di-F | 1H-[1,2,3]triazol-1-yl | 446 | |
| 332 | A-1d | — | C—H | 3,5-di-F | 2H-[1,2,3]triazol-2-yl | 446 | |
| 333 | A-2b | — | C—H | 3-F-5-Me | 3-CF$_3$-1H-pyrazol-1-yl | ** | |
| 334 | A-1h | — | C—H | 3-F-5-Me | 3-CF$_3$-1H-pyrazol-1-yl | ** | |
| 335 | A-2b | — | C—H | 3,5-di-Cl | 3-CF$_3$-1H-pyrazol-1-yl | ** | |
| 336 | A-2b | — | C—H | 3-Br-5-F | 3-CF$_3$-1H-pyrazol-1-yl | ** | |
| 337 | A-1h | — | C—H | 3-Br-5-F | 3-CF$_3$-1H-pyrazol-1-yl | ** | |
| 345 | A-1e | — | C—H | 3-F | 3-CF$_3$-1H-pyrazol-1-yl | ** | |
| 346 | A-1e | — | C—H | 3,5-di-F | 3-CF$_3$-1H-pyrazol-1-yl | ** | |
| 347 | A-2b | — | C—H | 3,5-di-F | 1-isobutyl-1H-pyrazol-4-yl | 486 | |
| 348 | A-1d | — | C—H | 3,5-di-F | 1-Me-1H-pyrazol-4-yl | 459 | |
| 349 | A-2a | — | C—H | 3-F | 3-CF$_3$-1H-pyrazol-1-yl | ** | |
| 350 | A-4a | — | C—H | 3,5-di-F | 3-CF$_3$-1H-pyrazol-1-yl | ** | |
| 351 | A-2a | — | C—H | 3,5-di-F | 3-CF$_3$-1H-pyrazol-1-yl | ** | |
| 352 | A-7a | — | C—H | 3-F | 3-CF$_3$-1H-pyrazol-1-yl | ** | |
| 353 | A-6b | — | C—H | 3,5-di-F | 3-CF$_3$-1H-pyrazol-1-yl | ** | |
| 354 | A-6a | — | C—H | 3,5-di-F | 3-CF$_3$-1H-pyrazol-1-yl | ** | |
| 355 | A-1a | — | C—H | 3-F | 3-CF$_3$-1H-pyrazol-1-yl | ** | |
| 356 | A-3c | — | C—H | 3,5-di-F | 3-CF$_3$-1H-pyrazol-1-yl | ** | |
| 357 | A-1a | — | C—H | 3,5-di-F | 3-CF$_3$-1H-pyrazol-1-yl | ** | |
| 358 | A-1d | — | C—H | 3,5-di-F | 3-CF$_3$-5-Me-1H-pyrazol-1-yl | 527 | |
| 359 | A-1d | — | C—H | 3,5-di-F | 3,5-di-Br-1H-[1,2,4]triazol-1-yl | 604 | |
| 360 | A-1d | — | C—H | 3,5-di-F | 3-(EtOC(=O))-1H-pyrazol-1-yl | 517 | |
| 361 | A-1d | — | C—H | 3,5-di-F | 4-(EtOC(=O))-1H-pyrazol-1-yl | 517 | |
| 362 | A-2b | — | C—H | 3,5-di-F | 3-CF$_3$-5-Me-1H-pyrazol-1-yl | | 510 |
| 363 | A-2b | — | C—H | 3,5-di-F | 3,5-di-Br-1H-[1,2,4]triazol-1-yl | | 587 |
| 364 | A-2b | — | C—H | 3,5-di-F | 3-(EtOC(=O))-1H-pyrazol-1-yl | 502 | |
| 365 | A-2b | — | C—H | 3,5-di-F | 4-(EtOC(=O))-1H-pyrazol-1-yl | 502 | |
| 366 | A-1h | — | C—H | 3,5-di-F | 3-CF$_3$-5-Me-1H-pyrazol-1-yl | 528 | |
| 367 | A-1h | — | C—H | 3,5-di-F | 3,5-di-Br-1H-[1,2,4]triazol-1-yl | 605 | |
| 368 | A-1h | — | C—H | 3,5-di-F | 3-(EtOC(=O))-1H-pyrazol-1-yl | 518 | |
| 369 | A-1h | — | C—H | 3,5-di-F | 4-(EtOC(=O))-1H-pyrazol-1-yl | 518 | |
| 370 | A-2b | — | C—H | 3,5-di-F | 3-Ph-4,5-dihydro-isoxazol-5-yl | 509 | |
| 371 | A-1d | — | C—H | 3,5-di-F | 3-Ph-4,5-dihydro-isoxazol-5-yl | 524 | |
| 372 | A-2b | — | C—H | 3,5-di-F | 5-Me-furan-2-yl | 444 | |
| 373 | A-1d | — | C—H | 3,5-di-F | 5-(MeC(=O))-thien-2-yl | 503 | |
| 374 | A-6a | — | C—H | 3-F | 3-CF$_3$-1H-pyrazol-1-yl | ** | |
| 375 | A-6b | — | C—H | 3-F | 3-CF$_3$-1H-pyrazol-1-yl | ** | |
| 378 | A-8a | — | C—H | — | 3-CF$_3$-1H-pyrazol-1-yl | 483 | |

*$^1$H NMR data found in Index Table 7
**MP data found in Index Table 8
***MS, $^1$H NMR or MP data found in the Synthesis Examples

INDEX TABLE 5

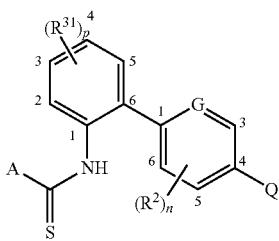

| Cmpd No. | A | $(R^{31})_p$ | G | $(R^2)_n$ | Q | M + 1 | M − 1 |
|---|---|---|---|---|---|---|---|
| 314[f] | A-1d | — | C—H | — | 3-CF₃-1H-pyrazol-1-yl | 491 | |

[f] Prepared compound may contain a small amount of Compound No. 198 as an impurity.

INDEX TABLE 6

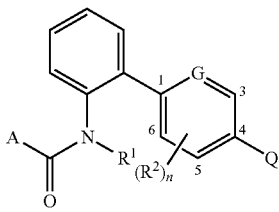

| Cmpd No. | A | $R^1$ | G | $(R^2)_n$ | Q | M + 1 | M − 1 |
|---|---|---|---|---|---|---|---|
| 376 | A-2b | c-Pr | C—H | 3,5-di-F | 3-CF₃-1H-pyrazol-1-yl | 538 | |
| 377 | A-1d | c-Pr | C—H | 3,5-di-F | 4-CF₃-1H-pyrazol-1-yl | ** | |

INDEX TABLE 7

| Cmpd No. | ¹H NMR Data (CDCl₃) |
|---|---|
| 140 | δ 8.75 (d, 1H), 8.12 (d, 1H), 7.83 (d, 1H), 7.80 (s, 1H), 7.58 (m, 2H), 7.48 (m, 2H), 6.37 (s, 1H), 4.78 (s, 1H), 4.49 (m, 1H), 3.35 (s, 3H), 1.42 (d, 3H). |
| 141 | δ 7.78 (d, 1H), 8.17 (d, 1H), 7.82 (d, 2H), 7.70 (s, 1H), 7.55 (m, 3H), 6.41 (s, 1H), 4.80 (d, 1H), 4.60 (m, 1H), 3.35 (s, 3H), 1.25 (d, 3H). |
| 142 | δ 8.75 (d, 1H), 8.02 (d, 1H), 7.83 (d, 1H), 7.78 (s, 1H), 7.62 (s, 1H), 7.58 (m, 2H), 6.44 (s, 1H), 6.22 (s, 1H), 4.77 (d, 1H), 4.46 (m, 1H), 3.42 (s, 3H), 2.34 (s, 3H), 1.40 (d, 3H). |
| 143 | δ 8.76 (d, 1H), 8.10 (d, 1H), 7.83 (d, 1H), 7.78 (s, 1H), 7.62 (s, 1H), 7.56 (m, 2H), 7.46 (s, 1H), 6.21 (s, 1H), 4.76 (d, 1H), 4.46 (m, 1H), 3.34 (s, 3H), 2.34 (s, 3H), 1.41 (d, 3H). |
| 148 | δ 8.62 (s, 1H), 8.48 (d, 2H), 7.44 (d, 2H), 7.19 (d, 2H), 6.77 (s, 1H), 3.76 (t, 2H), 3.04 (m, 2H), 2.64 (m, 1H), 0.60 (m, 2H), 0.40 (m, 2H). |
| 149 | δ 8.78 (d, 2H), 7.63 (s, 1H), 7.47 (d, 2H), 7.19 (d, 2H), 6.61 (s, 1H), 3.78 (t, 2H), 3.00 (t, 2H), 2.60 (m, 1H), 0.45 (m, 4H). |
| 158 | δ 9.72 (br s, 1H), 8.57 (d, 1H), 8.51 (d, 1H), 8.33 (d, 1H), 7.92 (d, 1H), 7.80-7.76 (m, 2H), 7.56-7.52 (m, 2H), 7.49-7.44 (m, 1H), 7.34-7.25 (m, 2H), 6.45 (d, 1H). |
| 285 | δ 8.77 (s, 1H), 8.36 (m, 1H), 7.99 (br s, 1H), 7.63 (d, 1H), 7.55 (m, 1H), 7.50 (s, 1H), 7.40 (d, 1H), 6.47 (s, 1H), 4.94 (m, 1H), 3.99 (m, 1H), 3.57 (m, 1H), 3.56 (s, 3H), 2.38 (s, 3H). |
| 288 | δ 7.90 (s, 1H), 7.83 (s, 1H), 7.74 (s, 1H), 7.56 (m, 2H), 6.84 (t, 1H), 6.81 (br s, 1H), 6.50 (s, 1H), 4.81 (m, 1H), 3.93 (m, 4H), 3.40 (m, 1H), 3.33 (s, 3H). |
| 289 | δ 7.95 (s, 1H), 7.90 (s, 1H), 7.74 (s, 1H), 7.68 (m, 1H), 7.55 (m, 2H), 6.82 (t, 1H), 6.79 (br s, 1H), 4.82 (m, 1H), 3.92 (m, 4H), 3.99 (m, 1H), 3.33 (s, 3H). |
| 292 | δ 7.94 (s, 1H), 7.70 (d, 1H), 7.57 (s, 1H), 7.45 (m, 1H), 7.12 (m, 1H), 6.84 (t, 1H), 6.81 (m, 1H), 4.85 (m, 1H), 4.02 (m, 1H), 3.93 (m, 3H), 3.39 (m, 1H), 3.36 (s, 3H). |

[a] ¹H NMR data are in ppm downfield from tetramethylsilane. Couplings are designated by (s)—singlet, (br s)—broad singlet, (d)—doublet, (t)—triplet, (q)—quartet, (m)—multiplet and (br m)—broad multiplet.

INDEX TABLE 8

| Cmpd No. | Melting Point[a] |
|---|---|
| 1 | 140-142 |
| 61 | 134-136 |
| 62 | 183-185 |
| 63 | 124-127 |
| 72 | 152-154 |
| 73 | 191-194 |
| 74 | 188-189 |
| 75 | 196-198 |
| 76 | 204-205 |
| 77 | 130-132 |
| 78 | 204-206 |
| 79 | 175-176 |
| 80 | 158-162 |
| 81 | 162-163 |
| 82 | 211-212 |
| 83 | 178-180 |
| 85 | 118-120 |
| 89 | 132-134 |
| 90 | 152-154 |
| 91 | 143-145 |
| 92 | 154-156 |
| 93 | 155-157 |
| 135 | 170-175 |
| 137 | 166-168 |
| 282 | 135-136 |
| 283 | 140-141 |
| 284 | 147-148 |
| 286 | 114-116 |
| 290 | 132-133 |
| 291 | 118-120 |
| 293 | 113-115 |
| 294 | 165-166 |
| 295 | 159-160 |
| 296 | 157-158 |
| 297 | 115-117 |
| 298 | 154-156 |
| 299 | 154-156 |
| 300 | 130-133 |
| 301 | 137-139 |
| 302 | 136-139 |
| 303 | 164-167 |
| 304 | 140-143 |
| 315 | 135-137 |
| 316 | 134-136 |
| 317 | 157-159 |

INDEX TABLE 8-continued

| Cmpd No. | Melting Point [a] |
|---|---|
| 318 | 90-92 |
| 319 | 73-75 |
| 320 | 160-162 |
| 321 | 132-134 |
| 322 | 104-106 |
| 323 | 169-171 |
| 324 | 151-154 |
| 325 | 136-139 |
| 327 | 120-123 |
| 328 | 140-142 |
| 329 | 102-104 |
| 333 | 135-138 |
| 334 | 147-149 |
| 335 | 118-120 |
| 336 | 86-89 |
| 337 | 143-145 |
| 340 | 170-172 |
| 341 | 217-221 |
| 342 | 157-159 |
| 343 | 180-182 |
| 345 | 144-147 |
| 346 | 180-182 |
| 349 | 122-124 |
| 350 | 140-142 |
| 351 | 147-149 |
| 352 | 111-113 |
| 353 | 176-177 |
| 354 | 132-134 |
| 355 | 177-179 |
| 356 | 100-102 |
| 357 | 161-163 |
| 374 | 112-114 |
| 375 | 162-164 |
| 377 | 110-113 |

[a] Melting point data are °C.

Biological Examples of the Invention

General protocol for preparing test suspensions for Tests A-H: the test compounds were first dissolved in acetone in an amount equal to 3% of the final volume and then suspended at the desired concentration (in ppm) in acetone and purified water (50/50 mix by volume) containing 250 ppm of the surfactant Trem® 014 (polyhydric alcohol esters). The resulting test suspensions were then used in Tests A-H. Spraying a 200 ppm test suspension to the point of run-off on the test plants was the equivalent of a rate of 600 g/ha. Unless otherwise indicated, the rating values indicate a 200 ppm test suspension was used. (In Table A, an asterisk "*" next to the rating value indicates a 40 ppm test suspension was used; a double asterisk "**" next to the rating value indicates a 130 ppm.)

Test A

Grape seedlings were inoculated with a spore suspension of *Plasmopara viticola* (the causal agent of grape downy mildew) and incubated in a saturated atmosphere at 20° C. for 24 h. After a short drying period, the test suspension was sprayed to the point of run-off on the grape seedlings, and then the seedlings were moved to a growth chamber at 20° C. for 4 days, after which time the seedlings were moved back to a saturated atmosphere at 20° C. for 24 h. Upon removal, visual disease ratings were made.

Test B

The test suspension was sprayed to the point of run-off on tomato seedlings. The following day the seedlings were inoculated with a spore suspension of *Botrytis cinerea* (the causal agent of tomato botrytis) and incubated in saturated atmosphere at 20° C. for 48 h, and then moved to a growth chamber at 24-27° C. for 2-3 days, after which time visual disease ratings were made.

Test C

The test suspension was sprayed to the point of run-off on tomato seedlings. The following day the seedlings were inoculated with a spore suspension of *Alternaria solani* (the causal agent of tomato early blight) and incubated in a saturated atmosphere at 27° C. for 48 h, and then moved to a growth chamber at 20° C. for 5 days, after which time visual disease ratings were made.

Test D

The test suspension was sprayed to the point of run-off on tomato seedlings. The following day the seedlings were inoculated with a spore suspension of *Phytophthora infestans* (the causal agent of tomato late blight) and incubated in a saturated atmosphere at 20° C. for 24 h, and then moved to a growth chamber at 20° C. for 5 days, after which time visual disease ratings were made.

Test E

The test suspension was sprayed to the point of run-off on wheat seedlings. The following day the seedlings were inoculated with a spore suspension of *Septoria nodorum* (also known as *Stagonosopora nodorum*; the causal agent of Septoria glume blotch) and incubated in a saturated atmosphere at 20-24° C. for 48 h, and then moved to a growth chamber at 20° C. for 6 days, after which time visual disease ratings were made.

Test F

The test suspension was sprayed to the point of run-off on wheat seedlings. The following day the seedlings were inoculated with a spore suspension of *Septoria tritici* (the causal agent of wheat leaf blotch) and incubated in saturated atmosphere at 24° C. for 48 h, and then moved to a growth chamber at 20° C. for 19 days, after which time visual disease ratings were made.

Test G

The test suspension was sprayed to the point of run-off on wheat seedlings. The following day the seedlings were inoculated with a spore suspension of *Puccinia recondita* f. sp. *tritici* (the causal agent of wheat leaf rust) and incubated in a saturated atmosphere at 20° C. for 24 h, and then moved to a growth chamber at 20° C. for 6 days, after which time visual disease ratings were made.

Test H

The test suspension was sprayed to the point of run-off on wheat seedlings. The following day the seedlings were inoculated with a spore dust of *Blumeria graminis* f. sp. *tritici* (also known as *Erysiphe graminis* f. sp. *tritici*, the causal agent of wheat powdery mildew) and incubated in a growth chamber at 20° C. for 8 days, after which time visual disease ratings were made.

Results for Tests A-H are given in Table A. In the Table, a rating of 100 indicates 100% disease control and a rating of 0 indicates no disease control (relative to the controls). A dash (-) indicates no test results. An asterisk "*" next to the rating value indicates a 40 ppm test suspension was used, a double asterisk "**" next to the rating value indicates a 130 ppm test suspension was used.

TABLE A

| Cmpd No. | Test A | Test B | Test C | Test D | Test E | Test F | Test G | Test H |
|---|---|---|---|---|---|---|---|---|
| 1 | — | 99 | — | 0 | 100 | 100 | 54 | 100 |
| 2 | — | 64 | — | 0 | — | 100 | 0 | 95 |
| 3 | — | 26 | — | 0 | — | 100 | 0 | 95 |
| 4 | — | 24 | — | 0 | — | 100 | 0 | 97 |
| 5 | — | 17 | 83 | 0 | 0 | 100 | 0 | 96 |
| 6 | 0 | 68 | 99 | 0 | 0 | 99 | 70 | 93 |
| 7 | — | 58 | — | 0 | — | 99 | 0 | 98 |
| 8 | — | 0 | — | 0 | 0 | 100 | 0 | 0 |
| 9 | — | 0 | — | 0 | 0 | 100 | 0 | 0 |
| 10 | — | 0 | — | 0 | 60 | 100 | 0 | 50 |
| 11 | — | 0 | — | 0 | 0 | 100 | 0 | 0 |
| 12 | — | 40 | — | 0 | — | 100 | 0 | 90 |
| 13 | — | 0 | — | 0 | — | 88 | 0 | 26 |
| 14 | 33 | 0 | — | 0 | 0 | 95 | 0 | 21 |
| 15 | 7 | 0 | — | 0 | 0 | 100 | 0 | 95 |
| 16 | — | 95 | — | 0 | 98 | 100 | 0 | 99 |
| 17 | — | 0 | — | 0 | — | 100 | 0 | 96 |
| 18 | — | 0 | — | 0 | — | 100 | 0 | 96 |
| 19 | — | 0 | — | 0 | — | 71 | 0 | 79 |
| 20 | — | 36 | — | 0 | — | 71 | 0 | 0 |
| 21 | — | 38 | — | 0 | — | 0 | 0 | 0 |
| 22 | — | 0 | — | 0 | — | 0 | 0 | 0 |
| 23 | — | 8 | — | 0 | — | 93 | 0 | 93 |
| 24 | — | 15 | — | 0 | — | 50 | 0 | 0 |
| 25 | — | 31 | — | 0 | — | 99 | 0 | 0 |
| 26 | — | 31 | — | 0 | — | 99 | 0 | 87 |
| 27 | — | 99 | — | 0 | — | 100 | 28 | 99 |
| 28 | 0 | 0 | — | 0 | — | 0 | 0 | 0 |
| 29 | — | 47 | — | 0 | 0 | 97 | 68 | 72 |
| 31 | — | 92 | — | 0 | 100 | 100 | 0 | 100 |
| 32 | — | 82 | — | 0 | 0 | 100 | 0 | 95 |
| 33 | — | 67 | — | 0 | 100 | 100 | 68 | 100 |
| 34 | — | 32 | — | 0 | 0 | 100 | 28 | 99 |
| 35 | 7 | 85 | — | 0 | 94 | 100 | 0 | 100 |
| 36 | — | 99 | — | 0 | 99 | 100 | 41 | 100 |
| 37 | — | 99 | — | 0 | 0 | 100 | 0 | 99 |
| 38 | — | 9 | — | 0 | 0 | 100 | 0 | 87 |
| 39 | — | 0 | — | 0 | 0 | 100 | 0 | 96 |
| 40 | — | 66 | — | 0 | 100 | 100 | 0 | 100 |
| 41 | — | 46 | — | 0 | 66 | 99 | 0 | 95 |
| 42 | — | 98 | — | 0 | 100 | 100 | 0 | 99 |
| 43 | 6 | 0 | — | 0 | 0 | 89 | 84 | 43 |
| 44 | — | 0 | — | 0 | 0 | 28 | 0 | 0 |
| 45 | — | 9 | — | 0 | 0 | 100 | 0 | 94 |
| 46 | — | 53 | — | 0 | 60 | 100 | 0 | 99 |
| 47 | — | 68 | — | 0 | 95 | 100 | 0 | 99 |
| 48 | — | 31 | — | 0 | 0 | 99 | 0 | 97 |
| 49 | — | 60 | — | 0 | 0 | 100 | 28 | 99 |
| 50 | — | 0 | — | 0 | 92 | 100 | 0 | 99 |
| 51 | — | 0 | — | 0 | 75 | 99 | 0 | 98 |
| 52 | — | 9 | — | 0 | 78 | 100 | 0 | 50 |
| 53 | — | 88 | — | 0 | 99 | 100 | 0 | 100 |
| 54 | — | 80 | — | 0 | 100 | 100 | 0 | 100 |
| 55 | — | 97 | — | 0 | 100 | 100 | 0 | 100 |
| 56 | — | 57 | — | 0 | 100 | 100 | 0 | 100 |
| 57 | — | — | — | 0 | 75 | 99 | 0 | 98 |
| 59 | — | 16 | — | 0 | 92 | 100 | 0 | 99 |
| 60 | — | 29 | — | 0 | 69 | 100 | 0 | 100 |
| 61 | 0 | 53 | — | 0 | 100 | — | 0 | 100 |
| 62 | 0 | 33 | — | 0 | 100 | 100 | 27 | 99 |
| 63 | 0 | 73 | — | 47 | 99 | 100 | 0 | 99 |
| 64 | 15 | 0 | — | 0 | 0 | 94 | 0 | 0 |
| 65 | 25 | 0 | — | 0 | 0 | 82 | 0 | 0 |
| 66 | 7 | 0 | — | 0 | 0 | 85 | 0 | 0 |
| 67 | 7 | 0 | — | 0 | 0 | 31 | 0 | 0 |
| 68 | — | 79 | — | 0 | 95 | 100 | 0 | 100 |
| 69 | — | 40 | — | 0 | — | 99 | 0 | 98 |
| 70 | — | 24 | — | 0 | 0 | 100 | 0 | 98 |
| 71 | 0 | 0 | — | 0 | 0 | 99 | 0 | 100 |
| 72 | 7 | 0 | — | 0 | 97 | 100 | 0 | 98 |
| 73 | 0 | 0 | — | 0 | 40 | 97 | 0 | 0 |

TABLE A-continued

| Cmpd No. | Test A | Test B | Test C | Test D | Test E | Test F | Test G | Test H |
|---|---|---|---|---|---|---|---|---|
| 74 | 0 | 66 | — | 0 | 98 | 99 | 0 | 90 |
| 75 | 0 | 0 | — | 0 | 0 | 99 | 0 | 76 |
| 76 | 0 | 39 | — | 0 | 89 | 99 | 0 | 21 |
| 77 | 0 | 0 | — | 0 | 0 | 28 | 0 | 0 |
| 78 | 7 | 39 | — | 0 | 0 | 94 | 0 | 0 |
| 79 | 37 | 9 | — | 0 | 0 | 82 | 0 | 0 |
| 80 | 0 | 0 | — | 0 | 0 | 87 | 0 | 47 |
| 81 | 49 | 88 | — | 0 | 100 | 100 | 0 | 100 |
| 82 | 0 | 0 | — | 0 | 0 | 92 | 0 | 73 |
| 83 | 15 | 86 | — | 0 | 98 | 99 | 0 | 99 |
| 84 | 0 | 61 | — | 0 | 73 | 100 | 0 | 90 |
| 85 | 0 | 95 | — | 0 | 100 | 100 | 0 | 100 |
| 86 | 8 | 96 | — | 0 | 100 | 99 | 0 | 99 |
| 87 | 16 | 15 | — | 0 | 0 | 99 | 0 | 96 |
| 88 | 8 | — | — | 0 | 100 | 99 | 68 | 99 |
| 89 | 17 | — | — | 0 | 92 | 100 | 0 | 100 |
| 90 | 8 | — | — | 0 | 67 | 100 | 0 | 98 |
| 91 | 0 | — | — | 0 | 95 | 100 | 0 | 100 |
| 92 | 0 | — | — | 0 | 100 | 100 | 0 | 100 |
| 93 | 0 | 0 | — | 0 | 99 | 98 | 0 | 97 |
| 94 | 0** | 30** | — | 0** | 82** | 100** | 0** | 100** |
| 95 | 0 | 77 | — | 0 | 89 | 99 | 0 | 99 |
| 96 | — | — | — | — | 99 | 100 | 0 | 100 |
| 97 | — | — | — | — | 100 | 100 | 0 | 100 |
| 98 | 0 | 100 | — | 0 | 99 | 100 | 0 | 99 |
| 99 | 0 | 99 | — | 0 | 100 | 100 | 0 | 100 |
| 100 | 0 | 99 | — | 0 | 100 | 100 | 0 | 100 |
| 101 | — | — | — | — | 100 | 100 | 0 | 100 |
| 102 | 0 | 99 | — | 0 | 100 | 99 | 0 | 95 |
| 103 | — | — | — | — | 100 | 100 | 55 | 100 |
| 104 | — | — | — | — | 100 | 100 | 0 | 100 |
| 105 | — | — | — | — | 100 | 100 | 41 | 100 |
| 106 | 0 | 99 | — | 0 | 99 | 99 | 0 | 99 |
| 107 | — | — | — | — | 100 | 100 | 94 | 100 |
| 108 | — | — | — | — | 100 | 100 | 91 | 100 |
| 109 | 0 | 99 | — | 0 | 99 | 100 | 0 | 99 |
| 110 | — | — | — | — | 100 | 100 | 98 | 99 |
| 111 | — | — | — | — | 100 | 100 | 17 | 100 |
| 112 | — | — | — | — | 100 | 100 | 9 | 100 |
| 113 | — | — | — | — | 100 | 100 | 0 | 100 |
| 114 | — | — | — | 0 | 100 | 100 | 0 | 100 |
| 115 | — | — | — | — | 100 | 99 | 0 | 100 |
| 116 | — | — | — | 0 | 100 | 100 | 0 | 100 |
| 117 | — | — | — | 0 | 94 | 82 | 0 | 97 |
| 118 | — | — | — | 0 | 100 | 100 | 0 | 100 |
| 119 | — | — | — | 0 | 100 | 100 | 0 | 100 |
| 120 | — | — | — | 0 | 100 | 99 | 0 | 100 |
| 121 | — | — | — | 0 | 100 | 100 | 0 | 100 |
| 122 | 0 | 50 | 100 | 0 | 0 | 100 | 0 | 94 |
| 123 | 0 | 0 | 99 | 0 | 90 | 99 | 41 | 97 |
| 124 | 31 | 0 | 9 | 0 | 0 | 0 | 0 | 0 |
| 125 | 78 | 0 | 91 | 0 | 29 | 98 | 94 | 99 |
| 127 | 0 | 0 | — | 0 | — | 94 | 0 | 0 |
| 128 | 8 | 94 | — | 0 | — | 100 | 0 | 93 |
| 130 | 17 | 21 | — | 0 | — | 95 | 0 | 0 |
| 131 | 17 | 33 | — | 0 | — | 100 | 0 | 91 |
| 132 | 0 | 0 | — | 0 | — | 0 | 0 | 0 |
| 133 | 8 | 91 | — | 53 | — | 100 | 0 | 94 |
| 134 | 0 | 0 | — | 0 | — | 96 | 0 | 21 |
| 135 | 0 | 0 | — | 0 | — | 96 | 0 | 95 |
| 136 | 0 | 0 | — | 0 | — | 71 | 0 | 0 |
| 137 | 8 | 56 | — | 17 | — | 99 | 0 | 98 |
| 138 | — | — | — | — | 100* | 100* | 0* | 100* |
| 139 | — | — | — | — | 100* | 100* | 0* | 100* |
| 140 | — | — | — | — | 100* | 100* | 0* | 100* |
| 141 | — | — | — | — | 100* | 100* | 0* | 100* |
| 142 | — | — | — | — | 100* | 100* | 0* | 100* |
| 143 | — | — | — | — | 100* | 100* | 0* | 100* |
| 144 | — | 67 | — | — | 0 | 100 | 0 | 94 |
| 145 | — | 8 | — | — | 0 | 97 | 0 | 64 |
| 146 | — | 99 | — | — | 100 | 100 | 73 | 100 |
| 147 | — | 0 | — | — | 97 | 100 | 94 | 84 |
| 148 | — | 17 | — | 0 | 0 | 97 | 74 | 0 |
| 149 | — | 95 | — | 0 | 99 | 100 | 55 | 96 |
| 150 | — | — | — | — | 100* | 100* | 0* | 100* |
| 151 | — | 95 | — | 0 | — | 99 | 100 | 98 |
| 152 | 2 | 42 | — | 0 | — | 100 | 100 | 100 |
| 153 | 4 | 8 | — | 0 | — | 100 | 100 | 97 |

TABLE A-continued

| Cmpd No. | Test A | Test B | Test C | Test D | Test E | Test F | Test G | Test H |
|---|---|---|---|---|---|---|---|---|
| 154 | 15 | 0 | — | 0 | — | 74 | 99 | 91 |
| 155 | 15 | 57 | — | 0 | — | 100 | 100 | 99 |
| 156 | — | 91 | — | 0 | 100 | 100 | 100 | 100 |
| 157 | — | 0 | — | — | 0 | 100 | 100 | 97 |
| 158 | — | 0 | — | 0 | 0 | 100 | 99 | 26 |
| 159 | — | 39 | — | 0 | 0 | 100 | 100 | 97 |
| 160 | — | 0 | — | 0 | 0 | 56 | 99 | 0 |
| 161 | — | 70 | — | 0 | 0 | 98 | 99 | 26 |
| 162 | — | 94 | — | 0 | 99 | 100 | 100 | 100 |
| 163 | — | 26 | — | 0 | 0 | 97 | 99 | 98 |
| 164 | — | 0 | — | 0 | 0 | 89 | 99 | 0 |
| 165 | — | 0 | — | 0 | 0 | 97 | 100 | 0 |
| 166 | — | 99 | — | 0 | 0 | 100 | 99 | 99 |
| 167 | — | 99 | — | 0 | 100 | 100 | 100 | 100 |
| 168 | 0 | 37 | — | 0 | 100 | 100 | 100 | 100 |
| 169 | — | 33 | — | 0 | 60 | 98 | 99 | 99 |
| 170 | 0 | 0 | — | 0 | 0 | 100 | 100 | 100 |
| 171 | 8 | 17 | — | 0 | 0 | 100 | 100 | 100 |
| 172 | 0 | 65 | — | 0 | 100 | 100 | 100 | 100 |
| 173 | 0 | 72 | — | 0 | 100 | 100 | 100 | 100 |
| 174 | 15 | 0 | — | 0 | 60 | 96 | 98 | 43 |
| 175 | 8 | 86 | — | 0 | 100 | 100 | 100 | 100 |
| 176 | 0 | 0 | — | 0 | 0 | 47 | 92 | 0 |
| 177 | 0 | 0 | — | 0 | 0 | 58 | 95 | 43 |
| 178 | 8 | 0 | — | 0 | 60 | 100 | 100 | 98 |
| 179 | 0 | 0 | — | 0 | 20 | — | 100 | 100 |
| 180 | 0 | 0 | — | 0 | 98 | 100 | 100 | 100 |
| 181 | 25 | 71 | — | 0 | 100 | 100 | 100 | 100 |
| 182 | 0 | 97 | — | 0 | 99 | 100 | 100 | 100 |
| 183 | 87 | 99 | — | 0 | 100 | 100 | 100 | 100 |
| 184 | 0 | 87 | — | 0 | 100 | 100 | 100 | 100 |
| 185 | 0 | 0 | — | 0 | 0 | — | 99 | 47 |
| 186 | 0 | 65 | — | 0 | 99 | — | 100 | 91 |
| 187 | 0 | 0 | — | 0 | 0 | — | 94 | 0 |
| 188 | 0 | 0 | — | 0 | 0 | — | 100 | 99 |
| 189 | 0 | 96 | — | 0 | 100 | 100 | 100 | 100 |
| 190 | 8 | 17 | — | 0 | 0 | 100 | 100 | 99 |
| 191 | 23 | 94 | — | 0 | 0 | 100 | 100 | 91 |
| 192 | 0 | — | — | 0 | 0 | 99 | 100 | 69 |
| 193 | 0 | — | — | 0 | 0 | 100 | 100 | 99 |
| 194 | 0 | — | — | 0 | 92 | 99 | 100 | 97 |
| 195 | 8 | 73 | — | 0 | 95 | 100 | 100 | 100 |
| 196 | 0 | 0 | — | 0 | 87 | 100 | 100 | 100 |
| 197 | 0 | 100 | — | 0 | 100 | 99 | 100 | 100 |
| 198 | — | — | — | — | 98 | 100 | 100 | 100 |
| 199 | — | 58 | — | — | 0 | 100 | 99 | 87 |
| 200 | — | — | — | — | 73* | 100* | 100* | 100* |
| 201 | — | — | — | — | 78* | 100* | 100* | 100* |
| 202 | — | — | — | — | 87* | 97* | 100* | 100* |
| 203 | — | — | — | — | 0* | 100* | 100* | 99* |
| 204 | — | — | — | — | 0* | 97* | 100* | 99* |
| 205 | — | — | — | — | 94* | 100* | 100* | 99* |
| 206 | — | — | — | — | 0* | 100* | 100* | 91* |
| 207 | — | — | — | — | 73* | 100* | 100* | 99* |
| 208 | — | — | — | — | 0* | 0* | 96* | 21* |
| 209 | — | — | — | — | 0* | 100* | 8* | 98* |
| 210 | — | — | — | — | 95* | 100* | 100* | 100* |
| 211 | — | — | — | — | 97* | 100* | 100* | 100* |
| 212 | — | — | — | — | 100* | 100* | 100* | 100* |
| 213 | — | — | — | — | 100* | 100* | 100* | 100* |
| 214 | — | — | — | — | 100* | 100* | 100* | 100* |
| 215 | — | — | — | — | 100* | 100* | 100* | 100* |
| 216 | — | — | — | — | 60* | 100* | 100* | 99* |
| 217 | — | — | — | — | 73* | 100* | 100* | 99* |
| 218 | — | — | — | — | 73* | 100* | 100* | 99* |
| 219 | — | — | — | — | 99* | 100* | 100* | 100* |
| 220 | — | — | — | — | 82* | 87* | 88* | 99* |
| 221 | — | — | — | — | 73* | 100* | 100* | 100* |
| 222 | — | — | — | — | 100* | 100* | 100* | 100* |
| 223 | — | — | — | — | 100* | 100* | 100* | 100* |
| 224 | — | 72 | — | — | 78 | 100 | 100 | 100 |
| 225 | — | — | — | — | 69* | 0* | 98* | 100* |
| 226 | — | — | — | — | 97* | 100* | 100* | 98* |
| 227 | — | 92 | — | — | 99 | 100 | 100 | 100 |
| 228 | — | — | — | — | 0 | 0 | 82 | 0 |
| 229 | — | 0* | — | — | 0* | 20* | 0* | 8* |
| 230 | — | 0 | — | — | 0 | 27 | 79 | 29 |
| 231 | — | 0 | — | — | 0 | 0 | 38 | 90 |

TABLE A-continued

| Cmpd No. | Test A | Test B | Test C | Test D | Test E | Test F | Test G | Test H |
|---|---|---|---|---|---|---|---|---|
| 232 | — | 81 | — | — | — | — | 100 | 97 |
| 233 | — | 96 | — | — | — | 98 | 100 | 99 |
| 234 | — | 0 | — | — | 0 | 0 | 0 | 0 |
| 235 | — | 41 | — | — | 60 | 23 | 89 | 97 |
| 236 | — | 95 | — | — | 99 | 100 | 100 | 97 |
| 237 | — | 99* | — | — | 100* | 100* | 100* | 100* |
| 238 | — | 97* | — | — | 94* | 100* | 100* | 100* |
| 239 | — | 99* | — | — | 98* | 100* | 100* | 99* |
| 240 | — | 99* | — | — | 90* | 100* | 100* | 99* |
| 241 | — | 92* | — | — | 0* | 100* | 99* | 100* |
| 242 | — | 29* | — | — | 0* | 97* | 95* | 100* |
| 243 | — | 73* | — | — | 0* | 100* | 100* | 98* |
| 244 | — | 99* | — | — | 99* | 100* | 100* | 100* |
| 245 | — | 98* | — | — | 87* | 88* | 73* | 96* |
| 246 | — | 99* | — | — | 94* | 100* | 100* | 99* |
| 247 | — | 99* | — | — | 100* | 100* | 100* | 100* |
| 248 | — | 100* | — | — | 100* | 100* | 100* | 100* |
| 249 | — | 15* | — | — | 0* | 0* | 0* | 0* |
| 250 | — | 15* | — | — | 0* | 0* | 0* | 0* |
| 251 | — | 28* | — | — | 60* | 70* | 82* | 0* |
| 252 | — | 15 | — | — | 0 | — | 0 | 64 |
| 253 | — | 15* | — | — | 0* | 0* | 79* | 0* |
| 254 | — | 46* | — | — | 0* | — | 97* | 87* |
| 255 | — | 0* | — | — | 0* | 100* | 96* | 100* |
| 256 | — | 54* | — | — | 78* | — | 100* | 100* |
| 257 | — | 71 | — | — | 0 | 100 | 99 | 0 |
| 258 | — | 21 | — | — | 0 | 77 | 0 | 98 |
| 259 | — | 49* | — | — | 87* | — | 100* | 95* |
| 260 | — | 0 | — | 0 | 0 | 30 | 80 | 0 |
| 261 | — | 60* | — | — | 73* | 100* | 100* | 99* |
| 262 | — | 51* | — | — | 0* | 79* | 100* | 90* |
| 263 | — | 9* | — | — | 0* | — | 100* | 94* |
| 264 | — | 94* | — | — | 99* | — | 100* | 99* |
| 265 | — | 83* | — | — | 84* | 100* | 100* | 93* |
| 266 | — | 53* | — | — | 0* | 53* | 85* | 0* |
| 267 | — | 0* | — | — | 0* | 43* | 99* | 0* |
| 268 | — | 100* | — | — | 90* | 100* | 100* | 100* |
| 269 | — | 99* | — | — | 100* | 100* | 0* | 100* |
| 270 | — | 99* | — | — | 100* | 100* | 0* | 100* |
| 271 | — | 85* | — | — | 98* | 100* | 0* | 97* |
| 272 | — | 99* | — | — | 100* | 100* | 68* | 100* |
| 273 | — | 99* | — | — | 100* | 100* | 0* | 100* |
| 274 | — | 44* | — | — | 0* | 100* | 0* | 95* |
| 275 | — | 89* | — | — | 100* | 100* | 0* | 100* |
| 276 | — | 99* | — | — | 100* | 100* | 0* | 100* |
| 277 | — | 73* | — | — | 87* | 100* | 0* | 99* |
| 278 | — | 78* | — | — | 100* | 100* | 0* | 99* |
| 279 | — | 97* | — | — | 100* | 100* | 68* | 99* |
| 280 | — | 95* | — | — | 100* | 100* | 28* | 93* |
| 281 | — | 87* | — | — | 100* | 100* | 28* | 99* |
| 282 | — | 99* | — | — | 100* | 100* | 0* | 100* |
| 283 | — | 100* | — | — | 100* | 100* | 0* | 100* |
| 284 | — | 99* | — | — | 100* | 100* | 0* | 100* |
| 285 | — | 91* | — | — | 100* | 100* | 0* | 98* |
| 286 | — | — | — | — | 99* | 100* | 0* | 99* |
| 287 | — | — | — | — | 100* | 100* | 17* | 96* |
| 288 | — | — | — | — | 100* | 100* | 26* | 100* |
| 289 | — | — | — | — | 100* | 100* | 0* | 99* |
| 290 | — | — | — | — | 100* | 100* | 0* | 95* |
| 291 | — | — | — | — | 100* | 100* | 0* | 96* |
| 292 | — | — | — | — | 100* | 100* | 0* | 73* |
| 293 | — | — | — | — | 100* | 100* | 17* | 93* |
| 294 | — | — | — | — | 100* | 100* | 0* | 98* |
| 295 | — | — | — | — | 100* | 100* | 0* | 91* |
| 296 | — | — | — | — | 100* | 100* | 0* | 96* |
| 297 | — | — | — | — | 100* | 100* | 0* | 56* |
| 298 | — | — | — | — | 98* | 100* | 0* | 79* |
| 299 | — | 100* | — | — | 100* | 89* | 100* | 99* |
| 300 | — | 100* | — | — | 100* | 99* | 86* | 99* |
| 301 | — | 100* | — | — | 100* | 99* | 86* | 99* |
| 302 | — | 99* | — | — | 100* | 95* | 0* | 85* |
| 303 | — | 69* | — | — | 87* | 37* | 0* | 0* |
| 304 | — | 99* | — | — | 100* | 100* | 19* | 100* |
| 305 | — | 100 | — | — | 100 | 100 | 67 | 100 |
| 306 | — | 100 | — | — | 100 | 100 | 67 | 97 |
| 307 | — | 99 | — | — | 99 | 100 | 0 | 90 |
| 308 | — | 98 | — | — | 100 | 100 | 85 | 95 |
| 309 | — | 46 | — | — | 99 | 100 | 28 | 0 |
| 310 | — | 97 | — | — | 96 | 100 | 9 | 0 |

TABLE A-continued

| Cmpd No. | Test A | Test B | Test C | Test D | Test E | Test F | Test G | Test H |
|---|---|---|---|---|---|---|---|---|
| 311 | — | 89 | — | — | 99 | 100 | 68 | 98 |
| 312 | — | — | — | — | 100* | 100* | 26* | 100* |
| 313 | — | 99 | — | — | 99 | 100 | 53 | 100 |
| 314 | — | 8 | — | — | 0 | 100 | 100 | 98 |
| 315 | — | 46* | — | — | 95* | 100* | 99* | 81* |
| 316 | — | 73* | — | — | 99* | 100* | 100* | 99* |
| 317 | — | 77* | — | — | 100* | 100* | 100* | 100* |
| 318 | — | 99* | — | — | 99* | 100* | 100* | 100* |
| 320 | — | 86* | — | — | 99* | 100* | 100* | 100* |
| 321 | — | 99* | — | — | 100* | 100* | 100* | 100* |
| 322 | — | 88* | — | — | 99* | 100* | 100* | 100* |
| 326 | — | 6* | — | — | 11* | 39* | 68* | 0* |
| 327 | — | 94* | — | — | 99* | 100* | 100* | 96* |
| 328 | — | 92* | — | — | 100* | 100* | 100* | 99* |
| 329 | — | 67* | — | — | 0* | 100* | 100* | 99* |
| 330 | — | 56* | — | — | 82* | 28* | 0* | 0* |
| 331 | — | 81 | — | — | 99 | 100 | 100 | 96 |
| 332 | — | 94 | — | — | 99 | 100 | 100 | 100 |
| 333 | — | 99* | — | — | 100* | 100* | 100* | 100* |
| 334 | — | 99* | — | — | 100* | 100* | 100* | 99* |
| 335 | — | 61* | — | — | 99* | 100* | 100* | 100* |
| 336 | — | — | — | — | 99* | 100* | 100* | 99* |
| 337 | — | 89* | — | — | 100* | 100* | 100* | 100* |
| 338 | 0 | 100 | — | — | 99 | 100 | 0 | 99 |
| 339 | 0 | 99 | — | — | 99 | 100 | 200 | 99 |
| 340 | — | 0* | — | — | 0* | 22* | 0* | 0* |
| 341 | — | 0* | — | — | 0* | 4* | 0* | 0* |
| 342 | — | 33* | — | — | 0* | 47* | 25* | 0* |
| 343 | — | 0* | — | — | 0* | 10* | 53* | 0* |
| 344 | — | — | — | — | 100 | 100 | 85 | 98 |
| 345 | — | 0* | — | — | 0* | 0* | 0* | 0* |
| 346 | — | 0* | — | — | 0* | 0* | 0* | 0* |
| 347 | — | 78* | — | — | 97* | 100* | 100* | 43* |
| 348 | — | 0* | — | — | 98* | 46* | 86* | 0* |
| 349 | — | 97* | — | — | 99* | 100* | 100* | 99* |
| 350 | — | 81* | — | — | — | 100* | 100* | 97* |
| 351 | — | 28* | — | — | 99* | 100* | 100* | 99* |
| 352 | — | 40* | — | — | 0* | 100* | 100* | 90* |
| 353 | — | 0* | — | — | 0* | 10* | 99* | 0* |
| 354 | — | 99* | — | — | 0* | 97* | 99* | 0* |
| 355 | — | 20* | — | — | 0* | 43* | 88* | 69* |
| 356 | — | 0* | — | — | 60* | 100* | 100* | 96* |
| 357 | — | 0* | — | — | 0* | 100* | 100* | 98* |
| 358 | — | 41* | — | — | 90* | 100* | 97* | 100* |
| 359 | — | 99* | — | — | 99* | 100* | 100* | 100* |
| 360 | — | 62* | — | — | 90* | 100* | 98* | 0* |
| 361 | — | 0* | — | — | 0* | 100* | 97* | 91* |
| 362 | — | 62* | — | — | 99* | 100* | 100* | 100* |
| 363 | — | 99* | — | — | 98* | 100* | 100* | 100* |
| 364 | — | 31* | — | — | 99* | 100* | 96* | 26* |
| 365 | — | 98* | — | — | 69* | 100* | 100* | 98* |
| 366 | — | 87* | — | — | 99* | 100* | 100* | 100* |
| 367 | — | 66* | — | — | 100* | 100* | 100* | 100* |
| 368 | — | 68* | — | — | 51* | 100* | 98* | 21* |
| 369 | — | 97* | — | — | 95* | 100* | 100* | 99* |
| 370 | — | — | — | — | 69 | 100 | 100 | 96 |
| 371 | — | — | — | — | 0 | 100 | 99 | 96 |
| 372 | — | — | — | — | 100 | 100 | 100 | 99 |
| 373 | — | — | — | — | 0* | 88* | 79* | 0* |
| 374 | — | 99* | — | — | 0* | 88* | 100* | 0* |
| 375 | — | — | — | — | 0* | 100* | 100* | 0* |
| 376 | — | 28* | — | — | 0* | 76* | 99* | 0* |
| 377 | — | 43* | — | — | 100* | 23* | 100* | 0* |
| 378 | — | — | — | — | 0 | 100 | 100 | 100 |

Test I

Control of the southern root-knot nematode (*Meloidogyne incognita*) through contact and/or systemic means was evaluated in test units consisting of small open containers filled with a sandy soil mixture and cucumber seedlings.

Test compounds were formulated using a solution containing 50% acetone and 50% water. Test compounds were applied directly to the soil of the test units at concentrations of 250 or 50 ppm active ingredient. Each test was replicated 3 times. After treatment, the test units were allowed to dry for 1 h, after which time about 250 second-stage juvenile (J2) larvae were pipetted into the soil. The test units were held at 27° C. and watered as needed for 7 days.

Nematocidal efficacy was determined by the amount of root gall formation observed when compared to an untreated control. No gall formation was indicative of 100% nematode control. Gall formation equivalent to that found in the untreated control was indicative of 0% control. No nematode control rating was given to compounds showing significant phytotoxicity.

Of the compounds tested at a concentration of 250 ppm, the following provided good levels of plant protection (50% or more reduction in root galling, compared to solvent-treated controls) and exhibited no significant phytotoxicity: 1, 2, 3, 4, 5, 6, 7, 9, 10, 17, 27, 29, 31, 33, 34, 35, 36, 37, 40, 50, 51, 53, 54, 55, 56, 58, 59, 60, 62, 69, 70, 71, 75, 84, 85, 86, 89, 92, 93, 96, 97, 99, 100, 101, 103, 105, 112, 128, 129, 130, 131, 133, 134, 135, 137, 142, 144 and 150.

What is claimed is:

1. A compound selected from Formula 1, N-oxides and salts thereof,

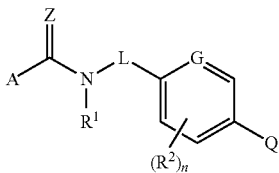

wherein

A is a radical selected from the group consisting of

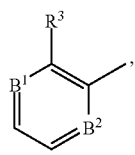
A-1

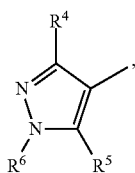
A-2

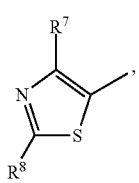
A-3

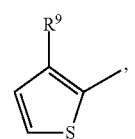
A-4

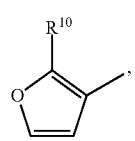
A-5

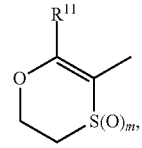
A-6

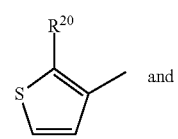
A-7

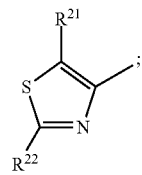
A-8

$R^1$ is H, cyclopropyl or $C_1$-$C_2$ alkoxy;
Z is O or S;
L is —C($R^{12a}$)$R^{12b}$—C($R^{13a}$)$R^{13b}$—, wherein the carbon atom bonded to $R^{12a}$ and $R^{12b}$ is also bonded to the carboxamide nitrogen atom in Formula 1; or 1,2-phenylene optionally substituted with up to 4 substituents independently selected from halogen and $C_1$-$C_2$ alkyl;
G is N or C—$R^{2a}$;
each $R^2$ is independently halogen, nitro, cyano, $C_1$-$C_2$ alkyl, $C_1$-$C_2$ haloalkyl, $C_1$-$C_2$ alkoxy or $C_1$-$C_2$ haloalkoxy;
n is 0, 1, 2 or 3;
$R^{2a}$ is H, halogen, nitro, cyano, $C_1$-$C_2$ alkyl, $C_1$-$C_2$ haloalkyl, $C_1$-$C_2$ alkoxy or $C_1$-$C_2$ haloalkoxy;
$B^1$ is CH or N;
$B^2$ is CH or N;
$R^3$ is halogen, $C_1$-$C_3$ alkyl or $C_1$-$C_3$ haloalkyl;
$R^4$ is halogen, $C_1$-$C_3$ alkyl or $C_1$-$C_3$ haloalkyl;
$R^5$ is H, halogen, $C_1$-$C_3$ alkyl or $C_1$-$C_3$ haloalkyl;
$R^6$ is $C_1$-$C_2$ alkyl;
$R^7$ is halogen, $C_1$-$C_3$ alkyl or $C_1$-$C_3$ haloalkyl;
$R^8$ is H, $C_1$-$C_2$ alkyl or $C_1$-$C_2$ haloalkyl;
$R^9$ is halogen, $C_1$-$C_3$ alkyl or $C_1$-$C_3$ haloalkyl;
$R^{10}$ is halogen, $C_1$-$C_3$ alkyl or $C_1$-$C_3$ haloalkyl;
$R^{11}$ is halogen, $C_1$-$C_3$ alkyl or $C_1$-$C_3$ haloalkyl;
m is 0, 1 or 2;
$R^{12a}$ and $R^{12b}$ are each independently H, $C_1$-$C_2$ alkyl or $C_1$-$C_2$ haloalkyl;
$R^{12a}$ and $R^{12b}$ are taken together as $C_2$-$C_4$ alkanediyl;
$R^{13a}$ is H, halogen, $C_1$-$C_2$ alkyl, $C_1$-$C_2$ haloalkyl, $C_1$-$C_2$ alkoxy, $C_1$-$C_2$ haloalkoxy, $C_1$-$C_2$ alkylthio or $C_1$-$C_2$ alkoxyamino;
$R^{13b}$ is H, halogen, $C_1$-$C_2$ alkyl or $C_1$-$C_2$ haloalkyl; or
$R^{13a}$ and $R^{13b}$ are taken together as $C_2$-$C_4$ alkanediyl;
Q is a 5-membered unsaturated heterocyclic ring containing ring members selected from carbon atoms and up to 4 heteroatoms independently selected from up to 1O, up to 1S and up to 4N atoms, wherein up to 2 carbon atom ring members are independently selected from C(=O), the ring optionally substituted with one substituent on a ring member distal relative to the ring member connecting the heteroaromatic ring to the remainder of Formula 1, said optional substituent selected from $R^{14c}$ on carbon atom ring members and from $R^{14n}$ on nitrogen atom ring members, the heterocyclic ring further optionally substituted with substituents selected from $R^{15c}$ on carbon atom ring members and $R^{15n}$ on nitrogen atom ring members;

each $R^{14c}$ is independently halogen, cyano, $C_1$-$C_3$ alkyl, $C_1$-$C_3$ haloalkyl, $C_1$-$C_3$ alkoxy, $C_1$-$C_3$ haloalkoxy, $C_2$-$C_3$ alkoxycarbonyl or $C_2$-$C_4$ alkylcarbonyl; or a phenyl ring optionally substituted with up to 5 substituents independently selected from $R^{16}$; or a heteroaromatic ring optionally substituted with up to 4 substituents independently selected from $R^{17c}$ on carbon atom ring members and from $R^{17n}$ on nitrogen atom ring members;

each $R^{14n}$ is independently $C_1$-$C_3$ alkyl, $C_1$-$C_3$ haloalkyl or $C_1$-$C_3$ alkoxy; or a phenyl ring optionally substituted with up to 5 substituents independently selected from $R^{18}$; or a heteroaromatic ring optionally substituted with up to 4 substituents independently selected from $R^{19c}$ on carbon atom ring members and from $R^{19n}$ on nitrogen atom ring members;

each $R^{15c}$ is independently halogen, $C_1$-$C_3$ alkyl, $C_1$-$C_3$ haloalkyl or $C_1$-$C_3$ alkoxy;

each $R^{15n}$ is independently $C_1$-$C_3$ alkyl, $C_1$-$C_3$ haloalkyl or $C_1$-$C_3$ alkoxy;

each $R^{16}$, $R^{17c}$, $R^{18}$ and $R^{19c}$ is independently halogen, cyano, $C_1$-$C_2$ alkyl, $C_1$-$C_2$ haloalkyl, $C_1$-$C_2$ alkoxy or $C_1$-$C_2$ haloalkoxy;

each $R^{17n}$ and $R^{19n}$ is independently $C_1$-$C_2$ alkyl, $C_1$-$C_2$ haloalkyl or $C_1$-$C_2$ alkoxy;

$R^{20}$ is halogen, $C_1$-$C_3$ alkyl or $C_1$-$C_3$ haloalkyl;

$R^{21}$ is halogen, $C_1$-$C_3$ alkyl or $C_1$-$C_3$ haloalkyl; and $R^{22}$ is H, $C_1$-$C_2$ alkyl or $C_1$-$C_2$ haloalkyl;

provided that the compound of Formula 1 is other than: 2-methyl-N-[2-[4-(1H-pyrazol-1-yl)phenyl]ethyl]-5-thiazolecarboxamide, N-[2-[4-(3,5-dimethyl-1H-pyrazol-1-yl)phenyl]ethyl]-1,3,5-trimethyl-1H-pyrazole-4-carboxamide, 2-bromo-N-[2-[4-(1H-pyrazol-1-yl)phenyl]ethyl]benzamide, 3-methyl-N-[2-[4-(1H-pyrazol-1-yl)phenyl]ethyl]-2-thiophenecarboxamide, 2-methyl-N-[2-[4-(1H-pyrazol-1-yl)phenyl]ethyl]benzamide, 2-iodo-N-[2-[4-(1H-pyrazol-1-yl)phenyl]ethyl]benzamide, 2-fluoro-N-[2-[4-(1H-pyrazol-1-yl)phenyl]ethyl]benzamide, 2-chloro-N-[2-[4-(1H-pyrazol-1-yl)phenyl]ethyl]benzamide, 5-chloro-1,3-dimethyl-N-[2-[4-(2-methyl-4-thiazolyl)phenyl]ethyl]-1H-pyrazole-4-carboxamide, 2-methyl-N-[2-[4-(2-methyl-4-thiazolyl)phenyl]ethyl]benzamide, 2-methyl-N-[2-[4-(2-methyl-4-thiazolyl)phenyl]ethyl]-3-furancarboxamide, 2-fluoro-N-[2-[4-(2-methyl-4-thiazolyl)phenyl]ethyl]benzamide, 2-bromo-N-[2-[4-(2-methyl-4-thiazolyl)phenyl]ethyl]benzamide, 2-iodo-N-[2-[4-(2-methyl-4-thiazolyl)phenyl]ethyl]benzamide, N-[2-[4-(2-methyl-4-thiazolyl)phenyl]ethyl]-2-(trifluoromethyl)benzamide, and 2-chloro-N-[2-[4-(2-methyl-4-thiazolyl)phenyl]ethyl]benzamide.

2. A compound of claim 1 wherein:

Z is O;

L is —$C(R^{12a})R^{12b}$—$C(R^{13a})R^{13b}$—; or 1,2-phenylene optionally substituted with up to 2 substituents independently selected from F, Cl, Br and $CH_3$;

each $R^2$ is independently F, Cl, Br or $CH_3$;

$R^{2a}$ is H, F, Cl, Br or $CH_3$;

$R^3$ is F, Cl Br, $CH_3$, $CHF_2$ or $CF_3$;

$R^4$ is F, Cl Br, $CH_3$, $CHF_2$ or $CF_3$;

$R^5$ is H, F, Cl Br, $CH_3$, $CHF_2$ or $CF_3$;

$R^6$ is $CH_3$;

$R^7$ is F, Cl Br, $CH_3$, $CHF_2$ or $CF_3$;

$R^8$ is H or $CH_3$;

$R^9$ is F, Cl Br, $CH_3$, $CHF_2$ or $CF_3$;

$R^{10}$ is F, Cl Br, $CH_3$, $CHF_2$ or $CF_3$;

$R^{11}$ is F, Cl Br, $CH_3$, $CHF_2$ or $CF_3$;

$R^{12a}$ is H or $CH_3$;

$R^{12b}$ is H;

$R^{13a}$ is H, $CH_3$, or $OCH_3$;

$R^{13b}$ is H;

each $R^{16}$, $R^{17c}$; $R^{18}$ and $R^{19c}$ is independently F, Cl, Br, $CH_3$, $CHF_2$ or $CF_3$; and each $R^{17n}$ and $R^{19n}$ is $CH_3$.

3. A compound of claim 2 wherein:

A is A-1, A-2, A-3 or A-4;

each $R^{14c}$ is independently F, Cl, Br, $CH_3$, $CHF_2$ or $CF_3$;

each $R^{14n}$ is $CH_3$;

each $R^{15c}$ is independently F, Cl, Br, $CH_3$, $CHF_2$ or $CF_3$; and each $R^{15n}$ is $CH_3$.

4. A compound of claim 3 wherein:

A is A-1, A-2 or A-4;

$B^2$ is N; and

Q is Q-9A or Q-9B.

5. A compound of claim 4 wherein:

L is —$C(R^{12a})R^{12b}$—$C(R^{13a})R^{13b}$—;

$R^{2a}$ is H, F or Cl; and each $R^2$ is F or Cl;

provided that when G is N or $R^{2a}$ is H, then the ring comprising G is substituted with $R^2$ ortho to the bond to L.

6. A compound of claim 4 wherein:

L is 1,2-phenylene optionally substituted with up to 2 substituents independently selected from F, Cl, Br and $CH_3$;

$R^{2a}$ is H, F or Cl;

each $R^2$ is F or Cl; and the ring comprising G is substituted with at least one $R^2$ ortho to the bond to Q.

7. A compound of claim 1, provided that when G is N or $R^{2a}$ is H, then the ring comprising G is substituted with at least one instance of $R^2$.

8. A compound of claim 1 wherein L is —$C(R^{12a})R^{12b}$—$C(R^{13a})R^{13b}$—.

9. A compound of claim 1 which is selected from the group consisting of:

3-chloro-N-[2-chloro-4-(3-trifluoromethyl)-1H-pyrazol-1-yl]phenyl-1-methylethyl]-2-pyrazinecarboxamide, N-[2-[2-chloro-4-[3-(trifluoromethyl)-1H-pyrazol-1-yl]phenyl]ethyl-3-(trifluoromethyl)-2-pyridinecarboxamide, N-[3',5'-difluoro-4'-[3-(trifluoromethyl)-1H-pyrazol-1-yl][1,1'-biphenyl]-2-yl]-3-(trifluoromethyl)-2-pyridinecarboxamide, 3-(difluoromethyl)-N-[3',5'-difluoro-4'-[3-(trifluoromethyl)-1H-pyrazol-1-yl][1,1'-biphenyl]-2-yl]-1-methyl-1H-pyrazole-4-carboxamide, and N-[2-[3-chloro-5-[3-(trifluoromethyl)-1H-pyrazol-1-yl]-2-pyridinyl]ethyl]-2-(trifluoromethyl)benzamide.

10. A fungicidal composition comprising (a) a compound of claim 1; and (b) at least one other fungicide.

11. A fungicidal composition comprising (a) a compound of claim 1; and (b) at least one additional component selected from the group consisting of surfactants, solid diluents and liquid diluents.

12. A method for protecting a plant or plant seed from diseases caused by fungal pathogens comprising applying a fungicidally effective amount of a compound of claim 1 to the plant or plant seed.

13. A method for controlling a phytophagous nematode comprising contacting the nematode or its environment with a nematocidally effective amount of a compound of claim 8.

\* \* \* \* \*